US011692194B2

(12) United States Patent
Shah et al.

(10) Patent No.: US 11,692,194 B2
(45) Date of Patent: Jul. 4, 2023

(54) MODULATING EXPRESSION OF POLYPEPTIDES VIA NEW GENE SWITCH EXPRESSION SYSTEMS

(71) Applicant: Precigen, Inc., Germantown, MD (US)

(72) Inventors: Rutul R. Shah, Blacksburg, VA (US); Thomas D. Reed, Blacksburg, VA (US); Cheryl G. Bolinger, Blacksburg, VA (US)

(73) Assignee: PRECIGEN, INC., Germantown, MD (US)

( * ) Notice: Subject to any disclaimer, the term of this patent is extended or adjusted under 35 U.S.C. 154(b) by 0 days.

(21) Appl. No.: 15/867,500

(22) Filed: Jan. 10, 2018

(65) Prior Publication Data

US 2018/0291384 A1 Oct. 11, 2018

Related U.S. Application Data

(60) Provisional application No. 62/464,958, filed on Feb. 28, 2017, provisional application No. 62/444,775, filed on Jan. 10, 2017.

(51) Int. Cl.

| | |
|---|---|
| ***C12N 15/63*** | (2006.01) |
| ***G01N 33/68*** | (2006.01) |
| ***C12N 15/10*** | (2006.01) |
| ***C07K 14/54*** | (2006.01) |
| ***C07K 14/725*** | (2006.01) |
| ***C12N 15/85*** | (2006.01) |

(52) U.S. Cl.

CPC ........ *C12N 15/635* (2013.01); *C07K 14/5443* (2013.01); *C07K 14/7051* (2013.01); *C12N 15/1055* (2013.01); *C12N 15/63* (2013.01); *C12N 15/85* (2013.01); *G01N 33/6845* (2013.01); *C07K 2319/80* (2013.01); *C12N 2800/90* (2013.01)

(58) Field of Classification Search

CPC .. C12N 15/635; C12N 15/1055; C12N 15/63; C12N 15/85; C12N 2800/90; C07K 2319/80; C07K 14/5443; C07K 14/7051; G01N 33/6845

See application file for complete search history.

(56) References Cited

U.S. PATENT DOCUMENTS 7,847,064 B2 * 12/2010 Beachy .............. C07K 14/4702 435/235.1
8,124,084 B2 2/2012 Lefrancois et al.
8,173,786 B2 5/2012 Weiner et al.
8,202,718 B2 6/2012 Palli et al.
8,556,882 B2 * 10/2013 Morgan .................. A61P 35/00 604/522
8,598,409 B2 12/2013 Kapitskaya et al.
8,715,959 B2 5/2014 Palli et al.
8,822,754 B2 9/2014 Palli et al.
8,927,518 B1 1/2015 Heller et al.
9,163,256 B2 10/2015 Palli et al.
9,322,026 B2 4/2016 Palli et al.
9,629,877 B2 4/2017 Cooper et al.
9,877,990 B2 * 1/2018 Krishnan ............ A61K 9/0014
10,358,477 B2 * 7/2019 Jacques .................. A61P 37/04
11,020,429 B2 * 6/2021 Thompson ......... A61K 39/0011
2009/0136465 A1 5/2009 Merenick et al.
2013/0071414 A1 3/2013 Dotti et al.
2013/0149290 A1 6/2013 Braughler et al.
2014/0057349 A1 2/2014 Hormann et al.
2016/0008398 A1 1/2016 Sadelain et al.
2016/0165861 A1 6/2016 Hering et al.
2016/0257964 A1 9/2016 Palli et al.
2016/0317678 A1 11/2016 Roeth et al.
2017/0088597 A1 3/2017 Wong et al.
2017/0096673 A1 4/2017 Kapitskaya et al.
2017/0128569 A1 5/2017 Beech et al.
2017/0151310 A1 6/2017 Felber et al.
2017/0183654 A1 6/2017 Wong et al.
2017/0202924 A1 7/2017 Felber et al.
2017/0342440 A1 11/2017 Palli et al.

FOREIGN PATENT DOCUMENTS

EP 1934353 B1 10/2011
EP 1809321 B1 3/2012
WO WO-0078951 A1 12/2000
WO WO-2007146959 A2 * 12/2007 ............ C07K 14/71
WO 2014/186469 A2 11/2014
WO WO-2015079053 A2 * 6/2015 ............ C12N 15/85
WO WO-2015142675 A2 9/2015

(Continued)

OTHER PUBLICATIONS

Grunseich et al. (Molecular Therapy, vol. 19, No. 7, p. 1369, Jul. 2011). (Year: 2011).*
Kumar and Katakam (Gene Transfer: Delivery and Expression of DNA and RNA, A Laboratory Manual, 2007, Chapter 64, pp. 643-651) (Year: 2007).*
Szymczak et al. (Nature Biotechnology, 2004. vol. 22, No. 5, pp. 589-594). (Year: 2004).*
Barrett et al (Cell Biology, 2016, vol. 5, No. 2, pp. 1-7) (Year: 2016).*
Sahm et al (Cancer Immunology and Immunotherapy 2012, vol. 61, pp. 1451-1461). (Year: 2012).*
Sauer et al (Proceedings of National Academy of Science, 1988, vol. 85, pp. 5166-5170).*

(Continued)

*Primary Examiner* — Antonio Galisteo Gonzalez
*Assistant Examiner* — Khaleda B Hasan
(74) *Attorney, Agent, or Firm* — Gene J. Yao; Barnes & Thornburg LLP

(57) ABSTRACT

Disclosed herein are polynucleotides encoding ligand-inducible gene switch polypeptides, and systems comprising gene switch polypeptides for modulating the expression of a heterologous gene and an interleukin in a host cell. The compositions, methods and systems described herein facilitate ligand dependent expression of polypeptides including but not limited to cytokines and antigen binding polypeptides.

32 Claims, 68 Drawing Sheets

Specification includes a Sequence Listing.

(56) References Cited

FOREIGN PATENT DOCUMENTS

| | | | | |
|---|---|---|---|---|
| WO | WO-2015168547 A2 * | 11/2015 | ........... | C12N 15/113 |
| WO | WO-2015174928 A1 | 11/2015 | | |
| WO | WO-2016126608 A1 | 8/2016 | | |
| WO | WO-2017083750 A1 | 5/2017 | | |
| WO | WO-2017177063 A1 | 10/2017 | | |
| WO | 2018/226897 A1 | 12/2018 | | |

OTHER PUBLICATIONS

Tosic et al.: Interleukin-15 (IL-15) and IL-15 receptor alpha fusion protein enhances antitumor activity of myxoma virus. Journal for ImmunoTherapy of Cancer 2013 1(Suppl 1):P137 (Year: 2013).*

Donnelly, et al., Analysis of the apthovirus 2A/2B polyprotein 'cleavage' mechanism indicates not a proteolytic reaction, but a novel translational effect: a putative ribosomal 'skip'. Journal of General Virology 2001;82:1013-1025.

Kim et al., PLoS One, 6:e18556 (2011).

Nakanishi et al., Yakugaku Zasshi, 129:1433-1443 (2009).

Uchibori et al., Molecular Therapy, vol. 23, Suppl. 1, p. S89 (2015).

Hurton, Proc. Natl. Acad. Sci. U S A., 113:E7788-E7797 (2016).

Kang et al., PNAS, 112:12893-12898 (2015).

Chan et al., Chapter 25—Therapeutic Efficacy and Systemic Anti-tumor T Cell Immunity Induced by Rheoswitch-Regulated IL-12 Expression after Intratumoral Injection of Adenovirus Vector or Vector-Transduced Dendritic Cells. Gene Therapy of Cancer (Third Edition), 2013, pp. 363-376.

Liu et al., Scientific Reports, 7:2193 (2017).

Minskaia et al., Biomed. Res. Int., 2013:291730 (2013).

Gary Luke, Translating 2A Research into Practice, in Innovations in Biotechnology (Eddy Agbo ed., 2012).

Smith MCM 2014, Phage-encoded Serine Integrases and Other Large Serine Recombinases, Microbiol Spectrum, 3(4): MDMA3-0059-2014 (2015).

Chicaybam et al., PloS One, 8:e60298 (2013).

* cited by examiner

| # | Vector 1 | Vector 2 |
|---|---|---|
| 16 | EF1A → 5'UTR – CAR – pA | EF1A → 5'UTR – Cell Tag – IRES – mbIL-15 – pA |
| 17 | EF1A → 5'UTR – CAR – 2A – VP16/RXR – IRES – Gal4/EcR – pA | IP → 5'UTR – mbIL-15 – 2A – Cell Tag – pA |
| 18 | EF1A → 5'UTR – CAR – 2A – VP16/RXR – IRES – Gal4/EcR – pA | IP → 5'UTR – Cell Tag – 2A – mbIL-15 – pA |
| 19 | EF1A → 5'UTR – CAR – 2A – VP16/RXR – IRES – Gal4/EcR – pA | IP → 5'UTR – Cell Tag – IRES – mbIL-15 – pA |
| 20 | EF1A → 5'UTR – CAR – 2A – VP16/RXR – 2A – Gal4/EcR – pA | IP → 5'UTR – Cell Tag – IRES – mbIL-15 – pA |
| 21 | EF1A → 5'UTR – CAR – 2A – VP16/RXR – 2A – Gal4/EcR – pA | IP → 5'UTR – mbIL-15 – 2A – Cell Tag – pA |
| 22 | EF1A → 5'UTR – CAR – 2A – VP16/RXR – 2A – Gal4/EcR – pA | IP → 5'UTR – Cell Tag – 2A – mbIL-15 – pA |
| 23 | IP → 5'UTR – CAR – 2A – mbIL-15 – 2A – Cell Tag – pA | EF1A → 5'UTR – VP16/RXR – IRES/2A – Gal4/EcR – pA |

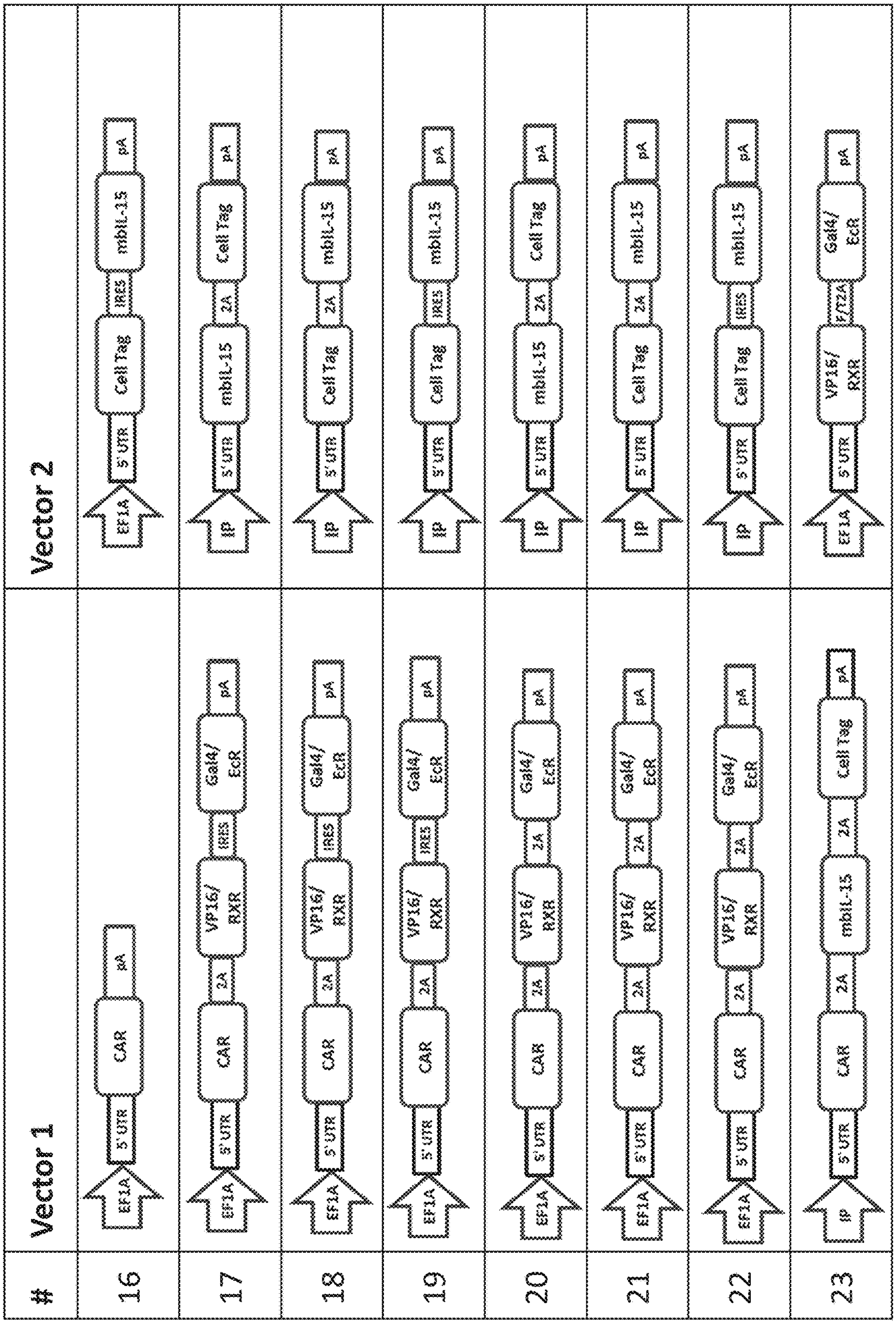

FIG. 2C

| Sample Description | | % CAR+ | | |
|---|---|---|---|---|
| | | Day 1 | Day 8 | Day 15 |
| RTS-mbIL15 construct | Serine Recombinase | 4.8 | 39.8 | 45.6 |
| Promoterless mbIL15 negative control | Serine Recombinase | 7.7 | 47.6 | 60.3 |
| RTS-mbIL15 construct | No recombinase | 6.4 | 0.2 | 0 |
| Promoterless mbIL15 negative control | No recombinase | 12.3 | 0.2 | 0.1 |

FIG. 18A

| # | Vector 1 | Vector 2 |
|---|---|---|
| 1 | EF1A → 5'UTR - CAR - BGHpA - 5'UTR - mbIL-15 - IP | NFAT-IL2 → 5'UTR - VP16/RXR - 2A - Gal4/EcR - pA |
| 2 | IP → 5'UTR - CAR - 2A - mbIL-15 - pA | NFAT-IL2 → 5'UTR - VP16/RXR - 2A - Gal4/EcR - pA |
| 3 | EF1A → 5'UTR - CAR - pA ← IP → 5'UTR - mbIL-15 - pA | NFAT-IL2 → 5'UTR - VP16/RXR - 2A - Gal4/EcR - pA |
| 4 | EF1A → 5'UTR - CAR - 2A - Cell Tag - pA ← IP → 5'UTR - mbIL-15 - pA | NFAT-IL2 → 5'UTR - VP16/RXR - 2A - Gal4/EcR - pA |
| 5 | IP → 5'UTR - CAR - pA | NFAT-IL2 → 5'UTR - VP16/RXR - 2A - Gal4/EcR - pA |
| 6 | EF1A → 5'UTR - mbIL-15 - pA ← EF1A → 5'UTR - CAR - 2A - Cell Tag - pA | NFAT-IL2 → 5'UTR - VP16/RXR - 2A - Gal4/EcR - pA |
| 7 | IP → 5'UTR - mbIL-15 - pA ← EF1A → 5'UTR - CAR - 2A - Cell Tag - pA | IL2 → 5'UTR - VP16/RXR - 2A - Gal4/EcR - pA |
| 8 | IP → 5'UTR - mbIL-15 - pA ← EF1A → 5'UTR - CAR - 2A - Cell Tag - pA | RO3 → 5'UTR - VP16/RXR - 2A - Gal4/EcR - pA |

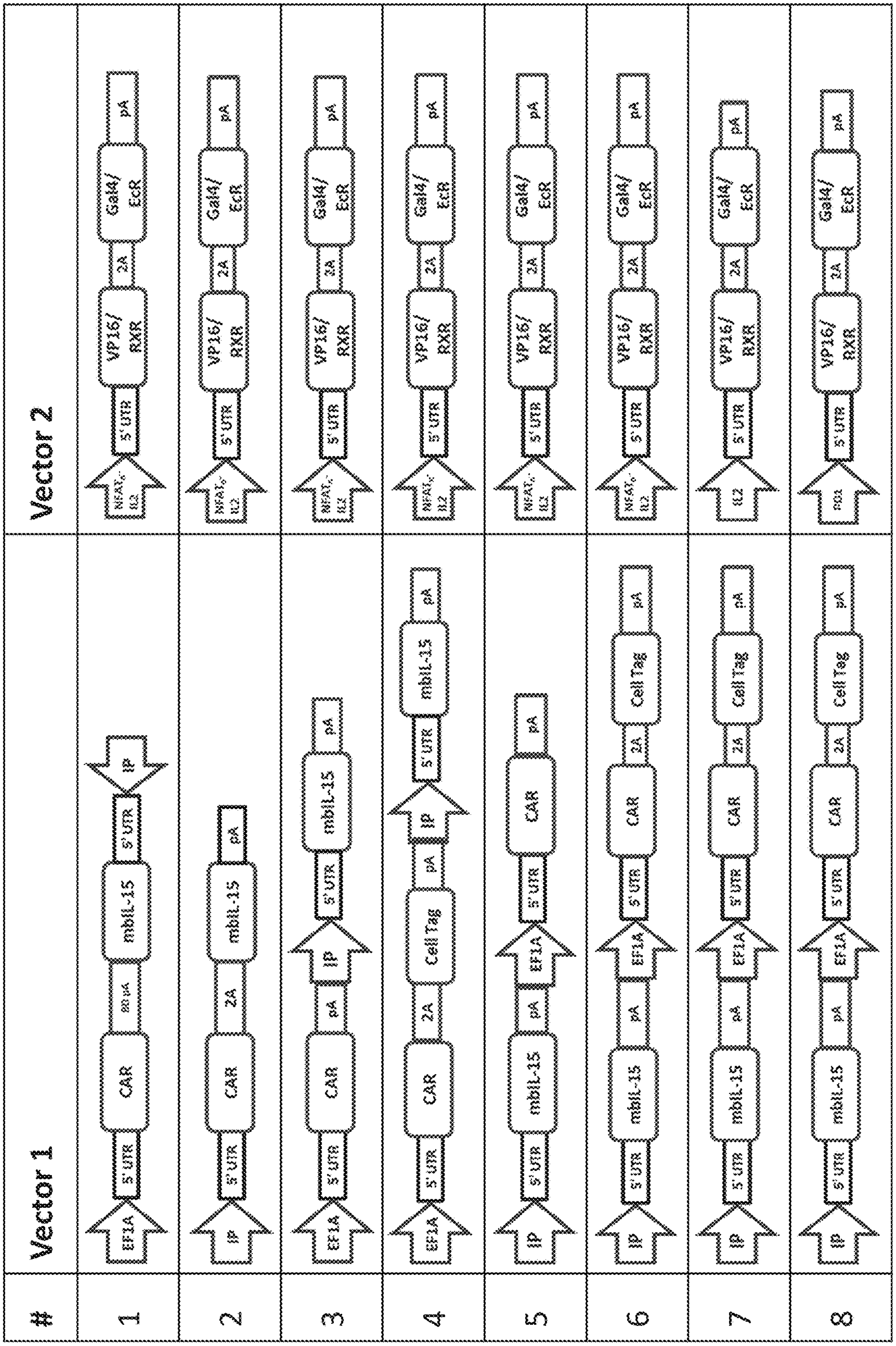

FIG. 19A

| # | Vector 1 | Vector 2 |
|---|---|---|
| 8 | EF1A → 5'UTR - CAR - 2A - VP16/RXR - 2A - Gal4/EcR - pA | IP → 5'UTR - scIL-12 - 2A - Cell Tag - pA |
| 9 | EF1A → 5'UTR - CAR - 2A - VP16/RXR - pA - Gal4/EcR | IP → 5'UTR - scIL-12 - pA |
| 10 | EF1A → 5'UTR - VP16/RXR - 2A - CAR - pA - Gal4/EcR | IP → 5'UTR - scIL-12 - pA |
| 11 | EF1A → 5'UTR - scIL-12 - pA  IP → 5'UTR - CAR - pA | EF1A → 5'UTR - VP16/RXR - 2A - Gal4/EcR - pA |
| 12 | EF1A → 5'UTR - CAR - pA - VP16/RXR - 2A - scIL-12 - pA | IP → 5'UTR - scIL-12 - 2A - Gal4/EcR - pA ← EF1A |
| 13 | EF1A → 5'UTR - CAR - 2A - Cell Tag - IRES - VP16/RXR - pA | IP → 5'UTR - scIL-12 - 2A - Gal4/EcR - pA ← EF1A |
| 14 | EF1A → 5'UTR - CAR - 2A - Gal4/EcR - pA | EF1A → 5'UTR - scIL-12 - 2A - Cell Tag - pA |
| 15 | IP → 5'UTR - scIL-12 - pA - EF1A → CAR | EF1A → 5'UTR - VP16/RXR - 2A - Gal4/EcR - pA |

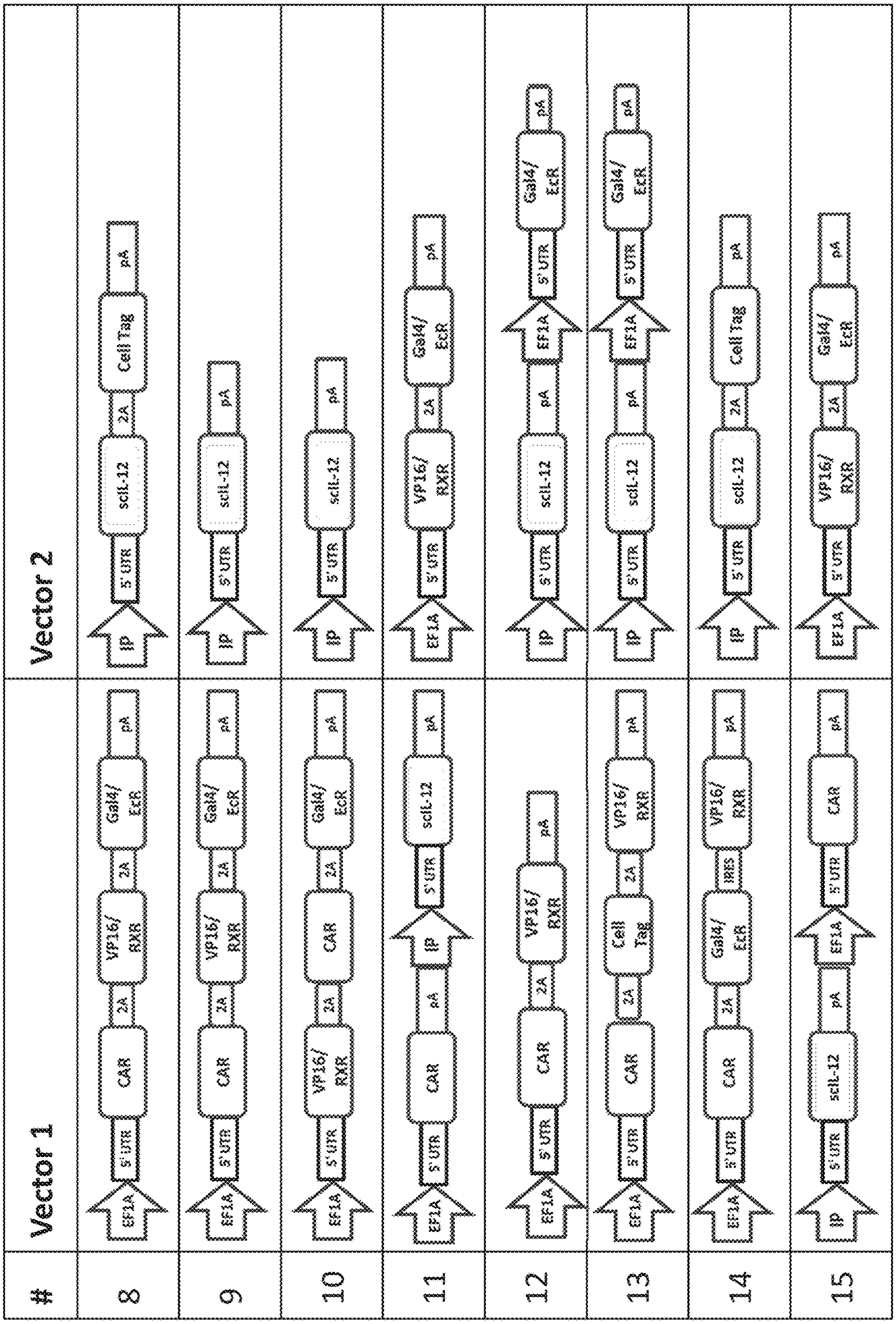

FIG. 24B

SEQUENCE LISTING

```
<160> NUMBER OF SEQ ID NOS: 244

<210> SEQ ID NO 1
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Whitlow Linker"
```

```
<400> SEQUENCE: 1

ggcagcacct ccggcagcgg caagcctggc agcggcgagg gcagcaccaa gggc          54


<210> SEQ ID NO 2
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Linker"

<400> SEQUENCE: 2

tctggcggag gatctggagg aggcggatct ggaggaggag gcagtggagg cggaggatct    60

ggcggaggat ctctgcag                                                   78


<210> SEQ ID NO 3
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="GSG linker"

<400> SEQUENCE: 3

ggaagcgga                                                              9


<210> SEQ ID NO 4
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="SGSG linker"

<400> SEQUENCE: 4

agtggcagcg gc                                                         12


<210> SEQ ID NO 5
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="(G4S)3 linker"

<400> SEQUENCE: 5

ggtggcggtg gctcgggcgg tggtgggtcg ggtggcggcg gatct                     45


<210> SEQ ID NO 6
<211> LENGTH: 12
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Furin cleavage site/ Furinlink1"

<400> SEQUENCE: 6

cgtgcaaagc gt                                                         12


<210> SEQ ID NO 7
<211> LENGTH: 84
<212> TYPE: DNA
<213> ORGANISM: Foot-and-mouth disease virus
<220> FEATURE:
<221> NAME/KEY: source
<223> OTHER INFORMATION: /note="Fmdv"

<400> SEQUENCE: 7

agagccaaga gggcaccggt gaaacagact ttgaattttg accttctgaa gttggcagga     60

gacgttgagt ccaaccctgg gccc                                            84


<210> SEQ ID NO 8
<211> LENGTH: 54
<212> TYPE: DNA
<213> ORGANISM: Thosea asigna virus
<220> FEATURE:
<221> NAME/KEY: source
<223> OTHER INFORMATION: /note="Thosea asigna virus 2A region (T2A)"

<400> SEQUENCE: 8

gagggcagag gaagtctgct aacatgcggt gacgtcgagg agaatcctgg acct           54


<210> SEQ ID NO 9
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Furin-GSG-T2A"

<400> SEQUENCE: 9

agagctaaga ggggaagcgg agagggcaga ggaagtctgc taacatgcgg tgacgtcgag     60

gagaatcctg gacct                                                      75


<210> SEQ ID NO 10
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Furin-SGSG-T2A"

<400> SEQUENCE: 10

agggccaaga ggagtggcag cggcgagggc agaggaagtc ttctaacatg cggtgacgtg     60

gaggagaatc ccggccct                                                   78
```

<210> SEQ ID NO 11
<211> LENGTH: 57
<212> TYPE: DNA
<213> ORGANISM: Porcine teschovirus
<220> FEATURE:
<221> NAME/KEY: source
<223> OTHER INFORMATION: /note="Porcine teschovirus-1 2A region (P2A)"

<400> SEQUENCE: 11
gcaacgaact tctctctcct aaaacaggct ggtgatgtgg aggagaatcc tggtcca 57

<210> SEQ ID NO 12
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="GSG-P2A"

<400> SEQUENCE: 12
ggaagcggag ctactaactt cagcctgctg aagcaggctg gagacgtgga ggagaaccct 60
ggacct 66

<210> SEQ ID NO 13
<211> LENGTH: 60
<212> TYPE: DNA
<213> ORGANISM: Equine rhinitis A virus
<220> FEATURE:
<221> NAME/KEY: source
<223> OTHER INFORMATION: /note="Equine rhinitis A virus 2A region (E2A)"

<400> SEQUENCE: 13
cagtgtacta attatgctct cttgaaattg gctggagatg ttgagagcaa ccctggacct 60

<210> SEQ ID NO 14
<211> LENGTH: 66
<212> TYPE: DNA
<213> ORGANISM: Foot-and-mouth disease virus
<220> FEATURE:
<221> NAME/KEY: source
<223> OTHER INFORMATION: /note="Foot-and-mouth disease virus 2A region (F2A)"

<400> SEQUENCE: 14
gtcaaacaga ccctaaactt tgatctgcta aaactggccg gggatgtgga aagtaatccc 60
ggcccc 66

<210> SEQ ID NO 15
<211> LENGTH: 93
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FP2A"

<400> SEQUENCE: 15
cgtgcaaagc gtgcaccggt gaaacaggga agcggagcta ctaacttcag cctgctgaag 60
caggctggag acgtggagga gaaccctgga cct 93

<210> SEQ ID NO 16
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Linker-GSG"

<400> SEQUENCE: 16
gcaccggtga aacagggaag cgga 24

<210> SEQ ID NO 17
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Linker"

<400> SEQUENCE: 17
gcaccggtga aacag 15

<210> SEQ ID NO 18
<211> LENGTH: 570
<212> TYPE: DNA
<213> ORGANISM: Encephalomyocarditis virus
<220> FEATURE:
<221> NAME/KEY: source
<223> OTHER INFORMATION: /note="EMCV IRES"

<400> SEQUENCE: 18 cccccctctcc ctcccccccc cctaacgtta ctggccgaag ccgcttggaa taaggccggt 60
gtgcgtttgt ctatatgtta ttttccacca tattgccgtc ttttggcaat gtgagggccc 120
ggaaacctgg ccctgtcttc ttgacgagca ttcctagggg tctttcccct ctcgccaaag 180
gaatgcaagg tctgttgaat gtcgtgaagg aagcagttcc tctggaagct tcttgaagac 240
aaacaacgtc tgtagcgacc ctttgcaggc agcggaaccc cccacctggc gacaggtgcc 300
tctgcggcca aaagccacgt gtataagata cacctgcaaa ggcggcacaa ccccagtgcc 360
acgttgtgag ttggatagtt gtggaaagag tcaaatggct ctcctcaagc gtattcaaca 420
aggggctgaa ggatgcccag aaggtacccc attgtatggg atctgatctg gggcctcggt 480
gcacatgctt tacatgtgtt tagtcgaggt taaaaaacgt ctaggccccc cgaaccacgg 540
ggacgtggtt ttcctttgaa aaacacgatc 570

<210> SEQ ID NO 19
<211> LENGTH: 73
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="2xRbm3 IRES"

<400> SEQUENCE: 19
actagtttta taatttcttc ttccagaatt tctgacattt tataatttct tcttccagaa 60
gactcacaac ctc 73

<210> SEQ ID NO 20
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="GM-CSFR-alpha signal peptide"

<400> SEQUENCE: 20
atgcttctcc tggtgacaag ccttctgctc tgtgagttac cacacccagc attcctcctg 60
atccca 66

<210> SEQ ID NO 21
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="GM-CSFR-alpha signal peptide"

<400> SEQUENCE: 21
atgctgctgc tggtgaccag cctgctgctg tgtgagctgc cccaccccgc ctttctgctg 60
atcccc 66

<210> SEQ ID NO 22
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Ig Kappa signal peptide"

<400> SEQUENCE: 22
atgaggctcc ctgctcagct cctggggctg ctaatgctct gggtcccagg atccagtggg 60

<210> SEQ ID NO 23
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="IgE signal peptide"

<400> SEQUENCE: 23
atggattgga cctggattct gtttctggtg gccgctgcca caagagtgca cagc 54

<210> SEQ ID NO 24
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="CD8-alpha signal peptide"

<400> SEQUENCE: 24
atggcgctgc ccgtgaccgc cttgctcctg ccgctggcct tgctgctcca cgccgccagg 60
ccg 63

<210> SEQ ID NO 25
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="CD8-alpha signal peptide"

<400> SEQUENCE: 25
atggccttac cagtgaccgc cttgctcctg ccgctggcct tgctgctcca cgccgccagg 60
ccg 63

<210> SEQ ID NO 26
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="TVB2(T21A)signal peptide"

<400> SEQUENCE: 26
atgggcacca gcctcctctg ctggatggcc ctgtgtctcc tgggggcaga tcacgcagat 60
gct 63

<210> SEQ ID NO 27
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="CD52 signal peptide"

<400> SEQUENCE: 27
atgaagcgct tcctcttcct cctactcacc atcagcctcc tggttatggt acagatacaa 60
actggactct ca 72

<210> SEQ ID NO 28
<211> LENGTH: 84
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Low-affinity nerve growth factor receptor (LNGFR, TNFRSF16) signal peptide"

<400> SEQUENCE: 28
atgggggcag gtgccaccgg ccgcgccatg gacgggccgc gcctgctgct gttgctgctt 60
ctgggggtgt cccttggagg tgcc 84

<210> SEQ ID NO 29
<211> LENGTH: 141
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="CD8-alpha hinge region"

<400> SEQUENCE: 29
aagcccacca ccacccctgc ccctagacct ccaaccccag cccctacaat cgccagccag 60
cccctgagcc tgaggcccga agcctgtaga cctgccgctg gcggagccgt gcacaccaga 120
ggcctggatt tcgcctgcga c 141

<210> SEQ ID NO 30
<211> LENGTH: 282
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="CD8 alpha 2x"

<400> SEQUENCE: 30
aaacctacta caactcctgc cccccggcct cctacaccag ctcctactat cgcctcccag 60
ccactcagtc tcagacccga ggcttctagg ccagcggccg gaggcgcggt ccacacccgc 120
gggctggact ttgcatccga taagcccacc accacccctg cccctagacc tccaacccca 180
gcccctacaa tcgccagcca gcccctgagc ctgaggcccg aagcctgtag acctgccgct 240
ggcggagccg tgcacaccag aggcctggat ttcgcctgcg ac 282

<210> SEQ ID NO 31
<211> LENGTH: 423
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="CD8 alpha 3x"

<400> SEQUENCE: 31
aagcctacca ccaccccgc acctcgtcct ccaacccctg cacctacgat tgccagtcag 60

```
cctctttcac tgcggcctga ggccagcaga ccagctgccg gcggtgccgt ccatacaaga    120

ggactggact tcgcgtccga taaacctact accactccag ccccaaggcc cccaacccca    180

gcaccgacta tcgcatcaca gcctttgtca ctgcgtcctg aagccagccg gccagctgca    240

gggggggccg tccacacaag gggactcgac tttgcgagtg ataagcccac caccacccct    300

gcccctagac ctccaacccc agcccctaca atcgccagcc agcccctgag cctgaggccc    360

gaagcctgta gacctgccgc tggcggagcc gtgcacacca gaggcctgga tttcgcctgc    420

gac                                                                  423
```

<210> SEQ ID NO 32
<211> LENGTH: 564
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="CD8 alpha 4x"

<400> SEQUENCE: 32

```
aagcctacca ccaccccgc acctcgtcct ccaacccctg cacctacgat tgccagtcag      60

cctctttcac tgcggcctga ggccagcaga ccagctgccg gcggtgccgt ccatacaaga    120

ggactggact tcgcgtccga taaacctact accactccag ccccaaggcc cccaacccca    180

gcaccgacta tcgcatcaca gcctttgtca ctgcgtcctg aagccagccg gccagctgca    240

gggggggccg tccacacaag gggactcgac tttgcgagtg ataaacctac tacaactcct    300

gcccccggc ctcctacacc agctcctact atcgcctccc agccactcag tctcagaccc    360

gaggcttcta ggccagcggc cggaggcgcg gtccacaccc gcgggctgga ctttgcatcc    420

gataagccca ccaccacccc tgcccctaga cctccaaccc cagcccctac aatcgccagc    480

cagcccctga gcctgaggcc cgaagcctgt agacctgccg ctggcggagc cgtgcacacc    540

agaggcctgg atttcgcctg cgac                                           564
```

<210> SEQ ID NO 33
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="CD8-alpha TM domain"

<400> SEQUENCE: 33

```
atctacatct gggcccctct ggccggcacc tgtggcgtgc tgctgctgag cctggtcatc     60

accctgtact gcaaccaccg gaat                                            84
```

<210> SEQ ID NO 34
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="CD28 TM domain"

<400> SEQUENCE: 34
ttttgggtgc tggtggtggt tggtggagtc ctggcttgct atagcttgct agtaacagtg 60
gcctttatta ttttctgggt g 81

<210> SEQ ID NO 35
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="CD28 signaling domain"

<400> SEQUENCE: 35
aggagcaagc ggagcagagg cggccacagc gactacatga acatgacccc ccggaggcct 60
ggccccaccc ggaagcacta ccagccctac gccccctccca gggacttcgc cgcctaccgg 120
agc 123

<210> SEQ ID NO 36
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="CD3 zeta signaling domain"

<400> SEQUENCE: 36
cgggtgaagt tcagccggag cgccgacgcc cctgcctacc agcagggcca gaaccagctg 60
tacaacgagc tgaacctggg ccggagggag gagtacgacg tgctggacaa gcggagaggc 120
cgggaccctg agatgggcgg caagccccgg agaaagaacc ctcaggaggg cctgtataac 180
gaactgcaga aagacaagat ggccgaggcc tacagcgaga tcggcatgaa gggcgagcgg 240
cggaggggca agggccacga cggcctgtac cagggcctga gcaccgccac caaggatacc 300
tacgacgccc tgcacatgca ggccctgccc cccaga 336

<210> SEQ ID NO 37
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="4-1BB signaling domain"

<400> SEQUENCE: 37
aagagaggcc ggaagaaact gctgtacatc ttcaagcagc ccttcatgcg gcccgtgcag 60
accacccagg aagaggacgg ctgcagctgc cggttccccg aggaagagga aggcggctgc 120
gaactg 126

<210> SEQ ID NO 38

<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="DNAX-activation protein 10 (DAP 10) Signaling Domain"

<400> SEQUENCE: 38
ctgtgcgcac gcccacgccg cagccccgcc caagaagatg gcaaagtcta catcaacatg 60
ccaggcaggg gc 72

<210> SEQ ID NO 39
<211> LENGTH: 156
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="DNAX-activation protein 12 (DAP12) Signaling Domain"

<400> SEQUENCE: 39
tacttcctgg gccggctggt ccctcggggg cgaggggctg cggaggcagc gacccggaaa 60
cagcgtatca ctgagaccga gtcgccttat caggagctcc agggtcagag gtcggatgtc 120
tacagcgacc tcaacacaca gaggccgtat tacaaa 156

<210> SEQ ID NO 40
<211> LENGTH: 114
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="IL-2 core promoter"

<400> SEQUENCE: 40
acattttgac acccccataa tatttttcca gaattaacag tataaattgc atctcttgtt 60
caagagttcc ctatcactct ctttaatcac tactcacagt aacctcaact cctg 114

<210> SEQ ID NO 41
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="IL-2 minimal promoter"

<400> SEQUENCE: 41
tcaagagttc cctatcactc tctttaatca ctactcacag taacctcaac tcctg 55

<210> SEQ ID NO 42
<211> LENGTH: 380

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="IL-2 enhancer and promoter variant"

<400> SEQUENCE: 42
tgatatcttt tctgagttac ttttgtatcc ccaccccctt aaagaaagga ggaaaaactg 60
tttcatacag aaggcgttaa ttgcatgaat tagagctatc acctaagtgt gggctaatgt 120
aacaaagagg gatttcacct acatccattc agtcagtctt tgggggttta aagaaattcc 180
aaagagtcat cagaagagga aaaatgaagg taatgttttt tcagactggt aaagtctttg 240
aaaatatgtg taatatgtaa aacattttga cacccccata atatttttcc agaattaaca 300
gtataaattg catctcttgt tcaagagttc cctatcactc tctttaatca ctactcacag 360
taacctcaac tcctgccaca 380

<210> SEQ ID NO 43
<211> LENGTH: 373
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="IL-2 enhancer and promoter variant"

<400> SEQUENCE: 43
ttttctgagt tacttttgta tccccacccc cttaaagaaa ggaggaaaaa ctgtttcata 60
cagaaggcgt taattgcatg aattagagct atcacctaag tgtgggctaa tgtaacaaag 120
agggatttca cctacatcca ttcagtcagt ctttgggggt ttaaagaaat tccaaagagt 180
catcagaaga ggaaaaatga aggtaatgtt ttttcagact ggtaaagtct ttgaaaatat 240
gtgtaatatg taaaacattt tgacaccccc ataatatttt tccagaatta acagtataaa 300
ttgcatctct tgttcaagag ttccctatca ctctctttaa tcactactca cagtaacctc 360
aactcctgcc aca 373

<210> SEQ ID NO 44
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="NF-kappa-B binding site"

<400> SEQUENCE: 44
aagagggatt tcacctacat 20

<210> SEQ ID NO 45
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="NF-kappa-B binding site"

<400> SEQUENCE: 45
aagagggatt t    11

<210> SEQ ID NO 46
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="NF-kappa-B binding site"

<400> SEQUENCE: 46
agagggattt cacctacatc    20

<210> SEQ ID NO 47
<211> LENGTH: 161
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="(NF-kappa-B)1-IL2 promoter variant"

<400> SEQUENCE: 47
aattggtccc atcgaagagg gatttcacct acataattgg tcccgggaca ttttgacacc    60
cccataatat ttttccagaa ttaacagtat aaattgcatc tcttgttcaa gagttcccta    120
tcactctctt taatcactac tcacagtaac ctcaactcct g    161

<210> SEQ ID NO 48
<211> LENGTH: 201
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="(NF-kappa-B)3-IL2 promoter variant"

<400> SEQUENCE: 48
aattggtccc atcgaagagg gatttcacct acataagagg gatttcacct acataagagg    60
gatttcacct acataattgg tcccgggaca ttttgacacc cccataatat ttttccagaa    120
ttaacagtat aaattgcatc tcttgttcaa gagttcccta tcactctctt taatcactac    180
tcacagtaac ctcaactcct g    201

<210> SEQ ID NO 49
<211> LENGTH: 268
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"
<220> FEATURE:
<221> NAME/KEY: source
<223> OTHER INFORMATION: /note="(NF-kappa-B)6-IL2 promoter variant"

<400> SEQUENCE: 49
aattggtccc atcgaagagg gatttcacct acataagagg gatttcacct acataagagg 60
gatttcacct acataattgg taagagggat ttcacctaca taagagggat ttcacctaca 120
taagagggat ttcacctaca taattggtcc cgggacattt tgacaccccc ataatatttt 180
tccagaatta acagtataaa ttgcatctct tgttcaagag ttccctatca ctctctttaa 240
tcactactca cagtaacctc aactcctg 268

<210> SEQ ID NO 50
<211> LENGTH: 177
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="1X NFAT Response Elements-IL2 Promoter
variant"

<400> SEQUENCE: 50
aattggtccc atcgaattag gaggaaaaac tgtttcatac agaaggcgtc aattggtccc 60
gggacatttt gacaccccca taatattttt ccagaattaa cagtataaat tgcatctctt 120
gttcaagagt tccctatcac tctctttaat cactactcac agtaacctca actcctg 177

<210> SEQ ID NO 51
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Nuclear factor of activated T-cells
(NFAT) response element"

<400> SEQUENCE: 51
aattaggagg aaaaactgtt tcatacagaa ggcgtc 36

<210> SEQ ID NO 52
<211> LENGTH: 358
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="6X NFAT Response Elements-IL2 Promoter
variant"

<400> SEQUENCE: 52
gaattaggag gaaaaactgt ttcatacaga aggcgtcaat taggaggaaa aactgtttca 60
tacagaaggc gtcaattagg aggaaaaact gtttcataca gaaggcgtca attggtccca 120
tcgaattagg aggaaaaact gtttcataca gaaggcgtca attaggagga aaaactgttt 180
catacagaag gcgtcaatta ggaggaaaaa ctgtttcata cagaaggcgt caattggtcc 240
cgggacattt tgacaccccc ataatatttt tccagaatta acagtataaa ttgcatctct 300
tgttcaagag ttccctatca ctctccttaa tcactactca cagtaacctc aactcctg 358

<210> SEQ ID NO 53
<211> LENGTH: 374
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="6X NFAT Response Elements-IL2 Promoter variant"

<400> SEQUENCE: 53
tgatatcgaa ttaggaggaa aaactgtttc atacagaagg cgtcaattag gaggaaaaac 60
tgtttcatac agaaggcgtc aattaggagg aaaaactgtt tcatacagaa ggcgtcaatt 120
ggtcccatcg aattaggagg aaaaactgtt tcatacagaa ggcgtcaatt aggaggaaaa 180
actgtttcat acagaaggcg tcaattagga ggaaaaactg tttcatacag aaggcgtcaa 240
ttggtcccgg gacattttga cacccccata atatttttcc agaattaaca gtataaattg 300
catctcttgt tcaagagttc cctatcactc tctttaatca ctactcacag taacctcaac 360
tcctgaattc catg 374

<210> SEQ ID NO 54
<211> LENGTH: 358
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="6X NFAT Response Elements-IL2 Promoter variant"

<400> SEQUENCE: 54
gaattaggag gaaaaactgt ttcatacaga aggcgtcaat taggaggaaa aactgtttca 60
tacagaaggc gtcaattagg aggaaaaact gtttcataca gaaggcgtca attggtccca 120
tcgaattagg aggaaaaact gtttcataca gaaggcgtca attaggagga aaaactgttt 180
catacagaag gcgtcaatta ggaggaaaaa ctgtttcata cagaaggcgt caattggtcc 240
cgggacattt tgacaccccc ataatatttt tccagaatta acagtataaa ttgcatctct 300
tgttcaagag ttccctatca ctctctttaa tcactactca cagtaacctc aactcctg 358

<210> SEQ ID NO 55
<211> LENGTH: 365
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="6X NFAT Response Elements-IL2 Promoter variant"

<400> SEQUENCE: 55
tgatatcgaa ttaggaggaa aaactgtttc atacagaagg cgtcaattag gaggaaaaac 60
tgtttcatac agaaggcgtc aattaggagg aaaaactgtt tcatacagaa ggcgtcaatt 120
ggtcccatcg aattaggagg aaaaactgtt tcatacagaa ggcgtcaatt aggaggaaaa 180
actgtttcat acagaaggcg tcaattagga ggaaaaactg tttcatacag aaggcgtcaa 240
ttggtcccgg gacattttga cacccccata atatttttcc agaattaaca gtataaattg 300
catctcttgt tcaagagttc cctatcactc tctttaatca ctactcacag taacctcaac 360
tcctg 365

<210> SEQ ID NO 56
<211> LENGTH: 256
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="3X NFAT Response Elements-IL2 Promoter variant"

<400> SEQUENCE: 56
tgatatcaat tggtcccatc gaattaggag gaaaaactgt ttcatacaga aggcgtcaat 60
taggaggaaa aactgtttca tacagaaggc gtcaattagg aggaaaaact gtttcataca 120
gaaggcgtca attggtcccg ggacattttg acacccccat aatatttttc cagaattaac 180
agtataaatt gcatctcttg ttcaagagtt ccctatcact ctctttaatc actactcaca 240
gtaacctcaa ctcctg 256

<210> SEQ ID NO 57
<211> LENGTH: 249
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="3X NFAT Response Elements-IL2 Promoter variant"

<400> SEQUENCE: 57
aattggtccc atcgaattag gaggaaaaac tgtttcatac agaaggcgtc aattaggagg 60
aaaaactgtt tcatacagaa ggcgtcaatt aggaggaaaa actgtttcat acagaaggcg 120
tcaattggtc ccgggacatt ttgacacccc cataatattt ttccagaatt aacagtataa 180
attgcatctc ttgttcaaga gttccctatc actctcttta atcactactc acagtaacct 240
caactcctg 249

<210> SEQ ID NO 58
<211> LENGTH: 244
<212> TYPE: DNA
<213> ORGANISM: Homo sapiens
<220> FEATURE:
<221> NAME/KEY: source
<223> OTHER INFORMATION: /note="human EEF1A1 promoter variant"

<400> SEQUENCE: 58
gagcgtgcgt gaggctccgg tgcccgtcag tgggcagagc gcacatcgcc cacagtcccc 60

```
gagaagttgg ggggaggggg tcggcgattg aaccggtgcc tagagaaggt ggcgcggggt    120

aaactgggaa agtgatgtcg tgtactggct ccgccttttt cccgagggtg ggggagaacc    180

gtatataagt gcagtagtcg ccgtgaacgt tctttttcgc aacgggtttg ccgccagaac    240

acag                                                                 244


<210> SEQ ID NO 59
<211> LENGTH: 236
<212> TYPE: DNA
<213> ORGANISM: Homo sapiens
<220> FEATURE:
<221> NAME/KEY: source
<223> OTHER INFORMATION: /note="human EEF1A1 promoter variant"

<400> SEQUENCE: 59

gcgtgaggct ccggtgcccg tcagtgggca gagcgcacat cgcccacagt ccccgagaag     60

ttggggggag gggtcggcaa ttgaaccggt gcctagagaa ggtggcgcgg ggtaaactgg    120

gaaagtgatg tcgtgtactg gctccgcctt tttcccgagg gtgggggaga accgtatata    180

agtgcagtag tcgccgtgaa cgttcttttt cgcaacgggt ttgccgccag aacaca        236


<210> SEQ ID NO 60
<211> LENGTH: 1266
<212> TYPE: DNA
<213> ORGANISM: Homo sapiens
<220> FEATURE:
<221> NAME/KEY: source
<223> OTHER INFORMATION: /note="human EEF1A1 promoter and enhancer"

<400> SEQUENCE: 60

gagctttgca aagatggata aagttttaaa cagagaggaa tctttgcagc taatggacct     60

tctaggtctt gaaaggagtg ggaattggct ccggtgcccg tcagtgggca gagcgcacat    120

cgcccacagt ccccgagaag ttggggggag gggtcggcaa ttgaaccggt gcctagagaa    180

ggtggcgcgg ggtaaactgg gaaagtgatg tcgtgtactg gctccgcctt tttcccgagg    240

gtgggggaga accgtatata agtgcagtag tcgccgtgaa cgttcttttt cgcaacgggt    300

ttgccgccag aacacaggta agtgccgtgt gtggttcccg cgggcctggc ctctttacgg    360

gttatggccc ttgcgtgcct tgaattactt ccacctggct gcagtacgtg attcttgatc    420

ccgagcttcg ggttggaagt gggtgggaga gttcgaggcc ttgcgcttaa ggagcccctt    480

cgcctcgtgc ttgagttgag gcctggcctg ggcgctgggg ccgccgcgtg cgaatctggt    540

ggcaccttcg cgcctgtctc gctgctttcg ataagtctct agccatttaa aatttttgat    600

gacctgctgc gacgcttttt ttctggcaag atagtcttgt aaatgcgggc caagatctgc    660

acactggtat ttcggttttt ggggccgcgg gcggcgacgg ggcccgtgcg tcccagcgca    720

catgttcggc gaggcggggc ctgcgagcgc ggccaccgag aatcggacgg gggtagtctc    780

aagctggccg gcctgctctg gtgcctggcc tcgcgccgcc gtgtatcgcc ccgccctggg    840

cggcaaggct ggcccggtcg gcaccagttg cgtgagcgga aagatggccg cttcccggcc    900

ctgctgcagg gagctcaaaa tggaggacgc ggcgctcggg agagcgggcg ggtgagtcac    960

ccacacaaag gaaaagggcc tttccgtcct cagccgtcgc ttcatgtgac tccacggagt   1020

accgggcgcc gtccaggcac ctcgattagt tctcgagctt ttggagtacg tcgtctttag   1080

gttgggggga ggggttttat gcgatggagt ttccccacac tgagtgggtg gagactgaag   1140

ttaggccagc ttggcacttg atgtaattct ccttggaatt tgcccttttt gagtttggat   1200
```

-continued cttggttcat tctcaagcct cagacagtgg ttcaaagttt ttttcttcca tttcaggtgt 1260
cgtgag 1266

<210> SEQ ID NO 61
<211> LENGTH: 571
<212> TYPE: DNA
<213> ORGANISM: Homo sapiens
<220> FEATURE:
<221> NAME/KEY: source
<223> OTHER INFORMATION: /note="Human UBC promoter"

<400> SEQUENCE: 61
ggcctccgcg ccgggttttg gcgcctcccg cgggcgcccc cctcctcacg gcgagcgctg 60
ccacgtcaga cgaagggcgc agcgagcgtc ctgatccttc cgcccggacg ctcaggacag 120
cggcccgctg ctcataagac tcggccttag aaccccagta tcagcagaag gacattttag 180
gacgggactt gggtgactct agggcactgg ttttctttcc agagagcgga acaggcgagg 240
aaaagtagtc ccttctcggc gattctgcgg agggatctcc gtggggcggt gaacgccgat 300
gattatataa ggacgcgccg ggtgtggcac agctagttcc gtcgcagccg ggatttgggt 360
cgcggttctt gtttgtggat cgctgtgatc gtcacttggt gagtagcggg ctgctgggct 420
gggtacgtgc gctcggggtt ggcgagtgtg ttttgtgaag ttttttaggc accttttgaa 480
atgtaatcat ttgggtcaat atgtaatttt cagtgttaga ctagtaaatt gtccgctaaa 540
ttctggccgt ttttggcttt tttgttagac g 571

<210> SEQ ID NO 62
<211> LENGTH: 148
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="6 site GAL4-inducible proximal factor binding element (PFB)"

<400> SEQUENCE: 62
attgttcgga gcagtgcggc gcgtttagcg gagtactgtc ctccgatatt aatcggggca 60
gactattccg ggtttaccg gcgcactctc gcccgaactt caccggcggt ctttcgtccg 120
tgctttatcg gggcggatca ctccgaac 148

<210> SEQ ID NO 63
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Synthetic minimal promoter 1 [Inducible Promoter]"

<400> SEQUENCE: 63
aggtctatat aagcagagct cgtttagtga accctcattc tggagacgga tcccgagccg 60
agtgttttga cctccataga a 81

<210> SEQ ID NO 64

-continued

<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Synthetic 5' UTR based on RPL6"

<400> SEQUENCE: 64
cagccgctaa atccaaggta aggtcagaag a 31

<210> SEQ ID NO 65
<211> LENGTH: 132
<212> TYPE: DNA
<213> ORGANISM: Simian virus 40
<220> FEATURE:
<221> NAME/KEY: source
<223> OTHER INFORMATION: /note="SV40e polyA"

<400> SEQUENCE: 65
aacttgttta ttgcagctta taatggttac aaataaagca atagcatcac aaatttcaca 60
aataaagcat ttttttcact gcattctagt tgtggtttgt ccaaactcat caatgtatct 120
tatcatgtct gg 132

<210> SEQ ID NO 66
<211> LENGTH: 275
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Bidirectional aCA polyA [bidirectional polyA]"

<400> SEQUENCE: 66
atcgattaat ctagcggccc tagacgagca gacatgataa gatacattga tgagtttgga 60
caaaccacaa ctagaatgca gtgaaaaaaa tgctttattt gtgaaatttg tgatgctatt 120
gctttatttg taaccattat aagctgcaat aaacaagtta acaacaacaa ttgcattcat 180
tttatgtttc aggttcaggg ggagatgtgg gaggtttttt aaagcaagta aaacctctac 240
aaatgtggta aaatccgata agcgtaccta gaggc 275

<210> SEQ ID NO 67
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="PA2 polyA"

<400> SEQUENCE: 67
ggccgcaata aaatatcttt attttcatta catctgtgtg ttggtttttt gtgtgag 57

<210> SEQ ID NO 68
<211> LENGTH: 258
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="VP16 activation domain"

<400> SEQUENCE: 68
ggccccaaga agaaaaggaa ggtggccccc cccaccgacg tgagcctggg cgacgagctg 60
cacctggacg gcgaggacgt ggccatggcc cacgccgacg ccctggacga cttcgacctg 120
gacatgctgg gcgacggcga cagccccggc cccggcttca ccccccacga cagcgccccc 180
tacggcgccc tggacatggc cgacttcgag ttcgagcaga tgttcaccga cgccctgggc 240
atcgacgagt acggcggc 258

<210> SEQ ID NO 69
<211> LENGTH: 705
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="Retinoid x receptor (RxR)"

<400> SEQUENCE: 69
gagatgcccg tggacaggat tctggaggcc gaactcgccg tggagcagaa aagcgaccag 60
ggcgtggagg gccccggcgg aaccggcggc agcggcagca gccccaacga ccccgtgacc 120
aacatctgcc aggccgccga caagcagctg ttcaccctgg tggagtgggc caagaggatt 180
ccccacttca gcagcctgcc cctggacgac caggtgatcc tgctgagggc cggatggaac 240
gagctgctga tcgccagctt cagccacagg agcatcgacg tgagggacgg catcctgctg 300
gccaccggcc tgcacgtcca taggaacagc gcccacagcg ccggagtggg cgccatcttc 360
gacagggtgc tgaccgagct ggtgagcaag atgagggaca tgaggatgga caagaccgag 420
ctgggctgcc tgagggccat catcctgttc aaccccgagg tgaggggcct gaaaagcgcc 480
caggaggtgg agctgctgag ggagaaggtg tacgccgccc tggaggagta caccaggacc 540
acccaccccg acgagcccgg cagattcgcc aagctgctgc tgaggctgcc cagcctgagg 600
agcatcggcc tgaagtgcct ggagcacctg ttcttcttca ggctgatcgg cgacgtgccc 660
atcgacacct tcctgatgga gatgctggag agccccagcg acagc 705

<210> SEQ ID NO 70
<211> LENGTH: 969
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="VP16-linker-RxR"

<400> SEQUENCE: 70
ggccccaaga agaaaaggaa ggtggccccc cccaccgacg tgagcctggg cgacgagctg 60
cacctggacg gcgaggacgt ggccatggcc cacgccgacg ccctggacga cttcgacctg 120

```
gacatgctgg gcgacggcga cagccccggc cccggcttca ccccccacga cagcgccccc    180

tacggcgccc tggacatggc cgacttcgag ttcgagcaga tgttcaccga cgccctgggc    240

atcgacgagt acggcggcga attcgagatg cccgtggaca ggattctgga ggccgaactc    300

gccgtggagc agaaaagcga ccagggcgtg gagggccccg gcggaaccgg cggcagcggc    360

agcagcccca acgaccccgt gaccaacatc tgccaggccg ccgacaagca gctgttcacc    420

ctggtggagt gggccaagag gattccccac ttcagcagcc tgcccctgga cgaccaggtg    480

atcctgctga gggccggatg gaacgagctg ctgatcgcca gcttcagcca caggagcatc    540

gacgtgaggg acggcatcct gctggccacc ggcctgcacg tccataggaa cagcgcccac    600

agcgccggag tgggcgccat cttcgacagg gtgctgaccg agctggtgag caagatgagg    660

gacatgagga tggacaagac cgagctgggc tgcctgaggg ccatcatcct gttcaacccc    720

gaggtgaggg gcctgaaaag cgcccaggag gtggagctgc tgagggagaa ggtgtacgcc    780

gccctggagg agtacaccag gaccacccac cccgacgagc ccggcagatt cgccaagctg    840

ctgctgaggc tgcccagcct gaggagcatc ggcctgaagt gcctggagca cctgttcttc    900

ttcaggctga tcggcgacgt gcccatcgac accttcctga tggagatgct ggagagcccc    960

agcgacagc                                                            969
```

```
<210> SEQ ID NO 71
<211> LENGTH: 450
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="GAL4 DNA Binding Domain"

<400> SEQUENCE: 71

atgaagctgc tgagcagcat cgagcaggct tgcgacatct gcaggctgaa gaagctgaag     60

tgcagcaagg agaagcccaa gtgcgccaag tgcctgaaga acaactggga gtgcagatac    120

agccccaaga ccaagaggag ccccctgacc agggcccacc tgaccgaggt ggagagcagg    180

ctggagaggc tggagcagct gttcctgctg atcttcccca gggaggacct ggacatgatc    240

ctgaagatgg acagcctgca agacatcaag gccctgctga ccggcctgtt cgtgcaggac    300

aacgtgaaca aggacgccgt gaccgacagg ctggccagcg tggagaccga catgcccctg    360

accctgaggc agcacaggat cagcgccacc agcagcagcg aggagagcag caacaagggc    420

cagaggcagc tgaccgtgag ccccgagttt                                     450
```

```
<210> SEQ ID NO 72
<211> LENGTH: 1008
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="Ecdysone Receptor Ligand Binding Domain
      - VY variant (EcR)"

<400> SEQUENCE: 72

atcaggcccg agtgcgtggt gcccgagacc cagtgcgcca tgaaaaggaa ggagaagaag     60
```

-continued

```
gcccagaagg agaaggacaa gctgcccgtg agcaccacca ccgtcgatga ccacatgccc    120

cccatcatgc agtgcgagcc cccccccccc gaggccgcca ggattcacga ggtcgtgccc    180

aggttcctga gcgacaagct gctggtgacc aacaggcaga agaacatccc ccagctgacc    240

gccaaccagc agttcctgat cgccaggctg atctggtatc aggacggcta cgagcagccc    300

agcgacgagg acctgaaaag gatcacccag acctggcagc aggccgacga cgagaacgag    360

gagagcgaca ccccccttcag gcagatcacc gagatgacca tcctgaccgt gcagctgatc    420

gtggagttcg ccaagggcct gcccggattc gccaagatca gccagcccga ccagatcacc    480

ctgctgaagg cttgcagcag cgaggtgatg atgctgaggg tggccaggag gtacgacgcc    540

gccagcgaca gcatcctgtt cgccaacaac caggcttaca ccagggacaa ctacaggaag    600

gctggcatgg ccgaggtgat cgaggacctc ctgcacttct gcagatgtat gtacagcatg    660

gccctggaca acatccacta cgccctgctg accgccgtgg tgatcttcag cgacaggccc    720

ggcctggagc agccccagct ggtggaggag atccagaggt actacctgaa caccctgagg    780

atctacatcc tgaaccagct gagcggcagc gccaggagca gcgtgatcta cggcaagatc    840

ctgagcatcc tgagcgagct gaggaccctg ggaatgcaga acagcaatat gtgtatcagc    900

ctgaagctga agaacaggaa gctgcccccc ttcctggagg agatttggga cgtggccgac    960

atgagccaca cccagccccc ccccatcctg gagagcccca ccaacctg                1008
```

<210> SEQ ID NO 73
<211> LENGTH: 1008
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Ecdysone Receptor Ligand Binding Domain - VY variant (EcR)"

<400> SEQUENCE: 73

```
cggcctgagt gcgtagtacc cgagactcag tgcgccatga agcggaaaga gaagaaagca     60

cagaaggaga aggacaaact gcctgtcagc acgacgacgg tggacgacca catgccgccc    120

attatgcagt gtgaacctcc acctcctgaa gcagcaagga ttcacgaagt ggtcccaagg    180

tttctctccg acaagctgtt ggtgacaaac cggcagaaaa acatccccca gttgacagcc    240

aaccagcagt tccttatcgc caggctcatc tggtaccagg acgggtacga gcagccttct    300

gatgaagatt tgaagaggat tacgcagacg tggcagcaag cggacgatga aaacgaagag    360

tcggacactc ccttccgcca gatcacagag atgactatcc tcacggtcca acttatcgtg    420

gagttcgcga agggattgcc agggttcgcc aagatctcgc agcctgatca aattacgctg    480

cttaaggctt gctcaagtga ggtaatgatg ctccgagtcg cgcgacgata cgatgcggcc    540

tcagacagta ttctgttcgc gaacaaccaa gcgtacactc gcgacaacta ccgcaaggct    600

ggcatggccg aggtcatcga ggatctactg cacttctgcc ggtgcatgta ctctatggcg    660

ttggacaaca tccattacgc gctgctcacg gctgtcgtca tcttttctga ccggccaggg    720

ttggagcagc cgcaactggt ggaagagatc cagcggtact acctgaatac gctccgcatc    780

tatatcctga accagctgag cgggtcggcg cgttcgtccg tcatatacgg caagatcctc    840

tcaatcctct ctgagctacg cacgctcggc atgcaaaact ccaacatgtg catctccctc    900

aagctcaaga acagaaagct gccgcctttc ctcgaggaga tctgggatgt ggcggacatg    960
```

tcgcacaccc aaccgccgcc tatcctcgag tcccccacga atctctag 1008

<210> SEQ ID NO 74
<211> LENGTH: 1467
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="GAL4-Linker-EcR"

<400> SEQUENCE: 74
atgaagctac tgtcttctat cgaacaagca tgcgatattt gccgacttaa aaagctcaag 60
tgctccaaag aaaaaccgaa gtgcgccaag tgtctgaaga acaactggga gtgtcgctac 120
tctcccaaaa ccaaaaggtc tccgctgact agggcacatc tgacagaagt ggaatcaagg 180
ctagaaagac tggaacagct atttctactg atttttcctc gagaagacct tgacatgatt 240
ttgaaaatgg attctttaca ggatataaaa gcattgttaa caggattatt tgtacaagat 300
aatgtgaata aagatgccgt cacagataga ttggcttcag tggagactga tatgcctcta 360
acattgagac agcatagaat aagtgcgaca tcatcatcgg aagagagtag taacaaaggt 420
caaagacagt tgactgtatc gccggaattc ccggggatcc ggcctgagtg cgtagtaccc 480
gagactcagt gcgccatgaa gcggaaagag aagaaagcac agaaggagaa ggacaaactg 540
cctgtcagca cgacgacggt ggacgaccac atgccgccca ttatgcagtg tgaacctcca 600
cctcctgaag cagcaaggat tcacgaagtg gtcccaaggt ttctctccga caagctgttg 660
gtgacaaacc ggcagaaaaa catcccccag ttgacagcca accagcagtt ccttatcgcc 720
aggctcatct ggtaccagga cgggtacgag cagccttctg atgaagattt gaagaggatt 780
acgcagacgt ggcagcaagc ggacgatgaa aacgaagagt cggacactcc cttccgccag 840
atcacagaga tgactatcct cacggtccaa cttatcgtgg agttcgcgaa gggattgcca 900
gggttcgcca agatctcgca gcctgatcaa attacgctgc ttaaggcttg ctcaagtgag 960
gtaatgatgc tccgagtcgc gcgacgatac gatgcggcct cagacagtat tctgttcgcg 1020
aacaaccaag cgtacactcg cgacaactac cgcaaggctg gcatggccga ggtcatcgag 1080
gatctactgc acttctgccg gtgcatgtac tctatggcgt tggacaacat ccattacgcg 1140
ctgctcacgg ctgtcgtcat cttttctgac cggccagggt tggagcagcc gcaactggtg 1200
gaagagatcc agcggtacta cctgaatacg ctccgcatct atatcctgaa ccagctgagc 1260
gggtcggcgc gttcgtccgt catatacggc aagatcctct caatcctctc tgagctacgc 1320
acgctcggca tgcaaaactc caacatgtgc atctccctca agctcaagaa cagaaagctg 1380
ccgcctttcc tcgaggagat ctgggatgtg gcggacatgt cgcacaccca accgccgcct 1440
atcctcgagt cccccacgaa tctctag 1467

<210> SEQ ID NO 75
<211> LENGTH: 1464
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="GAL4-Linker-EcR"

<400> SEQUENCE: 75
atgaagctgc tgagcagcat cgagcaggct tgcgacatct gcaggctgaa gaagctgaag 60
tgcagcaagg agaagcccaa gtgcgccaag tgcctgaaga acaactggga gtgcagatac 120
agccccaaga ccaagaggag cccccctgacc agggcccacc tgaccgaggt ggagagcagg 180
ctggagaggc tggagcagct gttcctgctg atcttcccca gggaggacct ggacatgatc 240
ctgaagatgg acagcctgca agacatcaag gccctgctga ccggcctgtt cgtgcaggac 300
aacgtgaaca aggacgccgt gaccgacagg ctggccagcg tggagaccga catgcccctg 360
accctgaggc agcacaggat cagcgccacc agcagcagcg aggagagcag caacaagggc 420
cagaggcagc tgaccgtgag ccccgagttt cccgggcggc ctgagtgcgt agtacccgag 480
actcagtgcg ccatgaagcg gaaagagaag aaagcacaga aggagaagga caaactgcct 540
gtcagcacga cgacggtgga cgaccacatg ccgcccatta tgcagtgtga acctccacct 600
cctgaagcag caaggattca cgaagtggtc ccaaggtttc tctccgacaa gctgttggtg 660
acaaaccggc agaaaaacat cccccagttg acagccaacc agcagttcct tatcgccagg 720
ctcatctggt accaggacgg gtacgagcag ccttctgatg aagatttgaa gaggattacg 780
cagacgtggc agcaagcgga cgatgaaaac gaagagtcgg acactccctt ccgccagatc 840
acagagatga ctatcctcac ggtccaactt atcgtggagt tcgcgaaggg attgccaggg 900
ttcgccaaga tctcgcagcc tgatcaaatt acgctgctta aggcttgctc aagtgaggta 960
atgatgctcc gagtcgcgcg acgatacgat gcggcctcag acagtattct gttcgcgaac 1020
aaccaagcgt acactcgcga caactaccgc aaggctggca tggccgaggt catcgaggat 1080
ctactgcact tctgccggtg catgtactct atggcgttgg acaacatcca ttacgcgctg 1140
ctcacggctg tcgtcatctt ttctgaccgg ccagggttgg agcagccgca actggtggaa 1200
gagatccagc ggtactacct gaatacgctc cgcatctata tcctgaacca gctgagcggg 1260
tcggcgcgtt cgtccgtcat atacggcaag atcctctcaa tcctctctga gctacgcacg 1320
ctcggcatgc aaaactccaa catgtgcatc tccctcaagc tcaagaacag aaagctgccg 1380
cctttcctcg aggagatctg ggatgtggcg gacatgtcgc acacccaacc gccgcctatc 1440
ctcgagtccc ccacgaatct ctag 1464

<210> SEQ ID NO 76
<211> LENGTH: 1005
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Truncated EGFR (huEGFRt) (Her1t)"

<400> SEQUENCE: 76
cgcaaagtgt gtaacggaat aggtattggt gaatttaaag actcactctc cataaatgct 60
acgaatatta aacacttcaa aaactgcacc tccatcagtg gcgatctcca catcctgccg 120
gtggcattta ggggtgactc cttcacacat actcctcctc tggatccaca ggaactggat 180
attctgaaaa ccgtaaagga aatcacaggg tttttgctga ttcaggcttg gcctgaaaac 240
aggacggacc tccatgcctt tgagaaccta gaaatcatac gcggcaggac caagcaacat 300

-continued

```
ggtcagtttt ctcttgcagt cgtcagcctg aacataacat ccttgggatt acgctccctc    360

aaggagataa gtgatggaga tgtgataatt tcaggaaaca aaaatttgtg ctatgcaaat    420

acaataaact ggaaaaaact gtttgggacc tccggtcaga aaaccaaaat tataagcaac    480

agaggtgaaa acagctgcaa ggccacaggc caggtctgcc atgccttgtg ctcccccgag    540

ggctgctggg gcccggagcc cagggactgc gtctcttgcc ggaatgtcag ccgaggcagg    600

gaatgcgtgg acaagtgcaa ccttctggag ggtgagccaa gggagtttgt ggagaactct    660

gagtgcatac agtgccaccc agagtgcctg cctcaggcca tgaacatcac ctgcacagga    720

cggggaccag acaactgtat ccagtgtgcc cactacattg acggccccca ctgcgtcaag    780

acctgcccgg caggagtcat gggagaaaac aacaccctgg tctggaagta cgcagacgcc    840

ggccatgtgt gccacctgtg ccatccaaac tgcacctacg gatgcactgg gccaggtctt    900

gaaggctgtc caacgaatgg gcctaagatc ccgtccatcg ccactgggat ggtgggggcc    960

ctcctcttgc tgctggtggt ggccctgggg atcggcctct tcatg                   1005
```

<210> SEQ ID NO 77
<211> LENGTH: 732
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFR truncated design 1 (Her1 truncated design 1) (HER1t1)"

<400> SEQUENCE: 77

```
cgcaaagtgt gtaacggaat aggtattggt gaatttaaag actcactctc cataaatgct     60

acgaatatta aacacttcaa aaactgcacc tccatcagtg gcgatctcca catcctgccg    120

gtggcattta ggggtgactc cttcacacat actcctcctc tggatccaca ggaactggat    180

attctgaaaa ccgtaaagga aatcacaggg tttttgctga ttcaggcttg gcctgaaaac    240

aggacggacc tccatgcctt tgagaaccta gaaatcatac gcggcaggac caagcaacat    300

ggtcagtttt ctcttgcagt cgtcagcctg aacataacat ccttgggatt acgctccctc    360

aaggagataa gtgatggaga tgtgataatt tcaggaaaca aaaatttgtg ctatgcaaat    420

acaataaact ggaaaaaact gtttgggacc tccggtcaga aaaccaaaat tataagcaac    480

agaggtgaaa acagctgcaa ggccacaggc caggtctgcc atgccttgtg ctcccccgag    540

ggctgctggg gcccggagcc cagggactgc gtctctggtg gcggtggctc gggcggtggt    600

gggtcgggtg gcggcggatc tggtggcggt ggctcgtttt gggtgctggt ggtggttggt    660

ggagtcctgg cttgctatag cttgctagta acagtggcct ttattatttt ctgggtgagg    720

agtaagagga gc                                                        732
```

<210> SEQ ID NO 78
<211> LENGTH: 771
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFR truncated design 2 (Her1 truncated design 2) (HER1t2)"

<400> SEQUENCE: 78
cgcaaagtgt gtaacggaat aggtattggt gaatttaaag actcactctc cataaatgct 60
acgaatatta aacacttcaa aaactgcacc tccatcagtg gcgatctcca catcctgccg 120
gtggcattta ggggtgactc cttcacacat actcctcctc tggatccaca ggaactggat 180
attctgaaaa ccgtaaagga aatcacaggg tttttgctga ttcaggcttg gcctgaaaac 240
aggacggacc tccatgcctt tgagaaccta gaaatcatac gcggcaggac caagcaacat 300
ggtcagtttt ctcttgcagt cgtcagcctg aacataacat ccttgggatt acgctccctc 360
aaggagataa gtgatggaga tgtgataatt tcaggaaaca aaaatttgtg ctatgcaaat 420
acaataaact ggaaaaaact gtttgggacc tccggtcaga aaaccaaaat tataagcaac 480
agaggtgaaa acagctgcaa ggccacaggc caggtctgcc atgccttgtg ctcccccgag 540
ggctgctggg gcccggagcc cagggactgc gtctcttgcc ggaatgtcag ccgaggcagg 600
gaatgcgtgg acaagggtgg cggtggctcg ggcggtggtg ggtcgggtgg cggcggatct 660
ggtggcggtg gctcgttttg ggtgctggtg gtggttggtg gagtcctggc ttgctatagc 720
ttgctagtaa cagtggcctt tattattttc tgggtgagga gtaagaggag c 771

<210> SEQ ID NO 79
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFR truncated design 3 (Her1 truncated design 3) (HER1t3)"

<400> SEQUENCE: 79
cgcaaagtgt gtaacggaat aggtattggt gaatttaaag actcactctc cataaatgct 60
acgaatatta aacacttcaa aaactgcacc tccatcagtg gcgatctcca catcctgccg 120
gtggcattta ggggtgactc cttcacacat actcctcctc tggatccaca ggaactggat 180
attctgaaaa ccgtaaagga aatcacaggg tttttgctga ttcaggcttg gcctgaaaac 240
aggacggacc tccatgcctt tgagaaccta gaaatcatac gcggcaggac caagcaacat 300
ggtcagtttt ctcttgcagt cgtcagcctg aacataacat ccttgggatt acgctccctc 360
aaggagataa gtgatggaga tgtgataatt tcaggaaaca aaaatttgtg ctatgcaaat 420
acaataaact ggaaaaaact gtttgggacc tccggtcaga aaaccaaaat tataagcaac 480
agaggtgaaa acagctgcaa ggccacaggc caggtctgcc atgccttgtg ctcccccgag 540
ggctgctggg gcccggagcc cagggactgc gtctcttgcc ggaatgtcag ccgaggcagg 600
gaatgcgtgg acaagtgcaa ccttctggag ggtgagccaa gggagtttgt ggagaactct 660
gagtgcatac agggtggcgg tggctcgggc ggtggtgggt cgggtggcgg cggatctggt 720
ggcggtggct cgttttgggt gctggtggtg gttggtggag tcctggcttg ctatagcttg 780
ctagtaacag tggcctttat tattttctgg gtgaggagta agaggagc 828

<210> SEQ ID NO 80
<211> LENGTH: 885
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="EGFR truncated design 4 (Her1 truncated
      design 4) (HER1t4)"

<400> SEQUENCE: 80
cgcaaagtgt gtaacggaat aggtattggt gaatttaaag actcactctc cataaatgct      60
acgaatatta aacacttcaa aaactgcacc tccatcagtg gcgatctcca catcctgccg     120
gtggcattta ggggtgactc cttcacacat actcctcctc tggatccaca ggaactggat     180
attctgaaaa ccgtaaagga aatcacaggg tttttgctga ttcaggcttg gcctgaaaac     240
aggacggacc tccatgcctt tgagaaccta gaaatcatac gcggcaggac caagcaacat     300
ggtcagtttt ctcttgcagt cgtcagcctg aacataacat ccttgggatt acgctccctc     360
aaggagataa gtgatggaga tgtgataatt tcaggaaaca aaaatttgtg ctatgcaaat     420
acaataaact ggaaaaaact gtttgggacc tccggtcaga aaaccaaaat tataagcaac     480
agaggtgaaa acagctgcaa ggccacaggc caggtctgcc atgccttgtg ctcccccgag     540
ggctgctggg gcccggagcc cagggactgc gtctcttgcc ggaatgtcag ccgaggcagg     600
gaatgcgtgg acaagtgcaa ccttctggag ggtgagccaa gggagtttgt ggagaactct     660
gagtgcatac agtgccaccc agagtgcctg cctcaggcca tgaacatcac ctgcacagga     720
cggggaccag acaactgtat ccagggcgga ggcggaagcg gaggcggagg ctccggcgga     780
ggcggaagct tttgggtgct ggtggtggtt ggtggagtcc tggcttgcta tagcttgcta     840
gtaacagtgg cctttattat tttctgggtg aggagtaaga ggagc                     885

<210> SEQ ID NO 81
<211> LENGTH: 924
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="EGFR truncated design 5 (Her1 truncated
      design 5) (HER1t5)"

<400> SEQUENCE: 81
cgcaaagtgt gtaacggaat aggtattggt gaatttaaag actcactctc cataaatgct      60
acgaatatta aacacttcaa aaactgcacc tccatcagtg gcgatctcca catcctgccg     120
gtggcattta ggggtgactc cttcacacat actcctcctc tggatccaca ggaactggat     180
attctgaaaa ccgtaaagga aatcacaggg tttttgctga ttcaggcttg gcctgaaaac     240
aggacggacc tccatgcctt tgagaaccta gaaatcatac gcggcaggac caagcaacat     300
ggtcagtttt ctcttgcagt cgtcagcctg aacataacat ccttgggatt acgctccctc     360
aaggagataa gtgatggaga tgtgataatt tcaggaaaca aaaatttgtg ctatgcaaat     420
acaataaact ggaaaaaact gtttgggacc tccggtcaga aaaccaaaat tataagcaac     480
agaggtgaaa acagctgcaa ggccacaggc caggtctgcc atgccttgtg ctcccccgag     540
ggctgctggg gcccggagcc cagggactgc gtctcttgcc ggaatgtcag ccgaggcagg     600
gaatgcgtgg acaagtgcaa ccttctggag ggtgagccaa gggagtttgt ggagaactct     660
gagtgcatac agtgccaccc agagtgcctg cctcaggcca tgaacatcac ctgcacagga     720
cggggaccag acaactgtat ccagtgtgcc cactacattg acggccccca ctgcgtcaag 780
accggcggag gcggaagcgg aggcggaggc tccggcggag gcggaagctt ttgggtgctg 840
gtggtggttg gtggagtcct ggcttgctat agcttgctag taacagtggc ctttattatt 900
ttctgggtga ggagtaagag gagc 924

<210> SEQ ID NO 82
<211> LENGTH: 984
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFR truncated design 6 (Her1 truncated design 6) (HER1t6)"

<400> SEQUENCE: 82
cgcaaagtgt gtaacggaat aggtattggt gaatttaaag actcactctc cataaatgct 60
acgaatatta aacacttcaa aaactgcacc tccatcagtg gcgatctcca catcctgccg 120
gtggcattta ggggtgactc cttcacacat actcctcctc tggatccaca ggaactggat 180
attctgaaaa ccgtaaagga aatcacaggg tttttgctga ttcaggcttg gcctgaaaac 240
aggacggacc tccatgcctt tgagaaccta gaaatcatac gcggcaggac caagcaacat 300
ggtcagtttt ctcttgcagt cgtcagcctg aacataacat ccttgggatt acgctccctc 360
aaggagataa gtgatggaga tgtgataatt tcaggaaaca aaaatttgtg ctatgcaaat 420
acaataaact ggaaaaaact gtttgggacc tccggtcaga aaaccaaaat tataagcaac 480
agaggtgaaa acagctgcaa ggccacaggc caggtctgcc atgccttgtg ctcccccgag 540
ggctgctggg gcccggagcc cagggactgc gtctcttgcc ggaatgtcag ccgaggcagg 600
gaatgcgtgg acaagtgcaa ccttctggag ggtgagccaa gggagtttgt ggagaactct 660
gagtgcatac agtgccaccc agagtgcctg cctcaggcca tgaacatcac ctgcacagga 720
cggggaccag acaactgtat ccagtgtgcc cactacattg acggccccca ctgcgtcaag 780
acctgcccgg caggagtcat gggagaaaac aacaccctgg tctggaagta cgcagacgcc 840
ggccatgtgt gccacctggg cggaggcgga agcggaggcg gaggctcctt ttgggtgctg 900
gtggtggttg gtggagtcct ggcttgctat agcttgctag taacagtggc ctttattatt 960
ttctgggtga ggagtaagag gagc 984

<210> SEQ ID NO 83
<211> LENGTH: 1032
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFR truncated design 7 (Her1 truncated design 7) (HER1t7)"

<400> SEQUENCE: 83
cgcaaagtgt gtaacggaat aggtattggt gaatttaaag actcactctc cataaatgct 60
acgaatatta aacacttcaa aaactgcacc tccatcagtg gcgatctcca catcctgccg 120

```
gtggcattta ggggtgactc cttcacacat actcctcctc tggatccaca ggaactggat    180

attctgaaaa ccgtaaagga aatcacaggg tttttgctga ttcaggcttg gcctgaaaac    240

aggacggacc tccatgcctt tgagaaccta gaaatcatac gcggcaggac caagcaacat    300

ggtcagtttt ctcttgcagt cgtcagcctg aacataacat ccttgggatt acgctccctc    360

aaggagataa gtgatggaga tgtgataatt tcaggaaaca aaaatttgtg ctatgcaaat    420

acaataaact ggaaaaaact gtttgggacc tccggtcaga aaaccaaaat tataagcaac    480

agaggtgaaa acagctgcaa ggccacaggc caggtctgcc atgccttgtg ctcccccgag    540

ggctgctggg gcccggagcc cagggactgc gtctcttgcc ggaatgtcag ccgaggcagg    600

gaatgcgtgg acaagtgcaa ccttctggag ggtgagccaa gggagtttgt ggagaactct    660

gagtgcatac agtgccaccc agagtgcctg cctcaggcca tgaacatcac ctgcacagga    720

cggggaccag acaactgtat ccagtgtgcc cactacattg acggccccca ctgcgtcaag    780

acctgcccgg caggagtcat gggagaaaac aacaccctgg tctggaagta cgcagacgcc    840

ggccatgtgt gccacctgtg ccatccaaac tgcacctacg gatgcactgg gccaggtctt    900

gaaggctgtc caggtggcgg tggcggcgga tctttttggg tgctggtggt ggttggtgga    960

gtcctggctt gctatagctt gctagtaaca gtggccttta ttattttctg ggtgaggagt   1020

aagaggagct aa                                                       1032
```

```
<210> SEQ ID NO 84
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="EGFR truncated design 8 (Her1 truncated
      design 8) (HER1t8)"

<400> SEQUENCE: 84

cgcaaagtgt gtaacggaat aggtattggt gaatttaaag actcactctc cataaatgct     60

acgaatatta aacacttcaa aaactgcacc tccatcagtg gcgatctcca catcctgccg    120

gtggcattta ggggtgactc cttcacacat actcctcctc tggatccaca ggaactggat    180

attctgaaaa ccgtaaagga aatcacaggg tttttgctga ttcaggcttg gcctgaaaac    240

aggacggacc tccatgcctt tgagaaccta gaaatcatac gcggcaggac caagcaacat    300

ggtcagtttt ctcttgcagt cgtcagcctg aacataacat ccttgggatt acgctccctc    360

aaggagataa gtgatggaga tgtgataatt tcaggaaaca aaaatttgtg ctatgcaaat    420

acaataaact ggaaaaaact gtttgggacc tccggtcaga aaaccaaaat tataagcaac    480

agaggtgaaa acagctgcaa ggccacaggc caggtctgcc atgccttgtg ctcccccgag    540

ggctgctggg gcccggagcc cagggactgc gtctctggtg gcggtggctc gggcggtggt    600

gggtcgggtg gcggcggatc tggtggcggt ggctcggaga taacactcat tatttttggg    660

gtgatggctg gtgttattgg aacgatcctc ttaatttctt acggtattcg ccgaggaggt    720

ggaagc                                                               726
```

```
<210> SEQ ID NO 85
<211> LENGTH: 717
<212> TYPE: DNA
<213> ORGANISM: Artificial Sequence
```

<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFR truncated design 9 (Her1 truncated design 9) (HER1t9)"

<400> SEQUENCE: 85

```
cgcaaagtgt gtaacggaat aggtattggt gaatttaaag actcactctc cataaatgct     60

acgaatatta aacacttcaa aaactgcacc tccatcagtg gcgatctcca catcctgccg    120

gtggcattta ggggtgactc cttcacacat actcctcctc tggatccaca ggaactggat    180

attctgaaaa ccgtaaagga aatcacaggg tttttgctga ttcaggcttg gcctgaaaac    240

aggacggacc tccatgcctt tgagaaccta gaaatcatac gcggcaggac caagcaacat    300

ggtcagtttt ctcttgcagt cgtcagcctg aacataacat ccttgggatt acgctccctc    360

aaggagataa gtgatggaga tgtgataatt tcaggaaaca aaaatttgtg ctatgcaaat    420

acaataaact ggaaaaaact gtttgggacc tccggtcaga aaaccaaaat tataagcaac    480

agaggtgaaa acagctgcaa ggccacaggc caggtctgcc atgccttgtg ctcccccgag    540

ggctgctggg gcccggagcc cagggactgc gtctctggtg gcggtggctc gggcggtggt    600

gggtcgggtg gcggcggatc tggtggcggt ggctcgataa cactcattat ttttggggtg    660

atggctggtg ttattggaac gatcctctta atttcttacg gtattggagg tggaagc       717
```

<210> SEQ ID NO 86
<211> LENGTH: 717
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFR truncated design 10 (Her1 truncated design 10) (HER1t10)"

<400> SEQUENCE: 86

```
cgcaaagtgt gtaacggaat aggtattggt gaatttaaag actcactctc cataaatgct     60

acgaatatta aacacttcaa aaactgcacc tccatcagtg gcgatctcca catcctgccg    120

gtggcattta ggggtgactc cttcacacat actcctcctc tggatccaca ggaactggat    180

attctgaaaa ccgtaaagga aatcacaggg tttttgctga ttcaggcttg gcctgaaaac    240

aggacggacc tccatgcctt tgagaaccta gaaatcatac gcggcaggac caagcaacat    300

ggtcagtttt ctcttgcagt cgtcagcctg aacataacat ccttgggatt acgctccctc    360

aaggagataa gtgatggaga tgtgataatt tcaggaaaca aaaatttgtg ctatgcaaat    420

acaataaact ggaaaaaact gtttgggacc tccggtcaga aaaccaaaat tataagcaac    480

agaggtgaaa acagctgcaa ggccacaggc caggtctgcc atgccttgtg ctcccccgag    540

ggctgctggg gcccggagcc cagggactgc gtctctggtg gcggtggctc gggcggtggt    600

gggtcgggtg gcggcggatc tggtggcggt ggctcgataa cactcattat ttttggggtg    660

atggctggtg ttattggaac gatcctctta gccctgctca tctggggagg tggaagc       717
```

<210> SEQ ID NO 87
<211> LENGTH: 711
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="EGFR truncated design 11 (Her1 truncated
      design 11) (HER1t11)"

<400> SEQUENCE: 87

cgcaaagtgt gtaacggaat aggtattggt gaatttaaag actcactctc cataaatgct     60

acgaatatta aacacttcaa aaactgcacc tccatcagtg gcgatctcca catcctgccg    120

gtggcattta ggggtgactc cttcacacat actcctcctc tggatccaca ggaactggat    180

attctgaaaa ccgtaaagga aatcacaggg tttttgctga ttcaggcttg gcctgaaaac    240

aggacggacc tccatgcctt tgagaaccta gaaatcatac gcggcaggac caagcaacat    300

ggtcagtttt ctcttgcagt cgtcagcctg aacataacat ccttgggatt acgctccctc    360

aaggagataa gtgatggaga tgtgataatt tcaggaaaca aaaatttgtg ctatgcaaat    420

acaataaact ggaaaaaact gtttgggacc tccggtcaga aaaccaaaat tataagcaac    480

agaggtgaaa acagctgcaa ggccacaggc caggtctgcc atgccttgtg ctcccccgag    540

ggctgctggg gcccggagcc cagggactgc gtctctggtg gcggtggctc gggcggtggt    600

gggtcgggtg gcggcggatc tggtggcggt ggctcgctct gctacctgct ggatggaatc    660

ctcttcatct atggtgtcat tctcactgcc ttgttcctgg gaggtggaag c             711


<210> SEQ ID NO 88
<211> LENGTH: 891
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="FL CD20"

<400> SEQUENCE: 88

atgacaacac ccagaaattc agtaaatggg actttcccgg cagagccaat gaaaggccct     60

attgctatgc aatctggtcc aaaaccactc ttcaggagga tgtcttcact ggtgggcccc    120

acgcaaagct tcttcatgag ggaatctaag actttggggg ctgtccagat tatgaatggg    180

ctcttccaca ttgccctggg gggtcttctg atgatcccag cagggatcta tgcacccatc    240

tgtgtgactg tgtggtaccc tctctgggga ggcattatgt atattatttc cggatcactc    300

ctggcagcaa cggagaaaaa ctccaggaag tgtttggtca aaggaaaaat gataatgaat    360

tcattgagcc tctttgctgc catttctgga atgattcttt caatcatgga catacttaat    420

attaaaattt cccatttttt aaaaatggag agtctgaatt ttattagagc tcacacacca    480

tatattaaca tatacaactg tgaaccagct aatccctctg agaaaaactc cccatctacc    540

caatactgtt acagcataca atctctgttc ttgggcattt tgtcagtgat gctgatcttt    600

gccttcttcc aggaacttgt aatagctggc atcgttgaga atgaatggaa aagaacgtgc    660

tccagaccca aatctaacat agttctcctg tcagcagaag aaaaaaaaga acagactatt    720

gaaataaaag aagaagtggt tgggctaact gaaacatctt cccaaccaaa gaatgaagaa    780

gacattgaaa ttattccaat ccaagaagag gaagaagaag aaacagagac gaactttcca    840
```

gaacctcccc aagatcagga atcctcacca atagaaaatg acagctctcc t 891

<210> SEQ ID NO 89
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Truncated CD20 design 1 (CD20t1) [CD20(M1-E263]"

<400> SEQUENCE: 89
atgaccacac cacggaactc tgtgaatggc accttcccag cagagccaat gaagggacca 60
atcgcaatgc agagcggacc caagcctctg tttcggagaa tgagctccct ggtgggccca 120
acccagtcct tctttatgag agagtctaag acactgggcg ccgtgcagat catgaacgga 180
ctgttccaca tcgccctggg aggactgctg atgatcccag ccggcatcta cgcccctatc 240
tgcgtgaccg tgtggtaccc tctgtggggc ggcatcatgt atatcatctc cggctctctg 300
ctggccgcca cagagaagaa cagcaggaag tgtctggtga agggcaagat gatcatgaat 360
agcctgtccc tgtttgccgc catctctggc atgatcctga gcatcatgga catcctgaac 420
atcaagatca gccacttcct gaagatggag agcctgaact tcatcagagc ccacacccct 480
tacatcaaca tctataattg cgagcctgcc aacccatccg agaagaattc tccaagcaca 540
cagtactgtt attccatcca gtctctgttc ctgggcatcc tgtctgtgat gctgatcttt 600
gccttctttc aggagctggt catcgccggc atcgtggaga acgagtggaa gaggacctgc 660
agccgcccca agtccaatat cgtgctgctg tccgccgagg agaagaagga gcagacaatc 720
gagatcaagg aggaggtggt gggcctgacc gagacatcta gccagcctaa gaatgaggag 780
gatatcgag 789

<210> SEQ ID NO 90
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Interleukin-15"

<400> SEQUENCE: 90
aactgggtga atgtgatcag cgacctgaag aagatcgagg atctgatcca gagcatgcac 60
attgatgcca ccctgtacac agaatctgat gtgcacccta gctgtaaagt gaccgccatg 120 aagtgtttc tgctggagct gcaggtgatt tctctggaaa gcggagatgc ctctatccac 180
gacacagtgg agaatctgat catcctggcc aacaatagcc tgagcagcaa tggcaatgtg 240
acagagtctg gctgtaagga gtgtgaggag ctggaggaga agaacatcaa ggagtttctg 300
cagagctttg tgcacatcgt gcagatgttc atcaatacaa gc 342

<210> SEQ ID NO 91
<211> LENGTH: 711
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="Interleukin-15 receptor alpha"

<400> SEQUENCE: 91

attacatgcc ctcctccaat gtctgtggag cacgccgata tttgggtgaa gtcctacagc     60

ctgtacagca gagagagata catctgcaac agcggcttta agagaaaggc cggcacctct    120

tctctgacag agtgcgtgct gaataaggcc acaaatgtgg cccactggac aacacctagc    180

ctgaagtgca ttagagatcc tgccctggtc caccagaggc ctgcccctcc atctacagtg    240

acaacagccg gagtgacacc tcagcctgaa tctctgagcc cttctggaaa agaacctgcc    300

gccagctctc ctagctctaa taataccgcc gccacaacag ccgccattgt gcctggatct    360

cagctgatgc ctagcaagtc tcctagcaca ggcacaacag agatcagcag ccacgaatct    420

tctcacggaa caccttctca gaccaccgcc aagaattggg agctgacagc ctctgcctct    480

caccagcctc caggagtgta tcctcagggc cactctgata caacagtggc catcagcaca    540

tctacagtgc tgctgtgtgg actgtctgcc gtgtctctgc tggcctgtta cctgaagtct    600

agacagacac ctcctctggc ctctgtggag atggaggcca tggaagccct gcctgtgaca    660

tggggaacaa gcagcagaga tgaggacctg gagaattgtt ctcaccacct g             711


<210> SEQ ID NO 92
<211> LENGTH: 1185
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="Membrane bound Interleukin-15 with
      signal peptide"

<400> SEQUENCE: 92

atggattgga cctggattct gtttctggtg gccgctgcca caagagtgca cagcaactgg     60

gtgaatgtga tcagcgacct gaagaagatc gaggatctga tccagagcat gcacattgat    120

gccaccctgt acacagaatc tgatgtgcac cctagctgta aagtgaccgc catgaagtgt    180

tttctgctgg agctgcaggt gatttctctg gaaagcggag atgcctctat ccacgacaca    240

gtggagaatc tgatcatcct ggccaacaat agcctgagca gcaatggcaa tgtgacagag    300

tctggctgta aggagtgtga ggagctggag gagaagaaca tcaaggagtt tctgcagagc    360

tttgtgcaca tcgtgcagat gttcatcaat acaagctctg gcggaggatc tggaggaggc    420

ggatctggag gaggaggcag tggaggcgga ggatctggcg gaggatctct gcagattaca    480

tgccctcctc caatgtctgt ggagcacgcc gatatttggg tgaagtccta cagcctgtac    540

agcagagaga gatacatctg caacagcggc tttaagagaa aggccggcac ctcttctctg    600

acagagtgcg tgctgaataa ggccacaaat gtggcccact ggacaacacc tagcctgaag    660

tgcattagag atcctgccct ggtccaccag aggcctgccc ctccatctac agtgacaaca    720

gccggagtga cacctcagcc tgaatctctg agcccttctg gaaaagaacc tgccgccagc    780

tctcctagct ctaataatac cgccgccaca acagccgcca ttgtgcctgg atctcagctg    840

atgcctagca agtctcctag cacaggcaca acagagatca gcagccacga atcttctcac    900
```

-continued

```
ggaacacctt ctcagaccac cgccaagaat tgggagctga cagcctctgc ctctcaccag    960

cctccaggag tgtatcctca gggccactct gatacaacag tggccatcag cacatctaca   1020

gtgctgctgt gtggactgtc tgccgtgtct ctgctggcct gttacctgaa gtctagacag   1080

acacctcctc tggcctctgt ggagatggag gccatggaag ccctgcctgt gacatgggga   1140

acaagcagca gagatgagga cctggagaat tgttctcacc acctg                   1185
```

<210> SEQ ID NO 93
<211> LENGTH: 1605
<212> TYPE: DNA
<213> ORGANISM: Mus sp.
<220> FEATURE:
<221> NAME/KEY: source
<223> OTHER INFORMATION: /note="Murine single chain IL-12 (p40-linker-p35)"

<400> SEQUENCE: 93

```
atgtgtcctc agaagctaac catctcctgg tttgccatcg ttttgctggt gtctccactc     60

atggccatgt gggagctgga gaaagacgtt tatgttgtag aggtggactg gactcccgat    120

gcccctggag aaacagtgaa cctcacctgt gacacgcctg aagaagatga catcacctgg    180

acctcagacc agagacatgg agtcataggc tctggaaaga ccctgaccat cactgtcaaa    240

gagtttctag atgctggcca gtacacctgc cacaaaggag gcgagactct gagccactca    300

catctgctgc tccacaagaa ggaaaatgga atttggtcca ctgaaattct gaagaacttc    360

aaaaacaaga ctttcctgaa gtgtgaagca ccaaattaca gcggccggtt cacgtgctca    420

tggctggtgc aaagaaacat ggacttgaag ttcaacatca agagcagtag cagttcccct    480

gactctcggg cagtgacatg tggaatggcg tctctgagcg ccgagaaggt cacactggac    540

cagagagact atgagaagta ttcagtgtcc tgccaggagg atgtcacctg cccaactgcc    600

gaggagaccc tgcccattga actggcgttg gaagcacggc agcagaacaa gtatgagaac    660

tacagcacca gcttcttcat cagggacatc atcaaaccag acccgcccaa gaacttgcag    720

atgaagcctt tgaagaactc acaggtggag gtcagctggg agtaccctga ctcctggagc    780

actccccatt cctacttctc cctcaagttc tttgtgagaa tccagcgcaa gaaagaaaag    840

atgaaggaga cagaggaggg gtgtaaccag aaaggtgcgt tcctcgtaga gaagacatct    900

accgaagtcc aatgcaaagg cgggaatgtc tgcgtgcaag ctcaggatcg ctattacaat    960

tcctcatgca gcaagtgggc atgtgttccc tgccgcgtcc gatccggtgg cggtggcggc   1020

ggatctaggg tcattccagt ctctggacct gccaggtgtc ttagccagtc ccgaaacctg   1080

ctgaagacca cagatgacat ggtgaagacg gccagagaaa aactgaaaca ttattcctgc   1140

actgctgaag acattgacca tgaagacatc acacgggacc aaaccagcac attgaagacc   1200

tgtttaccac tggaactaca caagaacgag agttgcctgg ctactagaga gacttcttcc   1260

acaacaagag ggagctgcct gcccccacag aagaccagct tgatgatgac cctgtgcctt   1320

ggtagcatct atgaggactt gaagatgtac cagacagagt tccaggccat caacgcagca   1380

cttcagaatc acaaccatca gcagatcatt ctagacaagg gcatgttggt ggccatcgac   1440

gagctgatgc agtctctgaa tcataatggc gagactctgc gccagaaacc tcctgtggga   1500

gaagcagacc cttacagagt gaaaatgaag ctctgcatcc tgcttcacgc cttcagcacc   1560

cgcgtcgtga ccatcaacag ggtgatgggc tatctgagca gcgcc                   1605
```

<210> SEQ ID NO 94
<211> LENGTH: 1596

<212> TYPE: DNA
<213> ORGANISM: Homo sapiens
<220> FEATURE:
<221> NAME/KEY: source
<223> OTHER INFORMATION: /note="Human single chain IL-12 (p40-linker-p35)"

<400> SEQUENCE: 94
atgtgtcacc agcagttggt catctcttgg ttcagcctgg tttttctggc atctcccctc 60
gtggccatct gggaactgaa gaaagatgtt tatgtcgtag aattggattg gtatcccgac 120
gcccctggag aaatggtggt cctgacatgt gacacccctg aagaagatgg tatcacctgg 180
accttggacc agagcagtga ggtcttaggc tctggcaaga ccctgaccat ccaagtcaaa 240
gagtttggag atgctggcca gtacacctgt cacaaaggag gcgaggttct aagccattcg 300
ctcctgctgc ttcacaaaaa ggaagatgga atttggtcca ctgacattct gaaggaccag 360
aaagaaccca agaataagac ctttctaaga tgcgaggcca agaattattc tggacgtttc 420
acctgctggt ggctgacgac aatcagtact gatttgacat tcagtgtcaa aagcagcaga 480
ggctcttctg acccccaagg ggtgacgtgc ggagctgcta cactcagcgc cgagagagtc 540
agaggggaca acaaggagta tgagtactca gtggagtgcc aggaggacag tgcctgccca 600
gctgctgagg agagtctgcc cattgaggtc atggtggatg ccgttcacaa gctcaagtat 660
gaaaactaca ccagcagctt cttcatcagg gacatcatca aacctgaccc acccaagaac 720
ttgcagctga agcccctgaa gaacagcaga caggtggagg tcagctggga gtaccctgac 780
acctggagta ctccacattc ctacttctcc ctgacattct gcgttcaggt ccagggcaag 840
agcaagagag aaaagaaaga tagagtcttc acggacaaga cctcagccac ggtcatctgc 900
cgcaaaaatg ccagcattag cgtgcgggcc caggaccgct actatagctc atcttggagc 960
gaatgggcat ctgtgccctg ctccggtggc ggtggcggcg gatctagaaa cctccccgtg 1020
gccactccag acccaggaat gttcccatgc cttcaccaca gccagaacct gctgagggcc 1080
gtcagcaaca tgctccagaa ggccagacaa actctagaat tttacccttg cacttctgaa 1140
gagattgatc atgaagatat cacaaaagat aaaaccagca cagtggaggc ctgtttacca 1200
ttggaattaa ccaagaatga gagttgccta aattccagag agacctcttt cataactaat 1260
gggagttgcc tggcctccag aaagacctct tttatgatgg ccctgtgcct tagtagtatt 1320
tatgaagact tgaagatgta ccaggtggag ttcaagacca tgaatgcaaa gctgctgatg 1380
gaccccaaga ggcagatctt tctagatcaa aacatgctgg cagttattga tgagctgatg 1440
caggccctga atttcaacag tgagactgtg ccacaaaaat cctcccttga agaaccggat 1500
ttttataaaa ctaaaatcaa gctctgcata cttcttcatg ctttcagaat cagagcagtg 1560
actattgata gagtgatgag ctatctgaat gcttcc 1596

<210> SEQ ID NO 95
<211> LENGTH: 6684
<212> TYPE: DNA
<213> ORGANISM: Homo sapiens
<220> FEATURE:
<221> NAME/KEY: source
<223> OTHER INFORMATION: /note="Human interleukin-2 (IL-2) gene and 5'-flanking region"

<400> SEQUENCE: 95
agtggttttt ggagtcagta cattctcttt tcaaatcctt ctctgcccct tactggcaat 60
aagggctgag tgacctagag gcaaattact taacttctct gagcctcagt tttctaatct 120

-continued

```
gcaaaatagg agccatcact tcacaagtct gtaagactta tattagacta agtgcctgcc    180
tgtacactgt tctctttttc tctctttcta tatacctgaa ggcattatag tgctagatgt    240
ctgtttaaag accagacaat attgtcttaa aaaaacaaac aaaaacacag acaataccat    300
ctttaaaaaa aaaaaaaaag tccaggtaag aaataaataa ggccatagaa tggaagcttt    360
acaaggactc tctttgagac aggatctcct caagtgtccc caggttaaat tagaagtata    420
tatccgtaca attgttcagc cagtttgtgc actgtactga ggatgaatga acacctatcc    480
taaatatcct agtcttctga ctaaaaacaa gatcatattt cataacgatt attgttacat    540
tcatagtgtc ccaggtgatt tagaggataa ataaaaatcc attaaagagg taaagacata    600
aaaacgagaa acatggactg gtttacacat aacacataca aagtctatta taaaactagc    660
atcagtatcc ttgaatcgaa accttttttct gagtatttaa caatcgcacc ctttaaaaaa    720
tgtacataga cattaagaga cttaaacaga tatataatca ttttaaatta aaatagcgtt    780
aaacagtacc tcaagctcaa taagcatttt aagtattcta atcttagtat ttctctagct    840
gacatgtaag aagcaatcta tcttattgta tgcaattagc tctttgtgtg gataaaaagg    900
taaaaccatt ctgaaacagg aaaccaatac acttcctgtt taatcaacaa atctaaacat    960
ttattctttt catctgttta ctcttgctct tgtccaccac aatatgctat tcacatgttc   1020
agtgtagttt tatgacaaag aaaattttct gagttacttt tgtatcccca ccccccttaaa   1080
gaaaggagga aaaactgttt catacagaag gcgttaattg catgaattag agctatcacc   1140
taagtgtggg ctaatgtaac aaagagggat ttcacctaca tccattcagt cagtctttgg   1200
gggtttaaag aaattccaaa gagtcatcag aagaggaaaa atgaaggtaa tgtttttttca   1260
gactggtaaa gtctttgaaa atatgtgtaa tatgtaaaac attttgacac ccccataata   1320
tttttccaga attaacagta taaattgcat ctcttgttca agagttccct atcactcttt   1380
aatcactact cacagtaacc tcaactcctg ccacaatgta caggatgcaa ctcctgtctt   1440
gcattgcact aagtcttgca cttgtcacaa acagtgcacc tacttcaagt tctacaaaga   1500
aaacacagct acaactggag catttactgc tggatttaca gatgattttg aatggaatta   1560
atgtaagtat atttcctttc ttactaaaat tattacattt agtaatctag ctggagatca   1620
tttcttaata acaatgcatt atactttctt agaattacaa gaatcccaaa ctcaccagga   1680
tgctcacatt taagttttac atgcccaaga aggtaagtac aatattttat gttcaatttc   1740
tgttttaata aaattcaaag taatatgaaa atttgcacag atgggactaa tagcagctca   1800
tctgaggtaa agagtaactt taatttgttt ttttgaaaac ccaagtttga taatgaagcc   1860
tctattaaaa cagttttacc tatattttta atatatattt gtgtgttggt gggggtggga   1920
gaaaacataa aaataatatt ctctcacttt atcgataaga caattctaaa caaaaatgtt   1980
catttatggt ttcatttaaa aatgtaaaac tctaaaatat ttgattatgt cattttagta   2040
tgtaaaatac caaaatctat ttccaaggag cccactttta aaaatctttt cttgttttag   2100
gaaaggtttc taagtgagag gcagcataac actaatagca cagagtctgg ggccagatat   2160
ctgaagtgaa atctcagctc tgccatgtcc tagctttcat gatctttggc aaattaccta   2220
ctctgtttgt gattcagttt catgtctact taaatgaata actgtatata cttaatatgg   2280
ctttgtgaga attagtaagt aaatgtaaag cactcagaac cgtgtctggc ataaggtaaa   2340
taccatacaa gcattagcta ttattagtag tattaaagat aaaattttca ctgagaaata   2400
caaagtaaaa ttttggactt tatcttttta ccaatagaac ttgagattta taatgctata   2460
tgacttattt tccaagatta aaagcttcat taggttgttt ttggattcag atagagcata   2520
```

-continued

```
agcataatca tccaagctcc taggctacat taggtgtgta aagctaccta gtagctgtgc   2580
cagttaagag agaatgaaca aaatctggtg ccagaaagag cttgtgccag ggtgaatcca   2640
agcccagaaa ataataggat ttaaggggac acagatgcaa tcccattgac tcaaattcta   2700
ttaattcaag acaaatctgc ttctaactac ccttctgaaa gatgtaaagg agacagctta   2760
cagatgttac tctagtttaa tcagagccac ataatgcaac tccagcaaca taaagatact   2820
agatgctgtt ttctgaagaa aatttctcca cattgttcat gccaaaaact taaacccgaa   2880
tttgtagaat ttgtagtggt gaattgaaag cgcaatagat ggacatatca ggggattggt   2940
attgtcttga cctacctttc ccactaaaga gtgttagaaa gatgagatta tgtgcataat   3000
ttaggggtgg tagaattcat ggaaatctaa gtttgaaacc aaaagtaatg ataaactcta   3060
ttcatttgtt catttaaccc tcattgcaca tttacaaaag attttagaaa ctaataaaaa   3120
tatttgattc caaggatgct atgttaatgc tataatgaga aagaaatgaa atctaattct   3180
ggctctacct acttatgtgg tcaaattctg agatttagtg tgcttattta taaagtggag   3240
atgatacttc actgcctact tcaaaagatg actgtgagaa gtaaatgggc ctattttgga   3300
gaaaattctt ttaaattgta atataccata gaaatatgaa atattatata taatatagaa   3360
tcaagaggcc tgtccaaaag tcctcccaaa gtattataat cttttatttc actgggacaa   3420
acatttttaa aatgcatctt aatgtagtga ttgtagaaaa gtaaaaattt aagacatatt   3480
taaaaatgtg tcttgctcaa ggctatattg agagccacta ctacatgatt attgttacct   3540
agtgtaaaat gttgggattg tgatagatgg catccaagag ttccttctct ctcaacattc   3600
tgtgattctt aactcttaga ctatcaaata ttataatcat agaatgtgat ttttatgcct   3660
tccacattct aatctcatct ggttctaatg attttctatg cagattggaa aagtaatcag   3720
cctacatctg taataggcat ttagatgcag aaagtctaac attttgcaaa gccaaattaa   3780
gctaaaacca gtgagtcaac tatcacttaa cgctagtcat aggtacttga gccctagttt   3840
ttccagtttt ataatgtaaa ctctactggt ccatctttac agtgacattg agaacagaga   3900
gaatggtaaa aactacatac tgctactcca aataaaataa attggaaatt aatttctgat   3960
tctgacctct atgtaaactg agctgatgat aattattatt ctaggccaca gaactgaaac   4020
atcttcagtg tctagaagaa gaactcaaac ctctggagga agtgctaaat ttagctcaaa   4080
gcaaaaactt tcacttaaga cccagggact taatcagcaa tatcaacgta atagttctgg   4140
aactaaaggt aaggcattac tttatttgct ctcctggaaa taaaaaaaaa aaagtagggg   4200
gaaaagtacc acattttaaa gtgacataac atttttggta tttgtaaagt acccatgcat   4260
gtaattagcc tacattttaa gtacactgtg aacatgaatc atttctaatg ttaaatgatt   4320
aactggggag tataagctac tgagtttgca cctaccatct actaatggac aagcctcatc   4380
ccaaactcca tcacctttca tattaacaca aaactgggag tgagagagaa gtgactgagt   4440
tgagtttcac agaaacgcag gcaagatttt attatatatt tttcaagttc cttcacagat   4500
catttactgg aatagccaat actgagttac ctgaaaggct tttcaaatgg tgtttcctta   4560
tcatttgatg gaaggactac ccataagaga tttgtcttaa aaaaaaaaac tggagccatt   4620
aaaatggcca gtggactaaa caaacaacaa tctttttaga ggcaatccca ctttcagaat   4680
cttaagtatt tttaaatgca caggaagcat aaaatatgca agggactcag gtgatgtaaa   4740
agagattcac ttttgtcttt ttatatcccg tctcctaagg tataaaattc atgagttaat   4800
aggtatccta aataagcagc ataagtatag tagtaaaaga cattcctaaa agtaactcca   4860
```

gttgtgtcca aatgaatcac ttattagtgg actgtttcag ttgaattaaa aaaatacatt 4920
gagatcaatg tcatctagac attgacagat tcagttcctt atctatggca agagttttac 4980
tctaaaataa ttaacatcag aaaactcatt cttaactctt gatacaaatt taagacaaaa 5040
ccatgcaaaa atctgaaaac tgtgtttcaa aagccaaaca ctttttaaaa taaaaaaatc 5100
ccaagatatg acaatattta aacaattatg cttaagagga tacagaacac tgcaacagtt 5160
ttttaaaaga gaatacttat ttaaagggaa cactctatct cacctgcttt tgttcccagg 5220
gtaggaatca cttcaaattt gaaaagctct cttttaaatc tcactatata tcaaaatagt 5280
tgcctcctta gcttatcaac tagaggaagc gtttaaatag ctcctttcag cagagaagcc 5340
taatttctaa aaagccagtc cacagaacaa aatttctaat gtttaaagct tttaaaagtt 5400
ggcaaattca cctgcattga tactatgatg gggtagggat aggtgtaagt atttatgaag 5460
atgttcattc acacaaattt acccaaacag gaagcatgtc ctacctagct tactctagtg 5520
tagctcgttt cgtctttggg gaaaatataa ggagattcac ttaagtagaa aaataggaga 5580
ctctaatcaa gatttagaaa agaagaaagt ataatgtgca tatcaattca tacatttaac 5640
ttacacaaat ataggtgtac attcagagga aaagcgatca agtttatttc acatccagca 5700
tttaatattt gtctagatct atttttattt aaatctttat ttgcacccaa tttagggaaa 5760
aaatttttgt gttcattgac tgaattaaca aatgaggaaa atctcagctt ctgtgttact 5820
atcatttggt atcataacaa aatacgcaat tttggcattc attttgatca tttcaagaaa 5880
atgtgaataa ttaatatgtt tggtaagctt gaaaataaag gcaacaggcc tataagactt 5940
caattgggaa taactgtata taaggtaaac tactctgtac tttaaaaaat taacattttt 6000
cttttatagg gatctgaaac aacattcatg tgtgaatatg ctgatgagac agcaaccatt 6060
gtagaatttc tgaacagatg gattaccttt tgtcaaagca tcatctcaac actgacttga 6120
taattaagtg cttcccactt aaaacatatc aggccttcta tttatttaaa tatttaaatt 6180
ttatatttat tgttgaatgt atggtttgct acctattgta actattattc ttaatcttaa 6240
aactataaat atggatcttt tatgattctt tttgtaagcc ctaggggctc taaaatggtt 6300
tcacttattt atcccaaaat atttattatt atgttgaatg ttaaatatag tatctatgta 6360
gattggttag taaaactatt taataaattt gataaatata aacaagcctg gatatttgtt 6420
attttggaaa cagcacagag taagcattta aatatttctt agttacttgt gtgaactgta 6480
ggatggttaa aatgcttaca aaagtcactc tttctctgaa gaaatatgta gaacagagat 6540
gtagacttct caaaagccct tgctttgtcc tttcaagggc tgatcagacc cttagttctg 6600
gcatctctta gcagattata ttttccttct tcttaaaatg ccaaacacaa acactcttga 6660
aactcttcat agatttggtg tggc 6684

<210> SEQ ID NO 96
<211> LENGTH: 1419
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="CD19-specific chimeric antigen receptor (CD19-CD8a-CD28-CD3z)"

<400> SEQUENCE: 96
gacatccaga tgacccagac cacctccagc ctgagcgcca gcctgggcga ccgggtgacc 60

```
atcagctgcc gggccagcca ggacatcagc aagtacctga actggtatca gcagaagccc    120

gacggcaccg tcaagctgct gatctaccac accagccggc tgcacagcgg cgtgcccagc    180

cggtttagcg gcagcggctc cggcaccgac tacagcctga ccatctccaa cctggagcag    240

gaggacatcg ccacctactt ttgccagcag ggcaacacac tgccctacac ctttggcggc    300

ggaacaaagc tggagatcac cggcagcacc tccggcagcg gcaagcctgg cagcggcgag    360

ggcagcacca agggcgaggt gaagctgcag gagagcggcc ctggcctggt ggcccccagc    420

cagagcctga gcgtgacctg taccgtgtcc ggcgtgtccc tgcccgacta cggcgtgtcc    480

tggatccggc agccccctag gaagggcctg gagtggctgg gcgtgatctg gggcagcgag    540

accacctact acaacagcgc cctgaagagc cggctgacca tcatcaagga caacagcaag    600

agccaggtgt tcctgaagat gaacagcctg cagaccgacg acaccgccat ctactactgt    660

gccaagcact actactacgg cggcagctac gccatggact actggggcca gggcaccagc    720

gtgaccgtgt ccagcaagcc caccaccacc cctgccccta gacctccaac cccagcccct    780

acaatcgcca gccagcccct gagcctgagg cccgaagcct gtagacctgc cgctggcgga    840

gccgtgcaca ccagaggcct ggatttcgcc tgcgacatct acatctgggc ccctctggcc    900

ggcacctgtg gcgtgctgct gctgagcctg gtcatcaccc tgtactgcaa ccaccggaat    960

aggagcaagc ggagcagagg cggccacagc gactacatga acatgacccc ccggaggcct   1020

ggccccaccc ggaagcacta ccagccctac gcccctccca gggacttcgc cgcctaccgg   1080

agccgggtga agttcagccg gagcgccgac gcccctgcct accagcaggg ccagaaccag   1140

ctgtacaacg agctgaacct gggccggagg gaggagtacg acgtgctgga caagcggaga   1200

ggccgggacc ctgagatggg cggcaagccc cggagaaaga accctcagga gggcctgtat   1260

aacgaactgc agaaagacaa gatggccgag gcctacagcg agatcggcat gaagggcgag   1320

cggcggaggg gcaagggcca cgacggcctg taccagggcc tgagcaccgc caccaaggat   1380

acctacgacg ccctgcacat gcaggccctg ccccccaga                          1419
```

```
<210> SEQ ID NO 97
<211> LENGTH: 1485
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="CD19-specific chimeric antigen receptor
      (CD19-CD8a-CD28-CD3z) with Signal peptide"

<400> SEQUENCE: 97

atgctgctgc tggtgaccag cctgctgctg tgtgagctgc cccaccccgc ctttctgctg     60

atccccgaca tccagatgac ccagaccacc tccagcctga gcgccagcct gggcgaccgg    120

gtgaccatca gctgccgggc cagccaggac atcagcaagt acctgaactg gtatcagcag    180

aagcccgacg gcaccgtcaa gctgctgatc taccacacca gccggctgca cagcggcgtg    240

cccagccggt ttagcggcag cggctccggc accgactaca gcctgaccat ctccaacctg    300

gagcaggagg acatcgccac ctacttttgc cagcagggca acacactgcc ctacaccttt    360

ggcggcggaa caaagctgga gatcaccggc agcacctccg gcagcggcaa gcctggcagc    420

ggcgagggca gcaccaaggg cgaggtgaag ctgcaggaga gcggccctgg cctggtggcc    480
```

cccagccaga gcctgagcgt gacctgtacc gtgtccggcg tgtccctgcc cgactacggc 540
gtgtcctgga tccggcagcc ccctaggaag ggcctggagt ggctgggcgt gatctggggc 600
agcgagacca cctactacaa cagcgccctg aagagccggc tgaccatcat caaggacaac 660
agcaagagcc aggtgttcct gaagatgaac agcctgcaga ccgacgacac cgccatctac 720
tactgtgcca agcactacta ctacggcggc agctacgcca tggactactg gggccagggc 780
accagcgtga ccgtgtccag caagcccacc accacccctg cccctagacc tccaacccca 840
gcccctacaa tcgccagcca gcccctgagc ctgaggcccg aagcctgtag acctgccgct 900
ggcggagccg tgcacaccag aggcctggat ttcgcctgcg acatctacat ctgggcccct 960
ctggccggca cctgtggcgt gctgctgctg agcctggtca tcaccctgta ctgcaaccac 1020
cggaatagga gcaagcggag cagaggcggc cacagcgact acatgaacat gacccccccgg 1080 aggcctggcc ccacccggaa gcactaccag ccctacgccc ctcccaggga cttcgccgcc 1140
taccggagcc gggtgaagtt cagccggagc gccgacgccc ctgcctacca gcagggccag 1200
aaccagctgt acaacgagct gaacctgggc cggagggagg agtacgacgt gctggacaag 1260
cggagaggcc gggaccctga gatgggcggc aagccccgga gaaagaaccc tcaggagggc 1320
ctgtataacg aactgcagaa agacaagatg gccgaggcct acagcgagat cggcatgaag 1380
ggcgagcggc ggaggggcaa gggccacgac ggcctgtacc agggcctgag caccgccacc 1440
aaggatacct acgacgccct gcacatgcag gccctgcccc ccaga 1485

<210> SEQ ID NO 98
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Anti-CD19 monoclonal antibody clone FMC63 variable heavy chain"

<400> SEQUENCE: 98
gaggtgaagc tgcaggagag cggccctggc ctggtggccc ccagccagag cctgagcgtg 60
acctgtaccg tgtccggcgt gtccctgccc gactacggcg tgtcctggat ccggcagccc 120
cctaggaagg gcctggagtg gctgggcgtg atctggggca gcgagaccac ctactacaac 180
agcgccctga agagccggct gaccatcatc aaggacaaca gcaagagcca ggtgttcctg 240
aagatgaaca gcctgcagac cgacgacacc gccatctact actgtgccaa gcactactac 300
tacggcggca gctacgccat ggactactgg ggccagggca ccagcgtgac cgtgtccagc 360

<210> SEQ ID NO 99
<211> LENGTH: 735
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Anti-CD19 clone FMC63 single chain fragment variable (scFv) with Whitlow linker"

<400> SEQUENCE: 99
gacatccaga tgacccagac cacctccagc ctgagcgcca gcctgggcga ccgggtgacc 60
atcagctgcc gggccagcca ggacatcagc aagtacctga actggtatca gcagaagccc 120
gacggcaccg tcaagctgct gatctaccac accagccggc tgcacagcgg cgtgcccagc 180
cggtttagcg gcagcggctc cggcaccgac tacagcctga ccatctccaa cctggagcag 240
gaggacatcg ccacctactt ttgccagcag ggcaacacac tgccctacac ctttggcggc 300
ggaacaaagc tggagatcac cggcagcacc tccggcagcg gcaagcctgg cagcggcgag 360
ggcagcacca agggcgaggt gaagctgcag gagagcggcc ctggcctggt ggcccccagc 420
cagagcctga gcgtgacctg taccgtgtcc ggcgtgtccc tgcccgacta cggcgtgtcc 480
tggatccggc agccccctag gaagggcctg gagtggctgg gcgtgatctg gggcagcgag 540
accacctact acaacagcgc cctgaagagc cggctgacca tcatcaagga caacagcaag 600
agccaggtgt tcctgaagat gaacagcctg cagaccgacg acaccgccat ctactactgt 660
gccaagcact actactacgg cggcagctac gccatggact actggggcca gggcaccagc 720
gtgaccgtgt ccagc 735

<210> SEQ ID NO 100
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="hM195 VL"

<400> SEQUENCE: 100
gacattcaga tgacccagtc tccgagctct ctgtccgcat cagtaggaga cagggtcacc 60
atcacatgca gagccagcga aagtgtcgac aattatggca ttagctttat gaactggttc 120
caacagaaac ccgggaaggc tcctaagctt ctgatttacg ctgcatccaa ccaaggctcc 180
ggggtaccct ctcgcttctc aggcagtgga tctgggacag acttcactct caccatttca 240
tctctgcagc ctgatgactt cgcaacctat tactgtcagc aaagtaagga ggttccgtgg 300
acgttcggtc aagggaccaa ggtggagatc aaa 333

<210> SEQ ID NO 101
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="hM195 VH"

<400> SEQUENCE: 101
caggttcagc tggtgcagtc tggagctgag gtgaagaagc ctgggagctc agtgaaggtt 60
tcctgcaaag cttctggcta caccttcact gactacaaca tgcactgggt gaggcaggct 120
cctggccaag gcctggaatg gattggatat atttatcctt acaatggtgg taccggctac 180
aaccagaagt tcaagagcaa ggccacaatt acagcagacg agagtactaa cacagcctac 240
atggaactct ccagcctgag gtctgaggac actgcagtct attactgcgc aagagggcgc 300
cccgctatgg actactgggg ccaagggact ctggtcactg tctcttca 348

<210> SEQ ID NO 102
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="hM195 scFv with linker"

<400> SEQUENCE: 102
gacattcaga tgacccagtc tccgagctct ctgtccgcat cagtaggaga cagggtcacc 60
atcacatgca gagccagcga aagtgtcgac aattatggca ttagctttat gaactggttc 120
caacagaaac ccgggaaggc tcctaagctt ctgatttacg ctgcatccaa ccaaggctcc 180
ggggtaccct ctcgcttctc aggcagtgga tctgggacag acttcactct caccatttca 240
tctctgcagc ctgatgactt cgcaacctat tactgtcagc aaagtaagga ggttccgtgg 300
acgttcggtc aagggaccaa ggtggagatc aaaggtggcg gtggctcggg cggtggtggg 360
tcgggtggcg gcggatctca ggttcagctg gtgcagtctg gagctgaggt gaagaagcct 420
gggagctcag tgaaggtttc ctgcaaagct tctggctaca ccttcactga ctacaacatg 480
cactgggtga ggcaggctcc tggccaaggc ctggaatgga ttggatatat ttatccttac 540
aatggtggta ccggctacaa ccagaagttc aagagcaagg ccacaattac agcagacgag 600
agtactaaca cagcctacat ggaactctcc agcctgaggt ctgaggacac tgcagtctat 660
tactgcgcaa gagggcgccc cgctatggac tactggggcc aagggactct ggtcactgtc 720
tcttca 726

<210> SEQ ID NO 103
<211> LENGTH: 2773
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFR variant III (EGFRvIII)"

<400> SEQUENCE: 103
atgcgaccct ccgggacggc cggggcagcg ctcctggcgc tgctggctgc gctctgcccg 60
gcgagtcggg ctctggagga aaagaaaggt aattatgtgg tgacagatca cggctcgtgc 120
gtccgagcct gtggggccga cagctatgag atggaggaag acggcgtccg caagtgtaag 180
aagtgcgaag ggccttgccg caaagtgtgt aacggaatag gtattggtga atttaaagac 240
tcactctcca taaatgctac gaatattaaa cacttcaaaa actgcacctc catcagtggc 300
gatctccaca tcctgccggt ggcatttagg ggtgactcct tcacacatac tcctcctctg 360
gatccacagg aactggatat tctgaaaacc gtaaaggaaa tcacagggtt tttgctgatt 420
caggcttggc ctgaaaacag gacggacctc catgcctttg agaacctaga aatcatacgc 480
ggcaggacca agcaacatgg tcagttttct cttgcagtcg tcagcctgaa cataacatcc 540
ttgggattac gctccctcaa ggagataagt gatggagatg tgataatttc aggaaacaaa 600
aatttgtgct atgcaaatac aataaactgg aaaaaactgt ttgggacctc cggtcagaaa 660
accaaaatta taagcaacag aggtgaaaac agctgcaagg ccacaggcca ggtctgccat 720

```
gccttgtgct cccccgaggg ctgctggggc ccggagccca gggactgcgt ctcttgccgg    780

aatgtcagcc gaggcaggga atgcgtggac aagtgcaacc ttctggaggg tgagccaagg    840

gagtttgtgg agaactctga gtgcatacag tgccacccag agtgcctgcc tcaggccatg    900

aacatcacct gcacaggacg gggaccagac aggagtcatg ggagaaaaca acaccctggt    960

ctggaagtac gcagacgccg gccatgtgtg ccacctgtgc catccaaact gcacctacgg   1020

atgcactggg ccaggtcttg aaggctgtcc aacgaatggg cctaagatcc cgtccatcgc   1080

cactgggatg gtgggggccc tcctcttgct gctggtggtg gccctgggga tcggcctctt   1140

catgcgaagg cgccacatcg ttcggaagcg cacgctgcgg aggctgctgc aggagaggga   1200

gcttgtggag cctcttacac ccagtggaga agctcccaac caagctctct tgaggatctt   1260

gaaggaaact gaattcaaaa agatcaaagt gctgggctcc ggtgcgttcg gcacggtgta   1320

taagggactc tggatcccag aaggtgagaa agttaaaatt cccgtcgcta tcaaggaatt   1380

aagagaagca acatctccga aagccaacaa ggaaatcctc gatgaagcct acgtgatggc   1440

cagcgtggac aacccccacg tgtgccgcct gctgggcatc tgcctcacct ccaccgtgca   1500

gctcatcacg cagctcatgc ccttcggctg cctcctggac tatgtccggg aacacaaaga   1560

caatattggc tcccagtacc tgctcaactg gtgtgtgcag atcgcaaagg gcatgaacta   1620

cttggaggac cgtcgcttgg tgcaccgcga cctggcagcc aggaacgtac tggtgaaaac   1680

accgcagcat gtcaagatca cagattttgg gctggccaaa ctgctgggtg cggaagagaa   1740

agaataccat gcagaaggag gcaaagtgcc tatcaagtgg atggcattgg aatcaatttt   1800

acacagaatc tatacccacc agagtgatgt ctggagctac ggggtgactg tttgggagtt   1860

gatgaccttt ggatccaagc catatgacgg aatccctgcc agcgagatct cctccatcct   1920

ggagaaagga gaacgcctcc ctcagccacc catatgtacc atcgatgtct acatgatcat   1980

ggtcaagtgc tggatgatag acgcagatag tcgcccaaag ttccgtgagt tgatcatcga   2040

attctccaaa atggcccgag acccccagcg ctaccttgtc attcaggggg atgaaagaat   2100

gcatttgcca agtcctacag actccaactt ctaccgtgcc ctgatggatg aagaagacat   2160

ggacgacgtg gtggatgccg acgagtacct catcccacag cagggcttct tcagcagccc   2220

ctccacgtca cggactcccc tcctgagctc tctgagtgca accagcaaca attccaccgt   2280

ggcttgcatt gatagaaatg ggctgcaaag ctgtcccatc aaggaagaca gcttcttgca   2340

gcgatacagc tcagacccca caggcgcctt gactgaggac agcatagacg acaccttcct   2400

cccagtgcct gaatacataa accagtccgt tcccaaaagg cccgctggct ctgtgcagaa   2460

tcctgtctat cacaatcagc ctctgaaccc cgcgcccagc agagacccac actaccagga   2520

cccccacagc actgcagtgg gcaaccccga gtatctcaac actgtccagc ccacctgtgt   2580

caacagcaca ttcgacagcc ctgcccactg ggcccagaaa ggcagccacc aaattagcct   2640

ggacaaccct gactaccagc aggacttctt tcccaaggaa gccaagccaa atggcatctt   2700

taagggctcc acagctgaaa atgcagaata cctaagggtc gcgccacaaa gcagtgaatt   2760

tattggagca tga                                                      2773
```

<210> SEQ ID NO 104
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"
<220> FEATURE:
<221> NAME/KEY: source
<223> OTHER INFORMATION: /note="Anti- EGFRvIII Clone 139 VH"

<400> SEQUENCE: 104
gaagtgcagg tgctggaaag cggcggagga ctggtgcagc ctggcggatc tctgagactg 60
agctgtgccg ccagcggctt caccttcagc agctacgcca tgagctgggt gcgccaggcc 120
cctggaaaag gcctggaatg ggtgtccgcc atctctggct ccggcggcag caccaattac 180
gccgatagcg tgaagggccg gttcaccatc agccgggaca acagcaagaa caccctgtac 240
ctgcagatga acagcctgag agccgaggac accgccgtgt actactgtgc cggaagctct 300
gggtggagcg agtattgggg ccagggcaca ctcgtgaccg tgtccagc 348

<210> SEQ ID NO 105
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Anti- EGFRvIII Clone 139 VL"

<400> SEQUENCE: 105
gacatccaga tgacccagag ccccagcagc ctgtctgcca gcgtgggcga cagagtgacc 60
atcacctgta gagccagcca gggcatccgg aacaacctgg cctggtatca gcagaagccc 120
ggcaaggccc ccaagcggct gatctacgcc gccagcaatc tgcagagcgg cgtgccctct 180
agattcaccg gctctggcag cggcaccgag ttcaccctga tcgtgtctag cctgcagccc 240
gaggacttcg ccacctacta ctgcctgcag caccacagct accccctgac atctggcgga 300
ggcaccaagg tggaaatcaa g 321

<210> SEQ ID NO 106
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Anti- EGFRvIII Clone MR1 VH"

<400> SEQUENCE: 106
caagtgaagc tgcagcagtc tggcggaggc ctcgtgaaac ctggcgcctc tctgaagctg 60
agctgcgtga ccagcggctt caccttcaga aagttcggca tgagctgggt gcgccagacc 120
agcgacaagc ggctggaatg ggtggccagc atcagcaccg gcggctacaa cacctactac 180
agcgacaacg tgaagggcag attcaccatc agcagagaga acgccaagaa taccctgtac 240
ctgcagatga gcagcctgaa gtccgaggac accgccctgt actactgcac cagaggctac 300
agcagcacca gctacgccat ggactattgg ggccagggca ccaccgtgac cgtgtctagt 360

<210> SEQ ID NO 107
<211> LENGTH: 321
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Anti- EGFRvIII Clone MR1 VL"

<400> SEQUENCE: 107
gacatcgagc tgacacagag ccctgccagc ctgtctgtgg ccaccggcga gaaagtgacc 60
atccggtgca tgaccagcac cgacatcgac gacgacatga actggtatca gcagaagccc 120
ggcgagcccc ccaagttcct gatcagcgag ggcaacacac tgcggcctgg cgtgccaagc 180
agattcagca gctctggcac cggcaccgac ttcgtgttca ccatcgagaa caccctgagc 240
gaggacgtgg gcgactacta ctgcctgcag agcttcaacg tgcccctgac ctttggcgac 300
ggcaccaagc tggaaatcaa g 321

<210> SEQ ID NO 108
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Anti- EGFRvIII Clone MR1-1 VH"

<400> SEQUENCE: 108
caagtgaagc tgcagcagtc tggcggaggc ctcgtgaaac ctggcgcctc tctgaagctg 60
agctgcgtga ccagcggctt caccttcaga aagttcggca tgagctgggt gcgccagacc 120
agcgacaagc ggctggaatg ggtggccagc atcagcaccg gcggctacaa cacctactac 180
agcgacaacg tgaagggcag attcaccatc agcagagaga acgccaagaa taccctgtac 240
ctgcagatga gcagcctgaa gtccgaggac accgccctgt actactgcac cagaggctac 300
agcccctaca gctacgccat ggactattgg ggccagggca ccaccgtgac cgtgtctagt 360

<210> SEQ ID NO 109
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Anti- EGFRvIII Clone MR1-1 VL"

<400> SEQUENCE: 109
gacatcgagc tgacacagag ccctgccagc ctgtctgtgg ccaccggcga gaaagtgacc 60
atccggtgca tgaccagcac cgacatcgac gacgacatga actggtatca gcagaagccc 120
ggcgagcccc ccaagttcct gatcagcgag ggcaacacac tgcggcctgg cgtgccaagc 180
agattcagca gctctggcac cggcaccgac ttcgtgttca ccatcgagaa caccctgagc 240
gaggacgtgg gcgactacta ctgcctgcag agctggaacg tgcccctgac ctttggcgac 300
ggcaccaagc tggaaatcaa g 321

<210> SEQ ID NO 110
<211> LENGTH: 360
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="Anti- EGFRvIII Clone humMR1-1 VH"

<400> SEQUENCE: 110
caggtgcagc tgcaggaatc tggcggaggg ctcgtgaagc ctggcggaag cctgaagctg 60
agctgtgccg ccagcggctt caccttcagc aagttcggca tgagctgggt gcgccagacc 120
cccgacaaga gactggaatg ggtggccagc atcagcaccg gcggctacaa tacctactac 180
agcgacaacg tgaagggccg gttcaccatc tcccgggaca acgccaagaa caccctgtac 240
ctgcagatga gcagcctgaa gtccgaggac accgccatgt actactgtgc cagaggctac 300
agcccctaca gctacgccat ggattactgg ggccagggca caatggtcac cgtgtcctct 360

<210> SEQ ID NO 111
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="Anti- EGFRvIII Clone humMR1-1 VL"

<400> SEQUENCE: 111
gacatccaga tgacccagag ccccagcagc ctgtctgcca gcgtgggcga cagagtgacc 60
atcacctgta tgaccagcac cgacatcgac gacgacatga actggtatca gcagaagccc 120
ggcaagaccc ccaagctgct gatctacgag ggcaacaccc tgaggcctgg cgtgcccagc 180
agattttctg gcagcggctc cggcaccgac ttcatcttca ccatcagctc cctgcagccc 240
gaggatatcg ccacctacta ctgcctgcag agctggaacg tgcccctgac ctttggcgga 300
ggcaccaagg tggaaatcaa g 321

<210> SEQ ID NO 112
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="Anti- EGFRvIII Clone humMR1-2 VH"

<400> SEQUENCE: 112
caggtgcagc tgcaggaatc tggcggaggg ctcgtgaagc ctggcggaag cctgaagctg 60
agctgtgccg ccagcggctt caccttcagc aagttcggca tgagctgggt gcgccagacc 120
cccgacaaga gactggaatg ggtggccagc atcagcaccg gcggctacaa caccttctac 180
agcgacaacg tgaagggccg gttcaccatc tcccgggaca acgccaagaa caccctgtac 240
ctgcagatga gcagcctgaa gtccgaggac accgccatgt actactgtgc cagaggctac 300
agcccctaca gcttcgccat ggattactgg ggccagggca caatggtcac cgtgtcctct 360

<210> SEQ ID NO 113

<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Anti- EGFRvIII Clone humMR1-2 VL"

<400> SEQUENCE: 113
gacatccaga tgacccagag ccccagcagc ctgtctgcca gcgtgggcga cagagtgacc 60
atcacctgta tgaccagcac cgacatcgac gacgacatga actggtatca gcagaagccc 120
ggcaagaccc ccaagctgct gatctacgag ggcaacaccc tgaggcctgg cgtgcccagc 180
agattttctg gcagcggctc cggcaccgac ttcatcttca ccatcagctc cctgcagccc 240
gaggatatcg ccacctacta ctgcctgcag agctggaacg tgcccctgac ctttggcgga 300
ggcaccaagg tggaaatcaa g 321

<210> SEQ ID NO 114
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Anti- EGFRvIII scFv Clone 139"

<400> SEQUENCE: 114
gacatccaga tgacccagag ccccagcagc ctgtctgcca gcgtgggcga cagagtgacc 60
atcacctgta gagccagcca gggcatccgg aacaacctgg cctggtatca gcagaagccc 120
ggcaaggccc ccaagcggct gatctacgcc gccagcaatc tgcagagcgg cgtgccctct 180
agattcaccg gctctggcag cggcaccgag ttcaccctga tcgtgtctag cctgcagccc 240
gaggacttcg ccacctacta ctgcctgcag caccacagct acccccctgac atctggcgga 300 ggcaccaagg tggaaatcaa gggcagcaca agcggcagcg gaaaacctgg atctggcgag 360
ggctctacca agggcgaagt gcaggtgctg gaaagcggcg gaggactggt gcagcctggc 420
ggatctctga gactgagctg tgccgccagc ggcttcacct tcagcagcta cgccatgagc 480
tgggtgcgcc aggcccctgg aaaaggcctg gaatgggtgt ccgccatctc tggctccggc 540
ggcagcacca attacgccga tagcgtgaag ggccggttca ccatcagccg ggacaacagc 600
aagaacaccc tgtacctgca gatgaacagc ctgagagccg aggacaccgc cgtgtactac 660
tgtgccggaa gctctgggtg gagcgagtat tggggccagg gcacactcgt gaccgtgtcc 720
agc 723

<210> SEQ ID NO 115
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Anti-EGFRvIII scFv clone MR1"

<400> SEQUENCE: 115
gacatcgagc tgacacagag ccctgccagc ctgtctgtgg ccaccggcga gaaagtgacc 60
atccggtgca tgaccagcac cgacatcgac gacgacatga actggtatca gcagaagccc 120
ggcgagcccc ccaagttcct gatcagcgag ggcaacacac tgcggcctgg cgtgccaagc 180
agattcagca gctctggcac cggcaccgac ttcgtgttca ccatcgagaa caccctgagc 240
gaggacgtgg gcgactacta ctgcctgcag agcttcaacg tgcccctgac ctttggcgac 300
ggcaccaagc tggaaatcaa gggcggaggc ggatctggcg gcggaggatc tgggggaggc 360
ggctctcaag tgaagctgca gcagtctggc ggaggcctcg tgaaacctgg cgcctctctg 420
aagctgagct gcgtgaccag cggcttcacc ttcagaaagt tcggcatgag ctgggtgcgc 480
cagaccagcg acaagcggct ggaatgggtg gccagcatca gcaccggcgg ctacaacacc 540
tactacagcg acaacgtgaa gggcagattc accatcagca gagagaacgc caagaatacc 600
ctgtacctgc agatgagcag cctgaagtcc gaggacaccg ccctgtacta ctgcaccaga 660
ggctacagca gcaccagcta cgccatggac tattggggcc agggcaccac cgtgaccgtg 720
tctagt 726

<210> SEQ ID NO 116
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="Anti EGFRvIII scFv clone MR1-1"

<400> SEQUENCE: 116
gacatcgagc tgacacagag ccctgccagc ctgtctgtgg ccaccggcga gaaagtgacc 60
atccggtgca tgaccagcac cgacatcgac gacgacatga actggtatca gcagaagccc 120
ggcgagcccc ccaagttcct gatcagcgag ggcaacacac tgcggcctgg cgtgccaagc 180
agattcagca gctctggcac cggcaccgac ttcgtgttca ccatcgagaa caccctgagc 240
gaggacgtgg gcgactacta ctgcctgcag agctggaacg tgcccctgac ctttggcgac 300
ggcaccaagc tggaaatcaa gggcggaggc ggatctggcg gcggaggatc tgggggaggc 360
ggctctcaag tgaagctgca gcagtctggc ggaggcctcg tgaaacctgg cgcctctctg 420
aagctgagct gcgtgaccag cggcttcacc ttcagaaagt tcggcatgag ctgggtgcgc 480
cagaccagcg acaagcggct ggaatgggtg gccagcatca gcaccggcgg ctacaacacc 540
tactacagcg acaacgtgaa gggcagattc accatcagca gagagaacgc caagaatacc 600
ctgtacctgc agatgagcag cctgaagtcc gaggacaccg ccctgtacta ctgcaccaga 660
ggctacagcc cctacagcta cgccatggac tattggggcc agggcaccac cgtgaccgtg 720
tctagt 726

<210> SEQ ID NO 117
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:

<221> NAME/KEY: source
<223> OTHER INFORMATION: /note="Anti-EGFRvIII scFv clone huMR1-1"

<400> SEQUENCE: 117
gacatccaga tgacccagag ccccagcagc ctgtctgcca gcgtgggcga cagagtgacc 60
atcacctgta tgaccagcac cgacatcgac gacgacatga actggtatca gcagaagccc 120
ggcaagaccc ccaagctgct gatctacgag ggcaacaccc tgaggcctgg cgtgcccagc 180
agattttctg gcagcggctc cggcaccgac ttcatcttca ccatcagctc cctgcagccc 240
gaggatatcg ccacctacta ctgcctgcag agctggaacg tgcccctgac ctttggcgga 300
ggcaccaagg tggaaatcaa gggcggaggc ggatctggcg gcggaggatc tgggggaggc 360
ggctctcagg tgcagctgca ggaatctggc ggagggctcg tgaagcctgg cggaagcctg 420
aagctgagct gtgccgccag cggcttcacc ttcagcaagt tcggcatgag ctgggtgcgc 480
cagacccccg acaagagact ggaatgggtg gccagcatca gcaccggcgg ctacaatacc 540
tactacagcg acaacgtgaa gggccggttc accatctccc gggacaacgc caagaacacc 600
ctgtacctgc agatgagcag cctgaagtcc gaggacaccg ccatgtacta ctgtgccaga 660
ggctacagcc cctacagcta cgccatggat tactggggcc agggcacaat ggtcaccgtg 720
tcctct 726

<210> SEQ ID NO 118
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="Anti-EGFRvIII scFv clone huMR1-2"

<400> SEQUENCE: 118
gacatccaga tgacccagag ccccagcagc ctgtctgcca gcgtgggcga cagagtgacc 60
atcacctgta tgaccagcac cgacatcgac gacgacatga actggtatca gcagaagccc 120
ggcaagaccc ccaagctgct gatctacgag ggcaacaccc tgaggcctgg cgtgcccagc 180
agattttctg gcagcggctc cggcaccgac ttcatcttca ccatcagctc cctgcagccc 240
gaggatatcg ccacctacta ctgcctgcag agctggaacg tgcccctgac ctttggcgga 300
ggcaccaagg tggaaatcaa gggcggaggc ggatctggcg gcggaggatc tgggggaggc 360
ggctctcagg tgcagctgca ggaatctggc ggagggctcg tgaagcctgg cggaagcctg 420
aagctgagct gtgccgccag cggcttcacc ttcagcaagt tcggcatgag ctgggtgcgc 480
cagacccccg acaagagact ggaatgggtg gccagcatca gcaccggcgg ctacaacacc 540
ttctacagcg acaacgtgaa gggccggttc accatctccc gggacaacgc caagaacacc 600
ctgtacctgc agatgagcag cctgaagtcc gaggacaccg ccatgtacta ctgtgccaga 660
ggctacagcc cctacagctt cgccatggat tactggggcc agggcacaat ggtcaccgtg 720
tcctct 726

<210> SEQ ID NO 119
<211> LENGTH: 1410
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="EGFRvIII CAR (clone 139 scFv.CD8alpha
      hinge &TM.4-1BB.CD3-zeta)"

<400> SEQUENCE: 119
gacatccaga tgacccagag ccccagcagc ctgtctgcca gcgtgggcga cagagtgacc 60
atcacctgta gagccagcca gggcatccgg aacaacctgg cctggtatca gcagaagccc 120
ggcaaggccc ccaagcggct gatctacgcc gccagcaatc tgcagagcgg cgtgccctct 180
agattcaccg gctctggcag cggcaccgag ttcaccctga tcgtgtctag cctgcagccc 240
gaggacttcg ccacctacta ctgcctgcag caccacagct accccctgac atctggcgga 300
ggcaccaagg tggaaatcaa gggcagcaca agcggcagcg gaaaacctgg atctggcgag 360
ggctctacca agggcgaagt gcaggtgctg gaaagcggcg gaggactggt gcagcctggc 420
ggatctctga gactgagctg tgccgccagc ggcttcacct tcagcagcta cgccatgagc 480
tgggtgcgcc aggcccctgg aaaaggcctg gaatgggtgt ccgccatctc tggctccggc 540
ggcagcacca attacgccga tagcgtgaag ggccggttca ccatcagccg ggacaacagc 600
aagaacaccc tgtacctgca gatgaacagc ctgagagccg aggacaccgc cgtgtactac 660
tgtgccggaa gctctgggtg gagcgagtat tggggccagg gcacactcgt gaccgtgtcc 720
agcaagccca ccaccacccc tgcccctaga cctccaaccc cagcccctac aatcgccagc 780
cagcccctga gcctgaggcc cgaagcctgt agacctgccg ctggcggagc cgtgcacacc 840
agaggcctgg atttcgcctg cgacatctac atctgggccc ctctggccgg cacctgtggc 900
gtgctgctgc tgagcctggt catcaccctg tactgcaacc accggaataa gagaggccgg 960
aagaaactgc tgtacatctt caagcagccc ttcatgcggc ccgtgcagac cacccaggaa 1020
gaggacggct gcagctgccg gttccccgag gaagaggaag gcggctgcga actgcgggtg 1080
aagttcagcc ggagcgccga cgcccctgcc taccagcagg gccagaacca gctgtacaac 1140
gagctgaacc tgggccggag ggaggagtac gacgtgctgg acaagcggag aggccgggac 1200
cctgagatgg gcggcaagcc ccggagaaag aaccctcagg agggcctgta taacgaactg 1260
cagaaagaca agatggccga ggcctacagc gagatcggca tgaagggcga gcggcggagg 1320
ggcaagggcc acgacggcct gtaccagggc ctgagcaccg ccaccaagga tacctacgac 1380
gccctgcaca tgcaggccct gccccccaga 1410

<210> SEQ ID NO 120
<211> LENGTH: 1413
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="EGFRvIII CAR (MR1 scFv.CD8alpha hinge
      &TM.4-1BB.CD3-zeta)"

<400> SEQUENCE: 120
gacatcgagc tgacacagag ccctgccagc ctgtctgtgg ccaccggcga gaaagtgacc 60
atccggtgca tgaccagcac cgacatcgac gacgacatga actggtatca gcagaagccc 120
ggcgagcccc ccaagttcct gatcagcgag ggcaacacac tgcggcctgg cgtgccaagc 180

```
agattcagca gctctggcac cggcaccgac ttcgtgttca ccatcgagaa caccctgagc    240

gaggacgtgg gcgactacta ctgcctgcag agcttcaacg tgcccctgac ctttggcgac    300

ggcaccaagc tggaaatcaa gggcggaggc ggatctggcg gcggaggatc tgggggaggc    360

ggctctcaag tgaagctgca gcagtctggc ggaggcctcg tgaaacctgg cgcctctctg    420

aagctgagct gcgtgaccag cggcttcacc ttcagaaagt tcggcatgag ctgggtgcgc    480

cagaccagcg acaagcggct ggaatgggtg gccagcatca gcaccggcgg ctacaacacc    540

tactacagcg acaacgtgaa gggcagattc accatcagca gagagaacgc caagaatacc    600

ctgtacctgc agatgagcag cctgaagtcc gaggacaccg ccctgtacta ctgcaccaga    660

ggctacagca gcaccagcta cgccatggac tattggggcc agggcaccac cgtgaccgtg    720

tctagtaagc ccaccaccac ccctgcccct agacctccaa ccccagcccc tacaatcgcc    780

agccagcccc tgagcctgag gcccgaagcc tgtagacctg ccgctggcgg agccgtgcac    840

accagaggcc tggatttcgc ctgcgacatc tacatctggg cccctctggc cggcacctgt    900

ggcgtgctgc tgctgagcct ggtcatcacc ctgtactgca accaccggaa taagagaggc    960

cggaagaaac tgctgtacat cttcaagcag cccttcatgc ggcccgtgca gaccacccag   1020

gaagaggacg gctgcagctg ccggttcccc gaggaagagg aaggcggctg cgaactgcgg   1080

gtgaagttca gccggagcgc cgacgcccct gcctaccagc agggccagaa ccagctgtac   1140

aacgagctga acctgggccg gagggaggag tacgacgtgc tggacaagcg gagaggccgg   1200

gaccctgaga tgggcggcaa gccccggaga aagaaccctc aggagggcct gtataacgaa   1260

ctgcagaaag acaagatggc cgaggcctac agcgagatcg gcatgaaggg cgagcggcgg   1320

aggggcaagg gccacgacgg cctgtaccag ggcctgagca ccgccaccaa ggatacctac   1380

gacgccctgc acatgcaggc cctgcccccc aga                                1413
```

```
<210> SEQ ID NO 121
<211> LENGTH: 1413
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="EGFRvIII CAR (MR1-1 scFv.CD8alpha hinge
      &TM.4-1BB.CD3-zeta)"

<400> SEQUENCE: 121

gacatcgagc tgacacagag ccctgccagc ctgtctgtgg ccaccggcga gaaagtgacc     60

atccggtgca tgaccagcac cgacatcgac gacgacatga actggtatca gcagaagccc    120

ggcgagcccc ccaagttcct gatcagcgag ggcaacacac tgcggcctgg cgtgccaagc    180

agattcagca gctctggcac cggcaccgac ttcgtgttca ccatcgagaa caccctgagc    240

gaggacgtgg gcgactacta ctgcctgcag agctggaacg tgcccctgac ctttggcgac    300

ggcaccaagc tggaaatcaa gggcggaggc ggatctggcg gcggaggatc tgggggaggc    360

ggctctcaag tgaagctgca gcagtctggc ggaggcctcg tgaaacctgg cgcctctctg    420

aagctgagct gcgtgaccag cggcttcacc ttcagaaagt tcggcatgag ctgggtgcgc    480

cagaccagcg acaagcggct ggaatgggtg gccagcatca gcaccggcgg ctacaacacc    540

tactacagcg acaacgtgaa gggcagattc accatcagca gagagaacgc caagaatacc    600

ctgtacctgc agatgagcag cctgaagtcc gaggacaccg ccctgtacta ctgcaccaga    660
```

```
ggctacagcc cctacagcta cgccatggac tattggggcc agggcaccac cgtgaccgtg    720

tctagtaagc ccaccaccac ccctgcccct agacctccaa ccccagcccc tacaatcgcc    780

agccagcccc tgagcctgag gcccgaagcc tgtagacctg ccgctggcgg agccgtgcac    840

accagaggcc tggatttcgc ctgcgacatc tacatctggg cccctctggc cggcacctgt    900

ggcgtgctgc tgctgagcct ggtcatcacc ctgtactgca accaccggaa taagagaggc    960

cggaagaaac tgctgtacat cttcaagcag cccttcatgc ggcccgtgca gaccacccag   1020

gaagaggacg gctgcagctg ccggttcccc gaggaagagg aaggcggctg cgaactgcgg   1080

gtgaagttca gccggagcgc cgacgcccct gcctaccagc agggccagaa ccagctgtac   1140

aacgagctga acctgggccg gagggaggag tacgacgtgc tggacaagcg gagaggccgg   1200

gaccctgaga tgggcggcaa gccccggaga aagaaccctc aggagggcct gtataacgaa   1260

ctgcagaaag acaagatggc cgaggcctac agcgagatcg gcatgaaggg cgagcggcgg   1320

aggggcaagg gccacgacgg cctgtaccag ggcctgagca ccgccaccaa ggatacctac   1380

gacgccctgc acatgcaggc cctgcccccc aga                                1413
```

<210> SEQ ID NO 122
<211> LENGTH: 1413
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFRvIII CAR (humMR1-1 scFv.CD8alpha hinge &TM.4-1BB.CD3-zeta)"

<400> SEQUENCE: 122

```
gacatccaga tgacccagag ccccagcagc ctgtctgcca gcgtgggcga cagagtgacc     60

atcacctgta tgaccagcac cgacatcgac gacgacatga actggtatca gcagaagccc    120

ggcaagaccc ccaagctgct gatctacgag ggcaacaccc tgaggcctgg cgtgcccagc    180

agattttctg gcagcggctc cggcaccgac ttcatcttca ccatcagctc cctgcagccc    240

gaggatatcg ccacctacta ctgcctgcag agctggaacg tgcccctgac ctttggcgga    300

ggcaccaagg tggaaatcaa gggcggaggc ggatctggcg gcggaggatc tgggggaggc    360

ggctctcagg tgcagctgca ggaatctggc ggagggctcg tgaagcctgg cggaagcctg    420

aagctgagct gtgccgccag cggcttcacc ttcagcaagt tcggcatgag ctgggtgcgc    480

cagacccccg acaagagact ggaatgggtg gccagcatca gcaccggcgg ctacaatacc    540

tactacagcg acaacgtgaa gggccggttc accatctccc gggacaacgc caagaacacc    600

ctgtacctgc agatgagcag cctgaagtcc gaggacaccg ccatgtacta ctgtgccaga    660

ggctacagcc cctacagcta cgccatggat tactggggcc agggcacaat ggtcaccgtg    720

tcctctaagc ccaccaccac ccctgcccct agacctccaa ccccagcccc tacaatcgcc    780

agccagcccc tgagcctgag gcccgaagcc tgtagacctg ccgctggcgg agccgtgcac    840

accagaggcc tggatttcgc ctgcgacatc tacatctggg cccctctggc cggcacctgt    900

ggcgtgctgc tgctgagcct ggtcatcacc ctgtactgca accaccggaa taagagaggc    960

cggaagaaac tgctgtacat cttcaagcag cccttcatgc ggcccgtgca gaccacccag   1020

gaagaggacg gctgcagctg ccggttcccc gaggaagagg aaggcggctg cgaactgcgg   1080
```

-continued

```
gtgaagttca gccggagcgc cgacgcccct gcctaccagc agggccagaa ccagctgtac   1140

aacgagctga acctgggccg gagggaggag tacgacgtgc tggacaagcg gagaggccgg   1200

gaccctgaga tgggcggcaa gccccggaga aagaaccctc aggagggcct gtataacgaa   1260

ctgcagaaag acaagatggc cgaggcctac agcgagatcg gcatgaaggg cgagcggcgg   1320

aggggcaagg gccacgacgg cctgtaccag ggcctgagca ccgccaccaa ggatacctac   1380

gacgccctgc acatgcaggc cctgcccccc aga                                1413
```

```
<210> SEQ ID NO 123
<211> LENGTH: 1413
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="EGFRvIII CAR (humMR1-2 scFv.CD8alpha
      hinge &TM.4-1BB.CD3-zeta)"

<400> SEQUENCE: 123

gacatccaga tgacccagag ccccagcagc ctgtctgcca gcgtgggcga cagagtgacc     60

atcacctgta tgaccagcac cgacatcgac gacgacatga actggtatca gcagaagccc    120

ggcaagaccc ccaagctgct gatctacgag ggcaacaccc tgaggcctgg cgtgcccagc    180

agattttctg gcagcggctc cggcaccgac ttcatcttca ccatcagctc cctgcagccc    240

gaggatatcg ccacctacta ctgcctgcag agctggaacg tgcccctgac ctttggcgga    300

ggcaccaagg tggaaatcaa gggcggaggc ggatctggcg gcggaggatc tgggggaggc    360

ggctctcagg tgcagctgca ggaatctggc ggagggctcg tgaagcctgg cggaagcctg    420

aagctgagct gtgccgccag cggcttcacc ttcagcaagt tcggcatgag ctgggtgcgc    480

cagacccccg acaagagact ggaatgggtg gccagcatca gcaccggcgg ctacaacacc    540

ttctacagcg acaacgtgaa gggccggttc accatctccc gggacaacgc caagaacacc    600

ctgtacctgc agatgagcag cctgaagtcc gaggacaccg ccatgtacta ctgtgccaga    660

ggctacagcc cctacagctt cgccatggat tactggggcc agggcacaat ggtcaccgtg    720

tcctctaagc ccaccaccac ccctgcccct agacctccaa ccccagcccc tacaatcgcc    780

agccagcccc tgagcctgag gcccgaagcc tgtagacctg ccgctggcgg agccgtgcac    840

accagaggcc tggatttcgc ctgcgacatc tacatctggg cccctctggc cggcacctgt    900

ggcgtgctgc tgctgagcct ggtcatcacc ctgtactgca accaccggaa taagagaggc    960

cggaagaaac tgctgtacat cttcaagcag cccttcatgc ggcccgtgca gaccacccag   1020

gaagaggacg gctgcagctg ccggttcccc gaggaagagg aaggcggctg cgaactgcgg   1080

gtgaagttca gccggagcgc cgacgcccct gcctaccagc agggccagaa ccagctgtac   1140

aacgagctga acctgggccg gagggaggag tacgacgtgc tggacaagcg gagaggccgg   1200

gaccctgaga tgggcggcaa gccccggaga aagaaccctc aggagggcct gtataacgaa   1260

ctgcagaaag acaagatggc cgaggcctac agcgagatcg gcatgaaggg cgagcggcgg   1320

aggggcaagg gccacgacgg cctgtaccag ggcctgagca ccgccaccaa ggatacctac   1380

gacgccctgc acatgcaggc cctgcccccc aga                                1413


<210> SEQ ID NO 124
<211> LENGTH: 1554
```

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFRvIII CAR (MR1-1 scFv.CD8alpha 2x hinge &TM.4-1BB.CD3-zeta)"

<400> SEQUENCE: 124

```
gacatcgagc tgacacagag ccctgccagc ctgtctgtgg ccaccggcga gaaagtgacc     60
atccggtgca tgaccagcac cgacatcgac gacgacatga actggtatca gcagaagccc    120
ggcgagcccc ccaagttcct gatcagcgag ggcaacacac tgcggcctgg cgtgccaagc    180
agattcagca gctctggcac cggcaccgac ttcgtgttca ccatcgagaa caccctgagc    240
gaggacgtgg gcgactacta ctgcctgcag agctggaacg tgcccctgac ctttggcgac    300
ggcaccaagc tggaaatcaa gggcggaggc ggatctggcg gcggaggatc tgggggaggc    360
ggctctcaag tgaagctgca gcagtctggc ggaggcctcg tgaaacctgg cgcctctctg    420
aagctgagct gcgtgaccag cggcttcacc ttcagaaagt tcggcatgag ctgggtgcgc    480
cagaccagcg acaagcggct ggaatgggtg gccagcatca gcaccggcgg ctacaacacc    540
tactacagcg acaacgtgaa gggcagattc accatcagca gagagaacgc caagaatacc    600
ctgtacctgc agatgagcag cctgaagtcc gaggacaccg ccctgtacta ctgcaccaga    660
ggctacagcc cctacagcta cgccatggac tattggggcc agggcaccac cgtgaccgtg    720
tctagtaaac ctactacaac tcctgccccc cggcctccta caccagctcc tactatcgcc    780
tcccagccac tcagtctcag acccgaggct tctaggccag cggccggagg cgcggtccac    840
acccgcgggc tggactttgc atccgataag cccaccacca cccctgcccc tagacctcca    900
accccagccc ctacaatcgc cagccagccc ctgagcctga ggcccgaagc ctgtagacct    960
gccgctggcg gagccgtgca caccagaggc ctggatttcg cctgcgacat ctacatctgg   1020
gcccctctgg ccggcacctg tggcgtgctg ctgctgagcc tggtcatcac cctgtactgc   1080
aaccaccgga ataagagagg ccggaagaaa ctgctgtaca tcttcaagca gcccttcatg   1140
cggcccgtgc agaccaccca ggaagaggac ggctgcagct gccggttccc cgaggaagag   1200
gaaggcggct gcgaactgcg ggtgaagttc agccggagcg ccgacgcccc tgcctaccag   1260
cagggccaga accagctgta caacgagctg aacctgggcc ggagggagga gtacgacgtg   1320
ctggacaagc ggagaggccg ggaccctgag atgggcggca agccccggag aaagaaccct   1380
caggagggcc tgtataacga actgcagaaa gacaagatgg ccgaggccta cagcgagatc   1440
ggcatgaagg gcgagcggcg gaggggcaag ggccacgacg gcctgtacca gggcctgagc   1500
accgccacca aggataccta cgacgccctg cacatgcagg ccctgccccc caga         1554
```

<210> SEQ ID NO 125
<211> LENGTH: 1695
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFRvIII CAR (MR1-1 scFv.CD8alpha 3x hinge &TM.4-1BB.CD3-zeta)"

<400> SEQUENCE: 125
gacatcgagc tgacacagag ccctgccagc ctgtctgtgg ccaccggcga gaaagtgacc 60
atccggtgca tgaccagcac cgacatcgac gacgacatga actggtatca gcagaagccc 120
ggcgagcccc ccaagttcct gatcagcgag ggcaacacac tgcggcctgg cgtgccaagc 180
agattcagca gctctggcac cggcaccgac ttcgtgttca ccatcgagaa caccctgagc 240
gaggacgtgg gcgactacta ctgcctgcag agctggaacg tgcccctgac ctttggcgac 300
ggcaccaagc tggaaatcaa gggcggaggc ggatctggcg gcggaggatc tgggggaggc 360
ggctctcaag tgaagctgca gcagtctggc ggaggcctcg tgaaacctgg cgcctctctg 420
aagctgagct gcgtgaccag cggcttcacc ttcagaaagt tcggcatgag ctgggtgcgc 480
cagaccagcg acaagcggct ggaatgggtg gccagcatca gcaccggcgg ctacaacacc 540
tactacagcg acaacgtgaa gggcagattc accatcagca gagagaacgc caagaatacc 600
ctgtacctgc agatgagcag cctgaagtcc gaggacaccg ccctgtacta ctgcaccaga 660
ggctacagcc cctacagcta cgccatggac tattggggcc agggcaccac cgtgaccgtg 720
tctagtaagc ctaccaccac ccccgcacct cgtcctccaa cccctgcacc tacgattgcc 780
agtcagcctc tttcactgcg gcctgaggcc agcagaccag ctgccggcgg tgccgtccat 840
acaagaggac tggacttcgc gtccgataaa cctactacca ctccagcccc aaggccccca 900
accccagcac cgactatcgc atcacagcct ttgtcactgc gtcctgaagc cagccggcca 960
gctgcagggg gggccgtcca cacaagggga ctcgactttg cgagtgataa gcccaccacc 1020
acccctgccc ctagacctcc aaccccagcc cctacaatcg ccagccagcc cctgagcctg 1080
aggcccgaag cctgtagacc tgccgctggc ggagccgtgc acaccagagg cctggatttc 1140
gcctgcgaca tctacatctg ggcccctctg gccggcacct gtggcgtgct gctgctgagc 1200
ctggtcatca ccctgtactg caaccaccgg aataagagag gccggaagaa actgctgtac 1260
atcttcaagc agcccttcat gcggcccgtg cagaccaccc aggaagagga cggctgcagc 1320
tgccggttcc ccgaggaaga ggaaggcggc tgcgaactgc gggtgaagtt cagccggagc 1380
gccgacgccc ctgcctacca gcagggccag aaccagctgt acaacgagct gaacctgggc 1440
cggagggagg agtacgacgt gctggacaag cggagaggcc gggaccctga gatgggcggc 1500
aagccccgga gaaagaaccc tcaggagggc ctgtataacg aactgcagaa agacaagatg 1560
gccgaggcct acagcgagat cggcatgaag ggcgagcggc ggaggggcaa gggccacgac 1620
ggcctgtacc agggcctgag caccgccacc aaggatacct acgacgccct gcacatgcag 1680
gccctgcccc ccaga 1695

<210> SEQ ID NO 126
<211> LENGTH: 1836
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFRvIII CAR (MR1-1 scFv.CD8alpha 4x hinge &TM.4-1BB.CD3-zeta)"

<400> SEQUENCE: 126
gacatcgagc tgacacagag ccctgccagc ctgtctgtgg ccaccggcga gaaagtgacc 60
atccggtgca tgaccagcac cgacatcgac gacgacatga actggtatca gcagaagccc 120
ggcgagcccc ccaagttcct gatcagcgag ggcaacacac tgcggcctgg cgtgccaagc 180
agattcagca gctctggcac cggcaccgac ttcgtgttca ccatcgagaa caccctgagc 240
gaggacgtgg gcgactacta ctgcctgcag agctggaacg tgcccctgac ctttggcgac 300
ggcaccaagc tggaaatcaa gggcggaggc ggatctggcg gcggaggatc tgggggaggc 360
ggctctcaag tgaagctgca gcagtctggc ggaggcctcg tgaaacctgg cgcctctctg 420
aagctgagct gcgtgaccag cggcttcacc ttcagaaagt tcggcatgag ctgggtgcgc 480
cagaccagcg acaagcggct ggaatgggtg gccagcatca gcaccggcgg ctacaacacc 540
tactacagcg acaacgtgaa gggcagattc accatcagca gagagaacgc caagaatacc 600
ctgtacctgc agatgagcag cctgaagtcc gaggacaccg ccctgtacta ctgcaccaga 660
ggctacagcc cctacagcta cgccatggac tattggggcc agggcaccac cgtgaccgtg 720
tctagtaagc ctaccaccac ccccgcacct cgtcctccaa cccctgcacc tacgattgcc 780
agtcagcctc tttcactgcg gcctgaggcc agcagaccag ctgccggcgg tgccgtccat 840
acaagaggac tggacttcgc gtccgataaa cctactacca ctccagcccc aaggccccca 900
accccagcac cgactatcgc atcacagcct ttgtcactgc gtcctgaagc cagccggcca 960
gctgcagggg gggccgtcca cacaagggga ctcgactttg cgagtgataa acctactaca 1020
actcctgccc cccggcctcc tacaccagct cctactatcg cctcccagcc actcagtctc 1080
agacccgagg cttctaggcc agcggccgga ggcgcggtcc acacccgcgg gctggacttt 1140
gcatccgata agcccaccac cacccctgcc cctagacctc caaccccagc ccctacaatc 1200
gccagccagc ccctgagcct gaggcccgaa gcctgtagac ctgccgctgg cggagccgtg 1260
cacaccagag gcctggattt cgcctgcgac atctacatct gggcccctct ggccggcacc 1320
tgtggcgtgc tgctgctgag cctggtcatc accctgtact gcaaccaccg gaataagaga 1380
ggccggaaga aactgctgta catcttcaag cagcccttca tgcggcccgt gcagaccacc 1440
caggaagagg acggctgcag ctgccggttc cccgaggaag aggaaggcgg ctgcgaactg 1500
cgggtgaagt tcagccggag cgccgacgcc cctgcctacc agcagggcca gaaccagctg 1560
tacaacgagc tgaacctggg ccggagggag gagtacgacg tgctggacaa gcggagaggc 1620
cgggaccctg agatgggcgg caagccccgg agaaagaacc ctcaggaggg cctgtataac 1680
gaactgcaga aagacaagat ggccgaggcc tacagcgaga tcggcatgaa gggcgagcgg 1740
cggaggggca agggccacga cggcctgtac cagggcctga gcaccgccac caaggatacc 1800
tacgacgccc tgcacatgca ggccctgccc cccaga 1836

<210> SEQ ID NO 127
<211> LENGTH: 1695
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFRvIII CAR (huMR1-1 scFv.CD8alpha 3x hinge & TM.4-1BB.CD3-zeta)"

<400> SEQUENCE: 127
gacatccaga tgacccagag ccccagcagc ctgtctgcca gcgtgggcga cagagtgacc 60
atcacctgta tgaccagcac cgacatcgac gacgacatga actggtatca gcagaagccc 120

```
ggcaagaccc ccaagctgct gatctacgag ggcaacaccc tgaggcctgg cgtgcccagc    180

agattttctg gcagcggctc cggcaccgac ttcatcttca ccatcagctc cctgcagccc    240

gaggatatcg ccacctacta ctgcctgcag agctggaacg tgcccctgac ctttggcgga    300

ggcaccaagg tggaaatcaa gggcggaggc ggatctggcg gcggaggatc tgggggaggc    360

ggctctcagg tgcagctgca ggaatctggc ggagggctcg tgaagcctgg cggaagcctg    420

aagctgagct gtgccgccag cggcttcacc ttcagcaagt tcggcatgag ctgggtgcgc    480

cagacccccg acaagagact ggaatgggtg gccagcatca gcaccggcgg ctacaatacc    540

tactacagcg acaacgtgaa gggccggttc accatctccc gggacaacgc caagaacacc    600

ctgtacctgc agatgagcag cctgaagtcc gaggacaccg ccatgtacta ctgtgccaga    660

ggctacagcc cctacagcta cgccatggat tactggggcc agggcacaat ggtcaccgtg    720

tcctctaagc ctaccaccac ccccgcacct cgtcctccaa cccctgcacc tacgattgcc    780

agtcagcctc tttcactgcg gcctgaggcc agcagaccag ctgccggcgg tgccgtccat    840

acaagaggac tggacttcgc gtccgataaa cctactacca ctccagcccc aaggccccca    900

accccagcac cgactatcgc atcacagcct ttgtcactgc gtcctgaagc cagccggcca    960

gctgcagggg gggccgtcca cacaagggga ctcgactttg cgagtgataa gcccaccacc   1020

acccctgccc ctagacctcc aaccccagcc cctacaatcg ccagccagcc cctgagcctg   1080

aggcccgaag cctgtagacc tgccgctggc ggagccgtgc acaccagagg cctggatttc   1140

gcctgcgaca tctacatctg ggcccctctg gccggcacct gtggcgtgct gctgctgagc   1200

ctggtcatca ccctgtactg caaccaccgg aataagagag gccggaagaa actgctgtac   1260

atcttcaagc agcccttcat gcggcccgtg cagaccaccc aggaagagga cggctgcagc   1320

tgccggttcc ccgaggaaga ggaaggcggc tgcgaactgc gggtgaagtt cagccggagc   1380

gccgacgccc ctgcctacca gcagggccag aaccagctgt acaacgagct gaacctgggc   1440

cggagggagg agtacgacgt gctggacaag cggagaggcc gggaccctga gatgggcggc   1500

aagccccgga gaaagaaccc tcaggagggc ctgtataacg aactgcagaa agacaagatg   1560

gccgaggcct acagcgagat cggcatgaag ggcgagcggc ggaggggcaa gggccacgac   1620

ggcctgtacc agggcctgag caccgccacc aaggatacct acgacgccct gcacatgcag   1680

gccctgcccc ccaga                                                     1695
```

```
<210> SEQ ID NO 128
<211> LENGTH: 1836
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="EGFRvIII CAR (huMR1-1 scFv.CD8alpha 4x
      hinge & TM.4-1BB.CD3-zeta)"

<400> SEQUENCE: 128

gacatccaga tgacccagag ccccagcagc ctgtctgcca gcgtgggcga cagagtgacc     60

atcacctgta tgaccagcac cgacatcgac gacgacatga actggtatca gcagaagccc    120

ggcaagaccc ccaagctgct gatctacgag ggcaacaccc tgaggcctgg cgtgcccagc    180

agattttctg gcagcggctc cggcaccgac ttcatcttca ccatcagctc cctgcagccc    240

gaggatatcg ccacctacta ctgcctgcag agctggaacg tgcccctgac ctttggcgga    300
```

ggcaccaagg tggaaatcaa gggcggaggc ggatctggcg gcggaggatc tgggggaggc 360
ggctctcagg tgcagctgca ggaatctggc ggagggctcg tgaagcctgg cggaagcctg 420
aagctgagct gtgccgccag cggcttcacc ttcagcaagt tcggcatgag ctgggtgcgc 480
cagacccccg acaagagact ggaatgggtg gccagcatca gcaccggcgg ctacaatacc 540
tactacagcg acaacgtgaa gggccggttc accatctccc gggacaacgc caagaacacc 600
ctgtacctgc agatgagcag cctgaagtcc gaggacaccg ccatgtacta ctgtgccaga 660
ggctacagcc cctacagcta cgccatggat tactggggcc agggcacaat ggtcaccgtg 720
tcctctaagc ctaccaccac ccccgcacct cgtcctccaa cccctgcacc tacgattgcc 780
agtcagcctc tttcactgcg gcctgaggcc agcagaccag ctgccggcgg tgccgtccat 840
acaagaggac tggacttcgc gtccgataaa cctactacca ctccagcccc aaggcccccca 900 accccagcac cgactatcgc atcacagcct ttgtcactgc gtcctgaagc cagccggcca 960
gctgcagggg gggccgtcca cacaagggga ctcgactttg cgagtgataa acctactaca 1020
actcctgccc cccggcctcc tacaccagct cctactatcg cctcccagcc actcagtctc 1080
agacccgagg cttctaggcc agcggccgga ggcgcggtcc acacccgcgg gctggacttt 1140
gcatccgata agcccaccac cacccctgcc cctagacctc caaccccagc ccctacaatc 1200
gccagccagc ccctgagcct gaggcccgaa gcctgtagac ctgccgctgg cggagccgtg 1260
cacaccagag gcctggattt cgcctgcgac atctacatct gggcccctct ggccggcacc 1320
tgtggcgtgc tgctgctgag cctggtcatc accctgtact gcaaccaccg gaataagaga 1380
ggccggaaga aactgctgta catcttcaag cagcccttca tgcggcccgt gcagaccacc 1440
caggaagagg acggctgcag ctgccggttc cccgaggaag aggaaggcgg ctgcgaactg 1500
cgggtgaagt tcagccggag cgccgacgcc cctgcctacc agcagggcca gaaccagctg 1560
tacaacgagc tgaacctggg ccggagggag gagtacgacg tgctggacaa gcggagaggc 1620
cgggaccctg agatgggcgg caagccccgg agaaagaacc ctcaggaggg cctgtataac 1680
gaactgcaga aagacaagat ggccgaggcc tacagcgaga tcggcatgaa gggcgagcgg 1740
cggaggggca agggccacga cggcctgtac cagggcctga gcaccgccac caaggatacc 1800
tacgacgccc tgcacatgca ggccctgccc cccaga 1836

<210> SEQ ID NO 129
<211> LENGTH: 1695
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFRvIII CAR (huMR1-2 scFv.CD8alpha 3x hinge & TM.4-1BB.CD3-zeta)"

<400> SEQUENCE: 129
gacatccaga tgacccagag ccccagcagc ctgtctgcca gcgtgggcga cagagtgacc 60
atcacctgta tgaccagcac cgacatcgac gacgacatga actggtatca gcagaagccc 120
ggcaagaccc ccaagctgct gatctacgag ggcaacaccc tgaggcctgg cgtgcccagc 180
agattttctg gcagcggctc cggcaccgac ttcatcttca ccatcagctc cctgcagccc 240
gaggatatcg ccacctacta ctgcctgcag agctggaacg tgcccctgac ctttggcgga 300

```
ggcaccaagg tggaaatcaa gggcggaggc ggatctggcg gcggaggatc tgggggaggc    360

ggctctcagg tgcagctgca ggaatctggc ggagggctcg tgaagcctgg cggaagcctg    420

aagctgagct gtgccgccag cggcttcacc ttcagcaagt tcggcatgag ctgggtgcgc    480

cagacccccg acaagagact ggaatgggtg gccagcatca gcaccggcgg ctacaacacc    540

ttctacagcg acaacgtgaa gggccggttc accatctccc gggacaacgc caagaacacc    600

ctgtacctgc agatgagcag cctgaagtcc gaggacaccg ccatgtacta ctgtgccaga    660

ggctacagcc cctacagctt cgccatggat tactggggcc agggcacaat ggtcaccgtg    720

tcctctaagc ctaccaccac ccccgcacct cgtcctccaa cccctgcacc tacgattgcc    780

agtcagcctc tttcactgcg gcctgaggcc agcagaccag ctgccggcgg tgccgtccat    840

acaagaggac tggacttcgc gtccgataaa cctactacca ctccagcccc aaggcccccca    900

accccagcac cgactatcgc atcacagcct ttgtcactgc gtcctgaagc cagccggcca    960

gctgcagggg gggccgtcca cacaagggga ctcgactttg cgagtgataa gcccaccacc   1020

acccctgccc ctagacctcc aaccccagcc cctacaatcg ccagccagcc cctgagcctg   1080

aggcccgaag cctgtagacc tgccgctggc ggagccgtgc acaccagagg cctggatttc   1140

gcctgcgaca tctacatctg ggcccctctg gccggcacct gtggcgtgct gctgctgagc   1200

ctggtcatca ccctgtactg caaccaccgg aataagagag gccggaagaa actgctgtac   1260

atcttcaagc agcccttcat gcggcccgtg cagaccaccc aggaagagga cggctgcagc   1320

tgccggttcc ccgaggaaga ggaaggcggc tgcgaactgc gggtgaagtt cagccggagc   1380

gccgacgccc ctgcctacca gcagggccag aaccagctgt acaacgagct gaacctgggc   1440

cggagggagg agtacgacgt gctggacaag cggagaggcc gggaccctga gatgggcggc   1500

aagccccgga gaaagaaccc tcaggagggc ctgtataacg aactgcagaa agacaagatg   1560

gccgaggcct acagcgagat cggcatgaag ggcgagcggc ggaggggcaa gggccacgac   1620

ggcctgtacc agggcctgag caccgccacc aaggatacct acgacgccct gcacatgcag   1680

gccctgcccc ccaga                                                    1695
```

<210> SEQ ID NO 130
<211> LENGTH: 1836
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="EGFRvIII CAR (huMR1-2 scFv.CD8alpha 4x hinge & TM.4-1BB.CD3-zeta"

<400> SEQUENCE: 130

```
gacatccaga tgacccagag ccccagcagc ctgtctgcca gcgtgggcga cagagtgacc     60

atcacctgta tgaccagcac cgacatcgac gacgacatga actggtatca gcagaagccc    120

ggcaagaccc ccaagctgct gatctacgag ggcaacaccc tgaggcctgg cgtgcccagc    180

agattttctg gcagcggctc cggcaccgac ttcatcttca ccatcagctc cctgcagccc    240

gaggatatcg ccacctacta ctgcctgcag agctggaacg tgcccctgac ctttggcgga    300

ggcaccaagg tggaaatcaa gggcggaggc ggatctggcg gcggaggatc tgggggaggc    360

ggctctcagg tgcagctgca ggaatctggc ggagggctcg tgaagcctgg cggaagcctg    420

aagctgagct gtgccgccag cggcttcacc ttcagcaagt tcggcatgag ctgggtgcgc    480
```

cagacccccg acaagagact ggaatgggtg gccagcatca gcaccggcgg ctacaacacc 540
ttctacagcg acaacgtgaa gggccggttc accatctccc gggacaacgc caagaacacc 600
ctgtacctgc agatgagcag cctgaagtcc gaggacaccg ccatgtacta ctgtgccaga 660
ggctacagcc cctacagctt cgccatggat tactggggcc agggcacaat ggtcaccgtg 720
tcctctaagc ctaccaccac ccccgcacct cgtcctccaa cccctgcacc tacgattgcc 780
agtcagcctc tttcactgcg gcctgaggcc agcagaccag ctgccggcgg tgccgtccat 840
acaagaggac tggacttcgc gtccgataaa cctactacca ctccagcccc aaggccccca 900
accccagcac cgactatcgc atcacagcct ttgtcactgc gtcctgaagc cagccggcca 960
gctgcagggg gggccgtcca cacaagggga ctcgactttg cgagtgataa acctactaca 1020
actcctgccc cccggcctcc tacaccagct cctactatcg cctcccagcc actcagtctc 1080
agacccgagg cttctaggcc agcggccgga ggcgcggtcc acacccgcgg gctggacttt 1140
gcatccgata agcccaccac cacccctgcc cctagacctc caaccccagc ccctacaatc 1200
gccagccagc ccctgagcct gaggcccgaa gcctgtagac ctgccgctgg cggagccgtg 1260
cacaccagag gcctggattt cgcctgcgac atctacatct gggcccctct ggccggcacc 1320
tgtggcgtgc tgctgctgag cctggtcatc accctgtact gcaaccaccg gaataagaga 1380
ggccggaaga aactgctgta catcttcaag cagcccttca tgcggcccgt gcagaccacc 1440
caggaagagg acggctgcag ctgccggttc cccgaggaag aggaaggcgg ctgcgaactg 1500
cgggtgaagt tcagccggag cgccgacgcc cctgcctacc agcagggcca gaaccagctg 1560
tacaacgagc tgaacctggg ccggagggag gagtacgacg tgctggacaa gcggagaggc 1620
cgggaccctg agatgggcgg caagccccgg agaaagaacc ctcaggaggg cctgtataac 1680
gaactgcaga aagacaagat ggccgaggcc tacagcgaga tcggcatgaa gggcgagcgg 1740
cggaggggca agggccacga cggcctgtac cagggcctga gcaccgccac caaggatacc 1800
tacgacgccc tgcacatgca ggccctgccc cccaga 1836

<210> SEQ ID NO 131
<211> LENGTH: 3224
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="XON-64"

<400> SEQUENCE: 131
gtggaatgtg tgtcagttag ggtgtggaaa gtccccaggc tccccagcag gcagaagtat 60
gcaaagcatc gagcggccgc aataaaatat ctttattttc attacatctg tgtgttggtt 120
ttttgtgtga atcgtaacta acatacgctc tccatcaaaa caaaacgaaa caaaacaaac 180
tagcaaaata ggctgtcccc agtgcaagtg caggtgccag aacatttctc tatcgaagga 240
tctgcgatcg ctccggtgcc cgtcagtggg cagagcgcac atcgcccaca gtccccgaga 300
agttgggggg aggggtcggc aattgaaccg gtgcctagag aaggtggcgc ggggtaaact 360
gggaaagtga tgtcgtgtac tggctccgcc tttttcccga gggtggggga gaaccgtata 420
taagtgcagt agtcgccgtg aacgttcttt ttcgcaacgg gtttgccgcc agaacacagc 480
tgaagcttcg aggggctcgc atctctcctt cacgcgcccg ccgccctacc tgaggccgcc 540

```
atccacgccg gttgagtcgc gttctgccgc ctcccgcctg tggtgcctcc tgaactgcgt    600
ccgccgtcta ggtaagttta aagctcaggt cgagaccggg cctttgtccg gcgctccctt    660
ggagcctacc tagactcagc cggctctcca cgctttgcct gaccctgctt gctcaactct    720
acgtctttgt ttcgttttct gttctgcgcc gttacagatc caagctgtga ccggcgccta    780
cctgagatca ccggcgaagg aggcctatca tgaagatcta tcgattgtac agctagccgc    840
caccatgctg ctgctggtga ccagcctgct gctgtgtgag ctgccccacc ccgcctttct    900
gctgatcccc gacatccaga tgacccagag ccccagcagc ctgtctgcca gcgtgggcga    960
cagagtgacc atcacctgta tgaccagcac cgacatcgac gacgacatga actggtatca   1020
gcagaagccc ggcaagaccc ccaagctgct gatctacgag ggcaacaccc tgaggcctgg   1080
cgtgcccagc agattttctg gcagcggctc cggcaccgac ttcatcttca ccatcagctc   1140
cctgcagccc gaggatatcg ccacctacta ctgcctgcag agctggaacg tgcccctgac   1200
ctttggcgga ggcaccaagg tggaaatcaa gggcggaggc ggatctggcg gcggaggatc   1260
tgggggaggc ggctctcagg tgcagctgca ggaatctggc ggagggctcg tgaagcctgg   1320
cggaagcctg aagctgagct gtgccgccag cggcttcacc ttcagcaagt tcggcatgag   1380
ctgggtgcgc cagacccccg acaagagact ggaatgggtg gccagcatca gcaccggcgg   1440
ctacaatacc tactacagcg acaacgtgaa gggccggttc accatctccc gggacaacgc   1500
caagaacacc ctgtacctgc agatgagcag cctgaagtcc gaggacaccg ccatgtacta   1560
ctgtgccaga ggctacagcc cctacagcta cgccatggat tactggggcc agggcacaat   1620
ggtcaccgtg tcctctaagc ctaccaccac ccccgcacct cgtcctccaa cccctgcacc   1680
tacgattgcc agtcagcctc tttcactgcg gcctgaggcc agcagaccag ctgccggcgg   1740
tgccgtccat acaagaggac tggacttcgc gtccgataaa cctactacca ctccagcccc   1800
aaggccccca accccagcac cgactatcgc atcacagcct ttgtcactgc gtcctgaagc   1860
cagccggcca gctgcagggg gggccgtcca cacaagggga ctcgactttg cgagtgataa   1920
gcccaccacc acccctgccc ctagacctcc aaccccagcc cctacaatcg ccagccagcc   1980
cctgagcctg aggcccgaag cctgtagacc tgccgctggc ggagccgtgc acaccagagg   2040
cctggatttc gcctgcgaca tctacatctg ggcccctctg gccggcacct gtggcgtgct   2100
gctgctgagc ctggtcatca ccctgtactg caaccaccgg aataagagag gccggaagaa   2160
actgctgtac atcttcaagc agcccttcat gcggcccgtg cagaccaccc aggaagagga   2220
cggctgcagc tgccggttcc ccgaggaaga ggaaggcggc tgcgaactgc gggtgaagtt   2280
cagccggagc gccgacgccc ctgcctacca gcagggccag aaccagctgt acaacgagct   2340
gaacctgggc cggagggagg agtacgacgt gctggacaag cggagaggcc gggaccctga   2400
gatgggcggc aagccccgga gaaagaaccc tcaggagggc ctgtataacg aactgcagaa   2460
agacaagatg gccgaggcct acagcgagat cggcatgaag ggcgagcggc ggaggggcaa   2520
gggccacgac ggcctgtacc agggcctgag caccgccacc aaggatacct acgacgccct   2580
gcacatgcag gccctgcccc ccagatgaga tatcactagt ctcgagtcga tcatgctcat   2640
agtggcaaga gagagccgta cgtgatcagc gggatctgct gtgccttcta gttgccagcc   2700
atctgttgtt tgcccctccc ccgtgccttc cttgaccctg gaaggtgcca ctcccactgt   2760
cctttcctaa taaaatgagg aaattgcatc gcattgtctg agtaggtgtc attctattct   2820
ggggggtggg gtggggcagg acagcaaggg ggaggattgg gaagacaata gcaggcatgc   2880
```

-continued

```
tggggatgcg gtgggctcta tgggtaccca ggtgctgaag aattgacccg gttcctcctg   2940

ggccagaaag aagcaggcac atccccttct ctgtgacaca ccctgtccac gcccctggtt   3000

cttagttcca gccccactca taggacactc atagctcagg agggctccgc cttcaatccc   3060

acccgctaaa gtacttggag cggtctctcc ctccctcatc agcccaccaa accaaaccta   3120

gcctccaaga gtgggaagaa attaaagcaa gataggctat taagtgcaga gggagagaaa   3180

atgcctccaa catgtgagga agtaatgaga gaaatcatag aatt                     3224


<210> SEQ ID NO 132
<211> LENGTH: 3319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="XON-30"

<400> SEQUENCE: 132

gtggaatgtg tgtcagttag ggtgtggaaa gtccccaggc tccccagcag gcagaagtat     60

gcaaagcatc gagcggccgc aataaaatat ctttattttc attacatctg tgtgttggtt    120

ttttgtgtga atcgtaacta acatacgctc tccatcaaaa caaaacgaaa caaaacaaac    180

tagcaaaata ggctgtcccc agtgcaagtg caggtgccag aacatttctc tatcgaagga    240

tctgcgatcg ctccggtgcc cgtcagtggg cagagcgcac atcgcccaca gtccccgaga    300

agttgggggg aggggtcggc aattgaaccg gtgcctagag aaggtggcgc ggggtaaact    360

gggaaagtga tgtcgtgtac tggctccgcc tttttcccga gggtggggga gaaccgtata    420

taagtgcagt agtcgccgtg aacgttcttt ttcgcaacgg gtttgccgcc agaacacagc    480

tgaagcttcg aggggctcgc atctctcctt cacgcgcccg ccgccctacc tgaggccgcc    540

atccacgccg gttgagtcgc gttctgccgc ctcccgcctg tggtgcctcc tgaactgcgt    600

ccgccgtcta ggtaagttta aagctcaggt cgagaccggg cctttgtccg gcgctccctt    660

ggagcctacc tagactcagc cggctctcca cgctttgcct gaccctgctt gctcaactct    720

acgtctttgt ttcgttttct gttctgcgcc gttacagatc caagctgtga ccggcgccta    780

cctgagatca ccggcgaagg aggcctatca tgaagatcta tcgattgtac agctagccgc    840

caccatgctg ctgctggtga ccagcctgct gctgtgtgag ctgccccacc ccgcctttct    900

gctgatcccc gacatccaga tgacccagag ccccagcagc ctgtctgcca gcgtgggcga    960

cagagtgacc atcacctgta tgaccagcac cgacatcgac gacgacatga actggtatca   1020

gcagaagccc ggcaagaccc ccaagctgct gatctacgag ggcaacaccc tgaggcctgg   1080

cgtgcccagc agattttctg gcagcggctc cggcaccgac ttcatcttca ccatcagctc   1140

cctgcagccc gaggatatcg ccacctacta ctgcctgcag agctggaacg tgcccctgac   1200

ctttggcgga ggcaccaagg tggaaatcaa gggcggaggc ggatctggcg gcggaggatc   1260

tgggggaggc ggctctcagg tgcagctgca ggaatctggc ggagggctcg tgaagcctgg   1320

cggaagcctg aagctgagct gtgccgccag cggcttcacc ttcagcaagt tcggcatgag   1380

ctgggtgcgc cagacccccg acaagagact ggaatgggtg gccagcatca gcaccggcgg   1440

ctacaatacc tactacagcg acaacgtgaa gggccggttc accatctccc gggacaacgc   1500

caagaacacc ctgtacctgc agatgagcag cctgaagtcc gaggacaccg ccatgtacta   1560
```

```
ctgtgccaga ggctacagcc cctacagcta cgccatggat tactggggcc agggcacaat   1620

ggtcaccgtg tcctctaagc ctaccaccac ccccgcacct cgtcctccaa cccctgcacc   1680

tacgattgcc agtcagcctc tttcactgcg gcctgaggcc agcagaccag ctgccggcgg   1740

tgccgtccat acaagaggac tggacttcgc gtccgataaa cctactacca ctccagcccc   1800

aaggccccca accccagcac cgactatcgc atcacagcct ttgtcactgc gtcctgaagc   1860

cagccggcca gctgcagggg gggccgtcca cacaagggga ctcgactttg cgagtgataa   1920

gcccaccacc acccctgccc ctagacctcc aaccccagcc cctacaatcg ccagccagcc   1980

cctgagcctg aggcccgaag cctgtagacc tgccgctggc ggagccgtgc acaccagagg   2040

cctggatttc gcctgcgaca tctacatctg ggcccctctg gccggcacct gtggcgtgct   2100

gctgctgagc ctggtcatca ccctgtactg caaccaccgg aataagagag gccggaagaa   2160

actgctgtac atcttcaagc agcccttcat gcggcccgtg cagaccaccc aggaagagga   2220

cggctgcagc tgccggttcc ccgaggaaga ggaaggcggc tgcgaactgc gggtgaagtt   2280

cagccggagc gccgacgccc ctgcctacca gcagggccag aaccagctgt acaacgagct   2340

gaacctgggc cggagggagg agtacgacgt gctggacaag cggagaggcc gggaccctga   2400

gatgggcggc aagccccgga gaaagaaccc tcaggagggc ctgtataacg aactgcagaa   2460

agacaagatg gccgaggcct acagcgagat cggcatgaag ggcgagcggc ggaggggcaa   2520

gggccacgac ggcctgtacc agggcctgag caccgccacc aaggatacct acgacgccct   2580

gcacatgcag gccctgcccc ccagaagggc caagaggagt ggcagcggcg agggcagagg   2640

aagtcttcta acatgcggtg acgtggagga gaatcccggc cctatgaggc tccctgctca   2700

gctcctgggg ctgctaatgc tctgggtccc aggatccagt gggcgcaaag tgtgtaacgg   2760

aataggtatt ggtgaattta aagactcact ctccataaat gctacgaata ttaaacactt   2820

caaaaactgc acctccatca gtggcgatct ccacatcctg ccggtggcat ttaggggtga   2880

ctccttcaca catactcctc ctctggatcc acaggaactg gatattctga aaaccgtaaa   2940

ggaaatcaca gggtttttgc tgattcaggc ttggcctgaa aacaggacgg acctccatgc   3000

ctttgagaac ctagaaatca tacgcggcag gaccaagcaa catggtcagt tttctcttgc   3060

agtcgtcagc ctgaacataa catccttggg attacgctcc ctcaaggaga taagtgatgg   3120

agatgtgata atttcaggaa acaaaaattt gtgctatgca aatacaataa actggaaaaa   3180

actgtttggg acctccggtc agaaaaccaa aattataagc aacagaggtg aaaacagctg   3240

caaggccaca ggccaggtct gccatgcctt gtgctccccc gagggctgct ggggcccgga   3300

gcccagggac tgcgtctct                                                3319
```

<210> SEQ ID NO 133
<211> LENGTH: 4763
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="XON-59"

<400> SEQUENCE: 133

```
gagcgtgcgt gaggctccgg tgcccgtcag tgggcagagc gcacatcgcc cacagtcccc     60

gagaagttgg ggggaggggg tcggcgattg aaccggtgcc tagagaaggt ggcgcggggt    120
```

-continued

```
aaactgggaa agtgatgtcg tgtactggct ccgccttttt cccgagggtg ggggagaacc    180
gtatataagt gcagtagtcg ccgtgaacgt tctttttcgc aacgggtttg ccgccagaac    240
acagcagccg ctaaatccaa ggtaaggtca gaagagctag cgccaccatg ctgctgctgg    300
tgaccagcct gctgctgtgt gagctgcccc accccgcctt tctgctgatc cccgacatcc    360
agatgaccca gagccccagc agcctgtctg ccagcgtggg cgacagagtg accatcacct    420
gtatgaccag caccgacatc gacgacgaca tgaactggta tcagcagaag cccggcaaga    480
cccccaagct gctgatctac gagggcaaca ccctgaggcc tggcgtgccc agcagatttt    540
ctggcagcgg ctccggcacc gacttcatct tcaccatcag ctccctgcag cccgaggata    600
tcgccaccta ctactgcctg cagagctgga acgtgcccct gacctttggc ggaggcacca    660
aggtggaaat caagggcgga ggcggatctg gcggcggagg atctgggggga ggcggctctc    720
aggtgcagct gcaggaatct ggcggagggc tcgtgaagcc tggcggaagc ctgaagctga    780
gctgtgccgc cagcggcttc accttcagca agttcggcat gagctgggtg cgccagaccc    840
ccgacaagag actggaatgg gtggccagca tcagcaccgg cggctacaat acctactaca    900
gcgacaacgt gaagggccgg ttcaccatct cccgggacaa cgccaagaac accctgtacc    960
tgcagatgag cagcctgaag tccgaggaca ccgccatgta ctactgtgcc agaggctaca   1020
gcccctacag ctacgccatg gattactggg gccagggcac aatggtcacc gtgtcctcta   1080
agcctaccac cacccccgca cctcgtcctc caacccctgc acctacgatt gccagtcagc   1140
ctctttcact gcggcctgag gccagcagac cagctgccgg cggtgccgtc catacaagag   1200
gactggactt cgcgtccgat aaacctacta ccactccagc cccaaggccc ccaaccccag   1260
caccgactat cgcatcacag cctttgtcac tgcgtcctga agccagccgg ccagctgcag   1320
ggggggccgt ccacacaagg ggactcgact ttgcgagtga taagcccacc accacccctg   1380
cccctagacc tccaacccca gcccctacaa tcgccagcca gcccctgagc ctgaggcccg   1440
aagcctgtag acctgccgct ggcggagccg tgcacaccag aggcctggat ttcgcctgcg   1500
acatctacat ctgggcccct ctggccggca cctgtggcgt gctgctgctg agcctggtca   1560
tcaccctgta ctgcaaccac cggaataaga gaggccggaa gaaactgctg tacatcttca   1620
agcagccctt catgcggccc gtgcagacca cccaggaaga ggacggctgc agctgccggt   1680
tccccgagga agaggaaggc ggctgcgaac tgcgggtgaa gttcagccgg agcgccgacg   1740
cccctgccta ccagcagggc cagaaccagc tgtacaacga gctgaacctg ggccggaggg   1800
aggagtacga cgtgctggac aagcggagag gccgggaccc tgagatgggc ggcaagcccc   1860
ggagaaagaa ccctcaggag ggcctgtata acgaactgca gaaagacaag atggccgagg   1920
cctacagcga gatcggcatg aagggcgagc ggcggagggg caagggccac gacggcctgt   1980
accagggcct gagcaccgcc accaaggata cctacgacgc cctgcacatg caggccctgc   2040
cccccagaag agctaagagg ggaagcggag agggcagagg aagtctgcta acatgcggtg   2100
acgtcgagga gaatcctgga cctggcccca agaagaaaag gaaggtggcc ccccccaccg   2160
acgtgagcct gggcgacgag ctgcacctgg acggcgagga cgtggccatg gcccacgccg   2220
acgccctgga cgacttcgac ctggacatgc tgggcgacgg cgacagcccc ggccccggct   2280
tcacccccca cgacagcgcc ccctacggcg ccctggacat ggccgacttc gagttcgagc   2340
agatgttcac cgacgccctg ggcatcgacg agtacggcgg cgaattcgag atgcccgtgg   2400
acaggattct ggaggccgaa ctcgccgtgg agcagaaaag cgaccagggc gtggagggcc   2460
ccggcggaac cggcggcagc ggcagcagcc ccaacgaccc cgtgaccaac atctgccagg   2520
```

ccgccgacaa gcagctgttc accctggtgg agtgggccaa gaggattccc cacttcagca 2580
gcctgcccct ggacgaccag gtgatcctgc tgagggccgg atggaacgag ctgctgatcg 2640
ccagcttcag ccacaggagc atcgacgtga gggacggcat cctgctggcc accggcctgc 2700
acgtccatag gaacagcgcc cacagcgccg gagtgggcgc catcttcgac agggtgctga 2760
ccgagctggt gagcaagatg agggacatga ggatggacaa gaccgagctg ggctgcctga 2820
gggccatcat cctgttcaac cccgaggtga ggggcctgaa aagcgcccag gaggtggagc 2880
tgctgaggga gaaggtgtac gccgccctgg aggagtacac caggaccacc caccccgacg 2940
agcccggcag attcgccaag ctgctgctga ggctgcccag cctgaggagc atcggcctga 3000
agtgcctgga gcacctgttc ttcttcaggc tgatcggcga cgtgcccatc gacaccttcc 3060
tgatggagat gctggagagc cccagcgaca gcagagctaa gaggggaagc ggagagggca 3120
gaggaagtct gctaacatgc ggtgacgtcg aggagaatcc tggacctaag ctgctgagca 3180
gcatcgagca ggcttgcgac atctgcaggc tgaagaagct gaagtgcagc aaggagaagc 3240
ccaagtgcgc caagtgcctg aagaacaact gggagtgcag atacagcccc aagaccaaga 3300
ggagcccccct gaccagggcc cacctgaccg aggtggagag caggctggag aggctggagc 3360
agctgttcct gctgatcttc cccagggagg acctggacat gatcctgaag atggacagcc 3420
tgcaagacat caaggccctg ctgaccggcc tgttcgtgca ggacaacgtg aacaaggacg 3480
ccgtgaccga caggctggcc agcgtggaga ccgacatgcc cctgaccctg aggcagcaca 3540
ggatcagcgc caccagcagc agcgaggaga gcagcaacaa gggccagagg cagctgaccg 3600
tgagccccga gtttcccggg atcaggcccg agtgcgtggt gcccgagacc cagtgcgcca 3660
tgaaaaggaa ggagaagaag gcccagaagg agaaggacaa gctgcccgtg agcaccacca 3720
ccgtcgatga ccacatgccc cccatcatgc agtgcgagcc cccccccccc gaggccgcca 3780
ggattcacga ggtcgtgccc aggttcctga gcgacaagct gctggtgacc aacaggcaga 3840
agaacatccc ccagctgacc gccaaccagc agttcctgat cgccaggctg atctggtatc 3900
aggacggcta cgagcagccc agcgacgagg acctgaaaag gatcacccag acctggcagc 3960
aggccgacga cgagaacgag gagagcgaca ccccccttcag gcagatcacc gagatgacca 4020
tcctgaccgt gcagctgatc gtggagttcg ccaagggcct gcccggattc gccaagatca 4080
gccagcccga ccagatcacc ctgctgaagg cttgcagcag cgaggtgatg atgctgaggg 4140
tggccaggag gtacgacgcc gccagcgaca gcatcctgtt cgccaacaac caggcttaca 4200
ccagggacaa ctacaggaag gctggcatgg ccgaggtgat cgaggacctc ctgcacttct 4260
gcagatgtat gtacagcatg gccctggaca acatccacta cgccctgctg accgccgtgg 4320
tgatcttcag cgacaggccc ggcctggagc agccccagct ggtggaggag atccagaggt 4380
actacctgaa caccctgagg atctacatcc tgaaccagct gagcggcagc gccaggagca 4440
gcgtgatcta cggcaagatc ctgagcatcc tgagcgagct gaggaccctg ggaatgcaga 4500
acagcaatat gtgtatcagc ctgaagctga agaacaggaa gctgcccccc ttcctggagg 4560
agatttggga cgtggccgac atgagccaca cccagccccc ccccatcctg gagagcccca 4620
ccaacctgtg aaacttgttt attgcagctt ataatggtta caaataaagc aatagcatca 4680
caaatttcac aaataaagca tttttttcac tgcattctag ttgtggtttg tccaaactca 4740
tcaatgtatc ttatcatgtc tgg 4763

<210> SEQ ID NO 134

```
<211> LENGTH: 4785
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="XON-60"

<400> SEQUENCE: 134

gagcgtgcgt gaggctccgg tgcccgtcag tgggcagagc gcacatcgcc cacagtcccc     60

gagaagttgg ggggaggggg tcggcgattg aaccggtgcc tagagaaggt ggcgcggggt    120

aaactgggaa agtgatgtcg tgtactggct ccgccttttt cccgagggtg ggggagaacc    180

gtatataagt gcagtagtcg ccgtgaacgt tctttttcgc aacgggtttg ccgccagaac    240

acagcagccg ctaaatccaa ggtaaggtca gaagagctag cgccaccatg ctgctgctgg    300

tgaccagcct gctgctgtgt gagctgcccc accccgcctt tctgctgatc cccgacatcc    360

agatgaccca gagccccagc agcctgtctg ccagcgtggg cgacagagtg accatcacct    420

gtatgaccag caccgacatc gacgacgaca tgaactggta tcagcagaag cccggcaaga    480

cccccaagct gctgatctac gagggcaaca ccctgaggcc tggcgtgccc agcagatttt    540

ctggcagcgg ctccggcacc gacttcatct tcaccatcag ctccctgcag cccgaggata    600

tcgccaccta ctactgcctg cagagctgga acgtgcccct gacctttggc ggaggcacca    660

aggtggaaat caagggcgga ggcggatctg gcggcggagg atctggggga ggcggctctc    720

aggtgcagct gcaggaatct ggcggagggc tcgtgaagcc tggcggaagc ctgaagctga    780

gctgtgccgc cagcggcttc accttcagca agttcggcat gagctgggtg cgccagaccc    840

ccgacaagag actggaatgg gtggccagca tcagcaccgg cggctacaat acctactaca    900

gcgacaacgt gaagggccgg ttcaccatct cccgggacaa cgccaagaac accctgtacc    960

tgcagatgag cagcctgaag tccgaggaca ccgccatgta ctactgtgcc agaggctaca   1020

gcccctacag ctacgccatg gattactggg gccagggcac aatggtcacc gtgtcctcta   1080

agcctaccac cacccccgca cctcgtcctc caacccctgc acctacgatt gccagtcagc   1140

ctctttcact gcggcctgag gccagcagac cagctgccgg cggtgccgtc catacaagag   1200

gactggactt cgcgtccgat aaacctacta ccactccagc cccaaggccc ccaaccccag   1260

caccgactat cgcatcacag cctttgtcac tgcgtcctga agccagccgg ccagctgcag   1320

ggggggccgt ccacacaagg ggactcgact ttgcgagtga taagcccacc accacccctg   1380

cccctagacc tccaacccca gcccctacaa tcgccagcca gcccctgagc ctgaggcccg   1440

aagcctgtag acctgccgct ggcggagccg tgcacaccag aggcctggat ttcgcctgcg   1500

acatctacat ctgggcccct ctggccggca cctgtggcgt gctgctgctg agcctggtca   1560

tcaccctgta ctgcaaccac cggaataaga gaggccggaa gaaactgctg tacatcttca   1620

agcagccctt catgcggccc gtgcagacca cccaggaaga ggacggctgc agctgccggt   1680

tccccgagga agaggaaggc ggctgcgaac tgcgggtgaa gttcagccgg agcgccgacg   1740

cccctgccta ccagcagggc cagaaccagc tgtacaacga gctgaacctg ggccggaggg   1800

aggagtacga cgtgctggac aagcggagag gccgggaccc tgagatgggc ggcaagcccc   1860

ggagaaagaa ccctcaggag ggcctgtata acgaactgca gaaagacaag atggccgagg   1920

cctacagcga gatcggcatg aagggcgagc ggcggagggg caagggccac gacggcctgt   1980
```

-continued

```
accagggcct gagcaccgcc accaaggata cctacgacgc cctgcacatg caggccctgc   2040
cccccagaag agctaagagg ggaagcggag agggcagagg aagtctgcta acatgcggtg   2100
acgtcgagga gaatcctgga cctggcccca agaagaaaag gaaggtggcc ccccccaccg   2160
acgtgagcct gggcgacgag ctgcacctgg acggcgagga cgtggccatg gcccacgccg   2220
acgccctgga cgacttcgac ctggacatgc tgggcgacgg cgacagcccc ggccccggct   2280
tcacccccca cgacagcgcc ccctacggcg ccctggacat ggccgacttc gagttcgagc   2340
agatgttcac cgacgccctg ggcatcgacg agtacggcgg cgaattcgag atgcccgtgg   2400
acaggattct ggaggccgaa ctcgccgtgg agcagaaaag cgaccagggc gtggagggcc   2460
ccggcggaac cggcggcagc ggcagcagcc ccaacgaccc cgtgaccaac atctgccagg   2520
ccgccgacaa gcagctgttc accctggtgg agtgggccaa gaggattccc cacttcagca   2580
gcctgcccct ggacgaccag gtgatcctgc tgagggccgg atggaacgag ctgctgatcg   2640
ccagcttcag ccacaggagc atcgacgtga gggacggcat cctgctggcc accggcctgc   2700
acgtccatag gaacagcgcc cacagcgccg gagtgggcgc catcttcgac agggtgctga   2760
ccgagctggt gagcaagatg agggacatga ggatggacaa gaccgagctg ggctgcctga   2820
gggccatcat cctgttcaac cccgaggtga ggggcctgaa aagcgcccag gaggtggagc   2880
tgctgaggga gaaggtgtac gccgccctgg aggagtacac caggaccacc caccccgacg   2940
agcccggcag attcgccaag ctgctgctga ggctgcccag cctgaggagc atcggcctga   3000
agtgcctgga gcacctgttc ttcttcaggc tgatcggcga cgtgcccatc gacaccttcc   3060
tgatggagat gctggagagc cccagcgaca gctgagcatg cactagtttt ataatttctt   3120
cttccagaat ttctgacatt ttataatttc ttcttccaga agactcacaa cctccatatg   3180
gccaccatga agctgctgag cagcatcgag caggcttgcg acatctgcag gctgaagaag   3240
ctgaagtgca gcaaggagaa gcccaagtgc gccaagtgcc tgaagaacaa ctgggagtgc   3300
agatacagcc ccaagaccaa gaggagcccc ctgaccaggg cccacctgac cgaggtggag   3360
agcaggctgg agaggctgga gcagctgttc ctgctgatct tccccaggga ggacctggac   3420
atgatcctga agatggacag cctgcaagac atcaaggccc tgctgaccgg cctgttcgtg   3480
caggacaacg tgaacaagga cgccgtgacc gacaggctgg ccagcgtgga gaccgacatg   3540
cccctgaccc tgaggcagca caggatcagc gccaccagca gcagcgagga gagcagcaac   3600
aagggccaga ggcagctgac cgtgagcccc gagtttcccg ggatcaggcc cgagtgcgtg   3660
gtgcccgaga cccagtgcgc catgaaaagg aaggagaaga aggcccagaa ggagaaggac   3720
aagctgcccg tgagcaccac caccgtcgat gaccacatgc cccccatcat gcagtgcgag   3780
cccccccccc ccgaggccgc caggattcac gaggtcgtgc ccaggttcct gagcgacaag   3840
ctgctggtga ccaacaggca gaagaacatc ccccagctga ccgccaacca gcagttcctg   3900
atcgccaggc tgatctggta tcaggacggc tacgagcagc ccagcgacga ggacctgaaa   3960
aggatcaccc agacctggca gcaggccgac gacgagaacg aggagagcga cacccccttc   4020
aggcagatca ccgagatgac catcctgacc gtgcagctga tcgtggagtt cgccaagggc   4080
ctgcccggat tcgccaagat cagccagccc gaccagatca ccctgctgaa ggcttgcagc   4140
agcgaggtga tgatgctgag ggtggccagg aggtacgacg ccgccagcga cagcatcctg   4200
ttcgccaaca accaggctta caccagggac aactacagga aggctggcat ggccgaggtg   4260
atcgaggacc tcctgcactt ctgcagatgt atgtacagca tggccctgga caacatccac   4320
tacgccctgc tgaccgccgt ggtgatcttc agcgacaggc ccggcctgga gcagccccag   4380
```

```
ctggtggagg agatccagag gtactacctg aacaccctga ggatctacat cctgaaccag   4440

ctgagcggca gcgccaggag cagcgtgatc tacggcaaga tcctgagcat cctgagcgag   4500

ctgaggaccc tgggaatgca gaacagcaat atgtgtatca gcctgaagct gaagaacagg   4560

aagctgcccc ccttcctgga ggagatttgg gacgtggccg acatgagcca cacccagccc   4620

ccccccatcc tggagagccc caccaacctg tgaaacttgt ttattgcagc ttataatggt   4680

tacaaataaa gcaatagcat cacaaatttc acaaataaag catttttttc actgcattct   4740

agttgtggtt tgtccaaact catcaatgta tcttatcatg tctgg                   4785


<210> SEQ ID NO 135
<211> LENGTH: 2009
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="XON-61"

<400> SEQUENCE: 135

attgttcgga gcagtgcggc gcgtttagcg gagtactgtc ctccgatatt aatcggggca     60

gactattccg gggtttaccg gcgcactctc gcccgaactt caccggcggt ctttcgtccg    120

tgctttatcg gggcggatca ctccgaaccc cgggaggtct atataagcag agctcgttta    180

gtgaaccctc attctggaga cggatcccga gccgagtgtt ttgacctcca tagaacagcc    240

gctaaatcca aggtaaggtc agaagagcta gcgccaccat gtgtcaccag cagttggtca    300

tctcttggtt cagcctggtt tttctggcat ctcccctcgt ggccatctgg gaactgaaga    360

aagatgttta tgtcgtagaa ttggattggt atcccgacgc ccctggagaa atggtggtcc    420

tgacatgtga cacccctgaa gaagatggta tcacctggac cttggaccag agcagtgagg    480

tcttaggctc tggcaagacc ctgaccatcc aagtcaaaga gtttggagat gctggccagt    540

acacctgtca caaaggaggc gaggttctaa gccattcgct cctgctgctt cacaaaaagg    600

aagatggaat ttggtccact gacattctga aggaccagaa agaacccaag aataagacct    660

ttctaagatg cgaggccaag aattattctg gacgtttcac ctgctggtgg ctgacgacaa    720

tcagtactga tttgacattc agtgtcaaaa gcagcagagg ctcttctgac ccccaagggg    780

tgacgtgcgg agctgctaca ctcagcgccg agagagtcag aggggacaac aaggagtatg    840

agtactcagt ggagtgccag gaggacagtg cctgcccagc tgctgaggag agtctgccca    900

ttgaggtcat ggtggatgcc gttcacaagc tcaagtatga aaactacacc agcagcttct    960

tcatcaggga catcatcaaa cctgacccac ccaagaactt gcagctgaag cccctgaaga   1020

acagcagaca ggtggaggtc agctgggagt accctgacac ctggagtact ccacattcct   1080

acttctccct gacattctgc gttcaggtcc agggcaagag caagagagaa aagaaagata   1140

gagtcttcac ggacaagacc tcagccacgg tcatctgccg caaaaatgcc agcattagcg   1200

tgcgggccca ggaccgctac tatagctcat cttggagcga atgggcatct gtgccctgct   1260

ccggtggcgg tggcggcgga tctagaaacc tccccgtggc cactccagac ccaggaatgt   1320

tcccatgcct tcaccacagc cagaacctgc tgagggccgt cagcaacatg ctccagaagg   1380

ccagacaaac tctagaattt tacccttgca cttctgaaga gattgatcat gaagatatca   1440

caaaagataa aaccagcaca gtggaggcct gtttaccatt ggaattaacc aagaatgaga   1500
```

```
gttgcctaaa ttccagagag acctctttca taactaatgg gagttgcctg gcctccagaa   1560

agacctcttt tatgatggcc ctgtgcctta gtagtattta tgaagacttg aagatgtacc   1620

aggtggagtt caagaccatg aatgcaaagc tgctgatgga ccccaagagg cagatctttc   1680

tagatcaaaa catgctggca gttattgatg agctgatgca ggccctgaat ttcaacagtg   1740

agactgtgcc acaaaaatcc tcccttgaag aaccggattt ttataaaact aaaatcaagc   1800

tctgcatact tcttcatgct ttcagaatca gagcagtgac tattgataga gtgatgagct   1860

atctgaatgc ttcctaaaac ttgtttattg cagcttataa tggttacaaa taaagcaata   1920

gcatcacaaa tttcacaaat aaagcatttt tttcactgca ttctagttgt ggtttgtcca   1980

aactcatcaa tgtatcttat catgtctgg                                      2009
```

<210> SEQ ID NO 136
<211> LENGTH: 2873
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="XON-62"

<400> SEQUENCE: 136

```
attgttcgga gcagtgcggc gcgtttagcg gagtactgtc ctccgatatt aatcggggca     60

gactattccg gggtttaccg gcgcactctc gcccgaactt caccggcggt ctttcgtccg    120

tgctttatcg ggcggatca ctccgaaccc cgggaggtct atataagcag agctcgttta     180

gtgaaccctc attctggaga cggatcccga gccgagtgtt ttgacctcca tagaacagcc    240

gctaaatcca aggtaaggtc agaagagcta gcgccaccat gtgtcaccag cagttggtca    300

tctcttggtt cagcctggtt tttctggcat ctcccctcgt ggccatctgg gaactgaaga    360

aagatgttta tgtcgtagaa ttggattggt atcccgacgc ccctggagaa atggtggtcc    420

tgacatgtga cacccctgaa gaagatggta tcacctggac cttggaccag agcagtgagg    480

tcttaggctc tggcaagacc ctgaccatcc aagtcaaaga gtttggagat gctggccagt    540

acacctgtca caaaggaggc gaggttctaa gccattcgct cctgctgctt cacaaaaagg    600

aagatggaat ttggtccact gacattctga aggaccagaa agaacccaag aataagacct    660

ttctaagatg cgaggccaag aattattctg gacgtttcac ctgctggtgg ctgacgacaa    720

tcagtactga tttgacattc agtgtcaaaa gcagcagagg ctcttctgac ccccaagggg    780

tgacgtgcgg agctgctaca ctcagcgccg agagagtcag aggggacaac aaggagtatg    840

agtactcagt ggagtgccag gaggacagtg cctgcccagc tgctgaggag agtctgccca    900

ttgaggtcat ggtggatgcc gttcacaagc tcaagtatga aaactacacc agcagcttct    960

tcatcaggga catcatcaaa cctgacccac ccaagaactt gcagctgaag cccctgaaga   1020

acagcagaca ggtggaggtc agctgggagt accctgacac ctggagtact ccacattcct   1080

acttctccct gacattctgc gttcaggtcc agggcaagag caagagagaa aagaaagata   1140

gagtcttcac ggacaagacc tcagccacgg tcatctgccg caaaaatgcc agcattagcg   1200

tgcgggccca ggaccgctac tatagctcat cttggagcga atgggcatct gtgccctgct   1260

ccggtggcgg tggcggcgga tctagaaacc tccccgtggc cactccagac ccaggaatgt   1320

tcccatgcct tcaccacagc cagaacctgc tgagggccgt cagcaacatg ctccagaagg   1380
```

ccagacaaac tctagaattt taccccttgca cttctgaaga gattgatcat gaagatatca 1440
caaaagataa aaccagcaca gtggaggcct gtttaccatt ggaattaacc aagaatgaga 1500
gttgcctaaa ttccagagag acctctttca taactaatgg gagttgcctg gcctccagaa 1560
agacctcttt tatgatggcc ctgtgcctta gtagtattta tgaagacttg aagatgtacc 1620
aggtggagtt caagaccatg aatgcaaagc tgctgatgga ccccaagagg cagatctttc 1680
tagatcaaaa catgctggca gttattgatg agctgatgca ggccctgaat ttcaacagtg 1740
agactgtgcc acaaaaatcc tcccttgaag aaccggattt ttataaaact aaaatcaagc 1800
tctgcatact tcttcatgct ttcagaatca gagcagtgac tattgataga gtgatgagct 1860
atctgaatgc ttccagagct aagaggggaa gcggagaggg cagaggaagt ctgctaacat 1920
gcggtgacgt cgaggagaat cctggaccta ggctccctgc tcagctcctg ggctgctaa 1980 tgctctgggt cccaggatcc agtgggcgca aagtgtgtaa cggaataggt attggtgaat 2040
ttaaagactc actctccata aatgctacga atattaaaca cttcaaaaac tgcacctcca 2100
tcagtggcga tctccacatc ctgccggtgg catttagggg tgactccttc acacatactc 2160
ctcctctgga tccacaggaa ctggatattc tgaaaaccgt aaaggaaatc acagggtttt 2220
tgctgattca ggcttggcct gaaaacagga cggacctcca tgcctttgag aacctagaaa 2280
tcatacgcgg caggaccaag caacatggtc agttttctct tgcagtcgtc agcctgaaca 2340
taacatcctt gggattacgc tccctcaagg agataagtga tggagatgtg ataatttcag 2400
gaaacaaaaa tttgtgctat gcaaatacaa taaactggaa aaaactgttt gggacctccg 2460
gtcagaaaac caaaattata agcaacagag gtgaaaacag ctgcaaggcc acaggccagg 2520
tctgccatgc cttgtgctcc cccgagggct gctggggccc ggagcccagg gactgcgtct 2580
ctggtggcgg tggctcgggc ggtggtgggt cgggtggcgg cggatctggt ggcggtggct 2640
cgttttgggt gctggtggtg gttggtggag tcctggcttg ctatagcttg ctagtaacag 2700
tggcctttat tattttctgg gtgaggagta agaggagcta aaacttgttt attgcagctt 2760
ataatggtta caaataaagc aatagcatca caaatttcac aaataaagca ttttttcac 2820 tgcattctag ttgtggtttg tccaaactca tcaatgtatc ttatcatgtc tgg 2873

<210> SEQ ID NO 137
<211> LENGTH: 3532
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="FLC-2B12/13-2"

<400> SEQUENCE: 137
attgttcgga gcagtgcggc gcgtttagcg gagtactgtc ctccgatatt aatcggggca 60
gactattccg ggtttaccg gcgcactctc gcccgaactt caccggcggt ctttcgtccg 120
tgctttatcg gggcggatca ctccgaaccc cgggaggtct atataagcag agctcgttta 180
gtgaaccctc attctggaga cggatcccga gccgagtgtt ttgacctcca tagaacagcc 240
gctaaatcca aggtaaggtc agaagagcta gcgccaccat ggattggacc tggattctgt 300
ttctggtggc cgctgccaca agagtgcaca gcaactgggt gaatgtgatc agcgacctga 360
agaagatcga ggatctgatc cagagcatgc acattgatgc caccctgtac acagaatctg 420
atgtgcaccc tagctgtaaa gtgaccgcca tgaagtgttt tctgctggag ctgcaggtga 480
tttctctgga aagcggagat gcctctatcc acgacacagt ggagaatctg atcatcctgg 540
ccaacaatag cctgagcagc aatggcaatg tgacagagtc tggctgtaag gagtgtgagg 600
agctggagga gaagaacatc aaggagtttc tgcagagctt tgtgcacatc gtgcagatgt 660
tcatcaatac aagctctggc ggaggatctg gaggaggcgg atctggagga ggaggcagtg 720
gaggcggagg atctggcgga ggatctctgc agattacatg ccctcctcca atgtctgtgg 780
agcacgccga tatttgggtg aagtcctaca gcctgtacag cagagagaga tacatctgca 840
acagcggctt taagagaaag gccggcacct cttctctgac agagtgcgtg ctgaataagg 900
ccacaaatgt ggcccactgg acaacaccta gcctgaagtg cattagagat cctgccctgg 960
tccaccagag gcctgcccct ccatctacag tgacaacagc cggagtgaca cctcagcctg 1020
aatctctgag cccttctgga aaagaacctg ccgccagctc tcctagctct aataataccg 1080
ccgccacaac agccgccatt gtgcctggat ctcagctgat gcctagcaag tctcctagca 1140
caggcacaac agagatcagc agccacgaat cttctcacgg aacaccttct cagaccaccg 1200
ccaagaattg ggagctgaca gcctctgcct ctcaccagcc tccaggagtg tatcctcagg 1260
gccactctga tacaacagtg gccatcagca catctacagt gctgctgtgt ggactgtctg 1320
ccgtgtctct gctggcctgt tacctgaagt ctagacagac acctcctctg gcctctgtgg 1380
agatggaggc catggaagcc ctgcctgtga catggggaac aagcagcaga gatgaggacc 1440
tggagaattg ttctcaccac ctgtgaaact tgtttattgc agcttataat ggttacaaat 1500
aaagcaatag catcacaaat ttcacaaata aagcattttt ttcactgcat tctagttgtg 1560
gtttgtccaa actcatcaat gtatcttatc atgtctggga gcgtgcgtga ggctccggtg 1620
cccgtcagtg ggcagagcgc acatcgccca cagtccccga gaagttgggg ggaggggtc 1680
ggcgattgaa ccggtgccta gagaaggtgg cgcggggtaa actgggaaag tgatgtcgtg 1740
tactggctcc gcctttttcc cgagggtggg ggagaaccgt atataagtgc agtagtcgcc 1800
gtgaacgttc tttttcgcaa cgggtttgcc gccagaacac agcagccgct aaatccaagg 1860
taaggtcaga agagctagcg ccaccatgaa gctgctgagc agcatcgagc aggcttgcga 1920
catctgcagg ctgaagaagc tgaagtgcag caaggagaag cccaagtgcg ccaagtgcct 1980
gaagaacaac tgggagtgca gatacagccc caagaccaag aggagccccc tgaccagggc 2040
ccacctgacc gaggtggaga gcaggctgga gaggctggag cagctgttcc tgctgatctt 2100
ccccagggag gacctggaca tgatcctgaa gatggacagc ctgcaagaca tcaaggccct 2160
gctgaccggc ctgttcgtgc aggacaacgt gaacaaggac gccgtgaccg acaggctggc 2220
cagcgtggag accgacatgc ccctgaccct gaggcagcac aggatcagcg ccaccagcag 2280
cagcgaggag agcagcaaca agggccagag gcagctgacc gtgagccccg agtttcccgg 2340
gatcaggccc gagtgcgtgg tgcccgagac ccagtgcgcc atgaaaagga aggagaagaa 2400
ggcccagaag gagaaggaca agctgcccgt gagcaccacc accgtcgatg accacatgcc 2460
ccccatcatg cagtgcgagc cccccccccc cgaggccgcc aggattcacg aggtcgtgcc 2520
caggttcctg agcgacaagc tgctggtgac caacaggcag aagaacatcc cccagctgac 2580
cgccaaccag cagttcctga tcgccaggct gatctggtat caggacggct acgagcagcc 2640
cagcgacgag gacctgaaaa ggatcaccca gacctggcag caggccgacg acgagaacga 2700
ggagagcgac accccccttca ggcagatcac cgagatgacc atcctgaccg tgcagctgat 2760

-continued cgtggagttc gccaagggcc tgcccggatt cgccaagatc agccagcccg accagatcac 2820
cctgctgaag gcttgcagca gcgaggtgat gatgctgagg gtggccagga ggtacgacgc 2880
cgccagcgac agcatcctgt tcgccaacaa ccaggcttac accagggaca actacaggaa 2940
ggctggcatg gccgaggtga tcgaggacct cctgcacttc tgcagatgta tgtacagcat 3000
ggccctggac aacatccact acgccctgct gaccgccgtg gtgatcttca gcgacaggcc 3060
cggcctggag cagccccagc tggtggagga gatccagagg tactacctga acaccctgag 3120
gatctacatc ctgaaccagc tgagcggcag cgccaggagc agcgtgatct acggcaagat 3180
cctgagcatc ctgagcgagc tgaggaccct gggaatgcag aacagcaata tgtgtatcag 3240
cctgaagctg aagaacagga agctgccccc cttcctggag gagatttggg acgtggccga 3300
catgagccac acccagcccc cccccatcct ggagagcccc accaacctgt gatgatgggt 3360
ggcatccctg tgacccctcc ccagtgcctc tcctggccct ggaagttgcc actccagtgc 3420
ccaccagcct tgtcctaata aaattaagtt gcatcatttt gtctgactag gtgtccttct 3480
ataatattat ggggtggagg ggggtggtat ggagcaaggg gcaagttggg aa 3532

<210> SEQ ID NO 138
<211> LENGTH: 4423
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="XON-02"

<400> SEQUENCE: 138
attgttcgga gcagtgcggc gcgtttagcg gagtactgtc ctccgatatt aatcggggca 60
gactattccg ggtttaccg gcgcactctc gcccgaactt caccggcggt ctttcgtccg 120
tgctttatcg gggcggatca ctccgaaccc cgggaggtct atataagcag agctcgttta 180
gtgaaccctc attctggaga cggatcccga gccgagtgtt ttgacctcca tagaacagcc 240
gctaaatcca aggtaaggtc agaagagcta gcgccaccat ggattggacc tggattctgt 300
ttctggtggc cgctgccaca agagtgcaca gcaactgggt gaatgtgatc agcgacctga 360
agaagatcga ggatctgatc cagagcatgc acattgatgc caccctgtac acagaatctg 420
atgtgcaccc tagctgtaaa gtgaccgcca tgaagtgttt tctgctggag ctgcaggtga 480
tttctctgga aagcggagat gcctctatcc acgacacagt ggagaatctg atcatcctgg 540
ccaacaatag cctgagcagc aatggcaatg tgacagagtc tggctgtaag gagtgtgagg 600
agctggagga gaagaacatc aaggagtttc tgcagagctt tgtgcacatc gtgcagatgt 660
tcatcaatac aagctctggc ggaggatctg gaggaggcgg atctggagga ggaggcagtg 720
gaggcggagg atctggcgga ggatctctgc agattacatg ccctcctcca atgtctgtgg 780
agcacgccga tatttgggtg aagtcctaca gcctgtacag cagagagaga tacatctgca 840
acagcggctt taagagaaag gccggcacct cttctctgac agagtgcgtg ctgaataagg 900
ccacaaatgt ggcccactgg acaacaccta gcctgaagtg cattagagat cctgccctgg 960
tccaccagag gcctgcccct ccatctacag tgacaacagc cggagtgaca cctcagcctg 1020
aatctctgag cccttctgga aaagaacctg ccgccagctc tcctagctct aataataccg 1080
ccgccacaac agccgccatt gtgcctggat ctcagctgat gcctagcaag tctcctagca 1140

-continued

```
caggcacaac agagatcagc agccacgaat cttctcacgg aacaccttct cagaccaccg   1200
ccaagaattg ggagctgaca gcctctgcct ctcaccagcc tccaggagtg tatcctcagg   1260
gccactctga tacaacagtg gccatcagca catctacagt gctgctgtgt ggactgtctg   1320
ccgtgtctct gctggcctgt tacctgaagt ctagacagac acctcctctg gcctctgtgg   1380
agatggaggc catggaagcc ctgcctgtga catggggaac aagcagcaga gatgaggacc   1440
tggagaattg ttctcaccac ctgtgaaact tgtttattgc agcttataat ggttacaaat   1500
aaagcaatag catcacaaat ttcacaaata aagcattttt ttcactgcat tctagttgtg   1560
gtttgtccaa actcatcaat gtatcttatc atgtctggga gcgtgcgtga ggctccggtg   1620
cccgtcagtg ggcagagcgc acatcgccca cagtccccga gaagttgggg ggaggggtc    1680
ggcgattgaa ccggtgccta gagaaggtgg cgcggggtaa actgggaaag tgatgtcgtg   1740
tactggctcc gcctttttcc cgagggtggg ggagaaccgt atataagtgc agtagtcgcc   1800
gtgaacgttc tttttcgcaa cgggtttgcc gccagaacac agcagccgct aaatccaagg   1860
taaggtcaga agagctagcg ccaccatgct gctgctggtg accagcctgc tgctgtgtga   1920
gctgccccac cccgcctttc tgctgatccc cgacatccag atgacccaga ccacctccag   1980
cctgagcgcc agcctgggcg accgggtgac catcagctgc cgggccagcc aggacatcag   2040
caagtacctg aactggtatc agcagaagcc cgacggcacc gtcaagctgc tgatctacca   2100
caccagccgg ctgcacagcg gcgtgcccag ccggtttagc ggcagcggct ccggcaccga   2160
ctacagcctg accatctcca acctggagca ggaggacatc gccacctact tttgccagca   2220
gggcaacaca ctgccctaca cctttggcgg cggaacaaag ctggagatca ccggcagcac   2280
ctccggcagc ggcaagcctg gcagcggcga gggcagcacc aagggcgagg tgaagctgca   2340
ggagagcggc cctggcctgg tggcccccag ccagagcctg agcgtgacct gtaccgtgtc   2400
cggcgtgtcc ctgcccgact acggcgtgtc ctggatccgg cagcccccta ggaagggcct   2460
ggagtggctg ggcgtgatct ggggcagcga gaccacctac tacaacagcg ccctgaagag   2520
ccggctgacc atcatcaagg acaacagcaa gagccaggtg ttcctgaaga tgaacagcct   2580
gcagaccgac gacaccgcca tctactactg tgccaagcac tactactacg gcggcagcta   2640
cgccatggac tactggggcc agggcaccag cgtgaccgtg tccagcaagc ccaccaccac   2700
ccctgcccct agacctccaa ccccagcccc tacaatcgcc agccagcccc tgagcctgag   2760
gcccgaagcc tgtagacctg ccgctggcgg agccgtgcac accagaggcc tggatttcgc   2820
ctgcgacatc tacatctggg cccctctggc cggcacctgt ggcgtgctgc tgctgagcct   2880
ggtcatcacc ctgtactgca accaccggaa taggagcaag cggagcagag gcggccacag   2940
cgactacatg aacatgaccc cccggaggcc tggccccacc cggaagcact accagcccta   3000
cgcccctccc agggacttcg ccgcctaccg gagccgggtg aagttcagcc ggagcgccga   3060
cgcccctgcc taccagcagg gccagaacca gctgtacaac gagctgaacc tgggccggag   3120
ggaggagtac gacgtgctgg acaagcggag aggccgggac cctgagatgg gcggcaagcc   3180
ccggagaaag aaccctcagg agggcctgta taacgaactg cagaaagaca agatggccga   3240
ggcctacagc gagatcggca tgaagggcga gcggcggagg ggcaagggcc acgacggcct   3300
gtaccagggc ctgagcaccg ccaccaagga tacctacgac gccctgcaca tgcaggccct   3360
gccccccaga agggccaaga ggagtggcag cggcgagggc agaggaagtc ttctaacatg   3420
cggtgacgtg gaggagaatc ccggccctat gaggctccct gctcagctcc tggggctgct   3480
aatgctctgg gtcccaggat ccagtgggcg caaagtgtgt aacggaatag gtattggtga   3540
```

```
atttaaagac tcactctcca taaatgctac gaatattaaa cacttcaaaa actgcacctc   3600

catcagtggc gatctccaca tcctgccggt ggcatttagg ggtgactcct tcacacatac   3660

tcctcctctg gatccacagg aactggatat tctgaaaacc gtaaaggaaa tcacagggtt   3720

tttgctgatt caggcttggc ctgaaaacag gacggacctc catgcctttg agaacctaga   3780

aatcatacgc ggcaggacca agcaacatgg tcagttttct cttgcagtcg tcagcctgaa   3840

cataacatcc ttgggattac gctccctcaa ggagataagt gatggagatg tgataatttc   3900

aggaaacaaa aatttgtgct atgcaaatac aataaactgg aaaaaactgt ttgggacctc   3960

cggtcagaaa accaaaatta taagcaacag aggtgaaaac agctgcaagg ccacaggcca   4020

ggtctgccat gccttgtgct cccccgaggg ctgctggggc ccggagccca gggactgcgt   4080

ctctggtggc ggtggctcgg gcggtggtgg gtcgggtggc ggcggatctg gtggcggtgg   4140

ctcgttttgg gtgctggtgg tggttggtgg agtcctggct tgctatagct tgctagtaac   4200

agtggccttt attattttct gggtgaggag taagaggagc taatgatggg tggcatccct   4260

gtgacccctc cccagtgcct ctcctggccc tggaagttgc cactccagtg cccaccagcc   4320

ttgtcctaat aaaattaagt tgcatcattt tgtctgacta ggtgtccttc tataatatta   4380

tggggtggag gggggtggta tggagcaagg ggcaagttgg gaa                     4423


<210> SEQ ID NO 139
<211> LENGTH: 4423
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="XON-02(h)"

<400> SEQUENCE: 139

gagcgtgcgt gaggctccgg tgcccgtcag tgggcagagc gcacatcgcc cacagtcccc     60

gagaagttgg ggggaggggg tcggcgattg aaccggtgcc tagagaaggt ggcgcggggt    120

aaactgggaa agtgatgtcg tgtactggct ccgccttttt cccgagggtg ggggagaacc    180

gtatataagt gcagtagtcg ccgtgaacgt tctttttcgc aacgggtttg ccgccagaac    240

acagcagccg ctaaatccaa ggtaaggtca gaagagctag cgccaccatg ctgctgctgg    300

tgaccagcct gctgctgtgt gagctgcccc accccgcctt tctgctgatc cccgacatcc    360

agatgaccca gaccacctcc agcctgagcg ccagcctggg cgaccgggtg accatcagct    420

gccgggccag ccaggacatc agcaagtacc tgaactggta tcagcagaag cccgacggca    480

ccgtcaagct gctgatctac cacaccagcc ggctgcacag cggcgtgccc agccggttta    540

gcggcagcgg ctccggcacc gactacagcc tgaccatctc caacctggag caggaggaca    600

tcgccaccta cttttgccag cagggcaaca cactgcccta cacctttggc ggcggaacaa    660

agctggagat caccggcagc acctccggca gcggcaagcc tggcagcggc gagggcagca    720

ccaagggcga ggtgaagctg caggagagcg gccctggcct ggtggccccc agccagagcc    780

tgagcgtgac ctgtaccgtg tccggcgtgt ccctgcccga ctacggcgtg tcctggatcc    840

ggcagccccc taggaagggc ctggagtggc tgggcgtgat ctggggcagc gagaccacct    900

actacaacag cgccctgaag agccggctga ccatcatcaa ggacaacagc aagagccagg    960

tgttcctgaa gatgaacagc ctgcagaccg acgacaccgc catctactac tgtgccaagc   1020
```

```
actactacta cggcggcagc tacgccatgg actactgggg ccagggcacc agcgtgaccg   1080
tgtccagcaa gcccaccacc acccctgccc ctagacctcc aaccccagcc cctacaatcg   1140
ccagccagcc cctgagcctg aggcccgaag cctgtagacc tgccgctggc ggagccgtgc   1200
acaccagagg cctggatttc gcctgcgaca tctacatctg ggcccctctg gccggcacct   1260
gtggcgtgct gctgctgagc ctggtcatca ccctgtactg caaccaccgg aataggagca   1320
agcggagcag aggcggccac agcgactaca tgaacatgac cccccggagg cctggcccca   1380
cccggaagca ctaccagccc tacgcccctc ccagggactt cgccgcctac cggagccggg   1440
tgaagttcag ccggagcgcc gacgcccctg cctaccagca gggccagaac cagctgtaca   1500
acgagctgaa cctgggccgg agggaggagt acgacgtgct ggacaagcgg agaggccggg   1560
accctgagat gggcggcaag ccccggagaa agaaccctca ggagggcctg tataacgaac   1620
tgcagaaaga caagatggcc gaggcctaca gcgagatcgg catgaagggc gagcggcgga   1680
ggggcaaggg ccacgacggc ctgtaccagg gcctgagcac cgccaccaag gatacctacg   1740
acgccctgca catgcaggcc ctgcccccca gaagggccaa gaggagtggc agcggcgagg   1800
gcagaggaag tcttctaaca tgcggtgacg tggaggagaa tcccggccct atgaggctcc   1860
ctgctcagct cctggggctg ctaatgctct gggtcccagg atccagtggg cgcaaagtgt   1920
gtaacggaat aggtattggt gaatttaaag actcactctc cataaatgct acgaatatta   1980
aacacttcaa aaactgcacc tccatcagtg gcgatctcca catcctgccg gtggcattta   2040
ggggtgactc cttcacacat actcctcctc tggatccaca ggaactggat attctgaaaa   2100
ccgtaaagga aatcacaggg tttttgctga ttcaggcttg gcctgaaaac aggacggacc   2160
tccatgcctt tgagaaccta gaaatcatac gcggcaggac caagcaacat ggtcagtttt   2220
ctcttgcagt cgtcagcctg aacataacat ccttgggatt acgctccctc aaggagataa   2280
gtgatggaga tgtgataatt tcaggaaaca aaaatttgtg ctatgcaaat acaataaact   2340
ggaaaaaact gtttgggacc tccggtcaga aaaccaaaat tataagcaac agaggtgaaa   2400
acagctgcaa ggccacaggc caggtctgcc atgccttgtg ctcccccgag ggctgctggg   2460
gcccggagcc cagggactgc gtctctggtg gcggtggctc gggcggtggt gggtcgggtg   2520
gcggcggatc tggtggcggt ggctcgtttt gggtgctggt ggtggttggt ggagtcctgg   2580
cttgctatag cttgctagta acagtggcct ttattatttt ctgggtgagg agtaagagga   2640
gctaatgatg ggtggcatcc ctgtgacccc tccccagtgc ctctcctggc cctggaagtt   2700
gccactccag tgcccaccag ccttgtccta ataaaattaa gttgcatcat tttgtctgac   2760
taggtgtcct tctataatat tatggggtgg aggggggtgg tatggagcaa ggggcaagtt   2820
gggaaattgt tcggagcagt gcggcgcgtt tagcggagta ctgtcctccg atattaatcg   2880
gggcagacta ttccggggtt taccggcgca ctctcgcccg aacttcaccg gcggtctttc   2940
gtccgtgctt tatcggggcg gatcactccg aaccccggga ggtctatata agcagagctc   3000
gtttagtgaa ccctcattct ggagacggat cccgagccga gtgttttgac ctccatagaa   3060
cagccgctaa atccaaggta aggtcagaag agctagcgcc accatggatt ggacctggat   3120
tctgtttctg gtggccgctg ccacaagagt gcacagcaac tgggtgaatg tgatcagcga   3180
cctgaagaag atcgaggatc tgatccagag catgcacatt gatgccaccc tgtacacaga   3240
atctgatgtg caccctagct gtaaagtgac cgccatgaag tgttttctgc tggagctgca   3300
ggtgatttct ctggaaagcg gagatgcctc tatccacgac acagtggaga atctgatcat   3360
```

```
cctggccaac aatagcctga gcagcaatgg caatgtgaca gagtctggct gtaaggagtg   3420

tgaggagctg gaggagaaga acatcaagga gtttctgcag agctttgtgc acatcgtgca   3480

gatgttcatc aatacaagct ctggcggagg atctggagga ggcggatctg gaggaggagg   3540

cagtggaggc ggaggatctg gcggaggatc tctgcagatt acatgccctc ctccaatgtc   3600

tgtggagcac gccgatattt gggtgaagtc ctacagcctg tacagcagag agagatacat   3660

ctgcaacagc ggctttaaga gaaaggccgg cacctcttct ctgacagagt gcgtgctgaa   3720

taaggccaca aatgtggccc actggacaac acctagcctg aagtgcatta gagatcctgc   3780

cctggtccac cagaggcctg cccctccatc tacagtgaca acagccggag tgacacctca   3840

gcctgaatct ctgagccctt ctggaaaaga acctgccgcc agctctccta gctctaataa   3900

taccgccgcc acaacagccg ccattgtgcc tggatctcag ctgatgccta gcaagtctcc   3960

tagcacaggc acaacagaga tcagcagcca cgaatcttct cacggaacac cttctcagac   4020

caccgccaag aattgggagc tgacagcctc tgcctctcac cagcctccag gagtgtatcc   4080

tcagggccac tctgatacaa cagtggccat cagcacatct acagtgctgc tgtgtggact   4140

gtctgccgtg tctctgctgg cctgttacct gaagtctaga cagacacctc ctctggcctc   4200

tgtggagatg gaggccatgg aagccctgcc tgtgacatgg ggaacaagca gcagagatga   4260

ggacctggag aattgttctc accacctgtg aaacttgttt attgcagctt ataatggtta   4320

caaataaagc aatagcatca caaatttcac aaataaagca tttttttcac tgcattctag   4380

ttgtggtttg tccaaactca tcaatgtatc ttatcatgtc tgg                      4423
```

<210> SEQ ID NO 140
<211> LENGTH: 4487
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="FLC-2B8-1"

<400> SEQUENCE: 140

```
gagcgtgcgt gaggctccgg tgcccgtcag tgggcagagc gcacatcgcc cacagtcccc     60

gagaagttgg ggggaggggg tcggcgattg aaccggtgcc tagagaaggt ggcgcggggt    120

aaactgggaa agtgatgtcg tgtactggct ccgccttttt cccgagggtg ggggagaacc    180

gtatataagt gcagtagtcg ccgtgaacgt tctttttcgc aacgggtttg ccgccagaac    240

acagcagccg ctaaatccaa ggtaaggtca gaagagctag cgccaccatg ctgctgctgg    300

tgaccagcct gctgctgtgt gagctgcccc accccgcctt tctgctgatc cccgacatcc    360

agatgaccca gaccacctcc agcctgagcg ccagcctggg cgaccgggtg accatcagct    420

gccgggccag ccaggacatc agcaagtacc tgaactggta tcagcagaag cccgacggca    480

ccgtcaagct gctgatctac cacaccagcc ggctgcacag cggcgtgccc agccggttta    540

gcggcagcgg ctccggcacc gactacagcc tgaccatctc caacctggag caggaggaca    600

tcgccaccta cttttgccag cagggcaaca cactgcccta cacctttggc ggcggaacaa    660

agctggagat caccggcagc acctccggca gcggcaagcc tggcagcggc gagggcagca    720

ccaagggcga ggtgaagctg caggagagcg gccctggcct ggtggccccc agccagagcc    780

tgagcgtgac ctgtaccgtg tccggcgtgt ccctgcccga ctacggcgtg tcctggatcc    840
```

```
ggcagccccc taggaagggc ctggagtggc tgggcgtgat ctggggcagc gagaccacct     900
actacaacag cgccctgaag agccggctga ccatcatcaa ggacaacagc aagagccagg     960
tgttcctgaa gatgaacagc ctgcagaccg acgacaccgc catctactac tgtgccaagc    1020
actactacta cggcggcagc tacgccatgg actactgggg ccagggcacc agcgtgaccg    1080
tgtccagcaa gcccaccacc acccctgccc ctagacctcc aaccccagcc cctacaatcg    1140
ccagccagcc cctgagcctg aggcccgaag cctgtagacc tgccgctggc ggagccgtgc    1200
acaccagagg cctggatttc gcctgcgaca tctacatctg ggcccctctg gccggcacct    1260
gtggcgtgct gctgctgagc ctggtcatca ccctgtactg caaccaccgg aataggagca    1320
agcggagcag aggcggccac agcgactaca tgaacatgac cccccggagg cctggcccca    1380
cccggaagca ctaccagccc tacgcccctc ccagggactt cgccgcctac cggagccggg    1440
tgaagttcag ccggagcgcc gacgcccctg cctaccagca gggccagaac cagctgtaca    1500
acgagctgaa cctgggccgg agggaggagt acgacgtgct ggacaagcgg agaggccggg    1560
accctgagat gggcggcaag ccccggagaa agaaccctca ggagggcctg tataacgaac    1620
tgcagaaaga caagatggcc gaggcctaca gcgagatcgg catgaagggc gagcggcgga    1680
ggggcaaggg ccacgacggc ctgtaccagg gcctgagcac cgccaccaag gatacctacg    1740
acgccctgca catgcaggcc ctgcccccca gaagagctaa gaggggaagc ggagagggca    1800
gaggaagtct gctaacatgc ggtgacgtcg aggagaatcc tggacctggc cccaagaaga    1860
aaaggaaggt ggcccccccc accgacgtga gcctgggcga cgagctgcac ctggacggcg    1920
aggacgtggc catggcccac gccgacgccc tggacgactt cgacctggac atgctgggcg    1980
acggcgacag ccccggcccc ggcttcaccc cccacgacag cgcccccctac ggcgccctgg    2040
acatggccga cttcgagttc gagcagatgt tcaccgacgc cctgggcatc gacgagtacg    2100
gcggcgaatt cgagatgccc gtggacagga ttctggaggc cgaactcgcc gtggagcaga    2160
aaagcgacca gggcgtggag ggccccggcg gaaccggcgg cagcggcagc agccccaacg    2220
accccgtgac caacatctgc caggccgccg acaagcagct gttcaccctg gtggagtggg    2280
ccaagaggat tccccacttc agcagcctgc ccctggacga ccaggtgatc ctgctgaggg    2340
ccggatggaa cgagctgctg atcgccagct tcagccacag gagcatcgac gtgagggacg    2400
gcatcctgct ggccaccggc ctgcacgtcc ataggaacag cgcccacagc gccggagtgg    2460
gcgccatctt cgacagggtg ctgaccgagc tggtgagcaa gatgagggac atgaggatgg    2520
acaagaccga gctgggctgc ctgagggcca tcatcctgtt caaccccgag gtgaggggcc    2580
tgaaaagcgc ccaggaggtg gagctgctga gggagaaggt gtacgccgcc ctggaggagt    2640
acaccaggac cacccacccc gacgagcccg gcagattcgc caagctgctg ctgaggctgc    2700
ccagcctgag gagcatcggc ctgaagtgcc tggagcacct gttcttcttc aggctgatcg    2760
gcgacgtgcc catcgacacc ttcctgatgg agatgctgga gagccccagc gacagcagag    2820
ctaagagggg aagcggagag ggcagaggaa gtctgctaac atgcggtgac gtcgaggaga    2880
atcctggacc taagctgctg agcagcatcg agcaggcttg cgacatctgc aggctgaaga    2940
agctgaagtg cagcaaggag aagcccaagt gcgccaagtg cctgaagaac aactgggagt    3000
gcagatacag ccccaagacc aagaggagcc ccctgaccag ggcccacctg accgaggtgg    3060
agagcaggct ggagaggctg gagcagctgt tcctgctgat cttccccagg gaggacctgg    3120
acatgatcct gaagatggac agcctgcaag acatcaaggc cctgctgacc ggcctgttcg    3180
tgcaggacaa cgtgaacaag gacgccgtga ccgacaggct ggccagcgtg gagaccgaca    3240
```

```
tgcccctgac cctgaggcag cacaggatca gcgccaccag cagcagcgag gagagcagca   3300

acaagggcca gaggcagctg accgtgagcc ccgagtttcc cgggatcagg cccgagtgcg   3360

tggtgcccga gacccagtgc gccatgaaaa ggaaggagaa gaaggcccag aaggagaagg   3420

acaagctgcc cgtgagcacc accaccgtcg atgaccacat gccccccatc atgcagtgcg   3480

agcccccccc ccccgaggcc gccaggattc acgaggtcgt gcccaggttc ctgagcgaca   3540

agctgctggt gaccaacagg cagaagaaca tcccccagct gaccgccaac cagcagttcc   3600

tgatcgccag gctgatctgg tatcaggacg gctacgagca gcccagcgac gaggacctga   3660

aaaggatcac ccagacctgg cagcaggccg acgacgagaa cgaggagagc gacaccccct   3720

tcaggcagat caccgagatg accatcctga ccgtgcagct gatcgtggag ttcgccaagg   3780

gcctgcccgg attcgccaag atcagccagc ccgaccagat caccctgctg aaggcttgca   3840

gcagcgaggt gatgatgctg agggtggcca ggaggtacga cgccgccagc gacagcatcc   3900

tgttcgccaa caaccaggct tacaccaggg acaactacag gaaggctggc atggccgagg   3960

tgatcgagga cctcctgcac ttctgcagat gtatgtacag catggccctg gacaacatcc   4020

actacgccct gctgaccgcc gtggtgatct tcagcgacag gcccggcctg gagcagcccc   4080

agctggtgga ggagatccag aggtactacc tgaacaccct gaggatctac atcctgaacc   4140

agctgagcgg cagcgccagg agcagcgtga tctacggcaa gatcctgagc atcctgagcg   4200

agctgaggac cctgggaatg cagaacagca atatgtgtat cagcctgaag ctgaagaaca   4260

ggaagctgcc ccccttcctg gaggagattt gggacgtggc cgacatgagc cacacccagc   4320

cccccccat cctggagagc cccaccaacc tgtgaaactt gtttattgca gcttataatg   4380

gttacaaata aagcaatagc atcacaaatt tcacaaataa agcatttttt tcactgcatt   4440

ctagttgtgg tttgtccaaa ctcatcaatg tatcttatca tgtctgg                 4487
```

<210> SEQ ID NO 141
<211> LENGTH: 4509
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="FLC-2A3-1"

<400> SEQUENCE: 141

```
gagcgtgcgt gaggctccgg tgcccgtcag tgggcagagc gcacatcgcc cacagtcccc     60

gagaagttgg ggggaggggg tcggcgattg aaccggtgcc tagagaaggt ggcgcggggt    120

aaactgggaa agtgatgtcg tgtactggct ccgccttttt cccgagggtg ggggagaacc    180

gtatataagt gcagtagtcg ccgtgaacgt tctttttcgc aacgggtttg ccgccagaac    240

acagcagccg ctaaatccaa ggtaaggtca gaagagctag cgccaccatg ctgctgctgg    300

tgaccagcct gctgctgtgt gagctgcccc accccgcctt tctgctgatc cccgacatcc    360

agatgaccca gaccacctcc agcctgagcg ccagcctggg cgaccgggtg accatcagct    420

gccgggccag ccaggacatc agcaagtacc tgaactggta tcagcagaag cccgacggca    480

ccgtcaagct gctgatctac cacaccagcc ggctgcacag cggcgtgccc agccggttta    540

gcggcagcgg ctccggcacc gactacagcc tgaccatctc caacctggag caggaggaca    600

tcgccaccta cttttgccag cagggcaaca cactgcccta cacctttggc ggcggaacaa    660
```

-continued

```
agctggagat caccggcagc acctccggca gcggcaagcc tggcagcggc gagggcagca    720
ccaagggcga ggtgaagctg caggagagcg gccctggcct ggtggccccc agccagagcc    780
tgagcgtgac ctgtaccgtg tccggcgtgt ccctgcccga ctacggcgtg tcctggatcc    840
ggcagccccc taggaagggc ctggagtggc tgggcgtgat ctggggcagc gagaccacct    900
actacaacag cgccctgaag agccggctga ccatcatcaa ggacaacagc aagagccagg    960
tgttcctgaa gatgaacagc ctgcagaccg acgacaccgc catctactac tgtgccaagc   1020
actactacta cggcggcagc tacgccatgg actactgggg ccagggcacc agcgtgaccg   1080
tgtccagcaa gcccaccacc acccctgccc ctagacctcc aaccccagcc cctacaatcg   1140
ccagccagcc cctgagcctg aggcccgaag cctgtagacc tgccgctggc ggagccgtgc   1200
acaccagagg cctggatttc gcctgcgaca tctacatctg ggcccctctg gccggcacct   1260
gtggcgtgct gctgctgagc ctggtcatca ccctgtactg caaccaccgg aataggagca   1320
agcggagcag aggcggccac agcgactaca tgaacatgac cccccggagg cctggcccca   1380
cccggaagca ctaccagccc tacgcccctc ccagggactt cgccgcctac cggagccggg   1440
tgaagttcag ccggagcgcc gacgcccctg cctaccagca gggccagaac cagctgtaca   1500
acgagctgaa cctgggccgg agggaggagt acgacgtgct ggacaagcgg agaggccggg   1560
accctgagat gggcggcaag ccccggagaa agaaccctca ggagggcctg tataacgaac   1620
tgcagaaaga caagatggcc gaggcctaca gcgagatcgg catgaagggc gagcggcgga   1680
ggggcaaggg ccacgacggc ctgtaccagg gcctgagcac cgccaccaag gatacctacg   1740
acgccctgca catgcaggcc ctgcccccca gaagagctaa gaggggaagc ggagagggca   1800
gaggaagtct gctaacatgc ggtgacgtcg aggagaatcc tggacctggc cccaagaaga   1860
aaaggaaggt ggcccccccc accgacgtga gcctgggcga cgagctgcac ctggacggcg   1920
aggacgtggc catggcccac gccgacgccc tggacgactt cgacctggac atgctgggcg   1980
acggcgacag ccccggcccc ggcttcaccc cccacgacag cgcccccctac ggcgccctgg   2040
acatggccga cttcgagttc gagcagatgt tcaccgacgc cctgggcatc gacgagtacg   2100
gcggcgaatt cgagatgccc gtggacagga ttctggaggc cgaactcgcc gtggagcaga   2160
aaagcgacca gggcgtggag ggccccggcg gaaccggcgg cagcggcagc agccccaacg   2220
accccgtgac caacatctgc caggccgccg acaagcagct gttcaccctg gtggagtggg   2280
ccaagaggat tccccacttc agcagcctgc ccctggacga ccaggtgatc ctgctgaggg   2340
ccggatggaa cgagctgctg atcgccagct tcagccacag gagcatcgac gtgagggacg   2400
gcatcctgct ggccaccggc ctgcacgtcc ataggaacag cgcccacagc gccggagtgg   2460
gcgccatctt cgacagggtg ctgaccgagc tggtgagcaa gatgagggac atgaggatgg   2520
acaagaccga gctgggctgc ctgagggcca tcatcctgtt caaccccgag gtgaggggcc   2580
tgaaaagcgc ccaggaggtg gagctgctga gggagaaggt gtacgccgcc ctggaggagt   2640
acaccaggac cacccacccc gacgagcccg gcagattcgc caagctgctg ctgaggctgc   2700
ccagcctgag gagcatcggc ctgaagtgcc tggagcacct gttcttcttc aggctgatcg   2760
gcgacgtgcc catcgacacc ttcctgatgg agatgctgga gagccccagc gacagctgag   2820
catgcactag ttttataatt tcttcttcca gaatttctga cattttataa tttcttcttc   2880
cagaagactc acaacctcca tatggccacc atgaagctgc tgagcagcat cgagcaggct   2940
tgcgacatct gcaggctgaa gaagctgaag tgcagcaagg agaagcccaa gtgcgccaag   3000
```

```
tgcctgaaga acaactggga gtgcagatac agccccaaga ccaagaggag ccccctgacc   3060

agggcccacc tgaccgaggt ggagagcagg ctggagaggc tggagcagct gttcctgctg   3120

atcttcccca gggaggacct ggacatgatc ctgaagatgg acagcctgca agacatcaag   3180

gccctgctga ccggcctgtt cgtgcaggac aacgtgaaca aggacgccgt gaccgacagg   3240

ctggccagcg tggagaccga catgcccctg accctgaggc agcacaggat cagcgccacc   3300

agcagcagcg aggagagcag caacaagggc cagaggcagc tgaccgtgag ccccgagttt   3360

cccgggatca ggcccgagtg cgtggtgccc gagacccagt gcgccatgaa aaggaaggag   3420

aagaaggccc agaaggagaa ggacaagctg cccgtgagca ccaccaccgt cgatgaccac   3480

atgcccccca tcatgcagtg cgagcccccc ccccccgagg ccgccaggat tcacgaggtc   3540

gtgcccaggt tcctgagcga caagctgctg gtgaccaaca ggcagaagaa catcccccag   3600

ctgaccgcca accagcagtt cctgatcgcc aggctgatct ggtatcagga cggctacgag   3660

cagcccagcg acgaggacct gaaaaggatc acccagacct ggcagcaggc cgacgacgag   3720

aacgaggaga gcgacacccc cttcaggcag atcaccgaga tgaccatcct gaccgtgcag   3780

ctgatcgtgg agttcgccaa gggcctgccc ggattcgcca agatcagcca gcccgaccag   3840

atcaccctgc tgaaggcttg cagcagcgag gtgatgatgc tgagggtggc caggaggtac   3900

gacgccgcca gcgacagcat cctgttcgcc aacaaccagg cttacaccag ggacaactac   3960

aggaaggctg gcatggccga ggtgatcgag gacctcctgc acttctgcag atgtatgtac   4020

agcatggccc tggacaacat ccactacgcc ctgctgaccg ccgtggtgat cttcagcgac   4080

aggcccggcc tggagcagcc ccagctggtg gaggagatcc agaggtacta cctgaacacc   4140

ctgaggatct acatcctgaa ccagctgagc ggcagcgcca ggagcagcgt gatctacggc   4200

aagatcctga gcatcctgag cgagctgagg accctgggaa tgcagaacag caatatgtgt   4260

atcagcctga agctgaagaa caggaagctg ccccccttcc tggaggagat ttgggacgtg   4320

gccgacatga gccacaccca gcccccccc atcctggaga gccccaccaa cctgtgaaac   4380

ttgtttattg cagcttataa tggttacaaa taaagcaata gcatcacaaa tttcacaaat   4440

aaagcatttt tttcactgca ttctagttgt ggtttgtcca aactcatcaa tgtatcttat   4500

catgtctgg                                                           4509
```

<210> SEQ ID NO 142
<211> LENGTH: 3155
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="FLC-2A7-1"

<400> SEQUENCE: 142

```
attgttcgga gcagtgcggc gcgtttagcg gagtactgtc ctccgatatt aatcggggca     60

gactattccg ggtttaccg gcgcactctc gcccgaactt caccggcggt ctttcgtccg    120

tgctttatcg gggcggatca ctccgaaccc cgggaggtct atataagcag agctcgttta    180

gtgaaccctc attctggaga cggatcccga gccgagtgtt ttgacctcca tagaacagcc    240

gctaaatcca aggtaaggtc agaagagcta gcgccaccat gctgctgctg gtgaccagcc    300

tgctgctgtg tgagctgccc caccccgcct ttctgctgat ccccgacatc cagatgaccc    360
```

```
agaccacctc cagcctgagc gccagcctgg gcgaccgggt gaccatcagc tgccgggcca    420
gccaggacat cagcaagtac ctgaactggt atcagcagaa gcccgacggc accgtcaagc    480
tgctgatcta ccacaccagc cggctgcaca gcggcgtgcc cagccggttt agcggcagcg    540
gctccggcac cgactacagc ctgaccatct ccaacctgga gcaggaggac atcgccacct    600
acttttgcca gcagggcaac acactgccct acacctttgg cggcggaaca aagctggaga    660
tcaccggcag cacctccggc agcggcaagc ctggcagcgg cgagggcagc accaagggcg    720
aggtgaagct gcaggagagc ggccctggcc tggtggcccc cagccagagc ctgagcgtga    780
cctgtaccgt gtccggcgtg tccctgcccg actacggcgt gtcctggatc cggcagcccc    840
ctaggaaggg cctggagtgg ctgggcgtga tctggggcag cgagaccacc tactacaaca    900
gcgccctgaa gagccggctg accatcatca aggacaacag caagagccag gtgttcctga    960
agatgaacag cctgcagacc gacgacaccg ccatctacta ctgtgccaag cactactact   1020
acggcggcag ctacgccatg gactactggg gccagggcac cagcgtgacc gtgtccagca   1080
agcccaccac cacccctgcc cctagacctc caaccccagc ccctacaatc gccagccagc   1140
ccctgagcct gaggcccgaa gcctgtagac ctgccgctgg cggagccgtg cacaccagag   1200
gcctggattt cgcctgcgac atctacatct gggcccctct ggccggcacc tgtggcgtgc   1260
tgctgctgag cctggtcatc accctgtact gcaaccaccg gaataggagc aagcggagca   1320
gaggcggcca cagcgactac atgaacatga ccccccggag gcctggcccc acccggaagc   1380
actaccagcc ctacgcccct cccagggact tcgccgccta ccggagccgg gtgaagttca   1440
gccggagcgc cgacgcccct gcctaccagc agggccagaa ccagctgtac aacgagctga   1500
acctgggccg gagggaggag tacgacgtgc tggacaagcg gagaggccgg gaccctgaga   1560
tgggcggcaa gccccggaga aagaaccctc aggagggcct gtataacgaa ctgcagaaag   1620
acaagatggc cgaggcctac agcgagatcg gcatgaaggg cgagcggcgg aggggcaagg   1680
gccacgacgg cctgtaccag ggcctgagca ccgccaccaa ggatacctac gacgccctgc   1740
acatgcaggc cctgcccccc agaagagcta agaggggaag cggagagggc agaggaagtc   1800
tgctaacatg cggtgacgtc gaggagaatc ctggacctga ttggacctgg attctgtttc   1860
tggtggccgc tgccacaaga gtgcacagca actgggtgaa tgtgatcagc gacctgaaga   1920
agatcgagga tctgatccag agcatgcaca ttgatgccac cctgtacaca gaatctgatg   1980
tgcaccctag ctgtaaagtg accgccatga agtgttttct gctggagctg caggtgattt   2040
ctctggaaag cggagatgcc tctatccacg acacagtgga gaatctgatc atcctggcca   2100
acaatagcct gagcagcaat ggcaatgtga cagagtctgg ctgtaaggag tgtgaggagc   2160
tggaggagaa gaacatcaag gagtttctgc agagctttgt gcacatcgtg cagatgttca   2220
tcaatacaag ctctggcgga ggatctggag gaggcggatc tggaggagga ggcagtggag   2280
gcggaggatc tggcggagga tctctgcaga ttacatgccc tcctccaatg tctgtggagc   2340
acgccgatat ttgggtgaag tcctacagcc tgtacagcag agagagatac atctgcaaca   2400
gcggctttaa gagaaaggcc ggcacctctt ctctgacaga gtgcgtgctg aataaggcca   2460
caaatgtggc ccactggaca acacctagcc tgaagtgcat tagagatcct gccctggtcc   2520
accagaggcc tgcccctcca tctacagtga caacagccgg agtgacacct cagcctgaat   2580
ctctgagccc ttctggaaaa gaacctgccg ccagctctcc tagctctaat aataccgccg   2640
ccacaacagc cgccattgtg cctggatctc agctgatgcc tagcaagtct cctagcacag   2700
gcacaacaga gatcagcagc cacgaatctt ctcacggaac accttctcag accaccgcca   2760
```

agaattggga gctgacagcc tctgcctctc accagcctcc aggagtgtat cctcagggcc 2820
actctgatac aacagtggcc atcagcacat ctacagtgct gctgtgtgga ctgtctgccg 2880
tgtctctgct ggcctgttac ctgaagtcta gacagacacc tcctctggcc tctgtggaga 2940
tggaggccat ggaagccctg cctgtgacat ggggaacaag cagcagagat gaggacctgg 3000
agaattgttc tcaccacctg tgaaacttgt ttattgcagc ttataatggt tacaaataaa 3060
gcaatagcat cacaaatttc acaaataaag catttttttc actgcattct agttgtggtt 3120
tgtccaaact catcaatgta tcttatcatg tctgg 3155

<210> SEQ ID NO 143
<211> LENGTH: 3476
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="FLC-2A5-2"

<400> SEQUENCE: 143
attgttcgga gcagtgcggc gcgtttagcg gagtactgtc ctccgatatt aatcggggca 60
gactattccg gggtttaccg gcgcactctc gcccgaactt caccggcggt ctttcgtccg 120
tgctttatcg gggcggatca ctccgaaccc cgggaggtct atataagcag agctcgttta 180
gtgaaccctc attctggaga cggatcccga gccgagtgtt ttgacctcca tagaacagcc 240
gctaaatcca aggtaaggtc agaagagcta gcgccaccat ggattggacc tggattctgt 300
ttctggtggc cgctgccaca agagtgcaca gcaactgggt gaatgtgatc agcgacctga 360
agaagatcga ggatctgatc cagagcatgc acattgatgc caccctgtac acagaatctg 420
atgtgcaccc tagctgtaaa gtgaccgcca tgaagtgttt tctgctggag ctgcaggtga 480
tttctctgga aagcggagat gcctctatcc acgacacagt ggagaatctg atcatcctgg 540
ccaacaatag cctgagcagc aatggcaatg tgacagagtc tggctgtaag gagtgtgagg 600
agctggagga gaagaacatc aaggagtttc tgcagagctt tgtgcacatc gtgcagatgt 660
tcatcaatac aagctctggc ggaggatctg gaggaggcgg atctggagga ggaggcagtg 720
gaggcggagg atctggcgga ggatctctgc agattacatg ccctcctcca atgtctgtgg 780
agcacgccga tatttgggtg aagtcctaca gcctgtacag cagagagaga tacatctgca 840
acagcggctt taagagaaag gccggcacct cttctctgac agagtgcgtg ctgaataagg 900
ccacaaatgt ggcccactgg acaacaccta gcctgaagtg cattagagat cctgccctgg 960
tccaccagag gcctgcccct ccatctacag tgacaacagc cggagtgaca cctcagcctg 1020
aatctctgag cccttctgga aaagaacctg ccgccagctc tcctagctct aataataccg 1080
ccgccacaac agccgccatt gtgcctggat ctcagctgat gcctagcaag tctcctagca 1140
caggcacaac agagatcagc agccacgaat cttctcacgg aacaccttct cagaccaccg 1200
ccaagaattg ggagctgaca gcctctgcct ctcaccagcc tccaggagtg tatcctcagg 1260
gccactctga tacaacagtg gccatcagca catctacagt gctgctgtgt ggactgtctg 1320
ccgtgtctct gctggcctgt tacctgaagt ctagacagac acctcctctg gcctctgtgg 1380
agatggaggc catggaagcc ctgcctgtga catggggaac aagcagcaga gatgaggacc 1440
tggagaattg ttctcaccac ctgtgaatcg attaatctag cggccctaga cgagcagaca 1500
tgataagata cattgatgag tttggacaaa ccacaactag aatgcagtga aaaaaatgct 1560
ttatttgtga aatttgtgat gctattgctt tatttgtaac cattataagc tgcaataaac 1620
aagttaacaa caacaattgc attcatttta tgtttcaggt tcagggggag atgtgggagg 1680 tttttaaag caagtaaaac ctctacaaat gtggtaaaat ccgataagcg tacctagagg 1740
ccgcctagag attcgtgggg gactcgagga taggcggcgg ttgggtgtgc gacatgtccg 1800
ccacatccca gatctcctcg aggaaaggcg gcagctttct gttcttgagc ttgagggaga 1860
tgcacatgtt ggagttttgc atgccgagcg tgcgtagctc agagaggatt gagaggatct 1920
tgccgtatat gacggacgaa cgcgccgacc cgctcagctg gttcaggata tagatgcgga 1980
gcgtattcag gtagtaccgc tggatctctt ccaccagttg cggctgctcc aaccctggcc 2040
ggtcagaaaa gatgacgaca gccgtgagca gcgcgtaatg gatgttgtcc aacgccatag 2100
agtacatgca ccggcagaag tgcagtagat cctcgatgac ctcggccatg ccagccttgc 2160
ggtagttgtc gcgagtgtac gcttggttgt tcgcgaacag aatactgtct gaggccgcat 2220
cgtatcgtcg cgcgactcgg agcatcatta cctcacttga gcaagcctta agcagcgtaa 2280
tttgatcagg ctgcgagatc ttggcgaacc ctggcaatcc cttcgcgaac tccacgataa 2340
gttggaccgt gaggatagtc atctctgtga tctggcggaa gggagtgtcc gactcttcgt 2400
tttcatcgtc cgcttgctgc cacgtctgcg taatcctctt caaatcttca tcagaaggct 2460
gctcgtaccc gtcctggtac cagatgagcc tggcgataag gaactgctgg ttggctgtca 2520
actgggggat gtttttctgc cggtttgtca ccaacagctt gtcggagaga aaccttggga 2580
ccacttcgtg aatccttgct gcttcaggag gtggaggttc acactgcata atgggcggca 2640
tgtggtcgtc caccgtcgtc gtgctgacag gcagtttgtc cttctccttc tgtgctttct 2700
tctctttccg cttcatggcg cactgagtct cgggtactac gcactcaggc cgcccgggaa 2760
actcggggct cacggtcagc tgcctctggc ccttgttgct gctctcctcg ctgctgctgg 2820
tggcgctgat cctgtgctgc ctcagggtca ggggcatgtc ggtctccacg ctggccagcc 2880
tgtcggtcac ggcgtccttg ttcacgttgt cctgcacgaa caggccggtc agcagggcct 2940
tgatgtcttg caggctgtcc atcttcagga tcatgtccag gtcctccctg ggaagatca 3000 gcaggaacag ctgctccagc ctctccagcc tgctctccac ctcggtcagg tgggccctgg 3060
tcagggggct cctcttggtc ttggggctgt atctgcactc ccagttgttc ttcaggcact 3120
tggcgcactt gggcttctcc ttgctgcact tcagcttctt cagcctgcag atgtcgcaag 3180
cctgctcgat gctgctcagc agcttcatgg tggcccgaaa agcacacaat gcctgtgttc 3240
tggcggcaaa cccgttgcga aaaagaacgt tcacggcgac tactgcactt atatacggtt 3300
ctcccccacc ctcgggaaaa aggcggagcc agtacacgac atcactttcc cagtttaccc 3360
cgcgccacct tctctaggca ccggttcaat cgccgacccc ctccccccaa cttctcgggg 3420
actgtgggcg atgtgcgctc tgcccactga cgggcaccgg agcctcacgc acgctc 3476

<210> SEQ ID NO 144
<211> LENGTH: 3503
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="FLC-2A6-1"

<400> SEQUENCE: 144
gagcgtgcgt gaggctccgg tgcccgtcag tgggcagagc gcacatcgcc cacagtcccc 60
gagaagttgg ggggaggggg tcggcgattg aaccggtgcc tagagaaggt ggcgcggggt 120
aaactgggaa agtgatgtcg tgtactggct ccgccttttt cccgagggtg ggggagaacc 180
gtatataagt gcagtagtcg ccgtgaacgt tctttttcgc aacgggtttg ccgccagaac 240
acagcagccg ctaaatccaa ggtaaggtca gaagagctag cgccaccatg ctgctgctgg 300
tgaccagcct gctgctgtgt gagctgcccc accccgcctt tctgctgatc cccgacatcc 360
agatgaccca gaccacctcc agcctgagcg ccagcctggg cgaccgggtg accatcagct 420
gccgggccag ccaggacatc agcaagtacc tgaactggta tcagcagaag cccgacggca 480
ccgtcaagct gctgatctac cacaccagcc ggctgcacag cggcgtgccc agccggttta 540
gcggcagcgg ctccggcacc gactacagcc tgaccatctc caacctggag caggaggaca 600
tcgccaccta cttttgccag cagggcaaca cactgcccta cacctttggc ggcggaacaa 660
agctggagat caccggcagc acctccggca gcggcaagcc tggcagcggc gagggcagca 720
ccaagggcga ggtgaagctg caggagagcg gccctggcct ggtggccccc agccagagcc 780
tgagcgtgac ctgtaccgtg tccggcgtgt ccctgcccga ctacggcgtg tcctggatcc 840
ggcagccccc taggaagggc ctggagtggc tgggcgtgat ctggggcagc gagaccacct 900
actacaacag cgccctgaag agccggctga ccatcatcaa ggacaacagc aagagccagg 960
tgttcctgaa gatgaacagc ctgcagaccg acgacaccgc catctactac tgtgccaagc 1020
actactacta cggcggcagc tacgccatgg actactgggg ccagggcacc agcgtgaccg 1080
tgtccagcaa gcccaccacc acccctgccc ctagacctcc aaccccagcc cctacaatcg 1140
ccagccagcc cctgagcctg aggcccgaag cctgtagacc tgccgctggc ggagccgtgc 1200
acaccagagg cctggatttc gcctgcgaca tctacatctg ggcccctctg gccggcacct 1260
gtggcgtgct gctgctgagc ctggtcatca ccctgtactg caaccaccgg aataggagca 1320
agcggagcag aggcggccac agcgactaca tgaacatgac cccccggagg cctggcccca 1380
cccggaagca ctaccagccc tacgcccctc ccagggactt cgccgcctac cggagccggg 1440
tgaagttcag ccggagcgcc gacgcccctg cctaccagca gggccagaac cagctgtaca 1500
acgagctgaa cctgggccgg agggaggagt acgacgtgct ggacaagcgg agaggccggg 1560
accctgagat gggcggcaag ccccggagaa agaaccctca ggagggcctg tataacgaac 1620
tgcagaaaga caagatggcc gaggcctaca gcgagatcgg catgaagggc gagcggcgga 1680
ggggcaaggg ccacgacggc ctgtaccagg gcctgagcac cgccaccaag gatacctacg 1740
acgccctgca catgcaggcc ctgcccccca gatgaatcga ttaatctagc ggccctagac 1800
gagcagacat gataagatac attgatgagt ttggacaaac cacaactaga atgcagtgaa 1860
aaaaatgctt tatttgtgaa atttgtgatg ctattgcttt atttgtaacc attataagct 1920
gcaataaaca agttaacaac aacaattgca ttcattttat gtttcaggtt cagggggaga 1980
tgtgggaggt tttttaaagc aagtaaaacc tctacaaatg tggtaaaatc cgataagcgt 2040
acctagaggc tcacaggtgg tgagaacaat tctccaggtc ctcatctctg ctgcttgttc 2100
cccatgtcac aggcagggct tccatggcct ccatctccac agaggccaga ggaggtgtct 2160
gtctagactt caggtaacag gccagcagag acacggcaga cagtccacac agcagcactg 2220
tagatgtgct gatggccact gttgtatcag agtggccctg aggatacact cctggaggct 2280
ggtgagaggc agaggctgtc agctcccaat tcttggcggt ggtctgagaa ggtgttccgt 2340
gagaagattc gtggctgctg atctctgttg tgcctgtgct aggagacttg ctaggcatca 2400
gctgagatcc aggcacaatg gcggctgttg tggcggcggt attattagag ctaggagagc 2460
tggcggcagg ttcttttcca gaagggctca gagattcagg ctgaggtgtc actccggctg 2520
ttgtcactgt agatggaggg gcaggcctct ggtggaccag ggcaggatct ctaatgcact 2580
tcaggctagg tgttgtccag tgggccacat ttgtggcctt attcagcacg cactctgtca 2640
gagaagaggt gccggccttt ctcttaaagc cgctgttgca gatgtatctc tctctgctgt 2700
acaggctgta ggacttcacc caaatatcgg cgtgctccac agacattgga ggagggcatg 2760
taatctgcag agatcctccg ccagatcctc cgcctccact gcctcctcct ccagatccgc 2820
ctcctccaga tcctccgcca gagcttgtat tgatgaacat ctgcacgatg tgcacaaagc 2880
tctgcagaaa ctccttgatg ttcttctcct ccagctcctc acactcctta cagccagact 2940
ctgtcacatt gccattgctg ctcaggctat tgttggccag gatgatcaga ttctccactg 3000
tgtcgtggat agaggcatct ccgctttcca gagaaatcac ctgcagctcc agcagaaaac 3060
acttcatggc ggtcacttta cagctagggt gcacatcaga ttctgtgtac agggtggcat 3120
caatgtgcat gctctggatc agatcctcga tcttcttcag gtcgctgatc acattcaccc 3180
agttgctgtg cactcttgtg gcagcggcca ccagaaacag aatccaggtc caatccatgg 3240
tggcgctagc ccgaaaagca cacaatgctt ctatggaggt caaaacactc ggctcgggat 3300
ccgtctccag aatgagggtt cactaaacga gctctgctta tatagacctc ccggggttcg 3360
gagtgatccg ccccgataaa gcacggacga aagaccgccg gtgaagttcg ggcgagagtg 3420
cgccggtaaa ccccggaata gtctgccccg attaatatcg gaggacagta ctccgctaaa 3480
cgcgccgcac tgctccgaac aat 3503

<210> SEQ ID NO 145
<211> LENGTH: 4079
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="XON-00(h)"

<400> SEQUENCE: 145
gagcgtgcgt gaggctccgg tgcccgtcag tgggcagagc gcacatcgcc cacagtcccc 60
gagaagttgg ggggaggggg tcggcgattg aaccggtgcc tagagaaggt ggcgcggggt 120
aaactgggaa agtgatgtcg tgtactggct ccgccttttt cccgagggtg ggggagaacc 180
gtatataagt gcagtagtcg ccgtgaacgt tctttttcgc aacgggtttg ccgccagaac 240
acagcagccg ctaaatccaa ggtaaggtca gaagagctag cgccaccatg ctgctgctgg 300
tgaccagcct gctgctgtgt gagctgcccc accccgcctt tctgctgatc cccgacatcc 360
agatgaccca gaccacctcc agcctgagcg ccagcctggg cgaccgggtg accatcagct 420
gccgggccag ccaggacatc agcaagtacc tgaactggta tcagcagaag cccgacggca 480
ccgtcaagct gctgatctac cacaccagcc ggctgcacag cggcgtgccc agccggttta 540
gcggcagcgg ctccggcacc gactacagcc tgaccatctc caacctggag caggaggaca 600
tcgccaccta cttttgccag cagggcaaca cactgcccta cacctttggc ggcggaacaa 660

```
agctggagat caccggcagc acctccggca gcggcaagcc tggcagcggc gagggcagca    720
ccaagggcga ggtgaagctg caggagagcg gccctggcct ggtggccccc agccagagcc    780
tgagcgtgac ctgtaccgtg tccggcgtgt ccctgcccga ctacggcgtg tcctggatcc    840
ggcagccccc taggaagggc ctggagtggc tgggcgtgat ctggggcagc gagaccacct    900
actacaacag cgccctgaag agccggctga ccatcatcaa ggacaacagc aagagccagg    960
tgttcctgaa gatgaacagc ctgcagaccg acgacaccgc catctactac tgtgccaagc   1020
actactacta cggcggcagc tacgccatgg actactgggg ccagggcacc agcgtgaccg   1080
tgtccagcaa gcccaccacc acccctgccc ctagacctcc aaccccagcc cctacaatcg   1140
ccagccagcc cctgagcctg aggcccgaag cctgtagacc tgccgctggc ggagccgtgc   1200
acaccagagg cctggatttc gcctgcgaca tctacatctg ggcccctctg gccggcacct   1260
gtggcgtgct gctgctgagc ctggtcatca ccctgtactg caaccaccgg aataggagca   1320
agcggagcag aggcggccac agcgactaca tgaacatgac cccccggagg cctggcccca   1380
cccggaagca ctaccagccc tacgcccctc ccagggactt cgccgcctac cggagccggg   1440
tgaagttcag ccggagcgcc gacgcccctg cctaccagca gggccagaac cagctgtaca   1500
acgagctgaa cctgggccgg agggaggagt acgacgtgct ggacaagcgg agaggccggg   1560
accctgagat gggcggcaag ccccggagaa agaaccctca ggagggcctg tataacgaac   1620
tgcagaaaga caagatggcc gaggcctaca gcgagatcgg catgaagggc gagcggcgga   1680
ggggcaaggg ccacgacggc ctgtaccagg gcctgagcac cgccaccaag gatacctacg   1740
acgccctgca catgcaggcc ctgcccccca gaagagctaa gaggggaagc ggagagggca   1800
gaggaagtct gctaacatgc ggtgacgtcg aggagaatcc tggacctatg cttctcctgg   1860
tgacaagcct tctgctctgt gagttaccac acccagcatt cctcctgatc ccacgcaaag   1920
tgtgtaacgg aataggtatt ggtgaattta aagactcact ctccataaat gctacgaata   1980
ttaaacactt caaaaactgc acctccatca gtggcgatct ccacatcctg ccggtggcat   2040
ttaggggtga ctccttcaca catactcctc ctctggatcc acaggaactg gatattctga   2100
aaaccgtaaa ggaaatcaca gggtttttgc tgattcaggc ttggcctgaa aacaggacgg   2160
acctccatgc ctttgagaac ctagaaatca tacgcggcag gaccaagcaa catggtcagt   2220
ttctcttgc agtcgtcagc ctgaacataa catccttggg attacgctcc ctcaaggaga   2280
taagtgatgg agatgtgata atttcaggaa acaaaaattt gtgctatgca aatacaataa   2340
actggaaaaa actgtttggg acctccggtc agaaaaccaa aattataagc aacagaggtg   2400
aaaacagctg caaggccaca ggccaggtct gccatgcctt gtgctccccc gagggctgct   2460
ggggcccgga gcccagggac tgcgtctctt gccggaatgt cagccgaggc agggaatgcg   2520
tggacaagtg caaccttctg gagggtgagc caagggagtt tgtggagaac tctgagtgca   2580
tacagtgcca cccagagtgc ctgcctcagg ccatgaacat cacctgcaca ggacggggac   2640
cagacaactg tatccagtgt gcccactaca ttgacggccc ccactgcgtc aagacctgcc   2700
cggcaggagt catgggagaa aacaacaccc tggtctggaa gtacgcagac gccggccatg   2760
tgtgccacct gtgccatcca aactgcacct acggatgcac tgggccaggt cttgaaggct   2820
gtccaacgaa tgggcctaag atcccgtcca tcgccactgg gatggtgggg gccctcctct   2880
tgctgctggt ggtggccctg gggatcggcc tcttcatgga gggcagagga agtctgctaa   2940
catgcggtga cgtcgaggag aatcctggac ctatgggccc caagaagaaa aggaaggtgg   3000
cccccccac cgacgtgagc ctgggcgacg agctgcacct ggacggcgag gacgtggcca   3060
```

tggcccacgc cgacgccctg gacgacttcg acctggacat gctgggcgac ggcgacagcc 3120
ccggccccgg cttcaccccc cacgacagcg ccccctacgg cgccctggac atggccgact 3180
tcgagttcga gcagatgttc accgacgccc tgggcatcga cgagtacggc ggcgaattcg 3240
agatgcccgt ggacaggatt ctggaggccg aactcgccgt ggagcagaaa agcgaccagg 3300
gcgtggaggg ccccggcgga accggcggca gcggcagcag ccccaacgac cccgtgacca 3360
acatctgcca ggccgccgac aagcagctgt tcaccctggt ggagtgggcc aagaggattc 3420
cccacttcag cagcctgccc ctggacgacc aggtgatcct gctgagggcc ggatggaacg 3480
agctgctgat cgccagcttc agccacagga gcatcgacgt gagggacggc atcctgctgg 3540
ccaccggcct gcacgtccat aggaacagcg cccacagcgc cggagtgggc gccatcttcg 3600
acagggtgct gaccgagctg gtgagcaaga tgagggacat gaggatggac aagaccgagc 3660
tgggctgcct gagggccatc atcctgttca accccgaggt gaggggcctg aaaagcgccc 3720
aggaggtgga gctgctgagg gagaaggtgt acgccgccct ggaggagtac accaggacca 3780
cccaccccga cgagcccggc agattcgcca agctgctgct gaggctgccc agcctgagga 3840
gcatcggcct gaagtgcctg gagcacctgt tcttcttcag gctgatcggc gacgtgccca 3900
tcgacacctt cctgatggag atgctggaga gccccagcga cagctgaaac ttgtttattg 3960
cagcttataa tggttacaaa taaagcaata gcatcacaaa tttcacaaat aaagcatttt 4020
tttcactgca ttctagttgt ggtttgtcca aactcatcaa tgtatcttat catgtctgg 4079

<210> SEQ ID NO 146
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Whitlow Linker"

<400> SEQUENCE: 146

Gly Ser Thr Ser Gly Ser Gly Lys Pro Gly Ser Gly Glu Gly Ser Thr
1 5 10 15

Lys Gly

<210> SEQ ID NO 147
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Linker"

<400> SEQUENCE: 147

Ser Gly Gly Gly Ser Gly Gly Gly Gly Ser Gly Gly Gly Gly Ser Gly
1 5 10 15

Gly Gly Gly Ser Gly Gly Gly Ser Leu Gln
20 25

<210> SEQ ID NO 148
<211> LENGTH: 3

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="GSG linker"

<400> SEQUENCE: 148

Gly Ser Gly
1

<210> SEQ ID NO 149
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="SGSG linker"

<400> SEQUENCE: 149

Ser Gly Ser Gly
1

<210> SEQ ID NO 150
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="(G4S)3 linker"

<400> SEQUENCE: 150

```
Gly Gly Gly Gly Ser Gly Gly Gly Gly Ser Gly Gly Gly Gly Ser
1               5                   10                  15
```

<210> SEQ ID NO 151
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Furin cleavage site/ Furinlink1"

<400> SEQUENCE: 151

Arg Ala Lys Arg
1

<210> SEQ ID NO 152
<211> LENGTH: 28
<212> TYPE: PRT
<213> ORGANISM: Foot-and-mouth disease virus
<220> FEATURE:
<221> NAME/KEY: source
<223> OTHER INFORMATION: /note="Fmdv"

<400> SEQUENCE: 152

```
Arg Ala Lys Arg Ala Pro Val Lys Gln Thr Leu Asn Phe Asp Leu Leu
1               5                   10                  15

Lys Leu Ala Gly Asp Val Glu Ser Asn Pro Gly Pro
            20                  25


<210> SEQ ID NO 153
<211> LENGTH: 18
<212> TYPE: PRT
<213> ORGANISM: Thosea asigna virus
<220> FEATURE:
<221> NAME/KEY: source
<223> OTHER INFORMATION: /note="Thosea asigna virus 2A region (T2A)"

<400> SEQUENCE: 153

Glu Gly Arg Gly Ser Leu Leu Thr Cys Gly Asp Val Glu Glu Asn Pro
1               5                   10                  15

Gly Pro


<210> SEQ ID NO 154
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Furin-GSG-T2A"

<400> SEQUENCE: 154

Arg Ala Lys Arg Gly Ser Gly Glu Gly Arg Gly Ser Leu Leu Thr Cys
1               5                   10                  15

Gly Asp Val Glu Glu Asn Pro Gly Pro
            20                  25


<210> SEQ ID NO 155
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Furin-SGSG-T2A"

<400> SEQUENCE: 155

Arg Ala Lys Arg Ser Gly Ser Gly Glu Gly Arg Gly Ser Leu Leu Thr
1               5                   10                  15

Cys Gly Asp Val Glu Glu Asn Pro Gly Pro
            20                  25


<210> SEQ ID NO 156
<211> LENGTH: 19
<212> TYPE: PRT
<213> ORGANISM: Porcine teschovirus
<220> FEATURE:
<221> NAME/KEY: source
<223> OTHER INFORMATION: /note="Porcine teschovirus-1 2A region (P2A)"

<400> SEQUENCE: 156

Ala Thr Asn Phe Ser Leu Leu Lys Gln Ala Gly Asp Val Glu Glu Asn
1               5                   10                  15
```

Pro Gly Pro

<210> SEQ ID NO 157
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="GSG-P2A"

<400> SEQUENCE: 157

```
Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 158
<211> LENGTH: 20
<212> TYPE: PRT
<213> ORGANISM: Equine rhinitis A virus
<220> FEATURE:
<221> NAME/KEY: source
<223> OTHER INFORMATION: /note="Equine rhinitis A virus 2A region (E2A)"

<400> SEQUENCE: 158

```
Gln Cys Thr Asn Tyr Ala Leu Leu Lys Leu Ala Gly Asp Val Glu Ser
1               5                   10                  15

Asn Pro Gly Pro
            20
```

<210> SEQ ID NO 159
<211> LENGTH: 22
<212> TYPE: PRT
<213> ORGANISM: Foot-and-mouth disease virus
<220> FEATURE:
<221> NAME/KEY: source
<223> OTHER INFORMATION: /note="Foot-and-mouth disease virus 2A region (F2A)"

<400> SEQUENCE: 159

```
Val Lys Gln Thr Leu Asn Phe Asp Leu Leu Lys Leu Ala Gly Asp Val
1               5                   10                  15

Glu Ser Asn Pro Gly Pro
            20
```

<210> SEQ ID NO 160
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="FP2A"

<400> SEQUENCE: 160

```
Arg Ala Lys Arg Ala Pro Val Lys Gln Gly Ser Gly Ala Thr Asn Phe
1               5                   10                  15

Ser Leu Leu Lys Gln Ala Gly Asp Val Glu Glu Asn Pro Gly Pro
            20                  25                  30
```

<210> SEQ ID NO 161
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Linker-GSG"

<400> SEQUENCE: 161

Ala Pro Val Lys Gln Gly Ser Gly
1               5

<210> SEQ ID NO 162
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Linker"

<400> SEQUENCE: 162

Ala Pro Val Lys Gln
1               5

<210> SEQ ID NO 163
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="GM-CSFR-alpha signal peptide"

<400> SEQUENCE: 163

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 164
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Ig Kappa signal peptide"

<400> SEQUENCE: 164

Met Arg Leu Pro Ala Gln Leu Leu Gly Leu Leu Met Leu Trp Val Pro
1               5                   10                  15

Gly Ser Ser Gly
            20

<210> SEQ ID NO 165
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="IgE signal peptide"

<400> SEQUENCE: 165

Met Asp Trp Thr Trp Ile Leu Phe Leu Val Ala Ala Ala Thr Arg Val
1               5                   10                  15

His Ser

<210> SEQ ID NO 166
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="CD8-alpha signal peptide"

<400> SEQUENCE: 166

Met Ala Leu Pro Val Thr Ala Leu Leu Leu Pro Leu Ala Leu Leu Leu
1               5                   10                  15

His Ala Ala Arg Pro
            20

<210> SEQ ID NO 167
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="TVB2(T21A)signal peptide"

<400> SEQUENCE: 167

Met Gly Thr Ser Leu Leu Cys Trp Met Ala Leu Cys Leu Leu Gly Ala
1               5                   10                  15

Asp His Ala Asp Ala
            20

<210> SEQ ID NO 168
<211> LENGTH: 24
<212> TYPE: PRT
<213> ORGANISM: Homo sapiens
<220> FEATURE:
<221> NAME/KEY: source
<223> OTHER INFORMATION: /note="CD52 signal peptide"

<400> SEQUENCE: 168

Met Lys Arg Phe Leu Phe Leu Leu Leu Thr Ile Ser Leu Leu Val Met
1               5                   10                  15

Val Gln Ile Gln Thr Gly Leu Ser
            20

<210> SEQ ID NO 169
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Low-affinity nerve growth factor receptor (LNGFR, TNFRSF16) signal peptide"

<400> SEQUENCE: 169

```
Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala
            20                  25
```

<210> SEQ ID NO 170
<211> LENGTH: 47
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="CD8-alpha hinge region"

<400> SEQUENCE: 170

```
Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp
        35                  40                  45
```

<210> SEQ ID NO 171
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="CD8 alpha 2x"

<400> SEQUENCE: 171

```
Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp Lys
        35                  40                  45

Pro Thr Thr Thr Pro Ala Pro Arg Pro Pro Thr Pro Ala Pro Thr Ile
    50                  55                  60

Ala Ser Gln Pro Leu Ser Leu Arg Pro Glu Ala Cys Arg Pro Ala Ala
65                  70                  75                  80

Gly Gly Ala Val His Thr Arg Gly Leu Asp Phe Ala Cys Asp
                85                  90
```

<210> SEQ ID NO 172
<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="CD8 alpha 3x"

<400> SEQUENCE: 172

```
Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp Lys
        35                  40                  45

Pro Thr Thr Thr Pro Ala Pro Arg Pro Pro Thr Pro Ala Pro Thr Ile
    50                  55                  60

Ala Ser Gln Pro Leu Ser Leu Arg Pro Glu Ala Ser Arg Pro Ala Ala
65                  70                  75                  80

Gly Gly Ala Val His Thr Arg Gly Leu Asp Phe Ala Ser Asp Lys Pro
                85                  90                  95

Thr Thr Thr Pro Ala Pro Arg Pro Pro Thr Pro Ala Pro Thr Ile Ala
            100                 105                 110

Ser Gln Pro Leu Ser Leu Arg Pro Glu Ala Cys Arg Pro Ala Ala Gly
        115                 120                 125

Gly Ala Val His Thr Arg Gly Leu Asp Phe Ala Cys Asp
    130                 135                 140
```

<210> SEQ ID NO 173
<211> LENGTH: 188
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="CD8 alpha 4x"

<400> SEQUENCE: 173

```
Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp Lys
        35                  40                  45

Pro Thr Thr Thr Pro Ala Pro Arg Pro Pro Thr Pro Ala Pro Thr Ile
    50                  55                  60

Ala Ser Gln Pro Leu Ser Leu Arg Pro Glu Ala Ser Arg Pro Ala Ala
65                  70                  75                  80

Gly Gly Ala Val His Thr Arg Gly Leu Asp Phe Ala Ser Asp Lys Pro
                85                  90                  95

Thr Thr Thr Pro Ala Pro Arg Pro Pro Thr Pro Ala Pro Thr Ile Ala
            100                 105                 110

Ser Gln Pro Leu Ser Leu Arg Pro Glu Ala Ser Arg Pro Ala Ala Gly
        115                 120                 125
```

```
Gly Ala Val His Thr Arg Gly Leu Asp Phe Ala Ser Asp Lys Pro Thr
    130                 135                 140

Thr Thr Pro Ala Pro Arg Pro Pro Thr Pro Ala Pro Thr Ile Ala Ser
145                 150                 155                 160

Gln Pro Leu Ser Leu Arg Pro Glu Ala Cys Arg Pro Ala Ala Gly Gly
                165                 170                 175

Ala Val His Thr Arg Gly Leu Asp Phe Ala Cys Asp
            180                 185


<210> SEQ ID NO 174
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="CD8-alpha TM domain"

<400> SEQUENCE: 174

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn
            20                  25


<210> SEQ ID NO 175
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="CD28 TM domain"

<400> SEQUENCE: 175

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 176
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="CD28 signaling domain"

<400> SEQUENCE: 176

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 177
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="CD3 zeta signaling domain"

<400> SEQUENCE: 177

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 178
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="4-1BB signaling domain"

<400> SEQUENCE: 178

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 179
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="DNAX-activation protein 10 (DAP 10) Signaling Domain"

<400> SEQUENCE: 179

```
Leu Cys Ala Arg Pro Arg Arg Ser Pro Ala Gln Glu Asp Gly Lys Val
1               5                   10                  15
```

```
Tyr Ile Asn Met Pro Gly Arg Gly
            20


<210> SEQ ID NO 180
<211> LENGTH: 52
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="DNAX-activation protein 12 (DAP12)
      Signaling Domain"

<400> SEQUENCE: 180

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
            20                  25                  30

Leu Gln Gly Gln Arg Ser Asp Val Tyr Ser Asp Leu Asn Thr Gln Arg
        35                  40                  45

Pro Tyr Tyr Lys
    50


<210> SEQ ID NO 181
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="VP16 activation domain"

<400> SEQUENCE: 181

Gly Pro Lys Lys Lys Arg Lys Val Ala Pro Pro Thr Asp Val Ser Leu
1               5                   10                  15

Gly Asp Glu Leu His Leu Asp Gly Glu Asp Val Ala Met Ala His Ala
            20                  25                  30

Asp Ala Leu Asp Asp Phe Asp Leu Asp Met Leu Gly Asp Gly Asp Ser
        35                  40                  45

Pro Gly Pro Gly Phe Thr Pro His Asp Ser Ala Pro Tyr Gly Ala Leu
    50                  55                  60

Asp Met Ala Asp Phe Glu Phe Glu Gln Met Phe Thr Asp Ala Leu Gly
65                  70                  75                  80

Ile Asp Glu Tyr Gly Gly
                85


<210> SEQ ID NO 182
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Retinoid x receptor (RxR)"

<400> SEQUENCE: 182
```

```
Glu Met Pro Val Asp Arg Ile Leu Glu Ala Glu Leu Ala Val Glu Gln
1               5                   10                  15

Lys Ser Asp Gln Gly Val Glu Gly Pro Gly Gly Thr Gly Gly Ser Gly
            20                  25                  30

Ser Ser Pro Asn Asp Pro Val Thr Asn Ile Cys Gln Ala Ala Asp Lys
        35                  40                  45

Gln Leu Phe Thr Leu Val Glu Trp Ala Lys Arg Ile Pro His Phe Ser
    50                  55                  60

Ser Leu Pro Leu Asp Asp Gln Val Ile Leu Leu Arg Ala Gly Trp Asn
65                  70                  75                  80

Glu Leu Leu Ile Ala Ser Phe Ser His Arg Ser Ile Asp Val Arg Asp
                85                  90                  95

Gly Ile Leu Leu Ala Thr Gly Leu His Val His Arg Asn Ser Ala His
            100                 105                 110

Ser Ala Gly Val Gly Ala Ile Phe Asp Arg Val Leu Thr Glu Leu Val
        115                 120                 125

Ser Lys Met Arg Asp Met Arg Met Asp Lys Thr Glu Leu Gly Cys Leu
    130                 135                 140

Arg Ala Ile Ile Leu Phe Asn Pro Glu Val Arg Gly Leu Lys Ser Ala
145                 150                 155                 160

Gln Glu Val Glu Leu Leu Arg Glu Lys Val Tyr Ala Ala Leu Glu Glu
                165                 170                 175

Tyr Thr Arg Thr Thr His Pro Asp Glu Pro Gly Arg Phe Ala Lys Leu
            180                 185                 190

Leu Leu Arg Leu Pro Ser Leu Arg Ser Ile Gly Leu Lys Cys Leu Glu
        195                 200                 205

His Leu Phe Phe Phe Arg Leu Ile Gly Asp Val Pro Ile Asp Thr Phe
    210                 215                 220

Leu Met Glu Met Leu Glu Ser Pro Ser Asp Ser
225                 230                 235
```

<210> SEQ ID NO 183
<211> LENGTH: 323
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="VP16-linker-RxR"

<400> SEQUENCE: 183

```
Gly Pro Lys Lys Lys Arg Lys Val Ala Pro Pro Thr Asp Val Ser Leu
1               5                   10                  15

Gly Asp Glu Leu His Leu Asp Gly Glu Asp Val Ala Met Ala His Ala
            20                  25                  30

Asp Ala Leu Asp Asp Phe Asp Leu Asp Met Leu Gly Asp Gly Asp Ser
        35                  40                  45

Pro Gly Pro Gly Phe Thr Pro His Asp Ser Ala Pro Tyr Gly Ala Leu
    50                  55                  60

Asp Met Ala Asp Phe Glu Phe Glu Gln Met Phe Thr Asp Ala Leu Gly
65                  70                  75                  80

Ile Asp Glu Tyr Gly Gly Glu Phe Glu Met Pro Val Asp Arg Ile Leu
                85                  90                  95

Glu Ala Glu Leu Ala Val Glu Gln Lys Ser Asp Gln Gly Val Glu Gly
```

```
            100                 105                 110

Pro Gly Gly Thr Gly Gly Ser Gly Ser Ser Pro Asn Asp Pro Val Thr
        115                 120                 125

Asn Ile Cys Gln Ala Ala Asp Lys Gln Leu Phe Thr Leu Val Glu Trp
    130                 135                 140

Ala Lys Arg Ile Pro His Phe Ser Ser Leu Pro Leu Asp Asp Gln Val
145                 150                 155                 160

Ile Leu Leu Arg Ala Gly Trp Asn Glu Leu Leu Ile Ala Ser Phe Ser
                165                 170                 175

His Arg Ser Ile Asp Val Arg Asp Gly Ile Leu Leu Ala Thr Gly Leu
            180                 185                 190

His Val His Arg Asn Ser Ala His Ser Ala Gly Val Gly Ala Ile Phe
        195                 200                 205

Asp Arg Val Leu Thr Glu Leu Val Ser Lys Met Arg Asp Met Arg Met
    210                 215                 220

Asp Lys Thr Glu Leu Gly Cys Leu Arg Ala Ile Ile Leu Phe Asn Pro
225                 230                 235                 240

Glu Val Arg Gly Leu Lys Ser Ala Gln Glu Val Glu Leu Leu Arg Glu
                245                 250                 255

Lys Val Tyr Ala Ala Leu Glu Glu Tyr Thr Arg Thr Thr His Pro Asp
            260                 265                 270

Glu Pro Gly Arg Phe Ala Lys Leu Leu Leu Arg Leu Pro Ser Leu Arg
        275                 280                 285

Ser Ile Gly Leu Lys Cys Leu Glu His Leu Phe Phe Phe Arg Leu Ile
    290                 295                 300

Gly Asp Val Pro Ile Asp Thr Phe Leu Met Glu Met Leu Glu Ser Pro
305                 310                 315                 320

Ser Asp Ser


<210> SEQ ID NO 184
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="GAL4 DNA Binding Domain"

<400> SEQUENCE: 184

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110
```

```
Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe
145                 150


<210> SEQ ID NO 185
<211> LENGTH: 336
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Ecdysone Receptor Ligand Binding Domain
      - VY variant (EcR)"

<400> SEQUENCE: 185

Ile Arg Pro Glu Cys Val Val Pro Glu Thr Gln Cys Ala Met Lys Arg
1               5                   10                  15

Lys Glu Lys Lys Ala Gln Lys Glu Lys Asp Lys Leu Pro Val Ser Thr
            20                  25                  30

Thr Thr Val Asp Asp His Met Pro Pro Ile Met Gln Cys Glu Pro Pro
        35                  40                  45

Pro Pro Glu Ala Ala Arg Ile His Glu Val Val Pro Arg Phe Leu Ser
    50                  55                  60

Asp Lys Leu Leu Val Thr Asn Arg Gln Lys Asn Ile Pro Gln Leu Thr
65                  70                  75                  80

Ala Asn Gln Gln Phe Leu Ile Ala Arg Leu Ile Trp Tyr Gln Asp Gly
                85                  90                  95

Tyr Glu Gln Pro Ser Asp Glu Asp Leu Lys Arg Ile Thr Gln Thr Trp
            100                 105                 110

Gln Gln Ala Asp Asp Glu Asn Glu Glu Ser Asp Thr Pro Phe Arg Gln
        115                 120                 125

Ile Thr Glu Met Thr Ile Leu Thr Val Gln Leu Ile Val Glu Phe Ala
    130                 135                 140

Lys Gly Leu Pro Gly Phe Ala Lys Ile Ser Gln Pro Asp Gln Ile Thr
145                 150                 155                 160

Leu Leu Lys Ala Cys Ser Ser Glu Val Met Met Leu Arg Val Ala Arg
                165                 170                 175

Arg Tyr Asp Ala Ala Ser Asp Ser Ile Leu Phe Ala Asn Asn Gln Ala
            180                 185                 190

Tyr Thr Arg Asp Asn Tyr Arg Lys Ala Gly Met Ala Glu Val Ile Glu
        195                 200                 205

Asp Leu Leu His Phe Cys Arg Cys Met Tyr Ser Met Ala Leu Asp Asn
    210                 215                 220

Ile His Tyr Ala Leu Leu Thr Ala Val Val Ile Phe Ser Asp Arg Pro
225                 230                 235                 240

Gly Leu Glu Gln Pro Gln Leu Val Glu Glu Ile Gln Arg Tyr Tyr Leu
                245                 250                 255

Asn Thr Leu Arg Ile Tyr Ile Leu Asn Gln Leu Ser Gly Ser Ala Arg
            260                 265                 270

Ser Ser Val Ile Tyr Gly Lys Ile Leu Ser Ile Leu Ser Glu Leu Arg
        275                 280                 285
```

```
Thr Leu Gly Met Gln Asn Ser Asn Met Cys Ile Ser Leu Lys Leu Lys
    290                 295                 300

Asn Arg Lys Leu Pro Pro Phe Leu Glu Glu Ile Trp Asp Val Ala Asp
305                 310                 315                 320

Met Ser His Thr Gln Pro Pro Pro Ile Leu Glu Ser Pro Thr Asn Leu
                325                 330                 335


<210> SEQ ID NO 186
<211> LENGTH: 335
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Ecdysone Receptor Ligand Binding Domain
      - VY variant (EcR)"

<400> SEQUENCE: 186

Arg Pro Glu Cys Val Val Pro Glu Thr Gln Cys Ala Met Lys Arg Lys
1               5                   10                  15

Glu Lys Lys Ala Gln Lys Glu Lys Asp Lys Leu Pro Val Ser Thr Thr
            20                  25                  30

Thr Val Asp Asp His Met Pro Pro Ile Met Gln Cys Glu Pro Pro Pro
        35                  40                  45

Pro Glu Ala Ala Arg Ile His Glu Val Val Pro Arg Phe Leu Ser Asp
    50                  55                  60

Lys Leu Leu Val Thr Asn Arg Gln Lys Asn Ile Pro Gln Leu Thr Ala
65                  70                  75                  80

Asn Gln Gln Phe Leu Ile Ala Arg Leu Ile Trp Tyr Gln Asp Gly Tyr
                85                  90                  95

Glu Gln Pro Ser Asp Glu Asp Leu Lys Arg Ile Thr Gln Thr Trp Gln
            100                 105                 110

Gln Ala Asp Asp Glu Asn Glu Glu Ser Asp Thr Pro Phe Arg Gln Ile
        115                 120                 125

Thr Glu Met Thr Ile Leu Thr Val Gln Leu Ile Val Glu Phe Ala Lys
    130                 135                 140

Gly Leu Pro Gly Phe Ala Lys Ile Ser Gln Pro Asp Gln Ile Thr Leu
145                 150                 155                 160

Leu Lys Ala Cys Ser Ser Glu Val Met Met Leu Arg Val Ala Arg Arg
                165                 170                 175

Tyr Asp Ala Ala Ser Asp Ser Ile Leu Phe Ala Asn Asn Gln Ala Tyr
            180                 185                 190

Thr Arg Asp Asn Tyr Arg Lys Ala Gly Met Ala Glu Val Ile Glu Asp
        195                 200                 205

Leu Leu His Phe Cys Arg Cys Met Tyr Ser Met Ala Leu Asp Asn Ile
    210                 215                 220

His Tyr Ala Leu Leu Thr Ala Val Val Ile Phe Ser Asp Arg Pro Gly
225                 230                 235                 240

Leu Glu Gln Pro Gln Leu Val Glu Glu Ile Gln Arg Tyr Tyr Leu Asn
                245                 250                 255

Thr Leu Arg Ile Tyr Ile Leu Asn Gln Leu Ser Gly Ser Ala Arg Ser
            260                 265                 270

Ser Val Ile Tyr Gly Lys Ile Leu Ser Ile Leu Ser Glu Leu Arg Thr
        275                 280                 285
```

Leu Gly Met Gln Asn Ser Asn Met Cys Ile Ser Leu Lys Leu Lys Asn
    290                 295                 300

Arg Lys Leu Pro Pro Phe Leu Glu Glu Ile Trp Asp Val Ala Asp Met
305                 310                 315                 320

Ser His Thr Gln Pro Pro Pro Ile Leu Glu Ser Pro Thr Asn Leu
                325                 330                 335

<210> SEQ ID NO 187
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="GAL4-Linker-EcR"

<400> SEQUENCE: 187

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Ile Arg Pro Glu Cys Val Val Pro
145                 150                 155                 160

Glu Thr Gln Cys Ala Met Lys Arg Lys Glu Lys Lys Ala Gln Lys Glu
                165                 170                 175

Lys Asp Lys Leu Pro Val Ser Thr Thr Thr Val Asp Asp His Met Pro
            180                 185                 190

Pro Ile Met Gln Cys Glu Pro Pro Pro Pro Glu Ala Ala Arg Ile His
        195                 200                 205

Glu Val Val Pro Arg Phe Leu Ser Asp Lys Leu Leu Val Thr Asn Arg
    210                 215                 220

Gln Lys Asn Ile Pro Gln Leu Thr Ala Asn Gln Gln Phe Leu Ile Ala
225                 230                 235                 240

Arg Leu Ile Trp Tyr Gln Asp Gly Tyr Glu Gln Pro Ser Asp Glu Asp
                245                 250                 255

Leu Lys Arg Ile Thr Gln Thr Trp Gln Gln Ala Asp Asp Glu Asn Glu
            260                 265                 270

Glu Ser Asp Thr Pro Phe Arg Gln Ile Thr Glu Met Thr Ile Leu Thr
        275                 280                 285

Val Gln Leu Ile Val Glu Phe Ala Lys Gly Leu Pro Gly Phe Ala Lys 290 295 300

Ile Ser Gln Pro Asp Gln Ile Thr Leu Leu Lys Ala Cys Ser Ser Glu
305 310 315 320

Val Met Met Leu Arg Val Ala Arg Arg Tyr Asp Ala Ala Ser Asp Ser
325 330 335

Ile Leu Phe Ala Asn Asn Gln Ala Tyr Thr Arg Asp Asn Tyr Arg Lys
340 345 350

Ala Gly Met Ala Glu Val Ile Glu Asp Leu Leu His Phe Cys Arg Cys
355 360 365

Met Tyr Ser Met Ala Leu Asp Asn Ile His Tyr Ala Leu Leu Thr Ala
370 375 380

Val Val Ile Phe Ser Asp Arg Pro Gly Leu Glu Gln Pro Gln Leu Val
385 390 395 400

Glu Glu Ile Gln Arg Tyr Tyr Leu Asn Thr Leu Arg Ile Tyr Ile Leu
405 410 415

Asn Gln Leu Ser Gly Ser Ala Arg Ser Ser Val Ile Tyr Gly Lys Ile
420 425 430

Leu Ser Ile Leu Ser Glu Leu Arg Thr Leu Gly Met Gln Asn Ser Asn
435 440 445

Met Cys Ile Ser Leu Lys Leu Lys Asn Arg Lys Leu Pro Pro Phe Leu
450 455 460

Glu Glu Ile Trp Asp Val Ala Asp Met Ser His Thr Gln Pro Pro Pro
465 470 475 480

Ile Leu Glu Ser Pro Thr Asn Leu
485

<210> SEQ ID NO 188
<211> LENGTH: 487
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="GAL4-Linker-EcR"

<400> SEQUENCE: 188

Met Lys Leu Leu Ser Ser Ile Glu Gln Ala Cys Asp Ile Cys Arg Leu
1 5 10 15

Lys Lys Leu Lys Cys Ser Lys Glu Lys Pro Lys Cys Ala Lys Cys Leu
20 25 30

Lys Asn Asn Trp Glu Cys Arg Tyr Ser Pro Lys Thr Lys Arg Ser Pro
35 40 45

Leu Thr Arg Ala His Leu Thr Glu Val Glu Ser Arg Leu Glu Arg Leu
50 55 60

Glu Gln Leu Phe Leu Leu Ile Phe Pro Arg Glu Asp Leu Asp Met Ile
65 70 75 80

Leu Lys Met Asp Ser Leu Gln Asp Ile Lys Ala Leu Leu Thr Gly Leu
85 90 95

Phe Val Gln Asp Asn Val Asn Lys Asp Ala Val Thr Asp Arg Leu Ala
100 105 110

Ser Val Glu Thr Asp Met Pro Leu Thr Leu Arg Gln His Arg Ile Ser
115 120 125

Ala Thr Ser Ser Ser Glu Glu Ser Ser Asn Lys Gly Gln Arg Gln Leu
130 135 140

```
Thr Val Ser Pro Glu Phe Pro Gly Arg Pro Glu Cys Val Val Pro Glu
145                 150                 155                 160

Thr Gln Cys Ala Met Lys Arg Lys Glu Lys Lys Ala Gln Lys Glu Lys
                165                 170                 175

Asp Lys Leu Pro Val Ser Thr Thr Thr Val Asp Asp His Met Pro Pro
            180                 185                 190

Ile Met Gln Cys Glu Pro Pro Pro Pro Glu Ala Ala Arg Ile His Glu
        195                 200                 205

Val Val Pro Arg Phe Leu Ser Asp Lys Leu Leu Val Thr Asn Arg Gln
    210                 215                 220

Lys Asn Ile Pro Gln Leu Thr Ala Asn Gln Gln Phe Leu Ile Ala Arg
225                 230                 235                 240

Leu Ile Trp Tyr Gln Asp Gly Tyr Glu Gln Pro Ser Asp Glu Asp Leu
                245                 250                 255

Lys Arg Ile Thr Gln Thr Trp Gln Gln Ala Asp Asp Glu Asn Glu Glu
            260                 265                 270

Ser Asp Thr Pro Phe Arg Gln Ile Thr Glu Met Thr Ile Leu Thr Val
        275                 280                 285

Gln Leu Ile Val Glu Phe Ala Lys Gly Leu Pro Gly Phe Ala Lys Ile
    290                 295                 300

Ser Gln Pro Asp Gln Ile Thr Leu Leu Lys Ala Cys Ser Ser Glu Val
305                 310                 315                 320

Met Met Leu Arg Val Ala Arg Arg Tyr Asp Ala Ala Ser Asp Ser Ile
                325                 330                 335

Leu Phe Ala Asn Asn Gln Ala Tyr Thr Arg Asp Asn Tyr Arg Lys Ala
            340                 345                 350

Gly Met Ala Glu Val Ile Glu Asp Leu Leu His Phe Cys Arg Cys Met
        355                 360                 365

Tyr Ser Met Ala Leu Asp Asn Ile His Tyr Ala Leu Leu Thr Ala Val
    370                 375                 380

Val Ile Phe Ser Asp Arg Pro Gly Leu Glu Gln Pro Gln Leu Val Glu
385                 390                 395                 400

Glu Ile Gln Arg Tyr Tyr Leu Asn Thr Leu Arg Ile Tyr Ile Leu Asn
                405                 410                 415

Gln Leu Ser Gly Ser Ala Arg Ser Ser Val Ile Tyr Gly Lys Ile Leu
            420                 425                 430

Ser Ile Leu Ser Glu Leu Arg Thr Leu Gly Met Gln Asn Ser Asn Met
        435                 440                 445

Cys Ile Ser Leu Lys Leu Lys Asn Arg Lys Leu Pro Pro Phe Leu Glu
    450                 455                 460

Glu Ile Trp Asp Val Ala Asp Met Ser His Thr Gln Pro Pro Pro Ile
465                 470                 475                 480

Leu Glu Ser Pro Thr Asn Leu
                485
```

<210> SEQ ID NO 189
<211> LENGTH: 335
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Truncated EGFR (huEGFRt) (Her1t)"

<400> SEQUENCE: 189

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Cys Arg Asn Val Ser Arg Gly Arg Glu Cys Val Asp Lys Cys Asn Leu
195 200 205

Leu Glu Gly Glu Pro Arg Glu Phe Val Glu Asn Ser Glu Cys Ile Gln
210 215 220

Cys His Pro Glu Cys Leu Pro Gln Ala Met Asn Ile Thr Cys Thr Gly
225 230 235 240

Arg Gly Pro Asp Asn Cys Ile Gln Cys Ala His Tyr Ile Asp Gly Pro
245 250 255

His Cys Val Lys Thr Cys Pro Ala Gly Val Met Gly Glu Asn Asn Thr
260 265 270

Leu Val Trp Lys Tyr Ala Asp Ala Gly His Val Cys His Leu Cys His
275 280 285

Pro Asn Cys Thr Tyr Gly Cys Thr Gly Pro Gly Leu Glu Gly Cys Pro
290 295 300

Thr Asn Gly Pro Lys Ile Pro Ser Ile Ala Thr Gly Met Val Gly Ala
305 310 315 320

Leu Leu Leu Leu Leu Val Val Ala Leu Gly Ile Gly Leu Phe Met
325 330 335

<210> SEQ ID NO 190
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="EGFR truncated design 1 (Her1 truncated design 1) (HER1t1)"

<400> SEQUENCE: 190

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Gly Gly Gly Gly Ser Gly Gly Gly Gly Ser Gly Gly Gly Gly Ser Gly
195 200 205

Gly Gly Gly Ser Phe Trp Val Leu Val Val Val Gly Gly Val Leu Ala
210 215 220

Cys Tyr Ser Leu Leu Val Thr Val Ala Phe Ile Ile Phe Trp Val Arg
225 230 235 240

Ser Lys Arg Ser

<210> SEQ ID NO 191
<211> LENGTH: 257
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="EGFR truncated design 2 (Her1 truncated design 2) (HER1t2)"

<400> SEQUENCE: 191

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn

```
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Gly Gly Gly
        195                 200                 205

Gly Ser Gly Gly Gly Gly Ser Gly Gly Gly Gly Ser Gly Gly Gly Gly
    210                 215                 220

Ser Phe Trp Val Leu Val Val Val Gly Gly Val Leu Ala Cys Tyr Ser
225                 230                 235                 240

Leu Leu Val Thr Val Ala Phe Ile Ile Phe Trp Val Arg Ser Lys Arg
                245                 250                 255

Ser


<210> SEQ ID NO 192
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="EGFR truncated design 3 (Her1 truncated
      design 3) (HER1t3)"

<400> SEQUENCE: 192

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140
```

```
Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Gly Gly Gly Gly Ser Gly Gly Gly Gly Ser Gly Gly Gly Gly Ser Gly
225                 230                 235                 240

Gly Gly Gly Ser Phe Trp Val Leu Val Val Val Gly Gly Val Leu Ala
                245                 250                 255

Cys Tyr Ser Leu Leu Val Thr Val Ala Phe Ile Ile Phe Trp Val Arg
            260                 265                 270

Ser Lys Arg Ser
        275
```

<210> SEQ ID NO 193
<211> LENGTH: 295
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="EGFR truncated design 4 (Her1 truncated design 4) (HER1t4)"

<400> SEQUENCE: 193

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190
```

```
Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Gly Gly Gly Gly Ser Gly Gly Gly
                245                 250                 255

Gly Ser Gly Gly Gly Gly Ser Phe Trp Val Leu Val Val Val Gly Gly
            260                 265                 270

Val Leu Ala Cys Tyr Ser Leu Leu Val Thr Val Ala Phe Ile Ile Phe
        275                 280                 285

Trp Val Arg Ser Lys Arg Ser
    290                 295


<210> SEQ ID NO 194
<211> LENGTH: 308
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="EGFR truncated design 5 (Her1 truncated
      design 5) (HER1t5)"

<400> SEQUENCE: 194

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220
```

```
Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Gly Gly Gly Gly Ser Gly Gly Gly Gly Ser Gly
            260                 265                 270

Gly Gly Gly Ser Phe Trp Val Leu Val Val Val Gly Gly Val Leu Ala
        275                 280                 285

Cys Tyr Ser Leu Leu Val Thr Val Ala Phe Ile Ile Phe Trp Val Arg
    290                 295                 300

Ser Lys Arg Ser
305


<210> SEQ ID NO 195
<211> LENGTH: 328
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="EGFR truncated design 6 (Her1 truncated
      design 6) (HER1t6)"

<400> SEQUENCE: 195

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240
```

Arg Gly Pro Asp Asn Cys Ile Gln Cys Ala His Tyr Ile Asp Gly Pro
245 250 255

His Cys Val Lys Thr Cys Pro Ala Gly Val Met Gly Glu Asn Asn Thr
260 265 270

Leu Val Trp Lys Tyr Ala Asp Ala Gly His Val Cys His Leu Gly Gly
275 280 285

Gly Gly Ser Gly Gly Gly Gly Ser Phe Trp Val Leu Val Val Val Gly
290 295 300

Gly Val Leu Ala Cys Tyr Ser Leu Leu Val Thr Val Ala Phe Ile Ile
305 310 315 320

Phe Trp Val Arg Ser Lys Arg Ser
325

<210> SEQ ID NO 196
<211> LENGTH: 343
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="EGFR truncated design 7 (Her1 truncated design 7) (HER1t7)"

<400> SEQUENCE: 196

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Cys Arg Asn Val Ser Arg Gly Arg Glu Cys Val Asp Lys Cys Asn Leu
195 200 205

Leu Glu Gly Glu Pro Arg Glu Phe Val Glu Asn Ser Glu Cys Ile Gln
210 215 220

Cys His Pro Glu Cys Leu Pro Gln Ala Met Asn Ile Thr Cys Thr Gly
225 230 235 240

```
Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Gly Gly Gly Gly Gly Gly Ser Phe Trp Val Leu Val Val Val Gly Gly
305                 310                 315                 320

Val Leu Ala Cys Tyr Ser Leu Leu Val Thr Val Ala Phe Ile Ile Phe
                325                 330                 335

Trp Val Arg Ser Lys Arg Ser
            340
```

<210> SEQ ID NO 197
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="EGFR truncated design 8 (Her1 truncated design 8) (HER1t8)"

<400> SEQUENCE: 197

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Gly Gly Gly Gly Ser Gly Gly Gly Gly Ser Gly Gly Gly Gly Ser Gly
        195                 200                 205

Gly Gly Gly Ser Glu Ile Thr Leu Ile Ile Phe Gly Val Met Ala Gly
    210                 215                 220
```

```
Val Ile Gly Thr Ile Leu Leu Ile Ser Tyr Gly Ile Arg Arg Gly Gly
225                 230                 235                 240

Gly Ser


<210> SEQ ID NO 198
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="EGFR truncated design 9 (Her1 truncated
      design 9) (HER1t9)"

<400> SEQUENCE: 198

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Gly Gly Gly Gly Ser Gly Gly Gly Gly Ser Gly Gly Gly Gly Ser Gly
        195                 200                 205

Gly Gly Gly Ser Ile Thr Leu Ile Ile Phe Gly Val Met Ala Gly Val
    210                 215                 220

Ile Gly Thr Ile Leu Leu Ile Ser Tyr Gly Ile Gly Gly Gly Ser
225                 230                 235


<210> SEQ ID NO 199
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="EGFR truncated design 10 (Her1 truncated
```

design 10) (HER1t10)"

<400> SEQUENCE: 199

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Gly Gly Gly Gly Ser Gly Gly Gly Gly Ser Gly Gly Gly Gly Ser Gly
195 200 205

Gly Gly Gly Ser Ile Thr Leu Ile Ile Phe Gly Val Met Ala Gly Val
210 215 220

Ile Gly Thr Ile Leu Leu Ala Leu Leu Ile Trp Gly Gly Gly Ser
225 230 235

<210> SEQ ID NO 200
<211> LENGTH: 237
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="EGFR truncated design 11 (Her1 truncated design 11) (HER1t11)"

<400> SEQUENCE: 200

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

-continued

```
Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Gly Gly Gly Gly Ser Gly Gly Gly Gly Ser Gly Gly Gly Gly Ser Gly
        195                 200                 205

Gly Gly Gly Ser Leu Cys Tyr Leu Leu Asp Gly Ile Leu Phe Ile Tyr
    210                 215                 220

Gly Val Ile Leu Thr Ala Leu Phe Leu Gly Gly Gly Ser
225                 230                 235


<210> SEQ ID NO 201
<211> LENGTH: 297
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="FL CD20"

<400> SEQUENCE: 201

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175
```

```
Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295


<210> SEQ ID NO 202
<211> LENGTH: 263
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Truncated CD20 design 1 (CD20t1)
      [CD20(M1-E263]"

<400> SEQUENCE: 202

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205
```

```
Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu
            260


<210> SEQ ID NO 203
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Interleukin-15"

<400> SEQUENCE: 203

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 204
<211> LENGTH: 237
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Interleukin-15 receptor alpha"

<400> SEQUENCE: 204

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80
```

Thr Thr Ala Gly Val Thr Pro Gln Pro Glu Ser Leu Ser Pro Ser Gly
85 90 95

Lys Glu Pro Ala Ala Ser Ser Pro Ser Ser Asn Asn Thr Ala Ala Thr
100 105 110

Thr Ala Ala Ile Val Pro Gly Ser Gln Leu Met Pro Ser Lys Ser Pro
115 120 125

Ser Thr Gly Thr Thr Glu Ile Ser Ser His Glu Ser Ser His Gly Thr
130 135 140

Pro Ser Gln Thr Thr Ala Lys Asn Trp Glu Leu Thr Ala Ser Ala Ser
145 150 155 160

His Gln Pro Pro Gly Val Tyr Pro Gln Gly His Ser Asp Thr Thr Val
165 170 175

Ala Ile Ser Thr Ser Thr Val Leu Leu Cys Gly Leu Ser Ala Val Ser
180 185 190

Leu Leu Ala Cys Tyr Leu Lys Ser Arg Gln Thr Pro Pro Leu Ala Ser
195 200 205

Val Glu Met Glu Ala Met Glu Ala Leu Pro Val Thr Trp Gly Thr Ser
210 215 220

Ser Arg Asp Glu Asp Leu Glu Asn Cys Ser His His Leu
225 230 235

<210> SEQ ID NO 205
<211> LENGTH: 395
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Membrane bound Interleukin-15 with signal peptide"

<400> SEQUENCE: 205

Met Asp Trp Thr Trp Ile Leu Phe Leu Val Ala Ala Ala Thr Arg Val
1 5 10 15

His Ser Asn Trp Val Asn Val Ile Ser Asp Leu Lys Lys Ile Glu Asp
20 25 30

Leu Ile Gln Ser Met His Ile Asp Ala Thr Leu Tyr Thr Glu Ser Asp
35 40 45

Val His Pro Ser Cys Lys Val Thr Ala Met Lys Cys Phe Leu Leu Glu
50 55 60

Leu Gln Val Ile Ser Leu Glu Ser Gly Asp Ala Ser Ile His Asp Thr
65 70 75 80

Val Glu Asn Leu Ile Ile Leu Ala Asn Asn Ser Leu Ser Ser Asn Gly
85 90 95

Asn Val Thr Glu Ser Gly Cys Lys Glu Cys Glu Glu Leu Glu Glu Lys
100 105 110

Asn Ile Lys Glu Phe Leu Gln Ser Phe Val His Ile Val Gln Met Phe
115 120 125

Ile Asn Thr Ser Ser Gly Gly Gly Ser Gly Gly Gly Gly Ser Gly Gly
130 135 140

Gly Gly Ser Gly Gly Gly Gly Ser Gly Gly Gly Ser Leu Gln Ile Thr
145 150 155 160

Cys Pro Pro Pro Met Ser Val Glu His Ala Asp Ile Trp Val Lys Ser
165 170 175

```
Tyr Ser Leu Tyr Ser Arg Glu Arg Tyr Ile Cys Asn Ser Gly Phe Lys
            180                 185                 190

Arg Lys Ala Gly Thr Ser Ser Leu Thr Glu Cys Val Leu Asn Lys Ala
        195                 200                 205

Thr Asn Val Ala His Trp Thr Thr Pro Ser Leu Lys Cys Ile Arg Asp
    210                 215                 220

Pro Ala Leu Val His Gln Arg Pro Ala Pro Pro Ser Thr Val Thr Thr
225                 230                 235                 240

Ala Gly Val Thr Pro Gln Pro Glu Ser Leu Ser Pro Ser Gly Lys Glu
                245                 250                 255

Pro Ala Ala Ser Ser Pro Ser Ser Asn Asn Thr Ala Ala Thr Thr Ala
            260                 265                 270

Ala Ile Val Pro Gly Ser Gln Leu Met Pro Ser Lys Ser Pro Ser Thr
        275                 280                 285

Gly Thr Thr Glu Ile Ser Ser His Glu Ser Ser His Gly Thr Pro Ser
    290                 295                 300

Gln Thr Thr Ala Lys Asn Trp Glu Leu Thr Ala Ser Ala Ser His Gln
305                 310                 315                 320

Pro Pro Gly Val Tyr Pro Gln Gly His Ser Asp Thr Thr Val Ala Ile
                325                 330                 335

Ser Thr Ser Thr Val Leu Leu Cys Gly Leu Ser Ala Val Ser Leu Leu
            340                 345                 350

Ala Cys Tyr Leu Lys Ser Arg Gln Thr Pro Pro Leu Ala Ser Val Glu
        355                 360                 365

Met Glu Ala Met Glu Ala Leu Pro Val Thr Trp Gly Thr Ser Ser Arg
    370                 375                 380

Asp Glu Asp Leu Glu Asn Cys Ser His His Leu
385                 390                 395
```

<210> SEQ ID NO 206
<211> LENGTH: 335
<212> TYPE: PRT
<213> ORGANISM: Mus sp.
<220> FEATURE:
<221> NAME/KEY: source
<223> OTHER INFORMATION: /note="Murine Interleukin-12 subunit beta (p40)"

<400> SEQUENCE: 206

```
Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125
```

```
Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                325                 330                 335


<210> SEQ ID NO 207
<211> LENGTH: 215
<212> TYPE: PRT
<213> ORGANISM: Mus sp.
<220> FEATURE:
<221> NAME/KEY: source
<223> OTHER INFORMATION: /note="Murine Interleukin-12 subunit alpha
      (p35)"

<400> SEQUENCE: 207

Met Cys Gln Ser Arg Tyr Leu Leu Phe Leu Ala Thr Leu Ala Leu Leu
1               5                   10                  15

Asn His Leu Ser Leu Ala Arg Val Ile Pro Val Ser Gly Pro Ala Arg
            20                  25                  30

Cys Leu Ser Gln Ser Arg Asn Leu Leu Lys Thr Thr Asp Asp Met Val
        35                  40                  45

Lys Thr Ala Arg Glu Lys Leu Lys His Tyr Ser Cys Thr Ala Glu Asp
    50                  55                  60

Ile Asp His Glu Asp Ile Thr Arg Asp Gln Thr Ser Thr Leu Lys Thr
65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
```

```
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
        195                 200                 205

Met Gly Tyr Leu Ser Ser Ala
    210                 215


<210> SEQ ID NO 208
<211> LENGTH: 535
<212> TYPE: PRT
<213> ORGANISM: Mus sp.
<220> FEATURE:
<221> NAME/KEY: source
<223> OTHER INFORMATION: /note="Murine single chain IL-12 (p40-linker-
      p35)"

<400> SEQUENCE: 208

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285
```

```
Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser Gly
                325                 330                 335

Gly Gly Gly Gly Gly Ser Arg Val Ile Pro Val Ser Gly Pro Ala Arg
            340                 345                 350

Cys Leu Ser Gln Ser Arg Asn Leu Leu Lys Thr Thr Asp Asp Met Val
        355                 360                 365

Lys Thr Ala Arg Glu Lys Leu Lys His Tyr Ser Cys Thr Ala Glu Asp
    370                 375                 380

Ile Asp His Glu Asp Ile Thr Arg Asp Gln Thr Ser Thr Leu Lys Thr
385                 390                 395                 400

Cys Leu Pro Leu Glu Leu His Lys Asn Glu Ser Cys Leu Ala Thr Arg
                405                 410                 415

Glu Thr Ser Ser Thr Thr Arg Gly Ser Cys Leu Pro Pro Gln Lys Thr
            420                 425                 430

Ser Leu Met Met Thr Leu Cys Leu Gly Ser Ile Tyr Glu Asp Leu Lys
        435                 440                 445

Met Tyr Gln Thr Glu Phe Gln Ala Ile Asn Ala Ala Leu Gln Asn His
    450                 455                 460

Asn His Gln Gln Ile Ile Leu Asp Lys Gly Met Leu Val Ala Ile Asp
465                 470                 475                 480

Glu Leu Met Gln Ser Leu Asn His Asn Gly Glu Thr Leu Arg Gln Lys
                485                 490                 495

Pro Pro Val Gly Glu Ala Asp Pro Tyr Arg Val Lys Met Lys Leu Cys
            500                 505                 510

Ile Leu Leu His Ala Phe Ser Thr Arg Val Val Thr Ile Asn Arg Val
        515                 520                 525

Met Gly Tyr Leu Ser Ser Ala
    530                 535
```

<210> SEQ ID NO 209
<211> LENGTH: 532
<212> TYPE: PRT
<213> ORGANISM: Homo sapiens
<220> FEATURE:
<221> NAME/KEY: source
<223> OTHER INFORMATION: /note="Human single chain IL-12 (p40-linker-p35)"

<400> SEQUENCE: 209

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95
```

```
Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Gly Gly Gly Ser Arg
                325                 330                 335

Asn Leu Pro Val Ala Thr Pro Asp Pro Gly Met Phe Pro Cys Leu His
            340                 345                 350

His Ser Gln Asn Leu Leu Arg Ala Val Ser Asn Met Leu Gln Lys Ala
        355                 360                 365

Arg Gln Thr Leu Glu Phe Tyr Pro Cys Thr Ser Glu Glu Ile Asp His
    370                 375                 380

Glu Asp Ile Thr Lys Asp Lys Thr Ser Thr Val Glu Ala Cys Leu Pro
385                 390                 395                 400

Leu Glu Leu Thr Lys Asn Glu Ser Cys Leu Asn Ser Arg Glu Thr Ser
                405                 410                 415

Phe Ile Thr Asn Gly Ser Cys Leu Ala Ser Arg Lys Thr Ser Phe Met
            420                 425                 430

Met Ala Leu Cys Leu Ser Ser Ile Tyr Glu Asp Leu Lys Met Tyr Gln
        435                 440                 445

Val Glu Phe Lys Thr Met Asn Ala Lys Leu Leu Met Asp Pro Lys Arg
    450                 455                 460

Gln Ile Phe Leu Asp Gln Asn Met Leu Ala Val Ile Asp Glu Leu Met
465                 470                 475                 480

Gln Ala Leu Asn Phe Asn Ser Glu Thr Val Pro Gln Lys Ser Ser Leu
                485                 490                 495

Glu Glu Pro Asp Phe Tyr Lys Thr Lys Ile Lys Leu Cys Ile Leu Leu
            500                 505                 510

His Ala Phe Arg Ile Arg Ala Val Thr Ile Asp Arg Val Met Ser Tyr
```

515 520 525

Leu Asn Ala Ser
530

<210> SEQ ID NO 210
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="CD19-specific chimeric antigen receptor (CD19-CD8a-CD28-CD3z)"

<400> SEQUENCE: 210

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Ser Thr Ser Gly
100 105 110

Ser Gly Lys Pro Gly Ser Gly Glu Gly Ser Thr Lys Gly Glu Val Lys
115 120 125

Leu Gln Glu Ser Gly Pro Gly Leu Val Ala Pro Ser Gln Ser Leu Ser
130 135 140

Val Thr Cys Thr Val Ser Gly Val Ser Leu Pro Asp Tyr Gly Val Ser
145 150 155 160

Trp Ile Arg Gln Pro Pro Arg Lys Gly Leu Glu Trp Leu Gly Val Ile
165 170 175

Trp Gly Ser Glu Thr Thr Tyr Tyr Asn Ser Ala Leu Lys Ser Arg Leu
180 185 190

Thr Ile Ile Lys Asp Asn Ser Lys Ser Gln Val Phe Leu Lys Met Asn
195 200 205

Ser Leu Gln Thr Asp Asp Thr Ala Ile Tyr Tyr Cys Ala Lys His Tyr
210 215 220

Tyr Tyr Gly Gly Ser Tyr Ala Met Asp Tyr Trp Gly Gln Gly Thr Ser
225 230 235 240

Val Thr Val Ser Ser Lys Pro Thr Thr Thr Pro Ala Pro Arg Pro Pro
245 250 255

Thr Pro Ala Pro Thr Ile Ala Ser Gln Pro Leu Ser Leu Arg Pro Glu
260 265 270

Ala Cys Arg Pro Ala Ala Gly Gly Ala Val His Thr Arg Gly Leu Asp
275 280 285

Phe Ala Cys Asp Ile Tyr Ile Trp Ala Pro Leu Ala Gly Thr Cys Gly
290 295 300

Val Leu Leu Leu Ser Leu Val Ile Thr Leu Tyr Cys Asn His Arg Asn 305 310 315 320

Arg Ser Lys Arg Ser Arg Gly Gly His Ser Asp Tyr Met Asn Met Thr
325 330 335

Pro Arg Arg Pro Gly Pro Thr Arg Lys His Tyr Gln Pro Tyr Ala Pro
340 345 350

Pro Arg Asp Phe Ala Ala Tyr Arg Ser Arg Val Lys Phe Ser Arg Ser
355 360 365

Ala Asp Ala Pro Ala Tyr Gln Gln Gly Gln Asn Gln Leu Tyr Asn Glu
370 375 380

Leu Asn Leu Gly Arg Arg Glu Glu Tyr Asp Val Leu Asp Lys Arg Arg
385 390 395 400

Gly Arg Asp Pro Glu Met Gly Gly Lys Pro Arg Arg Lys Asn Pro Gln
405 410 415

Glu Gly Leu Tyr Asn Glu Leu Gln Lys Asp Lys Met Ala Glu Ala Tyr
420 425 430

Ser Glu Ile Gly Met Lys Gly Glu Arg Arg Arg Gly Lys Gly His Asp
435 440 445

Gly Leu Tyr Gln Gly Leu Ser Thr Ala Thr Lys Asp Thr Tyr Asp Ala
450 455 460

Leu His Met Gln Ala Leu Pro Pro Arg
465 470

<210> SEQ ID NO 211
<211> LENGTH: 495
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="CD19-specific chimeric antigen receptor (CD19-CD8a-CD28-CD3z) with Signal peptide"

<400> SEQUENCE: 211

Met Leu Leu Leu Val Thr Ser Leu Leu Leu Cys Glu Leu Pro His Pro
1 5 10 15

Ala Phe Leu Leu Ile Pro Asp Ile Gln Met Thr Gln Thr Thr Ser Ser
20 25 30

Leu Ser Ala Ser Leu Gly Asp Arg Val Thr Ile Ser Cys Arg Ala Ser
35 40 45

Gln Asp Ile Ser Lys Tyr Leu Asn Trp Tyr Gln Gln Lys Pro Asp Gly
50 55 60

Thr Val Lys Leu Leu Ile Tyr His Thr Ser Arg Leu His Ser Gly Val
65 70 75 80

Pro Ser Arg Phe Ser Gly Ser Gly Ser Gly Thr Asp Tyr Ser Leu Thr
85 90 95

Ile Ser Asn Leu Glu Gln Glu Asp Ile Ala Thr Tyr Phe Cys Gln Gln
100 105 110

Gly Asn Thr Leu Pro Tyr Thr Phe Gly Gly Gly Thr Lys Leu Glu Ile
115 120 125

Thr Gly Ser Thr Ser Gly Ser Gly Lys Pro Gly Ser Gly Glu Gly Ser
130 135 140

Thr Lys Gly Glu Val Lys Leu Gln Glu Ser Gly Pro Gly Leu Val Ala
145 150 155 160

Pro Ser Gln Ser Leu Ser Val Thr Cys Thr Val Ser Gly Val Ser Leu

-continued

```
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Lys Pro Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Asn His Arg Asn Arg Ser Lys Arg Ser Arg Gly Gly His Ser
            340                 345                 350

Asp Tyr Met Asn Met Thr Pro Arg Arg Pro Gly Pro Thr Arg Lys His
        355                 360                 365

Tyr Gln Pro Tyr Ala Pro Pro Arg Asp Phe Ala Ala Tyr Arg Ser Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495
```

<210> SEQ ID NO 212
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Anti-CD19 monoclonal antibody clone FMC63 variable heavy chain"

<400> SEQUENCE: 212

```
Glu Val Lys Leu Gln Glu Ser Gly Pro Gly Leu Val Ala Pro Ser Gln
```

```
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120


<210> SEQ ID NO 213
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Anti-CD19 clone FMC63 single chain
      fragment variable (scFv) with Whitlow linker"

<400> SEQUENCE: 213

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
```

```
    210                 215                 220

Tyr Tyr Gly Gly Ser Tyr Ala Met Asp Tyr Trp Gly Gln Gly Thr Ser
225                 230                 235                 240

Val Thr Val Ser Ser
                245


<210> SEQ ID NO 214
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="hM195 VL"

<400> SEQUENCE: 214

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Lys
                85                  90                  95

Glu Val Pro Trp Thr Phe Gly Gln Gly Thr Lys Val Glu Ile Lys
            100                 105                 110


<210> SEQ ID NO 215
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="hM195 VH"

<400> SEQUENCE: 215

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110
```

Thr Val Ser Ser
115

<210> SEQ ID NO 216
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="hM195 scFv with linker"

<400> SEQUENCE: 216

Asp Ile Gln Met Thr Gln Ser Pro Ser Ser Leu Ser Ala Ser Val Gly
1 5 10 15

Asp Arg Val Thr Ile Thr Cys Arg Ala Ser Glu Ser Val Asp Asn Tyr
20 25 30

Gly Ile Ser Phe Met Asn Trp Phe Gln Gln Lys Pro Gly Lys Ala Pro
35 40 45

Lys Leu Leu Ile Tyr Ala Ala Ser Asn Gln Gly Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Asp Asp Phe Ala Thr Tyr Tyr Cys Gln Gln Ser Lys
85 90 95

Glu Val Pro Trp Thr Phe Gly Gln Gly Thr Lys Val Glu Ile Lys Gly
100 105 110

Gly Gly Gly Ser Gly Gly Gly Gly Ser Gly Gly Gly Gly Ser Gln Val
115 120 125

Gln Leu Val Gln Ser Gly Ala Glu Val Lys Lys Pro Gly Ser Ser Val
130 135 140

Lys Val Ser Cys Lys Ala Ser Gly Tyr Thr Phe Thr Asp Tyr Asn Met
145 150 155 160

His Trp Val Arg Gln Ala Pro Gly Gln Gly Leu Glu Trp Ile Gly Tyr
165 170 175

Ile Tyr Pro Tyr Asn Gly Gly Thr Gly Tyr Asn Gln Lys Phe Lys Ser
180 185 190

Lys Ala Thr Ile Thr Ala Asp Glu Ser Thr Asn Thr Ala Tyr Met Glu
195 200 205

Leu Ser Ser Leu Arg Ser Glu Asp Thr Ala Val Tyr Tyr Cys Ala Arg
210 215 220

Gly Arg Pro Ala Met Asp Tyr Trp Gly Gln Gly Thr Leu Val Thr Val
225 230 235 240

Ser Ser

<210> SEQ ID NO 217
<211> LENGTH: 943
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="EGFR variant III (EGFRvIII)"

<400> SEQUENCE: 217

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
        195                 200                 205

Asn Trp Lys Lys Leu Phe Gly Thr Ser Gly Gln Lys Thr Lys Ile Ile
    210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
        275                 280                 285

Ile Gln Cys His Pro Glu Cys Leu Pro Gln Ala Met Asn Ile Thr Cys
    290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
        355                 360                 365

Cys Pro Thr Asn Gly Pro Lys Ile Pro Ser Ile Ala Thr Gly Met Val
    370                 375                 380

Gly Ala Leu Leu Leu Leu Leu Val Val Ala Leu Gly Ile Gly Leu Phe
385                 390                 395                 400

Met Arg Arg Arg His Ile Val Arg Lys Arg Thr Leu Arg Arg Leu Leu
                405                 410                 415
```

```
Gln Glu Arg Glu Leu Val Glu Pro Leu Thr Pro Ser Gly Glu Ala Pro
            420                 425                 430

Asn Gln Ala Leu Leu Arg Ile Leu Lys Glu Thr Glu Phe Lys Lys Ile
        435                 440                 445

Lys Val Leu Gly Ser Gly Ala Phe Gly Thr Val Tyr Lys Gly Leu Trp
    450                 455                 460

Ile Pro Glu Gly Glu Lys Val Lys Ile Pro Val Ala Ile Lys Glu Leu
465                 470                 475                 480

Arg Glu Ala Thr Ser Pro Lys Ala Asn Lys Glu Ile Leu Asp Glu Ala
                485                 490                 495

Tyr Val Met Ala Ser Val Asp Asn Pro His Val Cys Arg Leu Leu Gly
            500                 505                 510

Ile Cys Leu Thr Ser Thr Val Gln Leu Ile Thr Gln Leu Met Pro Phe
        515                 520                 525

Gly Cys Leu Leu Asp Tyr Val Arg Glu His Lys Asp Asn Ile Gly Ser
    530                 535                 540

Gln Tyr Leu Leu Asn Trp Cys Val Gln Ile Ala Lys Gly Met Asn Tyr
545                 550                 555                 560

Leu Glu Asp Arg Arg Leu Val His Arg Asp Leu Ala Ala Arg Asn Val
                565                 570                 575

Leu Val Lys Thr Pro Gln His Val Lys Ile Thr Asp Phe Gly Leu Ala
            580                 585                 590

Lys Leu Leu Gly Ala Glu Glu Lys Glu Tyr His Ala Glu Gly Gly Lys
        595                 600                 605

Val Pro Ile Lys Trp Met Ala Leu Glu Ser Ile Leu His Arg Ile Tyr
    610                 615                 620

Thr His Gln Ser Asp Val Trp Ser Tyr Gly Val Thr Val Trp Glu Leu
625                 630                 635                 640

Met Thr Phe Gly Ser Lys Pro Tyr Asp Gly Ile Pro Ala Ser Glu Ile
                645                 650                 655

Ser Ser Ile Leu Glu Lys Gly Glu Arg Leu Pro Gln Pro Pro Ile Cys
            660                 665                 670

Thr Ile Asp Val Tyr Met Ile Met Val Lys Cys Trp Met Ile Asp Ala
        675                 680                 685

Asp Ser Arg Pro Lys Phe Arg Glu Leu Ile Ile Glu Phe Ser Lys Met
    690                 695                 700

Ala Arg Asp Pro Gln Arg Tyr Leu Val Ile Gln Gly Asp Glu Arg Met
705                 710                 715                 720

His Leu Pro Ser Pro Thr Asp Ser Asn Phe Tyr Arg Ala Leu Met Asp
                725                 730                 735

Glu Glu Asp Met Asp Asp Val Val Asp Ala Asp Glu Tyr Leu Ile Pro
            740                 745                 750

Gln Gln Gly Phe Phe Ser Ser Pro Ser Thr Ser Arg Thr Pro Leu Leu
        755                 760                 765

Ser Ser Leu Ser Ala Thr Ser Asn Asn Ser Thr Val Ala Cys Ile Asp
    770                 775                 780

Arg Asn Gly Leu Gln Ser Cys Pro Ile Lys Glu Asp Ser Phe Leu Gln
785                 790                 795                 800

Arg Tyr Ser Ser Asp Pro Thr Gly Ala Leu Thr Glu Asp Ser Ile Asp
                805                 810                 815

Asp Thr Phe Leu Pro Val Pro Glu Tyr Ile Asn Gln Ser Val Pro Lys
            820                 825                 830
```

```
Arg Pro Ala Gly Ser Val Gln Asn Pro Val Tyr His Asn Gln Pro Leu
        835                 840                 845

Asn Pro Ala Pro Ser Arg Asp Pro His Tyr Gln Asp Pro His Ser Thr
    850                 855                 860

Ala Val Gly Asn Pro Glu Tyr Leu Asn Thr Val Gln Pro Thr Cys Val
865                 870                 875                 880

Asn Ser Thr Phe Asp Ser Pro Ala His Trp Ala Gln Lys Gly Ser His
                885                 890                 895

Gln Ile Ser Leu Asp Asn Pro Asp Tyr Gln Gln Asp Phe Phe Pro Lys
            900                 905                 910

Glu Ala Lys Pro Asn Gly Ile Phe Lys Gly Ser Thr Ala Glu Asn Ala
        915                 920                 925

Glu Tyr Leu Arg Val Ala Pro Gln Ser Ser Glu Phe Ile Gly Ala
    930                 935                 940


<210> SEQ ID NO 218
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Anti- EGFRvIII Clone 139 VH"

<400> SEQUENCE: 218

Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Ser Ser Gly Trp Ser Glu Tyr Trp Gly Gln Gly Thr Leu Val
            100                 105                 110

Thr Val Ser Ser
        115


<210> SEQ ID NO 219
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Anti- EGFRvIII Clone 139 VL"

<400> SEQUENCE: 219

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
```

```
            20                  25                  30

Leu Ala Trp Tyr Gln Gln Lys Pro Gly Lys Ala Pro Lys Arg Leu Ile
        35                  40                  45

Tyr Ala Ala Ser Asn Leu Gln Ser Gly Val Pro Ser Arg Phe Thr Gly
    50                  55                  60

Ser Gly Ser Gly Thr Glu Phe Thr Leu Ile Val Ser Ser Leu Gln Pro
65                  70                  75                  80

Glu Asp Phe Ala Thr Tyr Tyr Cys Leu Gln His His Ser Tyr Pro Leu
                85                  90                  95

Thr Ser Gly Gly Gly Thr Lys Val Glu Ile Lys
            100                 105


<210> SEQ ID NO 220
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Anti- EGFRvIII Clone MR1 VH"

<400> SEQUENCE: 220

Gln Val Lys Leu Gln Gln Ser Gly Gly Gly Leu Val Lys Pro Gly Ala
1               5                   10                  15

Ser Leu Lys Leu Ser Cys Val Thr Ser Gly Phe Thr Phe Arg Lys Phe
            20                  25                  30

Gly Met Ser Trp Val Arg Gln Thr Ser Asp Lys Arg Leu Glu Trp Val
        35                  40                  45

Ala Ser Ile Ser Thr Gly Gly Tyr Asn Thr Tyr Tyr Ser Asp Asn Val
    50                  55                  60

Lys Gly Arg Phe Thr Ile Ser Arg Glu Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Thr Arg Gly Tyr Ser Ser Thr Ser Tyr Ala Met Asp Tyr Trp Gly Gln
            100                 105                 110

Gly Thr Thr Val Thr Val Ser Ser
        115                 120


<210> SEQ ID NO 221
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Anti- EGFRvIII Clone MR1 VL"

<400> SEQUENCE: 221

Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45
```

```
Ser Glu Gly Asn Thr Leu Arg Pro Gly Val Pro Ser Arg Phe Ser Ser
    50                  55                  60

Ser Gly Thr Gly Thr Asp Phe Val Phe Thr Ile Glu Asn Thr Leu Ser
65                  70                  75                  80

Glu Asp Val Gly Asp Tyr Tyr Cys Leu Gln Ser Phe Asn Val Pro Leu
                85                  90                  95

Thr Phe Gly Asp Gly Thr Lys Leu Glu Ile Lys
            100                 105


<210> SEQ ID NO 222
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Anti- EGFRvIII Clone MR1-1 VH"

<400> SEQUENCE: 222

Gln Val Lys Leu Gln Gln Ser Gly Gly Gly Leu Val Lys Pro Gly Ala
1               5                   10                  15

Ser Leu Lys Leu Ser Cys Val Thr Ser Gly Phe Thr Phe Arg Lys Phe
            20                  25                  30

Gly Met Ser Trp Val Arg Gln Thr Ser Asp Lys Arg Leu Glu Trp Val
        35                  40                  45

Ala Ser Ile Ser Thr Gly Gly Tyr Asn Thr Tyr Tyr Ser Asp Asn Val
    50                  55                  60

Lys Gly Arg Phe Thr Ile Ser Arg Glu Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Thr Arg Gly Tyr Ser Pro Tyr Ser Tyr Ala Met Asp Tyr Trp Gly Gln
            100                 105                 110

Gly Thr Thr Val Thr Val Ser Ser
        115                 120


<210> SEQ ID NO 223
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Anti- EGFRvIII Clone MR1-1 VL"

<400> SEQUENCE: 223

Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
    50                  55                  60
```

```
Ser Gly Thr Gly Thr Asp Phe Val Phe Thr Ile Glu Asn Thr Leu Ser
65                  70                  75                  80

Glu Asp Val Gly Asp Tyr Tyr Cys Leu Gln Ser Trp Asn Val Pro Leu
                85                  90                  95

Thr Phe Gly Asp Gly Thr Lys Leu Glu Ile Lys
            100                 105


<210> SEQ ID NO 224
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Anti- EGFRvIII Clone humMR1-1 VH"

<400> SEQUENCE: 224

Gln Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Lys Phe
            20                  25                  30

Gly Met Ser Trp Val Arg Gln Thr Pro Asp Lys Arg Leu Glu Trp Val
        35                  40                  45

Ala Ser Ile Ser Thr Gly Gly Tyr Asn Thr Tyr Tyr Ser Asp Asn Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gly Tyr Ser Pro Tyr Ser Tyr Ala Met Asp Tyr Trp Gly Gln
            100                 105                 110

Gly Thr Met Val Thr Val Ser Ser
        115                 120


<210> SEQ ID NO 225
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Anti- EGFRvIII Clone humMR1-1 VL"

<400> SEQUENCE: 225

Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
```

```
                85                  90                  95

Thr Phe Gly Gly Gly Thr Lys Val Glu Ile Lys
            100                 105
```

<210> SEQ ID NO 226
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Anti- EGFRvIII Clone humMR1-2 VH"

<400> SEQUENCE: 226

```
Gln Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Lys Phe
            20                  25                  30

Gly Met Ser Trp Val Arg Gln Thr Pro Asp Lys Arg Leu Glu Trp Val
        35                  40                  45

Ala Ser Ile Ser Thr Gly Gly Tyr Asn Thr Phe Tyr Ser Asp Asn Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gly Tyr Ser Pro Tyr Ser Phe Ala Met Asp Tyr Trp Gly Gln
            100                 105                 110

Gly Thr Met Val Thr Val Ser Ser
        115                 120
```

<210> SEQ ID NO 227
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Anti- EGFRvIII Clone humMR1-2 VL"

<400> SEQUENCE: 227

```
Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys
            100                 105
```

<210> SEQ ID NO 228
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Anti- EGFRvIII scFv Clone 139"

<400> SEQUENCE: 228

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Ala Trp Tyr Gln Gln Lys Pro Gly Lys Ala Pro Lys Arg Leu Ile
        35                  40                  45

Tyr Ala Ala Ser Asn Leu Gln Ser Gly Val Pro Ser Arg Phe Thr Gly
    50                  55                  60

Ser Gly Ser Gly Thr Glu Phe Thr Leu Ile Val Ser Ser Leu Gln Pro
65                  70                  75                  80

Glu Asp Phe Ala Thr Tyr Tyr Cys Leu Gln His His Ser Tyr Pro Leu
                85                  90                  95

Thr Ser Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Glu Val Gln
        115                 120                 125

Val Leu Glu Ser Gly Gly Gly Leu Val Gln Pro Gly Gly Ser Leu Arg
    130                 135                 140

Leu Ser Cys Ala Ala Ser Gly Phe Thr Phe Ser Ser Tyr Ala Met Ser
145                 150                 155                 160

Trp Val Arg Gln Ala Pro Gly Lys Gly Leu Glu Trp Val Ser Ala Ile
                165                 170                 175

Ser Gly Ser Gly Gly Ser Thr Asn Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Gly Ser
    210                 215                 220

Ser Gly Trp Ser Glu Tyr Trp Gly Gln Gly Thr Leu Val Thr Val Ser
225                 230                 235                 240

Ser
```

<210> SEQ ID NO 229
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Anti-EGFRvIII scFv clone MR1"

<400> SEQUENCE: 229

```
Asp Ile Glu Leu Thr Gln Ser Pro Ala Ser Leu Ser Val Ala Thr Gly
```

```
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
    50                  55                  60

Ser Gly Thr Gly Thr Asp Phe Val Phe Thr Ile Glu Asn Thr Leu Ser
65                  70                  75                  80

Glu Asp Val Gly Asp Tyr Tyr Cys Leu Gln Ser Phe Asn Val Pro Leu
                85                  90                  95

Thr Phe Gly Asp Gly Thr Lys Leu Glu Ile Lys Gly Gly Gly Gly Ser
            100                 105                 110

Gly Gly Gly Gly Ser Gly Gly Gly Gly Ser Gln Val Lys Leu Gln Gln
        115                 120                 125

Ser Gly Gly Gly Leu Val Lys Pro Gly Ala Ser Leu Lys Leu Ser Cys
    130                 135                 140

Val Thr Ser Gly Phe Thr Phe Arg Lys Phe Gly Met Ser Trp Val Arg
145                 150                 155                 160

Gln Thr Ser Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Glu Asn Ala Lys Asn Thr Leu Tyr Leu Gln Met Ser Ser Leu
        195                 200                 205

Lys Ser Glu Asp Thr Ala Leu Tyr Tyr Cys Thr Arg Gly Tyr Ser Ser
    210                 215                 220

Thr Ser Tyr Ala Met Asp Tyr Trp Gly Gln Gly Thr Thr Val Thr Val
225                 230                 235                 240

Ser Ser


<210> SEQ ID NO 230
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Anti EGFRvIII scFv clone MR1-1"

<400> SEQUENCE: 230

Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
    50                  55                  60

Ser Gly Thr Gly Thr Asp Phe Val Phe Thr Ile Glu Asn Thr Leu Ser
65                  70                  75                  80

Glu Asp Val Gly Asp Tyr Tyr Cys Leu Gln Ser Trp Asn Val Pro Leu
                85                  90                  95
```

Thr Phe Gly Asp Gly Thr Lys Leu Glu Ile Lys Gly Gly Gly Gly Ser
100 105 110

Gly Gly Gly Gly Ser Gly Gly Gly Gly Ser Gln Val Lys Leu Gln Gln
115 120 125

Ser Gly Gly Gly Leu Val Lys Pro Gly Ala Ser Leu Lys Leu Ser Cys
130 135 140

Val Thr Ser Gly Phe Thr Phe Arg Lys Phe Gly Met Ser Trp Val Arg
145 150 155 160

Gln Thr Ser Asp Lys Arg Leu Glu Trp Val Ala Ser Ile Ser Thr Gly
165 170 175

Gly Tyr Asn Thr Tyr Tyr Ser Asp Asn Val Lys Gly Arg Phe Thr Ile
180 185 190

Ser Arg Glu Asn Ala Lys Asn Thr Leu Tyr Leu Gln Met Ser Ser Leu
195 200 205

Lys Ser Glu Asp Thr Ala Leu Tyr Tyr Cys Thr Arg Gly Tyr Ser Pro
210 215 220

Tyr Ser Tyr Ala Met Asp Tyr Trp Gly Gln Gly Thr Thr Val Thr Val
225 230 235 240

Ser Ser

<210> SEQ ID NO 231
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Anti-EGFRvIII scFv clone huMR1-1"

<400> SEQUENCE: 231

Asp Ile Gln Met Thr Gln Ser Pro Ser Ser Leu Ser Ala Ser Val Gly
1 5 10 15

Asp Arg Val Thr Ile Thr Cys Met Thr Ser Thr Asp Ile Asp Asp Asp
20 25 30

Met Asn Trp Tyr Gln Gln Lys Pro Gly Lys Thr Pro Lys Leu Leu Ile
35 40 45

Tyr Glu Gly Asn Thr Leu Arg Pro Gly Val Pro Ser Arg Phe Ser Gly
50 55 60

Ser Gly Ser Gly Thr Asp Phe Ile Phe Thr Ile Ser Ser Leu Gln Pro
65 70 75 80

Glu Asp Ile Ala Thr Tyr Tyr Cys Leu Gln Ser Trp Asn Val Pro Leu
85 90 95

Thr Phe Gly Gly Gly Thr Lys Val Glu Ile Lys Gly Gly Gly Gly Ser
100 105 110

Gly Gly Gly Gly Ser Gly Gly Gly Gly Ser Gln Val Gln Leu Gln Glu
115 120 125

Ser Gly Gly Gly Leu Val Lys Pro Gly Gly Ser Leu Lys Leu Ser Cys
130 135 140

Ala Ala Ser Gly Phe Thr Phe Ser Lys Phe Gly Met Ser Trp Val Arg
145 150 155 160

Gln Thr Pro Asp Lys Arg Leu Glu Trp Val Ala Ser Ile Ser Thr Gly
165 170 175

Gly Tyr Asn Thr Tyr Tyr Ser Asp Asn Val Lys Gly Arg Phe Thr Ile
180 185 190

```
Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Tyr Ala Met Asp Tyr Trp Gly Gln Gly Thr Met Val Thr Val
225                 230                 235                 240

Ser Ser


<210> SEQ ID NO 232
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Anti-EGFRvIII scFv clone huMR1-2"

<400> SEQUENCE: 232

Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
                165                 170                 175

Gly Tyr Asn Thr Phe Tyr Ser Asp Asn Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Phe Ala Met Asp Tyr Trp Gly Gln Gly Thr Met Val Thr Val
225                 230                 235                 240

Ser Ser


<210> SEQ ID NO 233
<211> LENGTH: 470
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="EGFRvIII CAR (clone 139 scFv.CD8alpha hinge &TM.4-1BB.CD3-zeta)"

<400> SEQUENCE: 233

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Ala Trp Tyr Gln Gln Lys Pro Gly Lys Ala Pro Lys Arg Leu Ile
        35                  40                  45

Tyr Ala Ala Ser Asn Leu Gln Ser Gly Val Pro Ser Arg Phe Thr Gly
    50                  55                  60

Ser Gly Ser Gly Thr Glu Phe Thr Leu Ile Val Ser Ser Leu Gln Pro
65                  70                  75                  80

Glu Asp Phe Ala Thr Tyr Tyr Cys Leu Gln His His Ser Tyr Pro Leu
                85                  90                  95

Thr Ser Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Glu Val Gln
        115                 120                 125

Val Leu Glu Ser Gly Gly Gly Leu Val Gln Pro Gly Gly Ser Leu Arg
    130                 135                 140

Leu Ser Cys Ala Ala Ser Gly Phe Thr Phe Ser Ser Tyr Ala Met Ser
145                 150                 155                 160

Trp Val Arg Gln Ala Pro Gly Lys Gly Leu Glu Trp Val Ser Ala Ile
                165                 170                 175

Ser Gly Ser Gly Gly Ser Thr Asn Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Gly Ser
    210                 215                 220

Ser Gly Trp Ser Glu Tyr Trp Gly Gln Gly Thr Leu Val Thr Val Ser
225                 230                 235                 240

Ser Lys Pro Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Ile Tyr Ile Trp Ala Pro Leu Ala Gly Thr Cys Gly Val Leu Leu Leu
    290                 295                 300

Ser Leu Val Ile Thr Leu Tyr Cys Asn His Arg Asn Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365
```

```
Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470
```

<210> SEQ ID NO 234
<211> LENGTH: 471
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="EGFRvIII CAR (MR1 scFv.CD8alpha hinge &TM.4-1BB.CD3-zeta)"

<400> SEQUENCE: 234

```
Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
    50                  55                  60

Ser Gly Thr Gly Thr Asp Phe Val Phe Thr Ile Glu Asn Thr Leu Ser
65                  70                  75                  80

Glu Asp Val Gly Asp Tyr Tyr Cys Leu Gln Ser Phe Asn Val Pro Leu
                85                  90                  95

Thr Phe Gly Asp Gly Thr Lys Leu Glu Ile Lys Gly Gly Gly Gly Ser
            100                 105                 110

Gly Gly Gly Gly Ser Gly Gly Gly Gly Ser Gln Val Lys Leu Gln Gln
        115                 120                 125

Ser Gly Gly Gly Leu Val Lys Pro Gly Ala Ser Leu Lys Leu Ser Cys
    130                 135                 140

Val Thr Ser Gly Phe Thr Phe Arg Lys Phe Gly Met Ser Trp Val Arg
145                 150                 155                 160

Gln Thr Ser Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Glu Asn Ala Lys Asn Thr Leu Tyr Leu Gln Met Ser Ser Leu
        195                 200                 205

Lys Ser Glu Asp Thr Ala Leu Tyr Tyr Cys Thr Arg Gly Tyr Ser Ser
    210                 215                 220
```

```
Thr Ser Tyr Ala Met Asp Tyr Trp Gly Gln Gly Thr Thr Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Asn His Arg Asn Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470


<210> SEQ ID NO 235
<211> LENGTH: 471
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="EGFRvIII CAR (MR1-1 scFv.CD8alpha hinge
      &TM.4-1BB.CD3-zeta)"

<400> SEQUENCE: 235

Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
    50                  55                  60

Ser Gly Thr Gly Thr Asp Phe Val Phe Thr Ile Glu Asn Thr Leu Ser
65                  70                  75                  80
```

```
Glu Asp Val Gly Asp Tyr Tyr Cys Leu Gln Ser Trp Asn Val Pro Leu
                85                  90                  95

Thr Phe Gly Asp Gly Thr Lys Leu Glu Ile Lys Gly Gly Gly Gly Ser
            100                 105                 110

Gly Gly Gly Gly Ser Gly Gly Gly Gly Ser Gln Val Lys Leu Gln Gln
        115                 120                 125

Ser Gly Gly Gly Leu Val Lys Pro Gly Ala Ser Leu Lys Leu Ser Cys
    130                 135                 140

Val Thr Ser Gly Phe Thr Phe Arg Lys Phe Gly Met Ser Trp Val Arg
145                 150                 155                 160

Gln Thr Ser Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Glu Asn Ala Lys Asn Thr Leu Tyr Leu Gln Met Ser Ser Leu
        195                 200                 205

Lys Ser Glu Asp Thr Ala Leu Tyr Tyr Cys Thr Arg Gly Tyr Ser Pro
    210                 215                 220

Tyr Ser Tyr Ala Met Asp Tyr Trp Gly Gln Gly Thr Thr Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Asn His Arg Asn Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470
```

<210> SEQ ID NO 236
<211> LENGTH: 471

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="EGFRvIII CAR (humMR1-1 scFv.CD8alpha hinge &TM.4-1BB.CD3-zeta)"

<400> SEQUENCE: 236

```
Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Tyr Ala Met Asp Tyr Trp Gly Gln Gly Thr Met Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Asn His Arg Asn Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350
```

```
Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470


<210> SEQ ID NO 237
<211> LENGTH: 471
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="EGFRvIII CAR (humMR1-2 scFv.CD8alpha
      hinge &TM.4-1BB.CD3-zeta)"

<400> SEQUENCE: 237

Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
                165                 170                 175

Gly Tyr Asn Thr Phe Tyr Ser Asp Asn Val Lys Gly Arg Phe Thr Ile
            180                 185                 190

Ser Arg Asp Asn Ala Lys Asn Thr Leu Tyr Leu Gln Met Ser Ser Leu
        195                 200                 205
```

```
Lys Ser Glu Asp Thr Ala Met Tyr Tyr Cys Ala Arg Gly Tyr Ser Pro
    210                 215                 220

Tyr Ser Phe Ala Met Asp Tyr Trp Gly Gln Gly Thr Met Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Asn His Arg Asn Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470
```

<210> SEQ ID NO 238
<211> LENGTH: 518
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="EGFRvIII CAR (MR1-1 scFv.CD8alpha 2x hinge &TM.4-1BB.CD3-zeta)"

<400> SEQUENCE: 238

```
Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
    50                  55                  60
```

```
Ser Gly Thr Gly Thr Asp Phe Val Phe Thr Ile Glu Asn Thr Leu Ser
65                  70                  75                  80

Glu Asp Val Gly Asp Tyr Tyr Cys Leu Gln Ser Trp Asn Val Pro Leu
                85                  90                  95

Thr Phe Gly Asp Gly Thr Lys Leu Glu Ile Lys Gly Gly Gly Gly Ser
            100                 105                 110

Gly Gly Gly Gly Ser Gly Gly Gly Gly Ser Gln Val Lys Leu Gln Gln
        115                 120                 125

Ser Gly Gly Gly Leu Val Lys Pro Gly Ala Ser Leu Lys Leu Ser Cys
    130                 135                 140

Val Thr Ser Gly Phe Thr Phe Arg Lys Phe Gly Met Ser Trp Val Arg
145                 150                 155                 160

Gln Thr Ser Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Glu Asn Ala Lys Asn Thr Leu Tyr Leu Gln Met Ser Ser Leu
        195                 200                 205

Lys Ser Glu Asp Thr Ala Leu Tyr Tyr Cys Thr Arg Gly Tyr Ser Pro
    210                 215                 220

Tyr Ser Tyr Ala Met Asp Tyr Trp Gly Gln Gly Thr Thr Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Ser Arg
            260                 265                 270

Pro Ala Ala Gly Gly Ala Val His Thr Arg Gly Leu Asp Phe Ala Ser
        275                 280                 285

Asp Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Cys Arg Pro
305                 310                 315                 320

Ala Ala Gly Gly Ala Val His Thr Arg Gly Leu Asp Phe Ala Cys Asp
                325                 330                 335

Ile Tyr Ile Trp Ala Pro Leu Ala Gly Thr Cys Gly Val Leu Leu Leu
            340                 345                 350

Ser Leu Val Ile Thr Leu Tyr Cys Asn His Arg Asn Lys Arg Gly Arg
        355                 360                 365

Lys Lys Leu Leu Tyr Ile Phe Lys Gln Pro Phe Met Arg Pro Val Gln
    370                 375                 380

Thr Thr Gln Glu Glu Asp Gly Cys Ser Cys Arg Phe Pro Glu Glu Glu
385                 390                 395                 400

Glu Gly Gly Cys Glu Leu Arg Val Lys Phe Ser Arg Ser Ala Asp Ala
                405                 410                 415

Pro Ala Tyr Gln Gln Gly Gln Asn Gln Leu Tyr Asn Glu Leu Asn Leu
            420                 425                 430

Gly Arg Arg Glu Glu Tyr Asp Val Leu Asp Lys Arg Arg Gly Arg Asp
        435                 440                 445

Pro Glu Met Gly Gly Lys Pro Arg Arg Lys Asn Pro Gln Glu Gly Leu
    450                 455                 460

Tyr Asn Glu Leu Gln Lys Asp Lys Met Ala Glu Ala Tyr Ser Glu Ile
465                 470                 475                 480

Gly Met Lys Gly Glu Arg Arg Arg Gly Lys Gly His Asp Gly Leu Tyr
```

```
                485                 490                 495

Gln Gly Leu Ser Thr Ala Thr Lys Asp Thr Tyr Asp Ala Leu His Met
            500                 505                 510

Gln Ala Leu Pro Pro Arg
        515
```

<210> SEQ ID NO 239
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="EGFRvIII CAR (MR1-1 scFv.CD8alpha 3x hinge &TM.4-1BB.CD3-zeta)"

<400> SEQUENCE: 239

```
Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
    50                  55                  60

Ser Gly Thr Gly Thr Asp Phe Val Phe Thr Ile Glu Asn Thr Leu Ser
65                  70                  75                  80

Glu Asp Val Gly Asp Tyr Tyr Cys Leu Gln Ser Trp Asn Val Pro Leu
                85                  90                  95

Thr Phe Gly Asp Gly Thr Lys Leu Glu Ile Lys Gly Gly Gly Gly Ser
            100                 105                 110

Gly Gly Gly Gly Ser Gly Gly Gly Gly Ser Gln Val Lys Leu Gln Gln
        115                 120                 125

Ser Gly Gly Gly Leu Val Lys Pro Gly Ala Ser Leu Lys Leu Ser Cys
    130                 135                 140

Val Thr Ser Gly Phe Thr Phe Arg Lys Phe Gly Met Ser Trp Val Arg
145                 150                 155                 160

Gln Thr Ser Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Glu Asn Ala Lys Asn Thr Leu Tyr Leu Gln Met Ser Ser Leu
        195                 200                 205

Lys Ser Glu Asp Thr Ala Leu Tyr Tyr Cys Thr Arg Gly Tyr Ser Pro
    210                 215                 220

Tyr Ser Tyr Ala Met Asp Tyr Trp Gly Gln Gly Thr Thr Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Ser Arg
            260                 265                 270

Pro Ala Ala Gly Gly Ala Val His Thr Arg Gly Leu Asp Phe Ala Ser
        275                 280                 285

Asp Lys Pro Thr Thr Thr Pro Ala Pro Arg Pro Pro Thr Pro Ala Pro
```

```
    290                 295                 300

Thr Ile Ala Ser Gln Pro Leu Ser Leu Arg Pro Glu Ala Ser Arg Pro
305                 310                 315                 320

Ala Ala Gly Gly Ala Val His Thr Arg Gly Leu Asp Phe Ala Ser Asp
                325                 330                 335

Lys Pro Thr Thr Thr Pro Ala Pro Arg Pro Pro Thr Pro Ala Pro Thr
            340                 345                 350

Ile Ala Ser Gln Pro Leu Ser Leu Arg Pro Glu Ala Cys Arg Pro Ala
        355                 360                 365

Ala Gly Gly Ala Val His Thr Arg Gly Leu Asp Phe Ala Cys Asp Ile
    370                 375                 380

Tyr Ile Trp Ala Pro Leu Ala Gly Thr Cys Gly Val Leu Leu Leu Ser
385                 390                 395                 400

Leu Val Ile Thr Leu Tyr Cys Asn His Arg Asn Lys Arg Gly Arg Lys
                405                 410                 415

Lys Leu Leu Tyr Ile Phe Lys Gln Pro Phe Met Arg Pro Val Gln Thr
            420                 425                 430

Thr Gln Glu Glu Asp Gly Cys Ser Cys Arg Phe Pro Glu Glu Glu Glu
        435                 440                 445

Gly Gly Cys Glu Leu Arg Val Lys Phe Ser Arg Ser Ala Asp Ala Pro
    450                 455                 460

Ala Tyr Gln Gln Gly Gln Asn Gln Leu Tyr Asn Glu Leu Asn Leu Gly
465                 470                 475                 480

Arg Arg Glu Glu Tyr Asp Val Leu Asp Lys Arg Arg Gly Arg Asp Pro
                485                 490                 495

Glu Met Gly Gly Lys Pro Arg Arg Lys Asn Pro Gln Glu Gly Leu Tyr
            500                 505                 510

Asn Glu Leu Gln Lys Asp Lys Met Ala Glu Ala Tyr Ser Glu Ile Gly
        515                 520                 525

Met Lys Gly Glu Arg Arg Arg Gly Lys Gly His Asp Gly Leu Tyr Gln
    530                 535                 540

Gly Leu Ser Thr Ala Thr Lys Asp Thr Tyr Asp Ala Leu His Met Gln
545                 550                 555                 560

Ala Leu Pro Pro Arg
                565


<210> SEQ ID NO 240
<211> LENGTH: 612
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="EGFRvIII CAR (MR1-1 scFv.CD8alpha 4x
      hinge &TM.4-1BB.CD3-zeta)"

<400> SEQUENCE: 240

Asp Ile Glu Leu Thr Gln Ser Pro Ala Ser Leu Ser Val Ala Thr Gly
1               5                   10                  15

Glu Lys Val Thr Ile Arg Cys Met Thr Ser Thr Asp Ile Asp Asp Asp
            20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
```

```
    50                  55                  60

Ser Gly Thr Gly Thr Asp Phe Val Phe Thr Ile Glu Asn Thr Leu Ser
65                  70                  75                  80

Glu Asp Val Gly Asp Tyr Tyr Cys Leu Gln Ser Trp Asn Val Pro Leu
                85                  90                  95

Thr Phe Gly Asp Gly Thr Lys Leu Glu Ile Lys Gly Gly Gly Gly Ser
            100                 105                 110

Gly Gly Gly Gly Ser Gly Gly Gly Gly Ser Gln Val Lys Leu Gln Gln
        115                 120                 125

Ser Gly Gly Gly Leu Val Lys Pro Gly Ala Ser Leu Lys Leu Ser Cys
    130                 135                 140

Val Thr Ser Gly Phe Thr Phe Arg Lys Phe Gly Met Ser Trp Val Arg
145                 150                 155                 160

Gln Thr Ser Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Glu Asn Ala Lys Asn Thr Leu Tyr Leu Gln Met Ser Ser Leu
        195                 200                 205

Lys Ser Glu Asp Thr Ala Leu Tyr Tyr Cys Thr Arg Gly Tyr Ser Pro
    210                 215                 220

Tyr Ser Tyr Ala Met Asp Tyr Trp Gly Gln Gly Thr Thr Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Ser Arg
            260                 265                 270

Pro Ala Ala Gly Gly Ala Val His Thr Arg Gly Leu Asp Phe Ala Ser
        275                 280                 285

Asp Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Ser Arg Pro
305                 310                 315                 320

Ala Ala Gly Gly Ala Val His Thr Arg Gly Leu Asp Phe Ala Ser Asp
                325                 330                 335

Lys Pro Thr Thr Thr Pro Ala Pro Arg Pro Pro Thr Pro Ala Pro Thr
            340                 345                 350

Ile Ala Ser Gln Pro Leu Ser Leu Arg Pro Glu Ala Ser Arg Pro Ala
        355                 360                 365

Ala Gly Gly Ala Val His Thr Arg Gly Leu Asp Phe Ala Ser Asp Lys
    370                 375                 380

Pro Thr Thr Thr Pro Ala Pro Arg Pro Pro Thr Pro Ala Pro Thr Ile
385                 390                 395                 400

Ala Ser Gln Pro Leu Ser Leu Arg Pro Glu Ala Cys Arg Pro Ala Ala
                405                 410                 415

Gly Gly Ala Val His Thr Arg Gly Leu Asp Phe Ala Cys Asp Ile Tyr
            420                 425                 430

Ile Trp Ala Pro Leu Ala Gly Thr Cys Gly Val Leu Leu Leu Ser Leu
        435                 440                 445

Val Ile Thr Leu Tyr Cys Asn His Arg Asn Lys Arg Gly Arg Lys Lys
    450                 455                 460

Leu Leu Tyr Ile Phe Lys Gln Pro Phe Met Arg Pro Val Gln Thr Thr
465                 470                 475                 480
```

```
Gln Glu Glu Asp Gly Cys Ser Cys Arg Phe Pro Glu Glu Glu Glu Gly
                485                 490                 495

Gly Cys Glu Leu Arg Val Lys Phe Ser Arg Ser Ala Asp Ala Pro Ala
            500                 505                 510

Tyr Gln Gln Gly Gln Asn Gln Leu Tyr Asn Glu Leu Asn Leu Gly Arg
        515                 520                 525

Arg Glu Glu Tyr Asp Val Leu Asp Lys Arg Arg Gly Arg Asp Pro Glu
    530                 535                 540

Met Gly Gly Lys Pro Arg Arg Lys Asn Pro Gln Glu Gly Leu Tyr Asn
545                 550                 555                 560

Glu Leu Gln Lys Asp Lys Met Ala Glu Ala Tyr Ser Glu Ile Gly Met
                565                 570                 575

Lys Gly Glu Arg Arg Arg Gly Lys Gly His Asp Gly Leu Tyr Gln Gly
            580                 585                 590

Leu Ser Thr Ala Thr Lys Asp Thr Tyr Asp Ala Leu His Met Gln Ala
        595                 600                 605

Leu Pro Pro Arg
    610


<210> SEQ ID NO 241
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="EGFRvIII CAR (huMR1-1 scFv.CD8alpha 3x
      hinge & TM.4-1BB.CD3-zeta)"

<400> SEQUENCE: 241

Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190
```

```
Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Tyr Ala Met Asp Tyr Trp Gly Gln Gly Thr Met Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Ser Arg
            260                 265                 270

Pro Ala Ala Gly Gly Ala Val His Thr Arg Gly Leu Asp Phe Ala Ser
        275                 280                 285

Asp Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Ser Arg Pro
305                 310                 315                 320

Ala Ala Gly Gly Ala Val His Thr Arg Gly Leu Asp Phe Ala Ser Asp
                325                 330                 335

Lys Pro Thr Thr Thr Pro Ala Pro Arg Pro Pro Thr Pro Ala Pro Thr
            340                 345                 350

Ile Ala Ser Gln Pro Leu Ser Leu Arg Pro Glu Ala Cys Arg Pro Ala
        355                 360                 365

Ala Gly Gly Ala Val His Thr Arg Gly Leu Asp Phe Ala Cys Asp Ile
    370                 375                 380

Tyr Ile Trp Ala Pro Leu Ala Gly Thr Cys Gly Val Leu Leu Leu Ser
385                 390                 395                 400

Leu Val Ile Thr Leu Tyr Cys Asn His Arg Asn Lys Arg Gly Arg Lys
                405                 410                 415

Lys Leu Leu Tyr Ile Phe Lys Gln Pro Phe Met Arg Pro Val Gln Thr
            420                 425                 430

Thr Gln Glu Glu Asp Gly Cys Ser Cys Arg Phe Pro Glu Glu Glu Glu
        435                 440                 445

Gly Gly Cys Glu Leu Arg Val Lys Phe Ser Arg Ser Ala Asp Ala Pro
    450                 455                 460

Ala Tyr Gln Gln Gly Gln Asn Gln Leu Tyr Asn Glu Leu Asn Leu Gly
465                 470                 475                 480

Arg Arg Glu Glu Tyr Asp Val Leu Asp Lys Arg Arg Gly Arg Asp Pro
                485                 490                 495

Glu Met Gly Gly Lys Pro Arg Arg Lys Asn Pro Gln Glu Gly Leu Tyr
            500                 505                 510

Asn Glu Leu Gln Lys Asp Lys Met Ala Glu Ala Tyr Ser Glu Ile Gly
        515                 520                 525

Met Lys Gly Glu Arg Arg Arg Gly Lys Gly His Asp Gly Leu Tyr Gln
    530                 535                 540

Gly Leu Ser Thr Ala Thr Lys Asp Thr Tyr Asp Ala Leu His Met Gln
545                 550                 555                 560

Ala Leu Pro Pro Arg
                565
```

<210> SEQ ID NO 242
<211> LENGTH: 612
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="EGFRvIII CAR (huMR1-1 scFv.CD8alpha 4x hinge & TM.4-1BB.CD3-zeta)"

<400> SEQUENCE: 242

```
Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
                165                 170                 175

Gly Tyr Asn Thr Tyr Tyr Ser Asp Asn Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Tyr Ala Met Asp Tyr Trp Gly Gln Gly Thr Met Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Ser Arg
            260                 265                 270

Pro Ala Ala Gly Gly Ala Val His Thr Arg Gly Leu Asp Phe Ala Ser
        275                 280                 285

Asp Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Ser Arg Pro
305                 310                 315                 320

Ala Ala Gly Gly Ala Val His Thr Arg Gly Leu Asp Phe Ala Ser Asp
                325                 330                 335

Lys Pro Thr Thr Thr Pro Ala Pro Arg Pro Pro Thr Pro Ala Pro Thr
            340                 345                 350

Ile Ala Ser Gln Pro Leu Ser Leu Arg Pro Glu Ala Ser Arg Pro Ala
        355                 360                 365
```

Ala Gly Gly Ala Val His Thr Arg Gly Leu Asp Phe Ala Ser Asp Lys
370 375 380

Pro Thr Thr Thr Pro Ala Pro Arg Pro Pro Thr Pro Ala Pro Thr Ile
385 390 395 400

Ala Ser Gln Pro Leu Ser Leu Arg Pro Glu Ala Cys Arg Pro Ala Ala
405 410 415

Gly Gly Ala Val His Thr Arg Gly Leu Asp Phe Ala Cys Asp Ile Tyr
420 425 430

Ile Trp Ala Pro Leu Ala Gly Thr Cys Gly Val Leu Leu Leu Ser Leu
435 440 445

Val Ile Thr Leu Tyr Cys Asn His Arg Asn Lys Arg Gly Arg Lys Lys
450 455 460

Leu Leu Tyr Ile Phe Lys Gln Pro Phe Met Arg Pro Val Gln Thr Thr
465 470 475 480

Gln Glu Glu Asp Gly Cys Ser Cys Arg Phe Pro Glu Glu Glu Glu Gly
485 490 495

Gly Cys Glu Leu Arg Val Lys Phe Ser Arg Ser Ala Asp Ala Pro Ala
500 505 510

Tyr Gln Gln Gly Gln Asn Gln Leu Tyr Asn Glu Leu Asn Leu Gly Arg
515 520 525

Arg Glu Glu Tyr Asp Val Leu Asp Lys Arg Arg Gly Arg Asp Pro Glu
530 535 540

Met Gly Gly Lys Pro Arg Arg Lys Asn Pro Gln Glu Gly Leu Tyr Asn
545 550 555 560

Glu Leu Gln Lys Asp Lys Met Ala Glu Ala Tyr Ser Glu Ile Gly Met
565 570 575

Lys Gly Glu Arg Arg Arg Gly Lys Gly His Asp Gly Leu Tyr Gln Gly
580 585 590

Leu Ser Thr Ala Thr Lys Asp Thr Tyr Asp Ala Leu His Met Gln Ala
595 600 605

Leu Pro Pro Arg
610

<210> SEQ ID NO 243
<211> LENGTH: 565
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="EGFRvIII CAR (huMR1-2 scFv.CD8alpha 3x hinge & TM.4-1BB.CD3-zeta)"

<400> SEQUENCE: 243

Asp Ile Gln Met Thr Gln Ser Pro Ser Ser Leu Ser Ala Ser Val Gly
1 5 10 15

Asp Arg Val Thr Ile Thr Cys Met Thr Ser Thr Asp Ile Asp Asp Asp
20 25 30

Met Asn Trp Tyr Gln Gln Lys Pro Gly Lys Thr Pro Lys Leu Leu Ile
35 40 45

Tyr Glu Gly Asn Thr Leu Arg Pro Gly Val Pro Ser Arg Phe Ser Gly
50 55 60

Ser Gly Ser Gly Thr Asp Phe Ile Phe Thr Ile Ser Ser Leu Gln Pro
65 70 75 80

```
Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
                165                 170                 175

Gly Tyr Asn Thr Phe Tyr Ser Asp Asn Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Phe Ala Met Asp Tyr Trp Gly Gln Gly Thr Met Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Ser Arg
            260                 265                 270

Pro Ala Ala Gly Gly Ala Val His Thr Arg Gly Leu Asp Phe Ala Ser
        275                 280                 285

Asp Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Ser Arg Pro
305                 310                 315                 320

Ala Ala Gly Gly Ala Val His Thr Arg Gly Leu Asp Phe Ala Ser Asp
                325                 330                 335

Lys Pro Thr Thr Thr Pro Ala Pro Arg Pro Pro Thr Pro Ala Pro Thr
            340                 345                 350

Ile Ala Ser Gln Pro Leu Ser Leu Arg Pro Glu Ala Cys Arg Pro Ala
        355                 360                 365

Ala Gly Gly Ala Val His Thr Arg Gly Leu Asp Phe Ala Cys Asp Ile
    370                 375                 380

Tyr Ile Trp Ala Pro Leu Ala Gly Thr Cys Gly Val Leu Leu Leu Ser
385                 390                 395                 400

Leu Val Ile Thr Leu Tyr Cys Asn His Arg Asn Lys Arg Gly Arg Lys
                405                 410                 415

Lys Leu Leu Tyr Ile Phe Lys Gln Pro Phe Met Arg Pro Val Gln Thr
            420                 425                 430

Thr Gln Glu Glu Asp Gly Cys Ser Cys Arg Phe Pro Glu Glu Glu Glu
        435                 440                 445

Gly Gly Cys Glu Leu Arg Val Lys Phe Ser Arg Ser Ala Asp Ala Pro
    450                 455                 460

Ala Tyr Gln Gln Gly Gln Asn Gln Leu Tyr Asn Glu Leu Asn Leu Gly
465                 470                 475                 480

Arg Arg Glu Glu Tyr Asp Val Leu Asp Lys Arg Arg Gly Arg Asp Pro
                485                 490                 495

Glu Met Gly Gly Lys Pro Arg Arg Lys Asn Pro Gln Glu Gly Leu Tyr
```

```
            500                 505                 510

Asn Glu Leu Gln Lys Asp Lys Met Ala Glu Ala Tyr Ser Glu Ile Gly
        515                 520                 525

Met Lys Gly Glu Arg Arg Arg Gly Lys Gly His Asp Gly Leu Tyr Gln
    530                 535                 540

Gly Leu Ser Thr Ala Thr Lys Asp Thr Tyr Asp Ala Leu His Met Gln
545                 550                 555                 560

Ala Leu Pro Pro Arg
                565


<210> SEQ ID NO 244
<211> LENGTH: 612
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="EGFRvIII CAR (huMR1-2 scFv.CD8alpha 4x
      hinge & TM.4-1BB.CD3-zeta"

<400> SEQUENCE: 244

Asp Ile Gln Met Thr Gln Ser Pro Ser Ser Leu Ser Ala Ser Val Gly
1               5                   10                  15

Asp Arg Val Thr Ile Thr Cys Met Thr Ser Thr Asp Ile Asp Asp Asp
            20                  25                  30

Met Asn Trp Tyr Gln Gln Lys Pro Gly Lys Thr Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Leu Gln Ser Trp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Gly Gly Leu Val Lys Pro Gly Gly Ser Leu Lys Leu Ser Cys
    130                 135                 140

Ala Ala Ser Gly Phe Thr Phe Ser Lys Phe Gly Met Ser Trp Val Arg
145                 150                 155                 160

Gln Thr Pro Asp Lys Arg Leu Glu Trp Val Ala Ser Ile Ser Thr Gly
                165                 170                 175

Gly Tyr Asn Thr Phe Tyr Ser Asp Asn Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Met Tyr Tyr Cys Ala Arg Gly Tyr Ser Pro
    210                 215                 220

Tyr Ser Phe Ala Met Asp Tyr Trp Gly Gln Gly Thr Met Val Thr Val
225                 230                 235                 240

Ser Ser Lys Pro Thr Thr Thr Pro Ala Pro Arg Pro Pro Thr Pro Ala
                245                 250                 255

Pro Thr Ile Ala Ser Gln Pro Leu Ser Leu Arg Pro Glu Ala Ser Arg
```

-continued

```
            260                 265                 270

Pro Ala Ala Gly Gly Ala Val His Thr Arg Gly Leu Asp Phe Ala Ser
        275                 280                 285

Asp Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Ser Arg Pro
305                 310                 315                 320

Ala Ala Gly Gly Ala Val His Thr Arg Gly Leu Asp Phe Ala Ser Asp
                325                 330                 335

Lys Pro Thr Thr Thr Pro Ala Pro Arg Pro Pro Thr Pro Ala Pro Thr
            340                 345                 350

Ile Ala Ser Gln Pro Leu Ser Leu Arg Pro Glu Ala Ser Arg Pro Ala
        355                 360                 365

Ala Gly Gly Ala Val His Thr Arg Gly Leu Asp Phe Ala Ser Asp Lys
    370                 375                 380

Pro Thr Thr Thr Pro Ala Pro Arg Pro Pro Thr Pro Ala Pro Thr Ile
385                 390                 395                 400

Ala Ser Gln Pro Leu Ser Leu Arg Pro Glu Ala Cys Arg Pro Ala Ala
                405                 410                 415

Gly Gly Ala Val His Thr Arg Gly Leu Asp Phe Ala Cys Asp Ile Tyr
            420                 425                 430

Ile Trp Ala Pro Leu Ala Gly Thr Cys Gly Val Leu Leu Leu Ser Leu
        435                 440                 445

Val Ile Thr Leu Tyr Cys Asn His Arg Asn Lys Arg Gly Arg Lys Lys
    450                 455                 460

Leu Leu Tyr Ile Phe Lys Gln Pro Phe Met Arg Pro Val Gln Thr Thr
465                 470                 475                 480

Gln Glu Glu Asp Gly Cys Ser Cys Arg Phe Pro Glu Glu Glu Glu Gly
                485                 490                 495

Gly Cys Glu Leu Arg Val Lys Phe Ser Arg Ser Ala Asp Ala Pro Ala
            500                 505                 510

Tyr Gln Gln Gly Gln Asn Gln Leu Tyr Asn Glu Leu Asn Leu Gly Arg
        515                 520                 525

Arg Glu Glu Tyr Asp Val Leu Asp Lys Arg Arg Gly Arg Asp Pro Glu
    530                 535                 540

Met Gly Gly Lys Pro Arg Arg Lys Asn Pro Gln Glu Gly Leu Tyr Asn
545                 550                 555                 560

Glu Leu Gln Lys Asp Lys Met Ala Glu Ala Tyr Ser Glu Ile Gly Met
                565                 570                 575

Lys Gly Glu Arg Arg Arg Gly Lys Gly His Asp Gly Leu Tyr Gln Gly
            580                 585                 590

Leu Ser Thr Ala Thr Lys Asp Thr Tyr Asp Ala Leu His Met Gln Ala
        595                 600                 605

Leu Pro Pro Arg
    610
```

MODULATING EXPRESSION OF POLYPEPTIDES VIA NEW GENE SWITCH EXPRESSION SYSTEMS

CROSS-REFERENCE TO RELATED APPLICATION

The present application claims the benefit of U.S. provisional Patent Application Nos. 62/444,775 filed Jan. 10, 2017 and 62/464,958 filed Feb. 28, 2017, which are hereby incorporated by reference in their entirety.

REFERENCE TO SEQUENCE LISTING

The present application contains a Sequence Listing which has been filed electronically in ASCII format and is hereby incorporated by reference in its entirety. Said ASCII copy, created on Jan. 9, 2018, is named 50471_706_601_SL.txt and is 421,163 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE DISCLOSURE

Adoptive T cell immunotherapy using chimeric antigen receptors (CAR) and T-cell receptors (TCR) has been shown to successfully direct killing of tumor cells. While this innovative technology is promising, the administration of modified T cells into tumor bearing individuals has not been without safety issues, for instance tumor lysis and cytokine release syndrome. In addition, expressing CAR or TCR alone may not be sufficient for efficacy and additional expression of cytokines such as IL-2, IL-12, IL-15 or IL-21 may be needed to increase the efficacy of such treatments. However, this may lead to additional safety issues. It is therefore of interest to gain full control over expression of the therapeutic gene(s) of interest following patient administration.

SUMMARY OF THE DISCLOSURE

Disclosed herein, in certain embodiments, are systems, methods or compositions comprising gene switch polypeptides and polynucleotides encoding the same.

Provided herein is a composition that comprises a polynucleotide encoding gene switch polypeptides for ligand-inducible control of heterologous gene expression, wherein said gene switch polypeptides comprise: (a) a first gene switch polypeptide that comprises a DNA binding domain fused to a first nuclear receptor ligand binding domain; and (b) a second gene switch polypeptide that comprises a transactivation domain fused to a second nuclear receptor ligand binding domain, wherein said first gene switch polypeptide and said second gene switch polypeptide are connected by a linker.

Provided herein is a composition that comprises one or more polynucleotides encoding a gene switch system for ligand-inducible control of heterologous gene expression, wherein said gene switch system comprises: (a) a first gene switch polypeptide that comprises a transactivation domain; (b) a second gene switch polypeptide that comprises a DNA binding domain fused to a ligand binding domain; and (c) at least one heterologous gene polypeptide; wherein one of said first gene switch polypeptide, said second gene switch polypeptide and said heterologous gene polypeptide is connected by a polypeptide linker to another one of said first gene switch polypeptide, said second gene switch polypeptide and said heterologous gene polypeptide; and wherein said polypeptide linker comprises a cleavable linker or ribosome skipping linker sequence.

In some embodiments, the DNA binding domain of any of the compositions as provided herein comprises at least one of GAL4 (GAL4 DBD), a LexA DBD, a transcription factor DBD, a steroid/thyroid hormone nuclear receptor superfamily member DBD, a bacterial LacZ DBD, and a yeast DBD. In some embodiments, the DNA binding domain of any of the compositions as provided herein has a sequence as shown in SEQ ID NO: 184. In some embodiments, the transactivation domain of any of the compositions as provided herein comprises at least one of a VP16 transactivation domain and a B42 acidic activator transactivation domain. In some embodiments, the transactivation domain of any of the compositions as provided herein has a sequence as shown in SEQ ID NO: 181.

In some cases, at least one of the first nuclear receptor ligand binding domain, the second nuclear receptor ligand binding domain, and the ligand binding domain of any of the compositions as provided herein comprises at least one of an ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor. In other cases, at least one of the first nuclear receptor ligand binding domain, the second nuclear receptor ligand binding domain, and the ligand binding domain of any of the compositions as provided herein has a sequence as shown in any one of SEQ ID NOs: 185-186. In another case, the first gene switch polypeptide comprises a GAL4 DBD fused to an EcR nuclear receptor ligand binding domain, and said second gene switch polypeptide comprises a VP16 transactivation domain fused to a retinoid receptor X (RXR) nuclear receptor ligand binding domain. In yet another case, the Gal4 DBD fused to the EcR nuclear receptor ligand binding domain has a sequence as shown in any one of SEQ ID NOs: 185-186 or 187-188, and the VP16 transactivation domain fused to the retinoid receptor X (RXR) nuclear receptor ligand binding domain has a sequence as shown in SEQ ID NO: 183.

In some cases, the linker of any of the compositions as provided herein is a cleavable linker, a ribosome skipping linker sequence or an IRES linker. In some cases, the linker is an IRES linker and has a sequence as shown in any one of SEQ ID NOs: 18-19. In other cases, the linker is a cleavable linker or a ribosome skipping linker sequence. In some embodiments, the cleavable linker or the ribosome skipping linker sequence comprises one or more of a 2A linker, p2A linker, T2A linker, F2A linker, E2A linker, GSG-2A linker, GSG linker, SGSG linker, furinlink linker variants and derivatives thereof. In other embodiments, the cleavable linker or said ribosome skipping linker sequence has a sequence as shown in any one of SEQ ID NOs: 146-162.

In an embodiment, the polynucleotide or the one or more polynucleotides of any of the compositions as provided herein further encodes an antigen-binding polypeptide. In another embodiment, the antigen-binding polypeptide of any of the compositions as provided herein comprises at least one of a chimeric antigen receptor (CAR) and a T-cell receptor. In other embodiments, the antigen-binding polypeptide comprises a CAR and said CAR is capable of binding at least one of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MUC-16, MAGE-A1, h5T4, PSMA, TAG-72, EGFRvIII, CD123 and VEGF-R2. In another embodiment, the antigen-binding polypeptide comprises a CAR and the CAR has a sequence as shown in any one of SEQ ID NOs: 210-244.

In other embodiments, the polynucleotide or the one or more polynucleotides of any of the compositions as provided herein further encodes a cell tag. In some cases, the cell tag comprises at least one of a HER1 truncated variant or a CD20 truncated variant. In other cases, the cell tag has a sequence as shown in any one of SEQ ID NOs: 189-202.

In some embodiments, expression of at least one of the first gene switch polypeptide, the second gene switch polypeptide, the antigen-binding polypeptide, and the cell tag of any of the compositions as provided herein is modulated by a promoter, wherein the promoter is a tissue-specific promoter or an EF1A promoter or functional variant thereof. In some cases, the promoter is an EF1A promoter or functional variant thereof having a sequence as shown in any one of SEQ ID NOs: 58-60. In other cases, the promoter is a tissue-specific promoter comprising a T-cell-specific response element. In another case, the tissue-specific promoter comprises one or more NFAT response element(s). In yet another case, the NFAT response element has a sequence as shown in any one of SEQ ID NOs: 51-57.

In some examples, any of the compositions as provided herein further comprises a second polynucleotide encoding a heterologous gene polypeptide. In some cases, the heterologous gene polypeptide comprises at least one of a cytokine, a cell tag, and a chimeric antigen receptor (CAR). In some cases, the cytokine comprises a cytokine and said cytokine comprises at least one of IL-1, IL-2, IL-15, IL-12, IL-21, a fusion of IL-15, IL-15Rα, or an IL-15 variant. In other cases, the cytokine is in secreted form. In another case, the cytokine is in membrane-bound form. In yet another case, the cytokine has a sequence as shown in any one of SEQ ID NOs: 203-209.

In an embodiment, expression of the at least one heterologous gene polypeptide of any of the compositions as provided herein is modulated by an inducible promoter. In some embodiments, the inducible promoter has a sequence as shown in any of SEQ ID NOs: 40-64. In other embodiments, the inducible promoter is modulated by at least one of the first gene switch polypeptide and the second gene switch polypeptide.

Also provided herein is a vector that comprises the polynucleotide(s) of any of the compositions as provided herein. In an embodiment, the vector is a lentivirus vector, a retroviral vector, or a non-viral vector. In another embodiment, the non-viral vector is a Sleeping Beauty transposon.

Provided herein is a method of regulating the expression of a heterologous gene in an effector cell, the method comprising: (a) introducing into said effector cell one or more polynucleotides that encode (i) a first gene switch polypeptide that comprises a DNA-binding domain fused to a ligand binding domain, (ii) a second gene switch polypeptide that comprises a transactivation domain, (iii) a heterologous gene polypeptide encoded by said heterologous gene and (iv) a polypeptide linker that comprises a cleavable or ribosome skipping linker sequence, wherein said polypeptide linker connects one of said first gene switch polypeptide, said second gene switch polypeptide and said heterologous gene polypeptide to another one of said first gene switch polypeptide, said second gene switch polypeptide and said heterologous gene polypeptide, and (b) contacting said effector cell with a ligand in an amount sufficient to induce expression of said heterologous gene.

In an example, at least one of the one or more polynucleotides of the method of regulating the expression of the heterologous gene in the effector cell as provided herein further encodes an antigen-binding polypeptide. In some cases, the antigen-binding polypeptide selectively binds a predetermined cell surface protein of a target cell. In some cases, the target cell is a mammalian cell. In other cases, the target cell is a tumor cell.

In some embodiments, the predetermined cell surface protein of the method of regulating the expression of the heterologous gene in the effector cell as provided herein is a tumor antigen. In some cases, the antigen-binding polypeptide selectively binds the predetermined cell surface protein of the target cell prior to contacting the effector cell with the ligand. In some cases, the effector cell is exposed to the predetermined cell surface protein of the target cell for at least 7 days prior to contacting the effector cell with the ligand. In other cases, binding of the predetermined cell surface protein by the antigen-binding polypeptide activates the effector cell. In some embodiments, the method further comprises co-culturing said effector cell with an artificial antigen presenting cell (aAPC) expressing said predetermined cell surface protein, wherein binding of said antigen-binding polypeptide to said predetermined cell surface protein of said aAPC activates said effector cell. In some embodiments, the co-culturing is for at least 7 days, 14 days, 21 days or 28 days. In some cases, the aAPC is a transgenic K562 cell.

In other embodiments, the antigen-binding polypeptide in the method of regulating the expression of the heterologous gene in the effector cell as provided herein comprises at least one of a chimeric antigen receptor (CAR) and a T-cell receptor. In another embodiment, the antigen-binding polypeptide comprises a CAR and said CAR is capable of binding at least one of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MAGE-A1, MUC-16, h5T4, PSMA, TAG-72, EGFRvIII, CD123 and VEGF-R2. In yet another embodiment, the antigen-binding polypeptide comprises a CAR having a sequence as shown in any one of SEQ ID NOs: 210-244. In some embodiments, the heterologous gene polypeptide comprises the antigen-binding polypeptide.

In some cases, at least one of the one or more polynucleotides in the method of regulating the expression of the heterologous gene in the effector cell as provided herein further encodes a cell tag. In some cases, the cell tag comprises at least one of a HER1 truncated variant and a CD20 truncated variant. In other cases, the cell tag has a sequence as shown in any one of SEQ ID NOs: 189-202. In some cases, the heterologous gene polypeptide comprises the cell tag.

In other cases, at least one of the one or more polynucleotides in the method of regulating the expression of the heterologous gene in the effector cell as provided herein further encodes a cytokine. In some cases, the cytokine comprises at least one of IL-1, IL-2, IL-15, IL-12, IL-21, a fusion of IL-15, IL-15Rα, or an IL-15 variant. In an embodiment, the cytokine is in secreted form. In another embodiment, the cytokine is in membrane-bound form. In yet another embodiment, the cytokine has a sequence as shown in any one of SEQ ID NOs: 203-209. In other embodiments, the heterologous gene polypeptide comprises said cytokine.

In an embodiment, expression of the heterologous gene polypeptide in the method of regulating the expression of the heterologous gene in the effector cell as provided herein is modulated by an inducible promoter. In certain embodiments, the inducible promoter has a sequence as shown in any one of SEQ ID NOs: 40-64.

In another embodiment, the DNA-binding domain in the method of regulating the expression of the heterologous gene in the effector cell as provided herein comprises at least one of GAL4 (GAL4 DBD), a LexA DBD, a transcription factor DBD, a steroid/thyroid hormone nuclear receptor superfamily member DBD, a bacterial LacZ DBD, and a yeast DBD. In yet another embodiment, the DNA binding domain has a sequence as shown in SEQ ID NO: 184.

In yet another embodiment, the transactivation domain in the method of regulating the expression of the heterologous gene in the effector cell as provided herein comprises at least one of a VP16 transactivation domain, and a B42 acidic activator transactivation domain. In some cases, the transactivation domain has a sequence as shown in SEQ ID NO: 181. In other embodiments, at least one of said first and second gene switch polypeptides further comprises a response element capable of binding to said DNA-binding domain.

In some embodiments, the ligand binding domain in the method of regulating the expression of the heterologous gene in the effector cell as provided herein comprises at least one of an ecdysone receptor (EcR), a ubiquitous receptor, an orphan receptor 1, an NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor. In certain embodiments, the ligand binding domain has a sequence as shown in any one of SEQ ID NOs: 185-186. In certain embodiments, the first gene switch polypeptide comprises a GAL4 DBD fused to an EcR nuclear receptor ligand binding domain, and the second gene switch polypeptide comprises a VP16 transactivation domain fused to a retinoid receptor X (RXR) nuclear receptor ligand binding domain. In some embodiments, the Gal4 DBD fused to an EcR has a sequence as shown in any one of SEQ ID NOs: 185-186 and said VP16 transactivation domain fused to a retinoid receptor X (RXR) nuclear receptor ligand binding domain has a sequence as shown in SEQ ID NO: 183.

In certain embodiments, the ligand in the method of regulating the expression of the heterologous gene in the effector cell as provided herein comprises at least one of: (2S,3R,5R,9R,10R,13R,14S,17R)-17-[(2S,3R)-3,6-dihydroxy-6-methylheptan-2-yl]-2,3,14-trihydroxy-10,13-dimethyl-2,3,4,5,9,11,12,15,16,17-decahydro-1H-cyclopenta[a]phenanthren-6-one; N'-(3,5-Dimethylbenzoyl)-N'-[(3R)-2,2-dimethyl-3-hexanyl]-2-ethyl-3-methoxybenzohydrazide; 5-Methyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Methyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide; 5-Methyl-2,3-dihydro-benzo[1,4]dioxine-6-carboxylic acid N'-(1-tert-butyl-butyl)-N'-(3,5-dimethyl-benzoyl)-hydrazide; 5-Methyl-2,3-dihydro-benzo[1,4]dioxine-6-carboxylic acid N'-(1-tert-butyl-butyl)-N'-(3,5-dimethoxy-4-methyl-benzoyl)-hydrazide; 5-Ethyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Ethyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide; 5-Ethyl-2,3-dihydro-benzo[1,4]dioxine-6-carboxylic acid N'-(1-tert-butyl-butyl)-N'-(3,5-dimethyl-benzoyl)-hydrazide, 5-Ethyl-2,3-dihydro-benzo[1,4]dioxine-6-carboxylic acid N'-(1-tert-butyl-butyl)-N'-(3,5-dimethoxy-4-methyl-benzoyl)-hydrazide; 3,5-Dimethyl-benzoic acid N-(1-ethyl-2,2-dimethyl-propyl)-N'-(3-methoxy-2-methyl-benzoyl)-hydrazide; 3,5-Dimethoxy-4-methyl-benzoic acid N-(1-ethyl-2,2-dimethyl-propyl)-N'-(3-methoxy-2-methyl-benzoyl)-hydrazide; 3,5-Dimethyl-benzoic acid N-(1-tert-butyl-butyl)-N'-(3-methoxy-2-methyl-benzoyl)-hydrazide; 3,5-Dimethoxy-4-methyl-benzoic acid N-(1-tert-butyl-butyl)-N'-(3-methoxy-2-methyl-benzoyl)-hydrazide; 3,5-Dimethyl-benzoic acid N-(1-ethyl-2,2-dimethyl-propyl)-N'-(2-ethyl-3-methoxy-benzoyl)-hydrazide; 3,5-Dimethoxy-4-methyl-benzoic acid N-(1-ethyl-2,2-dimethyl-propyl)-N'-(2-ethyl-3-methoxy-benzoyl)-hydrazide; 3,5-Dimethyl-benzoic acid N-(1-tert-butyl-butyl)-N'-(2-ethyl-3-methoxy-benzoyl)-hydrazide; 3,5-Dimethoxy-4-methyl-benzoic acid N-(1-tert-butyl-butyl)-N'-(2-ethyl-3-methoxy-benzoyl)-hydrazide; 2-Methoxy-nicotinic acid N-(1-tert-butyl-pentyl)-N'-(4-ethyl-benzoyl)-hydrazide; 3,5-Dimethyl-benzoic acid N-(2,2-dimethyl-1-phenyl-propyl)-N'-(4-ethyl-benzoyl)-hydrazide; 3,5-Dimethyl-benzoic acid N-(1-tert-butyl-pentyl)-N'-(3-methoxy-2-methyl-benzoyl)-hydrazide; and 3,5-Dimethoxy-4-methyl-benzoic acid N-(1-tert-butyl-pentyl)-N'-(3-methoxy-2-methyl-benzoyl)-hydrazide.

In some cases, the expression of the heterologous gene in the method of regulating the expression of the heterologous gene in the effector cell as provided herein is reduced or eliminated in the absence of the ligand, as compared to the expression in the presence of the ligand. In certain cases, the expression of said heterologous gene is restored by providing additional amounts of the ligand.

In other cases, expression of at least one of the first gene switch polypeptide and the second gene switch polypeptide is modulated by a promoter in the method of regulating the expression of the heterologous gene in the effector cell as provided herein, wherein said promoter is a tissue-specific promoter or an EF1A promoter or functional variant thereof. In certain cases, the promoter is an EF1A promoter or functional variant thereof having a sequence as shown in any one of SEQ ID NOs: 58-60. In other cases, the promoter is a tissue-specific promoter, and the tissue-specific promoter comprises a T-cell-specific response element. In another case, the tissue-specific promoter comprises one or more NFAT response element(s). In yet another case, the NFAT response element has a sequence as shown in any one of SEQ ID NOs: 50-57.

In certain cases, the one or more polynucleotides of the method of regulating the expression of the heterologous gene in the effector cell as provided herein are comprised within a vector. In some cases, the vector is a lentivirus vector, a retroviral vector, or a non-viral vector. In certain cases, the non-viral vector is a Sleeping Beauty transposon.

Provided herein is a gene switch system for ligand-inducible control of heterologous gene expression, wherein said gene switch system comprises one or more expression cassettes, wherein said one or more expression cassettes comprise: (a) a sequence encoding a first gene switch polypeptide that comprises a DNA binding domain fused to a first nuclear receptor ligand binding domain; and (b) a sequence encoding a second gene switch polypeptide that comprises a transactivation domain fused to a second nuclear receptor ligand binding domain; wherein said first gene switch polypeptide and said second gene switch polypeptide are connected by a polypeptide linker.

Provided herein is a gene switch system for ligand-inducible control of heterologous gene expression, wherein said gene switch system comprises one or more expression cassettes, wherein said one or more expression cassettes comprise: (a) a sequence encoding a first gene switch polypeptide that comprises a transactivation domain; (b) a sequence encoding a second gene switch polypeptide that comprises a DNA binding domain fused to a ligand binding domain; and (c) a sequence encoding a heterologous gene polypeptide; wherein one of said transactivation domain, DNA binding domain fused to said ligand binding domain, and said heterologous gene polypeptide is connected by a polypeptide linker to another of said transactivation domain, DNA binding domain fused to said ligand binding domain, and said heterologous gene polypeptide, and wherein said polypeptide linker comprises a cleavable or ribosome skipping linker sequence.

In some embodiments, the one or more expression cassettes of the gene switch system as provided herein further comprise a sequence encoding a heterologous gene polypeptide. In some embodiments, the one or more expression cassettes further comprise one or more of the following: (a) one or more recombinase attachment sites; and (b) a sequence encoding a serine recombinase. In other embodiments, the one or more expression cassettes further comprise one or more of the following: (a) a non-inducible promoter; and (b) an inducible promoter.

In certain embodiments, the DNA binding domain of the gene switch system as provided herein has a sequence as shown in SEQ ID NO: 184. In other embodiments, the transactivation domain of the gene switch system as provided herein has a sequence as shown in SEQ ID NO: 181. In another embodiment, at least one of the first and second nuclear receptor ligand binding domains and the ligand binding domain has a sequence as shown in any one of SEQ ID NOs: 185-186. In certain embodiments, the non-inducible promoter has a sequence as shown in any one of SEQ ID NOs: 40-64. In certain embodiments, the inducible promoter has a sequence as shown in any one of SEQ ID NOs: 40-64. In certain embodiments, the polypeptide linker has a sequence as shown in any one of SEQ ID NOs: 146-162. In some embodiments, the polypeptide linker is a cleavable linker, a ribosome skipping linker or an IRES linker with a sequence as shown in any one of SEQ ID NOs: 18-19 and 146-162.

In some examples, the one or more expression cassettes of the gene switch system as provided herein include an expression cassette that comprises a sequence encoding a chimeric antigen receptor (CAR), wherein expression of the chimeric antigen receptor is modulated by a non-inducible promoter. In certain examples, the CAR is capable of binding at least one of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MAGE-A1, MUC-16, h5T4, PSMA, TAG-72, EGFRvIII, CD123 and VEGF-R2.

In other examples, the non-inducible promoter of the gene switch system as provided herein comprises EF1A or a variant thereof. In certain cases, the expression cassette has a sequence as shown in SEQ ID NO: 131. In other cases, the expression cassette further comprises a sequence encoding a cell tag, wherein the cell tag is connected to the CAR by a linker. In some cases, the cell tag comprises at least one of a HER truncated variant and a CD20 truncated variant.

In another example, the expression cassette of the gene switch system as provided herein has a sequence as shown in SEQ ID NO: 132. In some embodiments, the expression cassette further comprises a sequence encoding the first gene switch polypeptide and a sequence encoding the second gene switch polypeptide, wherein one of the first and second gene switch polypeptides is connected to the CAR by a linker.

In some embodiments, the first and second gene switch polypeptides of the gene switch system as provided herein are connected by said polypeptide linker, and the polypeptide linker is a cleavable linker. In some embodiments, the expression cassette has a sequence as shown in SEQ ID NO: 133. In some embodiments, the first and second gene switch polypeptides are connected by the polypeptide linker, and the polypeptide linker is an IRES linker.

In certain embodiments, the expression cassette of the gene switch system as provided herein has a sequence as shown in SEQ ID NO: 134. In other embodiments, the one or more expression cassettes includes an expression cassette that comprises a sequence encoding the heterologous gene polypeptide, wherein expression of said heterologous gene polypeptide is modulated by an inducible promoter. In other embodiments, the heterologous gene polypeptide comprises a cytokine. In some cases, the cytokine comprises at least one of IL-1, IL-2, IL-15, IL-12, IL-21, a fusion of IL-15, IL-15Rα, or an IL-15 variant.

In another embodiment, the expression cassette of the gene switch system as provided herein has a sequence as shown in SEQ ID NO: 135. In some embodiments, the expression cassette comprises a sequence encoding a second heterologous gene polypeptide, wherein the second heterologous gene polypeptide comprises a cell tag. In certain cases, the cell tag comprises at least one of a HER1 truncated variant and a CD20 truncated variant. In other cases, the cell tag is connected to the cytokine by a linker. In another case, the expression cassette has a sequence as shown in SEQ ID NO: 136.

In some cases, the gene switch system as provided herein is for integrating a heterologous gene in a host cell, wherein upon contacting the host cell with the one or more expression cassettes in the presence of the serine recombinase and the one or more recombinase attachment sites, the heterologous gene is integrated in the host cell. In certain cases, the gene switch system further comprises a ligand, wherein the heterologous gene is expressed in the host cell upon contacting the host cell with the ligand. In certain cases, the host cell is a T cell or an NK cell. In certain cases, the one or more recombinase attachment sites can comprise a phage genomic recombination attachment site (attP) or a bacterial genomic recombination attachment site (attB). In some cases, the serine recombinase can be SF370.

In certain cases, the inducible promoter of the gene switch system as provided herein is activated by the transactivation domain. In certain cases, the system is contained in one or more vectors. In certain cases, the system is contained in one vector.

Disclosed is a polynucleotide encoding one or more of the components of the gene switch system as provided herein. Also disclosed herein is a vector that comprises the polynucleotide encoding one or more of the components of the gene switch system as provided herein. In certain cases, the vector is any one of a lentivirus vector, a retroviral vector, or a non-viral vector. In certain cases, the vector is a non-viral vector and said non-viral vector is a Sleeping Beauty transposon.

Provided herein is a polynucleotide construct that comprises: a polynucleotide that encodes a first gene switch polypeptide, a polynucleotide that encodes a second gene switch polypeptide, and a polynucleotide that encodes a gene of interest (GOI), wherein the polynucleotide that encodes the GOI comprises a continuous open-reading frame (ORF) positioned between the polynucleotide that encodes the first gene switch polypeptide and the polynucleotide that encodes the second gene switch polypeptide, wherein the polynucleotide construct further comprises a polynucleotide that encodes a linker, and wherein said GOI is connected by said linker to each of said first and second gene switch polypeptides.

Provided herein is a polynucleotide that comprises at least one of: (i) a first sequence that encodes a first gene switch polypeptide that comprises a DNA binding domain fused to a first nuclear receptor ligand binding domain; and (ii) a second sequence that encodes a second gene switch polypeptide that comprises a transactivation domain fused to a second nuclear receptor ligand binding domain; wherein expression of at least one of said first sequence and said second sequence is modulated by one or more NFAT response element.

Provided herein is a-method of stimulating the proliferation and/or survival of engineered cells, the method comprising: (a) obtaining a sample of cells from a subject, and (b) transfecting cells of said sample of cells with one or more polynucleotides that comprise one or more transposons, wherein said one or more transposons encode: a chimeric antigen receptor (CAR) or a TCR, a cytokine, one or more cell tags, gene switch polypeptides for ligand-inducible control of said cytokine and a transposase effective to integrate said one or more polynucleotides into the genome of said cells, to provide a population of engineered cells; wherein said gene switch polypeptides comprise: i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein said first gene switch polypeptide and said second gene switch polypeptide are connected by a linker.

Provided herein is a method of enhancing in vivo persistence of engineered cells in a subject in need thereof, the method comprising: (a) obtaining a sample of cells from a subject, and (b) transfecting cells of said sample of cells with one or more polynucleotides that comprise one or more transposons, wherein said one or more transposons encode: a chimeric antigen receptor (CAR) or a TCR, a cytokine, one or more cell tags, gene switch polypeptides for ligand-inducible control of said cytokine and a transposase effective to integrate the DNA into the genome of said cells, to provide a population of engineered cells; wherein said gene switch polypeptides comprise: i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein said first gene switch polypeptide and said second gene switch polypeptide are connected by a linker.

In some embodiments, the transfecting cells in the methods provided herein comprises electroporating the cells. In certain embodiments, at least one polynucleotide of the one or more polynucleotides encodes the gene switch polypeptides, and the at least one polynucleotide is modulated by a promoter, wherein the promoter is a tissue-specific promoter or an EF1A promoter or functional variant thereof. In certain cases, the promoter is an EF1A promoter or functional variant thereof having a sequence as shown in any one of SEQ ID NOs: 58-60. In certain cases, the promoter is a tissue-specific promoter, and the tissue-specific promoter comprises a T-cell-specific response element. In certain cases, the promoter is a tissue-specific promoter, and the tissue-specific promoter comprises one or more NFAT response element. In certain cases, the NFAT response element has a sequence as shown in any one of SEQ ID NOs: 50-57. In certain cases, the cytokine comprises at least one of IL-1, IL-2, IL-15, IL-12, IL-21, a fusion of IL-15, IL-15Rα, or an IL-15 variant. In other cases, the cytokine is in secreted form. In another case, the cytokine is in membrane-bound form. In yet another case, the cytokine has a sequence as shown in any one of SEQ ID NOs: 203-209. In yet another case, the cells are NK cells, NKT cells, T-cells or T-cell progenitor cells.

In other cases, the method as provided herein further comprises administering an effective amount of the engineered cells to a subject in need thereof. In certain cases, administering comprises immediately infusing the subject with the engineered cells. In certain cases, the method further comprises administering an effective amount of the ligand to induce expression of the cytokine. In certain cases, the ligand is veledimex. In some cases, the CAR is capable of binding at least one of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MAGE-A1, MUC-16, h5T4, PSMA, TAG-72, EGFRvIII, CD123 and VEGF-R2. In certain cases, the CAR is capable of binding CD19. In certain cases, the CAR is capable of binding CD33. In certain cases, the transposase is salmonid-type Tc1-like transposase. In certain cases, the transposase is SB11 or SB100x transposase. In certain cases, the one or more cell tags comprises at least one of a HER1 truncated variant and a CD20 truncated variant. In certain cases, the one or more cell tags has a sequence as shown in any one of SEQ ID NOs: 189-202.

Provided herein is a method of treating a subject with a solid tumor, the method comprising: (a) obtaining a sample of cells from a subject, (b) transfecting cells of said sample of cells with one or more polynucleotides that comprise one or more transposons, wherein said one or more transposons encode: a chimeric antigen receptor (CAR) or a TCR, a cytokine, one or more cell tags, gene switch polypeptides for ligand-inducible control of said cytokine and a transposase effective to integrate the DNA into the genome of said cells, to provide a population of engineered cells; wherein said gene switch polypeptides comprise: i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein said first gene switch polypeptide and said second gene switch polypeptide are connected by a linker, and (c) administering said population of engineered cells to said subject.

In some embodiments, the cytokine in the method of treating comprises at least one of IL-1, IL-2, IL-15, IL-12, IL-21, a fusion of IL-15, IL-15Rα, or an IL-15 variant. In some embodiments, the cytokine comprises IL-12. In some embodiments, at least one polynucleotide of the one or more polynucleotides encodes the gene switch polypeptides, and the at least one polynucleotide is modulated by a promoter, wherein the promoter is a tissue-specific promoter or an EF1A promoter or functional variant thereof. In some embodiments, the promoter is an EF1A promoter or functional variant thereof having a sequence as shown in any one of SEQ ID NOs: 58-60. In certain embodiments, the promoter is a tissue-specific promoter, and the tissue-specific promoter comprises a T-cell-specific response element. In some embodiments, the promoter is a tissue-specific promoter, and the tissue-specific promoter comprises one or more NFAT response element. In some embodiments, the NFAT response element has a sequence as shown in any one of SEQ ID NOs: 50-57.

Also disclosed is an engineered effector cell, wherein said engineered effector cell comprises: (a) a first polynucleotide encoding an engineered receptor construct that selectively binds a predetermined cell surface protein expressed by a target cell; (b) one or more polynucleotides encoding one or more engineered gene switch polypeptides, wherein said engineered gene switch polypeptides comprise one or more of a transactivation domain, a DNA binding domain, and a ligand binding domain; and (c) a heterologous gene under the control of a ligand-inducible promoter modulated by said engineered gene switch polypeptides; wherein said heterologous gene encodes a cytokine.

In some embodiments, the target cell is a mammalian cell. In some embodiments, the target cell is a tumor cell. In some embodiments, the cell surface protein is expressed on the surface of said tumor cell. In some embodiments, the cell surface protein is expressed in an artificial antigen-presenting cell (aAPC). In some embodiments, the engineered receptor construct is a chimeric antigen receptor. In some embodiments, the chimeric antigen receptor binds CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MAGE-A1, h5T4, PSMA, TAG-72, EGFRvIII, CD123 or VEGF-R2. In some embodiments, the chimeric antigen receptor binds EGFRvIII.

In some embodiments, the engineered receptor construct is an engineered T-cell receptor. In some embodiments, the cytokine is IL-2, IL-15, IL-12, IL-21, or a fusion of IL-15 and IL-15Rα. In some embodiments, the cytokine is IL-12. In some embodiments, the effector cell further comprises a polynucleotide encoding a protein comprising a cell tag. In some embodiments, the cell tag is a truncated HER1 variant or a CD20 truncated variant. In some embodiments, the effector cell is an immune effector cell. In some embodiments, the effector cell is a T cell, an NK cell or a tumor infiltrating lymphocyte. In some embodiments, the one or more engineered gene switch polypeptides comprise a transactivation domain, a DNA binding domain and a ligand binding domain. In some embodiments, the one or more engineered gene switch polypeptides comprise a first gene switch polypeptide comprising said DNA-binding domain fused to a nuclear receptor ligand binding domain and a second gene switch polypeptide comprising said transactivation domain fused to a nuclear receptor ligand binding domain.

In some embodiments, the first gene switch polypeptide and said second gene switch polypeptide are connected by a polypeptide linker. In some embodiments, the polypeptide linker is a cleavable or ribosome skipping linker sequence. In some embodiments, the polypeptide linker comprises one of 2A, F/T2A, GSG-2A, GSG linker, SGSG linker, furinlink variants and derivatives thereof. In some embodiments, the transactivation domain comprises a VP16 transactivation domain. In some embodiments, the one or more engineered gene switch polypeptides comprise at least one of an ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor. In some embodiments, the DNA-binding domain (DBD) comprises at least one of GAL4 (GAL4 DBD), a LexA DBD, a transcription factor DBD, a steroid/thyroid hormone nuclear receptor superfamily member DBD, a bacterial LacZ DBD, and a yeast DBD.

Further disclosed herein is a method of modulating the expression of a heterologous gene, the method comprising contacting the target cell with an effector cell disclosed herein. In some cases, the modulating comprises increasing or decreasing expression of said heterologous gene. In some cases, the expression is reduced or eliminated in the absence of said ligand, as compared to the expression in the presence of said ligand. In some cases, the expression is resuscitated by providing additional amounts of said ligand.

Further disclosed is a method of regulating the expression of a heterologous in an effector cell, the method comprising: introducing into said effector cell polynucleotides encoding one or more engineered gene switch polypeptides, an engineered receptor construct, and said heterologous gene; wherein said heterologous gene is under the control of an inducible promoter; activating said effector cell via said engineered receptor construct; and presenting a ligand to said effector cell for inducing expression of said heterologous gene via said one or more engineered gene switch polypeptides after said activating said effector cell.

In some cases, the activating comprises contacting the effector cell with an antigen. In some cases, the antigen is a tumor antigen. In some cases, the effector cell is exposed to the tumor antigen for at least 7 days prior to presenting a ligand to the effector cell. In some cases, activating the effector cell comprises co-culturing the effector cell with an artificial antigen presenting cell (aAPC). In some cases, the co-culturing is for at least 7 days, 14 days, 21 days or 28 days. In some cases, the aAPC is a transgenic K562 cell. In some cases, the engineered receptor construct comprises a chimeric antigen receptor (CAR). In some cases, the CAR binds CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MAGE-A1, h5T4, PSMA, TAG-72, EGFRvIII, CD123, or VEGF-R2. In some cases, the engineered receptor construct comprises an engineered T-cell receptor (TCR). In some cases, the effector cell comprises contacting the effector cell with a TCR-binding polypeptide. In some cases, the TCR-binding polypeptide comprises a TCR-binding antibody or fragment thereof. In some cases, the effector cell is exposed to the TCR-binding polypeptide for at least 7 days prior to presenting a ligand to the effector cell. In some cases, the TCR-binding polypeptide is expressed by an aAPC. In some cases, the heterologous gene encodes a cytokine. In some cases, the cytokine is IL-2, IL-15, IL-12, IL-21, or a fusion of IL-15 and IL-15Rα. In some cases, the cytokine is IL-12.

In some cases, the heterologous gene encodes at least one cell tag. In some cases, the cell tag is a HER1 truncated variant or a CD20 truncated variant. In some cases, the one or more gene expression cassettes further comprise a nucleotide sequence encoding a cell tag. In some cases, the effector cell is an immune effector cell. In some cases, the immune effector cell is a T-cell, an NK cell or a tumor infiltrating lymphocyte. In some cases, the one or more engineered gene switch polypeptides comprise a transactivation domain, a DNA-binding domain, and a ligand-binding domain. In some cases, the ligand-binding domain comprises at least one of an ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a farnesol receptor. In some cases, the DNA-binding domain comprises at least one of GAL4 (GAL4 DBD), a LexA DBD, a transcription factor DBD, a steroid/thyroid hormone nuclear receptor superfamily member DBD, a bacterial LacZ DBD, and a yeast DBD. In some cases, the transactivation domain comprises a VP16 transactivation domain.

In some cases, the one or more engineered gene switch polypeptides further comprise a response element capable of binding to said DNA-binding domain. In some cases, the one or more engineered gene switch polypeptides further comprise at least one of ultraspiracle protein (USP), retinoid receptor X (RXR), or functional fragments and variants thereof, wherein said functional fragments and variants thereof are capable of binding to an EcR. In some cases, the one or more engineered gene switch polypeptides further comprise one or more polypeptide linkers. In some cases, the one or more polypeptide linkers further comprise at least one of 2A, GSG-2A, GSG linker, SGSG linker, furinlink variants and derivatives thereof. In some cases, the ligand comprises at least one of: (2S,3R,5R,9R,10R,13R,14S,17R)-17-[(2S,3R)-3,6-dihydroxy-6-methylheptan-2-yl]-2,3,14-trihydroxy-10,13-dimethyl-2,3,4,5,9,11,12,15,16,17-decahydro-1H-cyclopenta[a]phenanthren-6-one; N'-(3,5-Dimethylbenzoyl)-N'-[(3R)-2,2-dimethyl-3-hexanyl]-2-ethyl-3-methoxybenzohydrazide; 5-Methyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Methyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide; 5-Methyl-2,3-dihydro-benzo[1,4]dioxine-6-carboxylic acid N'-(1-tert-butyl-butyl)-N'-(3,5-dimethyl-benzoyl)-hydrazide; 5-Methyl-2,3-dihydro-benzo[1,4]dioxine-6-carboxylic acid N'-(1-tert-butyl-butyl)-N'-(3,5-dimethoxy-4-methyl-benzoyl)-hydrazide; 5-Ethyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Ethyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide; 5-Ethyl-2,3-dihydro-benzo[1,4]dioxine-6-carboxylic acid N'-(1-tert-butyl-butyl)-N'-(3,5-dimethyl-benzoyl)-hydrazide; 5-Ethyl-2,3-dihydro-benzo[1,4]dioxine-6-carboxylic acid N'-(1-tert-butyl-butyl)-N'-(3,5-dimethoxy-4-methyl-benzoyl)-hydrazide; 3,5-Dimethyl-benzoic acid N-(1-ethyl-2,2-dimethyl-propyl)-N'-(3-methoxy-2-methyl-benzoyl)-hydrazide; 3,5-Dimethoxy-4-methyl-benzoic acid N-(1-ethyl-2,2-dimethyl-propyl)-N'-(3-methoxy-2-methyl-benzoyl)-hydrazide; 3,5-Dimethyl-benzoic acid N-(1-tert-butyl-butyl)-N'-(3-methoxy-2-methyl-benzoyl)-hydrazide; 3,5-Dimethoxy-4-methyl-benzoic acid N-(1-tert-butyl-butyl)-N'-(3-methoxy-2-methyl-benzoyl)-hydrazide; 3,5-Dimethyl-benzoic acid N-(1-ethyl-2,2-dimethyl-propyl)-N'-(2-ethyl-3-methoxy-benzoyl)-hydrazide; 3,5-Dimethoxy-4-methyl-benzoic acid N-(1-ethyl-2,2-dimethyl-propyl)-N'-(2-ethyl-3-methoxy-benzoyl)-hydrazide; 3,5-Dimethyl-benzoic acid N-(1-tert-butyl-butyl)-N'-(2-ethyl-3-methoxy-benzoyl)-hydrazide; 3,5-Dimethoxy-4-methyl-benzoic acid N-(1-tert-butyl-butyl)-N'-(2-ethyl-3-methoxy-benzoyl)-hydrazide; 2-Methoxy-nicotinic acid N-(1-tert-butyl-pentyl)-N'-(4-ethyl-benzoyl)-hydrazide; 3,5-Dimethyl-benzoic acid N-(2,2-dimethyl-1-phenyl-propyl)-N'-(4-ethyl-benzoyl)-hydrazide; 3,5-Dimethyl-benzoic acid N-(1-tert-butyl-pentyl)-N'-(3-methoxy-2-methyl-benzoyl)-hydrazide; and 3,5-Dimethoxy-4-methyl-benzoic acid N-(1-tert-butyl-pentyl)-N'-(3-methoxy-2-methyl-benzoyl)-hydrazide.

Further disclosed herein is a polynucleotide for ligand-inducible control of heterologous gene expression in an engineered cell, wherein said polynucleotide comprises: (a) a first sequence encoding an engineered receptor construct capable of binding a predetermined cell surface protein expressed by a target cell; and (b) a second sequence encoding one or more engineered gene switch polypeptides for ligand-inducible control of said heterologous gene expression by modulating a promoter linked to said heterologous gene in response to the presence of said ligand; wherein said engineered receptor construct and said one or more engineered gene switch polypeptides are connected by a polypeptide linker.

In some embodiments, the polypeptide linker comprises a cleavable linker sequence. In some embodiments, the cleavable linker sequence is an F2A linker. In some embodiments, the one or more engineered gene switch polypeptides comprise a first gene switch polypeptide comprising a DNA-binding domain fused to a nuclear receptor ligand binding domain, and a second gene switch polypeptide comprising a transactivation domain fused to a nuclear receptor ligand binding domain. In some embodiments, the first gene switch polypeptide and the second gene switch polypeptide are connected by a linker. In some embodiments, the linker is a cleavable or ribosome skipping linker sequence. In some embodiments, the linker is a 2A linker, GSG-2A linker, GSG linker, SGSG linker, furinlink variants and derivatives thereof. In some embodiments, the 2A linker is an F2A linker. In some embodiments, the heterologous gene encodes a cytokine. In some embodiments, the cytokine is IL-2, IL-15, IL-12, IL-21, or a fusion of IL-15 and IL-15Rα. In some embodiments, the cytokine is IL-12. In some embodiments, the heterologous gene encodes at least one cell tag. In some embodiments, the cell tag is a HER1 truncated variant or a CD20 truncated variant. In some embodiments, the polynucleotide is incorporated into an engineered cell.

Further disclosed herein is a system for expressing a cytokine in a host cell in a vicinity of a target cell, wherein the system comprises: (a) the host cell encoding: (i) an engineered receptor construct that selectively binds a predetermined cell surface protein expressed in the target cell; (ii) an engineered gene switch polypeptide, wherein the engineered gene switch polypeptide comprises one or more of a transactivation domain, a DNA-binding domain, and a ligand-binding domain; and (iii) a cytokine expressed from a heterologous gene linked to a promoter modulated by the engineered gene switch polypeptide; and (b) a ligand; such that upon binding of the engineered receptor construct to the cell surface protein in the presence of the ligand, the cytokine is expressed by the host cell in the vicinity of the target cell.

In some cases, the engineered receptor construct comprises a chimeric antigen receptor. In some cases, the chimeric antigen receptor binds CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MAGE-A1, h5T4, PSMA, TAG-72, EGFRvIII, CD123 or VEGF-R2. In some cases, the chimeric antigen receptor binds EGFRvIII. In some cases, the engineered receptor construct comprises an engineered T-cell receptor. In some cases, the cytokine is IL-2, IL-15, IL-12, IL-21, or a fusion of IL-15 and IL-15Rα. In some cases, the cytokine is IL-12. In some cases, the host cell further encodes at least one cell tag. In some cases, the cell tag is a HER1 truncated variant or a CD20 truncated variant.

Further provided for herein is a method of expressing a cytokine from a host cell in the vicinity of a target cell, the method comprising contacting a system disclosed herein the said target cell in the presence of the ligand. Further provided for herein is a method of modulating the expression of a cytokine from a host cell in the vicinity of a target cell, the method comprising contacting a system disclosed herein with the target cell in the presence of the ligand, and regulating the amount of ligand. In some cases, the expression is reduced or eliminated in the absence of said ligand, as compared to expression in the presence of said ligand. In some cases, the expression is resuscitated by providing additional amounts of said ligand. In some cases, the host cell is an animal cell or a mammalian cell. In some cases, the mammalian cell is a human cell. In some cases, the mammalian cell is a T-cell, an NK cell, or a tumor-infiltrating lymphocyte. In some cases, the target cell is a tumor cell. In some cases, the system is contained in one or more vectors. In some cases, each vector comprises a plasmid. In some cases, each vector comprises an expression plasmid. In some cases, each vector is a lentivirus vector, a retroviral vector, or a non-viral vector. In some cases, the non-viral vector comprises a Sleeping Beauty transposase and a SB transposon.

Further disclosed herein is a polypeptide for binding to EGFRvIII, wherein the polypeptide comprises a polypeptide sequence which has at least 70%, 75%, 80%, 85%, 90%, 95%, 99% or 99.5% identity to a sequence shown in SEQ ID NOs: 233, 234, 235, 236, 237, 238, 239, 240, 241, 242, 243, or 244.

In some cases, the polypeptide is expressed in an engineered effector cell. In some cases, the effector cell is an immune effector cell. In some cases, the immune effector cell is a T-cell, an NK cell or a tumor-infiltrating lymphocyte. In some cases, the polypeptide comprises an antibody or fragment thereof. In some cases, the polypeptide comprises a chimeric antigen receptor (CAR). In some cases, the EGFRvIII binds an scFv antigen-binding domain of said antibody or fragment thereof or said CAR. In some cases, the polypeptide does not cross-react with wild-type EGFR.

Further disclosed herein is a polynucleotide encoding: a) an engineered receptor construct capable of binding EGFRvII; b) a first polypeptide comprising a transactivation domain and a nuclear receptor ligand binding domain; and (c) a second polypeptide comprising a DNA-binding domain and a nuclear receptor ligand binding domain; wherein an F/T2A linker connects at least two of the engineered receptor construct, the first polypeptide and the second polypeptide.

In some cases, the F/T2A linker connects said engineered receptor construct to at least one of said first polypeptide and said second polypeptide. In some cases, the F/T2A linker connects the first polypeptide to said second polypeptide. In some cases, the polynucleotide further encodes an IRES linker. In some cases, the IRES linker connects the first polypeptide to the second polypeptide.

Further disclosed herein is an effector cell comprising a polynucleotide disclosed herein. In some cases, the effector cell encodes a heterologous gene linked to an inducible promoter capable of being modulated by said first polypeptide or said second polypeptide.

Further disclosed herein is a chimeric antigen receptor (CAR) capable of binding EGFRvIII, wherein the CAR comprises: (a) an EGFRvIII-binding region; (b) a transmembrane region; and (c) a spacer region connecting the transmembrane region with the EGFRvIII binding region, wherein the spacer region comprises a stalk region comprising at least one dimerization site, and a stalk extension region comprising a sequence with at least 75% sequence identity to the stalk region.

Further disclosed herein is an engineered effector cell that comprises: (a) an EGFRvIII binding moiety at a surface of said engineered effector cell effective to bind an EGFRvIII molecule or variant thereof; (b) an engineered gene switch polypeptide, wherein the engineered gene switch polypeptide comprises one or more of a transactivation domain, a DNA binding domain, and a ligand binding domain; and (c) a heterologous gene encoding a cytokine, the heterologous gene controlled by a promoter modulated by the engineered gene switch polypeptide.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

Constructs 1, 4, 5, 6, 7 and 9 correspond to constructs as schematically depicted in FIG. 2A-2D.

Figure 7:
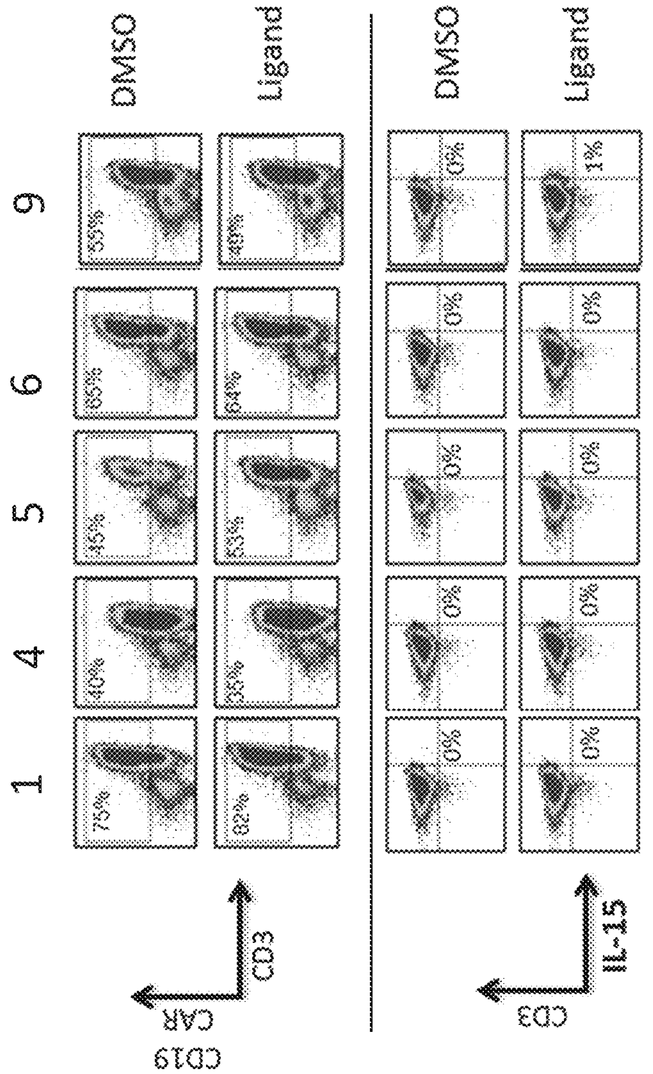

FIG. 7 shows quantitative flow cytometric analysis of cells transfected with ligand-inducible gene switch vector systems described herein, on day 35 of post nucleofection in presence/absence of veledimex ligand (solvent: DMSO), gated on CD19-specific CAR positive populations. The expression of mbIL-15 is turned off post ligand withdrawal. Constructs 1, 4, 5, 6 and 9 correspond to constructs as schematically depicted in FIG. 2A-2D.

Figure 8:
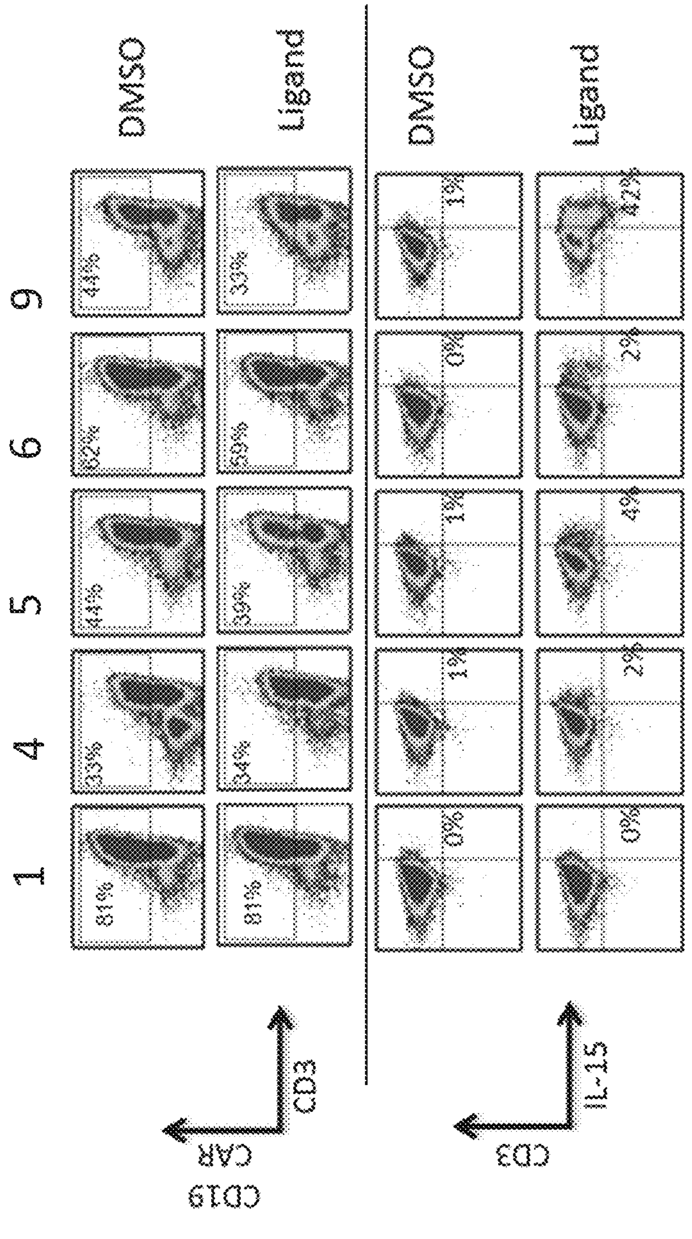

FIG. 8 shows quantitative flow cytometric analysis of cells transfected with ligand-inducible gene switch vector systems described herein, on day 40 of post nucleofection in presence/absence of veledimex ligand (solvent: DMSO), gated on CD19-specific CAR positive populations. The expression of mbIL-15 is maintained after re-introduction of ligand. Constructs 1, 4, 5, 6 and 9 correspond to constructs as schematically depicted in FIG. 2A-2D.

Figure 9:
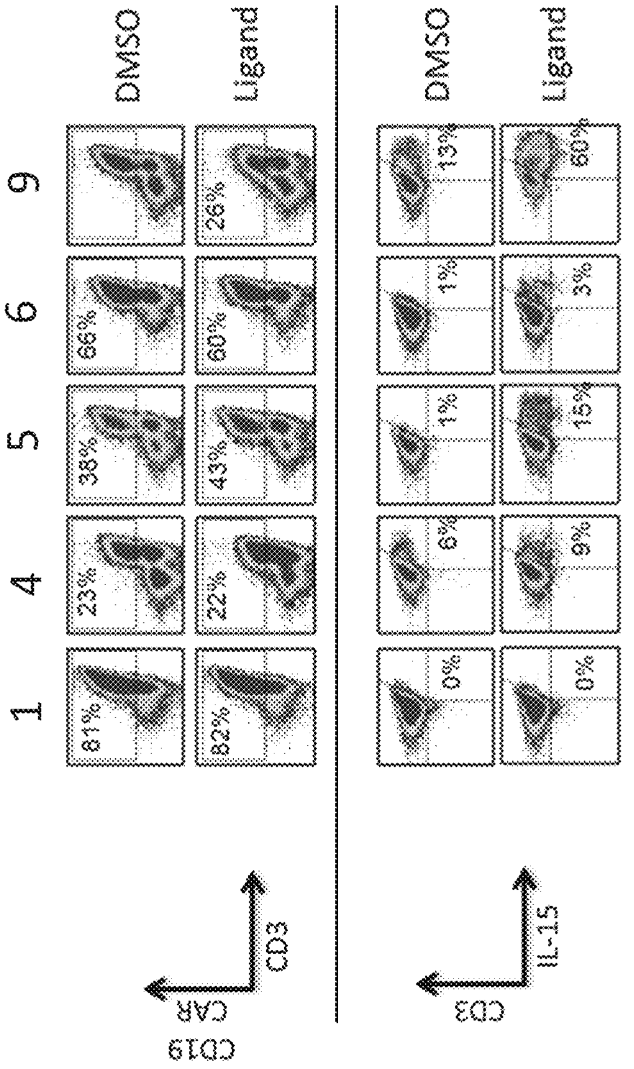

FIG. 9 shows quantitative flow cytometric analysis of cells transfected with ligand-inducible gene switch vector systems described herein, on day 48 of post nucleofection in presence/absence of veledimex ligand (solvent: DMSO), gated on CD19-specific CAR positive populations. The expression of mbIL-15 is continuously maintained after re-introduction of ligand. Constructs 1, 4, 5, 6 and 9 correspond to constructs as schematically depicted in FIG. 2A-2D.

Figure 10:
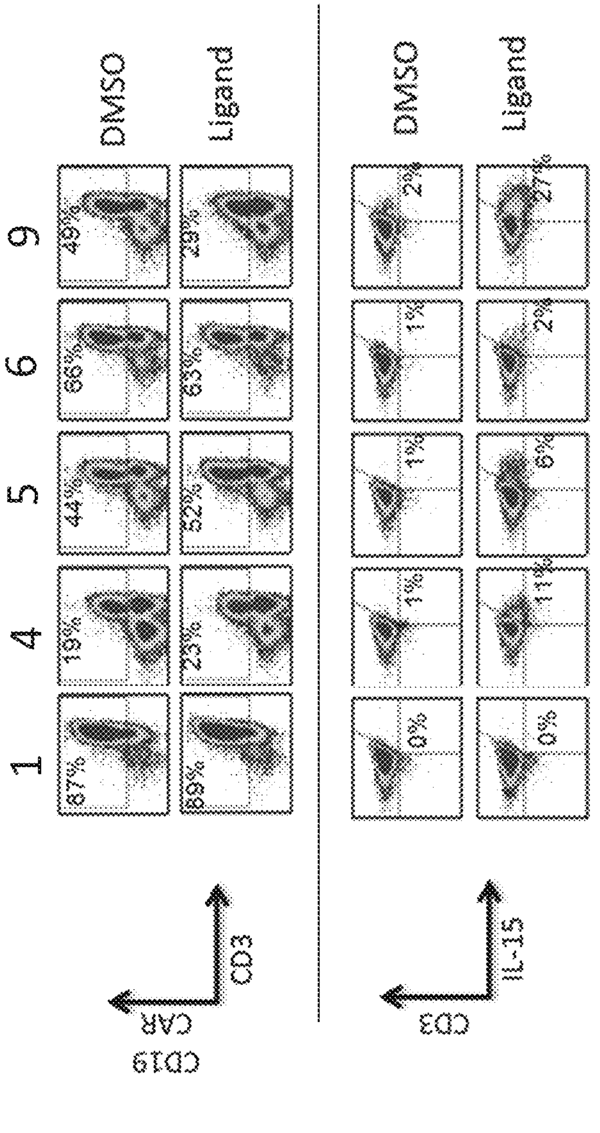

FIG. 10 shows quantitative flow cytometric analysis of cells transfected with ligand-inducible gene switch vector systems described herein, on day 50 of post nucleofection in presence/absence of veledimex ligand (solvent: DMSO), gated on CD19-specific CAR positive populations. The expression of mbIL-15 is continuously maintained after re-introduction of ligand. Constructs 1, 4, 5, 6 and 9 correspond to constructs as schematically depicted in FIG. 2A-2D.

Figure 11:
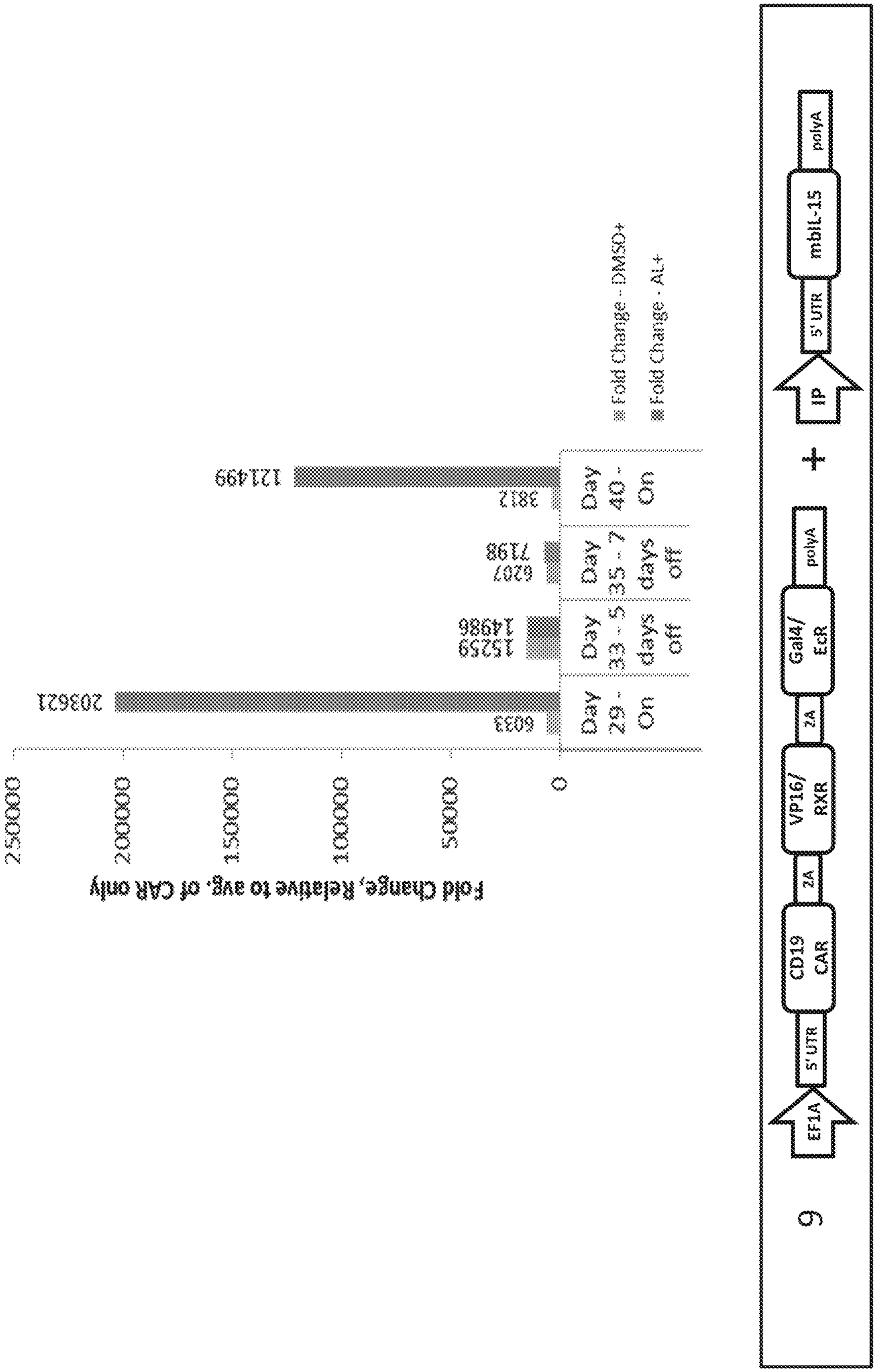

FIG. 11 shows quantitative RT-qPCR analysis of mbIL-15 expression in cells transfected with ligand-inducible gene switch vector systems described herein, on days 29, 33, 35, and 40 of post nucleofection in the presence and absence of a ligand described herein, demonstrating the ligand dependent regulation of expression of mbIL-15 by the gene switch.

Figure 12:
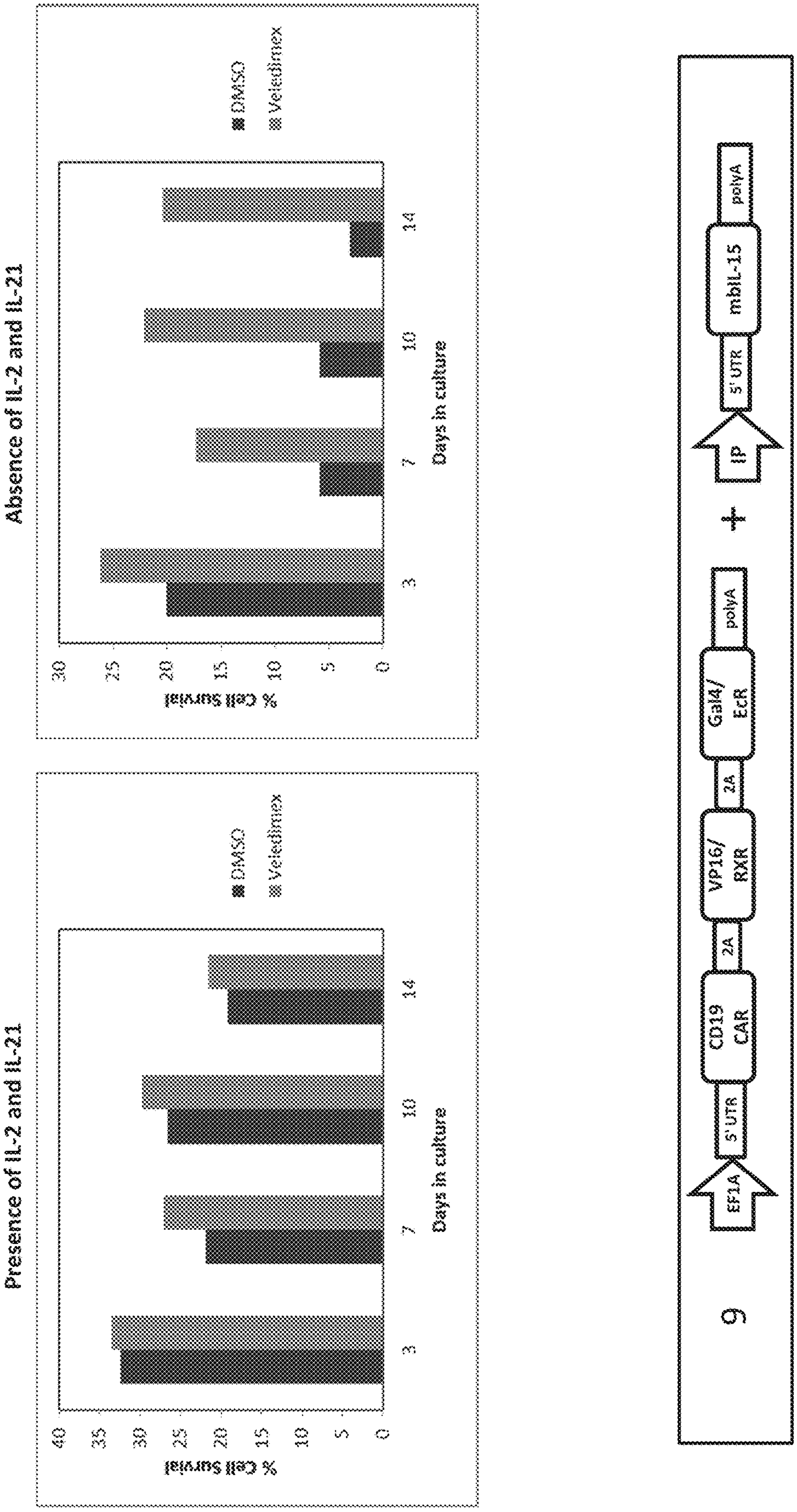

FIG. 12 shows results from a cell survival assay illustrating ligand regulated mbIL-15 expression promotes preferential CAR-T cell survival in the absence of IL-2 and IL-21 cytokines.

Figure 1:
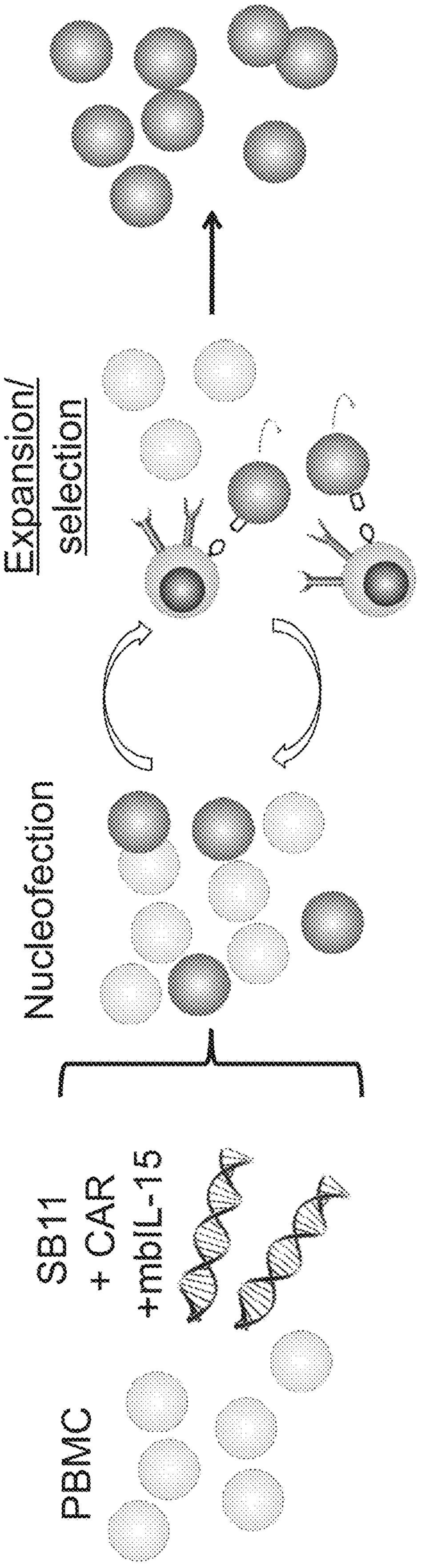
FIG. 1 is a schematic depiction of the Sleeping Beauty (SB) system adapted to genetically modify T cells. DNA plasmids expressing a SB transposon system, i.e. SB11, membrane bound IL-15 (mbIL-15), and chimeric antigen receptor (CAR), are transfected to peripheral blood mononuclear cells (PBMC) to redirect T cell specificity. T cells stably expressing integrants on designer activating and propagating cells (AaPC) are propagated and expanded.
Figure 2A:
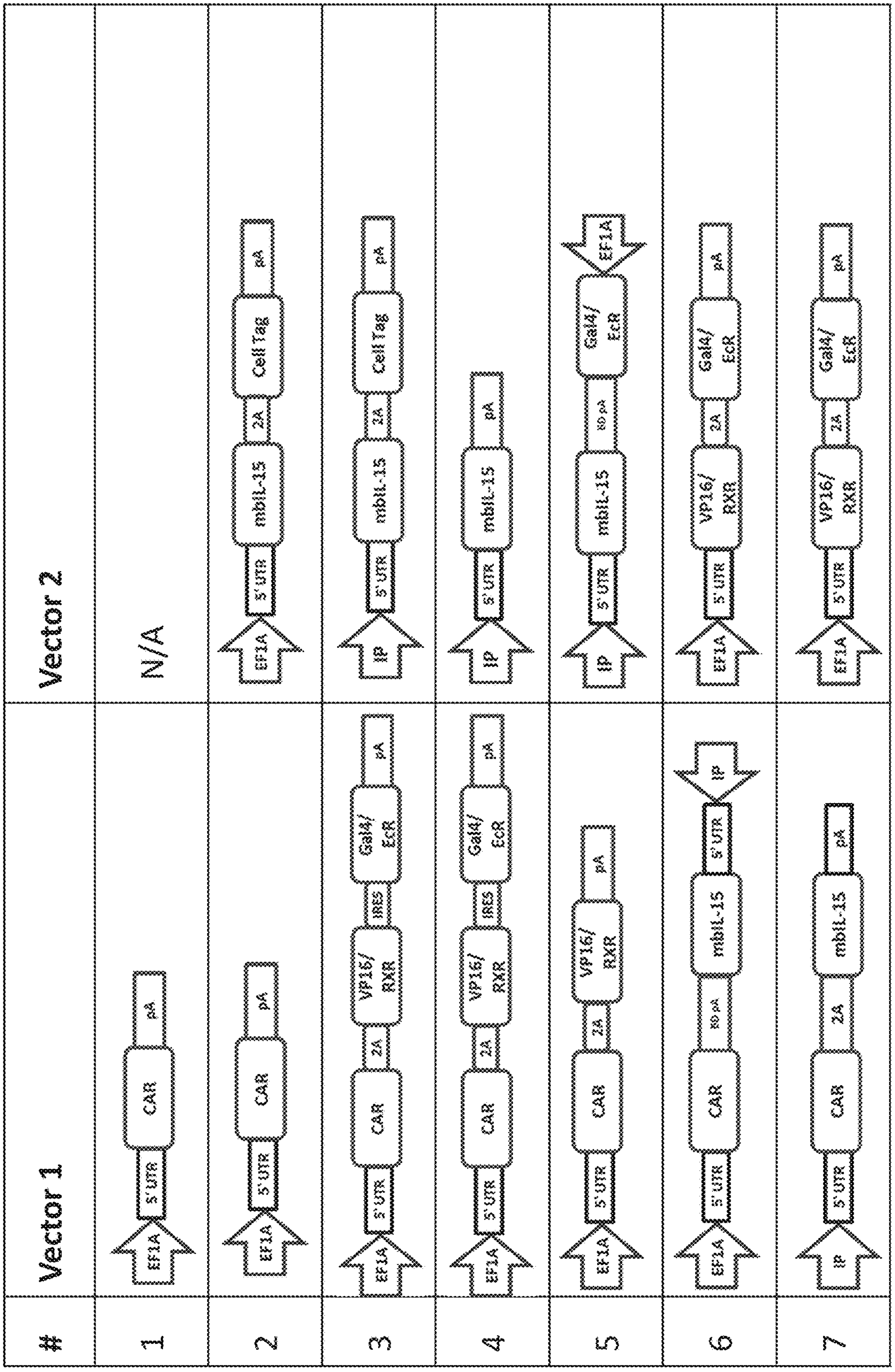
FIG. 2A-2D schematically illustrate various structural components of diverse ligand-inducible gene switch vector systems. Exemplary CAR as depicted can include CD19 CAR. EF1A promoter is an exemplary constitutive promoter.
Figure 2B:
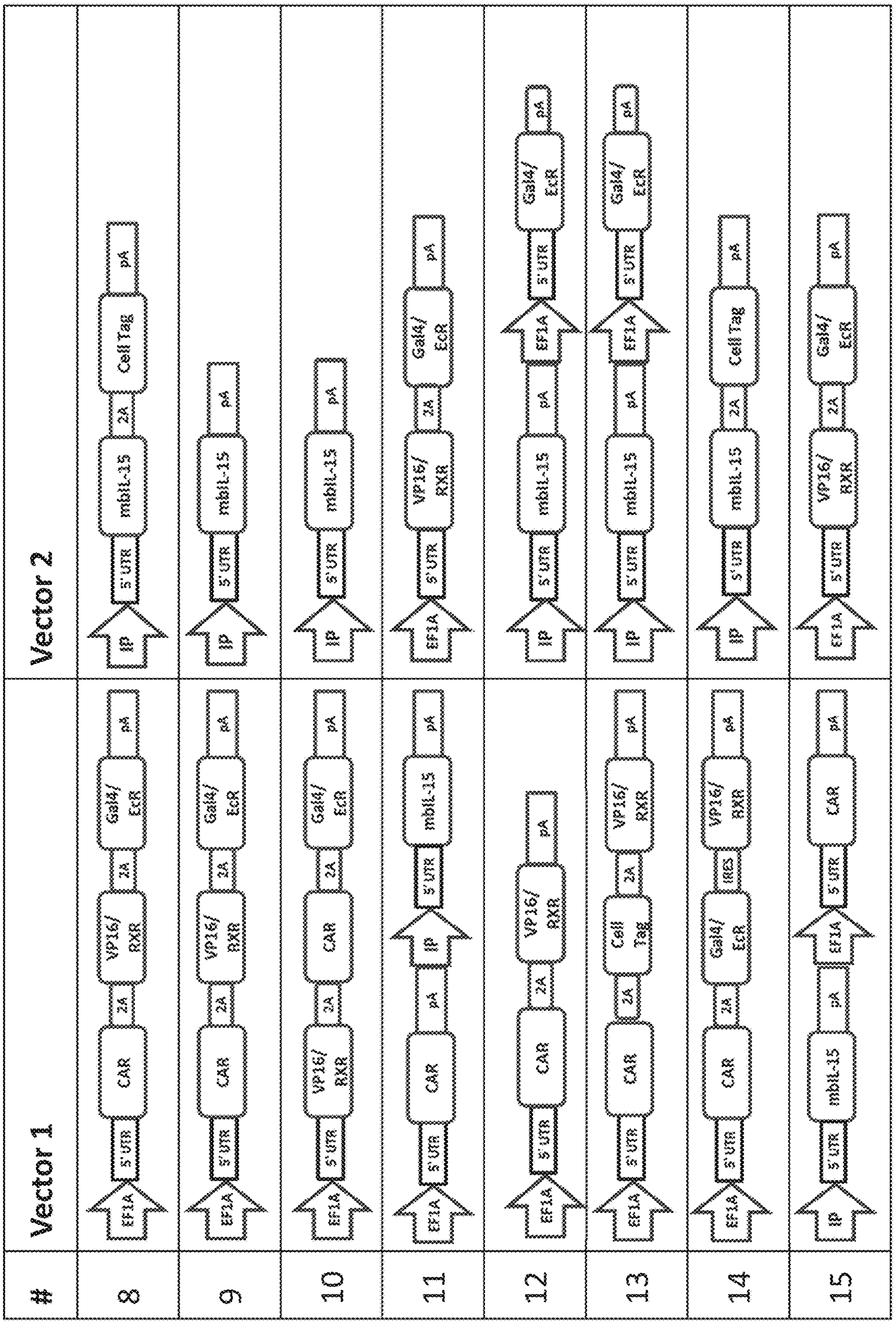
Figure 2D:
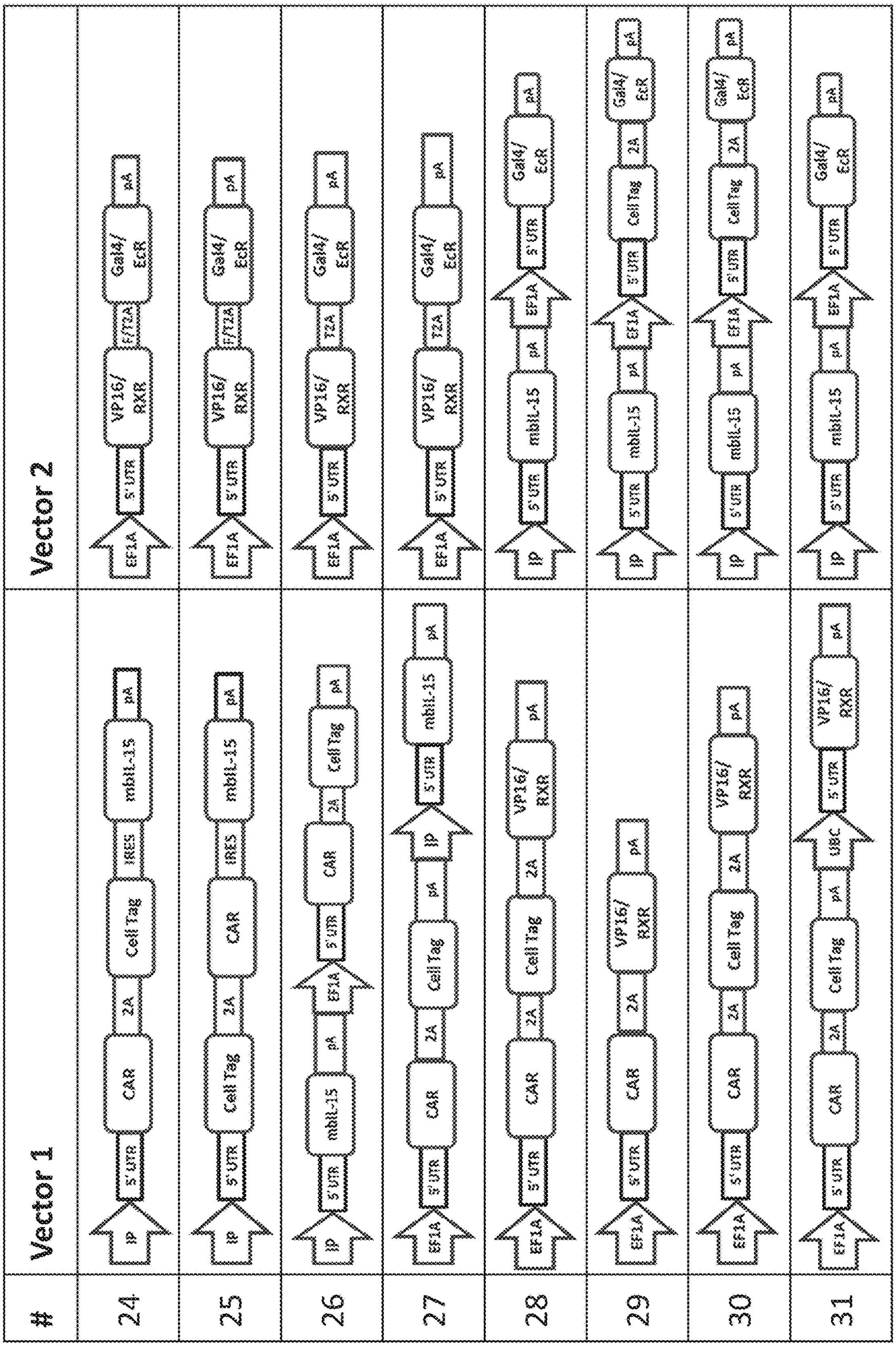
Figure 3:
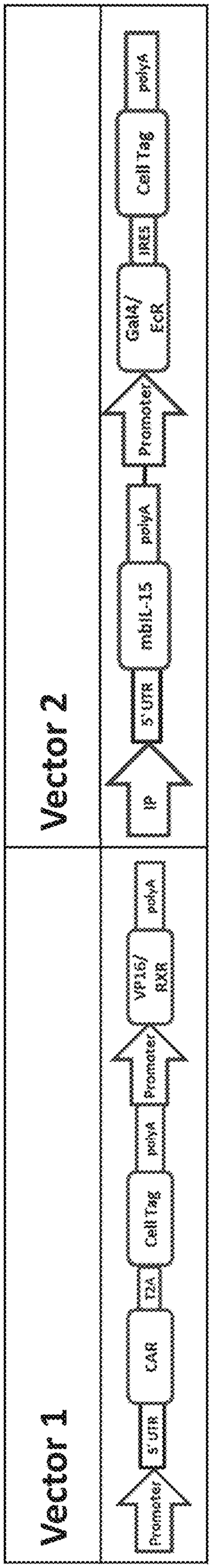
FIG. 3 is a schematic illustration of a multiple vector system for ligand-inducible gene switch polypeptides.
Figure 4:
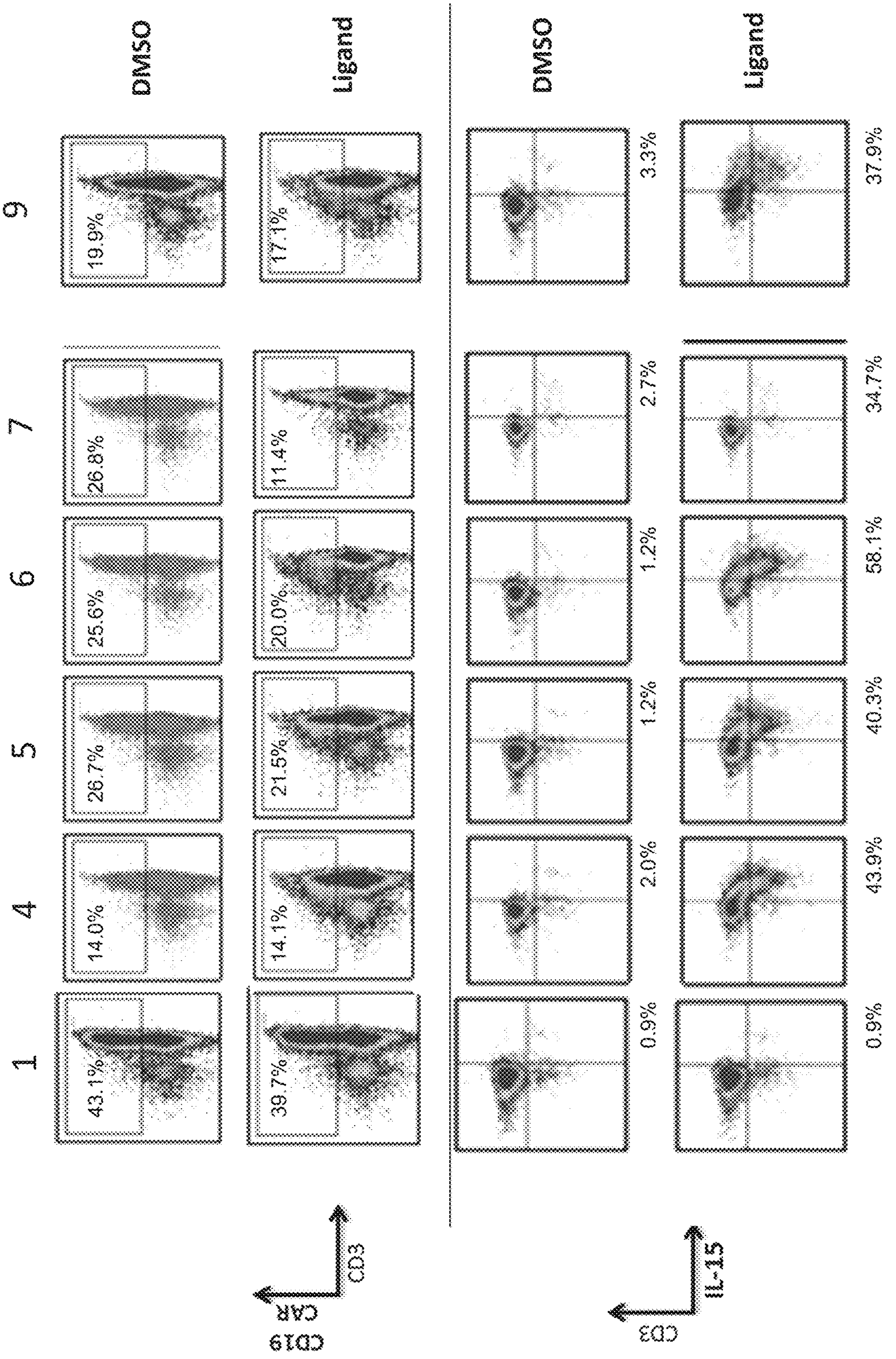
FIG. 4 depicts quantitative flow cytometric analysis of cells transfected with ligand-inducible gene switch vector systems described herein, on day 1 of post nucleofection in presence/absence of veledimex ligand (solvent: DMSO). Constructs 1, 4, 5, 6, 7 and 9 correspond to constructs as schematically depicted in FIG. 2A-2D.
Figure 5:
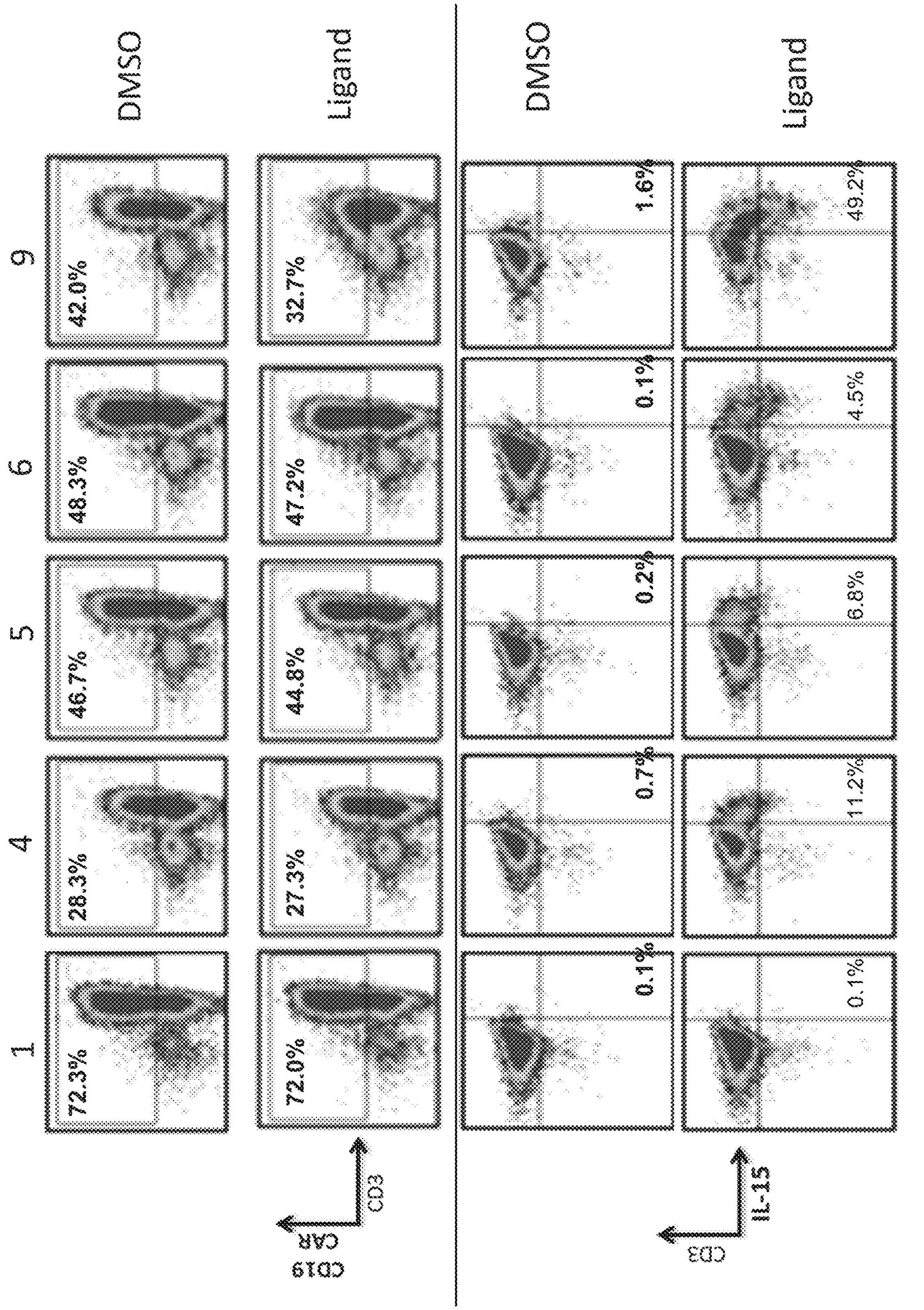
FIG. 5 depicts quantitative flow cytometric analysis of cells transfected with ligand-inducible gene switch vector systems described herein, on day 21 of post nucleofection in presence/absence of veledimex ligand (solvent: DMSO), gated on CD19-specific CAR positive populations. Ligand was added 48 hours prior to flow cytometric analysis. Constructs 1, 4, 5, 6 and 9 correspond to constructs as schematically depicted in FIG. 2A-2D.
Figure 6:
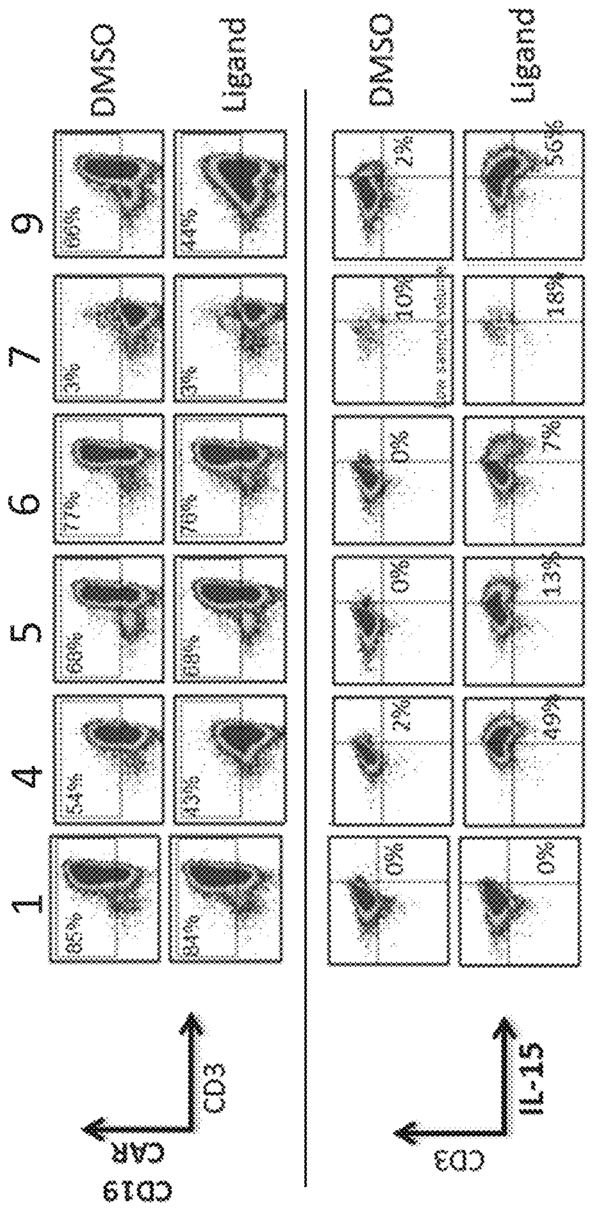
FIG. 6 depicts quantitative flow cytometric analysis of cells transfected with ligand-inducible gene switch vector systems described herein, on day 29 of post nucleofection in presence/absence of veledimex ligand (solvent: DMSO), gated on CD19-specific CAR positive populations. The expression of mbIL-15 is turned on post ligand addition.
Figures 1, 13A:
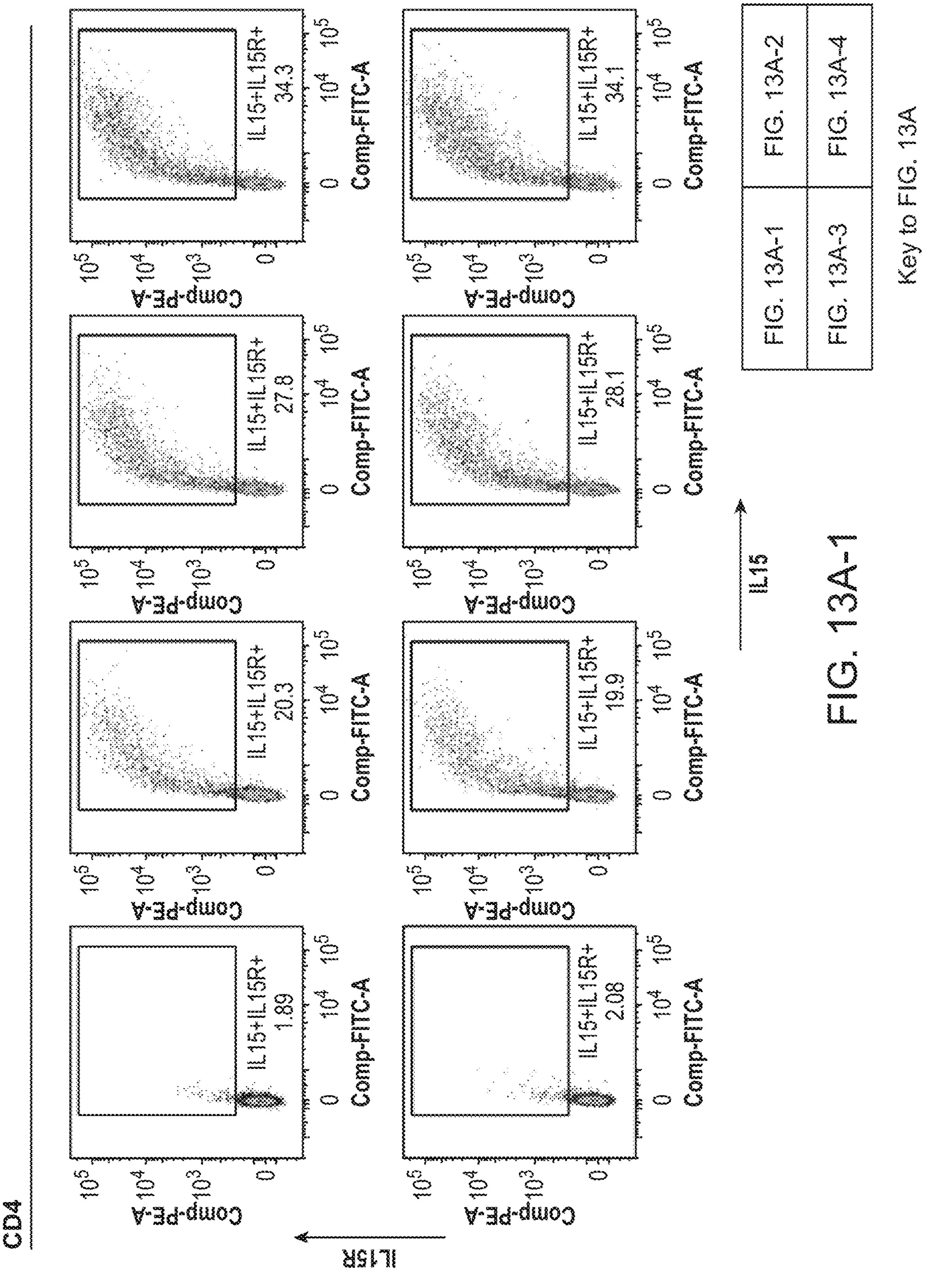
Figures 2, 13A:
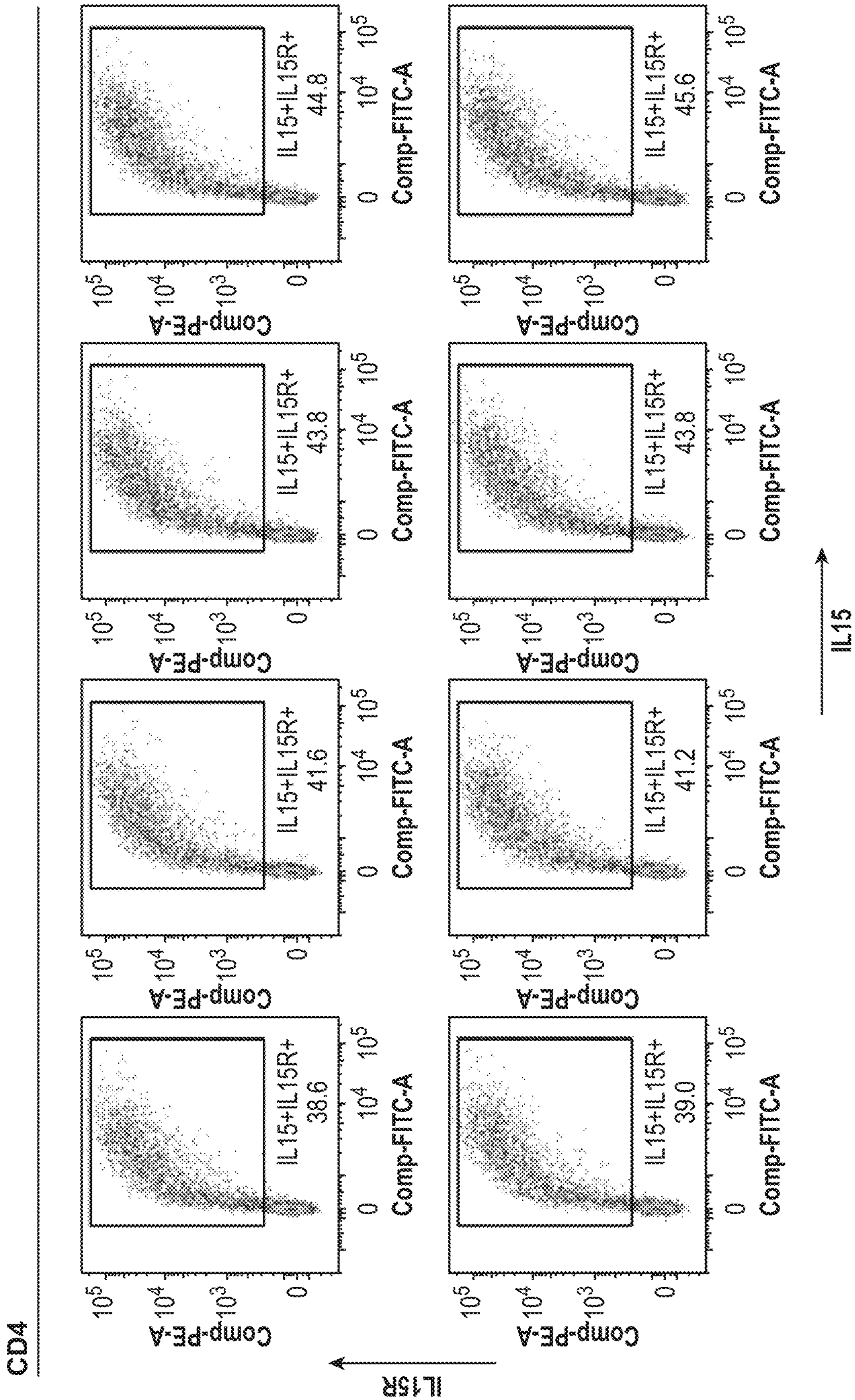
Figures 3, 13A:
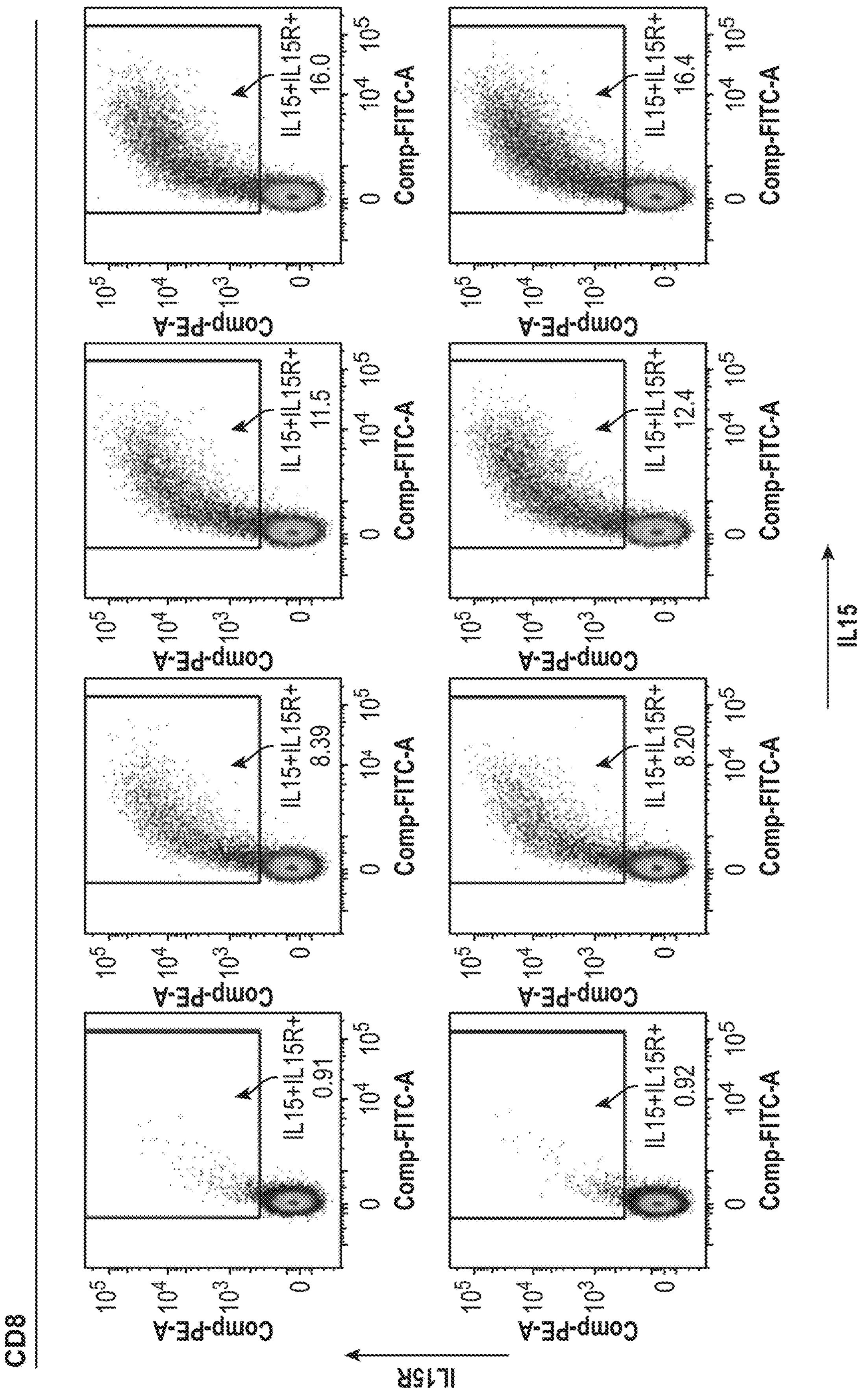
Figures 4, 13A:
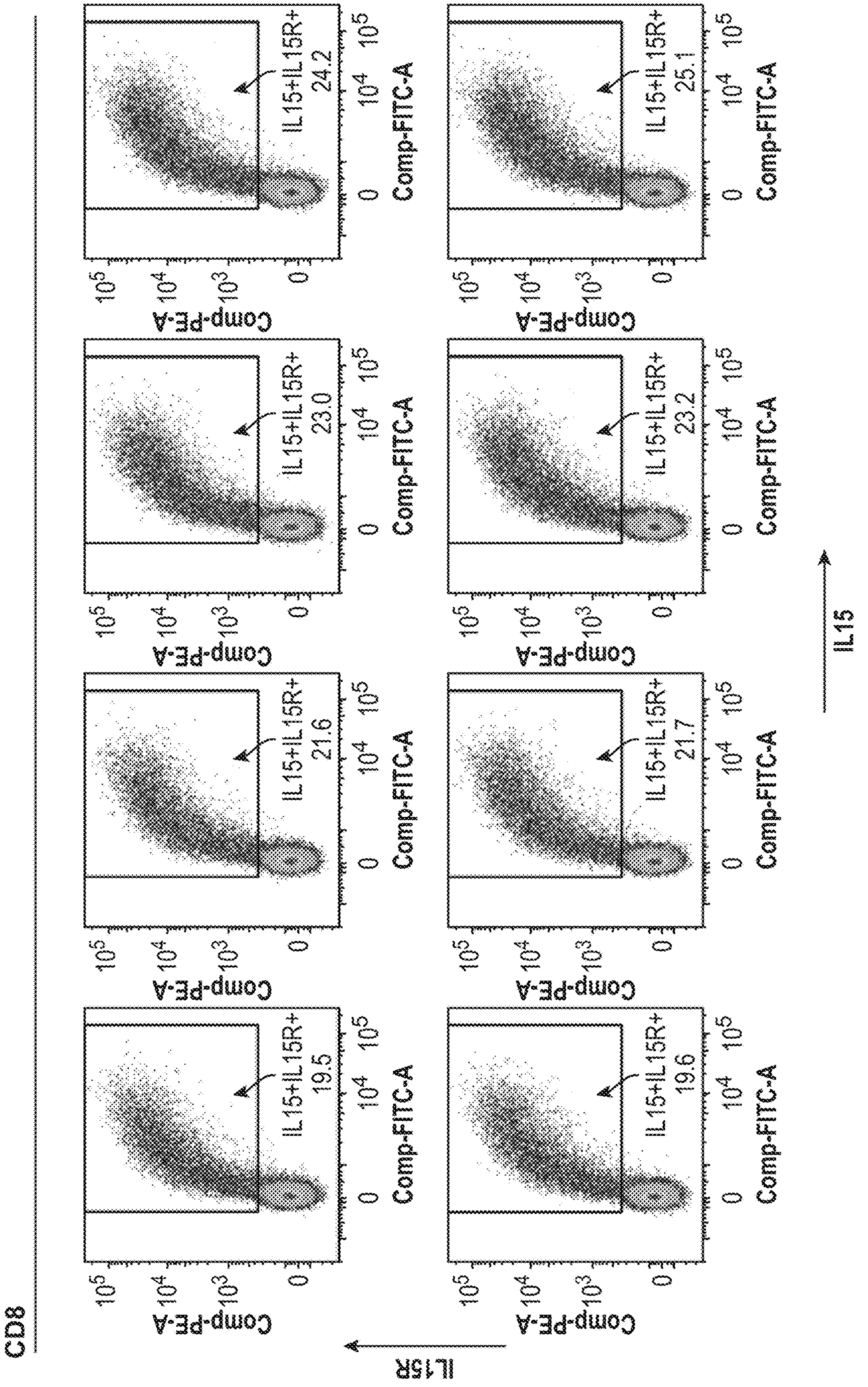
Figures 1, 13B:
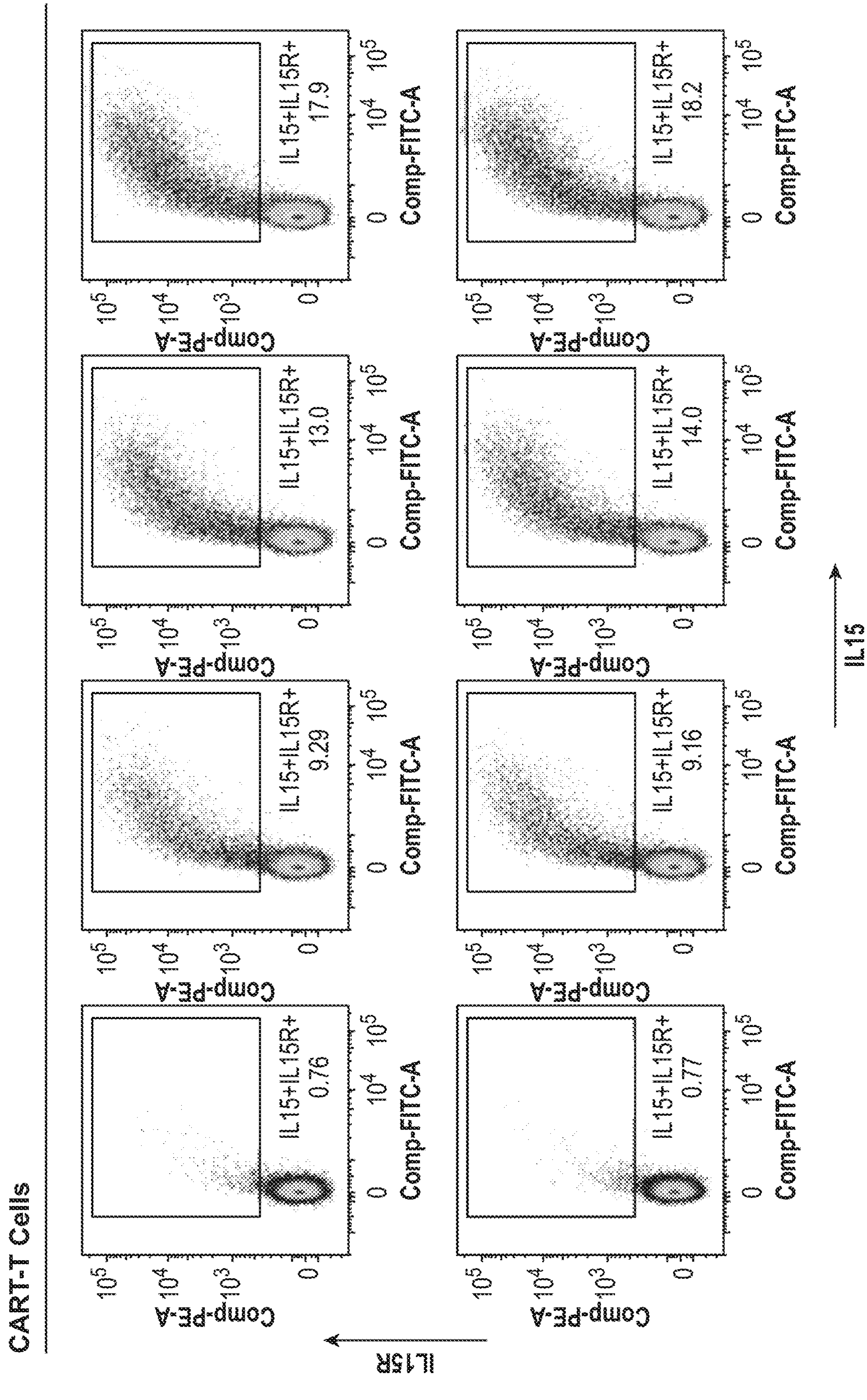
Figures 2, 13B:
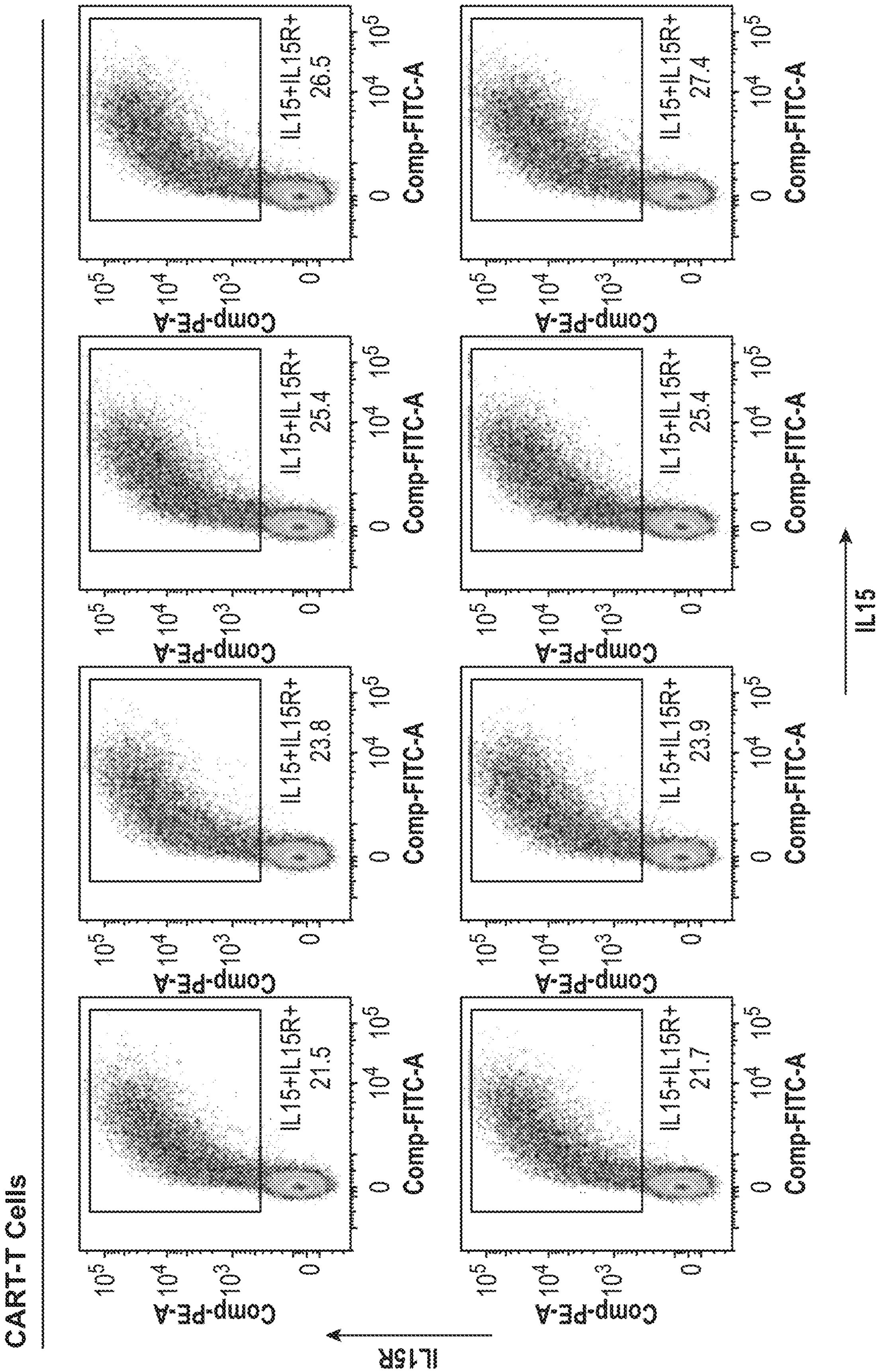
Figure 13C:
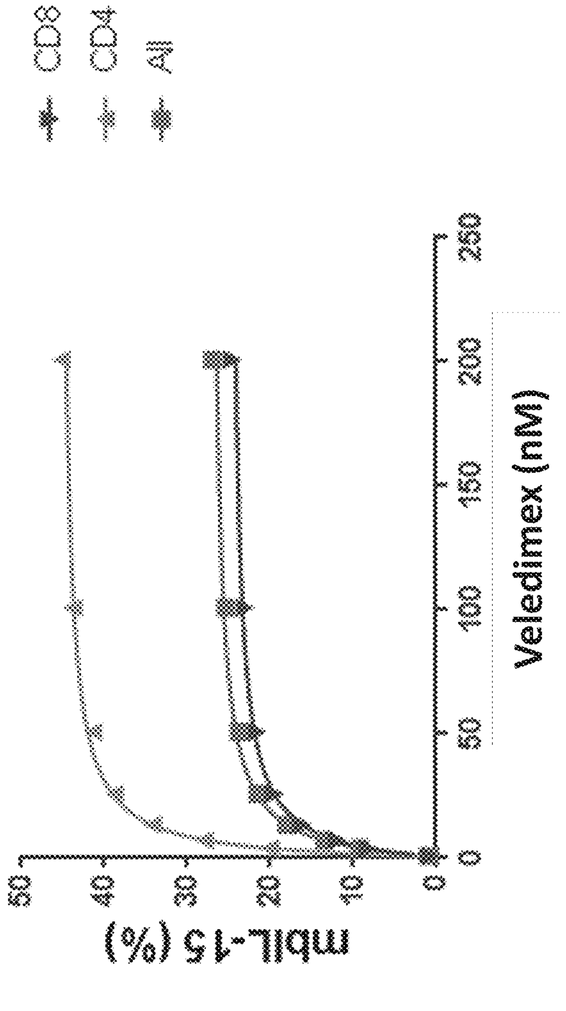
Figure 13D:
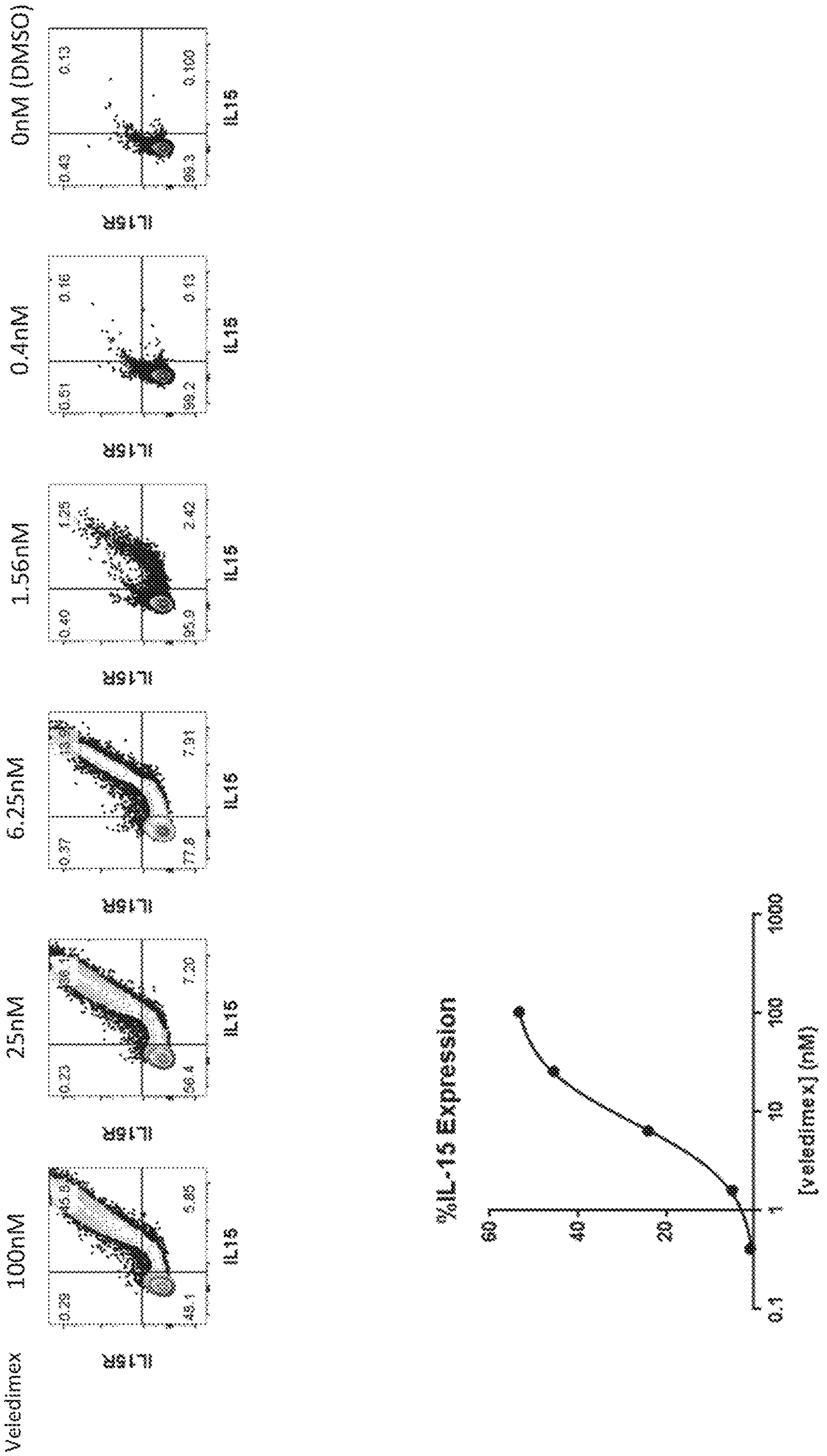

FIG. 13A-1, FIG. 13A-2, FIG. 13A-3, FIG. 13A-4, 13B-1, 13B-2, FIG. 13C and FIG. 13D show the quantitative flow cytometric analysis of cells transfected with ligand-inducible gene switch vector systems described herein, demonstrating veledimex ligand dose response. FIG. 13A-I is continued in FIG. 13A-2, FIG. 13A-3, and FIG. 13A-4. The key to assembling FIG. 13A-1 to FIG. 13A-4 is shown on FIG. 13A-1. FIG. 13B-1 is continued in FIG. 13B-2. FIG. 13D shows quantitative flow cytometric analyses of cells transfected with ligand-inducible gene switch vector systems described herein, demonstrating veledimex ligand dose response. The cells were gated on FSC/SSC/LIVE/CD3+. Samples were taken following a 2 day incubation with veledimex at 100 nM, 25 nM, 6.25 nM, 1.56 nM, 0.4 nM and 0 nM (DMSO control).

Figure 14:
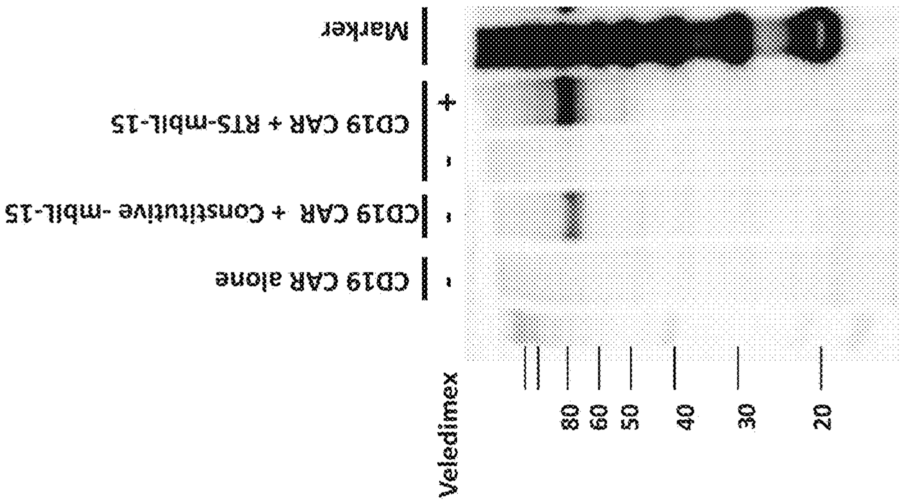

FIG. 14 is a western blot analysis of mb-IL-15 expression in cells transfected with ligand-inducible gene switch vector systems described herein, in the presence/absence of veledimex ligand.

Figure 15A:
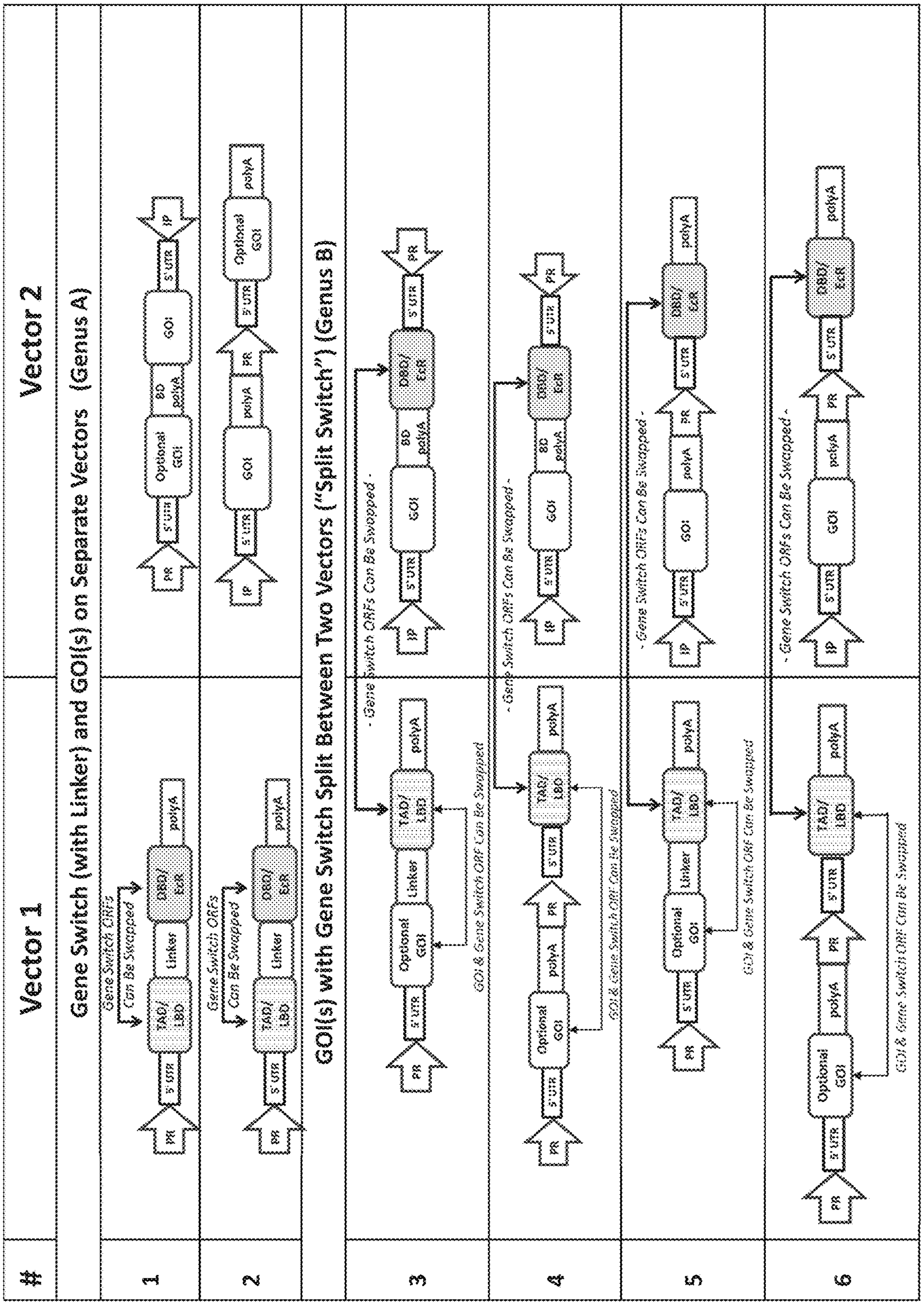
Figure 15B:
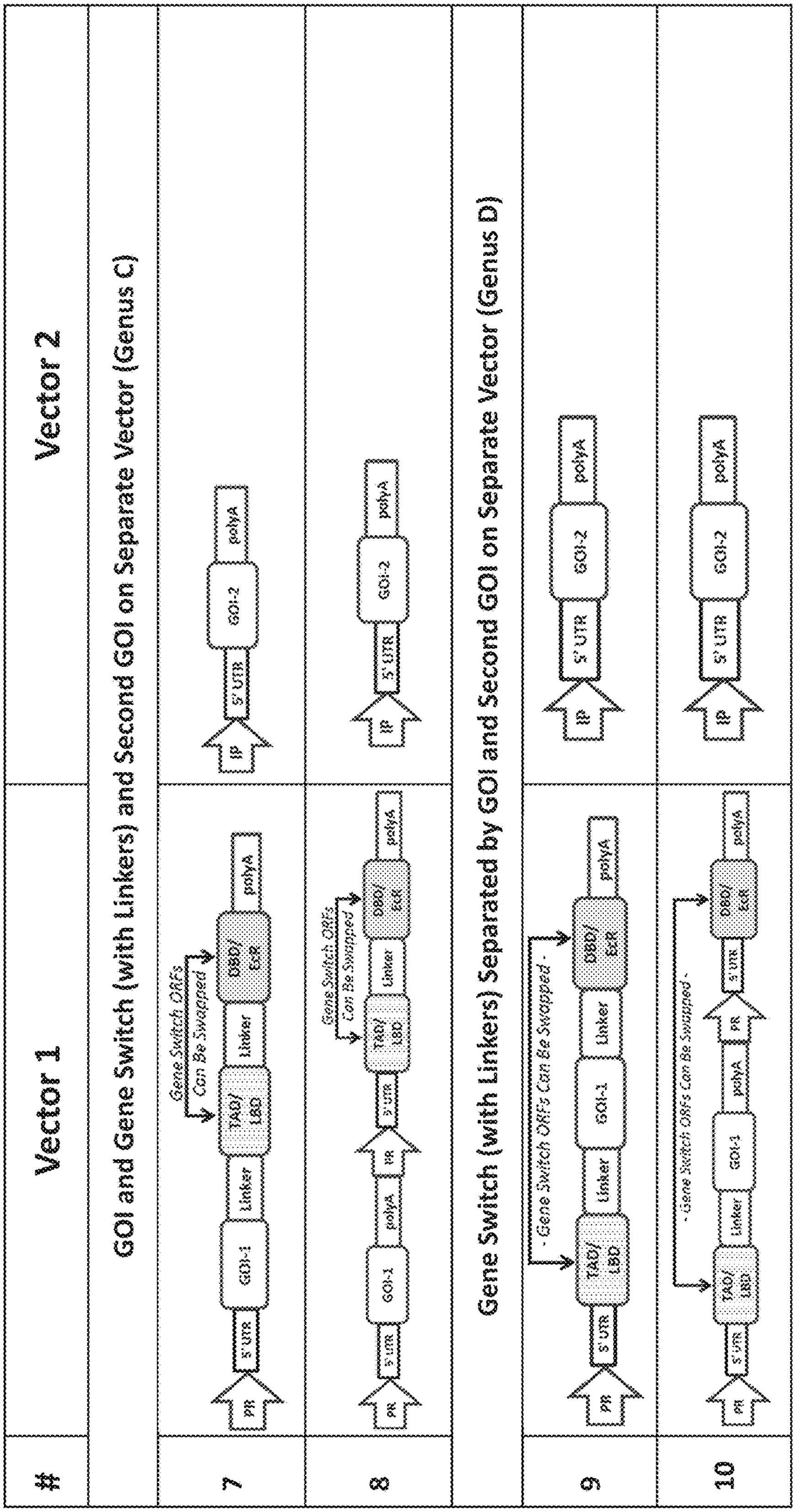

FIG. 15A and FIG. 15B are schematic depictions of varying structural components of generic diverse ligand-inducible gene switch vector systems described herein. In the schematic, “PR” stands for a promoter; “IP” is a gene switch ligand-inducible promoter for gene transcription; “5'UTR” is a 5' untranslated region (for transcription into mRNA); “GOI”, “GOI-1”, “GOI-2” are Gene(s) Of Interest (or first (GOI-1) and second GOI (GOI-2) to be transcribed and expressed as mRNA only (e.g., siRNA) or as mRNA and polypeptide; “Linker” is a cleavable or ribosome skipping linker sequence; “TAD” is a transcription transactivation domain (for instance, but not limited to a VP16 TAD from Herpes Virus); “LBD” is a nuclear receptor ligand binding domain (for instance, but not limited to a USP domain, an RXR domain, or chimeras (e.g., USP/RXR chimeras) and substitution mutated LBD domains derived from vertebrate and invertebrate species); “DBD” is a DNA binding domain (for instance, but not limited to a Gal4 DBD); “EcR” is an Ecdysone Receptor ligand binding domain, including truncated and substitution mutated EcR domains (such as EcR domains which confer in vitro and in vivo ability to form an active transcriptional activation complex in the presence of steroidal and/or non-steroidal ligands (agonists); including steroidal ligands (such as ponasterone A and muristerone A) and non-steroidal ligands (such as diacylhydrazines, tebufenozide and methoxyfenozide); “Optional GOI” is any optional gene of interest to be transcribed and expressed as mRNA or polypeptide; and “BD polyA” is a Bi-directional Poly-Adenosine tail sequence.

Figure 16A:
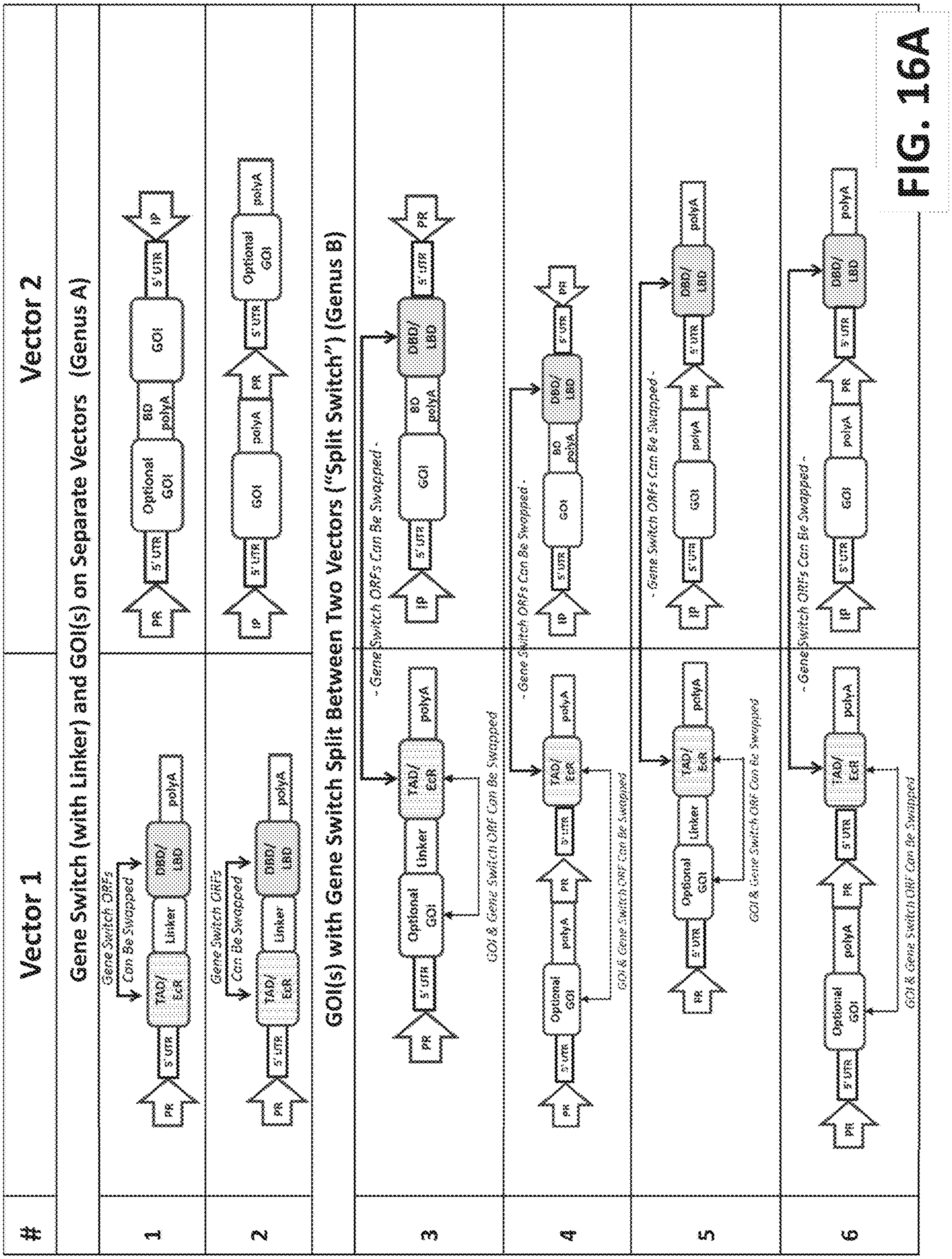
Figure 16B:
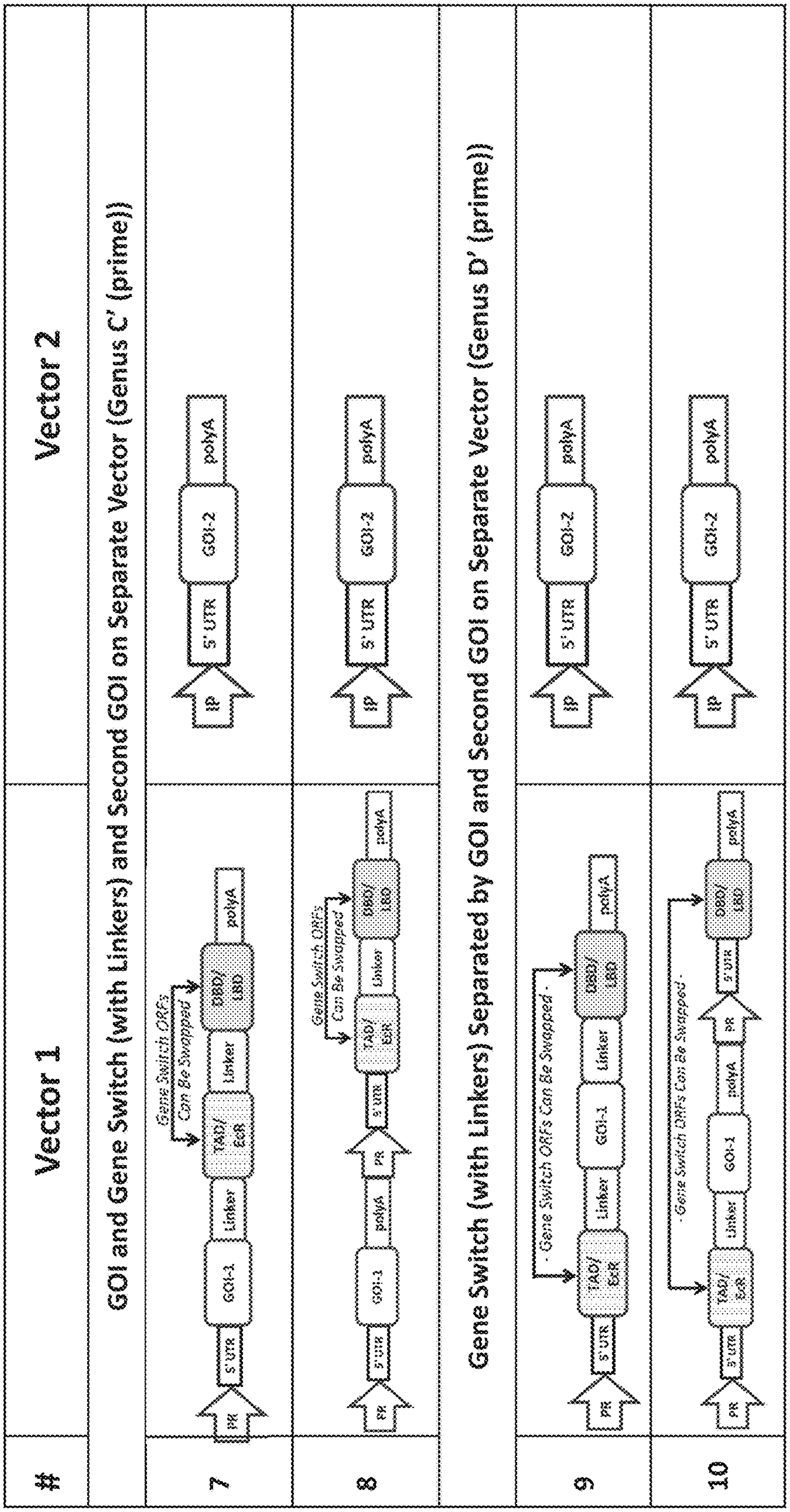

FIG. 16A and FIG. 16B are schematic depictions of varying structural components of diverse ligand-inducible gene switch vector systems described herein.

Figure 17:
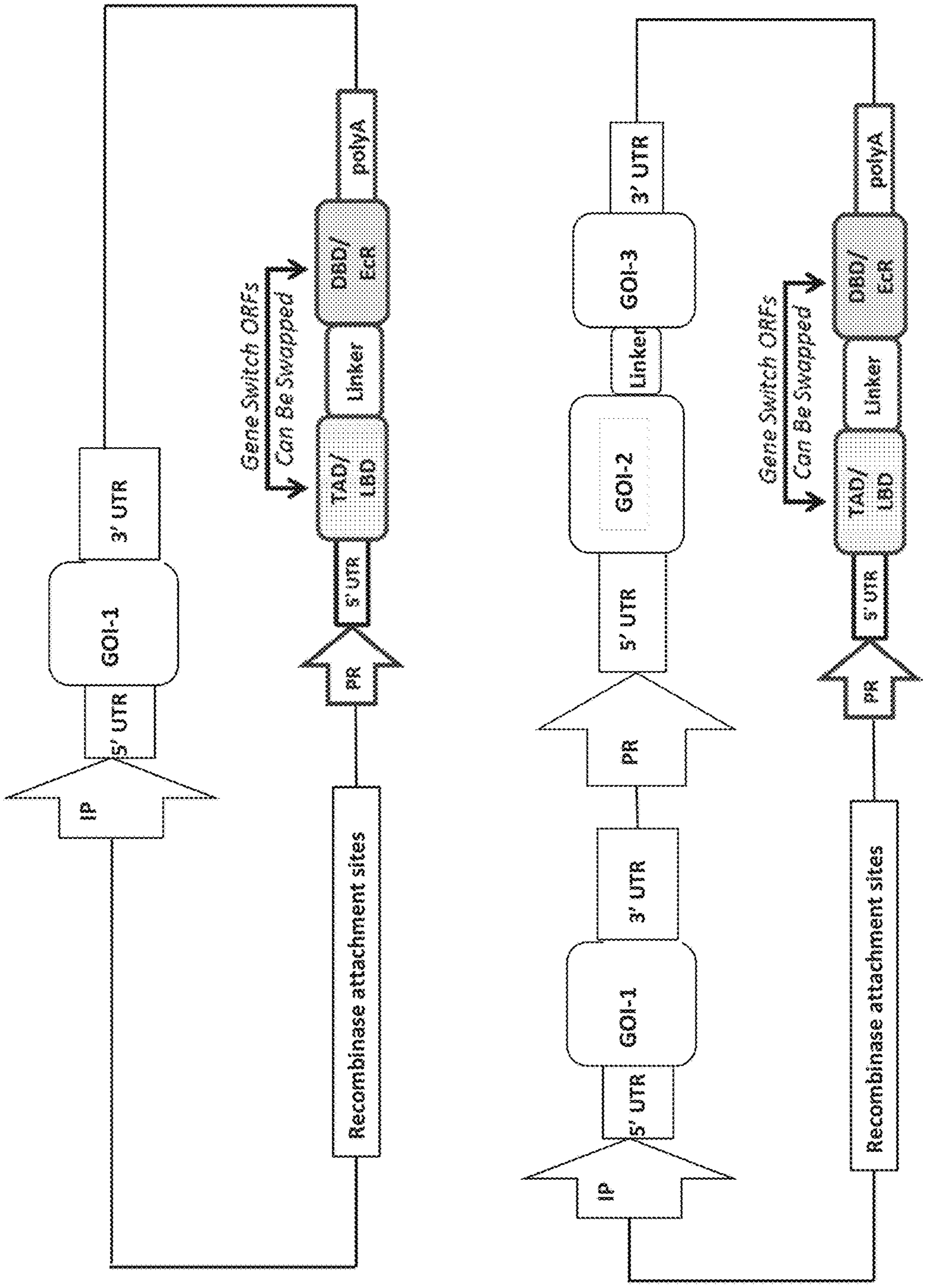

FIG. 17 is a schematic description of an exemplary ligand-inducible gene switch vector system with recombinase attachment sites. Such systems can utilize recombinases (such as serine recombinases) to integrate a single vector into an immune cell (e.g. T cell).

Figure 18B:
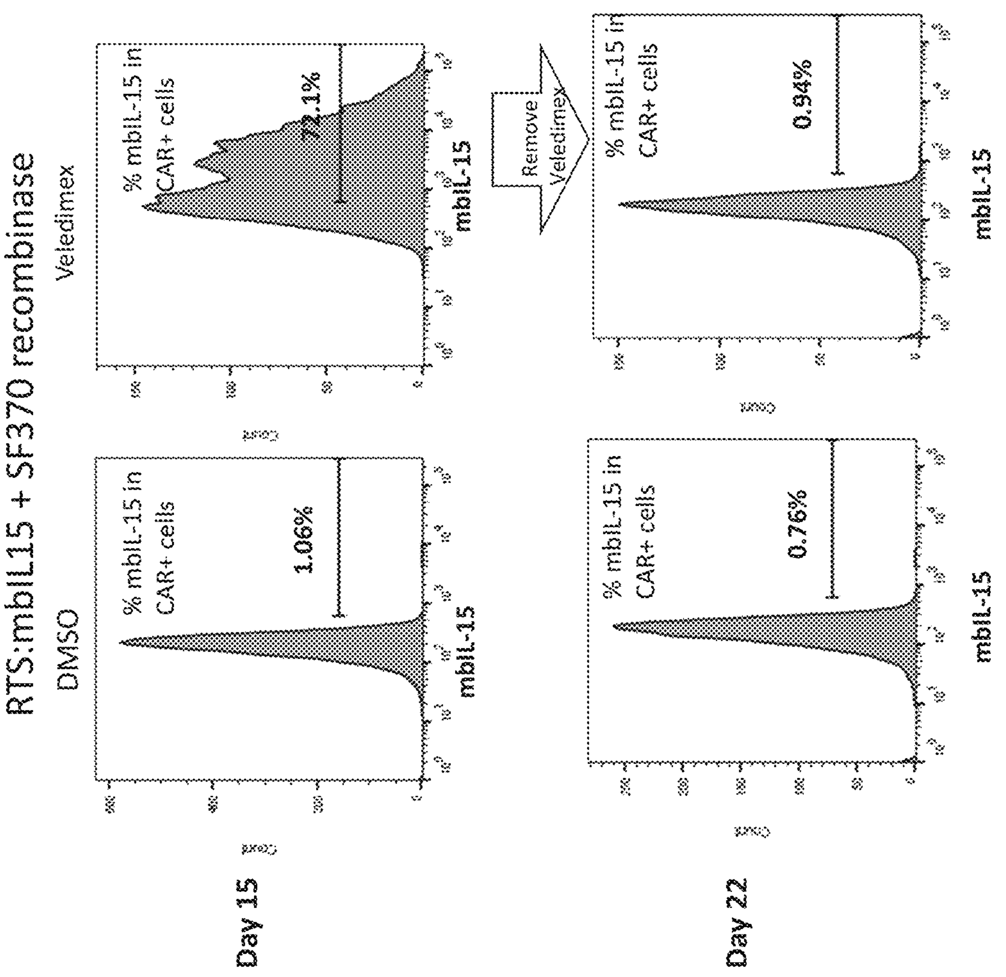
Figure 18C:
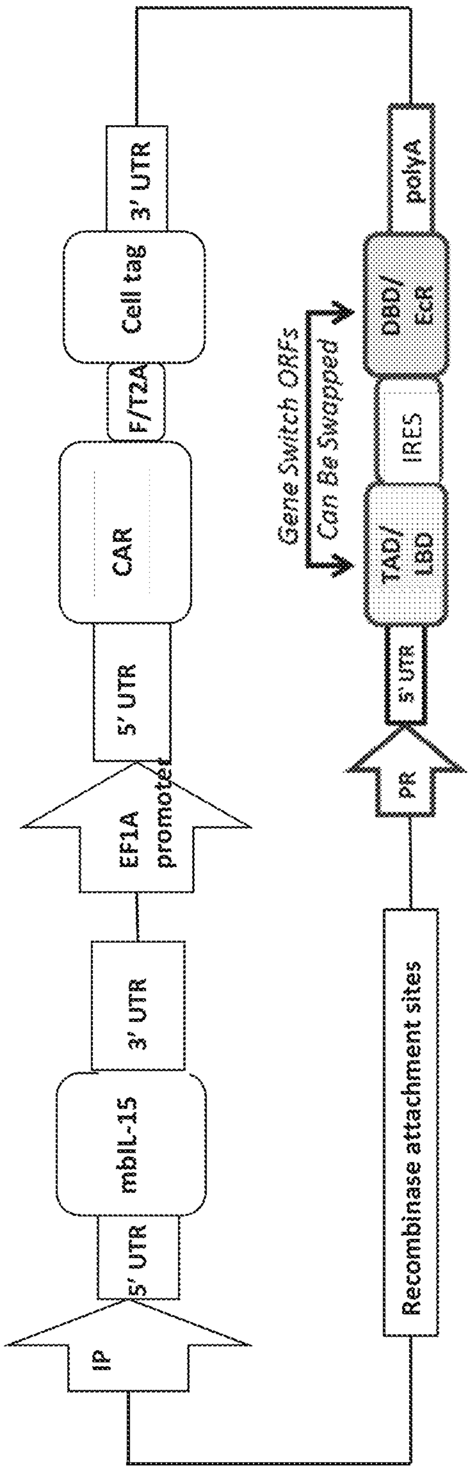

FIG. 18A is a table depicting % CAR positive T cells over Days 1, 8 and 15. Such T cells were modified to express CAR and gene switch controlled mbIL-15 (RTS-mbIL15) from a single vector using serine recombinase (SF370)-mediated integration. FIG. 18B depicts the induction of mbIl-15 expression in the presence and absence of veledimex at day 15. The figure also demonstrates the loss of mbIL15 expression upon removal of veledimex at day 22. FIG. 18C is an exemplary depiction of RTS-mbIL15-constitutive CAR construct.

Figure 19B:
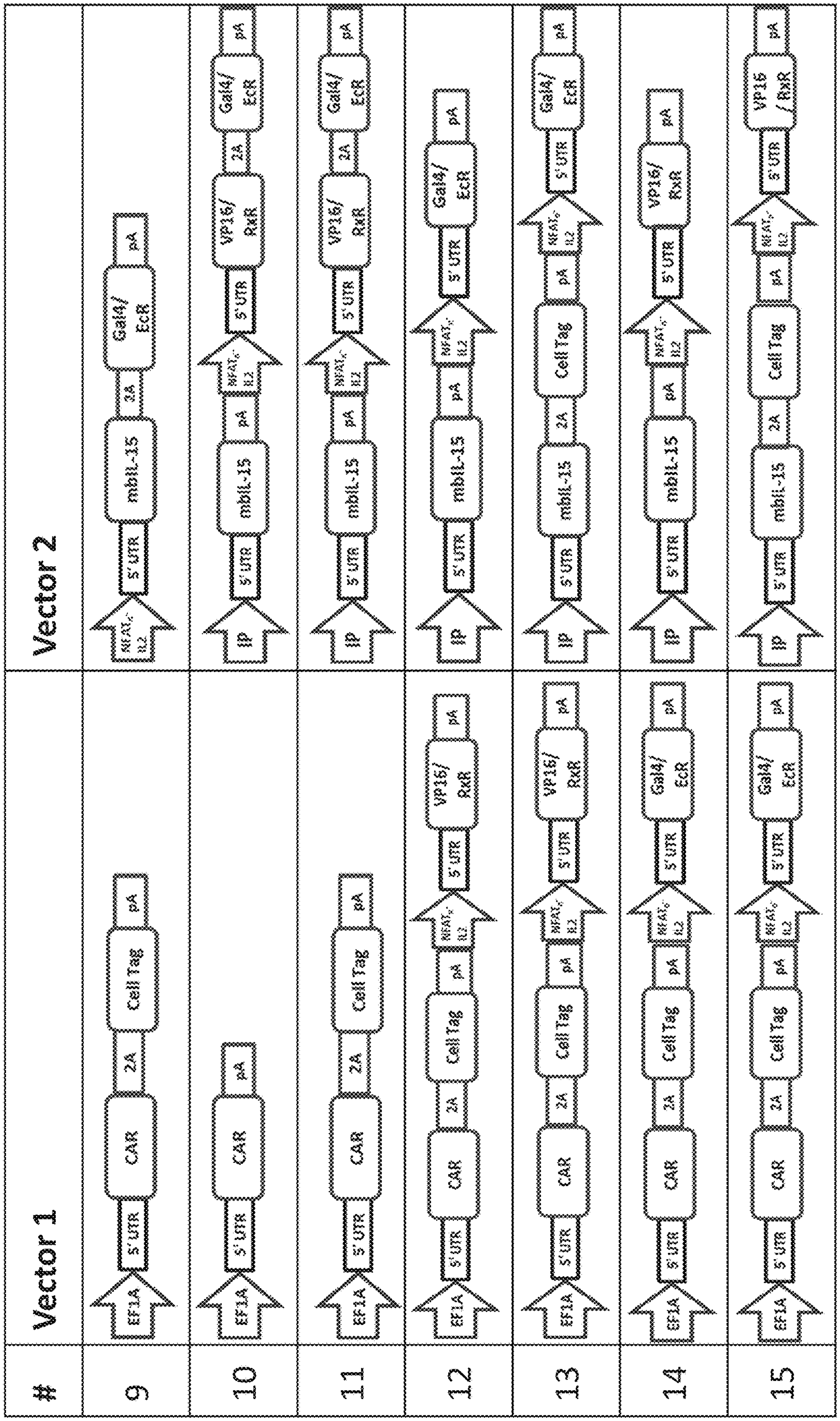

FIG. 19A-B schematically illustrate various structural components of diverse ligand-inducible gene switch vector systems under the control of constitutive or T cell specific promoters.

Figure 20A:
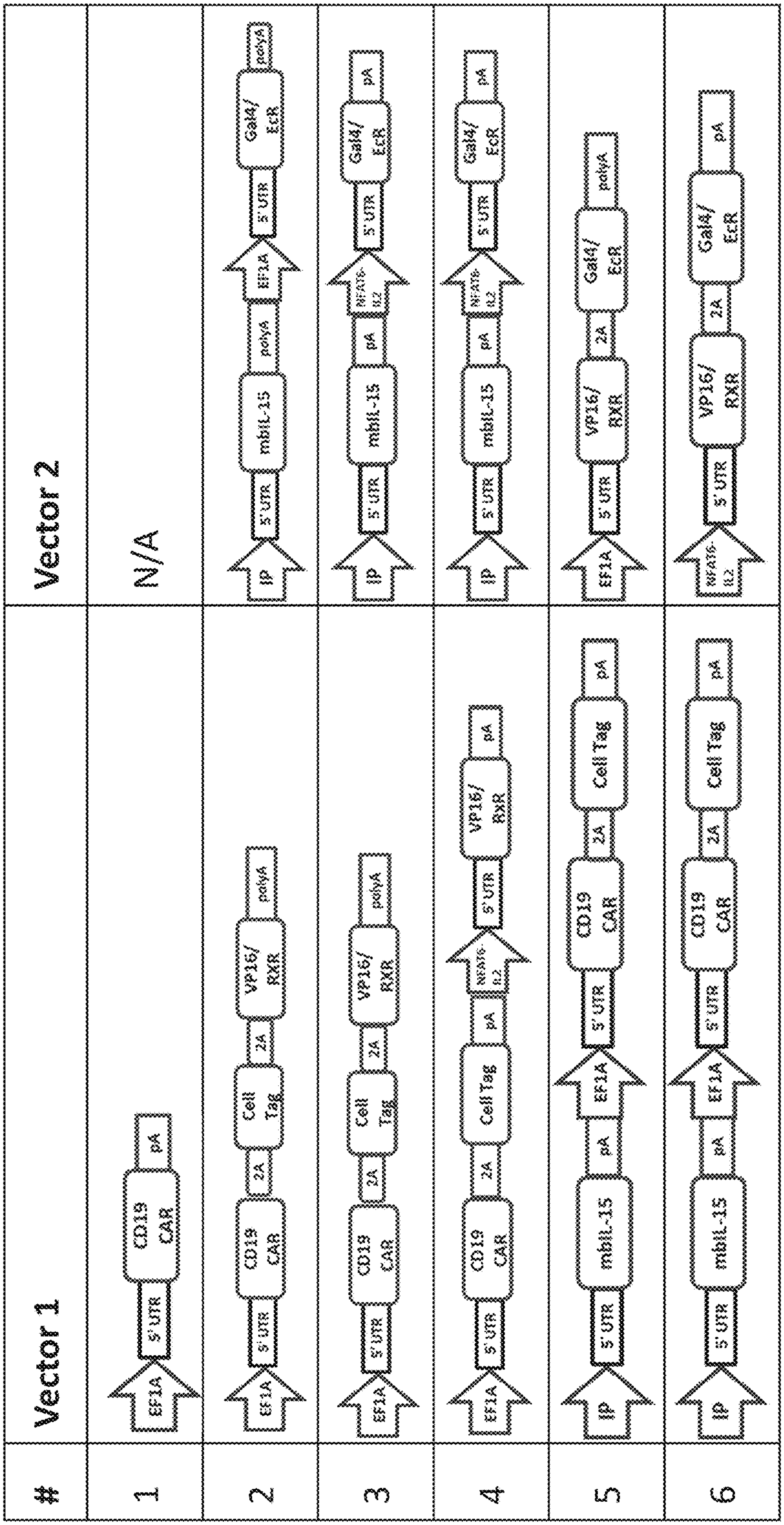
Figures 1, 20B:
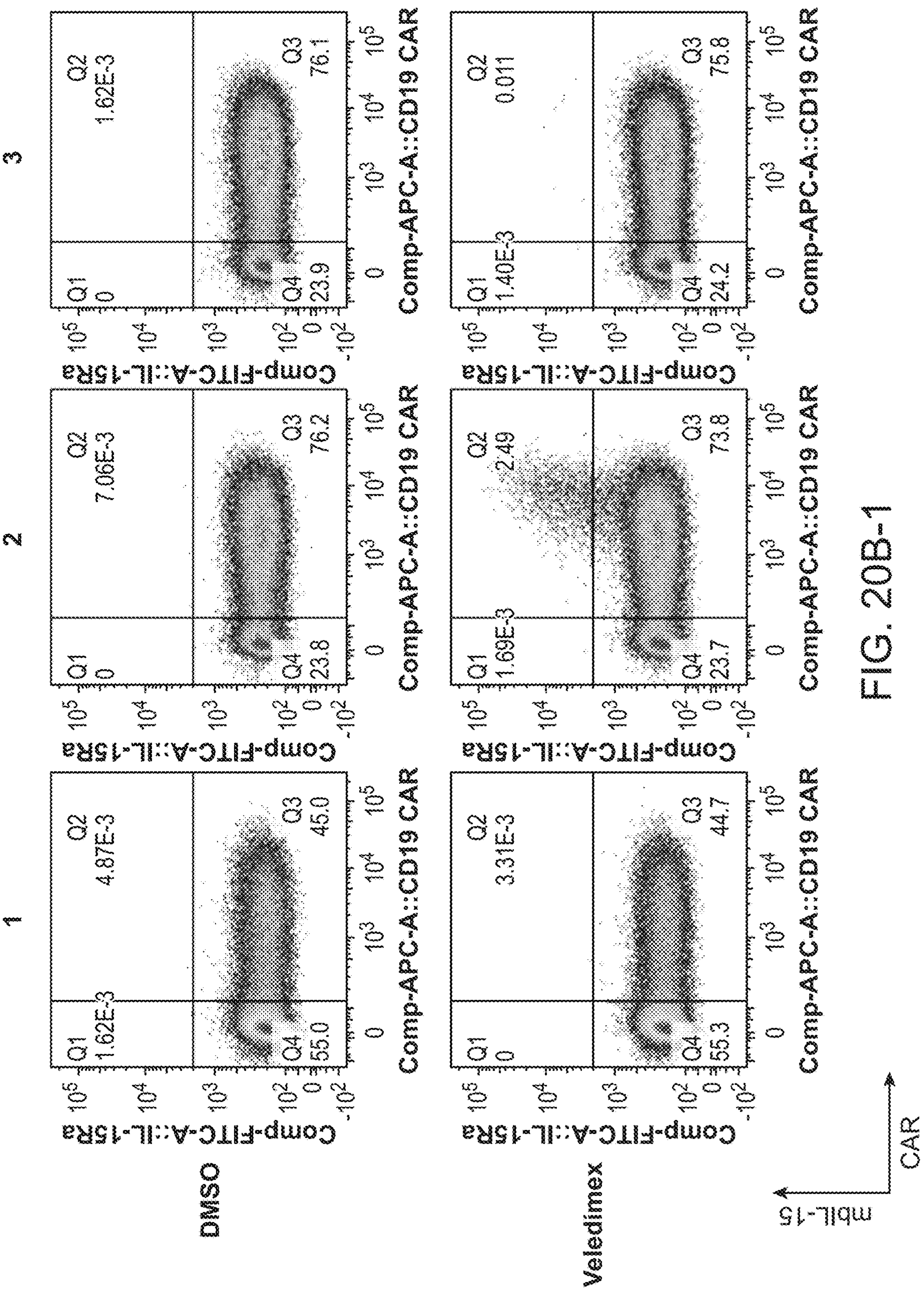
Figures 2, 20B:
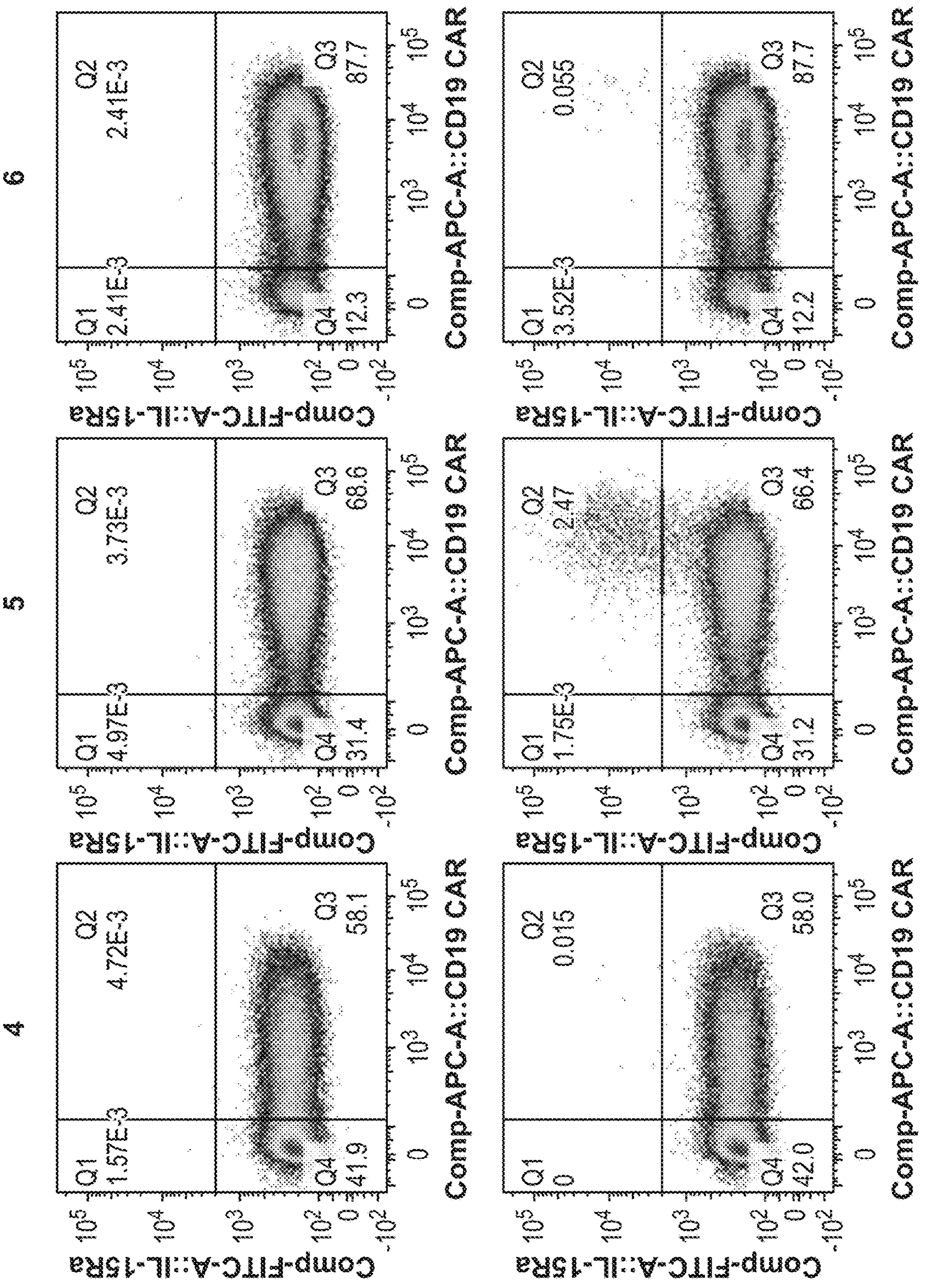
Figures 1, 20C:
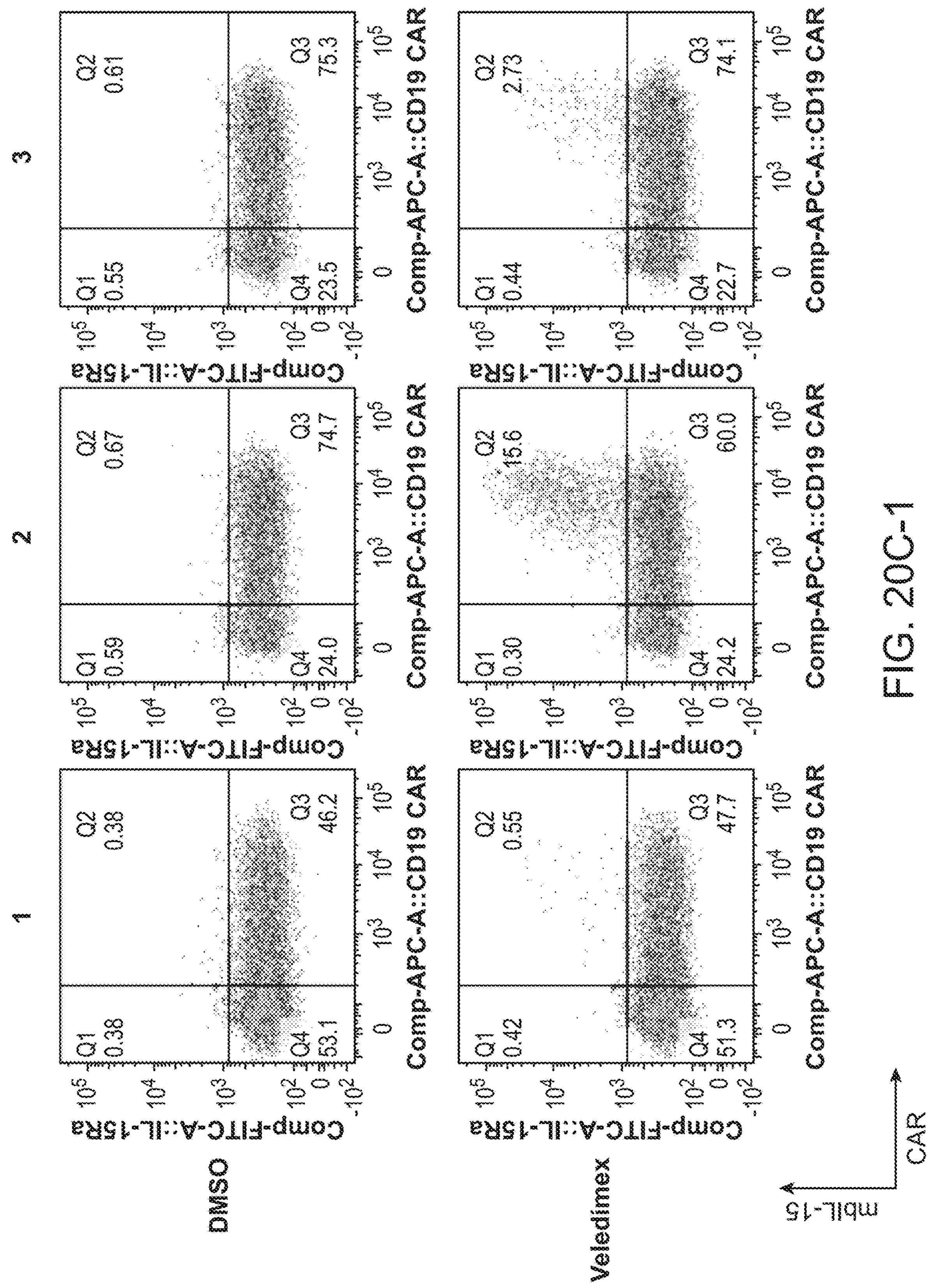
Figures 2, 20C:
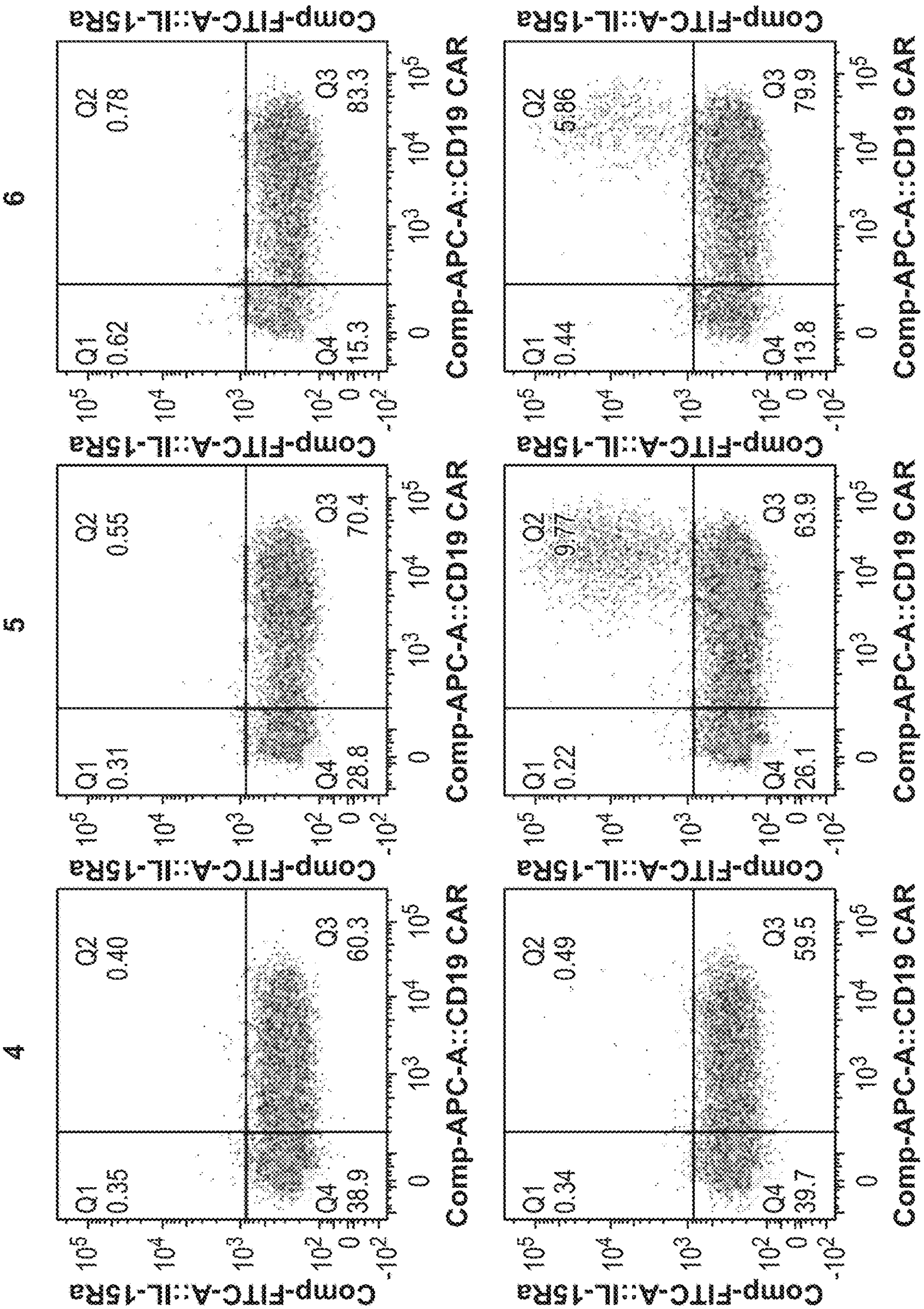
Figures 1, 20D:
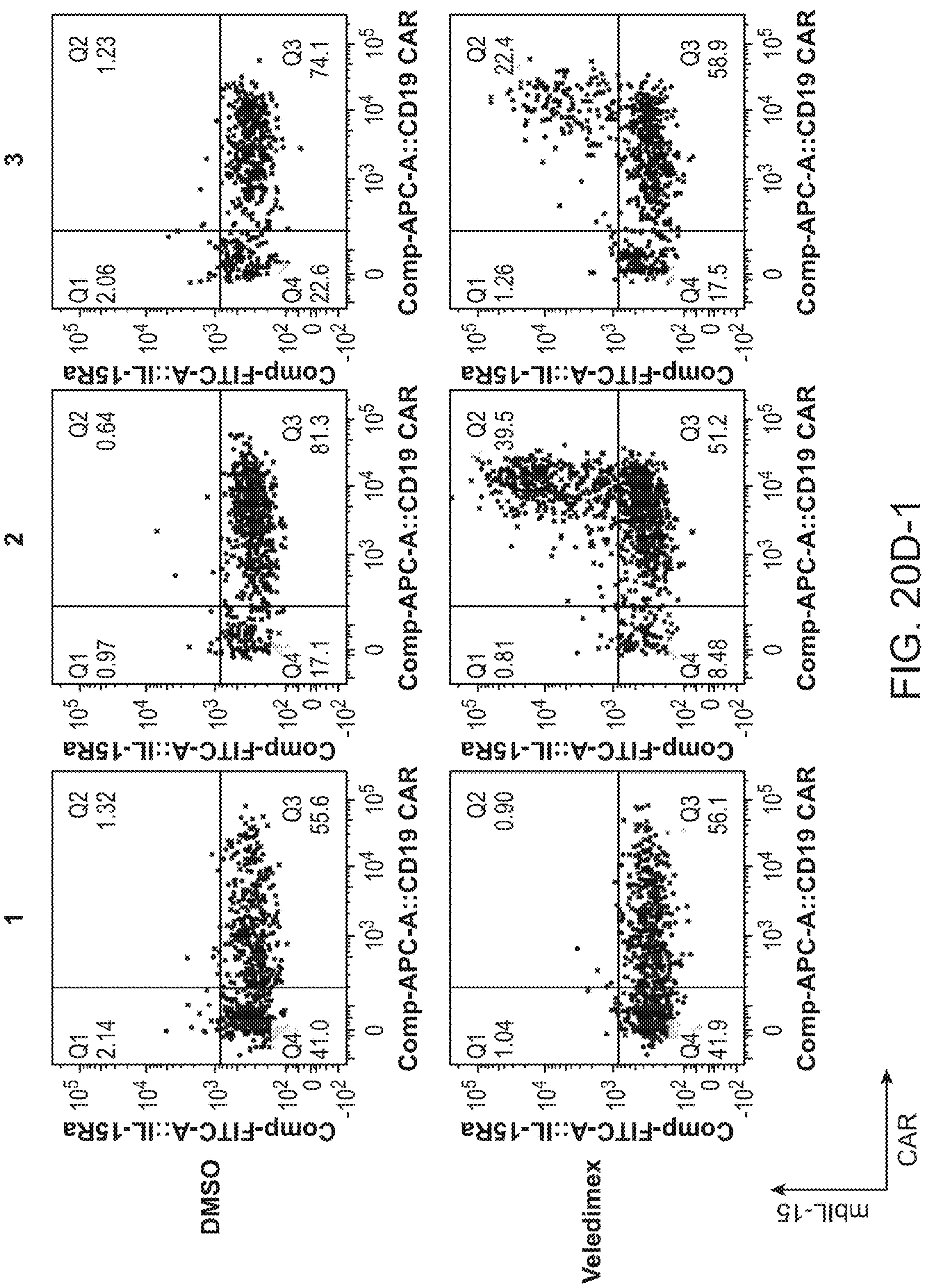
Figures 2, 20D:
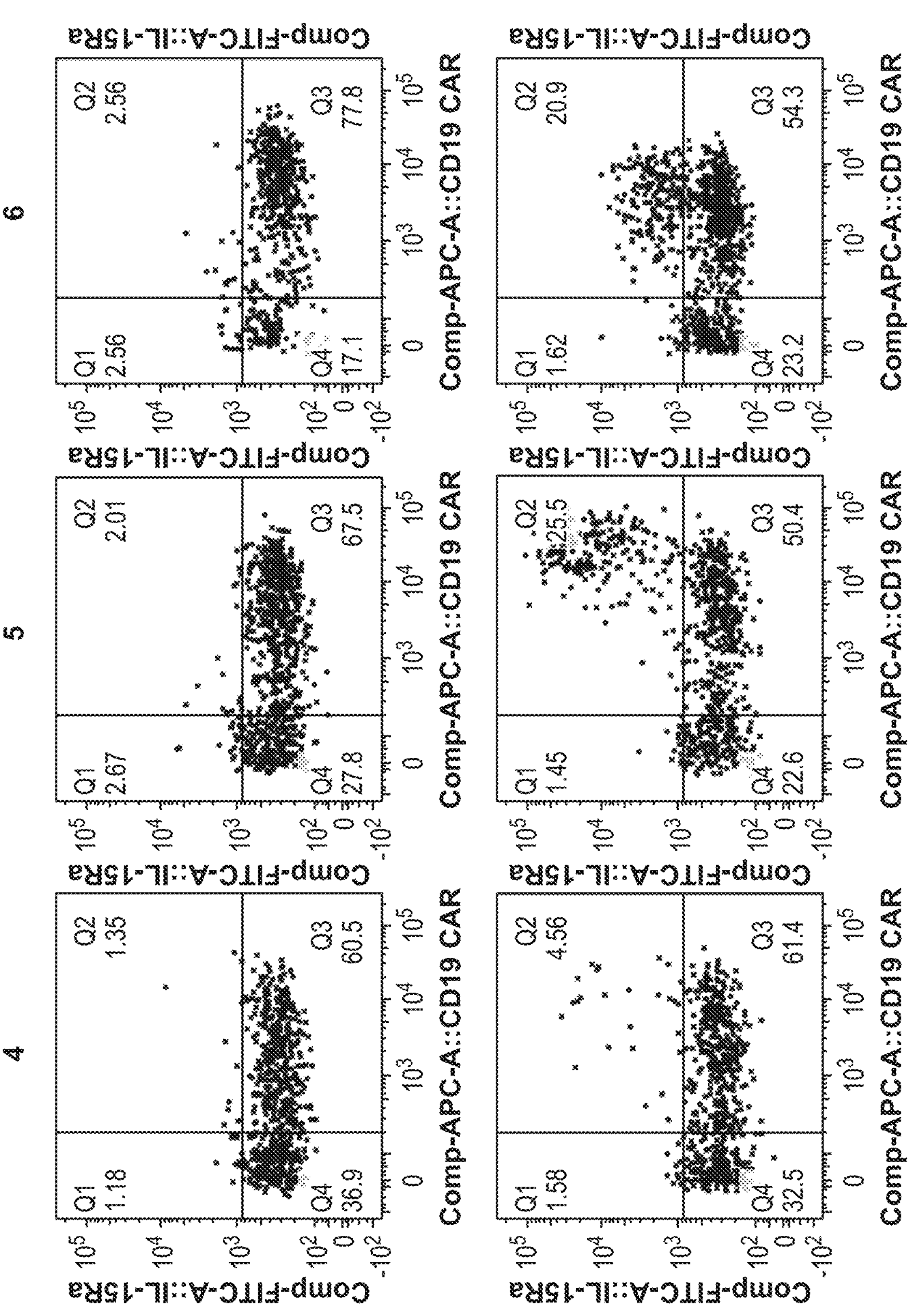
Figures 1, 20E:
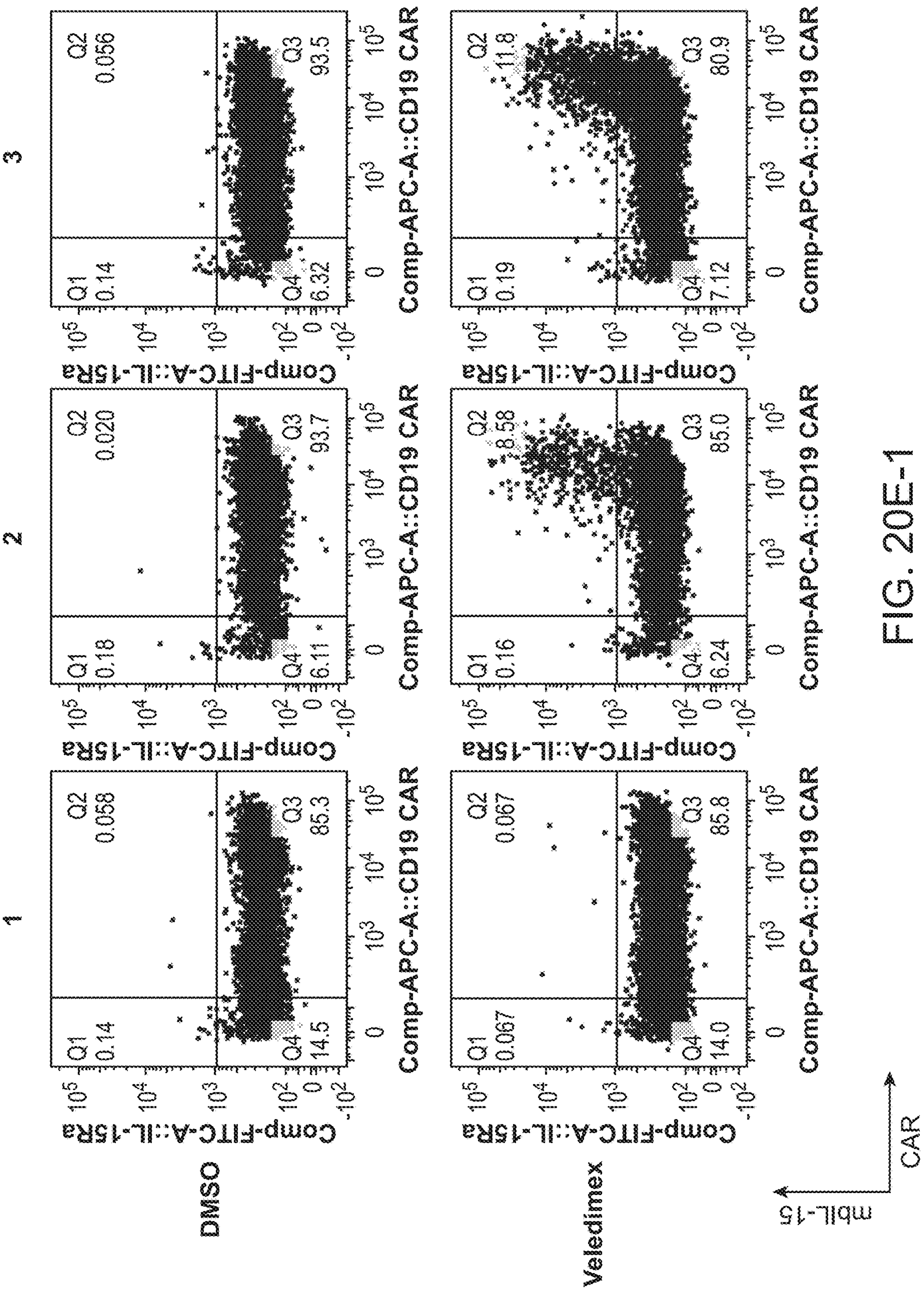
Figures 2, 20E:
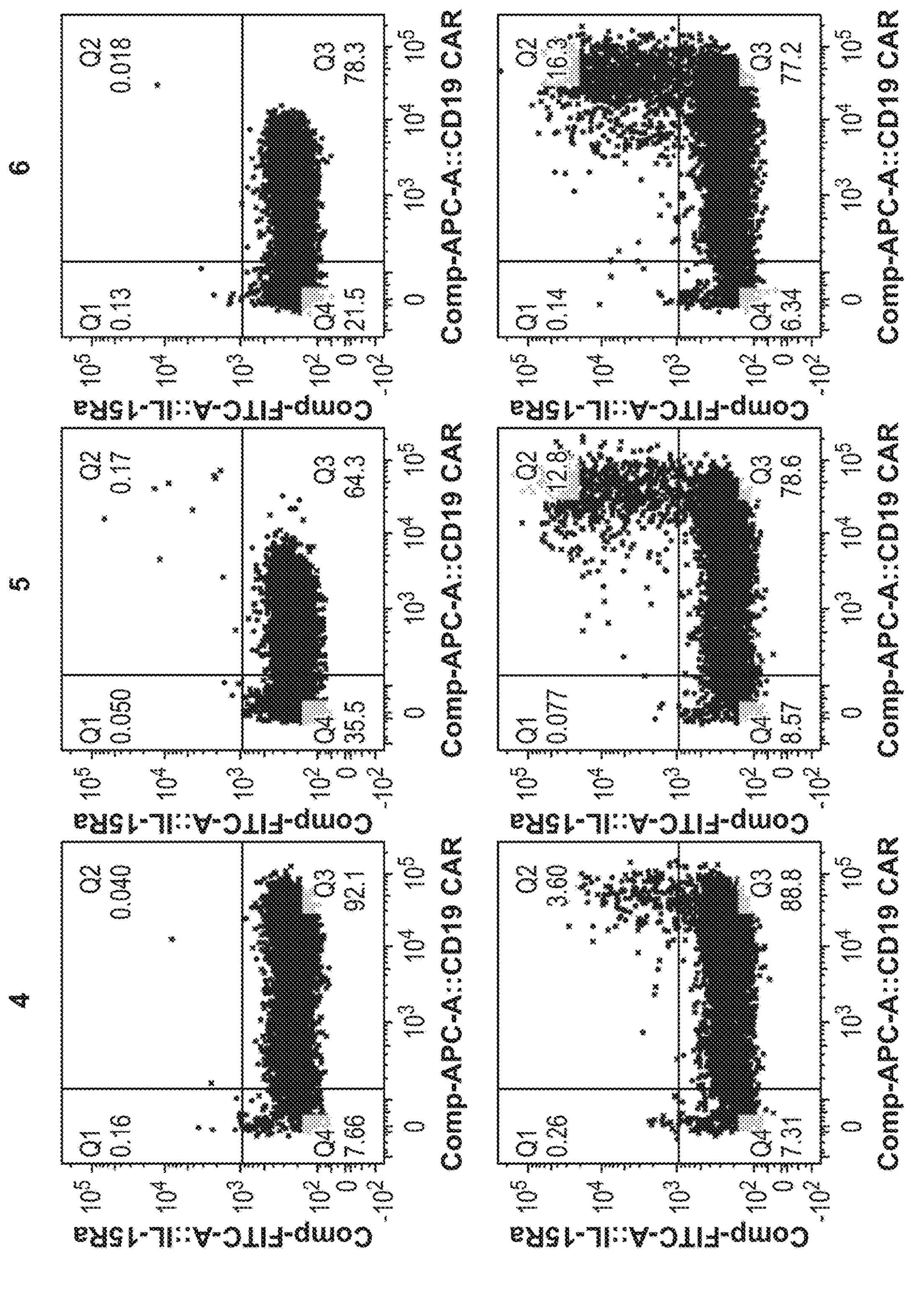

FIG. 20A schematically illustrates various structural components of diverse ligand-inducible gene switch vector systems under the control of constitutive or T cell specific promoters. FIG. 20B-1, FIG. 20B-2, FIG. 20C-1, FIG. 20C-2, FIG. 20D-1, FIG. 20D-2, FIG. 20E-1 and FIG. 20E-2 show the quantitative flow cytometric analysis of cells transfected with ligand-inducible gene switch vector systems described herein, demonstrating that expression of mbIL-15 is dependent on T cell activation (with addition of ConA) and presence of veledimex. Constructs 1-6 correspond to constructs as schematically depicted in FIG. 20A. FIG. 20B-1 is continued in FIG. 20B-2. FIG. 20C-1 is continued in FIG. 20C-2. FIG. 20D-1 is continued in FIG. 20D-2. FIG. 20E-1 is continued in FIG. 20E-2.

Figure 21A:
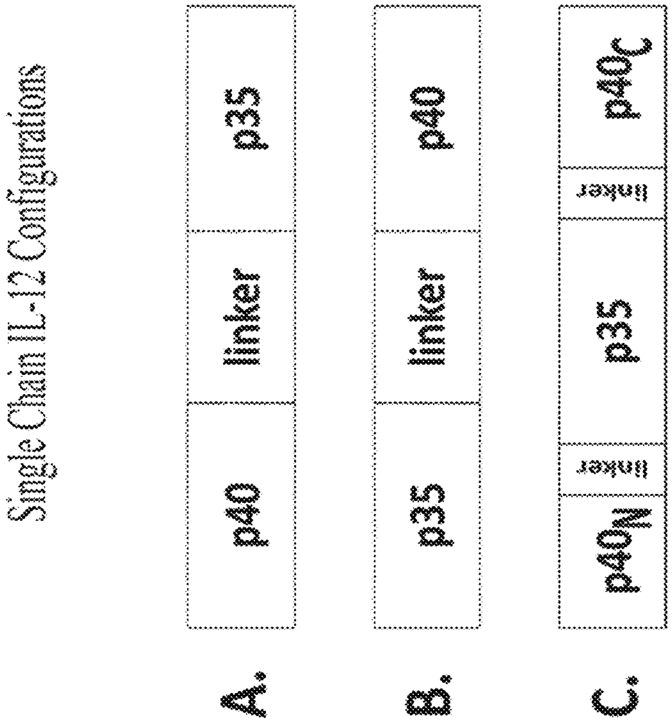
Figure 21B:
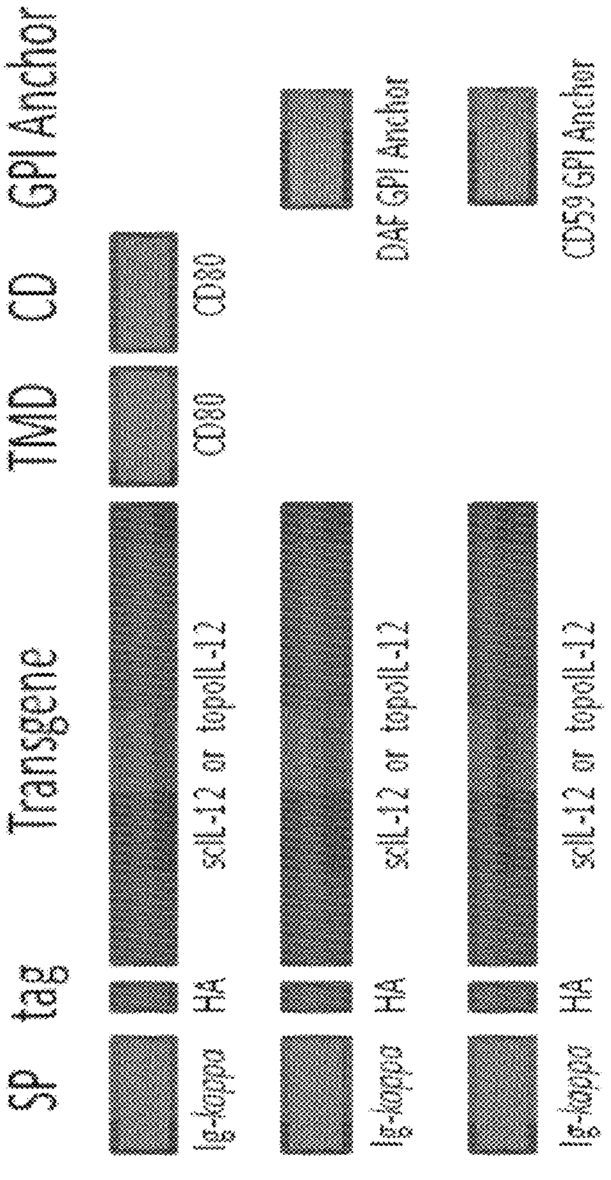

FIG. 21A-21B depicts various configurations of IL-12.

Figure 22:
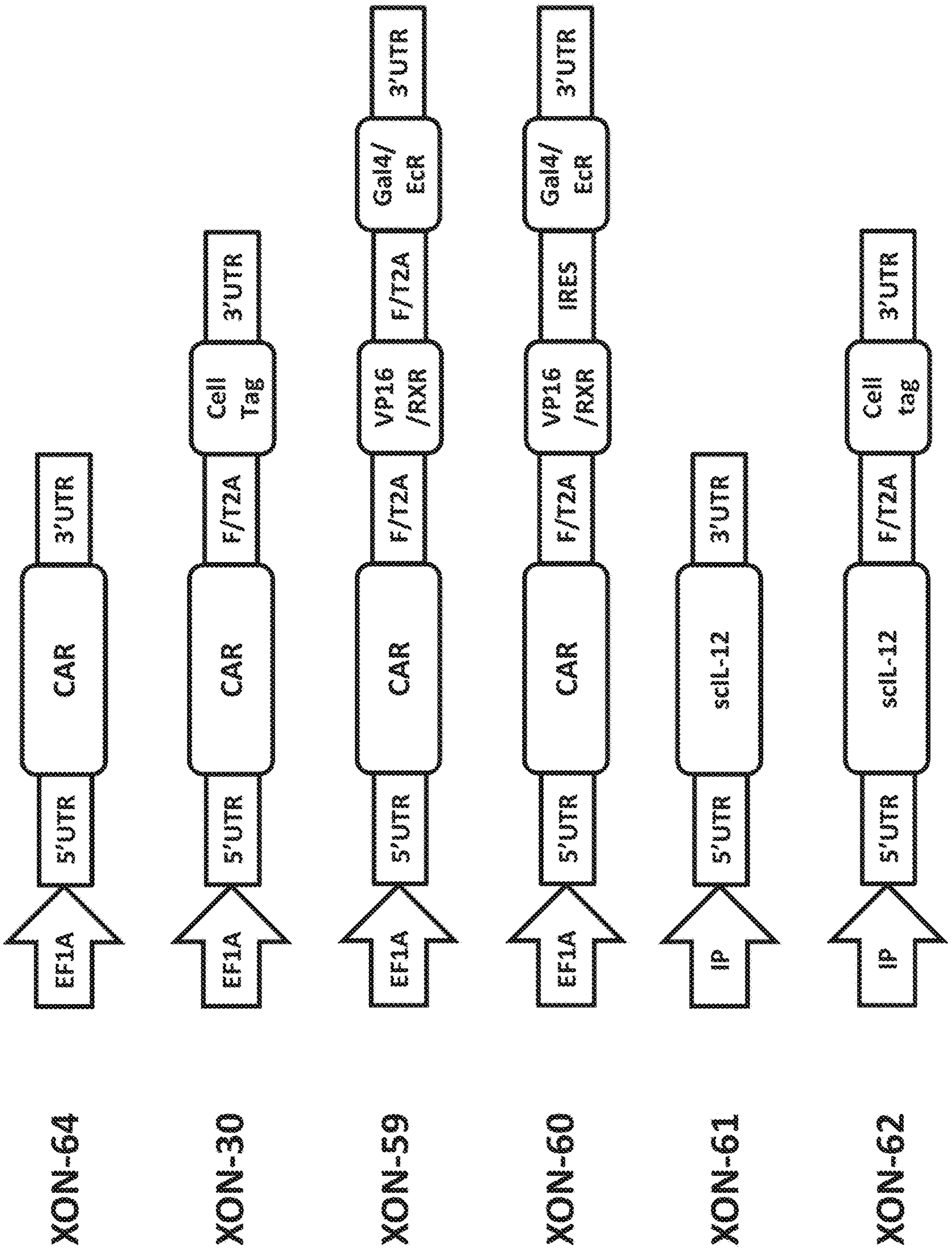

FIG. 22 schematically illustrates various structural components of diverse ligand-inducible gene switch vector systems under the control of constitutive or inducible promoters.

Figure 23:
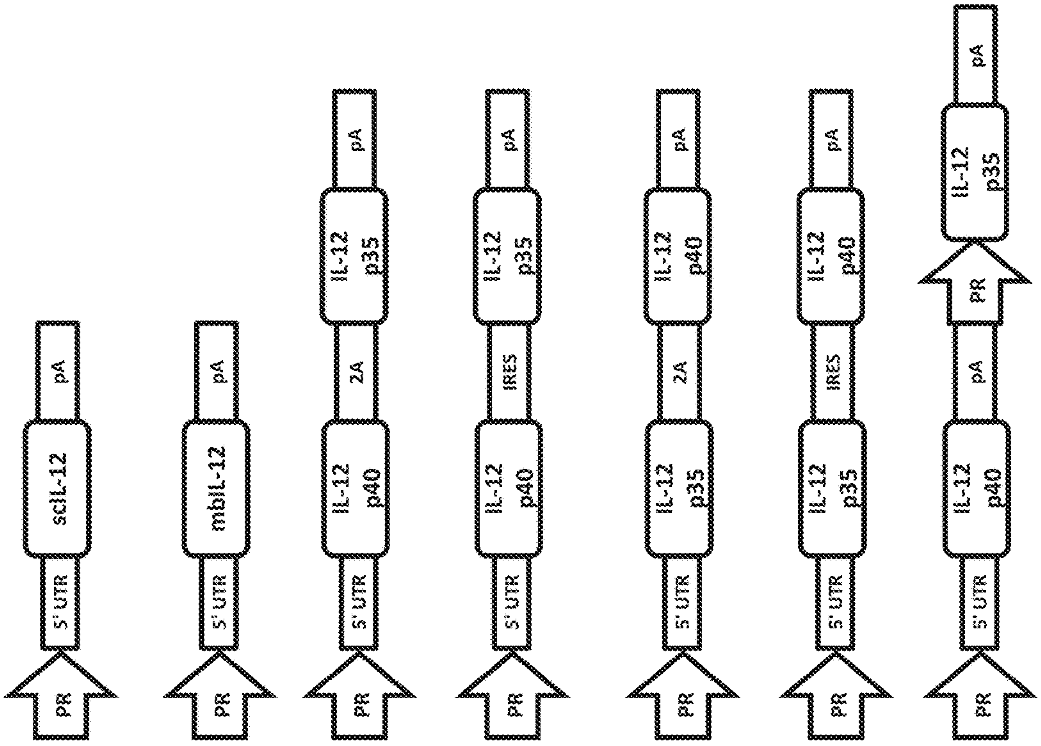
Figure 24A:
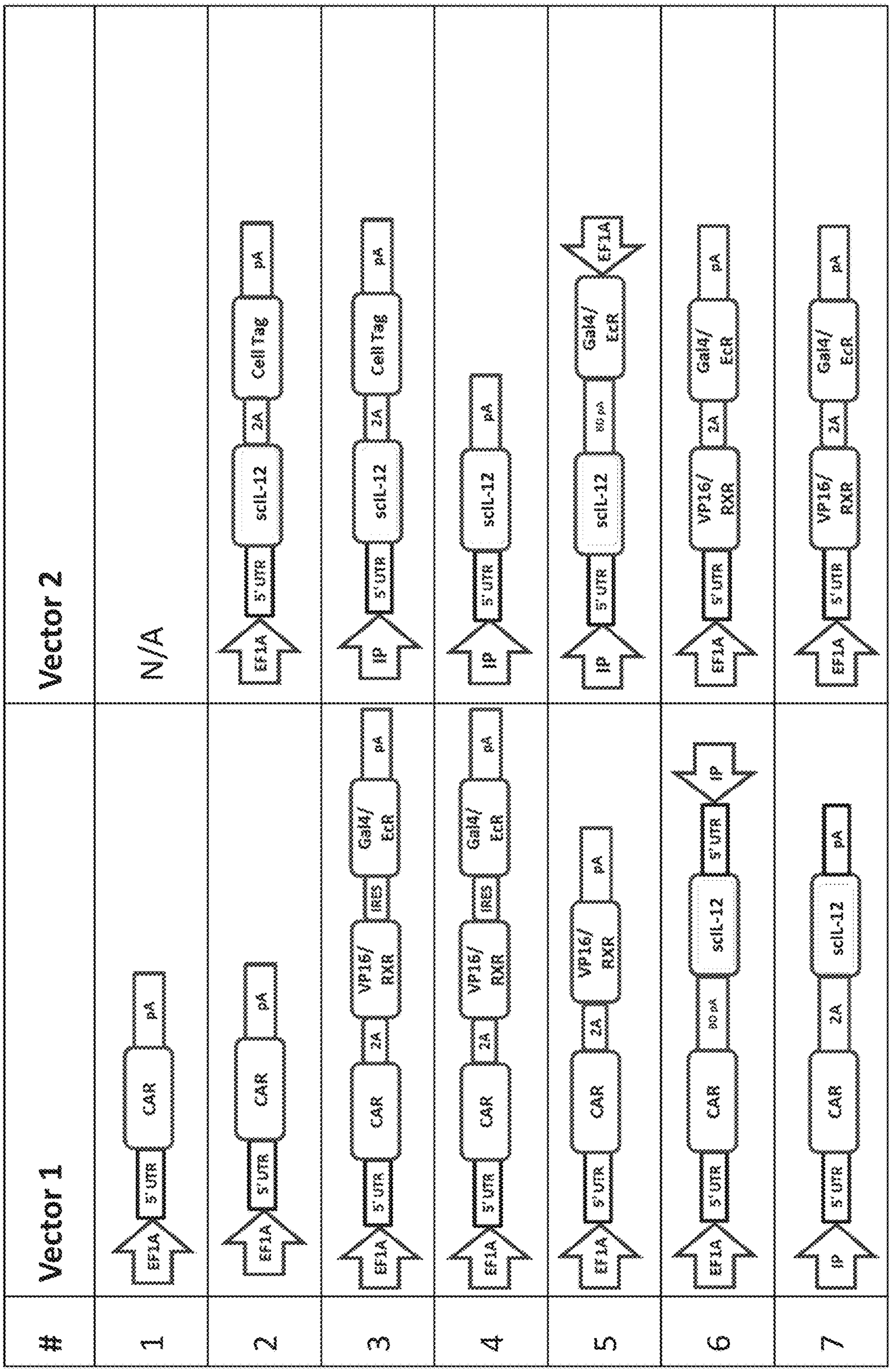
Figure 24C:
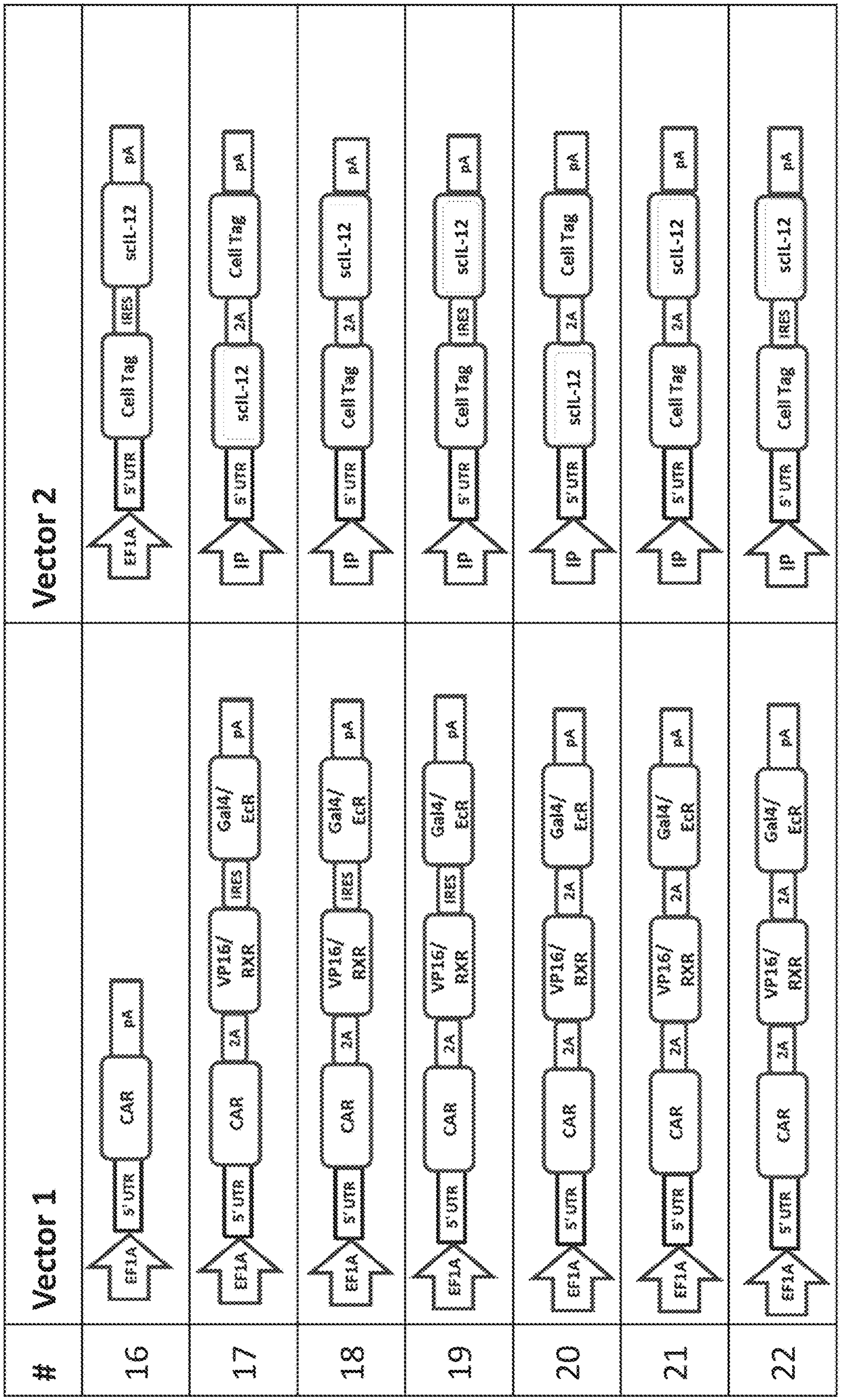
Figure 24D:
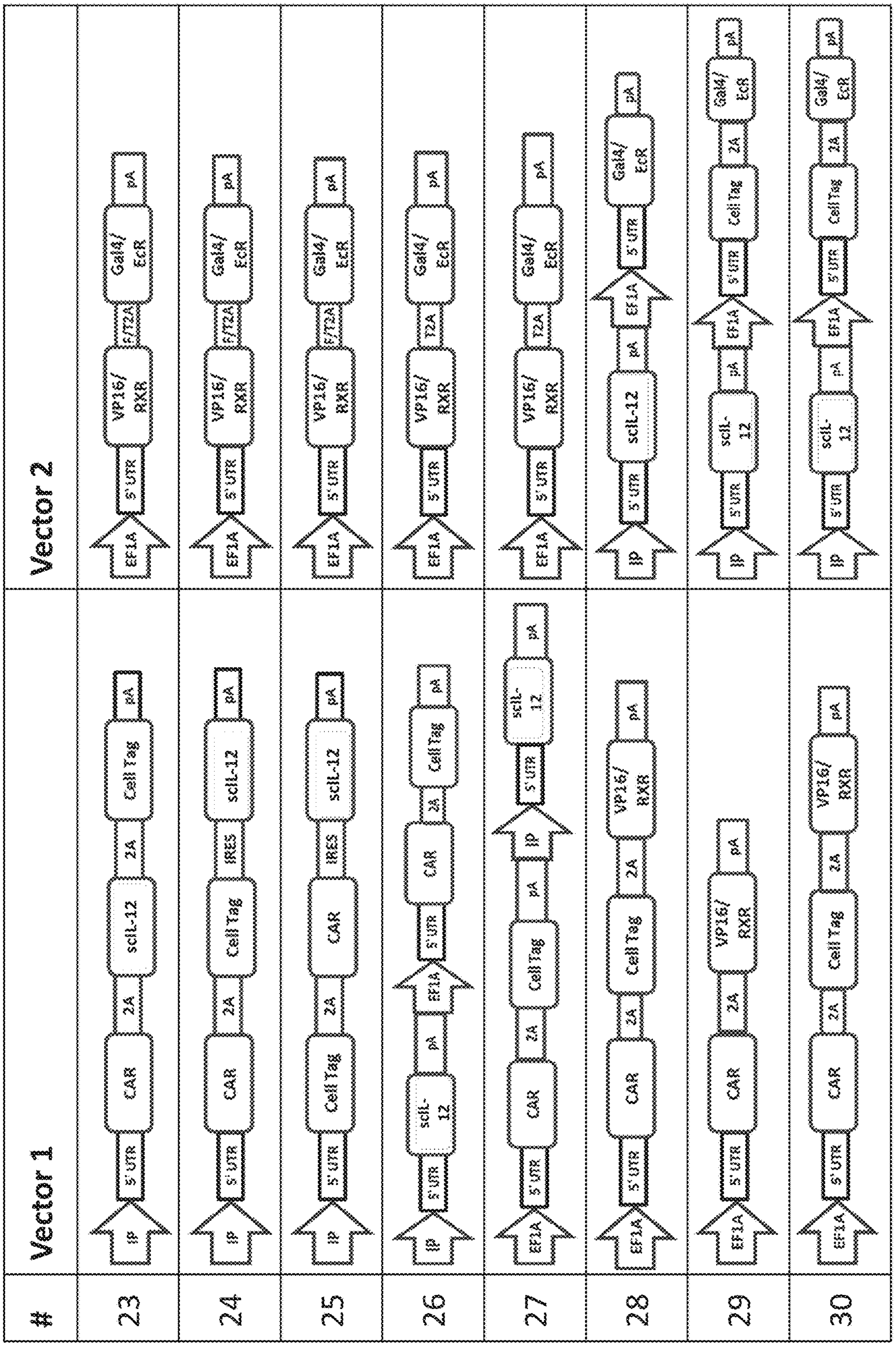

FIG. 23 schematically illustrates various structural components of diverse ligand-inducible gene switch vector systems to express different forms of IL-12 under the control of constitutive, inducible promoters or tissue-specific promoters (PR). IL-12 can be expressed as a single chain IL-12; membrane bound IL-12 or by individual expression of p35 and p40 domains.

FIG. 24A-24D schematically illustrate various structural components of diverse ligand-inducible gene switch vector systems under the control of constitutive or inducible promoters.

Figure 25A:
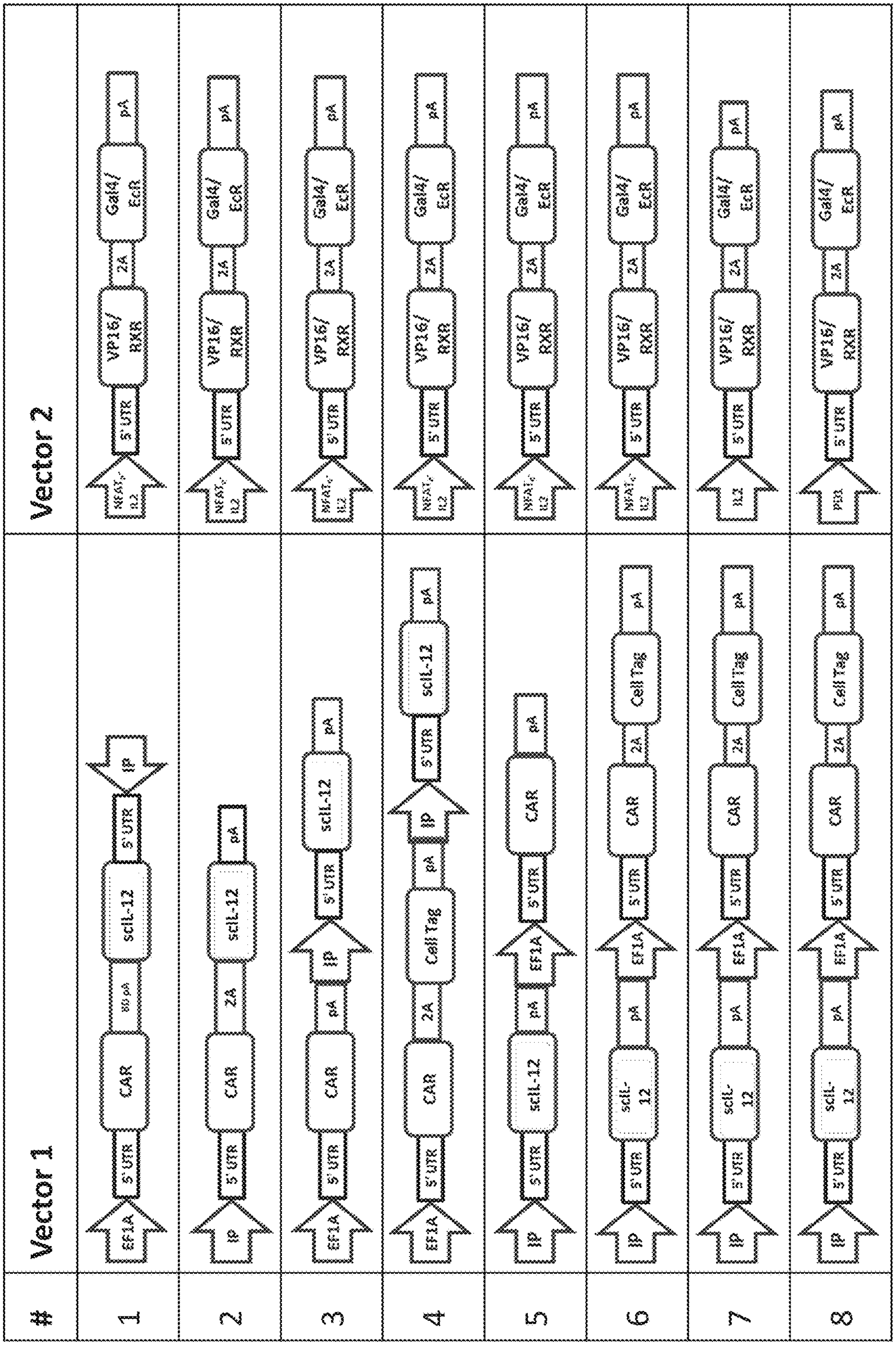
Figure 25B:
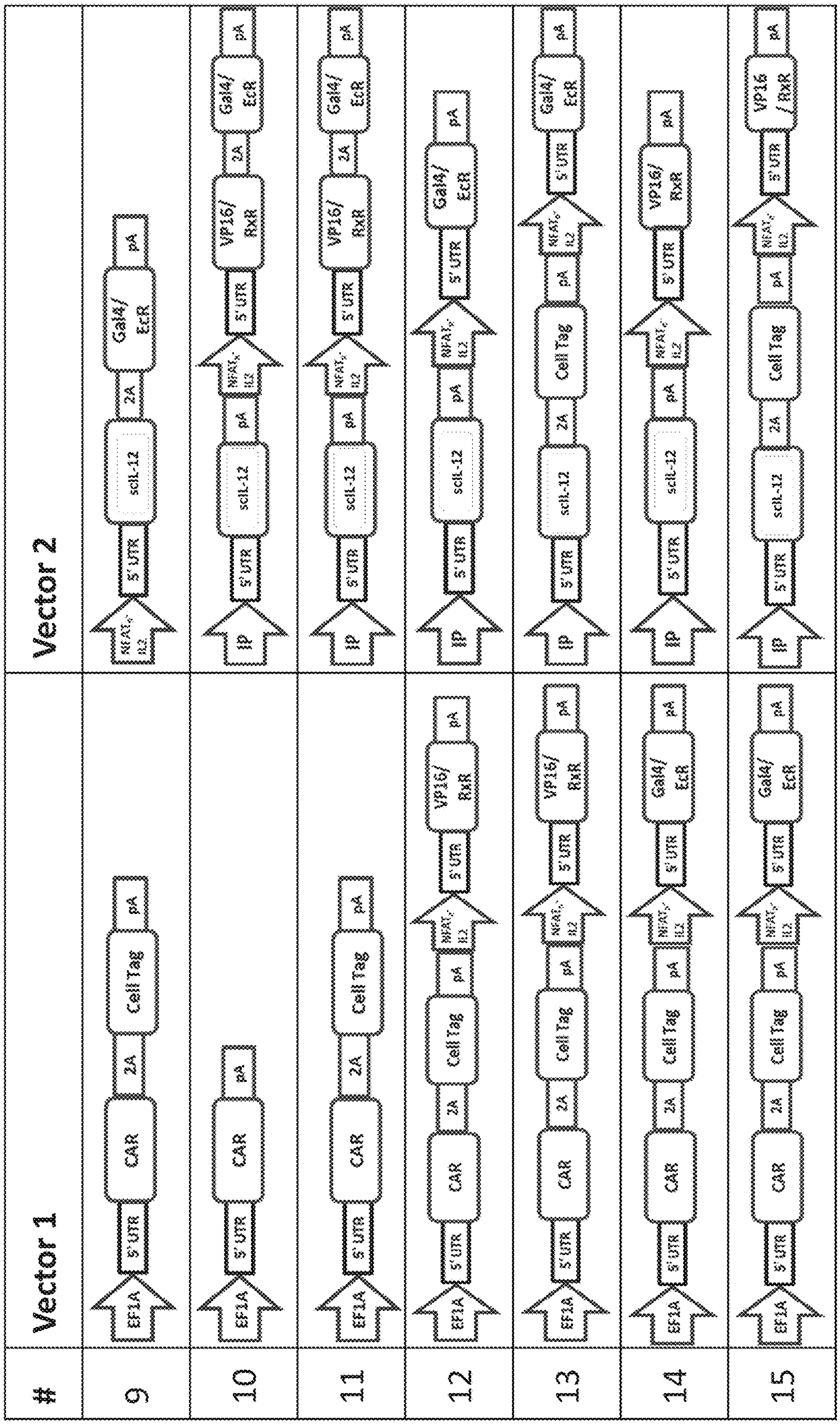

FIG. 25A-25B schematically illustrate various structural components of diverse ligand-inducible gene switch vector systems under the control of constitutive, inducible or T-cell specific promoters.

Figure 26:
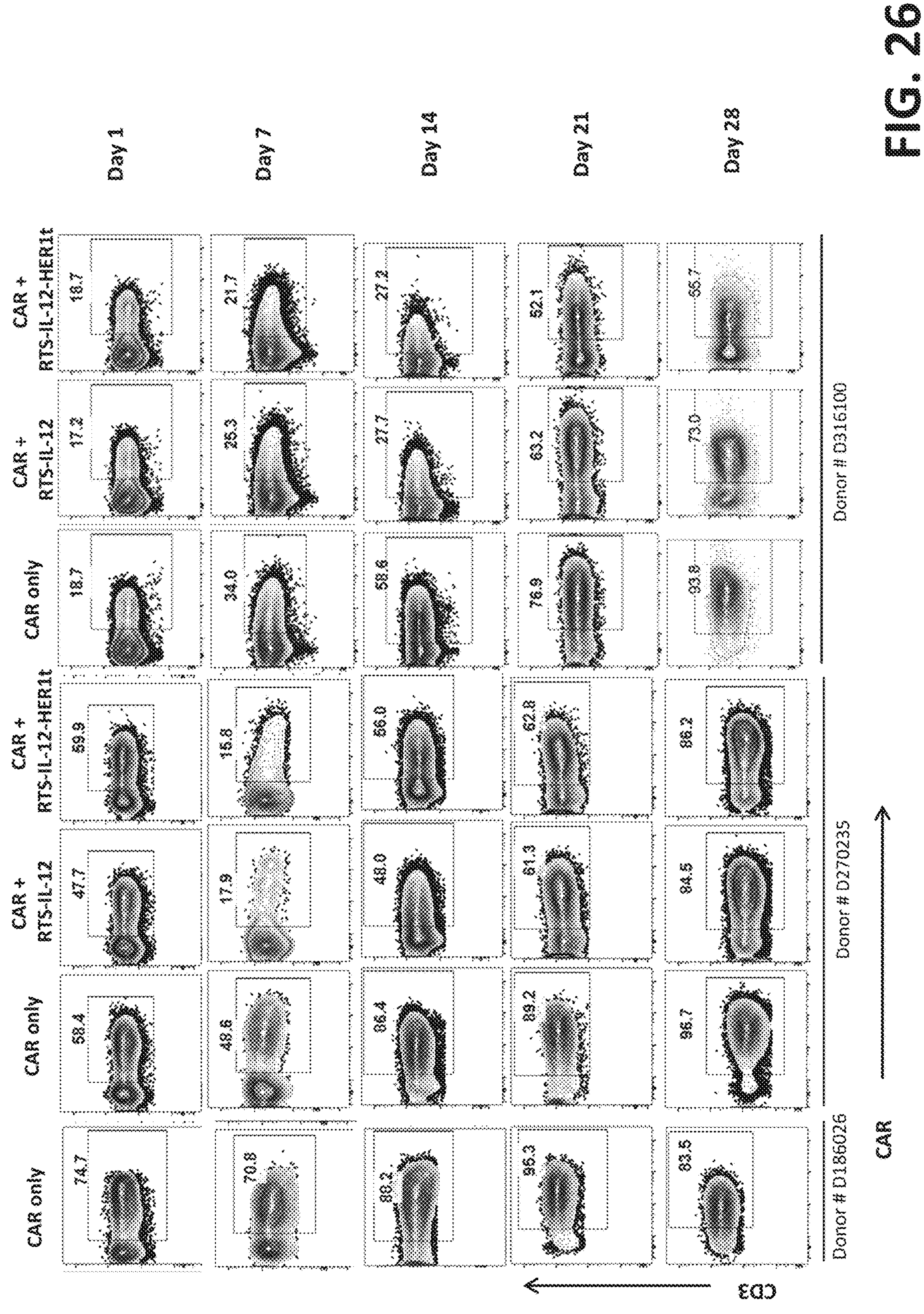

FIG. 26 show the quantitative flow cytometric analysis depicting expression of CAR in EGFRvIII CAR T cells expanded ex vivo by successive stimulations via co-culture with AaPC using multiple donors.

Figure 27:
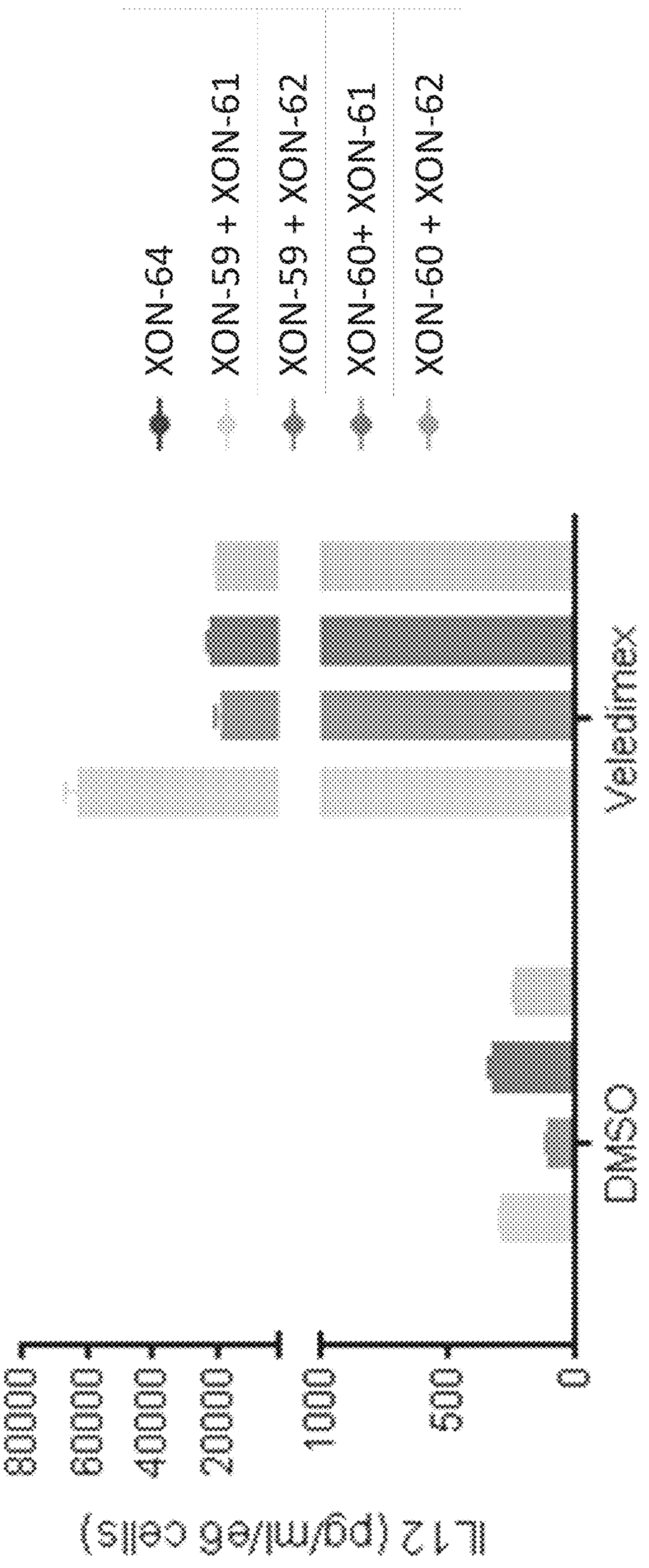

FIG. 27 shows production of IL-12 by cells transfected with ligand-inducible gene switch vector system described herein in presence/absence of veledimex ligand (solvent: DMSO).

Figure 28A:
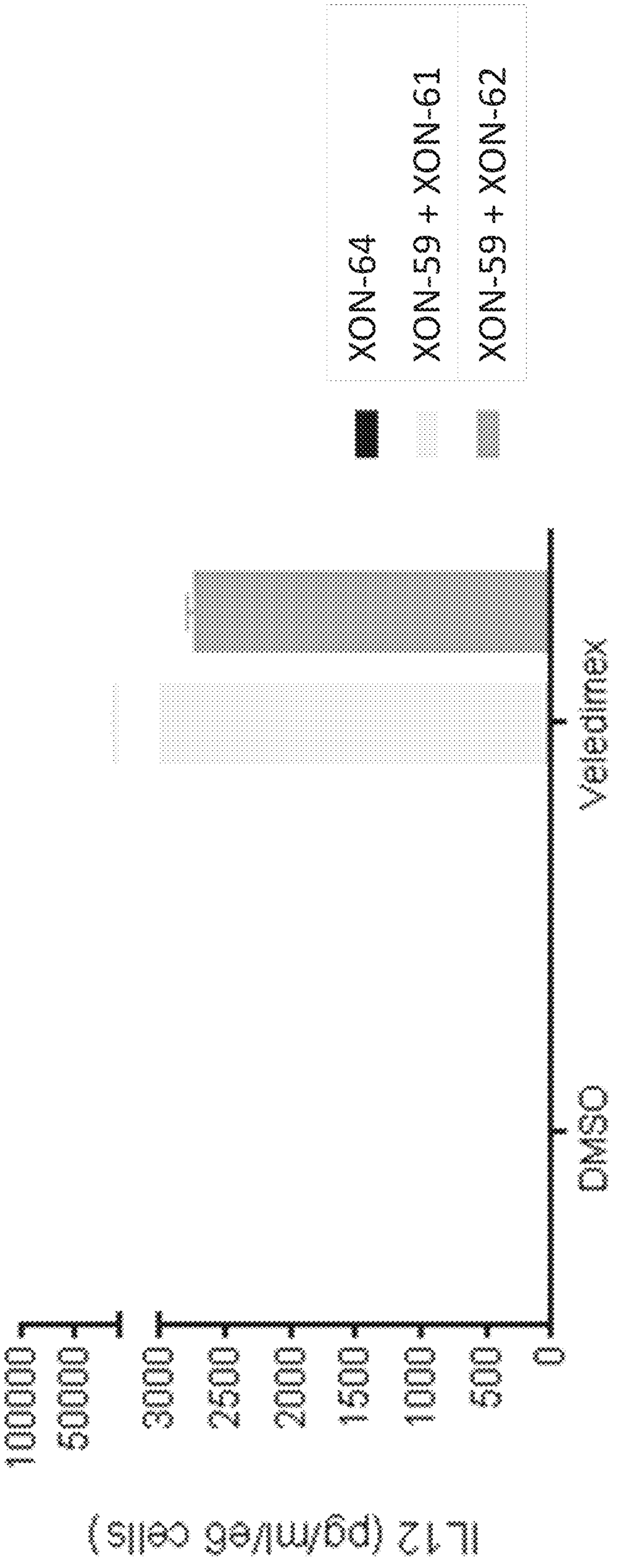
Figure 28B:
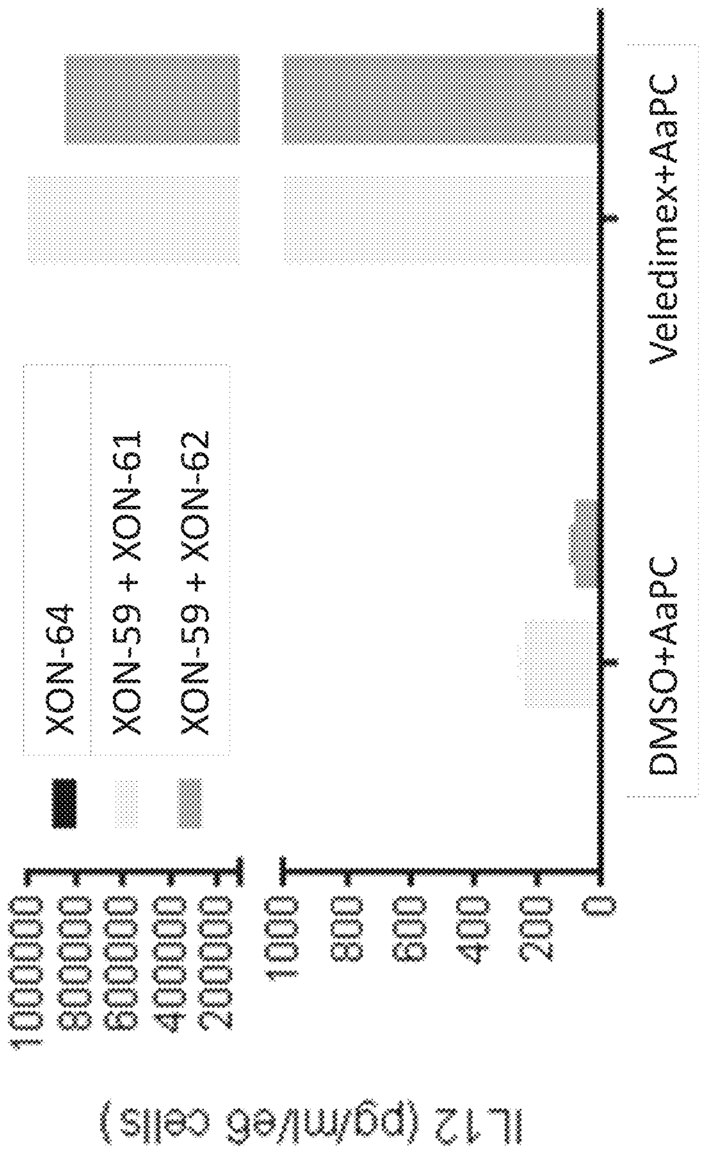

FIG. 28 show analyses of IL-12 expression levels. FIG. 28A shows expression levels of IL-12 by cells transfected with ligand-inducible gene switch vector system described herein in presence/absence of veledimex ligand (solvent: DMSO) in the absence of cell activation. FIG. 28B shows expression levels of IL-12 by cells transfected with ligand-inducible gene switch vector system described herein in presence/absence of veledimex ligand (solvent: DMSO) following antigen specific activation.

Figure 29:
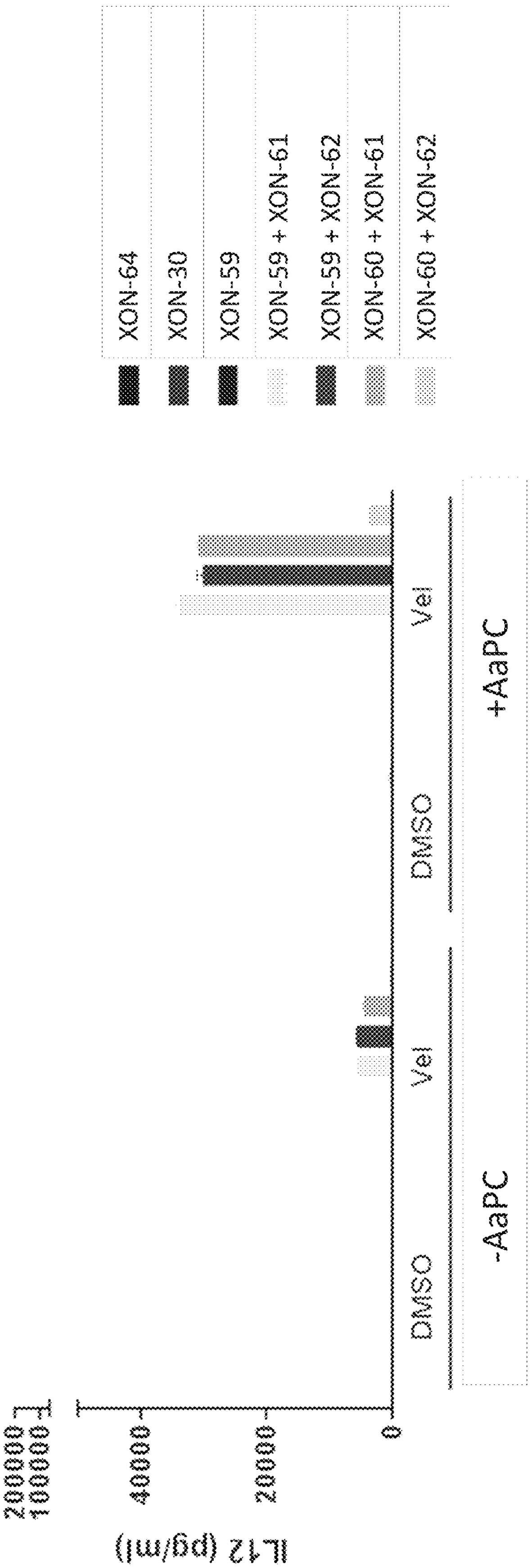

FIG. 29 show analyses of IL-12 expression levels in cells transfected with ligand-inducible gene switch vector system described herein and co-cultured in presence/absence of aAPCs and veledimex ligand (solvent: DMSO).

Figure 30A:
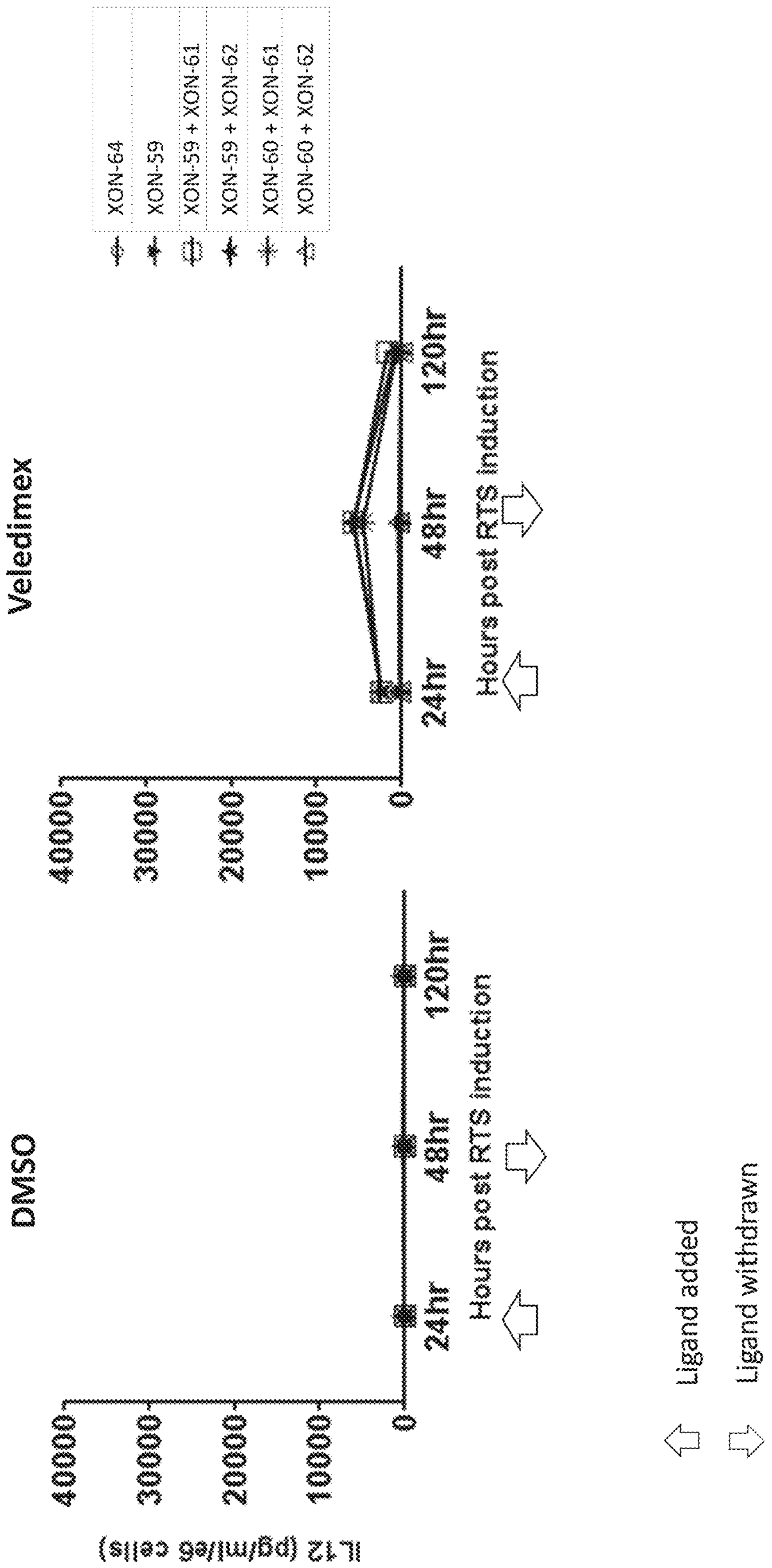
Figure 30B:
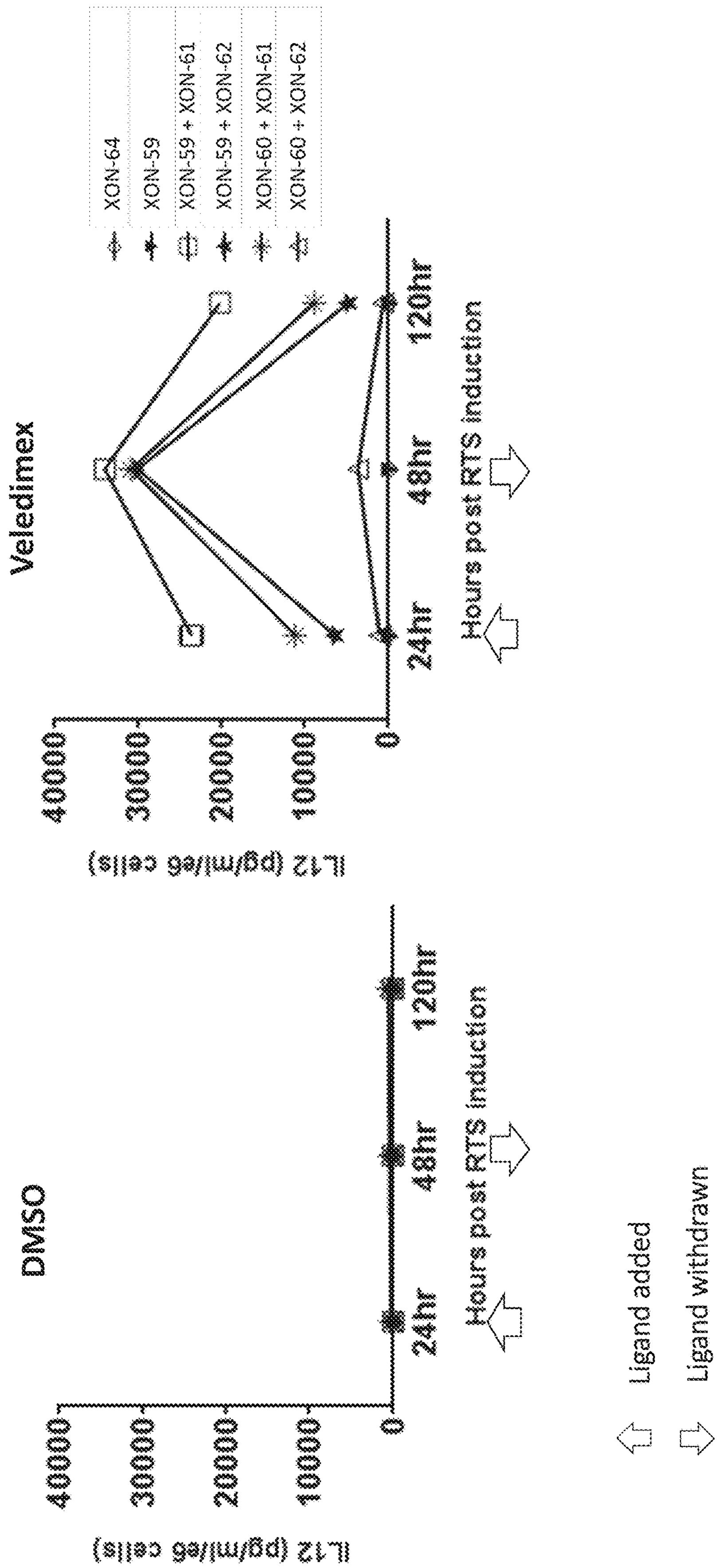

FIGS. 30A and 30B show time course analyses of IL-12 expression levels. FIG. 30 A shows expression levels of IL-12 by cells transfected with ligand-inducible gene switch vector system described herein and co-cultured in absence of AaPC s in presence/absence of veledimex ligand (solvent: DMSO). Ligand was added at 24 hours and withdrawn at 48 hours. FIG. 30B shows expression levels of IL-12 by cells transfected with ligand-inducible gene switch vector system described herein and co-cultured in presence of AaPC s in presence/absence of veledimex ligand (solvent: DMSO). Ligand was added at 24 hours and withdrawn at 48 hours. Expression of of IL-12 was quantified at 24, 48 and 120 hours post addition of ligand.

Figure 31A:
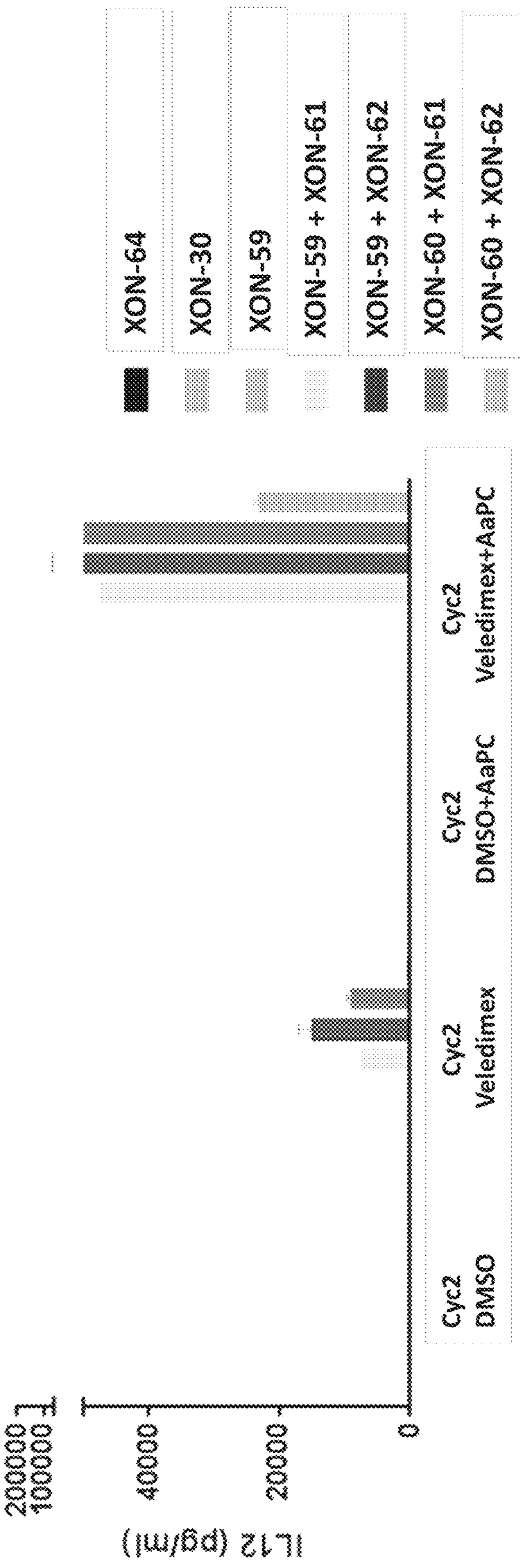
Figure 31B:
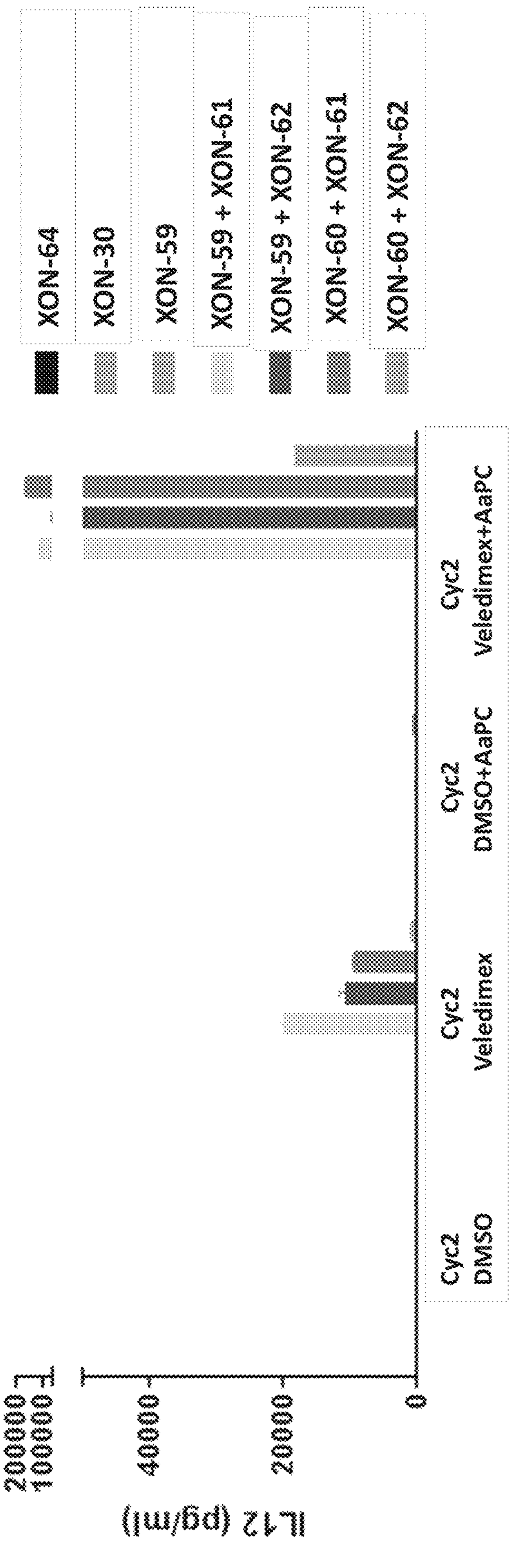

FIGS. 31A and 31B show analyses of IL-12 expression levels. FIG. 31A shows expression levels of IL-12 in presence/absence of veledimex and AaPCs by cells transfected with ligand-inducible gene switch vector system described herein and expanded by co-culture with AaPCs in media without veledimex previously (cycle 1). FIG. 31B shows production of IL-12 in presence/absence of veledimex and AaPCs by cells transfected with ligand-inducible gene switch vector system described herein and expanded by co-culture with AaPCs in media previously (cycle 1).

Figure 32B:
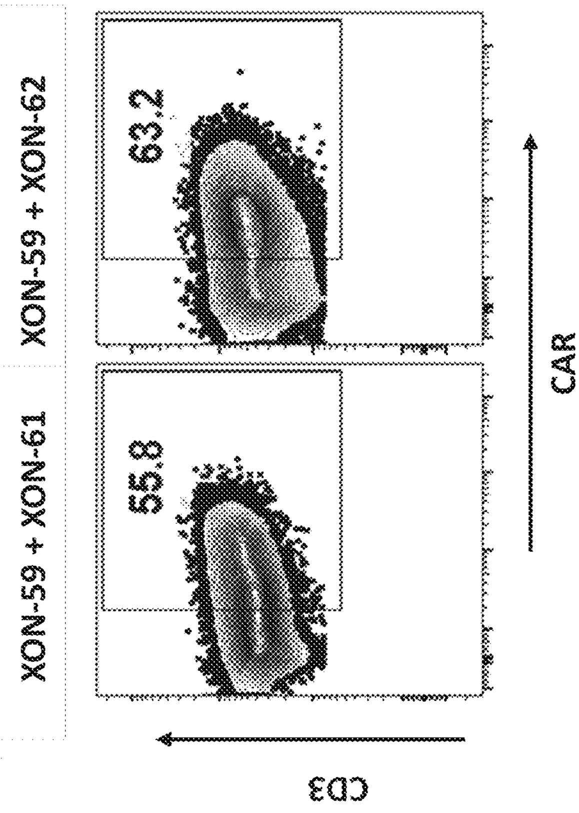
Figure 32A:
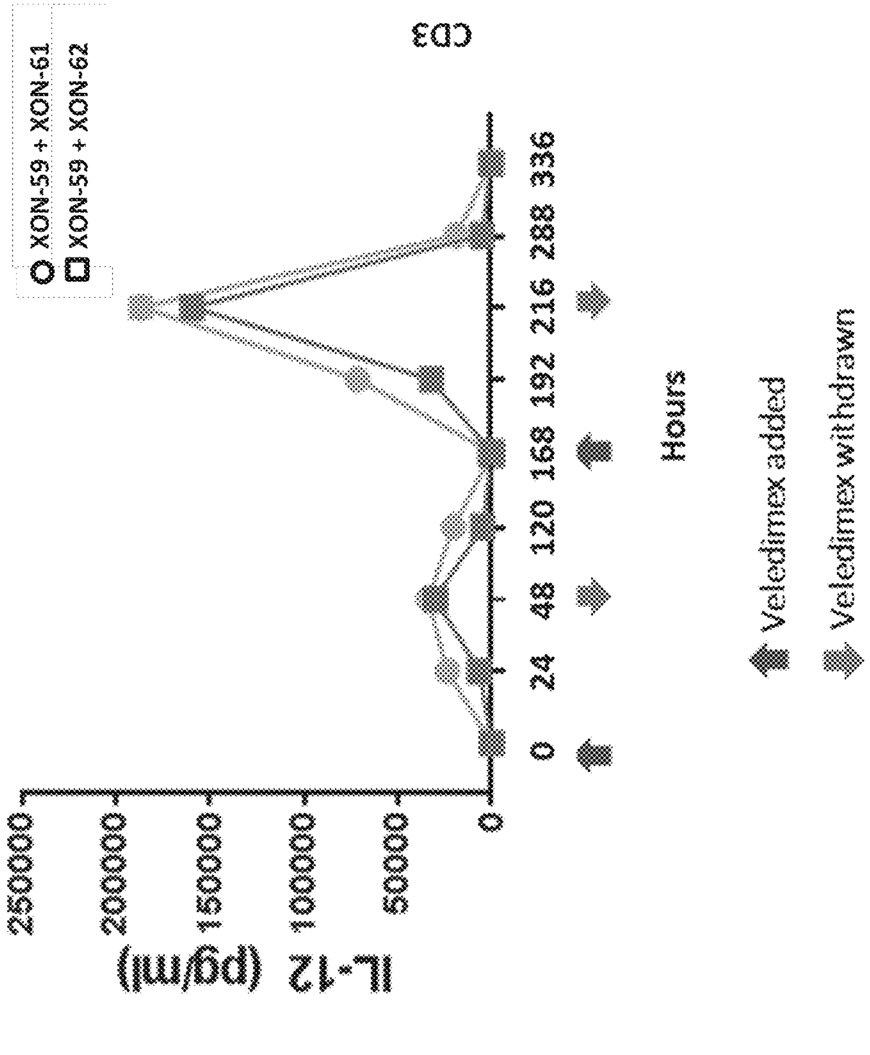

FIGS. 32A and 32B show analyses of IL-12 expression levels. FIG. 32A shows production of IL-12 by cells transfected with ligand-inducible gene switch vector system described herein. Veledimex ligand was added at time 0, withdrawn at time 48 hours, added again at time 168 hours and withdrawn at time 216 hours. FIG. 32B shows expression of CAR in cells transfected with ligand-inducible gene switch vector systems described herein by flow cytometry analysis. Cells are gated on CD3 positive population.

Figure 33:
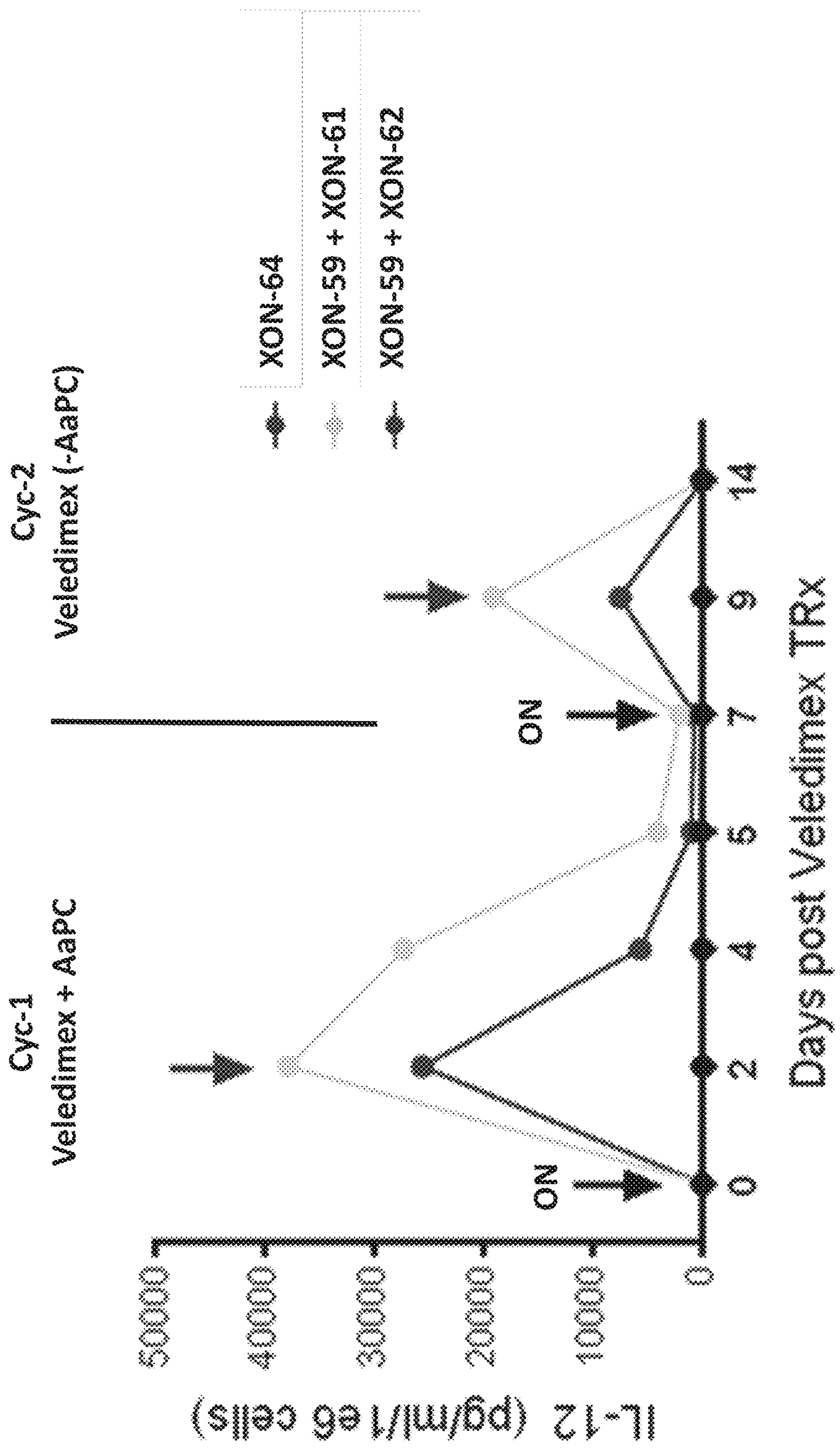

FIG. 33 shows expression levels of IL-12 by cells transfected with ligand-inducible gene switch vector system described herein in presence of veledimex and in presence (cycle 1)/absence (cycle 2) of AaPCs.

Figure 34:
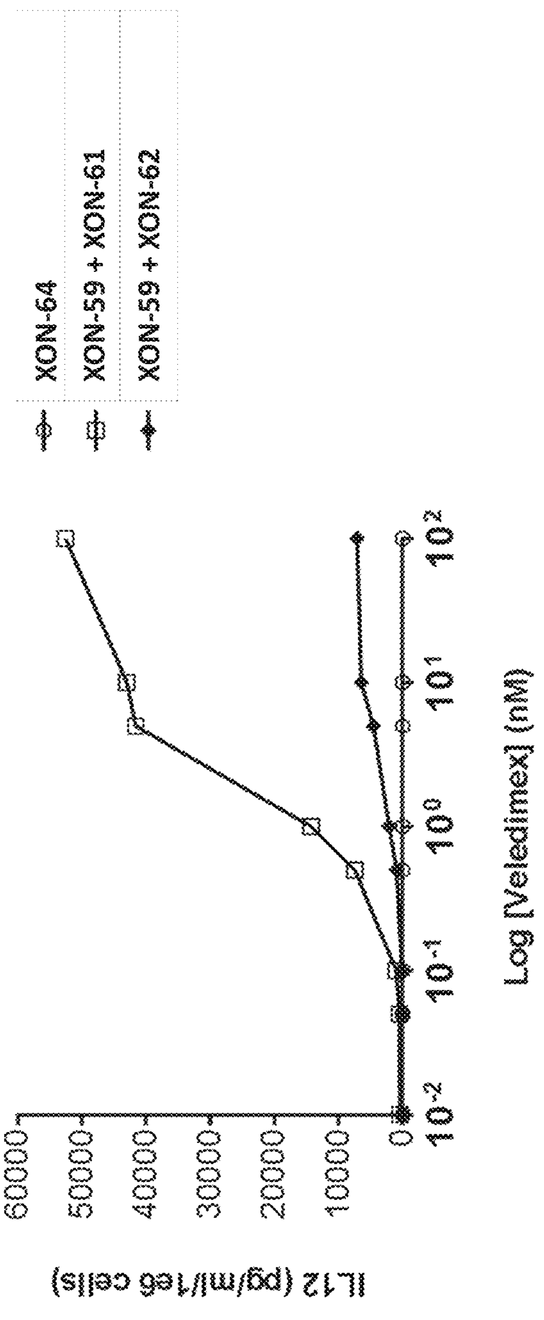

FIG. 34 shows veledimex dose dependent expression of IL-12 by cells transfected with ligand-inducible gene switch vector system described herein.

Figure 35:
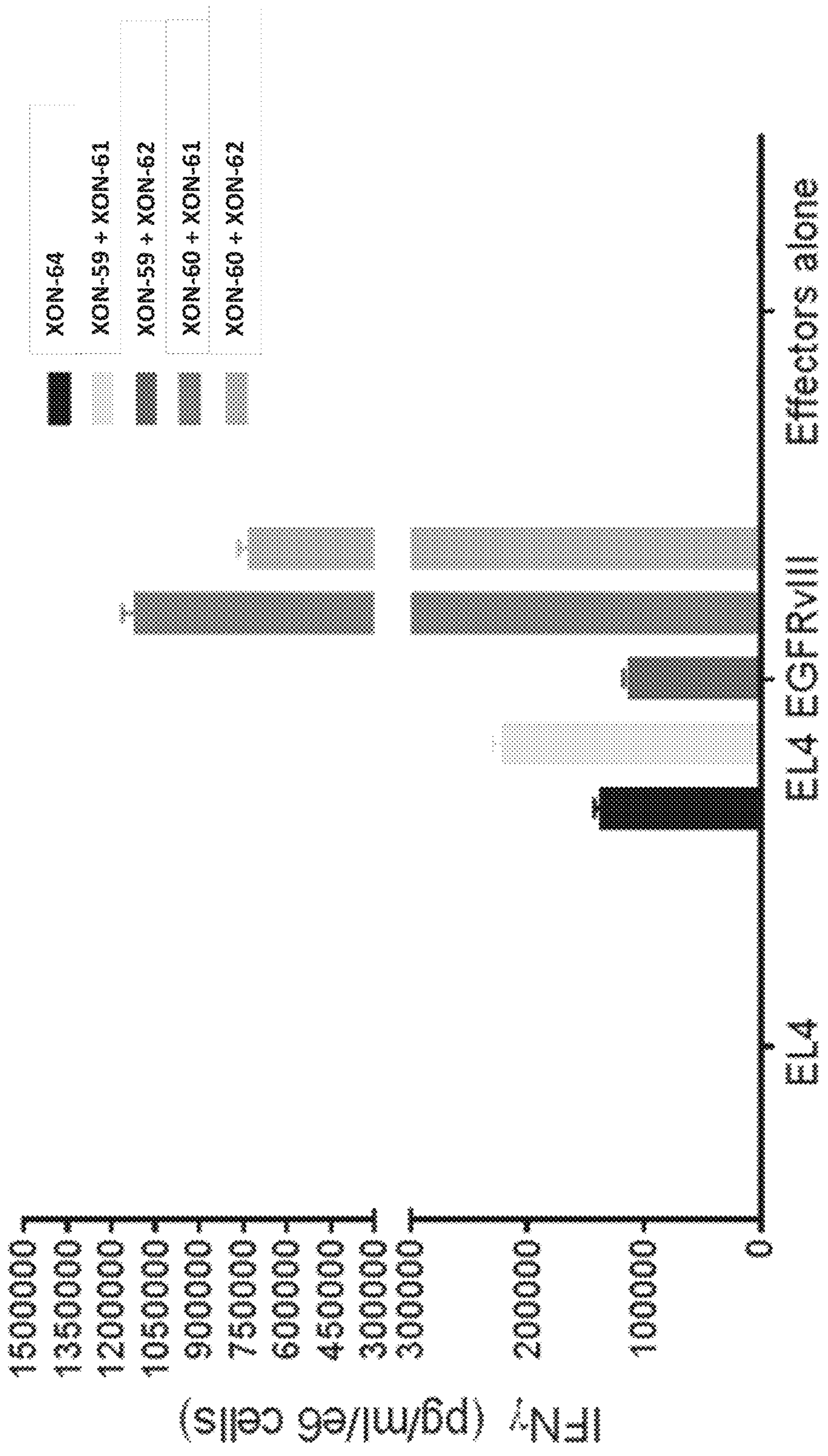

FIG. 35 shows production of IFNγ by CAR-T cells generated via transfection of ligand-inducible gene switch vector system described herein and co-cultured with target cells at 1:1 effector to target cell ratio. Production of IFNγ was measured using co-culture of CAR-T cells with EL4, EL4 EGFRvIII target cells as well as no target cell (effector alone) control.

Figure 36A:
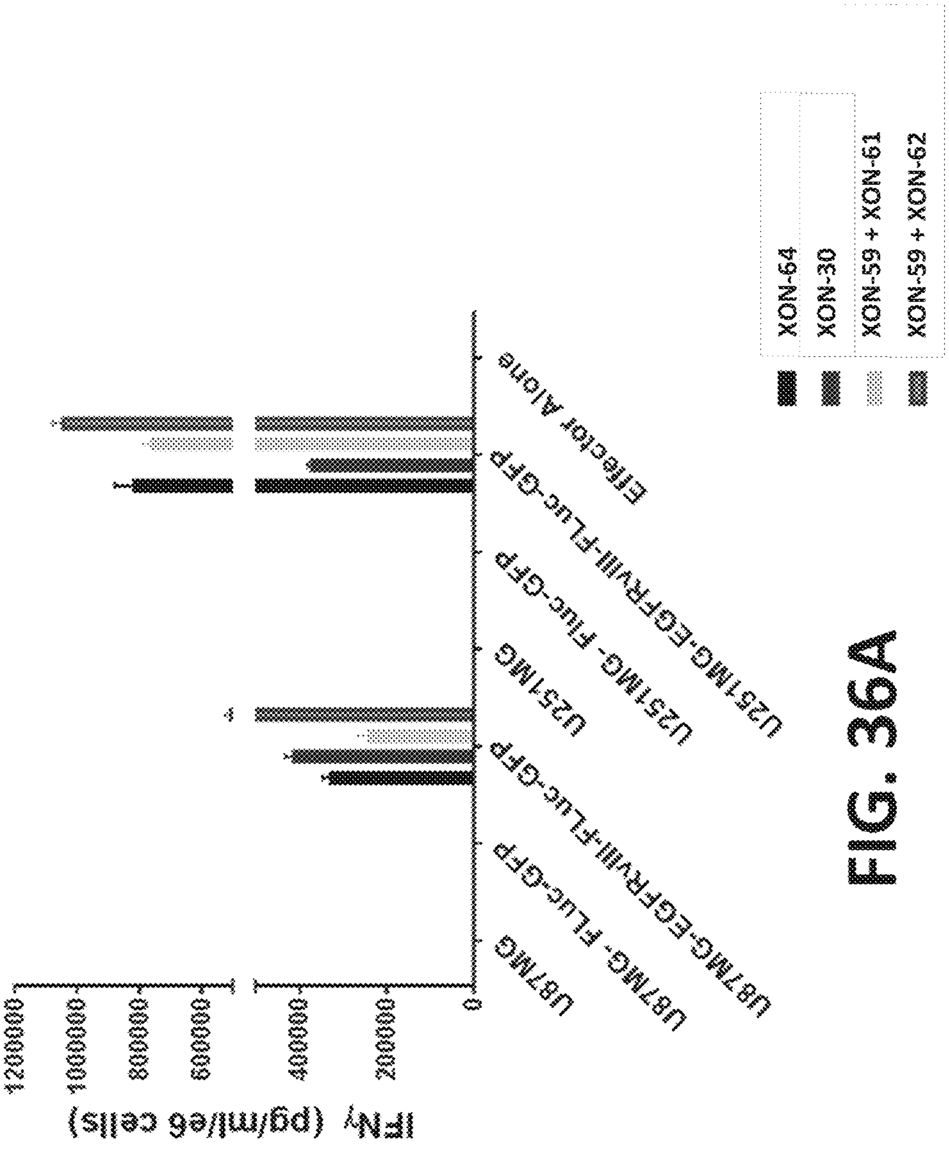
Figure 36B:
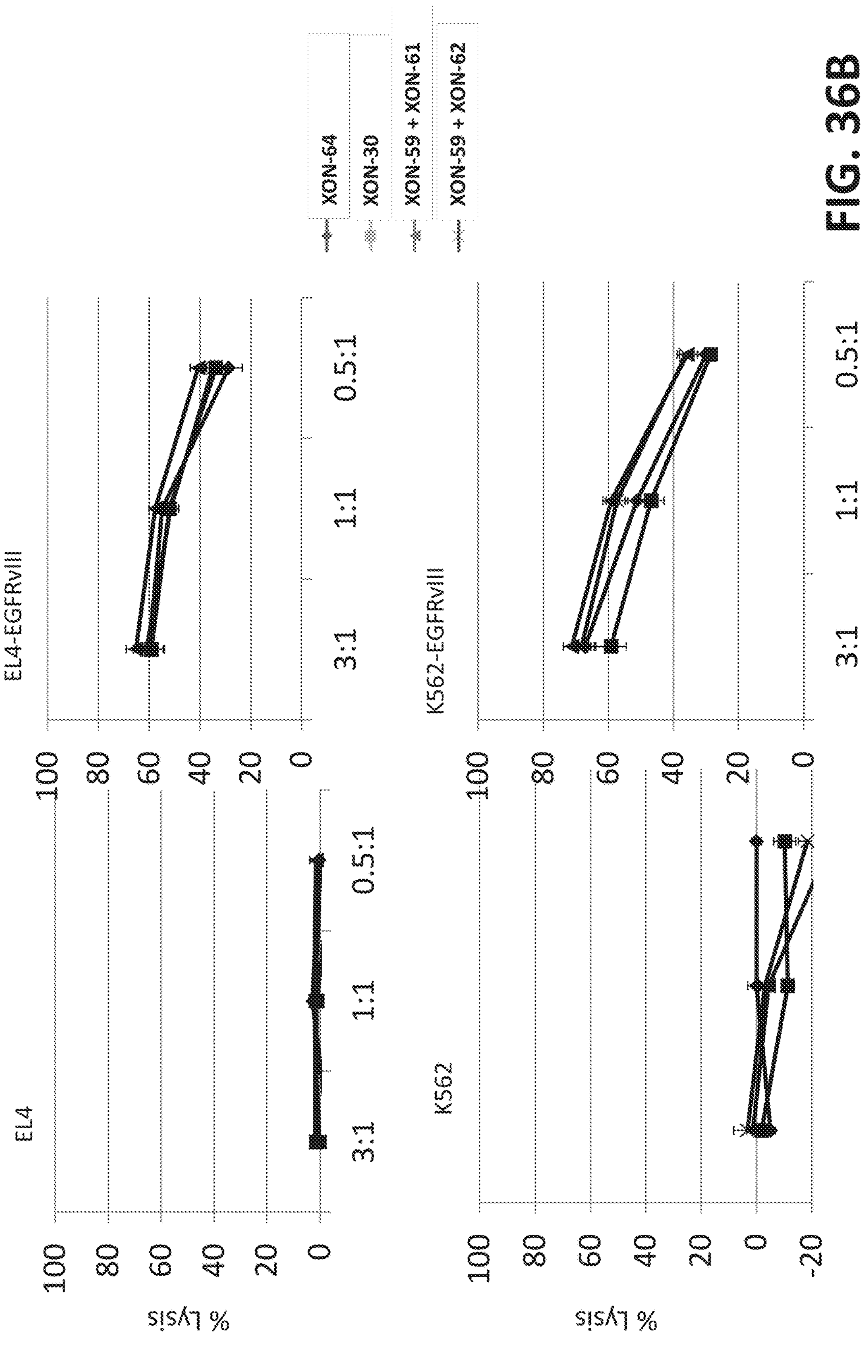

FIGS. 36A and 36B show specific cytotoxicity of CAR-T cells. FIG. 36A shows production of IFNγ by CAR-T cells generated via transfection of ligand-inducible gene switch vector system described herein. Effector CAR-T cells were co-cultured with U87MG, U87MG-FLuc-GFP, U87MG-EGFRvIII-FLuc-GFP, U251MG, U251MG-FLuc-GFP and U251MG-EGFRvIII-FLuc-GFP target cells at 1:1 effector: target cell ratio for 24 hours before analysis of IFNγ expression in culture supernatants. FIG. 36B shows % lysis of EGFRvIII expressing glioblastoma cells by CAR-T cells generated via transfection of ligand-inducible gene switch vector system described herein. Effector CAR-T cells were co-incubated with EL4, EL4 expressing EGFRvIII, K562 and K562 expressing EGFRvIII target cell lines at varying effector:target cell ratios.

DETAILED DESCRIPTION OF THE DISCLOSURE

The following description and examples illustrate embodiments of the present disclosure in detail. It is to be understood that this disclosure is not limited to the particular embodiments described herein and as such can vary. Those of skill in the art will recognize that there are numerous variations and modifications of this disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure may be described in the context of a single embodiment, the features may also be provided separately or in any suitable combination. Conversely, although the present disclosure may be described herein in the context of separate embodiments for clarity, the present disclosure may also be implemented in a single embodiment.

Definitions

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosure.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. In another example, the amount "about 10" includes 10 and any amounts from 9 to 11. In yet another example, the term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "isolated" and its grammatical equivalents as used herein refer to the removal of a nucleic acid from its natural environment. The term "purified" and its grammatical equivalents as used herein refer to a molecule or composition, whether removed from nature (including genomic DNA and mRNA) or synthesized (including cDNA) and/or amplified under laboratory conditions, that has been increased in purity, wherein "purity" is a relative term, not "absolute purity." It is to be understood, however, that nucleic acids and proteins may be formulated with diluents or adjuvants and still for practical purposes be isolated. For example, nucleic acids typically are mixed with an acceptable carrier or diluent when used for introduction into cells. The term "substantially purified" and its grammatical equivalents as used herein refer to a nucleic acid sequence, polypeptide, protein or other compound which is essentially free, i.e., is more than about 50% free of, more than about 70% free of, more than about 90% free of, the polynucleotides, proteins, polypeptides and other molecules that the nucleic acid, polypeptide, protein or other compound is naturally associated with.

"Polynucleotide" or "oligonucleotide" as used herein refers to a polymeric form of nucleotides or nucleic acids of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs.

"Polypeptide", "peptide", "protein" and their grammatical equivalents as used herein refers to a polymer of amino acid residues. A "mature protein" is a protein which is full-length and which, optionally, includes glycosylation or other modifications typical for the protein in a given cellular environment. Polypeptides and proteins disclosed herein (including functional portions and functional variants thereof) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbomane)-carboxylic acid, α,γ-diaminobutyric acid, α,β-diaminopropionic acid, homophenylalanine, and α-tert-butylglycine. The present disclosure further contemplates that expression of polypeptides described herein in an engineered cell can be associated with post-translational modifications of one or more amino acids of the polypeptide constructs. Non-limiting examples of post-translational modifications include phosphorylation, acylation including acetylation and formylation, glycosylation (including N-linked and O-linked), amidation, hydroxylation, alkylation including methylation and ethylation, ubiquitylation, addition of pyrrolidone carboxylic acid, formation of disulfide bridges, sulfation, myristoylation, palmitoylation, isoprenylation, farnesylation, geranylation, glypiation, lipoylation and iodination.

Nucleic acids and/or nucleic acid sequences are "homologous" when they are derived, naturally or artificially, from a common ancestral nucleic acid or nucleic acid sequence. Proteins and/or protein sequences are homologous when their encoding DNAs are derived, naturally or artificially, from a common ancestral nucleic acid or nucleic acid sequence. The homologous molecules can be termed homologs. For example, any naturally occurring proteins, as described herein, can be modified by any available mutagenesis method. When expressed, this mutagenized nucleic acid encodes a polypeptide that is homologous to the protein encoded by the original nucleic acid. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology. Methods for determining sequence identity percentages (e.g., BLASTP and BLASTN using default parameters) are described herein and are generally available.

The terms "identical" and its grammatical equivalents as used herein or "sequence identity" in the context of two nucleic acid sequences or amino acid sequences of polypeptides refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are aligned optimally. Methods of alignment of sequences for comparison are well-known in the art. Optimal alignment of sequences for comparison may be conducted by the local homology algorithm of Smith and Waterman, *Adv. Appl. Math.,* 2:482 (1981); by the alignment algorithm of Needleman and Wunsch, *J. Mol. Biol.,* 48:443 (1970); by the search for similarity method of Pearson and Lipman, *Proc. Nat. Acad. Sci U.S.A.,* 85:2444 (1988); by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.), the CLUSTAL program is well described by Higgins and Sharp, *Gene,* 73:237-244 (1988) and Higgins and Sharp, *CABIOS,* 5:151-153 (1989); Corpet et al., *Nucleic Acids Res.,* 16:10881-10890 (1988); Huang et al., *Computer Applications in the Biosciences,* 8:155-165 (1992); and Pearson et al., *Methods in Molecular Biology,* 24:307-331 (1994). Alignment is also often performed by inspection and manual alignment. In one class of embodiments, the polypeptides herein are at least 80%, 85%, 90%, 98% 99% or 100% identical to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or 100% identical to a reference nucleic acid or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, said percentage of residues in the smaller molecule finds a match residue in the larger molecule in accordance with the order by which the two molecules are optimally aligned.

The term "substantially identical" and its grammatical equivalents as applied to nucleic acid or amino acid sequences mean that a nucleic acid or amino acid sequence comprises a sequence that has at least 90% sequence identity or more, at least 95%, at least 98% and at least 99%, compared to a reference sequence using the programs described above, e.g., BLAST, using standard parameters. For example, the BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1992)). Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. In embodiments, the substantial identity exists over a region of the sequences that is at least about 50 residues in length, over a region of at least about 100 residues, and in embodiments, the sequences are substantially identical over at least about 150 residues. In embodiments, the sequences are substantially identical over the entire length of the coding regions.

"Transposon" or "transposable element" (TE) is a vector DNA sequence that can change its position within the genome, sometimes creating or reversing mutations and altering the cell's genome size. Transposition often results in duplication of the TE. Class I TEs are copied in two stages: first, they are transcribed from DNA to RNA, and the RNA produced is then reverse transcribed to DNA. This copied DNA is then inserted at a new position into the genome. The reverse transcription step is catalyzed by a reverse transcriptase, which may be encoded by the TE itself. The characteristics of retrotransposons are similar to retroviruses, such as HIV. The cut-and-paste transposition mechanism of class II TEs does not involve an RNA intermediate. The transpositions are catalyzed by several transposase enzymes. Some transposases non-specifically bind to any target site in DNA, whereas others bind to specific DNA sequence targets. The transposase makes a staggered cut at the target site resulting in single-strand 5' or 3' DNA overhangs (sticky ends). This step cuts out the DNA transposon, which is then ligated into a new target site; this process involves activity of a DNA polymerase that fills in gaps and of a DNA ligase that closes the sugar-phosphate backbone. This results in duplication of the target site. The insertion sites of DNA transposons may be identified by short direct repeats which may be created by the staggered cut in the target DNA and filling in by DNA polymerase, followed by a series of inverted repeats important for the TE excision by transposase. Cut-and-paste TEs may be duplicated if their transposition takes place during S phase of the cell cycle when a donor site has already been replicated, but a target site has not yet been replicated. Transposition can be classified as either "autonomous" or "non-autonomous" in both Class I and Class II TEs. Autonomous TEs can move by themselves while non-autonomous TEs require the presence of another TE to move. This is often because non-autonomous TEs lack transposase (for class II) or reverse transcriptase (for class I).

"Transposase" refers an enzyme that binds to the end of a transposon and catalyzes the movement of the transposon to another part of the genome by a cut and paste mechanism or a replicative transposition mechanism. In some embodiments, the transposase's catalytic activity can be utilized to move gene(s) from a vector to the genome. In some embodiments, the transposase's catalytic activity can be utilized to move gene(s) from a vector (e.g. a transposon) to the genome. In certain embodiments, the Sleeping Beauty transposase is provided as an mRNA. In some aspects, the mRNA comprises a cap and a poly-A tail.

The nucleic acid sequences and vectors disclosed or contemplated herein may be introduced into a cell by "transfection," "transformation," "nucleofection" or "transduction." "Transfection," "transformation," or "transduction," as used herein refers to the introduction of one or more exogenous polynucleotides into a host cell by using physical or chemical methods. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)); and nucleofection (Trompeter et al., J. Immunol. Methods 274:245-256 (2003). Phage or viral vectors can be introduced into host cells, after growth of infectious particles in suitable packaging cells, many of which are commercially available.

"Tumor antigen" as used herein refers to any antigenic substance produced or overexpressed in tumor cells. It may, for example, trigger an immune response in the host. Alternatively, for purposes of this disclosure, tumor antigens may be proteins that are expressed by both healthy and tumor cells but because they identify a certain tumor type, are a suitable therapeutic target. In embodiments, the tumor antigen is CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MAGE-A1, MUC16, h5T4, PSMA, TAG-72, EGFRvIII, CD123 or VEGF-R2. In one embodiment, the tumor antigen is EGFRvIII, which is a target for CAR T cell therapies for treating myeloid malignancies, for example, glioblastoma or glioblastoma multiforme (GBM). In another embodiment, the tumor antigen is CD19. In yet another embodiment, the tumor antigen is CD33.

The term "enhancer," as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), Fundamental Immunology, 3rd Edition, Raven Press, New York (1993), pages 353-363; and U.S. Pat. No. 5,885,827).

"Coding sequence" as used herein refers to a segment of a polynucleotide that codes for a polypeptide. The region or sequence is bounded nearer the 5' end by a start codon and nearer the 3' end with a stop codon. Coding sequences may also be referred to as open reading frames.

"Operably linked" as used herein refers to refers to the physical and/or functional linkage of a DNA segment to another DNA segment in such a way as to allow the segments to function in their intended manners. A DNA sequence encoding a gene product is operably linked to a regulatory sequence when it is linked to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence. Enhancers and silencers may be located upstream, downstream or embedded within the coding regions of the DNA sequence. A DNA for a signal sequence is operably linked to DNA coding for a polypeptide if the signal sequence is expressed as a preprotein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "induce", "induction" and its grammatical equivalents as used herein refer to an increase in nucleic acid sequence transcription, promoter activity and/or expression brought about by a transcriptional regulator, relative to some basal level of transcription.

A "target" gene or "heterologous" gene, or "gene of interest (GOI)" refers to a gene introduced into the host cell by gene transfer. Exemplary GOI can be an antigen binding polypeptide that can include an antigen binding polypeptide, chimeric receptor, CAR, TCR, a cytokine and/or a cell tag as described herein.

"Recombinase" as used herein refers to a group of enzymes that can facilitate site-specific recombination between defined sites, where the sites are physically separated on a single DNA molecule or where the sites reside on separate DNA molecules. The DNA sequences of the defined recombination sites are not necessarily identical. Initiation of recombination depends on protein-DNA interaction, within the group there are large number of proteins that catalyze phage integration and excision (e.g., λ integrase, ΦC31), resolution of circular plasmids (e.g., Tn3, gamma delta, Cre, Flp), DNA inversion for expression of alternate genes (e.g., Hin, Gin, Pin), assembly of genes during development (e.g., Anabaena nitrogen fixation genes), and transposition (e.g., IS607 transposon). Most site-specific recombinases fall into one of the two families, based on evolutionary and mechanistic relatedness. These are λ integrase family or tyrosine recombinases (e.g., Cre, Flp, Xer D) and resolvase/integrase family or serine recombinase family (e.g., ΦC31, TP901-1, Tn3, gamma delta).

"Recombination attachment sites" are specific polynucleotide sequences that are recognized by the recombinase enzymes described herein. Typically, two different sites are involved (termed "complementary sites"), one present in the target nucleic acid (e.g., a chromosome or episome of a eukaryote or prokaryote) and another on the nucleic acid that is to be integrated at the target recombination site. The terms "attB" and "attP," which refer to attachment (or recombination) sites originally from a bacterial target and a phage donor, respectively, are used herein although recombination sites for particular enzymes may have different names. The recombination sites typically include left and right arms separated by a core or spacer region. Thus, an attB recombination site consists of BOB', where B and B' are the left and right arms, respectively, and O is the core region. Similarly, attP is POP', where P and P' are the arms and O is again the core region. Upon recombination between the attB and attP sites, and concomitant integration of a nucleic acid at the target, the recombination sites that flank the integrated DNA are referred to as "attL" and "attR." The attL and attR sites, using the terminology above, thus consist of BOP' and POB', respectively. In some representations herein, the "O" is omitted and attB and attP, for example, are designated as BB' and PP', respectively.

Modulation of the Expression of Genes

In the field of genetic engineering, precise control of gene expression is a valuable tool for studying, manipulating, and controlling development and other physiological processes. Gene expression is a complex biological process involving a number of specific protein-protein interactions. Tightly regulated inducible gene expression systems or "gene switches" are useful for various applications such as gene therapy, large scale production of proteins in cells, cell based high throughput screening assays, functional genomics and regulation of traits in transgenic plants and animals. However, for therapy, regulated and localized expression is important to prevent off-target effects. Provided herein are means to regulate the expression of heterologous genes such as cytokines when required and at a specific vicinity of a target cell or location. Further provided herein is a method to regulate the expression of heterologous genes such as cytokines wherein the cytokine, for example, is under the control of a ligand inducible promoter. In some instances, the method results in a low or no basal level of heterologous gene expression in the absence of the ligand. In a further embodiment, the ligand inducible promoter is a gene switch ligand inducible promoter. Further provided herein are methods to regulate the expression of heterologous genes such as cytokines from an engineered cell. Herein an engineered cell is a cell which has been modified from its natural or endogenous state. An example of an engineered cell is a cell described herein which has been modified (e.g., by transfection of a polynucleotide into the cell). In some instances, the engineered cell can be an engineered immune effector cell. In one instance, the engineered cell is a T cell. In another instance, the engineered cell is a NK cell. In one instance, engineered cells are activated prior to inducing the expression of the heterologous gene with a ligand. In another instance, the engineered cells are activated by exposing the cells to an antigen. The antigen can be an antigen that is recognized by the antigen binding polypeptide expressed by the engineered cell. The antigen can be a tumor antigen or an infectious disease antigen. In one instance, the engineered cell can comprise an antigen binding polypeptide that binds such an antigen.

In a further instance, the gene switch components of a gene switch ligand inducible promoter can be further regulated by a tissue specific promoter. In such cases, the gene switch components are only expressed when the tissue specific promoter is activated, for example, in an activated T cell or an activated NK cell.

Vector

An "expression vector" or "vector" is any genetic element, e.g., a plasmid, chromosome, virus, transposon, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, transposons, bacteriophages and cosmids. Vectors may contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors may be capable of directly expressing nucleic acid sequence products encoded therein without ligation or integration of the vector into host cell DNA sequences.

Vector also can comprise a "selectable marker gene." The term "selectable marker gene," as used herein, refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., Proc. Natl. Acad. Sci. USA, 77: 3567 (1980); O'Hare et al., Proc. Natl. Acad. Sci. USA, 78: 1527 (1981); Mulligan & Berg, Proc. Natl. Acad. Sci. USA, 78: 2072 (1981); Colberre-Garapin et al., J. Mol. Biol., 150:1 (1981); Santerre et al., Gene, 30: 147 (1984); Kent et al., Science, 237: 901-903 (1987); Wigler et al., Cell, 11: 223 (1977); Szybalska & Szybalski, Proc. Natl. Acad. Sci. USA, 48: 2026 (1962); Lowy et al., Cell, 22: 817 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., Gene Therapy, 11:1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

As used herein, "a gene expression cassette" is part of a vector and can contain constitutive promoters such as EF1a or inducible promoters, 5' UTR, 3' UTR and polyA elements and one or more genes of interest (GOI). In one embodiment, the polyA element is SV40e polyA (SEQ ID NO 65). In another embodiment, the polyA element is bidirectional aCA polyA (SEQ ID NO 66). In yet another embodiment, the polyA is PA2 polyA (SEQ ID NO 67). In some aspects, a gene expression cassette may further comprise gene switch components such as a DNA-binding domain fused to a nuclear receptor ligand binding domain and/or a transactivation domain fused to a nuclear receptor ligand binding domain. A vector can include one or more gene expression cassette(s).

Vector Modifications

A polynucleotide vector useful for the methods and compositions described herein can be a good manufacturing practices (GMP) compatible vector. For example, a GMP vector may be purer than a non-GMP vector. In some cases, purity can be measured by bioburden. For example, bioburden can be the presence or absence of aerobes, anaerobes, sporeformers, fungi, or combinations thereof in a vector composition. In some cases, a pure vector can be endotoxin low or endotoxin free. Purity can also be measured by double-stranded primer-walking sequencing. Plasmid identity can be a source of determining purity of a vector. A GMP vector of the present disclosure can be from 10% to 99% more pure than a non-GMP vector. A GMP vector can be from 10%, 15%, 20%, 25%, 300, 35%, 40%, 45%, 50%, 55%, 60%, 65%, 70%, 75%, 80%, 85%, 90%, 95%, 96%, 97%, 98%, or 99% more pure than a non-GMP vector as measured by the presence of bioburden, endotoxin, sequencing, or combinations thereof.

In some cases, a terminator sequence at the end of the first gene program is used. A terminator sequence can ensure that a transcript is terminating prior to initiating a second gene program. For example, an expression vectors may contain sequences necessary for the termination of transcription and for stabilizing an mRNA. Such sequences are commonly available from the 5' and, occasionally 3', untranslated regions of eukaryotic or viral DNAs or cDNAs. These regions can contain nucleotide segments transcribed as polyadenylated fragments in the untranslated portion of the mRNA. Cells comprising the expression vector are grown under conditions that provide for expression of the desired polypeptide, either in vivo or in vitro.

In some cases, a spacer sequence can be used at the end of a first polypeptide encoded by a polynucleotide in a vector. In other cases, a spacer sequence can be used at the end of a second gene in a vector. A spacer sequence can also be used following a first gene and a second gene in a vector.

These vectors can be used to express a polypeptide encoded by a gene, or portion of a gene of interest. A gene of portion or a gene can be inserted by using any method, viral or non-viral. For example, a method can be a non-viral based technique.

IRES Elements

Also disclosed herein are constructs that comprise an IRES element to facilitate the expression and functionality of the polynucleotides and polypeptides described herein. The term "internal ribosome entry site (IRES)" as used herein can be intended to mean internal ribosomal entry site. In a vector comprising an IRES sequence, a first gene can be translated by a cap-dependent, ribosome scanning, mechanism with its own 5'-UTR, whereas translation of a subsequent gene can be accomplished by direct recruitment of a ribosome to an IRES in a cap-independent manner. An IRES sequence can allow eukaryotic ribosomes to bind and begin translation without binding to a 5' capped end. An IRES sequence can allow expression of multiple genes from one transcript (Mountford and Smith 1995).

The term "CAP" or "cap" as used herein refers to a modified nucleotide, generally a 7-methyl guanosine, linked 3' to 5' (7meG-ppp-G), to the 5' end of a eukaryotic mRNA, that serves as a required element in the normal translation initiation pathway during expression of protein from that mRNA.

In certain cases, an IRES region can be derived from a virus, such as picornavirus, encephalomyocarditis virus, hepatitis C virus IRES sequence. In other cases, an IRES sequence can be derived from an encephalomyocarditis virus. The term "EMCV" or "encephalomyocarditis virus" as used herein refers to any member isolate or strain of the encephalomyocarditis virus species of the genus of the family Picornaviridae. Examples are: EMCV-R (Rueckert) strain virus, Columbia-SK virus. In some cases, a cellular IRES element, such as eukaryotic initiation factor 4G, immunoglobulin heavy chain binding protein, c-myc proto-oncogene, vascular endothelial growth factor, fibroblast growth factor-1 IRES, or any combination or modification thereof can be used. In some cases, a cellular IRES can have increased gene expression when compared to a viral IRES.

An IRES sequence of viral, cellular or a combination thereof can be utilized in a vector. An IRES can be from encephalomyocarditis (EMCV) or poliovirus (PV). In some cases, an IRES element is selected from a group consisting of Poliovirus (PV), Encephalomyelitis virus (EMCV), Foot-and-mouth disease virus (FMDV), Porcine teschovirus-1 (PTV-1), Aichivirus (AiV), Seneca Valley virus (SVV), Hepatitis C virus (HCV), Classical swine fever virus (CSFV), Human immunodeficiency virus-2 (HIV-2), Human immunodeficiency virus-1 (HIV-1), Moloney murine leukemia virus (MoMLV), Feline immunodeficiency virus (FIV), Mouse mammary tumor virus (MMTV), Human cytomegalovirus latency (pUL138), Epstein-Barr virus (EBNA-1), Herpes virus Marek's disease (MDV RLORF9), SV40 polycistronic 19S (SV40 19S), Rhopalosiphum padi virus (RhPV), Cricket paralysis virus (CrPV), Ectropis obliqua picorna-like virus (EoPV), Plautia stali intestine virus (PSIV), Triatoma virus (TrV), Bee paralysis dicistrovirus (IAPV, KBV), Black currant reversion virus (BRV), Pelargonium flower break virus (PFBV), Hibiscus chlorotic ringspot virus (HCRSV), Crucifer-infecting tobamovirus (CrTMV), Potato leaf roll polerovirus (PLRV), Tobacco etch virus (TEV), Giardiavirus (GLV), Leishmania RNA virus-1 (LRV-1), and combinations or modifications thereof. In some cases, an IRES is selected from a group consisting of Apaf-1, XIAP, HIAP2/c-IAP1, DAP5, Bcl-2, c-myc, CAT-1, INR, Differentiation LEF-1, PDGF2, HIF-1a, VEGF, FGF2, BiP, BAG-1, CIRP, p53, SHMT1, PITSLREp58, CDK1, Rpr, hid, hsp70, grim, skl, Antennapedia, dFoxO, dInR, Adh-Adhr, HSP101, ADH, URE-2, GPR1, NCE102, YMR181a, MSN1, BOI1, FLO8, GIC1, and any combination or modification thereof. When an IRES element is included between two open reading frames (ORFs), initiation of translation can occur by a canonical 5'-m7GpppN cap-dependent mechanism in a first ORF and a cap-independent mechanism in a second ORF downstream of the IRES element.

In some cases, genes can be linked by an internal ribosomal entry site (IRES). An IRES can allow simultaneous expression of multiple genes. For example, an IRES sequence can permit production of multiple proteins from a single mRNA transcript. A ribosome can bind to an IRES in a 5'-cap independent manner and initiate translation.

In some cases, an IRES sequence can be or can be about 500 base pairs. An IRES sequence can be from 300 base pairs to 1000 base pairs. For example, an IRES can be 300, 350, 400, 450, 500, 550, 600, 650, 700, 750, 800, 850, 900, 950, or 1000 base pairs long.

In some cases, expression of a downstream gene within a vector comprising an IRES sequence can be reduced. For example, a gene following an IRES sequence can have reduced expression over a gene preceding an IRES sequence. Reduced expression can be from 1% to 99% reduction over a preceding gene.

In certain embodiments, an IRES is an EMCV IRES comprising a nucleotide sequence having at least 70%, 75%, 80%, 85%, 90%, 95%, 99%, 99.5% or 100% identity with the nucleotide sequence of SEQ ID NO 18.

Linkers

Also disclosed are constructs that comprise a linker to facilitate the expression and functionality of the polynucleotides and polypeptides described herein. In some embodiments, a polynucleotide linker can be utilized in a polynucleotide described herein. A polynucleotide linker can be a double-stranded segment of DNA containing desired restriction sites that may be added to create end structures that are compatible with a vector comprising a polynucleotide described herein. In some cases, a polynucleotide linker can be useful for modifying vectors comprising polynucleotides described herein. For example, a vector modification comprising a polynucleotide linker can be a change in a multiple cloning site, or the addition of a poly-histidine tail. Polynucleotide linkers can also be used to adapt the ends of blunt insert DNA for cloning into a vector cleaved with a restriction enzyme with cohesive end termini. The use of polynucleotide linkers can be more efficient than a blunt ligation into a vector and can provide a method of releasing an insert from a vector in downstream applications. In some cases an insert can be a polynucleotide sequence encoding polypeptides useful for therapeutic applications. In some cases, a linker can be a cleavable linker.

A polynucleotide linker can be an oligomer. A polynucleotide linker can be a DNA double strand, single strand, or a combination thereof. In some cases, a linker can be RNA. A polynucleotide linker can be ligated into a vector comprising a polynucleotide described herein by a T4 ligase in some cases. To facilitate a ligation an excess of polynucleotide linkers can be added to a composition comprising an insert and a vector. In some cases, an insert and vector are pre-treated before a linker is introduced. For example, pre-treatment with a methylase can prevent unwanted cleavage of insert DNA.

In certain embodiments, two or more polypeptides encoded by a polynucleotide described herein can be separated by an intervening sequence encoding an intervening linker polypeptide. Herein the term "intervening linker polypeptide" referring to an amino acid sequence separating two or more polypeptides encoded by a polynucleotide is distinguished from the term "peptide linker" which refers to the sequence of amino acids which is optionally included in a polypeptide construct disclosed herein to connect the transmembrane domain to the cell surface polypeptide (e.g., comprising a truncated variant of a natural polypeptide). In certain cases, the intervening linker is a cleavage-susceptible intervening linker polypeptide. In some embodiments, the linker is a cleavable or ribosome skipping linker. In some embodiments, the cleavable linker or ribosome skipping linker sequence is selected from the group consisting of 2A, GSG-2A, GSG linker, SGSG linker, furinlink variants and derivatives thereof. In some embodiments, the 2A linker is a p2A linker, a T2A linker, F2A linker or E2A linker. In some embodiments, polypeptides of interest are expressed as fusion proteins linked by a cleavage-susceptible intervening linker polypeptide. In certain embodiments, cleavage-susceptible intervening linker polypeptide(s) can be any one or more of: F/T2A, T2A, p2A, 2A, GSG-p2A, GSG linker, and furinlink variants. In certain embodiments, the linker polypeptide comprises disclosed in the table below:

TABLE 1

Linker amino acid sequences and polynucleotide sequences

| Linker Name | SEQ ID NO | Polynucleotide Sequence (5' to 3' where applicable) | SEQ ID NO | Amino Acids Sequence (5' to 3' where applicable) |
|---|---|---|---|---|
| Whitlow Linker | 1 | GGCAGCACCTCCGGCAGCG GCAAGCCTGGCAGCGGCGA GGGCAGCACCAAGGGC | 146 | GSTSGSGKPGSGEGSTKG |
| Linker | 2 | TCTGGCGGAGGATCTGGAG GAGGCGGATCTGGAGGAGG AGGCAGTGGAGGCGGAGGA TCTGGCGGAGGATCTCTGC AG | 147 | SGGGSGGGGSGGGGSGGG GSGGGSLQ |
| GSG linker | 3 | GGAAGCGGA | 148 | GSG |
| SGSG linker | 4 | AGTGGCAGCGGC | 149 | SGSG |
| (G4S)3 linker | 5 | GGTGGCGGTGGCTCGGGCG GTGGTGGGTCGGGTGGCGG CGGATCT | 150 | GGGGSGGGGSGGGGS |
| Furin cleavage site/Furinlink1 | 6 | CGTGCAAAGCGT | 151 | RAKR |
| Fmdv | 7 | AGAGCCAAGAGGGCACCGG TGAAACAGACTTTGAATTTT GACCTTCTGAAGTTGGCAG GAGACGTTGAGTCCAACCC TGGGCCC | 152 | RAKRAPVKQTLNFDLLKL AGDVESNPGP |

TABLE 1-continued

| Linker amino acid sequences and polynucleotide sequences | | | | |
|---|---|---|---|---|
| Linker Name | SEQ ID NO | Polynucleotide Sequence (5' to 3' where applicable) | SEQ ID NO | Amino Acids Sequence (5' to 3' where applicable) |
| Thosea asigna virus 2A region (T2A) | 8 | GAGGGCAGAGGAAGTCTGC TAACATGCGGTGACGTCGA GGAGAATCCTGGACCT | 153 | EGRGSLLTCGDVEENPGP |
| Furin-GSG-T2A | 9 | AGAGCTAAGAGGGGAAGCG GAGAGGGCAGAGGAAGTCT GCTAACATGCGGTGACGTC GAGGAGAATCCTGGACCT | 154 | RAKRGSGEGRGSLLTCGD VEENPGP |
| Furin-SGSG-T2A | 10 | AGGGCCAAGAGGAGTGGCA GCGGCGAGGGCAGAGGAA GTCTTCTAACATGCGGTGAC GTGGAGGAGAATCCCGGCC CT | 155 | RAKRSGSGEGRGSLLTCGD VEENPGP |
| Porcine teschovirus-1 2A region (P2A) | 11 | GCAACGAACTTCTCTCTCCT AAAACAGGCTGGTGATCATG GAGGAGAATCCTGGTCCA | 156 | ATNFSLLKQAGDVEENPGP |
| GSG-P2A | 12 | GGAAGCGGAGCTACTAACT TCAGCCTGCTGAAGCAGGC TGGAGACGTGGAGGAGAAC CCTGGACCT | 157 | GSGATNFSLLKQAGDVEE NPGP |
| Equine rhinitis A virus 2A region (E2A) | 13 | CAGTGTACTAATTATGCTCT CTTGAAATTGGCTGGAGAT GTTGAGAGCAACCCTGGAC CT | 158 | QCTNYALLKLAGDVESNP GP |
| Foot-and-mouth disease virus 2A region (F2A) | 14 | GTCAAACAGACCCTAAACT TTGATCTGCTAAAACTGGCC GGGGATGTGGAAAGTAATC CCGGCCCC | 159 | VKQTLNFDLLKLAGDVES NPGP |
| FP2A | 15 | CGTGCAAAGCGTGCACCGG TGAAACAGGGAAGCGGAGC TACTAACTTCAGCCTGCTGA AGCAGGCTGGAGACGTGGA GGAGAACCCTGGACCT | 160 | RAKRAPVKQGSGATNFSLL KQAGDVEENPGP |
| linker-GSG | 16 | GCACCGGTGAAACAGGGAA GCGGA | 161 | APVKQGSG |
| Linker | 17 | GCACCGGTGAAACAG | 162 | APVKQ |

In some embodiments, an intervening linker polypeptide comprises an amino acid sequence having at least 70%, 75%, 80%, 85%, 90%, 95%, 99%, 99.5% or 100% identity with the amino acid sequence of Whitlow linker (SEQ ID NO 146), GSG linker (SEQ ID NO 148), SGSG linker (SEQ ID NO 149), (G4S)3 linker (SEQ ID NO 150), Furin cleavage site/Furlink1 (SEQ ID NO 151), Fmdv linker (SEQ ID NO 152), *Thosea asigna* virus 2A region (T2A) (SEQ ID NO 153), Furin-GSG-T2A (SEQ ID NO 154), Furin-SGSG-T2A (SEQ ID NO 155), porcine teschovirus-1 2A region (P2A) (SEQ ID NO 156), GSG-P2A (SEQ ID NO 157), equine rhinitis A virus 2A region (E2A) (SEQ ID NO 158), or foot-and-mouth disease virus 2A region (F2A) (SEQ ID NO: 159). In some cases, an intervening linker polypeptide comprises an amino acid sequence having at least 70%, 75%, 80%, 85%, 90%, 95%, 99%, 99.5% or 100% identity with the amino acid sequence of linkers (SEQ ID NOS 147, 161 or 162) In some cases, a viral 2A sequence can be used. 2A elements can be shorter than IRES, having from 5 to 100 base pairs. In some cases, a 2A sequence can have 5, 10, 15, 20, 25, 30, 35, 40, 45, 50, 55, 60, 65, 70, 75, 80, 85, 90, or 100 nucleotides in length. 2A linked genes can be expressed in one single open reading frame and "self-cleavage" can occur co-translationally between the last two amino acids, GP, at the C-terminus of the 2A polypeptide, giving rise to equal amounts of co-expressed proteins.

A viral 2A sequence can be about 20 amino acids. In some cases, a viral 2A sequence can contain a consensus motif Asp-Val/Ile-Glu-X-Asn-Pro-Gly-Pro. A consensus motif sequence can act co-translationally. For example, formation of a normal peptide bond between a glycine and proline residue can be prevented, which can result in ribosomal skipping and cleavage of a nascent polypeptide. This effect can produce multiple genes at equimolar levels.

A 2A peptide can allow translation of multiple proteins in a single open reading frame into a polypeptide that can be subsequently cleaved into individual polypeptide through a ribosome-skipping mechanism (Funston, Kallioinen et al. 2008). In some embodiments, a 2A sequence can include: F/T2A, T2A, p2A, 2A, T2A, E2A, F2A, and BmCPV2A, BmIFV2A, and any combination thereof.

In some cases, a vector can comprise an IRES sequence and a 2A linker sequence. In other cases, expression of multiple genes linked with 2A peptides can be facilitated by a spacer sequence (GSG) ahead of the 2A peptides. In some cases, constructs can combine a spacers, linkers, adaptors, promotors, or combinations thereof. For example, a linker can have a spacer (SGSG or GSG or Whitlow linker) and furin linker (R-A-K-R) cleavage site with different 2A peptides. A spacer can be an I-Ceui. In some cases, a linker can be engineered. For example, a linker can be designed to comprise chemical characteristics such as hydrophobicity. In some cases, at least two linker sequences can produce the same protein. In other cases, multiple linkers can be used in a vector. For example, genes of interest can be separated by at least two linkers, as shown in FIG. 2 and FIG. 3.

In certain embodiments, two or more polypeptides encoded by a polynucleotide described herein can be separated by an intervening sequence encoding a linker polypeptide. In certain cases, the linker is a cleavage-susceptible linker. In some embodiments, polypeptides of interest are expressed as fusion proteins linked by a cleavage-susceptible linker polypeptide. In certain embodiments, cleavage-susceptible linker polypeptide(s) can be any one or two of: Furinlink, fmdv, p2a, GSG-p2a, and/or fp2a described below. In some cases, a linker is APVKQGSG (SEQ ID NO 161).

In certain cases, a linker polypeptide can comprise an amino acid sequence "RAKR" (SEQ ID NO 151). In certain cases, a Furin linker polypeptide can be encoded by a polynucleotide sequence polynucleotide sequence comprising "CGTGCAAAGCGT" (SEQ ID NO 6) or "AGAGCTAAGAGG." (SEQ ID NO 9).

In some embodiments, a linker can be utilized in a polynucleotide described herein. A linker can be a flexible linker, a rigid linker, an in vivo cleavable linker, or any combination thereof. In some cases, a linker may link functional domains together (as in flexible and rigid linkers) or releasing free functional domain in vivo as in in vivo cleavable linkers.

Linkers may improve biological activity, increase expression yield, and achieving desirable pharmacokinetic profiles. A linker can also comprise hydrazone, peptide, disulfide, or thioesther.

In some cases, a linker sequence described herein can include a flexible linker. Flexible linkers can be applied when a joined domain requires a certain degree of movement or interaction. Flexible linkers can be composed of small, non-polar (e.g., Gly) or polar (e.g., Ser or Thr) amino acids. A flexible linker can have sequences consisting primarily of stretches of Gly and Ser residues ("GS" linker). An example of a flexible linker can have the sequence of (Gly-Gly-Gly-Gly-Ser)n (SEQ ID NO 150). By adjusting the copy number "n", the length of this exemplary GS linker can be optimized to achieve appropriate separation of functional domains, or to maintain necessary inter-domain interactions. Besides GS linkers, other flexible linkers can be utilized for recombinant fusion proteins. In some cases, flexible linkers can also be rich in small or polar amino acids such as Gly and Ser, but can contain additional amino acids such as Thr and Ala to maintain flexibility. In other cases, polar amino acids such as Lys and Glu can be used to improve solubility.

Flexible linkers included in linker sequences described herein, can be rich in small or polar amino acids such as Gly and Ser to provide good flexibility and solubility. Flexible linkers can be suitable choices when certain movements or interactions are desired for fusion protein domains. In addition, although flexible linkers may not have rigid structures, they can serve as a passive linker to keep a distance between functional domains. The length of flexible linkers can be adjusted to allow for proper folding or to achieve optimal biological activity of the fusion proteins.

A linker described herein can further include a rigid linker in some cases. A rigid linker may be utilized to maintain a fixed distance between domains of a polypeptide. Examples of rigid linkers can be: Alpha helix-forming linkers, Pro-rich sequence, (XP)n, X-Pro backbone, A(EAAAK)nA (n=2-5), to name a few. Rigid linkers can exhibit relatively stiff structures by adopting α-helical structures or by containing multiple Pro residues in some cases.

A linker described herein can be cleavable in some cases. In other cases a linker is not cleavable. Linkers that are not cleavable may covalently join functional domains together to act as one molecule throughout an in vivo processes or an ex vivo process. A linker can also be cleavable in vivo. A cleavable linker can be introduced to release free functional domains in vivo. A cleavable linker can be cleaved by the presence of reducing reagents, proteases, to name a few. For example, a reduction of a disulfide bond may be utilized to produce a cleavable linker. In the case of a disulfide linker, a cleavage event through disulfide exchange with a thiol, such as glutathione, could produce a cleavage. In other cases, an in vivo cleavage of a linker in a recombinant fusion protein may also be carried out by proteases that can be expressed in vivo under pathological conditions (e.g. cancer or inflammation), in specific cells or tissues, or constrained within certain cellular compartments. In some cases, a cleavable linker may allow for targeted cleavage. For example, the specificity of many proteases can offer slower cleavage of a linker in constrained compartments. A cleavable linker can also comprise hydrazone, peptides, disulfide, or thioesther. For example, a hydrazone can confer serum stability. In other cases, a hydrazone can allow for cleavage in an acidic compartment. An acidic compartment can have a pH up to 7. A linker can also include a thioether. A thioether can be nonreducible A thioether can be designed for intracellular proteolytic degradation.

In certain embodiments, an fmdv linker polypeptide comprises a sequence that can be at least about 45%, 50%, 55%, 60%, 65%, 70%, 75%, 80%, 85%, 90%, 95%, 97%, 98%, 99% or 100% identical to SEQ ID NO 152. In certain embodiments, an fmdv linker polypeptide is one or more of the linkers encoded in a single vector linking two or more fusion proteins. In certain cases, an fmdv linker polypeptide can be encoded by a polynucleotide open reading frame (ORF) nucleic acid sequence. In some cases, an ORF encoding fmdv comprises or consists of a sequence of SEQ ID NO 7). In certain embodiments, a polynucleotide encoding fmdv is at least 45%, 50%, 55%, 60%, 65%, 70%, 75%, 80%, 85%, 90%, 95%, 97%, 98%, 99% or 100% identical to SEQ ID NO 7).

In certain cases, a linker polypeptide can be a "p2a" linker. In certain embodiments, a p2a polypeptide can comprise a sequence that can be about at least 45%, 50%, 55%, 60%, 65%, 70%, 75%, 80%, 85%, 90%, 95%, 97%, 98%, 99% or 100% identical to SEQ ID NO 156). In certain embodiments, the p2a linker polypeptide can be one or more of the linkers encoded in a single vector linking two or more fusion proteins. In some cases, a p2a linker polypeptide can be encoded by a polynucleotide open reading frame (ORF) nucleic acid sequence. In certain embodiments, an ORF encoding p2a comprises or consists of the sequence of SEQ ID NO 11). In certain cases, a polynucleotide encoding p2a can be or can be about at least 45%, 50%, 55%, 60%, 65%, 70%, 75%, 80%, 85%, 90%, 95%, 97%, 98%, 99% or 100% identical to SEQ ID NO 11).

In some cases, a linker polypeptide can be a "GSG-p2a" linker. In certain embodiments, a GSG-p2a linker polypeptide can comprise a sequence that can be about at least 45%, 50%, 55%, 60%, 65%, 70%, 75%, 80%, 85%, 90%, 95%, 97%, 98%, 99% or 100% identical to SEQ ID NO 157). In certain embodiments, a GSG-p2a linker polypeptide can be one or more of the linkers encoded in a single vector linking two or more fusion proteins. In some cases, a GSG-p2a linker polypeptide can be encoded by a polynucleotide open-reading frame (ORF) nucleic acid sequence. An ORF encoding GSG p2a can comprise the sequence of SEQ ID NO 12). In some cases, a polynucleotide encoding GSG-p2a can be or can be about at least 45%, 50%, 55%, 60%, 65%, 70%, 75%, 80%, 85%, 90%, 95%, 97%, 98%, 99% or 100% identical to SEQ ID NO 12).

A linker polypeptide can be an "fp2a" linker as provided herein. In certain embodiments, a fp2a linker polypeptide can comprise a sequence that can be about at least 45%, 50%, 55%, 60%, 65%, 70%, 75%, 80%, 85%, 90%, 95%, 97%, 98%, 99% or 100% identical to SEQ ID NO 160). In certain cases, an fp2a linker polypeptide can be one or more of the linkers encoded in a single vector linking two or more fusion proteins. In some cases, a fp2a linker polypeptide can be encoded by a polynucleotide open reading frame (ORF) nucleic acid sequence. In certain embodiments, a polynucleotide encoding an fp2a linker can be or can be about at least 45%, 50%, 55%, 60%, 65%, 70%, 75%, 80%, 85%, 90%, 95%, 97%, 98%, 99% or 100% identical to SEQ ID NO 15).

In some cases, a linker can be engineered. For example, a linker can be designed to comprise chemical characteristics such as hydrophobicity. In some cases, at least two linker sequences can produce the same protein. A sequence can be or can be about 45%, 50%, 55%, 60%, 65%, 70%, 75%, 80%, 85%, 90%, 95%, 96%, 97%, 98%, 99%, or 100% identical to a polypeptide sequence of SEQ ID NOS 147, 161 or 162. In other cases, multiple linkers can be used in a vector. For example, genes of interest, and one or more gene switch polypeptide sequences described herein can be separated by at least two linkers, as shown in FIG. 15 and FIG. 16. In some cases, genes can be separated by 2, 3, 4, 5, 6, 7, 8, 9, or up to 10 linkers.

A linker can be an engineered linker. Methods of designing linkers can be computational. In some cases, computational methods can include graphic techniques. Computation methods can be used to search for suitable peptides from libraries of three-dimensional peptide structures derived from databases. For example, a Brookhaven Protein Data Bank (PDB) can be used to span the distance in space between selected amino acids of a linker.

In some embodiments are polynucleotides encoding a polypeptide construct comprising a furin polypeptide and a 2A polypeptide, wherein the furin polypeptide and the 2A polypeptide are connected by a polypeptide linker comprising at least three hydrophobic amino acids. In some cases, at least three hydrophobic amino acids are selected from the list consisting of glycine (Gly)(G), alanine (Ala)(A), valine (Val)(V), leucine (Leu)(L), isoleucine (Ile)(I), proline (Pro) (P), phenylalanine (Phe)(F), methionine (Met)(M), tryptophan (Trp)(W). In some cases, a polypeptide linker may also include one or more GS linker sequences, for instance (GS)n, (SG)n, (GSG)n (SEQ ID NO: 78) and (SGSG)n (SEQ ID NO: 79) wherein n can be any number from zero to fifteen.

Provided are methods of obtaining an improved expression of a polypeptide construct comprising: providing a polynucleotide encoding said polypeptide construct comprising a first functional polypeptide and a second functional polypeptide, wherein said first functional polypeptide and second functional polypeptide are connected by a linker polypeptide comprising a sequence with at least 60% identity to the sequence APVKQ (SEQ ID NO 162); and expressing said polynucleotide in a host cell, wherein said expressing results in an improved expression of the polypeptide construct as compared to a corresponding polypeptide construct that does not have a linker polypeptide comprising a sequence with at least 60% identity to the sequence APVKQ.

Promoters

"Promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter. Yet other promoters are tissue specific or activated promoters, including but not limited to T-cell specific promoters.

The term "promoter activity" and its grammatical equivalents as used herein refer to the extent of expression of nucleotide sequence that is operably linked to the promoter whose activity is being measured. Promoter activity may be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Examples of inducible promoters are alcohol-regulated promoters, tetracycline-regulated promoters, steroid-regulated promoters, metal-regulated promoters, pathogenesis-regulated promoters, temperature-regulated promoters and light-regulated promoters. In one embodiment, the inducible promoter is part of a genetic switch. The inducible promoter can be a gene switch ligand inducible promoter. In some cases, an inducible promoter can be a small molecule ligand-inducible two polypeptide ecdysone receptor-based gene switch, such as RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/1J52002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/US2002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497,093; PCT/US2005/015089 (WO 2005/108617); U.S. Pat. Nos. 7,935,510; 8,076,454; PCT/US2008/011270 (WO 2009/045370); U.S. application Ser. No. 12/241,018 (U.S. Pub. No. 20090136465); PCT/US2008/011563 (WO 2009/

048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); and, U.S. Pat. No. 9,402,919 each of which is incorporated by reference in its entirety).

Provided herein are methods comprising administering to a subject at least one non-viral vector comprising a polynucleotide encoding a polypeptide sequence described herein comprising at least two functional proteins or portions thereof; at least one promotor; and at least one engineered recombination site; wherein said at least one promoter drives expression of said at least two functional proteins. In some cases, at least one promotor can be constitutive. In some cases, at least one promoter can be tissue-specific. In some cases, at least one promoter can be inducible. In some cases, an inducible promoter is a small molecule ligand-inducible two polypeptide ecdysone receptor-based gene switch. In other cases, a combination of promoters wherein at least one promoter can be inducible and at least one promoter can be activation specific can be utilized.

An inducible promoter utilizes a ligand for dose-regulated control of expression of said at least two genes. In some cases, a ligand can be selected from a group consisting of ecdysteroid, 9-cis-retinoic acid, synthetic analogs of retinoic acid, N,N'-diacylhydrazines, oxadiazolines, dibenzoylalkyl cyanohydrazines, N-alkyl-N,N'-diaroylhydrazines, N-acyl-N-alkylcarbonylhydrazines, N-aroyl-N-alkyl-N'-aroylhydrazines, arnidoketones, 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, framesol, bile acids, 1,1-biphosphonate esters, juvenile hormone III, RG-115819 (3,5-Dimethyl-benzoic acid N-(1-ethyl-2,2-dimethyl-propyl)-N'-(2-methyl-3-methoxy-benzoyl)-hydrazide-), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide), and any combination thereof.

In some embodiments, a promoter is an inducible promoter. In some embodiments, a promoter is a non-inducible promoter. In some cases, a promoter can be a tissue-specific promoter. Herein "tissue-specific" refers to regulated expression of a gene in a subset of tissues or cell types. In some cases, a tissue-specific promoter can be regulated spatially such that the promoter drives expression only in certain tissues or cell types of an organism. In other cases, a tissue-specific promoter can be regulated temporally such that the promoter drives expression in a cell type or tissue differently across time, including during development of an organism. In some cases, a tissue-specific promoter is regulated both spatially and temporally. In certain embodiments, a tissue-specific promoter is activated in certain cell types either constitutively or intermittently at particular times or stages of the cell type. For example, a tissue-specific promoter can be a promoter that is activated when a specific cell such as a T cell or a NK cell is activated. T cells can be activated in a variety of ways, for example, when presented with peptide antigens by MHC class II molecules or when an engineered T cells comprising an antigen binding polypeptide engages with an antigen. In one instance, such an engineered T cell or NK cell expresses a chimeric antigen receptor (CAR) or T-cell receptor (TCR).

In one case, at least one promoter is an engineered promoter or variants thereof. As described herein, the promoter can incorporate minimal promoter sequences from IL-2 and one or more of the following: nuclear factor of activated T-cells (NFAT) response element(s) such as SEQ ID NO 51; NFIL2D response element, NFkB/TCF response element, NF_AT/NFIL2B response element or NFIL2A/OCT response element. Examples of response elements are described in Mattila et al., EMBO J. 1990 December; 9(13): 4425-4433; incorporated herein in its entirety.

In some embodiments, at least one promoter comprises IL-2 core promoter (SEQ ID NO 40). In one embodiment, at least one promoter comprises IL-2 minimal promoter (SEQ ID NO 41). In another embodiment, at least one promoter comprises IL-2 enhancer and promoter variant (SEQ ID NOS 42-43). In yet another embodiment, at least one promoter comprises NF-κB binding site (SEQ ID NOS 44-46). In some embodiments, at least one promoter comprises $(NF\text{-}\kappa B)_1$-IL2 promoter variant (SEQ ID NO 47). In some embodiments, at least one promoter comprises $(NF\text{-}\kappa B)_3$-IL2 promoter variant (SEQ ID NO 48). In some embodiments, at least one promoter comprises $(NF\text{-}\kappa B)_6$-IL2 promoter variant (SEQ ID NO 49). In one embodiments, at least one promoter comprises 1×NFAT response elements-IL2 promoter variant (SEQ ID NO 50). In another embodiments, at least one promoter comprises nuclear factor of activated T-cells (NFAT) response element (SEQ ID NO 51). In yet another embodiment, at least one promoter comprises 6×NFAT response elements-IL2 promoter variant (SEQ ID NOS 52-55). In yet another embodiment, at least one promoter comprises 3×NFAT response elements-IL2 promoter variant (SEQ ID NOS 56-57). In some embodiments, at least one promoter comprises human EF1A1 promoter variant (SEQ ID NOS 58-59). In some embodiment, at least one promoter comprises human EF1A1 promoter and enhancer (SEQ ID NO 60). In some embodiments, at least one promoter comprises human UBC promoter (SEQ ID NO 61). In some embodiments, at least one promoter comprises 6 site GAL4-inducible proximal factor binding element (PFB) (SEQ ID NO 62). In some embodiment, at least one promoter comprises synthetic minimal promoter 1 (inducible promoter) (SEQ ID NO 63). Human IL-2 gene and 5' flanking region comprises a nucleotide sequence of SEQ ID NO 95.

Use of gene switch for ligand inducible control of IL-12 expression described herein can improve the safety profile of IL-12 by for example allowing for regulated expression and improving therapeutic index. However, a condition for ligand dose dependent expression of IL-12 using gene switch(es) is the presence or absence of activator ligand (e.g. veledimex). In certain embodiments, an additional conditional control for induction of IL-12 expression is contemplated. Gene switch components under the control of T cell activated specific promoters are provided. This results in conditional expression (e.g., T cell activation) of gene switch components necessary for veledimex controlled expression of transgene(s) under control of a gene switch. In some embodiments, this results in preferential expression of cytokines such as IL-12 or IL-15 by tumor specific T cells when veledimex is present and T cells are activated. This may lead to increased localized levels of gene switch controlled transgene expression.

For example, T cell activation specific expression of gene switch components can be controlled by promoter comprising Nuclear Factor of Activated T-cells (NFAT) response element(s). NFAT transcription factors are key modulators of effector T-cell states. NFATs are early transcriptional checkpoint progressively driving exhaustion. NFATs are quickly activated in T cells following TCR stimulation and form a protein complex with AP-1 induced by appropriate co-stimulation signaling and regulate effector genes and T-cell functions. NFAT response element(s) can be fused with other minimal promoter sequences (e.g. IL2 minimal promoter) to drive expression of transgenes in response to T cell activation.

Other examples of activation specific promoters include but are not limited to interleukin-2 (IL2) promoter and Programmed Death (PD)-1 (CD279) promoter. Gene switch components can also be conditionally expressed upon immune cell activation by fusing binding sites for other nuclear factors like NF-κB of proinflammatory signaling pathway to minimal promoter sequence (e.g. IL2).

In some embodiments, the promoter comprises NF-κB binding site (SEQ ID NOS 44-46), nuclear factor of activated T cells (NFAT) response element (SEQ ID NO 51), 6 site GAL4-inducible proximal factor binding element (PFB) (SEQ ID NO 62) or synthetic 5' UTR based on RPL6 (SEQ ID NO 64). In certain embodiments, the promoter can be any one or more of: IL-2 core promoter, IL-2 minimal promoter, IL-2 enhancer and promoter variant, $(NF\text{-}\kappa B)_1$-IL2 promoter variant, $(NF\text{-}\kappa B)_3$-IL2 promoter variant, $(NF\text{-}\kappa B)_6$-IL2 promoter variant, 1×NFAT response elements-IL2 promoter variant, 3×NFAT response elements-IL2 promoter variant, 6×NFAT response elements-IL2 promoter variant, human EEF1A1 promoter variant, human EEF1A1 promoter and enhancer, human UBC promoter and synthetic minimal promoter 1. In certain embodiments, the promoter nucleotides comprise disclosed in the table below:

TABLE 2

Promoter polynucleotide sequences

| SEQ ID NO | Promoter | Polynucleotide Sequence (5' to 3' where applicable) |
|---|---|---|
| 40 | IL-2 core promoter | ACATTTTGACACCCCCATAATATTTTTCCAGAATTAAC<br>AGTATAAATTGCATCTCTTGTTCAAGAGTTCCCTATCA<br>CTCTCTTTAATCACTACTCACAGTAACCTCAACTCCTG |
| 41 | IL-2 minimal promoter | TCAAGAGTTCCCTATCACTCTCTTTAATCACTACTCAC<br>AGTAACCTCAACTCCTG |
| 42 | IL-2 enhancer and promoter variant | TGATATCTTTTCTGAGTTACTTTTGTATCCCCACCCCC<br>TTAAAGAAAGGAGGAAAAACTGTTTCATACAGAAGG<br>CGTTAATTGCATTTAATTAGAGCTATCACCTAAGTGTG<br>GGCTAATGTAACAAAGAGGGATTTCACCTACATCCAT<br>TCAGTCAGTCTTTGGGGGTTTAAAGAAATTCCAAAGA<br>GTCATCAGAAGAGGAAAAATGAAGGTAATGTTTTTTC<br>AGACTGGTAAAGTCTTTGAAAATATGTGTAATATGTA<br>AAACATTTTGACACCCCCATAATATTTTTCCAGAATTA<br>ACAGTATAAATTGCATCTCTTGTTCAAGAGTTCCCTAT<br>CACTCTCTTTAATCACTACTCACAGTAACCTCAACTCC<br>TGCCACA |
| 43 | L-2 enhancer and promoter variant | TTTTCTGAGTTACTTTTGTATCCCCACCCCCTTAAAGA<br>AAGGAGGAAAAACTGTTTCATACAGAAGGCGTTAATT<br>GCATGAATTAGAGCTATCACCTAAGTGTGGGCTAATG<br>TAACAAAGAGGGATTTCACCTACATCCATTCAGTCAG<br>TCTTTGGGGGTTTAAAGAAATTCCAAAGAGTCATCAG<br>AAGAGGAAAAATGAAGGTAATGTTTTTTCAGACTGGT<br>AAAGTCTTTGAAAATATGTGTAATATGTAAAACATTT<br>TGACACCCCCATAATATTTTTCCAGAATTAACAGTAT<br>AAAGTCTTTGAAAATATGTGTAATATGTAAAACATTT<br>TTTAATCACTACTCACAGTAACCTCAACTCCTGCCAC<br>A |
| 47 | $(NF\text{-}\kappa B)_1$-IL2 promoter variant | AATTGGTCCCATCGAAGAGGGATTTCACCTACATAAT<br>TGGTCCCGGGACATTTTGACACCCCCATAATATTCTTTC<br>CAGAATTAACAGTATAAATTGCATCTCTTGTTCAAGA<br>GTTCCCTATCACTCTCTTTAATCACTACTCACAGTAAC<br>CTCAACTCCTG |
| 48 | $(INF\text{-}\kappa B)_3$-IL2 promoter variant | AATTGGTCCCATCGAAGAGGGATTTCACCTACATAAG<br>AGGGATTTCACCTACATAAGAGGGATTTCACCTACAT<br>AATTGGTCCCGGGACATTTTGACACCCCCATAATATT<br>TTTCCAGAATTCAACAGTATAAATTGCATCTCTTGTTCA<br>AGAGTTCCCTATCACTCTCTTTAATCACTACTCACAGT<br>AACCTCAACTCCTG |
| 49 | $(NF\text{-}\kappa B)_6$-IL2 promoter variant | AATTGGTCCCATCGAAGAGGGATTTCACCTACATAAG<br>AGGGATTTCACCTACATAAGAGGGATTTCACCTACAT<br>AATTGGTAAGAGGGATTTCACCTACATAAGAGGGATT<br>TCACCTACATAAGAGGGATTTCACCTACATAATTGGT<br>CCCGGGACATTTTGAGACCCCCATAATATTTTTCCAG<br>AATTAACAGTATAAATTGCATCTCTTGTTCAAGAGTT<br>CCCTATCACTCTCTTTAATCACTACTCACAGTAACCTC<br>AACTCCTG |

TABLE 2-continued

Promoter polynucleotide sequences

| SEQ ID NO | Promoter | Polynucleotide Sequence (5' to 3' where applicable) |
|---|---|---|
| 50 | 1X NFAT response elements-IL2 promoter variant | AATTGGTCCCATCGAATTAGGAGGAAAAACTGTTTCA TACAGAAGGCGTCAATTGGTCCCGGGACATTTTGACA CCCCCATAATATTTTTCCAGAATTAACAGTATAAATT GCATCTCTTGTTCAAGAGTTCCCTATCACTCTCTTTAA TCACTACTCACAGTAACCTCAACTCCTG |
| 56 | 3X NFAT response elements-IL2 promoter variant | TGATATCAATTGGTCCCATCGAATTAGGAGGAAAAAC TGTTTCATACAGAAGGCGTCAATTAGGAGGAAAAACT GTTTTCATACAGAAGGCGTCAATTAGGAGGAAAAACT GTTTCATACAGAAGGCGTCAATTGGTCCCGGGACATT TTGACACCCCCATAATATTTTTCCAGAATTAACAGTAT AAATTGCATCTCTTGTTCAAGAGTTCCCTATCACTCTC TTTAATCACTACTCACAGTAACCTCAACTCCTG |
| 57 | 3X NFAT response elements-IL2 promoter variant | AATTGGTCCCATCGAATTAGGAGGAAAAACTGTTTCA TACAGAAGGCGTCAATTAGGAGGAAAAACTGTTTCAT ACAGAAGGCGTCAATTAGGAGGAAAAACTGTTTCAT ACAGAAGGCGTCAATTGGTCCCGGGACATTTTGACAC CCCCATAATATTTTTCCAGAATTAACAGTATAAATTG CATCTCTTGTTCAAGAGTTCCCTATCACTCTCTTTAAT CACTACTCACAGTAACCTCAACTCCTG |
| 52 | 6X NFAT response elements-IL2 promoter variant | GAATTAGGAGGAAAAACTGTTTCATACAGAAGGCGT CAATTAGGAGGAAAAACTGTTTCATACAGAAGGCGTC AATTAGGAGGAAAAACTGTTTCATACAGAAGGCGTC AATTGGTCCCATCGAATTAGGAGGAAAAACTTGTTTTCA TACAGAAGGCGTCAATTAGGAGGAAAAACTGTTTCAT ACAGAAGGCGTCAATTAGGAGGAAAAACTGTTTCAT ACAGAAGGCGTCAATTGGTCCCGGGACATTTTGACAC CCCCATAATATTTTTCCAGAATTAACAGTATAAATTG CATCTCTTGTTCAAGAGTCTCCCTATCACTCTCCTTAAT CACTACTCACAGTAACCTCAACTCCTG |
| 53 | 6X NFAT response elements-IL2 promoter variant | TGATATCGAATTAGGAGGAAAAACTGTTTCATACAGA AGGCGTCAATTAGGAGGAAAAACTGTTTCATACAGA AGGCGTCAATTAGGAGGAAAAACTGTTTCATACAGA AGGCGTCAATTGGTCCCATCGAATTAGGAGGAAAAA CTGTTTCATACAGAAGGCGTCAATTAGGAGGAAAAAC TGTTTCATACAGAAGGCGTCAATTAGGAGGAAAAACT GTTTCATACAGAAGGCGTCAATTGGTCCCGGGACATT TTGACACCCCCATAATATTTTTCCAGAATTAACAGTAT AAATTGCATCTCTTGTTCAAGAGTTCCCTATCACTCTC TTTAATCACTACTCACAGTAACCTCAACTCCTGAATTC CATG |
| 54 | 6X NFAT response elements-IL2 promoter variant | GAATTAGGAGGAAAAACTGTTTCATACAGAAGGCGT CAATTAGGAGGAAAAACTGTTTCATACAGAAGGCGTC AATTAGGAGGAAAAACTGTTTCATACAGAAGGCGTC AATTGGTCCCATCGAATTAGGAGGAAAAACTGTTTCA TACAGAAGGCGTCAATTAGGAGGAAAAACTGTTTCAT ACAGAAGGCGTCAATTAGGAGGAAAAACTGTTTCAT ACAGAAGGCGTCAATTGGTCCCGGGACATTTTGACAC CCCCATAATATTTTTCCAGAATTAACAGTATAAATTG CATCTCTTGTTCAAGAGTTCCCTATCACTCTCTTTAAT CACTACTCACAGTAACCTCAACTCCTG |
| 55 | 6X NFAT response elements-IL2 promoter variant | TGATATCGAATTAGGAGGAAAAACTGTTTCATACAGA AGGCGTCAATTAGGAGGAAAAACTGTTTCATACAGA AGGCGTCAATTAGGAGGAAAAACTGTTTCATACAGA AGGCGTCAATTGGTCCCATCGAATTAGGAGGAAAAA CTGTTTCATACAGAAGGCGTCAATTAGGAGGAAAAAC TGTTTCATACAGAAGGCGTCAATTAGGAGGAAAAACT GTTTCATACAGAAGGCGTCAATTGGTCCCGGGACATT TTGACACCCCCATAATATTTTTCCAGAATTAACAGTAT AAATTGCATCTCTTGTTCAAGAGTTCCCTATCACTCTC TTTAATCACTACTCACAGTAACCTCAACTCCTG |

TABLE 2-continued

| SEQ ID NO | Promoter | Polynucleotide Sequence (5' to 3' where applicable) |
|---|---|---|
| Promoter polynucleotide sequences | | |
| 58 | human EEF1A1 promoter variant | GAGCGTGCGTGAGGCTCCGGTGCCCGTCAGTGGGCAG AGCGCACATCGCCCACAGTCCCCGAGAAGTTGGGGG GAGGGGGTCGGCGATTGAACCGGTGCCTAGAGAAGG TGGCGCGGGGTAAACTGGGAAAGTGATGTCGTGTACT GGCTCCGCCTTTTTCCCGAGGGTGGGGGAGAACCGTA TATAAGTGCAGTAGTCGCCGTGAACGTTCTTTTTCGC AACGGGTTTGCCGCCAGAACACAG |
| 59 | human EEF1A1 promoter variant | GCGTGAGGCTCCGGTGCCCGTCAGTGGGCAGAGCGC ACATCGCCCACAGTCCCCGAGAAGTTGGGGGGAGGG GTCGGCAATTGAACCGGTGCCTAGAGAAGGTGGCGC GGGGTAAACTGGGAAAGTGATGTCGTGTACTGGCTCC GCCTTTTTCCCGAGGGTGGGGGAGAACCGTATATAAG TGCAGTAGTCGCCGTGAACGTTCTTTTTCGCAACGGG TTTGCCGCCAGAACACA |
| 60 | human EFF1A1 promoter and enhancer | GAGCTTTGCAAAGATGGATAAAGTTTTAAACAGAGA GGAATCTTTGCAGCTAATGGACCTTCTAGGTCTFGAA AGGAGTGGGAATTGGCTCCGGTGCCCGTCAGTGGGCA GAGCGCACATCGCCCACAGTCCCCGAGAAGTTGGGG GGAGGGGTCGGCAATTGAACCGGTGCCTAGAGAAGG TGGCGCGGGGTAAACTGGGAAAGTGATGTCGTGTACT GGCTCCGCCTTTTTCCCGAGGGTGGGGGAGAACCGTA TATAAGTGCAGTAGTCGCCGTGAACGTTCTTTTTCGC AACGGGTTTGCCGCCAGAACACAGGTAAGTGCCGTGT GTGGTTCCCGCGGGCCTGGCCTCTTTACGGGTTATGG CCCTTGCGTGCCTTGAATTACTTCCACCTGGCTGCAGT ACGTGATTCTTGATCCCGAGCTTCGGGTTGGAAGTGG GTGGGAGAGTTCGAGGCCTTGCGCTTAAGGAGCCCCT TCGCCTCGTGCTTGAGTTGAGGCCTGGCCTGGGCGCT GGGGCCGCCGCGTGCGAATCTGGTGGCACCTTCGCGC CTGTCTCGCTGCTTTCGATAAGTCTCTAGCCATTTAAA ATTTTTGATGACCTGCTGCGACGCTTTTTTTCTGGCAA GATAGTCTTCTAAATGCGGGCCAAGATCTGCACACTG GTATTTCGGTTTTTGGGGCCGCGGGCGGCGACGGGGC CCGTGCGTCCCAGCGCACATGTTCGGCGAGGCGGGGC CTGCGAGCGCGGCCACCGAGAATCGGACGGGGGTAG TCTCAAGCTGGCCGGCCTGCTCTGGTGCCTGGCCTCG CGCCGCCGTGTATCGCCCCGCCCTGGGCGGCAAGGCT GGCCCGGTCGGCACCAGTTGCGTGAGCGGAAAGATG GCCGCTTCCCGGCCCTGCTGCAGGGAGCTCAAAATGG AGGACGCGGCGCTCGGGAGAGCGGGCGGGTGAGTCA CCCACACAAAGGAAAAGGGCCTTTCCGTCCTCAGCCG TCGCTTCATGTGACTCCACGGAGTACCGGGCGCCGTC CAGGCACCTCGATTAGTTCTCGAGCTTTTGGAGTACG TCGTCTTTAGGTTGGGGGGAGGGGTTTTATGCGATGG AGTTTCCCCACACTGAGTGGGTGGAGACTGAAGTTAG GCCAGCTTGGCACTTGATGTAATTCTCCTTGGAATTTG CCCTTTTTGAGTTTGGATCTTGGTTCATTCTCAAGCCT CAGACAGTGGTTCAAAGTTTTTTTCTTCCATTTCAGGT GTCGTGAG |
| 61 | human UBC promoter | GGCCTCCGCGCCGGGTTTTGGCGCCTCCCGCGGGCGC CCCCCTCCTCACGGCGAGCGCTGCCACGTCAGACGAA GGGCGCAGCGAGCGTCCTGATCCTTCCGCCCGGACGC TCAGGACAGCGGCCCGCTGCTCATAAGACTCGGCCTT AGAACCCCAGTATCAGCAGAAGGACATTTTAGGACG GGACTTGGGTGACTCTAGGGCACTGGTTTTCTTTCCA GAGAGCGGAACAGGCGAGGAAAAGTAGTCCCTTCTC GGCGATTCTGCGGAGGGATCTCCGTGGGGCGGTGAAC GCCGATGATTATATAAGGACGCGCCGGGTGTGGCACA GCTAGTTCCGTCGCAGCCGGGATTTGGGTCGCGGTTC TTGTTTGTGGATCGCTGTGATCGTCACTTGGTGAGTAG CGGGCTGCTGGGCTGGGTACGTGCGCTCGGGGTTGGC GAGTGTGTTTTGTGAAGTTTTTTAGGCACCTTTTGAAA TGTAATCATTTGGGTCAATATGTAATTTTCAGTGTTAG ACTAGTAAATTGTCCGCTAAATTCTGGCCGTTTTTGGC TTTTTTGTTAGACG |
| 63 | synthetic minimal promoter 1 | AGGTCTATATAAGCAGAGCTCGTTTAGTGAACCCTCA TTCTGGAGACGGATCCCGAGCCGAGTGTTTTGACCTC CATAGAA |

Gene Switch

Provided herein are gene switch polypeptides, polynucleotides encoding ligand-inducible gene switch polypeptides, and methods and systems incorporating these polypeptides and/or polynucleotides.

The term "gene switch" or "genetic switch" refers to the combination of a response element associated with a promoter, and for instance, an EcR based system which, in the presence of one or more ligands, modulates the expression of a gene into which the response element and promoter are incorporated. Tightly regulated inducible gene expression systems or gene switches are useful for various applications such as gene therapy, large scale production of proteins in cells, cell based high throughput screening assays, functional genomics and regulation of traits in transgenic plants and animals. Such inducible gene expression systems may include ligand inducible heterologous gene expression systems.

An early version of EcR-based gene switch used *Drosophila melanogaster* EcR (DmEcR) and *Mus musculus* RXR (MmRXR) polypeptides and showed that these receptors in the presence of steroid, ponasteroneA, transactivate reporter genes in mammalian cell lines and transgenic mice (Christopherson et al., 1992; No et al., 1996). Later, Suhr et al., 1998 showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. In this example, the ecdysone receptor was isolated from *Drosophila melanogaster*. Typically, such systems require the presence of the silent partner, preferably retinoid X receptor (RXR), in order to provide optimum activation. In mammalian cells, insect ecdysone receptor (EcR) is capable of heterodimerizing with mammalian retinoid X receptor (RXR) and, thereby, be used to regulate expression of target genes or heterologous genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner. In some embodiments, the RXR comprises a nucleotide at least 45%, 50%, 55%, 60%, 65%, 70%, 75%, 80%, 85%, 90%, 95%, 97%, 98%, 99% or 100% identical to SEQ ID NO 69 or a polypeptide at least 45%, 50%, 55%, 60%, 65%, 70%, 75%, 80%, 85%, 90%, 95%, 97%, 98%, 99% or 100% identical to SEQ ID NO 182. In some embodiments, the gene switch comprises VP16-linker-RxR, wherein the VP16-linker-RXR comprises a nucleotide at least 45%, 50%, 55%, 60%, 65%, 70%, 75%, 80%, 85%, 90%, 95%, 97%, 98%, 99% or 100% identical to SEQ ID NO 70 or a polypeptide at least 45%, 50%, 55%, 60%, 65%, 70%, 75%, 80%, 85%, 90%, 95%, 97%, 98%, 99% or 100% identical to SEQ ID NO 183.

U.S. Pat. No. 6,265,173 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state. In some embodiments, the gene switch comprises EcR ligand binding domain—VY variant, wherein the EcR ligand binding domain—VY variant comprises a nucleotide at least 45%, 50%, 55%, 60%, 65%, 70%, 75%, 80%, 85%, 90%, 95%, 97%, 98%, 99% or 100% identical to SEQ ID NO 72 or 73 or a polypeptide at least 45%, 50%, 55%, 60%, 65%, 70%, 75%, 80%, 85%, 90%, 95%, 97%, 98%, 99% or 100% identical to SEQ ID NO 185 or 186. In other embodiments, the gene switch comprises GAL4-linker-EcR, wherein the GAL4-linker-EcR comprises a nucleotide at least 45%, 50%, 55%, 60%, 65%, 70%, 75%, 80%, 85%, 90%, 95%, 97%, 98%, 99% or 100% identical to SEQ ID NO 74 or 75 or a polypeptide at least 45%, 50%, 55%, 60%, 65%, 70%, 75%, 80%, 85%, 90%, 95%, 97%, 98%, 99% or 100% identical to SEQ ID NO 187 or 188.

International Patent Application No. PCT/US01/0905 discloses an ecdysone receptor-based inducible gene expression system in which the transactivation and DNA binding domains are separated from each other by placing them on two different proteins results in greatly reduced background activity in the absence of a ligand and significantly increased activity over background in the presence of a ligand. This two-hybrid system is a significantly improved inducible gene expression modulation system compared to the two systems disclosed in applications PCT/US97/05330 and PCT/US98/14215. The two-hybrid system is believed to exploit the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). The two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, it is believed that a conformational change is induced which promotes interaction of the first polypeptide with the second polypeptide thereby resulting in dimerization of the DNA binding domain and the transactivation domain. Since the DNA binding and transactivation domains reside on two different molecules, the background activity in the absence of ligand is greatly reduced.

Another surprising discovery was that certain modifications of the two-hybrid system could also provide improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provided higher gene transcription activity at a lower ligand concentration. Furthermore, the two-hybrid system avoids some side effects due to overexpression of RXR that can occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell, thereby resulting in reduced side effects.

The ecdysone receptor (EcR) is a member of the nuclear receptor superfamily and is classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97: 161-163). In addition to the ecdysone receptor, other members of this nuclear receptor subfamily 1, group H include: ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1).

In some cases, an inducible promoter can be a small molecule ligand-inducible two polypeptide ecdysone receptor-based gene switch, such as Intrexon Corporation's RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/1J52002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/US2002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497,093; PCT/US2005/015089 (WO 2005/108617); U.S. Pat. Nos. 7,935,510; 8,076,454; PCT/US2008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); and, U.S. Pat. No. 9,402,919 each of which is incorporated by reference in its entirety.

Provided are systems for modulating the expression of a heterologous gene and an interleukin in a host cell, comprising polynucleotides expressing gene-switch polypeptides disclosed herein. Various structural components of non-limiting exemplary ligand-inducible gene switch vector system under the control of constitutive or inducible promoters are shown in FIG. 22.

In some embodiments, the expression cassette of the gene switch vector system is XON-64 and has a sequence as shown in SEQ ID NO: 131. In some embodiments, the expression cassette of the gene switch vector system is XON-30 and has a sequence as shown in SEQ ID NO: 132. In some embodiments, the expression cassette of the gene switch vector system is XON-59 and has a sequence as shown in SEQ ID NO: 133. In some embodiments, the expression cassette of the gene switch vector system is XON-60 and has a sequence as shown in SEQ ID NO: 134. In some embodiments, the expression cassette of the gene switch vector system is XON-61 and has a sequence as shown in SEQ ID NO: 135. In some embodiments, the expression cassette of the gene switch vector system is XON-62 and has a sequence as shown in SEQ ID NO: 136.

In some embodiments are systems for modulating the expression of a heterologous gene and a cytokine in a host cell, comprising a first gene expression cassette comprising a first polynucleotide encoding a first polypeptide; a second gene expression cassette comprising a second polynucleotide encoding a second polypeptide; and a ligand; wherein said first and second polypeptides comprise one or more of: (i) a transactivation domain; (ii) a DNA-binding domain; and (iii) a ligand binding domain; (iv) said heterologous gene; and (vi) said cytokine such that upon contacting said host cell with said first gene expression cassette and said second gene expression cassette in the presence of said ligand, said heterologous gene and said cytokine are expressed in said host cell. In some cases, the heterologous gene comprises an antigen binding polypeptide described herein. In some cases, the antigen binding polypeptide may be a CAR described herein, for instance, a CAR that binds at least one of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR MUC-1, MUC-16, MAGE-A1, MUC16, h5T4, PSMA, TAG-72, EGFRvIII, CD123 and VEGF-R2.

Cytokines

Provided herein are polynucleotides encoding gene-switch polypeptides and a cytokine, or variant or derivative thereof, and methods and systems incorporating the same. Cytokine is a category of small proteins between about 5-20 kDa that are involved in cell signaling. In some instances, cytokines include chemokines, interferons, interleukins, colony-stimulating factors or tumor necrosis factors. In some embodiments, chemokines play a role as a chemoattractant to guide the migration of cells, and is classified into four subfamilies: CXC, CC, CX3C, and XC. Exemplary chemokines include chemokines from the CC subfamily: CCL1, CCL2 (MCP-1), CCL3, CCL4, CCL5 (RANTES), CCL6, CCL7, CCL8, CCL9 (or CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28; the CXC subfamily: CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17; the XC subfamily: XCL1 and XCL2; and the CX3C subfamily CX3CL1.

Interferons (IFNs) comprise interferon type I (e.g. IFN-α, IFN-β, IFN-ε, IFN-κ, and IFN-ω), interferon type II (e.g. IFN-γ), and interferon type III. In some embodiments, IFN-α is further classified into about 13 subtypes including IFNA1, IFNA2, IFNA4, IFNA5, IFNA6, IFNA7, IFNA8, IFNA10, IFNA13, IFNA14, IFNA16, IFNA17, and IFNA21.

Interleukins are expressed by leukocytes or white blood cells and they promote the development and differentiation of T and B lymphocytes and hematopoietic cells. Exemplary interleukines include IL-1, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, and IL-36.

In some embodiments, an interleukin comprises mbIL-15. In some embodiments, a mbIL-15 is a membrane-bound chimeric IL-15 which can be co-expressed with a modified effector cell described herein. In some embodiments, the mbIL-15 comprises a full-length IL-15 (e.g., a native IL-15 polypeptide) or fragment or variant thereof, fused in frame with a full length IL-15Rα, functional fragment or variant thereof. In some cases, the IL-15 is indirectly linked to the IL-15Rα through a linker. In some instances, the mbIL-15 is as described in Hurton et al., "Tethered IL-15 augments antitumor activity and promotes a stem-cell memory subset in tumor-specific T cells," PNAS 2016.

Tumor necrosis factors (TNFs) are a group of cytokines that modulate apoptosis. In some instances, there are about 19 members within the TNF family, including, not limited to, TNFα, lymphotoxin-alpha (LT-alpha), lymphotoxin-beta (LT-beta), T cell antigen gp39 (CD40L), CD27L, CD30L, FASL, 4-1BBL, OX40L, and TNF-related apoptosis inducing ligand (TRAIL).

Colony-stimulating factors (CSFs) are secreted glycoproteins that interact with receptor proteins on the surface of hemopoietic stem cells, which subsequently modulates cell proliferation and differentiation into specific kind of blood cells. In some instances, a CSF comprises macrophage colony-stimulating factor, granulocyte macrophage colony-stimulating factor (GM-CSF), granulocyte colony-stimulating factor (G-CSF) or promegapoietin.

In some embodiments, the cytokine is a membrane-bound cytokine, which is co-expressed with a chimeric antigen receptor described herein.

In some embodiments, one or more methods described herein further comprise administration of a cytokine. In some instances, the cytokine comprises a chemokine, an interferon, an interleukin, a colony-stimulating factor or a tumor necrosis factor. In some instances, one or more methods described herein further comprise administration of a cytokine selected from a chemokine, an interferon, an interleukin, a colony-stimulating factor or a tumor necrosis factor. In some instances, one or more methods described herein further comprise administration of a cytokine selected from IL2, IL7, IL12, IL115, IL21 IFNγ or TNF-α.

In some cases, the cytokine comprises at least one chemokine, interferon, interleukin, lymphokine, tumor necrosis factor, or variant or combination thereof. In some cases, the cytokine is an interleukin. In some cases, the interleukin is at least one of IL-12, IL-2, IL-15, IL-21, and functional variants and fragments thereof. In some embodiments, the cytokine is at least one of IL-1, IL-2, IL-15, IL-12, IL-21, a fusion of IL-15, IL-15Rα, or an IL-15 variant. In one embodiment, the cytokine is a variant of IL-15 (SEQ ID NO 90; SEQ ID NO 203). In one embodiment, the cytokine comprises IL-15 receptor alpha (SEQ ID NO 91; SEQ ID NO 204). In some embodiments, the cytokines can be membrane bound or secreted. In other embodiments, the cytokines can be intracellular. The interleukin may comprise membrane bound IL-15 (mbIL-15), a fusion of IL-15 and IL-15Rα (SEQ ID NO 91; SEQ ID NO 204) or an IL-15 (SEQ ID NO 90; SEQ ID NO 203) variant. In some embodiments, a mbIL-15 is a membrane-bound chimeric IL-15 which can be co-expressed with a modified effector cell described herein. In some embodiments, the mbIL-15 comprises a full-length IL-15 (e.g., a native IL-15 polypeptide) or fragment or variant thereof, fused in frame with a full length IL-15Rα, functional fragment or variant thereof. In some cases, the IL-15 is indirectly linked to the IL-15Rα through a linker. In some embodiments, the mbIL-15 comprises a signal peptide (SEQ ID NO 92; SEQ ID NO 205). In some instances, the mbIL-15 is as described in Hurton et al., "Tethered IL-15 augments antitumor activity and promotes a stem-cell memory subset in tumor-specific T cells," PNAS 2016. In another aspect, the interleukin can comprise IL-12. In some embodiments, IL-12 can be a single chain IL-12 (scIL-12), protease sensitive IL-12, destabilized IL-12, membrane bound IL-12 or intercalated IL-12. In some embodiments, IL-12 is murine IL-12 subunit beta (p40) (SEQ ID NO 206). In some embodiments, IL-12 is murine IL-12 subunit alpha (p35) (SEQ ID NO 207). In some embodiments, IL-12 is murine single chain IL-12 (p40-linker-p35) (SEQ ID NO 93; SEQ ID NO 208). In some embodiments, IL-12 is human single chain IL-12 (p40-linker-p35) (SEQ ID NO 94; SEQ ID NO 209). In certain embodiments, IL-12 is single chain IL-12. In some instances, the IL-12 variants are as described in WO2015/095249, WO2016/048903, and WO2017/062953, all of which are incorporated by reference in their entireties.

Provided herein are polynucleotides encoding gene switch polypeptides, wherein said gene switch polypeptides comprise: a) a first gene switch polypeptide comprising a DNA-binding domain fused to a nuclear receptor ligand binding domain, and b) a second gene switch polypeptide comprising a transactivation domain fused to a nuclear receptor ligand binding domain, wherein the first gene switch polypeptide and the second gene switch polypeptide are connected by a linker. In some cases, the linker may be a linker described herein, for instance GSG linker, furinlink, a 2A linker such as F/T2A, T2A, p2A, GSG-p2A, variants and derivatives thereof. In other instances, the linker may be an IRES. In some embodiments, the IRES is EMCV IRES or 2xRbm3 IRES. Exemplary IRES sequences can be found in SEQ ID NO: 18 and 19. In certain cases, a polynucleotide encoding 2xRbm3 IRES a can be or can be about at least 45%, 50%, 55%, 60%, 65%, 70%, 75%, 80%, 85%, 90%, 95%, 97%, 98%, 99% or 100% identical to SEQ ID NO: 19. In certain cases, a polynucleotide encoding EMCV IRES a can be or can be about at least 45%, 50%, 55%, 60%, 65%, 70%, 75%, 80%, 85%, 90%, 95%, 97%, 98%, 99% or 100% identical to SEQ ID NO: 18.

In some cases, the DNA binding domain (DBD) comprises a DBD described herein, for instance at least one of GAL4 (GAL4 DBD) (SEQ ID NO 71, SEQ ID NO 184), a LexA DBD, a transcription factor DBD, a steroid/thyroid hormone nuclear receptor superfamily member DBD, a bacterial LacZ DBD, and a yeast DBD. The transactivation domain may comprise a transactivation domain described herein, for instance one of a VP16 transactivation domain (SEQ ID NO 68; SEQ ID NO 181), a p53 transactivation domain and a B42 acidic activator transactivation domain. The Nuclear receptor ligand binding domain may comprise at least one of a ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor.

In some cases, the gene switch polypeptides connected by a polypeptide linker or ribosome-skipping sequence exhibit improved dose-dependent ligand-inducible control of gene expression compared to a ligand-inducible gene switch wherein the gene switch polypeptides are connected by non-coding sequences, such as an IRES. In some cases, the gene switch polypeptides connected by a 2A linker may exhibit improved dose-dependent ligand-inducible control of heterologous gene expression compared to a gene switch wherein said gene switch polypeptides are separated by an IRES.

The polypeptides and polynucleotides as described herein can be expressed in an engineered cell. Herein an engineered cell is a cell which has been modified from its natural or endogenous state. An example of an engineered cell is a cell described herein which has been modified (e.g., by transfection of a polynucleotide into the cell) to encode for example, gene switch polypeptides, gene of interest (GOI), cell tags, heterologous genes and any other polypeptides and polynucleotides described herein.

Ligands

In some embodiments, a ligand used for inducible gene switch regulation can be selected from any of, but without limitation to, following: N-[(1R)-1-(1,1-dimethylethyl) butyl]-N'-(2-ethyl-3-methoxybenzoyl)-3,5-dimethylbenzohydrazide (also referred to as veledimex), (2S,3R,5R,9R, 10R,13R,14S,17R)-17-[(2S,3R)-3,6-dihydroxy-6-methylheptan-2-yl]-2,3,14-trihydroxy-10,13-dimethyl-2,3, 4,5,9,11,12,15,16,17-decahydro-1H-cyclopenta[a] phenanthren-6-one; N'-(3,5-Dimethylbenzoyl)-N'-[(3R)-2, 2-dimethyl-3-hexanyl]-2-ethyl-3-methoxybenzohydrazide; 5-Methyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Methyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide; 5-Methyl-2,3-dihydro-benzo[1,4]dioxine-6-carboxylic acid N'-(1-tert-butyl-butyl)-N'-(3,5-dimethyl-benzoyl)-hydrazide; 5-Methyl-2,3-dihydro-benzo[1,4]dioxine-6-carboxylic acid N'-(1-tert-butyl-butyl)-N'-(3,5-dimethoxy-4-methyl-benzoyl)-hydrazide; 5-Ethyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Ethyl-2,3-dihydro-benzo[1, 4]dioxine-6-carboxylic acid N'-(3,5-dimethoxy-4-methyl-benzoyl)-N'-(1-ethyl-2,2-dimethyl-propyl)-hydrazide; 5-Ethyl-2,3-dihydro-benzo[1,4]dioxine-6-carboxyli c acid N'-(1-tert-butyl-butyl)-N'-(3,5-dimethyl-benzoyl)-hydrazide; 5-Ethyl-2,3-dihydro-benzo[1,4]dioxine-6-carboxylic acid N'-(1-tert-butyl-butyl)-N'-(3,5-dimethoxy-4-methyl-benzoyl)-hydrazide; 3,5-Dimethyl-benzoic acid N-(1-ethyl-2,2-dimethyl-propyl)-N'-(3-methoxy-2-methyl-benzoyl)-hydrazide; 3,5-Dimethoxy-4-methyl-benzoic acid N-(1-ethyl-2,2-dimethyl-propyl)-N'-(3-methoxy-2-methyl-benzoyl)-hydrazide; 3,5-Dimethyl-benzoic acid N-(1-tert-butyl-butyl)-N'-(3-methoxy-2-methyl-benzoyl)-hydrazide; 3,5-Dimethoxy-4-methyl-benzoic acid N-(1-tert-butyl-butyl)-N'-(3-methoxy-2-methyl-benzoyl)-hydrazide; 3,5-Dimethyl-benzoic acid N-(1-ethyl-2,2-dimethyl-propyl)-N'-(2-ethyl-3-methoxy-benzoyl)-hydrazide; 3,5-Dimethoxy-4-methyl-benzoic acid N-(1-ethyl-2,2-dimethyl-propyl)-N'-(2-ethyl-3-methoxy-benzoyl)-hydrazide; 3,5-Dimethyl-benzoic acid N-(1-tert-butyl-butyl)-N'-(2-ethyl-3-methoxy-benzoyl)-hydrazide; 3,5-Dimethoxy-4-methyl-benzoic acid N-(1-tert-butyl-butyl)-N'-(2-ethyl-3-methoxy-benzoyl)-hydrazide; 2-Methoxy-nicotinic acid N-(1-tert-butyl-pentyl)-N'-(4-ethyl-benzoyl)-hydrazide; 3,5-Dimethyl-benzoic acid N-(2,2-dimethyl-1-phenyl-propyl)-N'-(4-ethyl-benzoyl)-hydrazide; 3,5-Dimethyl-benzoic acid N-(1-tert-butyl-pentyl)-N'-(3-methoxy-2-methyl-benzoyl)-hydrazide; and 3,5-Dimethoxy-4-methyl-benzoic acid N-(1-tert-butyl-pentyl)-N'-(3-methoxy-2-methyl-benzoyl)-hydrazide.

In some cases, a ligand used for dose-regulated control of ecdysone receptor-based inducible gene switch can be selected from any of, but without limitation to, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroylhydrazines such as those disclosed in U.S. Pat. No. 5,225, 443; N-acyl-N-alkylcarbonylhydrazines such as those disclosed in European Application No. 234,994; N-aroyl-N-alkyl-N'-aroylhydrazines such as those described in U.S. Pat. No. 4,985,461; arnidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, framesol, bile acids, 1,1-biphosphonate esters, juvenile hormone III, and the like. Examples of diacylhydrazine ligands useful in the present disclosure include RG-115819 (3,5-Dimethyl-benzoic acid N-(1-ethyl-2,2-dimethyl-propyl)-N'-(2-methyl-3-methoxy-benzoyl)-hydrazide-), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See, e.g., U.S. patent application Ser. No. 12/155,111, and PCT Appl. No. PCT/US2008/006757, both of which are incorporated herein by reference in their entireties.

Antigen Binding Polypeptides

Polypeptides and proteins disclosed herein (including functional portions and functional variants thereof) may comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

"Antibody" as used herein refers to monoclonal or polyclonal antibodies. The term "monoclonal antibodies," as used herein, refers to antibodies that are produced by a single clone of B-cells and bind to the same epitope. In contrast, "polyclonal antibodies" refer to a population of antibodies that are produced by different B-cells and bind to different epitopes of the same antigen. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have a similar general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding.

"Antigen recognition moiety" or "antibody recognition domain" refers to a molecule or portion of a molecule that specifically binds to an antigen. In one embodiment, the antigen recognition moiety is an antibody, antibody like molecule or fragment thereof and the antigen is a tumor antigen or an infectious disease antigen.

"Antibody like molecules" may be for example proteins that are members of the Ig-superfamily which are able to selectively bind a partner. MHC molecules and T cell receptors are such molecules. In one embodiment the antibody-like molecule is a TCR. In one embodiment the TCR has been modified to increase its MHC binding affinity.

The terms "fragment of an antibody," "antibody fragment," "functional fragment of an antibody," "antigen-binding portion" or their grammatical equivalents are used interchangeably herein to mean one or more fragments or portions of an antibody that retain the ability to specifically bind to an antigen (see, generally, Holliger et al., Nat. Biotech., 23(9): 1126-1129 (2005)). The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the VL, VH, CL, and CH1 domains; (ii) a F(ab')2 fragment, which is a bivalent fragment comprising two Fab fragments linked by a disulfide bridge at the stalk region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al., Science, 242: 423-426 (1988); Huston et al., Proc. Natl. Acad. Sci. USA, 85: 5879-5883 (1988); and Osbourn et al., Nat. Biotechnol., 16: 778 (1998)) and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites. Antibody fragments are known in the art and are described in more detail in, e.g., U.S. Pat. No. 8,603,950. Other antibody fragments can include variable fragments of heavy chain antibodies (VHH).

The term "functional portion," when used in reference to a CAR, refers to any part or fragment of the CAR of the present disclosure, which part or fragment retains the biological activity of the CAR of which it is a part (the parent CAR). In reference to a nucleic acid sequence encoding the parent CAR, a nucleic acid sequence encoding a functional portion of the CAR can encode a protein comprising, for example, about 10%, 25%, 30%, 50%, 68%, 80%, 90%, 95%, or more, of the parent CAR.

The term "functional variant," as used herein, refers to a polypeptide, or a protein having substantial or significant sequence identity or similarity to the reference polypeptide, and retains the biological activity of the reference polypeptide of which it is a variant. In some embodiments, a functional variant, for example, comprises the amino acid sequence of the reference protein with at least or about 1, 2, 3, 4, 5, 6, 7, 8, 9, 10, 11, 12, 13, 14, 15, 16, 17, 18, 19, or 20 conservative amino acid substitutions. Functional variants encompass, for example, those variants of the CAR described herein (the parent CAR) that retain the ability to recognize target cells to a similar extent, the same extent, or to a higher extent, as the parent CAR. In reference to a nucleic acid sequence encoding the parent CAR, a nucleic acid sequence encoding a functional variant of the CAR can be for example, about 10% identical, about 25% identical, about 30% identical, about 50% identical, about 65% identical, about 80% identical, about 90% identical, about 95% identical, or about 99% identical to the nucleic acid sequence encoding the parent CAR.

The term "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and Schirmer, R. H., Principles of Protein Structure, Springer-Verlag, New York (1979)). According to such analyses, groups of amino acids may be defined where amino acids within a group exchange preferentially with each other, and therefore resemble each other most in their impact on the overall protein structure (Schulz, G. E. and Schirmer, R. H., supra). Examples of conservative mutations include amino acid substitutions of amino acids within the sub-groups above, for example, lysine for arginine and vice versa such that a positive charge may be maintained; glutamic acid for aspartic acid and vice versa such that a negative charge may be maintained, serine for threonine such that a free —OH can be maintained; and glutamine for asparagine such that a free —$NH_2$ can be maintained. Alternatively or additionally, the functional variants can comprise the amino acid sequence of the reference protein with at least one non-conservative amino acid substitution.

The term "non-conservative mutations" involve amino acid substitutions between different groups, for example, lysine for tryptophan, or phenylalanine for serine, etc. In this case, it is preferable for the non-conservative amino acid substitution to not interfere with, or inhibit the biological activity of, the functional variant. The non-conservative amino acid substitution may enhance the biological activity of the functional variant, such that the biological activity of the functional variant is increased as compared to the parent CAR.

In some embodiments, the antigen binding moiety of a CAR described herein is specific to or binds CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MUC-16, MAGE-A1, MUC16, h5T4, PSMA, TAG-72, EGFRvIII, CD123 and VEGF-R2. In embodiments, the antigen binding domain comprises a single chain antibody fragment (scFv) comprising a variable domain light chain (VL) and variable domain heavy chain (VH) of a target antigen specific monoclonal antibody joined by a flexible linker, such as a glycine-serine linker or a Whitlow linker. In embodiments, the scFv is humanized. In some embodiments, the antigen binding moiety may comprise VH and VL that are directionally linked, for example, from N to C terminus, VH-linker-VL or VL-linker-VH. In some instances, the antigen binding domain recognizes an epitope of the target. In some embodiments, described herein include a CAR or a CAR-T cell, in which the antigen binding domain comprises a F(ab')2, Fab', Fab, Fv, or scFv.

In one embodiment, the antigen binding moiety of a CAR described herein is specific to CD19. In one embodiment, the antigen binding moiety of a CAR described herein is specific to CD33. In another embodiment, the antigen binding moiety of a CAR described herein is specific to BCMA. In yet another embodiment, the antigen binding moiety of a CAR described herein is specific to CD44. In some embodiments, the antigen binding moiety of a CAR described herein is specific to α-Folate receptor. In some embodiments, the antigen binding moiety of a CAR described herein is specific to CAIX. In one embodiment, the antigen binding moiety of a CAR described herein is specific to CD30. In some embodiments, the antigen binding moiety of a CAR described herein is specific to ROR1. In one embodiment, the antigen binding moiety of a CAR described herein is specific to CEA. In some embodiments, the antigen binding moiety of a CAR described herein is specific to EGP-2. In one embodiment, the antigen binding moiety of a CAR described herein is specific to EGP-40. In another embodiment, the antigen binding moiety of a CAR described herein is specific to HER2. In yet another embodiment, the antigen binding moiety of a CAR described herein is specific to HER3. In yet another embodiment, the antigen binding moiety of a CAR described herein is specific to Folate-binding protein. In some embodiments, the antigen binding moiety of a CAR described herein is specific to GD2. In some embodiments, the antigen binding moiety of a CAR described herein is specific to GD3. In one embodiment, the antigen binding moiety of a CAR described herein is specific to IL-13R-a2. In one embodiment, the antigen binding moiety of a CAR described herein is specific to KDR. In one embodiment, the antigen binding moiety of a CAR described herein is specific to EDB-F. In another embodiment, the antigen binding moiety of a CAR described herein is specific to mesothelin. In yet another embodiment, the antigen binding moiety of a CAR described herein is specific to CD22. In one embodiment, the antigen binding moiety of a CAR described herein is specific to EGFR. In one embodiment, the antigen binding moiety of a CAR described herein is specific to MUC-1. In one embodiment, the antigen binding moiety of a CAR described herein is specific to MUC-16. In one embodiment, the antigen binding moiety of a CAR described herein is specific to MAGE-A1. In some embodiments, the antigen binding moiety of a CAR described herein is specific to h5T4. In some embodiments, the antigen binding moiety of a CAR described herein is specific to PSMA. In another embodiment, the antigen binding moiety of a CAR described herein is specific to TAG-72. In yet one embodiment, the antigen binding moiety of a CAR described herein is specific to EGFRvIII. In another embodiment, the antigen binding moiety of a CAR described herein is specific to CD123. In yet embodiment, the antigen binding moiety of a CAR described herein is specific to VEGF-R2.

Chimeric Antigen Receptors (CARs)

In some embodiments, described herein includes a polynucleotide which encodes a chimeric receptor expressed on the surface of the cell. In some instances, the chimeric receptor comprises an antigen binding region that enables recognition and binding to an antigen, for instance, a tumor antigen such as a tumor-associated antigen or a tumor-specific antigen. In some instances, the antigen binding region comprises an antibody or binding fragment, for example, an Fab, an Fab', an F(ab')2, an F(ab')3, an scFv, an sc(Fv)2, a dsFv, a diabody, a minibody, and a nanobody or binding fragments thereof. In some cases, the antigen binding region comprises an scFv. In some cases, the chimeric receptor comprises an scFv (e.g., a chimeric antigen receptor (CAR)). In some instances, the chimeric antigen receptor comprises a pattern-recognition receptor. In other cases, the chimeric receptor comprises an engineered T-cell receptor (TCR).

The terms "chimeric antigen receptor (CAR)", "artificial T cell receptor", "chimeric T cell receptor" or "chimeric immunoreceptor" as used herein refer to an engineered receptor which grafts an exogenous specificity onto an immune effector cell. In some instances, a CAR comprises an extracellular domain (ectodomain) that comprises an antigen binding domain, a stalk region, a transmembrane domain and an intracellular (endodomain) domain. In some instances, the intracellular domain further comprises one or more intracellular signaling domains. In some instances, a CAR described herein comprises an antigen binding domain, a stalk region, a transmembrane domain, one or more costimulatory domains, and a signaling domain for T-cell activation.

In embodiments, the CAR of the present disclosure comprises a target-specific binding element otherwise referred to as an antigen-binding moiety. In embodiments, the CAR of the present disclosure is engineered to target a tumor antigen of interest by way of engineering a desired antigen-binding moiety that specifically binds to an antigen on a tumor cell. In the context of the present disclosure, "tumor antigen" or "hyperproliferative disorder antigen" or "antigen associated with a hyperproliferative disorder," refers to antigens that are common to specific hyperproliferative disorders such as cancer.

An antigen binding domain can comprise complementary determining regions of a monoclonal antibody, variable regions of a monoclonal antibody, and/or antigen binding fragments thereof. A complementarity determining region (CDR) is a short amino acid sequence found in the variable domains of antigen receptor (e.g., immunoglobulin and T-cell receptor) proteins that complements an antigen and therefore provides the receptor with its specificity for that particular antigen. Each polypeptide chain of an antigen receptor can contain three CDRs (CDR1, CDR2, and CDR3). In some instances, an antigen binding domain comprises F(ab')2, Fab', Fab, Fv, or scFv. In some cases, an antigen binding domain is a scFv. In some cases, an antigen binding domain is a Fab. In some cases, an antigen binding domain is a Fab'. In some cases, an antigen binding domain is F(ab')2. In some cases, an antigen binding domain is a Fv.

In some embodiments, a CAR described herein comprises an antigen binding domain that binds to an epitope on CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MUC-16, MAGE-A1, MUC16, h5T4, PSMA, TAG-72, EGFRvIII, CD123 and VEGF-R2. In some embodiments, a CAR described herein comprises an antigen binding domain that binds to an epitope on CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MUC-16, MAGE-A1, MUC16, h5T4, PSMA, TAG-72, EGFRvIII, CD123 and VEGF-R2. In some embodiments, a CAR described herein comprises an antigen binding domain that binds to an epitope on CD19, CD33 or EGFRvIII. In some instances, a CAR described herein comprises an antigen binding domain that binds to an epitope on CD19. In some cases, a CAR described herein comprises an antigen binding domain that binds to an epitope on CD33. In further embodiments, a CAR or a chimeric receptor or antigen binding polypeptide described herein comprises an autoantigen or an antigen binding region that binds to an epitope on HLA-A2, myelin oligodendrocyte glycoprotein (MOG), factor VIII (FVIII), MAdCAM1, SDF1, or collagen type II.

In another embodiment, a CAR described herein is a EGFRvIII specific CAR. "EGFRvIII", "EGFR variant III", "EGFR type III mutant", "EGFR.D2-7" or "de2-7EGFR" is a mutated form of epidermal growth factor receptor (EGFR; ErbB-1; HER1), a transmembrane protein that is a receptor for members of the epidermal growth factor (EGF) family of extracellular protein ligands in human and non-human subjects. EGFRvIII is characterized by a deletion of exons 2-7 of the wild type EGFR gene, which results in an in-frame deletion of 267 amino acids in the extracellular domain of the full length wild type EGFR protein. EGFRvII also contains a novel glycine residue inserted at the fusion junction. The truncated receptor EGFRvIII is unable to bind any known EGFR ligand; however, it shows constitutive tyrosine kinase activity. This constitutive activation is important to its pro-oncogenic effect. A kinase-deficient EGFRvIII is unable to confer a similar oncogenic advantage. EGFRvIII is highly expressed in glioblastoma (GBM) and can be detected in some other solid tumor types but not in normal tissues.

In some embodiments, the antigen binding moiety of a CAR described herein is specific to EGFRvIII (EGFRvIII CAR). The EGFRvIII-specific CAR, when expressed on the cell surface, redirects the specificity of T cells to human EGFRvIII. In embodiments, the antigen binding domain comprises a single chain antibody fragment (scFv) comprising a variable domain light chain (VL) and variable domain heavy chain (VH) of a target antigen specific monoclonal anti-EGFRvIII antibody joined by a flexible linker, such as a glycine-serine linker or a Whitlow linker. In embodiments, the scFv is murine MR1 IgG. In some embodiments, the scFv is anti-EGFRvIII scFv clone MR1 (SEQ ID NO 115; SEQ ID NO 229), anti-EGFRvIII scFv clone MR1-1 (SEQ ID NO 116; SEQ ID NO 230), anti-EGFRvII scFv clone huMR1-1 (SEQ ID NO 117; SEQ ID NO 231), anti-EGFRvIII scFv clone huMR1-2 (SEQ ID NO 118; SEQ ID NO 232). In some embodiments, the antigen binding moiety may comprise VH and VL that are directionally linked, for example, from N to C terminus, VH-linker-VL or VL-linker-VH.

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO 221 (anti-EGFRvIII clone MR1 VL). In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO 220 (anti-EGFRvIII clone MR1 VH). In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO 223 (anti-EGFRvIII clone MR1-1 VL). In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO 222 (anti-EGFRvIII clone MR1-1 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO 225 (anti-EGFRvIII clone humMR1-1 VL). In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO 224 (anti-EGFRvIII clone humMR1-1 VH). In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO 227 (anti-EGFRvIII clone humMR1-2 VL). In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO 226 (anti-EGFRvIII clone humMR1-2 VH).

In one embodiment, a CAR described herein is a CD19 specific CAR. "CD19", cluster of differentiation 19 or B-lymphocyte antigen CD19, is a protein that in human is encoded by the CD19 gene. The CD19 gene encodes a cell surface molecule that assembles with the antigen receptor of B lymphocytes in order to decrease the threshold for antigen receptor-dependent stimulation. CD19 is expressed on follicular dendritic cells and B cells. In fact, it is present on B cells from earliest recognizable B-lineage cells during development to B-cell blasts but is lost on maturation to plasma cells. It primarily acts as a B cell co-receptor in conjunction with CD21 and CD81. Upon activation, the cytoplasmic tail of CD19 becomes phosphorylated, which leads to binding by Src-family kinases and recruitment of PI-3 kinase. As on T cells, several surface molecules form the antigen receptor and form a complex on B lymphocytes. The (almost) B cell-specific CD19 phosphoglycoprotein is one of these molecules. The others are CD21 and CD81. These surface immunoglobulin (sIg)-associated molecules facilitate signal transduction. On B cells, anti-immunoglobulin antibody mimicking exogenous antigen causes CD19 to bind to sIg and internalize with it. The reverse process has not been demonstrated, suggesting that formation of this receptor complex is antigen-induced. This molecular association has been confirmed by chemical studies.

In yet another embodiment, a CAR descried herein is a CD33 specific CAR. "CD33", Siglec-3, sialic acid binding Ig-like lectin 3, SIGLEC3, SIGLEC-3, gp67, or p67 is a 67 kDa single pass transmembrane glycoprotein and is a member of the sialic acid-binding immunoglobulin-like lectins (Siglecs) super-family. CD33 is characterized by a V-set Ig-like domain responsible for sialic acid binding and a C2-set Ig-like domain in its extracellular domain. Alternative splicing of CD33 mRNA leads to a shorter isoform (CD33m) lacking the V-set Ig-like domain as well as the disulfide bond linking the V- and C2-set Ig-like domains. In healthy subjects. CD33 is primarily expressed as a myeloid differentiation antigen found on normal multipotent myeloid precursors, unipotent colony-forming cells, monocytes and maturing granulocytes. CD33 is expressed on more than 80% of myeloid leukemia cells but not on normal hematopoietic stem cells or mature granulocytes (Andrews, R. et al., The L4F3 antigen is expressed by unipotent and multipotent colony-forming cells but not by their precursors, *Blood,* 68(5):1030-5 (1986)). CD33 has been reported to be expressed on malignant myeloid cells, activated T cells and activated NK cells and is found on at least a subset of blasts in the vast majority of AML patients (Pollard, J. et al., Correlation of CD33 expression level with disease characteristics and response to gemtuzumab ozogamicin containing chemotherapy in childhood AML, *Blood,* 119(16):3705-11 (2012)). In addition to broad expression on AML blasts, CD33 may be expressed on stem cells underlying AML.

In embodiments, the antigen binding moiety of a CAR described herein is specific to CD33 (CD33 CAR). The CD33-specific CAR, when expressed on the cell surface, redirects the specificity of T cells to human CD33. In embodiments, the antigen binding domain comprises a single chain antibody fragment (scFv) comprising a variable domain light chain (VL) and variable domain heavy chain (VH) of a target antigen specific monoclonal anti-CD33 antibody joined by a flexible linker, such as a glycine-serine linker or a Whitlow linker. In embodiments, the scFv are M195, m2H12, DRB2, and/or My9-6. In embodiments, the scFv is humanized, for example, hM195. In some embodiments, the antigen binding moiety may comprise VH and VL that are directionally linked, for example, from N to C terminus, VH-linker-VL or VL-linker-VH. In some embodiments, the CD33 antigen binding domain comprises a polypeptide having at least 90%, 91%, 92%, 93%, 94%, 95%, 96%, 97%, 98%, 99% or 100% identity with the amino acid sequence of SEQ ID NO 214 (hM195 VL). In some embodiments, the CD33 antigen binding domain comprises a polypeptide having at least 90%, 91%, 92%, 93%, 94%, 95%, 96%, 97%, 98%, 99% or 100% identity with the amino acid sequence of SEQ ID NO 215 (hM195 VH). In some embodiments, the CD33 antigen binding domain comprises a polypeptide having at least 90%, 91%, 92%, 93%, 94%, 95%, 96%, 97%, 98%, 99% or 100% identity with the amino acid sequence of SEQ ID NO 216 (hM195 scFv with linker).

In some embodiments, the polynucleotides, polypeptides and methods described herein can be used for the treatment of a hyperproliferative disease, such as a cancer, an autoimmune disease or for the treatment of an infection, such as a viral, bacterial or parasitic infection. In some aspects, the antigen is an antigen that is elevated in cancer cells, in autoimmune cells or in cells that are infected by a virus, bacteria or parasite. Pathogens that may be targeted include, without limitation, Plasmodium, trypanosome, *Aspergillus, Candida*, Hepatitis A, Hepatitis B, Hepatitis C, HSV, HPV, RSV, EBV, CMV, JC virus, BK virus, or Ebola pathogens. Autoimmune diseases can include graft-versus-host disease, rheumatoid arthritis, lupus, celiac disease, Crohn's disease, Sjogren Syndrome, polymyalgia rheumatic, multiple sclerosis, neuromyelitis optica, ankylosing spondylitis, Type 1 diabetes, alopecia areata, vasculitis, temporal arteritis, bullous pemphigoid, psoriasis, pemphigus vulgaris, or autoimmune uveitis.

The pathogen recognized by a CAR may be essentially any kind of pathogen, but in some embodiments the pathogen is a fungus, bacteria, or virus. Exemplary viral pathogens include those of the families of Adenoviridae, Epstein-Barr virus (EBV), Cytomegalovirus (CMV), Respiratory Syncytial Virus (RSV), JC virus, BK virus, HPV, HSV, HHV family of viruses, Hepatitis family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis*, and *Stachybotrys*. Exemplary pathogenic bacteria include *Streptococcus, Pseudomonas, Shigella, Campylobacter, Staphylococcus, Helicobacter, E. coli, Rickettsia, Bacillus, Bordetella, Chlamydia, Spirochetes*, and *Salmonella*. In some embodiments the pathogen receptor Dectin-1 may be used to generate a CAR that recognizes the carbohydrate structure on the cell wall of fungi such as *Aspergillus*. In another embodiment, CARs can be made based on an antibody recognizing viral determinants (e.g., the glycoproteins from CMV and Ebola) to interrupt viral infections and pathology.

In some embodiments, a "stalk", "stalk region" or "stalk domain", which encompasses the terms "spacer", "spacer region" or "spacer domain" or "hinge", "hinge region" or "hinge domain", is used to link the antigen-binding domain to the transmembrane domain. In some instances, a "stalk domain" or "stalk region" comprise any oligonucleotide- or polypeptide that functions to link the transmembrane domain to, either the extracellular domain or, the cytoplasmic domain in the polypeptide chain. In some embodiments, it is flexible enough to allow the antigen-binding domain to orient in different directions to facilitate antigen recognition. In some instances, the stalk region comprises the hinge region from IgG. In alternative instances, the stalk region comprises the CH2CH3 region of immunoglobulin and optionally portions of CD3. In some cases, the stalk region comprises a CD8α hinge region (SEQ ID NO 29; SEQ ID NO 170), an IgG4-Fc 12 amino acid hinge region (ESKYGPPCPPCP) or IgG4 hinge regions as described in WO/2016/073755.

In some embodiments, the stalk region comprises at least one of a polypeptide having at least 90%, 91%, 92%, 93%, 94%, 95%, 96%, 97%, 98%, 99% or 100% identity with the amino acid sequence of CD8 alpha 2× (SEQ ID NO 30; SEQ ID NO 171), CD8 alpha 3× (SEQ ID NO 31; SEQ ID NO 172) or CD8 alpha 4× (SEQ ID NO 32; SEQ ID NO 173).

In other embodiments, between the extracellular domain and the transmembrane domain of the CAR, there is incorporated a spacer. A spacer can comprise a stalk region and a stalk extension region. In one embodiment, a spacer can include a single stalk region. In another embodiment, a spacer can comprise a stalk region and stalk extension region(s). For example, a spacer can comprise one (1) stalk region and 0, 1, 2, 3, 4, 5, 6, 7, 8, 9, 10, 11, 12, 13, 14, 15, 16, 17, 18, 19, or 20 stalk regions. In further embodiments, the stalk region can be linked to stalk extension region via a linker.

The transmembrane domain can be derived from either a natural or a synthetic source. Where the source is natural, the domain can be derived from any membrane-bound or transmembrane protein. Suitable transmembrane domains can include the transmembrane region(s) of alpha, beta or zeta chain of the T-cell receptor; or a transmembrane region from CD28, CD3 epsilon, CD3ζ, CD45, CD4, CD5, CD8alpha, CD9, CD16, CD22, CD33, CD37, CD64, CD80, CD86, CD134, CD137 or CD154. Alternatively the transmembrane domain can be synthetic, and can comprise hydrophobic residues such as leucine and valine. In some embodiments, a triplet of phenylalanine, tryptophan and valine is found at one or both termini of a synthetic transmembrane domain. Optionally, a short oligonucleotide or polypeptide linker, in some embodiments, between 2 and 10 amino acids in length may form the linkage between the transmembrane domain and the cytoplasmic signaling domain of a CAR. In some embodiments, the linker is a glycine-serine linker. In some embodiments, the transmembrane domain comprises a CD8α transmembrane domain or a CD3ζ transmembrane domain. In some embodiments, the transmembrane domain comprises a CD8α transmembrane domain. In other embodiments, the transmembrane domain comprises a CD3ζ transmembrane domain. In some embodiments, the transmembrane region comprises at least one of a polypeptide having at least 90%, 91%, 92%, 93%, 94%, 95%, 96%, 97%, 98%, 99% or 100% identity with the amino acid sequence of CD8 alpha transmembrane domain (SEQ ID NO 174). In some embodiments, the transmembrane region comprises at least one of a polypeptide having at least 90%, 91%, 92%, 93%, 94%, 95%, 96%, 97%, 98%, 99% or 100% identity with the amino acid sequence of CD28 transmembrane domain (SEQ ID NO 175).

The intracellular domain can comprise one or more costimulatory domains. Exemplary costimulatory domains include, but are not limited to, CD8, CD27, CD28, 4-1BB (CD137), ICOS, DAP10, DAP12, OX40 (CD134) or fragment or combination thereof. In some instances, a CAR described herein comprises one or more, or two or more of costimulatory domains selected from CD8, CD27, CD28, 4-1BB (CD137), ICOS, DAP10, DAP12, OX40 (CD134) or fragment or combination thereof. In some instances, a CAR described herein comprises one or more, or two or more of costimulatory domains selected from CD27, CD28, 4-1BB (CD137), ICOS, OX40 (CD134) or fragment or combination thereof. In some instances, a CAR described herein comprises one or more, or two or more of costimulatory domains selected from CD8, CD28, 4-1BB (CD137), or fragment or combination thereof. In some instances, a CAR described herein comprises one or more, or two or more of costimulatory domains selected from CD28, 4-1BB (CD137), or fragment or combination thereof. In some instances, a CAR described herein comprises costimulatory domains CD28 and 4-1BB (CD137) or their respective fragments thereof. In some instances, a CAR described herein comprises costimulatory domains CD28 and OX40 (CD134) or their respective fragments thereof. In some instances, a CAR described herein comprises costimulatory domains CD8 and CD28 or their respective fragments thereof. In some instances, a CAR described herein comprises costimulatory domains CD28 or a fragment thereof. In some instances, a CAR described herein comprises costimulatory domains 4-1BB (CD137) or a fragment thereof. In some instances, a CAR described herein comprises costimulatory domains OX40 (CD134) or a fragment thereof. In some instances, a CAR described herein comprises costimulatory domains CD8 or a fragment thereof.

The intracellular signaling domain, also known as cytoplasmic domain, of the CAR of the present disclosure, is responsible for activation of at least one of the normal effector functions of the immune cell in which the CAR has been placed. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal. In some embodiments, the intracellular domain further comprises a signaling domain for T-cell activation. In some instances, the signaling domain for T-cell activation comprises a domain derived from TCR zeta, FcR gamma, FcR beta, CD3 gamma, CD3 delta, CD3 epsilon, CD5, CD22, CD79a, CD79b or CD66d. In some cases, the signaling domain for T-cell activation comprises a domain derived from CD3ζ.

In some embodiments, the intracellular signaling domain comprises at least one of a polypeptide having at least 90%, 91%, 92%, 93%, 94%, 95%, 96%, 97%, 98%, 99% or 100% identity with the amino acid sequence of CD28 (SEQ ID NO 176), CD3 zeta signaling domain (SEQ ID NO 177), 4-1BB signaling domain (SEQ ID NO 178), DNAX-activation protein 10 (DAP 10) signaling domain (SEQ ID NO 179) or DNAX-activation protein 12 (DAP12) signaling domain (SEQ ID NO 180).

CD19 Specific CARs

CD19 is a cell surface glycoprotein of the immunoglobulin superfamily. In some instances, CD19 has been detected in solid tumors such as pancreatic cancer, liver cancer, and prostate cancer.

In some embodiments, the antigen binding moiety of a CAR described herein, is specific to CD19. A CD19-specific CAR, when expressed on the cell surface, may redirect the specificity of T cells to human CD19. In embodiments, the antigen binding domain comprises a single chain antibody fragment (scFv) comprising a variable domain light chain (VL) and variable domain heavy chain (VH) of a target antigen specific monoclonal anti-CD19 antibody joined by a flexible linker, such as a glycine-serine linker or a Whitlow linker. In embodiments, the scFv are SJ25C1 and/or FMC63. In embodiments, the scFv is humanized. In some embodiments, the antigen binding moiety may comprise VH and VL that are directionally linked, for example, from N to C terminus, VH-linker-VL or VL-linker-VH.

In some embodiments, described herein include a CD19-specific CAR, in which the antigen binding domain comprises a scFv that binds CD19. In some instances, the antigen binding domain recognizes an epitope on CD19.

In some embodiments, the antigen binding domain recognizes an epitope on CD19 that is also recognized by JCAR014, JCAR015, JCAR017, or 19-28z CAR (Juno Therapeutics). In some embodiments, described herein include a CD19-specific CAR-T cell, in which the antigen binding domain recognizes an epitope on CD19 that is also recognized by JCAR014, JCAR015, JCAR017, or 19-28z CAR (Juno Therapeutics). In some instances, the CD19-specific CAR-T cell further comprises a transmembrane domain selected from a CD8alpha transmembrane domain or a CD3ζ transmembrane domain, one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by JCAR014, JCAR015, JCAR017, or 19-28z CAR (Juno Therapeutics). In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, a CD19-specific CAR-T cell described herein comprises an anti-CD19 antibody described in US20160152723.

In some embodiments, the antigen binding domain recognizes an epitope on CD19 that is also recognized by KTE-C19 (Kite Pharma, Inc.). In some embodiments, described herein include a CD19-specific CAR-T cell, in which the antigen binding domain recognizes an epitope on CD19 that is also recognized by KTE-C19. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by KTE-C19. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, a CD19-specific CAR-T cell described herein comprises an anti-CD19 antibody described in WO2015187528 or fragment or derivative thereof.

In some embodiments, the antigen binding domain recognizes an epitope on CD19 that is also recognized by CTL019 (Novartis). In some embodiments, described herein include a CD19-specific CAR-T cell, in which the antigen binding domain recognizes an epitope on CD19 that is also recognized by CTL019. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by CTL019. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, the antigen binding domain recognizes an epitope on CD19 that is also recognized by UCART19 (Cellectis). In some embodiments, described herein include a CD19-specific CAR-T cell, in which the antigen binding domain recognizes an epitope on CD19 that is also recognized by UCART19. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by UCART19. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, OX40 (CD134) or fragment or combination thereof; and a signaling domain from CD3ζ.

In some embodiments, the antigen binding domain recognizes an epitope on CD19 that is also recognized by BPX-401 (Bellicum). In some embodiments, described herein include a CD19-specific CAR-T cell, in which the antigen binding domain recognizes an epitope on CD19 that is also recognized by BPX-401. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by BPX-401. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some cases, the antigen binding domain recognizes an epitope on CD19 that is also recognized by blinatumomab (Amgen), coltuximabravtansine (ImmunoGen Inc./Sanofi-aventis), MOR208 (Morphosys AG/Xencor Inc.), MEDI-551 (Medimmune), denintuzumabmafodotin (Seattle Genetics), B4 (or DI-B4) (Merck Serono), taplitumomabpaptox (National Cancer Institute), XmAb 5871 (Amgen/Xencor, Inc.), MDX-1342 (Medarex) or AFM11 (Affimed). In some instances, the CD19-specific CAR further comprises a transmembrane domain selected from a CD8alpha transmembrane domain or a CD3ζ transmembrane domain; one or more costimulatory domains selected from CD27, CD28, 4-1BB (CD137), ICOS, DAP10, OX40 (CD134) or fragment or combination thereof; and a signaling domain from CD3ζ.

In some embodiments, described herein include a CD19-specific CAR-T cell, in which the antigen binding domain comprises a F(ab')2, Fab', Fab, Fv, or scFv. In some instances, the antigen binding domain recognizes an epitope on CD19. In some cases, the antigen binding domain recognizes an epitope on CD19 that is also recognized by blinatumomab (Amgen), coltuximabravtansine (ImmunoGen Inc./Sanofi-aventis), MOR208 (Morphosys AG/Xencor Inc.), MEDI-551 (Medimmune), denintuzumabmafodotin (Seattle Genetics), B4 (or DI-B4) (Merck Serono), taplitumomabpaptox (National Cancer Institute), XmAb 5871 (Amgen/Xencor, Inc.), MDX-1342 (Medarex) or AFM11 (Affimed). In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some cases, a CD19-specific CAR-T cell described herein comprise a scFv antigen binding domain, and the antigen binding domain recognizes an epitope on CD19 that is also recognized by blinatumomab (Amgen), coltuximabravtansine (ImmunoGen Inc./Sanofi-aventis), MOR208 (Morphosys AG/Xencor Inc.), MEDI-551 (Medimmune), denintuzumabmafodotin (Seattle Genetics), B4 (or DI-B4) (Merck Serono), taplitumomabpaptox (National Cancer Institute), XmAb 5871 (Amgen/Xencor, Inc.), MDX-1342 (Medarex) or AFM11 (Affimed). In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, OX40 (CD134) or fragment or combination thereof, and a signaling domain from CD3ζ.

In embodiments, a CAR described herein comprises CD19 specific CAR (CD19-CD8α-CD28-CD3ζ) having at least 90%, 91%, 92%, 93%, 94%, 95%, 96%, 97%, 98%, 99% or 100% identity with the amino acid sequence of SEQ ID NO 210. In embodiments, a CAR described herein comprises CD19 specific CAR (CD19-CD8α-CD28-CD3ζ with signal peptide) having at least 90%, 91%, 92%, 93%, 94%, 95%, 96%, 97%, 98%, 99% or 100% identity with the amino acid sequence of SEQ ID NO 211.

In some embodiments, the antigen binding moiety of a CAR described herein is specific to CD19. The CD19-specific CAR, when expressed on the cell surface, redirects the specificity of T cells to human CD19. In embodiments, the antigen binding domain comprises a single chain antibody fragment (scFv) comprising a variable domain light chain (VL) and variable domain heavy chain (VH) of a target antigen specific monoclonal anti-CD19 antibody joined by a flexible linker, such as a glycine-serine linker or a Whitlow linker. In embodiments, the scFv is anti-CD19 clone FMC63 scFv with whitlow linker (SEQ ID NO 213). In embodiments, the anti-CD19 antibody comprises anti-CD19 monoclonal antibody clone FMC63 variable heavy chain (SEQ ID NO 212). In some embodiments, the antigen binding moiety may comprise VH and VL that are directionally linked, for example, from N to C terminus, VH-linker-VL or VL-linker-VH.

Engineered T Cell Receptor (TCR)

In some embodiments, the chimeric receptor encoded by a polynucleotide described herein, comprises an engineered T-cell receptor. The T cell receptor (TCR) is composed of two chains (αβ or γδ) that pair on the surface of the T cell to form a heterodimeric receptor. In some instances, the αβ TCR is expressed on most T cells in the body and is known to be involved in the recognition of specific MHC-restricted antigens. Each α and β chain are composed of two domains: a constant domain (C) which anchors the protein to the cell membrane and is associated with invariant subunits of the CD3 signaling apparatus; and a variable domain (V) that confers antigen recognition through six loops, referred to as complementarity determining regions (CDRs). In some instances, each of the V domains comprises three CDRs; e.g., CDR1, CDR2 and CDR3 with CDR3 as the hypervariable region. These CDRs interact with a complex formed between an antigenic peptide bound to a protein encoded by the major histocompatibility complex (pepMHC) (e.g., HLA-A, HLA-B, HLA-C, HLA-DPA1, HLA-DPB1, HLA-DQA1, HLA-DQB1, HLA-DRA, or HLA-DRB1 complex). In some instances, the constant domain further comprises a joining region that connects the constant domain to the variable domain. In some cases, the beta chain further comprises a short diversity region which makes up part of the joining region.

In some cases, such TCR are reactive to specific tumor antigen, e.g. NY-ESO, Mage A3, Titin. In other cases, such TCR are reactive to specific neoantigens expressed within a patient's tumor (i.e. patient-specific, somatic, non-synonymous mutations expressed by tumors). In some cases, engineered TCRs can be affinity-enhanced.

In some embodiments, a TCR is described using the International Immunogenetics (IMGT) TCR nomenclature, and links to the IMGT public database of TCR sequences. For example, there can be several types of alpha chain variable (Vα) regions and several types of beta chain variable (Vβ) regions distinguished by their framework, CDR1, CDR2, and CDR3 sequences. As such, a Vα type can be referred to in IMGT nomenclature by a unique TRAV number. For example, "TRAV21" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. Similarly, "TRBV5-1" defines a TCR Vβ region having unique framework and CDR1 and CDR2 sequences, but with only a partly defined CDR3 sequence.

In some cases, the beta chain diversity region is referred to in IMGT nomenclature by the abbreviation TRBD.

In some instances, the unique sequences defined by the IMGT nomenclature are widely known and accessible to those working in the TCR field. For example, they can be found in the IMGT public database and in "T cell Receptor Factsbook", (2001) LeFranc and LeFranc, Academic Press, ISBN 0-12-441352-8.

In some embodiments, an αβ heterodimeric TCR is, for example, transfected as full length chains having both cytoplasmic and transmembrane domains. In some cases, the TCRs contain an introduced disulfide bond between residues of the respective constant domains, as described, for example, in WO 2006/000830.

In some instances, TCRs described herein are in single chain format, for example see WO 2004/033685. Single chain formats include αβ TCR polypeptides of the Vα-L-Vβ, Vβ-L-Vα, Vα-Cα-L-Vβ, Vα-L-Vβ-Cβ, Vα-Cα-L-Vβ-Cβ types, wherein Vα and Vβ are TCR α and β variable regions respectively, Cα and Cβ are TCR α and β constant regions respectively, and L is a linker sequence. In certain embodiments single chain TCRs of the present disclosure may have an introduced disulfide bond between residues of the respective constant domains, as described in WO 2004/033685.

The TCR described herein may be associated with a detectable label, a therapeutic agent or a PK modifying moiety.

Exemplary detectable labels for diagnostic purposes include, but are not limited to, fluorescent labels, radiolabels, enzymes, nucleic acid probes and contrast reagents.

Additional Genetic Elements

Although cellular therapies hold great promise for the treatment of human disease, significant toxicities from the cells themselves or from their transgene products have hampered clinical investigation. In embodiments described herein, immune effector cells comprising a CAR or TCR described herein that have been infused into a mammalian subject, e.g., a human, can be ablated in order to regulate the effect of such immune effector cells should toxicity arise from their use. Therefore, certain in embodiments, in addition to the specific chimeric antigen receptor described herein, a second gene is also introduced into an engineered immune effector cell described herein. The second gene is effectively a "kill switch" or "cell tag" that allows for the depletion of CAR or TCR or antigen binding polypeptide containing cells. In certain embodiments, the "kill switch" is a truncated HER1 peptide (herein designated HER1t or EGFRt) which comprises at least an antibody binding epitope of HER1 or functional fragment thereof, and optionally a signal polypeptide sequence or fragment thereof.

In certain embodiments, the second gene is a HER1 tag which is Epidermal Growth Factor Receptor (HER1) or a fragment or variant thereof. In embodiments, the second gene is a HER1 tag which is truncated human Epidermal Growth Factor Receptor 1 (for instance HER1t) (SEQ ID NO 76; SEQ ID NO 189). In some cases, the second gene is a variant of a truncated human Epidermal Growth Factor Receptor 1. In some cases, the variant of a truncated HER1 is HER1t1 (SEQ ID NO 77; SEQ ID NO 190), HER1t2 (SEQ ID NO 78; SEQ ID NO 191), HER1t3 (SEQ ID NO 79; SEQ ID NO 192), HER1t4 (SEQ ID NO 80; SEQ ID NO 193), HER1t5 (SEQ ID NO 81; SEQ ID NO 194), HER1t6 (SEQ ID NO 82; SEQ ID NO 195), HER1t7 (SEQ ID NO 83; SEQ ID NO 196), HER1t8 (SEQ ID NO 84; SEQ ID NO 197), HER1t9 (SEQ ID NO 85; SEQ ID NO 198), HER1t10 (SEQ ID NO 86; SEQ ID NO 199) or HER1t11 (SEQ ID NO 87; SEQ ID NO 200). In embodiments, at least one of HER1, HER1t, HER1t1, HER1t2, HER1t3, HER1t4, HER1t5, HER1t6, HER1t7, HER1t8, HER1t9, HER1t10 and HER1t11 provide a safety mechanism by allowing for depletion of infused CAR-T cells through administering FDA approved cetuximab or any antibody that recognizes HER1, HER1t, HER1t1, HER1t2, HER1t3, HER1t4, HER1t5, HER1t6, HER1t7, HER1t8, HER1t9, HER1t10 and/or HER1t11.

In embodiments, the HER1t gene comprises a nucleotide sequence having at least 90%, 91%, 92%, 93%, 94%, 95%, 96%, 97%, 98%, 99% or 100% identity with the nucleic acid sequence of SEQ ID NO: 76. In embodiments, the HER1t1 gene comprises a nucleotide sequence having at least 90%, 91%, 92%, 93%, 94%, 95%, 96%, 97%, 98%, 99% or 100% identity with the nucleic acid sequence of SEQ ID NO: 77. In embodiments, the HER1t2 gene comprises a nucleotide sequence having at least 90%, 91%, 92%, 93%, 94%, 95%, 96%, 97%, 98%, 99% or 100% identity with the nucleic acid sequence of SEQ ID NO: 78. In embodiments, the HER1t3 gene comprises a nucleotide sequence having at least 90%, 91%, 92%, 93%, 94%, 95%, 96%, 97%, 98%, 99% or 100% identity with the nucleic acid sequence of SEQ ID NO: 79. In embodiments, the HER1t4 gene comprises a nucleotide sequence having at least 90%, 91%, 92%, 93%, 94%, 95%, 96%, 97%, 98%, 99% or 100% identity with the nucleic acid sequence of SEQ ID NO: 80. In embodiments, the HER1t5 gene comprises a nucleotide sequence having at least 90%, 91%, 92%, 93%, 94%, 95%, 96%, 97%, 98%, 99% or 100% identity with the nucleic acid sequence of SEQ ID NO: 81. In embodiments, the HER1t6 gene comprises a nucleotide sequence having at least 90%, 91%, 92%, 93%, 94%, 95%, 96%, 97%, 98%, 99% or 100% identity with the nucleic acid sequence of SEQ ID NO: 82. In embodiments, the HER1t7 gene comprises a nucleotide sequence having at least 90%, 91%, 92%, 93%, 94%, 95%, 96%, 97%, 98%, 99% or 100%, identity with the nucleic acid sequence of SEQ ID NO: 83. In embodiments, the HER1t8 gene comprises a nucleotide sequence having at least 90%, 91%, 92%, 93%, 94%, 95%, 96%, 97%, 98%, 99% or 100% identity with the nucleic acid sequence of SEQ ID NO: 84. In embodiments, the HER1t9 gene comprises a nucleotide sequence having at least 90%, 91%, 92%, 93%, 94%, 95%, 96%, 97%, 98%, 99% or 100% identity with the nucleic acid sequence of SEQ ID NO: 85. In embodiments, the HER1t10 gene comprises a nucleotide sequence having at least 90%, 91%, 92%, 93%, 94%, 95%, 96%, 97%, 98%, 99% or 100% identity with the nucleic acid sequence of SEQ ID NO: 86. In embodiments, the HER1t11 gene comprises a nucleotide sequence having at least 90%, 91%, 92%, 93%, 94%, 95%, 96%, 97%, 98%, 99% or 100%, identity with the nucleic acid sequence of SEQ ID NO: 87.

The truncated HER1 sequence, for instance HER1t, HER1t1, HER1t2, HER1t3, HER1t4, HER1t5, HER1t6, HER1t7, HER1t8, HER1t9, HER1t10 and/or HER1t11 eliminates the potential for EGF ligand binding, homo- and hetero-dimerization of EGFR, and EGFR mediated signaling while keeping cetuximab binding to the receptor intact (Ferguson, K., 2008. A structure-based view of Epidermal Growth Factor Receptor regulation. *Annu Rev Biophys*, Volume 37, pp. 353-373).

In further embodiments, in addition to the therapeutic target specific chimeric antigen receptor of the present disclosure the second gene introduced is a HER1 tag. In some cases, the HER1 tag is a full-length HER1 polypeptide, or a truncated HER1 polypeptide (HER1t1), HER1t2, HER1t3, HER1t4, HER1t5, HER1t6, HER1t7, HER1t8, HER1t9, HER1t10 or HER1t11. In some cases, the HER1 tag is a truncated HER1 variant. In some cases, the HER1 tag, for instance HER1, HER1t1, HER1t2, HER1t3, HER1t4, HER1t5, HER1t6, HER1t7, HER1t8, HER1t9, HER1t10 or HER1t11 also provides a safety mechanism by allowing for depletion of infused CAR-T cells through administering FDA-approved rituximab therapy. In certain embodiments, the HER1 tag has a polypeptide sequence having at least 90%, 91%, 92%, 93%, 94%, 95%, 96%, 97%, 98%, 99% or 100% identity with the sequence of SEQ ID NO: 189. In certain embodiments, the HER1 tag is a HER1t1 tag and has a polypeptide sequence having at least 90%, 91%, 92%, 93%, 94%, 95%, 96%, 97%, 98%, 99% or 100% identity with the sequence of SEQ ID NO: 190. In certain embodiments, the HER1 tag is a HER1t2 tag and has a polypeptide sequence having at least 90%, 91%, 92%, 93%, 94%, 95%, 96%, 97%, 98%, 99% or 100% identity with the sequence of SEQ ID NO: 191. In certain embodiments, the HER1 tag is a HER1t3 tag and has a polypeptide sequence having at least 90%, 91%, 92%, 93%, 94%, 95%, 96%, 970%, 98%, 99% or 100% identity with the sequence of SEQ ID NO: 192. In certain embodiments, the HER1 tag is a HER1t4 tag and has a polypeptide sequence having at least 90%, 91%, 92%, 93%, 940%, 95%, 96%, 97%, 98%, 99% or 100% identity with the sequence of SEQ ID NO: 193. In certain embodiments, the HER1 tag is a HER1t5 tag and has a polypeptide sequence having at least 90%, 91%, 92%, 93%, 94%, 95%, 96%, 97%, 98%, 99% or 100% identity with the sequence of SEQ ID NO: 194. In certain embodiments, the HER1 tag is a HER1t6 tag and has a polypeptide sequence having at least 90%, 91%, 92%, 93%, 94%, 95%, 96%, 97%, 98%, 99% or 100% identity with the sequence of SEQ ID NO: 195. In certain embodiments, the HER1 tag is a HER1t7 tag and has a polypeptide sequence having at least 90%, 91%, 92%, 93%, 94%, 95%, 96%, 97%, 98%, 99% or 100% identity with the sequence of SEQ ID NO: 196. In certain embodiments, the HER1 tag is a HER1t8 tag and has a polypeptide sequence having at least 90%, 91%, 92%, 93%, 94%, 95%, 96%, 97%, 98%, 99% or 100% identity with the sequence of SEQ ID NO: 197. In certain embodiments, the HER1 tag is a HER1t9 tag and has a polypeptide sequence having at least 90%, 91%, 92%, 93%, 94%, 95%, 96%, 97%, 98%, 99% or 100% identity with the sequence of SEQ ID NO: 198. In certain embodiments, the HER1 tag is a HER1t10 tag and has a polypeptide sequence having at least 90%, 91%, 92%, 93%, 94%, 95%, 96%, 97%, 98%, 99% or 100% identity with the sequence of SEQ ID NO: 199. In certain embodiments, the HER1 tag is a HER1t11 tag and has a polypeptide sequence having at least 90%, 91%, 92%, 93%, 94%, 95%, 96%, 97%, 98%, 99% or 100% identity with the sequence of SEQ ID NO: 200.

In certain embodiments, the second gene is a CD20 tag (SEQ ID NO 88; SEQ ID NO 201) which is an activated glycosylated phosphoprotein or a fragment or variant thereof. In some cases, the second gene is a variant of a truncated CD20, CD20t1 (SEQ ID NO 89; SEQ ID NO 202). In embodiments, the CD20 tag, the variant of CD20 tag (CD20t1) or the fragment of the CD20 or CD20t1 tag provides a safety mechanism by allowing for depletion of infused CAR-T cells through administering an antibody that recognizes CD20. In embodiments, the gene encoding the CD20 tag comprises a nucleotide sequence having at least 90%, 91%, 92%, 93%, 94%, 95%, 96%, 97%, 98%, 99% or 100% identity with the nucleic acid sequence of SEQ ID NO: 88. In embodiments, the gene encoding the CD20t1 tag comprises a nucleotide sequence having at least 90%, 91%, 92%, 93%, 94%, 95%, 96%, 97%, 98%, 99% or 100% identity with the nucleic acid sequence of SEQ ID NO: 89.

In further embodiments, in addition to the therapeutic target specific chimeric antigen receptor of the present disclosure the second gene introduced is a CD20 tag. In some cases, the CD20 tag is a full-length CD20 polypeptide or a truncated CD20 polypeptide (CD20t1).

In embodiments, a CAR vector comprising a CAR described herein further comprises a full length CD20 tag comprising a nucleic acid sequence having at least 90%, 91%, 92%, 93%, 94%, 95%, 96%, 97%, 98%, 99% or 100% identity with the nucleic acid sequence of SEQ ID NO: 88. In embodiments, a CAR vector comprising a CAR described herein further comprises a variant of CD20 tag (CD20t1) comprising a nucleic acid sequence having at least 90%, 91%, 92%, 93%, 94%, 95%, 96%, 97%, 98%, 99% or 100% identity with the nucleic acid sequence of SEQ ID NO: 89.

In embodiments, the gene encoding the kill tag, for instance the HER1t, HER1t1, HER1t2, HER1t3, HER1t4, HER1t5, HER1t6, HER1t7, HER1t8, HER1t9, HER1t10 or HER1t11 is genetically fused to the CAR or TCR or cytokine via in-frame with a self-cleaving peptide, for example but not restricted to *Thosea asigna* virus (T2A) peptide. In embodiments, the T2A peptide has an amino acid sequence having at least 90%, 91%, 92%, 93%, 94%, 95%, 96%, 97%, 98%, 99% or 100% identity with the amino acid sequence of SEQ ID NO 153. In other embodiments, the gene encoding the kill tag, for instance the HER1t, HER1t1, HER1t2, HER1t3, HER1t4, HER1t5, HER1t6, HER1t7, HER1t8, HER1t9, HER1t10 or HER1t11 is genetically fused to a cytokine at 3' end via in-frame with a self-cleaving peptide, for example but not restricted to *Thosea asigna* virus (T2A) peptide.

In embodiments, both genes are cloned into a plasmid. In other embodiments, the cell tag is cloned into a separate lentiviral vector. In other embodiments, the cell tag gene is cloned into the Sleeping Beauty transposon vector backbone in frame with the CAR gene. In yet other embodiments, the cell tag such as HER1t, HER1t1, HER1t2, HER1t3, HER1t4, HER1t5, HER1t6, HER1t7, HER1t8, HER1t9, HER1t10 or HER1t11 is cloned into multiple Sleeping Beauty transposon vectors.

In certain embodiments, the cell tags have a signal peptide, for instance, GM-CSFRα signal peptide wherein the GM-CSFRα signal peptide has at least 90%, 91%, 92%, 93%, 94%, 95%, 96%, 97%, 98%, 99% or 100% identity with the amino acid sequence of SEQ ID NO: 163. In certain embodiments, the signal peptide is IgK having a sequence at least 90%, 91%, 92%, 93%, 94%, 95%, 96%, 97%, 98%, 99% or 100% identity with the amino acid sequence of SEQ ID NO: 164. In certain embodiments, the signal peptide is IgE having a sequence at least 90%, 91%, 92%, 93%, 94%, 95%, 96%, 97%, 98%, 99% or 100% identity with the amino acid sequence of SEQ ID NO: 165. In certain embodiments, the signal peptide is CD8α having a sequence at least 90%, 91%, 92%, 93%, 94%, 95%, 96%, 97%, 98%, 99% or 100% identity with the amino acid sequence of SEQ ID NO: 166. In certain embodiments, the signal peptide is TVB2 (T21A) having a sequence at least 90%, 91%, 92%, 93%, 94%, 95%, 96%, 97%, 98%, 99% or 100% identity with the amino acid sequence of SEQ ID NO: 167. In certain embodiments, the signal peptide is CD52 having a sequence at least 90%, 91%, 92%, 93%, 94%, 95%, 96%, 97%, 98%, 99% or 100% identity with the amino acid sequence of SEQ ID NO: 168. In certain embodiments, the signal peptide is low-affinity nerve growth factor receptor (LNGFR, TNFRSF16) having a sequence at least 90%, 91%, 92%, 93%, 94%, 95%, 96%, 97%, 98%, 99% or 100% identity with the amino acid sequence of SEQ ID NO: 169. In some cases the signal peptide can be selected from GM-CSFRα, IgK, IgE, CD8α, T21A, CD52, low-affinity nerve growth factor receptor variants and fragments thereof.

In some embodiments, the cell tags have a signal peptide, for instance, GM-CSFRα signal peptide wherein the GM-CSFRα signal peptide is encoded from a nucleotide sequence having at least 90%, 91%, 92%, 93%, 94%, 95%, 96%, 97%, 98%, 99% or 100% identity with the nucleotide acid sequence of SEQ ID NO 20 or SEQ ID NO 21. In some embodiments, the cell tags have a signal peptide, for instance, IgK signal peptide wherein the IgK signal peptide is encoded from a nucleotide sequence having at least 90%, 91%, 92%, 93%, 94%, 95%, 96%, 97%, 98%, 99% or 100% identity with the nucleotide acid sequence of SEQ ID NO 22. In some embodiments, the cell tags have a signal peptide, for instance, IgE signal peptide wherein the IgK signal peptide is encoded from a nucleotide sequence having at least 90%, 91%, 92%, 93%, 94%, 95%, 96%, 97%, 98%, 99% or 100% identity with the nucleotide acid sequence of SEQ ID NO 23. In some embodiments, the cell tags have a signal peptide, for instance, CD8α signal peptide wherein the CD8α signal peptide is encoded from a nucleotide sequence having at least 90%, 91%, 92%, 93%, 94%, 95%, 96%, 97%, 98%, 99% or 100% identity with the nucleotide acid sequence of SEQ ID NO 24 or SEQ ID NO 25. In some embodiments, the cell tags have a signal peptide, for instance, TVB2 (T21A) signal peptide wherein the TVB2 (T21A) signal peptide is encoded from a nucleotide sequence having at least 90%, 91%, 92%, 93%, 94%, 95%, 96%, 97%, 98%, 99% or 100% identity with the nucleotide acid sequence of SEQ ID NO 26. In some embodiments, the cell tags have a signal peptide, for instance, CD52 signal peptide wherein the CD52 signal peptide is encoded from a nucleotide sequence having at least 90%, 91%, 92%, 93%, 94%, 95%, 96%, 97%, 98%, 99% or 100% identity with the nucleotide acid sequence of SEQ ID NO 27. In some embodiments, the cell tags have a signal peptide, for instance, low-affinity nerve growth factor receptor (LNGFR, TNFRSF16) signal peptide wherein the low-affinity nerve growth factor receptor (LNGFR, TNFRSF16) signal peptide is encoded from a nucleotide sequence having at least 90%, 91%, 92%, 93%, 94%, 95%, 96%, 97%, 98%, 99% or 100% identity with the nucleotide acid sequence of SEQ ID NO 28.

A signal peptide is a sequence of amino acids typically located at the N-terminus of a newly synthesized protein or polypeptide which directs the protein or polypeptide to the cell surface. In some embodiments, the signal peptide directs the polypeptide to the cell surface to be inserted (e.g., via a transmembrane domain) into the cellular membrane. In some embodiments, a polypeptide construct described herein is synthesized with the signal peptide, but then post-translationally processed to cleave the signal peptide such that the mature polypeptide construct lacks the signal peptide amino acid sequence. In other embodiments, the signal peptide sequence is not cleaved and remains in the mature polypeptide construct.

The present disclosure provides for a polypeptide construct comprising any known or unknown signal peptide capable of directing and/or trafficking the polypeptide construct to the cell surface. For example, in some embodiments, a polypeptide construct comprises a signal sequence corresponding to the signal peptide of GMCSFRα, Ig Kappa, Immunoglobulin E, CD8α, TVB2 (T21A), CD52 or Low-affinity nerve growth factor receptor (LNGFR, TNFRSF16).

In embodiments, the signal peptide is encoded by a polynucleotide comprising a nucleotide sequence which has at least 70%, 75%, 80%, 85%, 90%, 95%, 99%, or 100% identity with a nucleotide sequence selected from the list consisting of SEQ ID NO: 20-28. In embodiments, the signal peptide comprises an amino acid sequence which has at least 70%, 75%, 80%, 85%, 90%, 95%, 99%, or 100% identity with an amino acid sequence selected from the list consisting of SEQ ID NO: 163-169.

Modified Effector Cells

Provided are effector cells (also referred to as immune effector cells) modified to express one or more heterologous genes or genes regulated by gene-switch polypeptides disclosed herein.

"T cell" or "T lymphocyte" as used herein is a type of lymphocyte that plays a central role in cell-mediated immunity. They may be distinguished from other lymphocytes, such as B cells and natural killer cells (NK cells), by the presence of a T-cell receptor (TCR) on the cell surface.

In some embodiments, modified effector cells are modified immune cells that comprise T cells and/or natural killer cells. T cells or T lymphocytes are a subtype of white blood cells that are involved in cell-mediated immunity. Exemplary T cells include T helper cells, cytotoxic T cells, $T_H17$ cells, stem memory T cells (TSCM), naïve T cells, memory T cells, effector T cells, regulatory T cells, or natural killer T cells.

"T helper cells" ($T_H$ cells) assist other white blood cells in immunologic processes, including maturation of B cells into plasma cells and memory B cells, and activation of cytotoxic T cells and macrophages. In some instances, $T_H$ cells are known as CD4+ T cells due to expression of the CD4 glycoprotein on the cell surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_{FH}$, which secrete different cytokines to facilitate different types of immune responses. Signaling from the APC directs T cells into particular subtypes.

"Cytotoxic T cells" (TC cells or CTLs) destroy virus-infected cells and tumor cells, and are also implicated in transplant rejection. These cells are also known as CD8+ T cells since they express the CD8 glycoprotein on their surfaces. These cells recognize their targets by binding to antigen associated with MHC class I molecules, which are present on the surface of all nucleated cells. Through IL-10, adenosine, and other molecules secreted by regulatory T cells, the CD8+ cells can be inactivated to an anergic state, which prevents autoimmune diseases.

"Memory T cells" are a subset of antigen-specific T cells that persist long-term after an infection has resolved. They quickly expand to large numbers of effector T cells upon re-exposure to their cognate antigen, thus providing the immune system with "memory" against past infections. Memory T cells comprise subtypes: stem memory T cells (TSCM), central memory T cells (TCM cells) and two types of effector memory T cells (TEM cells and TEMRA cells). Memory cells may be either CD4+ or CD8+. Memory T cells may express the cell surface proteins CD45RO, CD45RA and/or CCR7.

"Regulatory T cells" (Treg cells), formerly known as suppressor T cells, play a role in the maintenance of immunological tolerance. Their major role is to shut down T cell-mediated immunity toward the end of an immune reaction and to suppress autoreactive T cells that escaped the process of negative selection in the thymus.

"Natural killer T cells" (NKT cells) bridge the adoptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both Th and Tc cells (i.e., cytokine production and release of cytolytic/cell killing molecules). They are also able to recognize and eliminate some tumor cells and cells infected with herpes viruses. Natural killer (NK) cells are a type of cytotoxic lymphocyte of the innate immune system. In some instances, NK cells provide a first line defense against viral infections and/or tumor formation. NK cells can detect MHC presented on infected or cancerous cells, triggering cytokine release, and subsequently induce lysis and apoptosis. NK cells can further detect stressed cells in the absence of antibodies and/or MHC, thereby allowing a rapid immune response.

Modified Effector Cell Doses

In some embodiments, an amount of modified effector cells is administered to a subject in need thereof and the amount is determined based on the efficacy and the potential of inducing a cytokine-associated toxicity. In some cases, an amount of modified effector cells comprises about $10^5$ to about $10^9$ modified effector cells/kg. In some cases, an amount of modified effector cells comprises about $10^5$ to about $10^8$ modified effector cells/kg. In some cases, an amount of modified effector cells comprises about $10^5$ to about $10^7$ modified effector cells/kg. In some cases, an amount of modified effector cells comprises about $10^6$ to about $10^9$ modified effector cells/kg. In some cases, an amount of modified effector cells comprises about $10^6$ to about $10^8$ modified effector cells/kg. In some cases, an amount of modified effector cells comprises about $10^7$ to about $10^9$ modified effector cells/kg. In some cases, an amount of modified effector cells comprises about $10^5$ to about $10^6$ modified effector cells/kg. In some cases, an amount of modified effector cells comprises about $10^6$ to about $10^7$ modified effector cells/kg. In some cases, an amount of modified effector cells comprises about $10^7$ to about $10^8$ modified effector cells/kg. In some cases, an amount of modified effector cells comprises about $10^8$ to about $10^9$ modified effector cells/kg. In some instances, an amount of modified effector cells comprises about $10^9$ modified effector cells/kg. In some instances, an amount of modified effector cells comprises about $10^8$ modified effector cells/kg. In some instances, an amount of modified effector cells comprises about $10^7$ modified effector cells/kg. In some instances, an amount of modified effector cells comprises about $10^6$ modified effector cells/kg. In some instances, an amount of modified effector cells comprises about $10^5$ modified effector cells/kg.

In some embodiments, the modified effector cells are modified T cells. In some instances, the modified T cells are CAR-T cells. In some cases, an amount of CAR-T cells comprises about $10^5$ to about $10^9$ CAR-T cells/kg. In some cases, an amount of CAR-T cells comprises about $10^5$ to about $10^8$ CAR-T cells/kg. In some cases, an amount of CAR-T cells comprises about $10^5$ to about $10^7$ CAR-T cells/kg. In some cases, an amount of CAR-T cells comprises about $10^6$ to about $10^9$ CAR-T cells/kg. In some cases, an amount of CAR-T cells comprises about $10^6$ to about $10^8$ CAR-T cells/kg. In some cases, an amount of CAR-T cells comprises about $10^7$ to about $10^9$ CAR-T cells/kg. In some cases, an amount of CAR-T cells comprises about $10^5$ to about $10^6$ CAR-T cells/kg. In some cases, an amount of CAR-T cells comprises about $10^6$ to about $10^7$ CAR-T cells/kg. In some cases, an amount of CAR-T cells comprises about $10^7$ to about $10^8$ CAR-T cells/kg. In some cases, an amount of CAR-T cells comprises about $10^8$ to about $10^9$ CAR-T cells/kg. In some instances, an amount of CAR-T cells comprises about $10^9$ CAR-T cells/kg. In some instances, an amount of CAR-T cells comprises about $10^8$ CAR-T cells/kg. In some instances, an amount of CAR-T cells comprises about $10^7$ CAR-T cells/kg. In some instances, an amount of CAR-T cells comprises about $10^6$ CAR-T cells/kg. In some instances, an amount of CAR-T cells comprises about $10^5$ CAR-T cells/kg.

In some embodiments, the CAR-T cells are CD19-specific CAR-T cells. In some cases, an amount of CD19-specific CAR-T cells comprises about $10^5$ to about $10^9$ CAR-T cells/kg. In some cases, an amount of CD19-specific CAR-T cells comprises about $10^5$ to about $10^8$ CAR-T cells/kg. In some cases, an amount of CD19-specific CAR-T cells comprises about $10^5$ to about $10^7$ CAR-T cells/kg. In some cases, an amount of CD19-specific CAR-T cells comprises about $10^6$ to about $10^9$ CAR-T cells/kg. In some cases, an amount of CD19-specific CAR-T cells comprises about $10^6$ to about $10^8$ CAR-T cells/kg. In some cases, an amount of CD19-specific CAR-T cells comprises about $10^7$ to about $10^9$ CAR-T cells/kg. In some cases, an amount of CD19-specific CAR-T cells comprises about $10^5$ to about $10^6$ CAR-T cells/kg. In some cases, an amount of CD19-specific CAR-T cells comprises about $10^6$ to about $10^7$ CAR-T cells/kg. In some cases, an amount of CD19-specific CAR-T cells comprises about $10^7$ to about $10^8$ CAR-T cells/kg. In some cases, an amount of CD19-specific CAR-T cells comprises about $10^8$ to about $10^9$ CAR-T cells/kg. In some instances, an amount of CD19-specific CAR-T cells comprises about $10^9$ CAR-T cells/kg. In some instances, an amount of CD19-specific CAR-T cells comprises about $10^8$ CAR-T cells/kg. In some instances, an amount of CD19-specific CAR-T cells comprises about $10^7$ CAR-T cells/kg. In some instances, an amount of CD19-specific CAR-T cells comprises about $10^6$ CAR-T cells/kg. In some instances, an amount of CD19-specific CAR-T cells comprises about $10^5$ CAR-T cells/kg.

In some embodiments, the modified T cells are engineered TCR T-cells. In some cases, an amount of engineered TCR T-cells comprises about $10^5$ to about $10^9$ TCR cells/kg. In some cases, an amount of engineered TCR cells comprises about $10^5$ to about $10^8$ TCR cells/kg. In some cases, an amount of engineered TCR cells comprises about $10^5$ to about $10^7$ TCR cells/kg. In some cases, an amount of engineered TCR cells comprises about $10^6$ to about $10^9$ TCR cells/kg. In some cases, an amount of engineered TCR cells comprises about $10^6$ to about $10^8$ TCR cells/kg. In some cases, an amount of engineered TCR cells comprises about $10^7$ to about $10^9$ TCR cells/kg. In some cases, an amount of engineered TCR cells comprises about $10^5$ to about $10^6$ TCR cells/kg. In some cases, an amount of engineered TCR cells comprises about $10^6$ to about $10^7$ TCR cells/kg. In some cases, an amount of engineered TCR cells comprises about $10^7$ to about $10^8$ TCR cells/kg. In some cases, an amount of engineered TCR cells comprises about $10^8$ to about $10^9$ TCR cells/kg. In some instances, an amount of engineered TCR cells comprises about $10^9$ TCR cells/kg. In some instances, an amount of engineered TCR cells comprises about $10^8$ TCR cells/kg. In some instances, an amount of engineered TCR cells comprises about $10^7$ TCR cells/kg. In some instances, an amount of engineered TCR cells comprises about $10^6$ TCR cells/kg. In some instances, an amount of engineered TCR cells comprises about $10^5$ TCR cells/kg.

Indications

In some embodiments, disclosed herein are methods of administering a modified effector cell encoding a polynucleotide described herein to a subject having a disorder, for instance a cancer or an infectious disease. In some cases, the cancer is a cancer associated with an expression of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MAGE-A1, MUC16, h5T4, PSMA, TAG-72, EGFRvIII, CD123 or VEGF-R2.

In some embodiments, disclosed herein are methods of administering a polynucleotide, polypeptide or a modified effector cell encoding a polynucleotide described herein, to a subject having a cancer associated with an overexpression of CD19. In some embodiments, disclosed herein are methods of administering a modified effector cell to a subject having a cancer associated with an overexpression of CD33. In some embodiments, disclosed herein are methods of administering a modified effector cell to a subject having a cancer associated with an overexpression of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MAGE-A1, MUC16, h5T4, PSMA, TAG-72, EGFRvIII, CD123 or VEGF-R2. In some cases, the cancer is a metastatic cancer. In other cases, the cancer is a relapsed or refractory cancer.

In some cases, a cancer is a solid tumor or a hematologic malignancy. In some instances, the cancer is a solid tumor. In other instances, the cancer is a hematologic malignancy. In some cases, the cancer is a metastatic cancer. In some cases, the cancer is a relapsed or refractory cancer.

In some instances, the cancer is a solid tumor. Exemplary solid tumors include, but are not limited to, anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; gastroenterological cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; vulvar cancer; or glioblastoma.

"Glioblastoma" or "glioblastoma multiforme" (GBM) is an aggressive neuroepithelial brain cancer. GBM may originate from glial type cells, astrocytes, oligodendrocyte progenitor cells, or neural stem cells. Four subtypes of glioblastoma have been identified. The classical subtype, a majority of GBM, carries extra copies of the epidermal growth factor receptor (EGFR) gene, and most have higher than normal expression of epidermal growth factor receptor (EGFR). In a subset of the cases, EGFR amplification is accompanied by gene rearrangement, the most common of which is EGFR variant III (EGFRvIII). The gene TP53 (p53), which is often mutated in glioblastoma, is rarely mutated in the classical subtype. The proneural subtype often has high rates of alterations in TP53 (p53), and in PDGFRA, the gene encoding platelet-derived growth factor receptor A, and in IDH1, the gene encoding isocitrate dehydrogenase-1. The Mesenchymal subtype is characterized by high rates of mutations or other alterations in NF1, the gene encoding neurofibromin 1 and fewer alterations in the EGFR gene and less expression of EGFR than other types. The Neural subtype was typified by the expression of neuron markers such as NEFL, GABRA1, SYT1 and SLC12A5. Other genetic alterations have been described in glioblastoma, and the majority of them are clustered in two pathways, the RB and the PI3K/AKT. Glioblastomas have alterations in 68-78% and 88% of these pathways, respectively.

In some instances, the cancer is a hematologic malignancy. In some cases, a hematologic malignancy comprises a lymphoma, a leukemia, a myeloma, or a B-cell malignancy. In some cases, a hematologic malignancy comprises a lymphoma, a leukemia or a myeloma. In some instances, exemplary hematologic malignancies include chronic lymphocytic leukemia (CLL), small lymphocytic lymphoma (SLL), high risk CLL, non-CLL/SLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the hematologic malignancy comprises a myeloid leukemia. In some embodiments, the hematologic malignancy comprises acute myeloid leukemia (AML) or chronic myeloid leukemia (CML).

In some instances, disclosed herein are methods of administering to a subject having a hematologic malignancy selected from chronic lymphocytic leukemia (CLL), small lymphocytic lymphoma (SLL), high risk CLL, non-CLL/SLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis a modified effector cell described herein. In some instances, disclosed herein are methods of administering to a subject having a hematologic malignancy selected from AML or CML a modified effector cell to the subject.

In other cases, disclosed herein are methods of administering to a subject having an infection due to an infectious disease. An infectious disease can be a disease resulting from a bacterial, viral or fungi infection. In other instances, exemplary viral pathogens include those of the families of Adenoviridae, Epstein-Barr virus (EBV), Cytomegalovirus (CMV), Respiratory Syncytial Virus (RSV), JC virus, BK virus, HSV, HHV family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis*, and *Stachybotrys*. Exemplary pathogenic bacteria include *Streptococcus, Pseudomonas, Shigella, Campylobacter, Staphylococcus, Helicobacter, E. coli, Rickettsia, Bacillus, Bordetella, Chlamydia, Spirochetes*, and *Salmonella*.

Viral Based Delivery System

The present disclosure also provides delivery systems, such as viral-based systems, in which a nucleic acid described herein is inserted. Representative viral expression vectors include, but are not limited to, adeno-associated viral vectors, adenovirus-based vectors (e.g., the adenovirus-based Per.C6 system available from Crucell, Inc. (Leiden, The Netherlands)), lentivirus-based vectors (e.g., the lentiviral-based pLPI from Life Technologies (Carlsbad, Calif.)), retroviral vectors (e.g., the pFB-ERV plus pCFB-EGSH), and herpes virus-based vectors. In an embodiment, the viral vector is a lentivirus vector. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In an additional embodiment, the viral vector is an adeno-associated viral vector. In a further embodiment, the viral vector is a retroviral vector. In general, and in embodiments, a suitable vector contains an origin of replication functional in at least one organism, a promoter sequence, convenient restriction endonuclease sites, and one or more selectable markers. (e.g., WO 01/96584, WO 01/29058, and U.S. Pat. No. 6,326,193).

Additional suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNATM5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.). Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto.

Another example of a suitable promoter is human elongation growth factor 1 alpha 1 (hEF1a1). In embodiments, the vector construct comprising the CARs and/or TCRs of the present disclosure comprises hEF1a1 functional variants.

However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the present disclosure should not be limited to the use of constitutive promoters. Inducible promoters are also contemplated as part of the present disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Other examples of inducible promoters include, but are not limited to tissue specific promoters as described herein. In some embodiments, the promoter comprises NF-κB binding site (SEQ ID NOS 44-46), nuclear factor of activated T cells (NFAT) response element (SEQ ID NO 51), 6 site GAL4-inducible proximal factor binding element (PFB) (SEQ ID NO 62) or synthetic 5' UTR based on RPL6 (SEQ ID NO 64). In certain embodiments, the promoter can be any one or more of: IL-2 core promoter, IL-2 minimal promoter, IL-2 enhancer and promoter variant, $(NF\text{-}\kappa B)_1$-IL2 promoter variant, $(NF\text{-}\kappa B)_3$-IL2 promoter variant, $(NF\text{-}\kappa B)_6$-IL2 promoter variant, 1×NFAT response elements-IL2 promoter variant, 3×NFAT response elements-IL2 promoter variant, 6×NFAT response elements-IL2 promoter variant, human EEF1A1 promoter variant, human EEF1A promoter and enhancer, human UBC promoter and synthetic minimal promoter 1. In certain embodiments, the promoter nucleotides comprise disclosed in Table 2.

In order to assess the expression of a CAR or TCR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neomycin resistance gene (neo) and ampicillin resistance gene and the like. In some embodiments, a truncated epidermal growth factor receptor (HER1t) tag may be used as a selectable marker gene.

Reporter genes can be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., FEBS Letters 479: 79-82 (2000)). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, the vectors comprise a hEF1a1 promoter to drive expression of transgenes, a bovine growth hormone polyA sequence to enhance transcription, a woodchuck hepatitis virus posttranscriptional regulatory element (WPRE), as well as LTR sequences derived from the pFUGW plasmid.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York (2001)). In embodiments, a method for the introduction of a polynucleotide into a host cell is calcium phosphate transfection or polyethylenimine (PEI) Transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., Glycobiology 5: 505-10 (1991)). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Non-Viral Based Delivery System

In some instances, polynucleotides encoding gene-switch polypeptides for expressing CARs and/or TCRs described herein can also be introduced into T cells using non-viral based delivery systems, such as the "Sleeping Beauty (SB) Transposon System," which refers a synthetic DNA transposon system for introducing DNA sequences into the chromosomes of vertebrates. Some exemplary embodiments of the system are described, for example, in U.S. Pat. Nos. 6,489,458, 8,227,432, 9,228,180 and WO2016/145146. The Sleeping Beauty transposon system is composed of a Sleeping Beauty (SB) transposase and a SB transposon. In embodiments, the Sleeping Beauty transposon system can include the SB11 transposon system, the SB100X transposon system, or the SB110 transposon system and any other variants thereof.

DNA transposons translocate from one DNA site to another in a simple, cut-and-paste manner. Transposition is a precise process in which a defined DNA segment is excised from one DNA molecule and moved to another site in the same or different DNA molecule or genome. As do other Tc1/mariner-type transposases, SB transposase inserts a transposon into a TA dinucleotide base pair in a recipient DNA sequence. The insertion site can be elsewhere in the same DNA molecule, or in another DNA molecule (or chromosome). In mammalian genomes, including humans, there are approximately 200 million TA sites. The TA insertion site is duplicated in the process of transposon integration. This duplication of the TA sequence is a hallmark of transposition and used to ascertain the mechanism in some experiments. The transposase can be encoded either within the transposon or the transposase can be supplied by another source, for instance a DNA or mRNA source, in which case the transposon becomes a non-autonomous element. Non-autonomous transposons are most useful as genetic tools because after insertion they cannot independently continue to excise and re-insert. SB transposons envisaged to be used as non-viral vectors for introduction of genes into genomes of vertebrate animals and for gene therapy. Briefly, the Sleeping Beauty (SB) system (Hackett et al., Mol Ther 18:674-83, (2010)) was adapted to genetically modify the T cells (Cooper et al., Blood 105:1622-31, (2005)). This involved two steps: (i) the electro-transfer of DNA plasmids expressing a SB transposon [i.e., chimeric antigen receptor (CAR) to redirect T-cell specificity (Jin et al., Gene Ther 18:849-56, (2011); Kebriaei et al., Hum Gene Ther 23:444-50, (2012)) and SB transposase and (ii) the propagation and expansion of T cells stably expressing integrants on designer artificial antigen-presenting cells (AaPC) derived from the K562 cell line (also known as AaPCs (Activating and Propagating Cells). In one embodiment, the SB transposon system includes coding sequence encoding tdIL-15, an IL-21 and/or a chimeric antigen receptor. Such systems are described for example in Singh et al., Cancer Res (8):68 (2008). Apr. 15, 2008 and Maiti et al., J Immunother. 36(2): 112-123 (2013), incorporated herein by reference in their entireties.

In some embodiments, a polynucleotide encoding a CAR or a TCR, one or more gene-switch polypeptides and mbIL-15 is encoded in one or more Sleeping Beauty transposon(s), and the SB transposase is encoded in a separate vector. In embodiments, the CD19 specific CAR is encoded in a transposon DNA plasmid vector, mb-IL15 is encoded in a second transposon DNA plasmid vector, and the SB transposase is encoded in a third DNA plasmid vector. In some embodiments, the mbIL-15 is encoded with a cell tag. Examples of cell tags can include truncated epidermal growth factor receptor tag (HER1t), HER1t1, HER1t2, HER1t3, HER1t4, HER1t5, HER1t6, HER1t7, HER1t8, HER1t9, HER1t10, HER1t11, CD20 and CD20t1. CD20 tag or any other appropriate cell tags for use as a depletion or kill switch, or enrichment marker. Non-limiting exemplary gene switch vector system comprising a cell tag is illustrated in FIG. 2A-2D, FIG. 3, FIG. 19A-19B, FIG. 20A, FIG. 22, FIG. 24A-24D, and FIG. 25A-25B.

In some embodiments, HER1t provides a safety mechanism by allowing for depletion of infused CAR-T cells through administering FDA approved cetuximab or any antibody that recognizes HER1t. In some embodiments, CD20 also provides a safety mechanism by allowing for depletion of infused CAR-T cells through administering FDA-approved rituximab therapy.

Regardless of the method used to introduce exogenous nucleic acids into a host cell or otherwise expose a cell to the inhibitor of the present disclosure, in order to confirm the presence of the recombinant DNA sequence in the host cell, a variety of assays may be performed. Such assays include, for example, molecular assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the present disclosure. In embodiments, a modified effector cell described herein and other genetic elements are delivered to a cell using the SB11 transposon system, the SB100X transposon system, the SB110 transposon system, the piggyBac transposon system (see, e.g., Wilson et al, "PiggyBac Transposon-mediated Gene Transfer in Human Cells," Molecular Therapy 15:139-145 (2007), incorporated herein by reference in its entirety) and/or the piggyBac transposon system (see, e.g., Mitra et al., "Functional characterization of piggyBac from the bat *Myotis lucifugus* unveils an active mammalian DNA transposon," Proc. Natl. Acad. Sci USA 110:234-239 (2013). Additional transposases and transposon systems are provided in U.S. Pat. Nos. 6,489,458; 6,613,752, 7,148,203; 7,985,739; 8,227,432; 9,228,180; U.S. Patent Publn. No. 2011/0117072; Mates et al., Nat Genet, 41(6):753-61 (2009). doi: 10.1038/ng.343. Epub 2009 May 3, Gene Ther., 18(9):849-56 (2011). doi: 10.1038/gt.2011.40. Epub 2011 Mar. 31 and in Ivics et al., Cell. 91(4):501-10, (1997), each of which is incorporated herein by reference in their entirety.

Additional suitable non-viral systems can include integrating expression vectors, which may randomly integrate into the host cell's DNA, or may include a recombination site to enable the specific recombination between the expression vector and the host cell's chromosome. Targeted integration of transgenes into predefined genetic loci is a desirable goal for many applications. First, a first recombination site for a site-specific recombinase is inserted at a genomic site, either at a random or at a predetermined location. Subsequently, the cells are transfected with a plasmid carrying the gene or DNA of interest and the second recombination site and a source for recombinase (expression plasmid, RNA, protein, or virus-expressing recombinase). Recombination between the first and second recombination sites leads to integration of plasmid DNA.

Such integrating expression vectors may utilize the endogenous expression control sequences of the host cell's chromosomes to effect expression of the desired protein. In some embodiments, targeted integration is promoted by the presence of sequences on the donor polynucleotide that are homologous to sequences flanking the integration site. For example, targeted integration using the donor polynucleotides described herein may be achieved following conventional transfection techniques, e.g. techniques used to create gene knockouts or knockins by homologous recombination. In other embodiments, targeted integration is promoted both by the presence of sequences on the donor polynucleotide that are homologous to sequences flanking the integration site, and by contacting the cells with donor polynucleotide in the presence of a site-specific recombinase. By a site-specific recombinase, or simply a recombinase, it is meant is a polypeptide that catalyzes conservative site-specific recombination between its compatible recombination sites. As used herein, a site-specific recombinase includes native polypeptides as well as derivatives, variants and/or fragments that retain activity, and native polynucleotides, derivatives, variants, and/or fragments that encode a recombinase that retains activity.

Also provided herein is a system for integrating heterologous genes in a host cell, said system comprising one or more gene expression cassettes. In some instances, the system includes a first gene expression cassette comprising a first polynucleotide encoding a first polypeptide construct. In other instances, the system can include a second gene expression cassette comprising a second polynucleotide encoding a second polypeptide construct. In yet other instances, the system can include a third gene expression cassette. In one embodiment, one of the gene expression cassettes can comprise a gene switch polynucleotide encoding one or more of: (i) a transactivation domain; (ii) nuclear receptor ligand binding domain; (iii) a DNA-binding domain; and (iv) ecdysone receptor binding domain. In another embodiment, the system further includes recombinant attachment sites; and a serine recombinase; such that upon contacting said host cell with at least said first gene expression cassette, in the presence of said serine recombinase, said heterologous genes are integrated in said host cell.

In some instances, the system further comprises a ligand; such that upon contacting said host cell, in the presence of said ligand, said heterologous gene are expressed in said host cell. In one instance, the system also includes recombinant attachment sites. In some instances, one recombination attachment site is a phage genomic recombination attachment site (attP) or a bacterial genomic recombination attachment site (attB). In one instance, the host cell is an eukaryotic cell. In another instance, the host cell is a human cell. In further instances, the host cell is a T cell or NK cell.

In one embodiment, the heterologous gene in the system described above comprises a CAR. In some embodiments, the CAR binds at least one of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MAGE-A1, MUC16, h5T4, PSMA, TAG-72, EGFRvIII, CD123 or VEGF-R2.

In another embodiment, the system includes a heterologous gene comprising a cytokine. In one instance, the cytokine comprises at least one of IL-15, IL-12, IL-21, and a fusion of IL-15 and IL-15Rα. In one embodiment, the system includes a heterologous gene comprising at least one cell tag. In one instance, said cell tag comprises at least one of HER1t and CD20. In some embodiments, the mbIL-15 is encoded with a cell tag. Examples of cell tags can include truncated epidermal growth factor receptor tag (HER1t), CD20 tag or any other appropriate cell tags for use as a depletion or kill switch, or enrichment marker. Exemplary sequences of cell tags are as below:

TABLE 3

Cell tag amino acid sequences and polynucleotide sequences

| Cell Tag Name | SEQ ID NO | Polynucleotide Sequence (5' to 3' where applicable) | SEQ ID NO | Amino Acids Sequence (5' to 3' where applicable) |
|---|---|---|---|---|
| Truncated EGFR (huEGFRt) (Merit) | 76 | CGCAAAGTGTGTAACGGAA<br>TAGGTATTGGTGAATTTAA<br>AGACTCACTCTCCATAAAT<br>GCTACGAATATTAAACACT<br>TCAAAAACTGCACCTCCAT<br>CAGTGGCGATCTCCACATC<br>CTGCCGGTGGCATTTAGGG<br>GTGACTCCTTCACACATACT<br>CCTCCTCTGGATCCACAGG<br>AACTGGATATTCTGAAAAC<br>CGTAAAGGAAATCACAGGG<br>TTTTTGCTGATTCAGGCTTG<br>GCCTGAAAACAGGACGGAC<br>CTCCATGCCTTTGAGAACCT<br>AGAAATCATACGCGGCAGG<br>ACCAAGCAACATGGTCAGT<br>TTTCTCTTGCAGTCGTCAGC<br>CTGAACATAACATCCTTGG<br>CTATTACGCTCCCTCAAGGA<br>GATAAGTGATGGAGATGTG<br>ATAATTTCAGGAAACAAAA<br>ATTTGTGCTATGCAAATACA<br>ATAAACTGGAAAAAACTGT<br>TTGGGACCTCCGGTCAGAA<br>AACCAAAATTATAAGCAAC<br>AGAGGTGAAAACAGCTGCA<br>AGGCCACAGGCCAGGTCTG<br>CCATGCCTTGTGCTCCCCCG<br>AGGGCTGCTGGGGCCCGGA<br>GCCCAGGGACTGCGTCTCTT<br>GCCGGAATGTCAGCCGAGG<br>CAGGGAATGCGTGGACAAG<br>TGCAACCTTCTGGAGGGTG<br>AGCCAAGGGAGTTTGTGGA<br>GAACTCTGAGTGCATACAG<br>TGCCACCCAGAGTGCCTGC<br>CTCAGGCCATGAACATCAC<br>CTGCACAGGACGGGGACCA<br>GACAACTGTATCCAGTGTG<br>CCCACTACATTGACGGCCC<br>CCACTGCGTCAAGACCTGC<br>CCGGCAGGAGTCATGGGAG<br>AAAACAACACCCTGGTCTG<br>GAAGTACGCAGACGCCGGC<br>CATGTGTGCCACCTGTGCCA<br>TCCAAACTGCACCTACGGA<br>TGCACTGGGCCAGGTCTTG<br>AAGGCTGTCCAACGAATGG<br>GCCTAAGATCCCGTCCATC<br>GCCACTGGGATGGTGGGGG<br>CCCTCCTCTTGCTGCTGGTG<br>GTGGCCCTGGGGATCGGCC<br>TCTTCATG | 189 | RKVCNGIGIGEFKDSLSINA<br>TNIKHFKNCTSISGDLHILP<br>VAFRGDSFTHTPPLDPQEL<br>DILKTVKEITGFLLIQAWPE<br>NRTDLHAFENLEIIRGRTK<br>QHGQFSLAVVSLNITSLGL<br>RSLKEISDGDVIISGNKNLC<br>YANTINWKKLFGTSGQKT<br>KIISNRGENSCKATGQVCH<br>ALCSPEGCWGPEPRDCVCH<br>RNVSRGRECVDKCNLLEG<br>EPREFVENSECIQCHPECLP<br>QAMNITCTGRGPDNCIQCA<br>HYIDGPHCVKTCPAGVMG<br>ENNTLVWKYADAGHVCH<br>LCHPNCTYGCTGPGLEGCP<br>TNGPKIPSIATGMVGALLL<br>LLVVALGIGLFM |
| EGFR truncated design 1 (Her1 truncated design 1)(HER1t1) | 77 | CGCAAAGTGTGTAACGGAA<br>TAGGTATTGGTGAATTTAA<br>AGACTCACTCTCCATAAAT<br>GCACGAATATTAAACACT<br>TCAAAAACTGCACCTCCAT<br>CAGTGGCGATCTCCACATC<br>CTGCCGGTGGCATTTAGGG<br>GTGACTCCTTCACACATACT<br>CCTCCCTCTGGATCCACAGG<br>AACTGGATATTCTGAAAAC<br>CGTAAAGGAAATCACAGGG<br>TTTTTGCTGATTCAGGCTTG<br>GCCTGAAAACAGGACGGAC<br>CTCCATGCCTTTGAGAACCT<br>AGAAATCATACGCGCAGG<br>ACCAAGCAACATGGTCAGT<br>TTTCTCTTGCAGTCGTCAGC<br>CTGAACATAACATCCTTGG<br>GATTACGCTCCCTCAAGGA<br>GATAAGTGATGGAGATGTG | 190 | RKVCNGIGIGEFKDSLSINA<br>TNIKHFKNCTSISGDLHILP<br>VAFRGDSFTHTPPLDPQEL<br>DILKTVKEITGFLLIQAWPE<br>NRTDLHAFENLEIIRGRTK<br>QHGQFSLAVVSLNITSLGL<br>RSLKEISDGDVIISGNKNLC<br>YANTINWKKLFGTSGQKT<br>KIISNRGENSCKATGQVCH<br>ALCSPEGCWGPEPRDCVSG<br>GGGSGGGGSGGGGSGGGG<br>SFWVLVVVGGVLACYSLL<br>VTVAFIIFWVRSKRS |

TABLE 3-continued

| Cell tag amino acid sequences and polynucleotide sequences | | | | |
|---|---|---|---|---|
| Cell Tag Name | SEQ ID NO | Polynucleotide Sequence (5' to 3' where applicable) | SEQ ID NO | Amino Acids Sequence (5' to 3' where applicable) |
| | | ATATTTCAGGAAACAAAA ATTTGTGCTATGCAAATACA ATAAACTGGAAAAAACTGT TTGGGACCTCCGGTCAGAA AACCAAAATTATAAGCAAC AGAGGTGAAAACAGCTGCA AGGCCACAGGCCAGGTCTG CCATGCCTGTGCTCCCCCG AGGGCTGCTGGGGCCCGGA GCCCAGGGACTGCGTCTCT GGTGGCGGTGGCTCGGGCG GTGGTGGGTCGGGTGGCGG CGGATCTGGTGGCGGTGGC TCGTTTTGGGTGCTGGTGGT GGTTGGTGGAGTCCTGGCTT GCTATAGCTTGCTAGTAAC AGTGGCCTTTATTATTTTCT GGGTGAGGAGTAAGAGGAG C | | |
| EGFR truncated design 2 (Her1 truncated design 2)(HER1t2) | 78 | CGCAAAGTGTGTAACGGAA TAGGTATTGGTGAATTTAA AGACTCACTCTCCATAAAT GCTACGAATATTAAACACT TCAAAAACTGCACCTCCAT CAGTGGCGATCTCCACATC CTGCCGGTGGCATTTAGGG GTGACTCCTTCACACATACT CCTCCTCTGGATCCACAGG AACTGGATATTCTGAAAAC CGTAAAGGAAATCACAGGG TTTTTGCTGATTCAGGCTTG GCCTGAAAACAGGACGGAC CTCCATGCCTTTGAGAACCT AGAAATCATACGCGGCAGG ACCAAGCAACATGGTCAGT TTTCTCTTGCAGTCGTCAGC CTGAACATAACATCCTTGG GATTACGCTCCCTCAAGGA GATAAGTGATGGAGATGTG ATAATTTCAGGAAACAAAA ATTTGTGCTATGCAAATACA ATAAACTGGAAAAAACTGT TTGGGACCTCCGGTCAGAA AACCAAAATTATAAGCAAC AGAGGTGAAAACAGCTGCA AGGCCACAGGCCAGGTCTG CCATGCCTTGTGCTCCCCCG AGGGCTGCTGGGGCCCGGA GCCCAGGGACTGCGTCTCTT GCCGGAATGTCAGCCGAGG CAGGGAATGCGTGGACAAG GGTGGCGGTGGCTCGGGCG GTGGTGGGTCGGGTGGCGG CGGATCTGGTGGCGGTGGC TCGTTTTGGGTGCTGGTGGT GGTTGGTGGAGTCCTGGCTT GCTATAGCTTGCTAGTAAC AGTGGCCTTTATTATTTTCT GGGTGAGGAGTAAGAGGAG C | 191 | RKVCNGIGIGEFKDSLSINA TNIKHFKNCTSISGDLHILP VAFRGDSFTHTPPLDPQEL DILKTVKEITGFLLIQAWPE NRTDLHAFENLEIIRGRTK QHGQFSLAVVSLNITSLGL RSLKEISDGDVIISGNKNLC YANTINWKKLFGTSGQKT KIISNRGENSCKATGQVCH ALCSPEGCWGPEPRDCVSC RNVSRGRECVDKGGGGSG GGGSGGGGSGGGGSFWVL VVVGGVLACYSLLVTVAFI IFWVRSKRS |
| EGFR truncated design 3 (Her1 truncated design 3)(HER1t3) | 79 | CGCAAAGTGTGTAACGGAA TAGGTATTGGTGAATTTAA AGACTCACTCTCCATAAAT GCTACGAATATTAAACACT TCAAAAACTGCACCTCCAT CAGTGGCGATCTCCACATC CTGCCGGTGGCATTTAGGG GTGACTCCTTCACACATACT CCTCCTCTGGATCCACAGG AACTGGATATTCTGAAAAC CGTAAAGGAAATCACAGGG TTTTTGCTGATTCAGGCTTG | 192 | RKVCNGIGIGEFKDSLSINA TNIKHFKNCTSISGDLHILP VAFRGDSFTHTPPLDPQEL DILKTVKEITGFLLIQAWPE NRTDLHAFENLEIIRGRTK QHGQFSLAVVSLNITSLGL RSLKEISDGDVIISGNKNLC YANTINWKKLFGTSGQKT KIISNRGENSCKATGQVCH ALCSPEGCWGPEPRDCVSC RNVSRGRECVDKCNLLEG EPREFVENSECIQGGGGSG |

TABLE 3-continued

| Cell tag amino acid sequences and polynucleotide sequences | | | | |
|---|---|---|---|---|
| Cell Tag Name | SEQ ID NO | Polynucleotide Sequence (5' to 3' where applicable) | SEQ ID NO | Amino Acids Sequence (5' to 3' where applicable) |
| | | GCCTGAAAACAGGACGGAC CTCCATGCGTTTGAGAACCT AGAAATCATACGCGGCAGG ACCAAGCAACATGGTCAGT TTTCTCTTGCAGTCGTCAGC CTGAACATAACATCCTTGG GATTACGCTCCCTCAAGGA GATAAGTGATGGAGATGTG ATAATTTCAGGAAACAAAA ATTTGTGCTATGCAAATACA ATAAACTGGAAAAAACTGT TTGGGACCTCCGGTCAGAA AACCAAAATTATAAGCAAC AGAGGTGAAAACAGCTGCA AGGCCACAGGCCAGGTCTG CCATGCCTTGTGCTCCCCCG AGGGCTGCTGGGGCCCGGA GCCCAGGGACTGCGTCTCTT GCCGGAATGTCAGCCGAGG CAGGGAATGCGTGGACAAG TGCAACCTTCTGGAGGGTG AGCCAAGGGAGTTTGTGGA GAACTCTGAGTGCATACAG GGTGGCGGTGGCTCGGGCG GTGGTGGGTCGGGTGGCGG CGGATCTGGTGGCGGTGGC TCGTTTTGGGTGCTGGTGGT GGTTGGTGGAGTCCTGGCTT GCTATAGCTTGCTAGTAAC AGTGGCCTTTATTATTTTCT GGGTGAGGAGTAAGAGGAG C | | GGGSGGGGSGGGGSFWVL VVVGGVLACYSLLVTVAFI IFWVRSKRS |
| EGFR truncated design 4 (Her1 truncated design 4)(HER1t4) | 8 | CGCAAAGTGTGTAACGGAA TAGGTATTGGTGAATTTAA AGACTCACTCTCCATAAAT GCTACGAATATTAAACACT TCAAAAACTGCACCTCCAT CAGTGGCGATCTCCACATC CTGCCGGTGGCATTTAGGG GTGACTCCTTCACACATACT CCTCCTCTGGATCCACAGG AACTGGATATTCTGAAAAC CGTAAAGGAAATCACAGGG TTTTTGCTGATTCAGGCTTG GCCTGAAAACAGGACGGAC CTCCATGCCTTTGAGAACCT AGAAATCATACGCGGCAGG ACCAAGCAACATGGTCAGT TTTCTCTTGCAGTCGTCAGC CTGAACATAACATCCTTGG GATTACGCTCCCTCAAGGA GATAAGTGATGGAGATGTG ATAATTTCAGGAAACAAAA ATTTGTGCTATGCAAATACA ATAAACTGGAAAAAACTGT TTGGGACCTCCGGTCAGAA AACCAAAATTATAAGCAAC AGAGGTGAAAACAGCTGCA AGGCCAGAGGCCAGGTCTG CCATGCCTTGTGCTCCCCCG AGGGCTGCTGGGGCCCGGA GCCCAGGGACTGCGTCTCTT GCCGGAATGTCAGCCGAGG CAGGGAATGCGTGGACAAG TGCAACCTTCTGGAGGGTG AGCCAAGGGAGTTTGTGGA GAACTCTGAGTGCATACAG TGCCACCCAGAGTGCCTGC CTCAGGCCATGAACATCAC CTGCACAGGACGGGGACCA GACAACTGTATCCAGGGCG GAGGCGGAAGCGGAGGCG GAGGCTCCGGCGGAGGCGG | 193 | RKVCNGIGIGEFKDSLSINA TNIKHFKNCTSISGDLHILP VAFRGDSFTHTPPLDPQEL DILKTVKEITGFLLIQAWPE NRTDLHAFENLEIIRGRTK QHGQFSLAVVSLNITSLGL RSLKEISDGDVIISGNKNLC YANTINWKKLFGTSGQKT KIISNRGENSCKATGQVCH ALCSPEGCWGPEPRDCVSC RNVSRGRECVDKCNLLEG EPREFVENSECIQCHPECLP QAMNITCTGRGPDNCIQGG GGSGGGGSGGGGSFWVLV VVGGVLACYSLLVTVAFII FWVRSKRS |

TABLE 3-continued

Cell tag amino acid sequences and polynucleotide sequences

| Cell Tag Name | SEQ ID NO | Polynucleotide Sequence (5' to 3' where applicable) | SEQ ID NO | Amino Acids Sequence (5' to 3' where applicable) |
|---|---|---|---|---|
| | | AAGCTTTTGGGTGCTGGTG<br>GTGGTTGGTGGAGTCCTGG<br>CTTGCTATAGCTTGCTAGTA<br>ACAGTGGCCTTTATTATTTT<br>CTGGGTGAGGAGTAAGAGG<br>AGC | | |
| EGFR truncated design 5 (Her1 truncated design 5)(HER1t5) | 81 | CGCAAAGTGTGTAACGGAA<br>TAGGTATTGGTGAATTTAA<br>AGACTCACTCTCCATAAAT<br>GCTACGAATATTAAACACT<br>TCAAAAACTGCACCTCCAT<br>CAGTGGCGATCTCCACATC<br>CTGCCGGTGGCATTTAGGG<br>GTGACTCCTTCACACATACT<br>CCTCCTCTGGATCCACAGG<br>AACTGGATATTCTGAAAAC<br>CGTAAAGGAAATCACAGGG<br>TTTTTGCTGATTCAGGCTTG<br>GCCTGAAAACAGGACGGAC<br>CTCCATGCCTTTGAGAACCT<br>AGAAATCATACGCGGCAGG<br>ACCAAGCAACATGGTCAGT<br>TTTCTCTTGCAGTCGTCAGC<br>CTGAACATAACATCCTTGG<br>GATTACGCTCCCTCAAGGA<br>GATAAGTGATGGAGATGTG<br>ATAATTTCAGGAAACAAAA<br>ATTTGTGCTATGCAAATACA<br>ATAAACTGGAAAAAACTGT<br>TTGGGACCTCCGGTCAGAA<br>AACCAAAATTATAAGCAAC<br>AGAGGTGAAAACAGCTGCA<br>AGGCCACAGGCCAGGTCTG<br>CCATGCCTTGTGCTCCCCCG<br>AGGGCTGCTGGGGCCCGGA<br>GCCCAGGGACTGCGTCTCTT<br>GCCGGAATGTCAGCCGAGG<br>CAGGGAATGCGTGGACAAG<br>TGCAACCTTCTGGAGGGTG<br>AGCCAAGGGAGTTTGTGGA<br>GAACTCTGAGTGCATACAG<br>TGCCACCCAGAGTGCCTGC<br>CTCAGGCCATGAACATCAC<br>CTGCACAGGACGGGGACCA<br>GACAACTGTATCCAGTGTG<br>CCCACTACATTGACGGCCC<br>CCACTGCGTCAAGACCGGC<br>GGAGGCGGAAGCGGAGGC<br>GGAGGCTCCGGCGGAGGCG<br>GAAGCTTTTGGGTGCTGGT<br>GGTGGTTGGTGGAGTCCTG<br>GCTTGCTATAGCTTGCTAGT<br>AACAGTGGCCTTTATTATTT<br>TCTGGGTGAGGAGTAAGAG<br>GAGC | 194 | RKVCNGIGIGEFKDSLSINA<br>TNIKHFKNCTSISGDLHILP<br>VAFRGDSFTHTPPLDPQEL<br>DILKTVKEITGFLLIQAWPE<br>NRTDLHAFENLEIIRGRTK<br>QHGQFSLAWSLNITSLGL<br>RSLKEISDGDVIISGNKNLC<br>YANTESTWKKLFGTSGQKT<br>KIISNRGENSCKATGQVCH<br>ALCSPEGCWGPEPRDCVSC<br>RNVSRGRECVDKCNLLEG<br>EPREFVENSEGQCHPECLP<br>QAMNITCTGRGPDNCIQCA<br>HYIDGPHCVKTGGGGSGG<br>GGSGGGGSFWVLVVVGGV<br>LACYLLVTVAFIIFWVRS<br>KRS |
| EGFR truncated design 6 (Her1 truncated design 6)(HER1t6) | 82 | CGCAAAGTGTGTAACGGAA<br>TAGGTATTGGTGAATTTAA<br>AGACTCACTCTCCATAAA<br>GCTACGAATATTAAACACT<br>TCAAAAACTGCACCTCCAT<br>CAGTGGCGATCTCCACATC<br>CTGCCGGTGGCATTTAGGG<br>CTTGACTCCTTCACACATACT<br>CCTCCTCTGGATCCACAGG<br>AACTGGATATTCTGAAAAC<br>CGTAAAGGAAATCACAGGG<br>TTTTTGCTGATTCAGGCTTG<br>GCCTGAAAACAGGACGGAC | 195 | RKVCNGIGIGEFKDSLSINA<br>TNIKHFKNCTSISGDLHILP<br>VAFRGDSFTHTPPLDPQE<br>DILKTVKEITGFLLIQAWPE<br>NRTDLFIAFENLEIIRGRTK<br>QHGQFSLAWSLNITSLGL<br>RSLKEISDGDVIISGNKNLC<br>YANTINWKKLFGTSGQKT<br>KIISNRGENSCKATGQVCH<br>ALCSPEGCWGPEPRDCVSC<br>RNVSRGRECVDKCNLLEG<br>EPREFVENSECIQCHPECLP<br>QAVINITCTGRGPDNCFQCA |

TABLE 3-continued

Cell tag amino acid sequences and polynucleotide sequences

| Cell Tag Name | SEQ ID NO | Polynucleotide Sequence (5' to 3' where applicable) | SEQ ID NO | Amino Acids Sequence (5' to 3' where applicable) |
|---|---|---|---|---|
| | | CTCCATGCCTTTGAGAACCT<br>AGAAATCATACGCGGCAGG<br>ACCAAGCAACATGGTCAGT<br>TTTCTCTTGCAGTCGTCAGC<br>CTGAACATAACATCCTTGG<br>GATTACGCTCCCTCAAGGA<br>GATAAGTGATGGAGATGTG<br>ATAATTTCAGGAAACAAAA<br>ATTTGTGCTATGCAAATACA<br>ATAAACTGGAAAAAACTGT<br>TTGGGACCTCCGGTCAGAA<br>AACCAAAATTATAAGCAAC<br>AGAGGTGAAAACAGCTGCA<br>AGGCCACAGGCCAGGTCTG<br>CCATGCCTTGTGCTCCCCCG<br>AGGGCTGCTGGGGCCCGGA<br>GCCCAGGGACTGCGTCTCTT<br>GCCGGAATGTCAGCCGAGG<br>CAGGGAATGCGTGGACAAG<br>TGCAACCTTCTGGAGGGTG<br>AGCCAAGGGAGTTTGTGGA<br>GAACTCTGAGTGCATACAG<br>TGCCACCCAGAGTGCCTGC<br>CTCAGGCCATGAACATCAC<br>CTGCACAGGACGGGGACCA<br>GACAACTGTATCCAGTGTG<br>CCCACTACATTGACGGCCC<br>CCACTGCGTCAAGACCTGC<br>CCGGCAGGAGTCATGGGAG<br>AAAACAACACCCTGGTCTG<br>GAAGTACGCAGACGCCGGC<br>CATGTGTGCCACCTGGGCG<br>GAGGCGGAAGCGGAGGCG<br>GAGGCTCCTTTTGGGTGCTG<br>GTGGTGGTTGGTGGAGTCC<br>TGGCTTGCTATAGCTTGCTA<br>GTAACAGTGGCCTTTATTAT<br>TTTCTGGGTGAGGAGTAAG<br>AGGAGC | | HYIDGPHCVKTCPAGVMG<br>ENNTLVWKYADAGHVCH<br>LGGGGSGGGGSFWVLVVV<br>GGVLACYSLLVTVAFIIFW<br>VRSKRS |
| EGFR truncated design 7 (Her1 truncated design 7)(HER1t7) | 83 | CGCAAAGTGTGTAACGGAA<br>TAGGTATTGGTGAATTTAA<br>AGACTCACTCTCCATAAAT<br>GCTACGAATATTAAACACT<br>TCAAAAACTGCACCTCCAT<br>CAGTGGCGATCTCCACATC<br>CTGCCGGTGGCATTTAGGG<br>GTGACTCCTTCACACATACT<br>CCTCCTCTGGATCCACAGG<br>AACTGGATATTCTGAAAAC<br>CGTAAAGGAAATCACAGGG<br>TTTTTGCTGATTCAGGCTTG<br>GCCTGAAAACAGGACGGAC<br>CTCCATGCCTTTGAGAACCT<br>AGAAATCATACGCGGCAGG<br>ACCAAGCAACATGGTCAGT<br>TTTCTCTTGCAGTCGTCAGC<br>CTGAACATAACATCCTTGG<br>GATTACGCTCCCTCAAGGA<br>GATAAGTGATGGAGATGTG<br>ATAATTTCAGGAAACAAAA<br>ATTTGTGCTATGCAAATACA<br>ATAAACTGGAAAAAACTGT<br>TTGGGACCTCCGGTCAGAA<br>AACCAAAATTATAAGCAAC<br>AGAGGTGAAAACAGCTGCA<br>AGGCCACAGGCCAGGTCTG<br>CCATGCCTTGTGCTCCCCCG<br>AGGGCTGCTGGGGCCCGGA<br>GCCCAGGGACTGCGTCTCTT<br>GCCGGAATGTCAGCCGAGG<br>CAGGGAATGCGTGGACAAG<br>TGCAACCTTCTGGAGGGTG<br>AGCCAAGGGAGTTTGTGGA | 196 | RKVCNGIGIGEFKDSLSINA<br>TNIKHFKNCTSISGDLHILP<br>VAFRGDSFTHTPPLDPQEL<br>DILKTVKEITGFLLIQAWPE<br>NRTDLHAFENLEIIRGRTK<br>QHGQFSLAWSLNITSLGL<br>RSLKEISDGDVIISGNKNLC<br>YANTINWKKLFGTSGQKT<br>KIISNRGENSCKATGQVCH<br>ALCSPEGCWGPEPRDCVSC<br>RNVSRGRECVDKCNLLEG<br>EPREFVENSECIQCHPECLP<br>QAVINITCTGRGPDNCFQCA<br>HYIDGPHCYTCTCPAGVMG<br>ENNTLVWKYADAGHVCH<br>LCHPNCTYGCTGPGLEGCP<br>GGGGGGSFWVLVVVGGV<br>LACYSLLVTVAFIIFWVRS<br>KRS* |

TABLE 3-continued

Cell tag amino acid sequences and polynucleotide sequences

| Cell Tag Name | SEQ ID NO | Polynucleotide Sequence (5' to 3' where applicable) | SEQ ID NO | Amino Acids Sequence (5' to 3' where applicable) |
|---|---|---|---|---|
| | | GAACTCTGAGTGCATACAG TGCCACCCAGAGTGCCTGC CTCAGGCCATGAACATCAC CTGCACAGGACGGGGACCA GACAACTGTATCCAGTGTG CCCACTACATTGACGGCCC CCACTGCGTCAAGACCTGC CCGGCAGGAGTCATGGGAG AAAACAACACCCTGGTCTG GAAGTACGCAGACGCCGGC CATGTGTGCCACCTGTGCCA TCCAAACTGCACCTACGGA TGCACTGGGCCAGGTCTTG AAGGCTGTCCAGGTGGCGG TGGCGGCGGATCTTTTTGGG TGCTGGTGGTGGTTGGTGG AGTCCTGGCTTGCTATAGCT TGCTAGTAACAGTGGCCTTT ATTATTTTCTGGGTGAGGAG TAAGAGGAGCTAA | | |
| EGFR truncated design 8 (Her1 truncated design 8)(HER1t8) | 84 | CGCAAAGTGTGTAACGGAA TAGGTATTGGTGAATTTAA AGACTCACTCTCCATAAAT GCTACGAATATTAAACACT TCAAAAACTGCACCTCCAT CAGTGGCGATCTCCACATC CTGCCGGTGGCATTTAGGG GTGACTCCTTCACACATACT CCTCCTCTGGATCCACAGG AACTGGATATTCTGAAAAC CGTAAAGGAAATCACAGGG TTTTTGCTGATTCAGGCTTG GCCTGAAAACAGGACGGAC CTCCATGCGTTTGAGAACCT AGAAATCATACGCGGCAGG ACCAAGCAACATGGTCAGT TTTCTCTTGCAGTCGTCAGC CTGAACATAACATCCTTGG GATTACGCTCCCTCAAGGA GATAAGTGATGGAGATGTG ATAATTTCAGGAAACAAAA ATTTGTGCTATGCAAATACA ATAAACTGGAAAAAACTGT TTGGGACCTCCGGTCAGAA AACCAAAATTATAAGCAAC AGAGGTGAAAACAGCTGCA AGGCCACAGGCCAGGTCTG CCATGCCTTGTGCTCCCCCG AGGGCTGCTGGGGCCCGGA GCCCAGGGACTGCGTCTCT GGTGGCGGTGGCTCGGGCG GTGGTGGGTCGGGTGGCGG CGGATCTGGTGGCGGTGGC TCGGAGATAACACTCATTA TTTTTGGGGTGATGGCTGGT GTTATTGGAACGATCCTCTT AATTTCTTACGGTATTCGCC GAGGAGGTGGAAGC | 197 | RKVCNGIGIGEFKDSLSINA TNIKHFKNCTSISGDLHILP VAFRGDSFTHTPPLDPQEL DILKTVKEITGFLLIQAWPE NRTDLHAFENLEIIRGRTK QHGQFSLAVVSLNITSLGL RSLKEISDGDVIISGNKNLC YANTINWKKLFGTSGQKT KIISNRGENSCKATGQVCH ALCSPEGCWGPEPRDCVSG GGGSGGGGSGGGGSGGGG SEITLIIFGVMAGVIGTILLIS YGIRRGGGS |
| EGFR truncated design 9 (Her1 truncated design 9)(HER1t9) | 85 | CGCAAAGTGTGTAACGGAA TAGGTATTGGTGAATTTAA AGACTCACTCTCCATAAAT GCTACGAATATTAAACACT TCAAAAACTGCACCTCCAT CAGTGGCGATCTCCACATC CTGCCGGTGGCATTTAGGG GTGACTCCTTCACACATACT CCTCCTCTGGATCCACAGG AACTGGATATTCTGAAAAC CGTAAAGGAAATCACAGGG TTTTTGCTGATTCAGGCTTG GCCTGAAAACAGGACGGAC CTCCATGCCTTTGAGAACCT | 198 | RKVCNGIGIGEFKDSLSINA TNIKHFKNCTSISGDLHILP VAFRGDSFTHTPPLDPQEL DILKTVKEITGFLLIQAWPE NRTDLHAFENLEIIRGRTK QHGQFSLAVVSLNITSLGL RSLKEISDGDVIISGNKNLC YANTINWKKLFGTSGQKT KIISNRGENSCKATGQVCH ALCSPEGCWGPEPRDCVSG GGGSGGGGSGGGGSGGGG SITLIIFGVMAGVIGTILLIS YGIGGGS |

TABLE 3-continued

Cell tag amino acid sequences and polynucleotide sequences

| Cell Tag Name | SEQ ID NO | Polynucleotide Sequence (5' to 3' where applicable) | SEQ ID NO | Amino Acids Sequence (5' to 3' where applicable) |
|---|---|---|---|---|
| | | AGAAATCATACGCGGCAGG ACCAAGCAACATGGTCAGT TTTCTCTTGCAGTCGTCAGC CTGAACATAACATCCTTGG GATTACGCTCCCTCAAGGA GATAAGTGATGGAGATGTG ATAATTTCAGGAAACAAAA ATTTGTGCTATGCAAATACA ATAAACTGGAAAAAACTGT TTGGGACCTCCGGTCAGAA AACCAAAATTATAAGCAAC AGAGGTGAAAACAGCTGCA AGGCCACAGGCCAGGTCTG CCATGCCTTGTGCTCCCCCG AGGGCTGCTGGGGCCCGGA GCCCAGGGACTGCGTCTCT GGTGGCGGTGGCTCGGGCG GTGGTGGGTCGGGTGGCGG CGGATCTGGTGGCGGTGG TCGATAACACTCATTATTTT TGGGGTGATGGCTGGTGTT ATTGGAACGATCCTCTTAAT TTCTTACGGTATTGGAGGTG GAAGC | | |
| EGFR truncated design 10 (Her1 truncated design 10)(HER1t10) | 86 | CGCAAAGTGTGTAACGGAA TAGGTATTGGTGAATTTAA AGACTCACTCTCCATAAAT GCTACGAATATTAAACACT TCAAAAACTGCACCTCCAT CAGTGGCGATCTCCACATC CTGCCGGTGGCATTTAGGG GTGACTCCTTCACACATACT CCTCCTCTGGATCCACAGG AACTGGATATTCTGAAAAC CGTAAAGGAAATCACAGGG TTTTTGCTGATTCAGGCTTG GCCTGAAAACAGGACGGAC CTCCATGCCTTTGAGAACCT AGAAATCATACGCGGCAGG ACCAAGCAACATGGTCAGT TTTCTCTTGCAGTCGTCAGC CTGAACATAACATCCTTGG GATTACGCTCCCTCAAGGA GATAAGTGATGGAGATGTG ATAATTTCAGGAAACAAAA ATTTGTGCTATGCAAATACA ATAAACTGGAAAAAACTGT TTGGGACCTCCGGTCAGAA AACCAAAATTATAAGCAAC AGAGGTGAAAACAGCTGCA AGGCCACAGGCCAGGTCTG CCATGCCTTGTGCTCCCCCG AGGGCTGCTGGGGCCCGGA GCCCAGGGACTGCGTCTCT GGTGGCGGTGGCTCGGGCG GTGGTGGGTCGGGTGGCGG CGGATCTGGTGGCGGTGGC TCGATAACACTCATTATTTT TGGGGTGATGGCTGGTGTT ATTGGAACGATCCTCTTAGC CCTGCTCATCTGGGGAGGT GGAAGC | 199 | RKVCNGIGIGEFKDSLSINA TNIKHFKNCTSISGDLHILP VAFRGDSFTHTPPLDPQEL DILKTVKEITGFLLIQAWPE NRTDLHAFENLEIIRGRT QHGQFSLAVVSLNITSLGL RSLKEISDGDVIISGNKNLC YANTINWKKLFGTSGQKT KIISNRGENSCKATGQVCH ALCSPEGCWGPEPRDCVSG GGGSGGGGSGGGGSGGGG SITLIIFGVMAGVIGTILLAL LIWGGGS |
| EGFR truncated design 11 (Her1 truncated design 11)(HER1t11) | 87 | CGCAAAGTGTGTAACGGAA TAGGTATTGGTGAATTTAA AGACTCACTCTCCATAAAT GCTACGAATATTAAACACT TCAAAAACTGCACCTCCAT CAGTGGCGATCTCCACATC CTGCCGGTGGCATTTAGGG GTGACTCCTTCACACATACT CCTCCTCTGGATCCACAGG AACTGGATATTCTGAAAAC | 200 | RKVCNGIGIGEFKDSLSINA TNIKHFKNCTSISGDLHILP VAFRGDSFTHTPPLDPQEL DILKTVKEITGFLLIQAWPE NRTDLHAFENLEIIRGRTK QHGQFSLAVVSLNITSLGL RSLKEISDGDVIISGNKNLC YANTINWKKLFGTSGQKT KIISNRGENSCKATGQVCH ALCSPEGCWGPEPRDCVSG |

TABLE 3-continued

| Cell tag amino acid sequences and polynucleotide sequences | | | | |
|---|---|---|---|---|
| Cell Tag Name | SEQ ID NO | Polynucleotide Sequence (5' to 3' where applicable) | SEQ ID NO | Amino Acids Sequence (5' to 3' where applicable) |
| | | CGTAAAGGAAATCACAGGG<br>TTTTTGCTGATTCAGGCTTG<br>GCCTGAAAACAGGACGGAC<br>CTCCATGCCTTTGAGAACCT<br>AGAAATCATACGCGGCAGG<br>ACCAAGCAACATGGTCAGT<br>TTTCTCTTGCAGTCGTCAGC<br>CTGAACATAACATCCTTGG<br>GATTACGCTCCCTCAAGGA<br>GATAAGTGATGGAGATGTG<br>ATAATTTCAGGAAACAAAA<br>ATTTGTGCTATGCAAATACA<br>ATAAACTGGAAAAAACTGT<br>TTGGGACCTCCGGTCAGAA<br>AACCAAAATTATAAGCAAC<br>AGAGGTGAAAACAGCTGCA<br>AGGCCACAGGCCAGGTCTG<br>CCATGCCTTGTGCTCCCCCG<br>AGGGCTGCTGGGGCCCGGA<br>GCCCAGGGACTGCGTCTCT<br>GGTGGCGGTGGCTCGGGCG<br>GTGGTGGGTCGGGTGGCGG<br>CGGATCTGGTGGCGGTGGC<br>TCGCTCTGCTACCTGCTGGA<br>TGGAATCCTCTTCATCTATG<br>GTGTCATTCTCACTGCCTTG<br>TTCCTGGGAGGTGGAAGA | | GGGSGGGGSGGGGSGGGG<br>SLCYLLDGILFIYGVILTAL<br>FLGGGS |
| FL CD20 | 88 | ATGACAACACCCAGAAATT<br>CAGTAAATGGGACTTTCCC<br>GGCAGAGCCAATGAAAGGC<br>CCTATTGCTATGCAATCTGG<br>TCCAAAACCACTCTTCAGG<br>AGGATGTCTTCACTGGTGG<br>GCCCCACGCAAAGCTTCTTC<br>ATGAGGGAATCTAAGACTT<br>TGGGGGCTGTCCAGATTAT<br>GAATGGGCTCTTCCACATTG<br>CCCTGGGGGGTCTTCTGATG<br>ATCCCAGCAGGGATCTATG<br>CACCCATCTGTGTGACTGTG<br>TGGTACCCTCTCTGGGGAG<br>GCATTATGTATATTATTTCC<br>GGATCACTCCTGGCAGCAA<br>CGGAGAAAAACTCCAGGAA<br>GTGTTTGGTCAAAGGAAAA<br>ATGATAATGAATTCATTGA<br>GCCTCTTTGCTGCCATTTCT<br>GGAATGATTCTTTCAATCAT<br>GGACATACTTAATATTAAA<br>ATTTCCCATTTTTTAAAAAT<br>GGAGAGTCTGAATTTTATTA<br>GAGCTCACACACCATATAT<br>TAACATATACAACTGTGAA<br>CCAGCTAATCCCTCTGAGA<br>AAAACTCCCCATCTACCCA<br>ATACTGTTACAGCATACAA<br>TCTCTGTTCTTGGGCATTTT<br>GTCAGTGATGCTGATCTTTG<br>CCTTCTTCCAGGAACTTGTA<br>ATAGCTGGCATCGTTGAGA<br>ATGAATGGAAAAGAACGTG<br>CTCCAGACCCAAATCTAAC<br>ATAGTTCTCCTGTCAGCAGA<br>AGAAAAAAAAGAACAGACT<br>ATTGAAATAAAAGAAGAAG<br>TGGTTGGGCTAACTGAAAC<br>ATCTTCCCAACCAAAGAAT<br>GAAGAAGACATTGAAATTA<br>TTCCAATCCAAGAAGAGGA<br>AGAAGAAGAAACAGAGAC<br>GAACTTTCCAGAACCTCCCC<br>AAGATCAGGAATCCTCACC<br>AATAGAAAATGACAGCTCT | 201 | MTTPRNSVNGTFPAEPMK<br>GPIAMQSGPKPLFRRMSSL<br>VGPTQSFFMRESKTLGAVQ<br>IMNGLFHIALGGLLMEPAGI<br>YAPICVTVWYPLWGGIMYI<br>ISGSLLAATEKNSRKCLVK<br>GKMTMNSLSLFAAISGMILS<br>IMDILNKISHFLKMESLNFI<br>RAHTPYINIYNCEPANPSEK<br>NSPSTQYCYSIQSLFLGILS<br>VMLIFAFFQELVIAGIVENE<br>WKRTCSRPKSNIVLLSAEE<br>KKEQTIEIKEEVVGLTETSS<br>QPKNEEDIEIIPIQEEEEEET<br>FTNFPEPPQDQESSPIENDS<br>SP |

TABLE 3-continued

Cell tag amino acid sequences and polynucleotide sequences

| Cell Tag Name | SEQ ID NO | Polynucleotide Sequence (5' to 3' where applicable) | SEQ ID NO | Amino Acids Sequence (5' to 3' where applicable) |
|---|---|---|---|---|
| | | CCT | | |
| Truncated CD20 design 1 (CD20t1) [CD20(M1-E263] | 89 | ATGACCACACCACGGAACT CTGTGAATGGCACCTTCCCA GCAGAGCCAATGAAGGGAC CAATCGCAATGCAGAGCGG ACCCAAGCCTCTGTTTCGGA GAATGAGCTCCCTGGTGGG CCCAACCCAGTCCTTCTTTA TGAGAGAGTCTAAGACACT GGGCGCCGTGCAGATCATG AACGGACTGTTCCACATCG CCCTGGGAGGACTGCTGAT GATCCCAGCCGGCATCTAC GCCCCTATCTGCGTGACCGT GTGGTACCCTCTGTGGGGC GGCATCATGTATATCATCTC CGGCTCTCTGCTGGCCGCCA CAGAGAAGAACAGCAGGA AGTGTCTGGTGAAGGGCAA GATGATCATGAATAGCCTG TCCCTGTTTGCCGCCATCTC TGGCATGATCCTGAGCATC ATGGACATCCTGAACATCA AGATCAGCCACTTCCTGAA GATGGAGAGCCTGAACTTC ATCAGAGCCCACACCCCTT ACATCAACATCTATAATTGC GAGCCTGCCAACCCATCCG AGAAGAATTCTCCAAGCAC ACAGTACTGTTATTCCATCC AGTCTCTGTTCCTGGGCATC CTGTCTGTGATGCTGATCTT TGCCTTCTTTCAGGAGCTGG TCATCGCCGGCATCGTGGA GAACGAGTGGAAGAGGACC TGCAGCCGCCCCAAGTCCA ATATCGTGCTGCTGTCCGCC GAGGAGAAGAAGGAGCAG ACAATCGAGATCAAGGAGG AGGTGGTGGGCCTGACCGA GACATCTAGCCAGCCTAAG AATGAGGAGGATATCGAG | 202 | MTTPRNSVNGTFPAEPMK GPIAMQSGPKPLFRRMSSL VGPTQSFFMRESKTLGAVQ IMNGLFHIALGGLLMIPAGI YAPICVTVWYPLWGGIMYI ISGSLLAATEKNSRKCLVK GKMIMNSLSLFAAISGMILS IMDIENIKISIIFLKMESLNFI RAHTPYINIYNCEPANPSEK NSPSTQYCYSIQSLFLGILS VMLIFAFFQELVIAGIVENE WKRTCSRPKSNIVLLSAEE KKEQTIEIKEEVVGLTETSS QPKNEEDIE |

In further embodiments, at least one of said gene expression cassettes comprises a polynucleotide encoding a promoter that is activated by the transactivation domain. In further embodiments, said system is contained in one or more vectors. In one instance, the system is contained in one vector. In one instance, the first gene expression cassette, the second gene expression cassette, and the recombinant attachment sites are contained in one vector. In one instance, the first gene expression cassette, the second gene expression cassette, the third gene expression cassette and the recombinant attachment sites are contained in one vector. In another instance, the serine recombinase is SF370. In other instances, the serine recombinase is in a separate vector.

The recombinases can be introduced into a target cell before, concurrently with, or after the introduction of a targeting vector. The recombinase can be directly introduced into a cell as a protein, for example, using liposomes, coated particles, or microinjection. Alternately, a polynucleotide, either DNA or messenger RNA, encoding the recombinase can be introduced into the cell using a suitable expression vector. The targeting vector components described above are useful in the construction of expression cassettes containing sequences encoding a recombinase of interest. However, expression of the recombinase can be regulated in other ways, for example, by placing the expression of the recombinase under the control of a regulatable promoter (i.e., a promoter whose expression can be selectively induced or repressed).

Recombinases for use in the practice of the present disclosure can be produced recombinantly or purified as previously described. Polypeptides having the desired recombinase activity can be purified to a desired degree of purity by methods known in the art of protein ammonium sulfate precipitation, purification, including, but not limited to, size fractionation, affinity chromatography, HPLC, ion exchange chromatography, heparin agarose affinity chromatography (e.g., Thorpe & Smith, Proc. Nat. Acad. Sci. 95:5505-5510, 1998.)

In one embodiment, the recombinases can be introduced into the eukaryotic cells that contain the recombination attachment sites at which recombination is desired by any suitable method. Methods of introducing functional proteins, e.g., by microinjection or other methods, into cells are well known in the art. Introduction of purified recombinase protein ensures a transient presence of the protein and its function, which is often a preferred embodiment. Alternatively, a gene encoding the recombinase can be included in an expression vector used to transform the cell, in which the recombinase-encoding polynucleotide is operably linked to a promoter which mediates expression of the polynucleotide in the eukaryotic cell. The recombinase polypeptide can also be introduced into the eukaryotic cell by messenger RNA that encodes the recombinase polypeptide. It is generally preferred that the recombinase be present for only such time as is necessary for insertion of the nucleic acid fragments into the genome being modified. Thus, the lack of permanence associated with most expression vectors is not expected to be detrimental. One can introduce the recombinase gene into the cell before, after, or simultaneously with, the introduction of the exogenous polynucleotide of interest. In one embodiment, the recombinase gene is present within the vector that carries the polynucleotide that is to be inserted; the recombinase gene can even be included within the polynucleotide. In other embodiments, the recombinase gene is introduced into a transgenic eukaryotic organism. Transgenic cells or animals can be made that express a recombinase constitutively or under cell-specific, tissue-specific, developmental-specific, organelle-specific, or small molecule-inducible or repressible promoters. The recombinases can be also expressed as a fusion protein with other peptides, proteins, nuclear localizing signal peptides, signal peptides, or organelle-specific signal peptides (e.g., mitochondrial or chloroplast transit peptides to facilitate recombination in mitochondria or chloroplast).

For example, a recombinase may be from the Integrase or Resolvase families. The Integrase family of recombinases has over one hundred members and includes, for example, FLP, Cre, and lambda integrase. The Integrase family, also referred to as the tyrosine family or the lambda integrase family, uses the catalytic tyrosine's hydroxyl group for a nucleophilic attack on the phosphodiester bond of the DNA. Typically, members of the tyrosine family initially nick the DNA, which later forms a double strand break. Examples of tyrosine family integrases include Cre, FLP, SSV1, and lambda (λ) integrase. In the resolvase family, also known as the serine recombinase family, a conserved serine residue forms a covalent link to the DNA target site (Grindley, et al., (2006) Ann Rev Biochem 16:16).

In one embodiment, the recombinase is an isolated polynucleotide sequence comprising a nucleic acid sequence that encodes a recombinase selecting from the group consisting of a SPβc2 recombinase, a SF370.1 recombinase, a Bxb1 recombinase, an A118 recombinase and a ΦRv1 recombinase. Examples of serine recombinases are described in detail in U.S. Pat. No. 9,034,652, hereby incorporated by reference in its entirety.

In one embodiment, a method for site-specific recombination comprises providing a first recombination site and a second recombination site; contacting the first and second recombination sites with a prokaryotic recombinase polypeptide, resulting in recombination between the recombination sites, wherein the recombinase polypeptide can mediate recombination between the first and second recombination sites, the first recombination site is attP or attB, the second recombination site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB Further embodiments provide for the introduction of a site-specific recombinase into a cell whose genome is to be modified. One embodiment relates to a method for obtaining site-specific recombination in an eukaryotic cell comprises providing a eukaryotic cell that comprises a first recombination attachment site and a second recombination attachment site; contacting the first and second recombination attachment sites with a prokaryotic recombinase polypeptide, resulting in recombination between the recombination attachment sites, wherein the recombinase polypeptide can mediate recombination between the first and second recombination attachment sites, the first recombination attachment site is a phage genomic recombination attachment site (attP) or a bacterial genomic recombination attachment site (attB), the second recombination attachment site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB. In an embodiment the recombinase is selected from the group consisting of an A118 recombinase, a SF370.1 recombinase, a SPβc2 recombinase, a ΦRv1 recombinase, and a Bxb1 recombinase. In one embodiment the recombination results in integration.

Immune Effector Cell Sources

In certain aspects, the embodiments described herein include methods of making and/or expanding the antigen-specific redirected immune effector cells (e.g., T-cells, NK-cell or NK T-cells) that comprises transfecting the cells with an expression vector containing a DNA (or RNA) construct encoding the CAR, then, optionally, stimulating the cells with feeder cells, recombinant antigen, or an antibody to the receptor to cause the cells to proliferate. In certain aspects, the cell (or cell population) engineered to express a CAR or TCR is a stem cell, iPS cell, immune effector cell or a precursor of these cells.

Sources of immune effector cells can include both allogeneic and autologous sources. In some cases immune effector cells may be differentiated from stem cells or induced pluripotent stem cells (iPSCs). Thus, cells for engineering according to the embodiments can be isolated from umbilical cord blood, peripheral blood, human embryonic stem cells, or iPSCs. For example, allogeneic T cells can be modified to include a chimeric antigen receptor (and optionally, to lack functional TCR). In some aspects, the immune effector cells are primary human T cells such as T cells derived from human peripheral blood mononuclear cells (PBMC). PBMCs can be collected from the peripheral blood or after stimulation with G-CSF (Granulocyte colony stimulating factor) from the bone marrow, or umbilical cord blood. Following transfection or transduction (e.g., with a CAR expression construct), the cells may be immediately infused or may be cryo-preserved. In certain aspects, following transfection, the cells may be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the chimeric antigen receptor is expanded ex vivo. The clone selected for expansion demonstrates the capacity to specifically recognize and lyse antigen-expressing target cells. The recombinant T cells may be expanded by stimulation with IL-2, or other cytokines that bind the common gamma-chain (e.g., IL-7, IL-12, IL-15, IL-21, and others). The recombinant T cells may be expanded by stimulation with artificial antigen presenting cells. The recombinant T cells may be expanded on artificial antigen presenting cell or with an antibody, such as OKT3, which cross links CD3 on the T cell surface. Subsets of the recombinant T cells may be further selected with the use of magnetic bead based isolation methods and/or fluorescence activated cell sorting technology and further cultured with the AaPCs. In a further aspect, the genetically modified cells may be cryopreserved.

T cells can also be obtained from a number of sources, including peripheral blood, bone marrow, lymph node tissue, cord blood, thymus tissue, tissue from a site of infection, ascites, pleural effusion, spleen tissue, and tumor (tumor-infiltrating lymphocytes). In certain embodiments of the present disclosure, any number of T cell lines available in the art, may be used. In certain embodiments of the present disclosure, T cells can be obtained from a unit of blood collected from a subject using any number of techniques known to the skilled artisan, such as Ficoll® separation. In embodiments, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the present disclosure, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca2+-free, Mg2+-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL® gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours. In one embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this disclosure. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, CD25+, CD62Lhi, GITR+, and FoxP3+. Alternatively, in certain embodiments, T regulatory cells are depleted by anti-CD25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is 5×106/ml. In other embodiments, the concentration used can be from about 1×105/ml to 1×106/ml, and any integer value in between.

In other embodiments, the cells may be incubated on a rotator for varying lengths of time at varying speeds at either 2-10° C. or at room temperature.

T cells for stimulation can also be frozen after a washing step. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present disclosure.

Also contemplated in the context of the present disclosure is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, (1991); Henderson et al., Immun 73:316-321, (1991); Bierer et al., Curr. Opin. Immun 5:763-773, (1993)). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present disclosure, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

In certain embodiments are T cells comprising polynucleotides encoding gene-switch polypeptides for expressing an interleukin, CARs and/or TCRs described herein Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

"Adoptive T cell transfer" refers to the isolation and ex vivo or in vivo expansion of tumor specific T cells to achieve greater number of T cells than what could be obtained by vaccination alone or the patient's natural tumor response. The tumor specific T cells are then infused into patients with cancer in an attempt to give their immune system the ability to overwhelm remaining tumor via T cells which can attack and kill cancer. There are many forms of adoptive T cell therapy being used for cancer treatment; culturing tumor infiltrating lymphocytes or TIL, isolating and expanding one particular T cell or clone, and even using T cells that have been engineered to potently recognize and attack tumors. In some aspects, adoptive T-cell therapy can include engineered antigen-specific T cells that are modified and immediately infused into a patient, thus allowing in vivo expansion of antigen-specific T cells to occur within the patient.

In some cases, T cells described herein are activated and/or expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, (1998); Haanen et al., J. Exp. Med. 190(9):13191328, (1999); Garland et al., J. Immunol Meth. 227(1-2):53-63, (1999)).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (AaPC) that are contemplated for use in activating and expanding T cells in the present disclosure.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4+ T cell expansion and T cell growth is used. In certain aspects of the present disclosure, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present disclosure, more anti-CD28 antibody is bound to the particles than anti-CD3 antibody, i.e., the ratio of CD3:CD28 is less than one. In certain embodiments of the present disclosure, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In embodiments, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one ratio being at least 1:1 particles per T cell. In one embodiment, a ratio of particles to cells of 1:1 or less is used. In one particular embodiment, the particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present disclosure. In particular, ratios will vary depending on particle size and on cell size and type.

In further embodiments of the present disclosure, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, 104 to 109 T cells) and beads (for example, DYNABEADS® M-450 CD3/CD28 T paramagnetic beads at a ratio of 1:1, or MACS® MicroBeads from Miltenyi Biotec) are combined in a buffer, for example, PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present disclosure. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present disclosure, the mixture may be cultured for several hours (about 3 hours) to about 14 days or any hourly integer value in between. In another embodiment, the mixture may be cultured for 21 days. In one embodiment of the present disclosure the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-.gamma., IL-4, IL-7, GM-CSF, IL-10, IL-12, IL-15, TGFbeta, and TNF-alpha or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, alpha-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2).

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In some cases, immune effector cells of the embodiments (e.g., T-cells) are co-cultured with activating and propagating cells (AaPCs), to aid in cell expansion. AaPCs can also be referred to as artificial Antigen Presenting cells (AaPCs). For example, antigen presenting cells (APCs) are useful in preparing therapeutic compositions and cell therapy products of the embodiments. In one aspect, the AaPCs may be transgenic K562 cells. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009, each of which is incorporated by reference. In yet a further aspect of the embodiments, culturing the transgenic CAR cells comprises culturing the transgenic CAR cells in the presence of dendritic cells or activating and propagating cells (AaPCs) that stimulate expansion of the CAR-expressing immune effector cells. In still further aspects, the AaPCs comprise a CAR-binding antibody or fragment thereof expressed on the surface of the AaPCs. In other embodiments, the AaPCS comprise a TCR-binding polypeptide or TCR binding antibody or fragment thereof expressed on the surface of the AaPCs. The AaPCs may comprise additional molecules that activate or co-stimulate T-cells in some cases. The additional molecules may, in some cases, comprise membrane-bound Cγ cytokines. In yet still further aspects, the AaPCs are inactivated or irradiated, or have been tested for and confirmed to be free of infectious material. In still further aspects, culturing the transgenic CAR cells in the presence of AaPCs comprises culturing the transgenic CAR cells in a medium comprising soluble cytokines, such as IL-15, IL-21 and/or IL-2. The cells may be cultured at a ratio of about 10:1 to about 1:10; about 3:1 to about 1:5; about 1:1 to about 1:3 (immune effector cells to AaPCs); or any range derivable therein. For example, the co-culture of T cells and AaPCs can be at a ratio of about 1:1, about 1:2 or about 1:3.

In one aspect, the AaPCs may express CD137L. In other aspects, the AaPCs may further express CD19, CD64, CD86, or mIL15. In certain aspects, the AaPCs may express at least one anti-CD3 antibody clone, such as, for example, OKT3 and/or UCHT1. In one aspect, the AaPCs may be treated (e.g. irradiated or mytomycin C) to eliminate their growth potential. In one aspect, the AaPCs may have been tested for and confirmed to be free of infectious material. Methods for producing such AaPCs are known in the art. In one aspect, culturing the CAR-modified T cell population with AaPCs may comprise culturing the cells at a ratio of about 10:1 to about 1:10; about 3:1 to about 1:5; about 1:1 to about 1:3 (T cells to AaPCs); or any range derivable therein. For example, the co-culture of T cells and AaPCs can be at a ratio of about 1:1, about 1:2 or about 1:3. In one aspect, the culturing step may further comprise culturing with an aminobisphosphonate (e.g., zoledronic acid).

In a further aspect, the population of CAR-T cells is cultured and/or stimulated for no more than 7, 14, 21, 28, 35 42 days, 49, 56, 63 or 70 days. In some embodiments, the population of CAR-T cells is cultured and/or stimulated for at least 0, 2, 4, 6, 8, 10, 12, 14, 16, 18, 20, 22, 24, 26, 28, 30 or more days. In some embodiments, the population of CAR-T cells is cultured and/or stimulated for at least 5, 10, 15, 20, 25, 30, 35, 40, 45, 50, 55, 60 or more days. In some embodiments, the population of CAR-T cells is cultured and/or stimulated for at least 7, 14, 21, 28, 35, 42, 49, 56, 63 or more days. In other embodiments, a stimulation includes the co-culture of the CAR-T cells with AaPCs to promote the growth of CAR positive T cells. In another aspect, the population of transgenic CAR cells is stimulated for not more than: 1× stimulation, 2× stimulation, 3× stimulation, 4× stimulation, 5× stimulation, 5× stimulation, 6× stimulation, 7× stimulation, 8× stimulation, 9× stimulation or 10× stimulation. In some instances, the transgenic cells are not cultured ex vivo in the presence of AaPCs. In some specific instances, the method of the embodiment further comprises enriching the cell population for CAR-expressing immune effector cells (e.g., T-cells) after the transfection and/or culturing step. The enriching may comprise fluorescence-activated cell sorting (FACS) and sorting for CAR-expressing cells. In a further aspect, the sorting for CAR-expressing cells comprises use of a CAR-binding antibody. The enriching may also comprise depletion of CD56+ cells. In yet still a further aspect of the embodiment, the method further comprises cryopreserving a sample of the population of transgenic CAR cells.

In some cases, AaPCs are incubated with a peptide of an optimal length that allows for direct binding of the peptide to the MHC molecule without additional processing. Alternatively, the cells can express an antigen of interest (i.e., in the case of MHC-independent antigen recognition). Furthermore, in some cases, APCs can express an antibody that binds to either a specific CAR polypeptide or to CAR polypeptides in general (e.g., a universal activating and propagating cell (uAPC). Such methods are disclosed in WO/2014/190273, which is incorporated herein by reference. In addition to peptide-MHC molecules or antigens of interest, the AaPC systems may also comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD70 and B7.1 (B7.1 was previously known as B7 and also known as CD80), which among other things, bind to CD28 and/or CTLA-4 molecules on the surface of T cells, thereby affecting, for example, T-cell expansion, Th1 differentiation, short-term T-cell survival, and cytokine secretion such as interleukin (IL)-2. Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001, incorporated herein by reference.

Cells selected to become AaPCs, preferably have deficiencies in intracellular antigen-processing, intracellular peptide trafficking, and/or intracellular MHC Class I or Class II molecule-peptide loading, or are poikilothermic (i.e., less sensitive to temperature challenge than mammalian cell lines), or possess both deficiencies and poikilothermic properties. Preferably, cells selected to become AaPCs also lack the ability to express at least one endogenous counterpart (e.g., endogenous MHC Class I or Class II molecule and/or endogenous assisting molecules as described above) to the exogenous MHC Class I or Class II molecule and assisting molecule components that are introduced into the cells. Furthermore, AaPCs preferably retain the deficiencies and poikilothermic properties that were possessed by the cells prior to their modification to generate the AaPCs. Exemplary AaPCs either constitute or are derived from a transporter associated with antigen processing (TAP)-deficient cell line, such as an insect cell line. An exemplary poikilothermic insect cells line is a *Drosophila* cell line, such as a Schneider 2 cell line (see, e.g., Schneider 1972 Illustrative methods for the preparation, growth, and culture of Schneider 2 cells, are provided in U.S. Pat. Nos. 6,225,042, 6,355,479, and 6,362,001.

In one embodiment, AaPCs are also subjected to a freeze-thaw cycle. In an exemplary freeze-thaw cycle, the AaPCs may be frozen by contacting a suitable receptacle containing the AaPCs with an appropriate amount of liquid nitrogen, solid carbon dioxide (i.e., dry ice), or similar low-temperature material, such that freezing occurs rapidly. The frozen APCs are then thawed, either by removal of the AaPCs from the low-temperature material and exposure to ambient room temperature conditions, or by a facilitated thawing process in which a lukewarm water bath or warm hand is employed to facilitate a shorter thawing time. Additionally, AaPCs may be frozen and stored for an extended period of time prior to thawing. Frozen AaPCs may also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing AaPCs that undergo the freeze-thaw cycle, or are essentially removed, such as by transfer of AaPCs to media that is essentially devoid of such preservatives.

In further embodiments, xenogenic nucleic acid and nucleic acid endogenous to the AaPCs, may be inactivated by crosslinking, so that essentially no cell growth, replication or expression of nucleic acid occurs after the inactivation. In one embodiment, AaPCs are inactivated at a point subsequent to the expression of exogenous MHC and assisting molecules, presentation of such molecules on the surface of the AaPCs, and loading of presented MHC molecules with selected peptide or peptides. Accordingly, such inactivated and selected peptide loaded AaPCs, while rendered essentially incapable of proliferating or replicating, retain selected peptide presentation function. Preferably, the crosslinking also yields AaPCs that are essentially free of contaminating microorganisms, such as bacteria and viruses, without substantially decreasing the antigen-presenting cell function of the AaPCs. Thus crosslinking maintains the important AaPC functions of while helping to alleviate concerns about safety of a cell therapy product developed using the AaPCs. For methods related to crosslinking and AaPCs, see for example, U.S. Patent Application Publication No. 20090017000, which is incorporated herein by reference.

In certain embodiments there are further provided an engineered antigen presenting cell (APC). Such cells may be used, for example, as described above, to propagate immune effector cells ex vivo. In further aspects, engineered APCs may, themselves be administered to a patient and thereby stimulate expansion of immune effector cells in vivo. Engineered APCs of the embodiments may, themselves, be used as a therapeutic agent. In other embodiments, the engineered APCs can used as a therapeutic agent that can stimulate activation of endogenous immune effector cells specific for a target antigen and/or to increase the activity or persistence of adoptively transferred immune effector cells specific to a target antigen.

As used herein the term "engineered APC" refers to cell(s) that comprises at least a first transgene, wherein the first transgene encodes a HLA. Such engineered APCs may further comprise a second transgene for expression of an antigen, such that the antigen is presented at the surface on the APC in complex with the HLA. In some aspects, the engineered APC can be a cell type that presented antigens (e.g., a dendritic cell). In further aspects, engineered APC can be produced from a cell type that does not normally present antigens, such a T-cell or T-cell progenitor (referred to as "T-APC"). Thus, in some aspects, an engineered APC of the embodiments comprises a first transgene encoding a target antigen and a second transgene encoding a human leukocyte antigen (HLA), such that the HLA is expressed on the surface of the engineered APC in complex with an epitope of the target antigen. In certain specific aspects, the HLA expressed in the engineered APC is HLA-A2.

In some aspects, an engineered APC of the embodiments may further comprise at least a third transgene encoding co-stimulatory molecule. The co-stimulatory molecule may be a co-stimulatory cytokine that may be a membrane-bound Cγ cytokine. In certain aspects, the co-stimulatory cytokine is IL-15, such as membrane-bound IL-15. In some further aspects, an engineered APC may comprise an edited (or deleted) gene. For example, an inhibitory gene, such as PD-1, LIM-3, CTLA-4 or a TCR, can be edited to reduce or eliminate expression of the gene. An engineered APC of the embodiments may further comprise a transgene encoding any target antigen of interest. For example, the target antigen can be an infectious disease antigen or a tumor-associated antigen (TAA).

Methods of Regulating Expression

In one embodiment, a method of regulating the expression of a heterologous gene in an engineered cell is provided. Polynucleotides encoding for gene switch polypeptides for ligand inducible control of a heterologous gene expression, an antigen binding polypeptide and a heterologous gene is provided. In some instances, the polynucleotides are in one or more gene expression cassettes as depicted in any one of FIGS. 1 through 16. In another instance, the polynucleotides are incorporated into an engineered cell via viral or non-viral vectors. Viral vectors can include lentiviral vectors, retroviral vectors or adenoviral vectors. Non-viral vectors can include Sleeping Beauty transposons. In other instances, the polynucleotides are incorporated into an engineered cell via recombinases or gene editing techniques. Examples of recombinases are serine recombinases as described herein. Examples of gene editing techniques can include CRISPR or Argnonaute systems. Herein a "CRISPR gene editing system" of "CRISPR system" refers to any RNA-guided Cas protein-mediated process for targeting a change in DNA sequence to a specific region of a genome. Herein "Argonaute gene editing system" refers to any single-stranded DNA guided Argonaute endonuclease-mediated process for targeting a change in DNA sequence to a specific region of a genome.

In some instances, the antigen binding polypeptide can be an antigen binding polypeptide or a ligand binding polypeptide. For example, an antigen binding polypeptide can be an antibody or a fragment thereof, F(ab')2, Fab', Fab, Fv, scFv, variable fragments of heavy chain antibodies (VHHs), a CAR, or an engineered TCR. As a further example, a ligand binding polypeptide can be a receptor. In certain aspects, the heterologous gene is a cytokine. The cytokine can be IL-2, IL-15, IL-12, IL-21, or a fusion of IL-15 and IL-15R (mbIL-15). In certain instances, the cytokine is IL-12. For example, the IL-12 is a single chain IL-12 (scIL-12), protease sensitive IL-12, destabilized IL-12, membrane bound IL-12, intercalated IL-12. In some cases, the heterologous gene is under the control of an inducible promoter. For example, the inducible promoter is a gene switch ligand-inducible promoter for gene transcription.

In certain instances, the cell is an engineered cell. Herein an engineered cell is a cell which has been modified from its natural or endogenous state. An example of an engineered cell is a cell described herein which has been modified (e.g., by transfection of a polynucleotide into the cell). In some instances, the engineered cell can be an engineered immune effector cell.

Provided herein is a method to regulate the expression of a heterologous gene wherein the heterologous gene is under the control of a ligand inducible promoter. In some instances, the method results in a low or no basal level of heterologous gene expression in the absence of the ligand. In one instance, the engineered cells are activated prior to inducing the expression of the heterologous gene with a ligand. In another instance, the engineered cells are activated by exposing the cells to an antigen. The antigen can be an antigen that is recognized by the antigen binding polypeptide expressed by the engineered cell. The antigen can be a tumor antigen or an infectious disease antigen.

The engineered cells can be exposed to the antigen for at least: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days. In some instances, the engineered cells can be exposed to the antigen for at least: 1, 2, 3, 4, 5, 6, 7, 8, 9, 10, 11, 12, 13, 14, 15, 16, 17, 18, 19, 20, 21, 22, 23, 24 hours.

In another instance, a population of immune effector cells that have been transduced with the vectors encompassing gene switch polypeptides and inducible gene of interest (described herein in FIG. 2A-2D, FIG. 3, FIG. 19A-19B, FIG. 20A, FIG. 22, FIG. 24A-24D, and FIG. 25A-25B) is cultured and/or stimulated with an engineered AaPC of the embodiments for at least 1× stimulation, 2× stimulation, 3× stimulation or 4× stimulation. In some instances, the engineered AaPC comprises an antigen or a ligand that is recognized by the binding polypeptide expressed on the engineered cells. Following the last stimulation, the cells are allowed to rest before infusion into a patient. The patient is then given the appropriate dose of a ligand used for inducible gene switch regulation to activate and express the gene of interest. In one aspect, the ligand is veledimex. In another aspect, veledimex is provided at 5 mg, 10 mg, 15 mg, 20 mg, 30 mg, 40 mg, 50 mg, 60 mg, 70 mg, 80 mg, 90 mg or 100 mg. In a further aspect, lower doses of veledimex are provided, for example, 0.5 mg, 1 mg, 5 mg, 10 mg, 15 mg or 20 mg.

Point-of-Care

In one embodiment of the present disclosure, the immune effector cells described herein are modified at a point-of-care site. In some cases, the point-of-care site is at a hospital or at a facility (e.g., a medical facility) near a subject in need of treatment. The subject undergoes apheresis and peripheral blood mononuclear cells (PBMCs) obtained can be enriched for example, by elutriation. In one instance, the elutriation process is performed using a buffer solution containing human serum albumin. Immune effector cells, such as T cells can be isolated by selection methods described herein. In one instance, the selection method for T cells includes beads specific for CD3 and CD8 on T cells. In one case, the beads can be paramagnetic beads. The harvested immune effector cells can be cryopreserved in any appropriate cryopreservation solution prior to modification. The immune effector cells can be thawed up to 24 hours, 36 hours, 48 hours. 72 hours or 96 hours ahead of infusion. The thawed cells can be placed in cell culture buffer, for example in cell culture buffer (e.g. RPMI) supplemented with fetal bovine serum (FBS) or placed in a buffer that includes IL-2 and IL-21, prior to modification. In another aspect, the harvested immune effector cells can be modified immediately without the need for cryopreservation.

In some cases, the immune effector cells are modified by engineering/introducing a chimeric receptor, one or more cell tag(s), and/or cytokine into the immune effector cells and then rapidly infused into a subject. In some cases, the sources of immune effector cells can include both allogeneic and autologous sources. In one case, the immune effector cells can be T cells or NK cells. In one case, the chimeric receptor can be a CAR or a TCR. In another case, the cytokine can be mbIL-15. In one case, the mbIL-15 is of SEQ ID NO: 15, or variant or fragment thereof. In yet another case, expression of mbIL-15 is modulated by ligand inducible gene-switch expression systems described herein. For example, a ligand such as veledimex can be delivered to the subject to modulate the expression of mbIL-15. In another aspect, veledimex is provided at 5 mg, 10 mg, 15 mg, 20 mg, 30 mg, 40 mg, 50 mg, 60 mg, 70 mg, 80 mg, 90 mg or 100 mg. In a further aspect, lower doses of veledimex are provided, for example, 0.5 mg, 1 mg, 5 mg, 10 mg, 15 mg or 20 mg. In one embodiment, veledimex is administered to the subject 0, 1, 2, 3, 4, 5, 6, 7, 8, 9, 10, 11, 12, 13, 14, 15, 16, 17, 18, 19, 20, or 21 days prior to infusion of the modified immune effector cells. In a further embodiment, veledimex is administered about once every 12 hours, about once every 24 hours, about once every 36 hours or about once every 48 hours, for an effective period of time to a subject post infusion of the modified immune effector cells. In one embodiment, an effective period of time for veledimex administration is about: 7, 8, 9, 10, 11, 12, 13, 14, 15, 16, 17, 18, 19, 20, 21, 22, 23, 24, 25, 26, 27, 28, 29, 30 days. In other embodiments, veledimex can be re-administered after a rest period, after a drug holiday or when the subject experiences a relapse.

In certain cases, where an adverse effect on a subject is observed or when treatment is not needed, the cell tag can be activated, for example via cetuximab, for conditional in vivo ablation of modified immune effector cells comprising cell tags such as truncated epidermal growth factor receptor tags as described herein.

In some embodiments, such immune effectors cells are modified by the constructs as described in FIG. 2A-2D, FIG. 3, FIG. 19A-19B, FIG. 20A, FIG. 22, FIG. 24A-24D, and FIG. 25A-25B through electroporation. In one instance, electroporation is performed with electroporators such as Lonza's Nucleofector™ electroporators. In other embodiments, the vector comprising the above-mentioned constructs is a non-viral or viral vector. In one case, the non-viral vector includes a Sleeping Beauty transposon-transposase system. In one instance, the immune effector cells are electroporated using a specific sequence. For example, the immune effector cells can be electroporated with one transposon followed by the DNA encoding the transposase followed by a second transposon. In another instance, the immune effector cells can be electroporated with all transposons and transposase at the same time. In another instance, the immune effector cells can be electroporated with a transposase followed by both transposons or one transposon at a time. While undergoing sequential electroporation, the immune effector cells may be rested for a period of time prior to the next electroporation step.

In some cases, the modified immune effector cells do not undergo a propagation and activation step. In some cases, the modified immune effector cells do not undergo an incubation or culturing step (e.g. ex vivo propagation). In certain cases, the modified immune effector cells are placed in a buffer that includes IL-2 and IL21 prior to infusion. In other instances, the modified immune effector cells are placed or rested in cell culture buffer, for example in cell culture buffer (e.g. RPMI) supplemented with fetal bovine serum (FBS) prior to infusion. Prior to infusion, the modified immune effector cells can be harvested, washed and formulated in saline buffer in preparation for infusion into the subject.

In one instance, the subject has been lymphodepleted prior to infusion. In other instances, lymphodepletion is not required and the modified immune effector cells are rapidly infused into the subject. Exemplary lymphodepletion regimens are listed in Tables 4 and 5 below:

TABLE 4

| Regimen 1 | |
|---|---|
| D-6 | Admit/IV Hydration |
| D-5 | Fludarabine 25 mg/m2, Cyclophosphamide 250 mg/m2 |
| D-4 | Fludarabine 25 mg/m2, Cyclophosphamide 250 mg/m2 |
| D-3 | Fludarabine 25 mg/m2 IV, Cyclophosphamide 250 mg/m2 |
| D-2 | REST |
| D-1 | REST |
| D0 | T-cell infusion |

TABLE 5

| Regimen 2 | |
|---|---|
| D-6 | Admit/IV Hydration |
| D-5 | Fludarabine 30 mg/m2, Cyclophosphamide 500 mg/m2 |
| D-4 | Fludarabine 30 mg/m2, Cyclophosphamide 500 mg/m2 |
| D-3 | Fludarabine 30 mg/m2 IV, Cyclophosphamide 500 mg/m2 |
| D-2 | REST |
| D-1 | REST |
| D0 | T-cell infusion |

In a further instance, the subject undergoes minimal lymphodepletion. Minimal lymphodepletion herein refers to a reduced lymphodepletion protocol such that the subject can be infused within 1 day, 2 days or 3 days following the lymphodepletion regimen. In one instance, a reduced lymphodepletion protocol can include lower doses of fludarabine and/or cyclophosphamide. In another instance, a reduced lymphodepetion protocol can include a shortened period of lymphodepletion, for example 1 day or 2 days.

In one embodiment, the immune effector cells are modified by engineering/introducing a chimeric receptor and a cytokine into said immune effector cells and then rapidly infused into a subject. In other cases, the immune effector cells are modified by engineering/introducing a chimeric receptor and a cytokine into said cells and then infused within at least: 0, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 hours into a subject. In other cases, immune effector cells are modified by engineering/introducing a chimeric receptor and a cytokine into the immune effector cells and then infused in 0 days, <1 day, <2 days, <3 days, <4 days, <5 days, <6 days or <7 days into a subject.

In some embodiments, an amount of modified effector cells is administered to a subject in need thereof and the amount is determined based on the efficacy and the potential of inducing a cytokine-associated toxicity. In another embodiment, the modified effector cells are $CAR^+$ or $TCR^+$ and $CD3^+$ cells. In some cases, an amount of modified effector cells comprises about $10^4$ to about $10^9$ modified effector cells/kg. In some cases, an amount of modified effector cells comprises about $10^4$ to about $10^5$ modified effector cells/kg. In some cases, an amount of modified effector cells comprises about $10^5$ to about $10^6$ modified effector cells/kg. In some cases, an amount of modified effector cells comprises about $10^6$ to about $10^7$ modified effector cells/kg. In some cases, an amount of modified effector cells comprises $>10^4$ but $\leq 10^5$ modified effector cells/kg. In some cases, an amount of modified effector cells comprises $>10^5$ but $\leq 10^6$ modified effector cells/kg. In some cases, an amount of modified effector cells comprises $>10^6$ but $\leq 10^7$ modified effector cells/kg.

In other embodiments, a method of stimulating the proliferation and/or survival of engineered cells comprises obtaining a sample of cells from a subject, and transfecting cells of the sample of cells with one or more polynucleotides that comprise one or more transposons. In an embodiment, the transposons encode a chimeric antigen receptor (CAR) or a TCR, a cytokine, one or more cell tags, gene switch polypeptides for ligand-inducible control of the cytokine and a transposase effective to integrate said one or more polynucleotides into the genome of said cells, to provide a population of engineered cells. In an embodiment, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain. In some embodiments, the first gene switch polypeptide and the second gene switch polypeptide are connected by a linker. In one instance, lymphodepletion is not required prior to administration of the engineered cells to a subject.

In one instance, a method of in vivo propagation of engineered cells comprises obtaining a sample of cells from a subject, and transfecting cells of the sample of cells with one or more polynucleotides that comprise one or more transposons. In an embodiment, the transposons encode a chimeric antigen receptor (CAR) or a TCR, a cytokine, one or more cell tags, gene switch polypeptides for ligand-inducible control of the cytokine and a transposase effective to integrate said one or more polynucleotides into the genome of said cells, to provide a population of engineered cells. In an embodiment, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain. In some embodiments, the first gene switch polypeptide and the second gene switch polypeptide are connected by a linker. In one instance, lymphodepletion is not required prior to administration of the engineered cells to a subject.

In another embodiment, a method of enhancing in vivo persistence of engineered cells in a subject in need thereof comprises obtaining a sample of cells from a subject, and transfecting cells of the sample of cells with one or more polynucleotides that comprise one or more transposons. In some cases, the transposons encode a chimeric antigen receptor (CAR) or a TCR, a cytokine, one or more cell tags, gene switch polypeptides for ligand-inducible control of the cytokine and a transposase effective to integrate the DNA into the genome of said cells, to provide a population of engineered cells. In some cases, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein the first gene switch polypeptide and the second gene switch polypeptide are connected by a linker. In one instance, lymphodepletion is not required prior to administration of the engineered cells to a subject.

In another embodiment, a method of treating a subject with a solid tumor comprises obtaining a sample of cells from a subject, transfecting cells of the sample with one or more polynucleotides that comprise one or more transposons, and administering the population of engineered cells to the subject. In one instance, lymphodepletion is not required prior to administration of the engineered cells to a subject. In some cases, the one or more transposons encode a chimeric antigen receptor (CAR) or a TCR, a cytokine, one or more cell tags, gene switch polypeptides for ligand-inducible control of the cytokine and a transposase effective to integrate the DNA into the genome of the cells. In some cases, the gene switch polypeptides comprise: i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein the first gene switch polypeptide and second gene switch polypeptide are connected by a linker. In some cases, the cells are transfected via electroporation. In some cases, the polynucleotides encoding the gene switch polypeptides are modulated by a promoter. In some cases, the promoter is a tissue-specific promoter or an EF1A promoter or functional variant thereof. In some cases, the tissue-specific promoter comprises a T cell specific response element or an NFAT response element. In some cases, the cytokine comprises at least one of IL-1, IL-2, IL-15, IL-12, IL-21, a fusion of IL-15, IL-15Rα, or an IL-15 variant. In some cases, the cytokine is in secreted form. In some cases, the cytokine is in membrane-bound form. In some cases, the cells are NK cells, NKT cells, T-cells or T-cell progenitor cells. In some cases, the cells are administered to a subject (e.g. by infusing the subject with the engineered cells). In some cases, the method further comprises administering an effective amount of a ligand (e.g. veledimex) to induce expression of the cytokine. In some cases, the CAR is capable of binding at least one of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MAGE-A1, MUC-16, h5T4, PSMA, TAG-72, EGFRvIII, CD123 and VEGF-R2. In some cases, the transposase is salmonid-type Tc1-like transposase. In some cases, the transposase is SB11 or SB100x transposase. In some cases, the cell tag comprise at least one of a HER1 truncated variant and a CD20 truncated variant.

Pharmaceutical Compositions and Dosage

In some embodiments, disclosed herein are compositions comprising a polynucleotide or polypeptide disclosed herein for administration in a subject. In some instances, are modified effector cell compositions encoding a polynucleotide or polypeptide disclosed herein, and optionally containing a cytokine and/or an additional therapeutic agent. In some instances, also included herein are vectors encoding gene-switch polypeptides for regulating expression of a chimeric antigen receptor for modification of an effector cell.

In some instances, pharmaceutical compositions of a modified effector cell or a vector encoding gene-switch polypeptides and a chimeric antigen receptor are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Pharmaceutical compositions are optionally manufactured in a conventional manner, such as, by way of example only, by means of conventional mixing, dissolving, granulating, dragee-making, levigating, emulsifying, encapsulating, entrapping or compression processes.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The pharmaceutical compositions described herein are administered by any suitable administration route, including but not limited to, oral, parenteral (e.g., intravenous, subcutaneous, intramuscular, intracerebral, intracerebroventricular, intra-articular, intraperitoneal, or intracranial), intranasal, buccal, sublingual, or rectal administration routes. In some instances, the pharmaceutical composition is formulated for parenteral (e.g., intravenous, subcutaneous, intramuscular, intracerebral, intracerebroventricular, intra-articular, intraperitoneal, or intracranial) administration.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the pharmaceutical compositions are formulated into capsules. In some embodiments, the pharmaceutical compositions are formulated into solutions (for example, for IV administration). In some cases, the pharmaceutical composition is formulated as an infusion. In some cases, the pharmaceutical composition is formulated as an injection.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated. In some embodiments, the compositions are formulated into particles (for example for administration by capsule) and some or all of the particles are not microencapsulated and are uncoated.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

"Proliferative disease" as referred to herein means a unifying concept that excessive proliferation of cells and turnover of cellular matrix contribute significantly to the pathogenesis of several diseases, including cancer is presented.

"Patient" or "subject" as used herein refers to a mammalian subject diagnosed with or suspected of having or developing a physiological condition, for instance a cancer or an autoimmune condition or an infection. In some embodiments, the term "patient" refers to a mammalian subject with a higher than average likelihood of developing cancer. Exemplary patients may be humans, apes, dogs, pigs, cattle, cats, horses, goats, sheep, rodents and other mammalians that can benefit from the therapies disclosed herein. Exemplary human patients can be male and/or female.

"Patient in need thereof" or "subject in need thereof" is referred to herein as a patient diagnosed with or suspected of having a disease or disorder, for instance, but not restricted to a proliferative disorder such as cancer. In some cases, a cancer is a solid tumor or a hematologic malignancy. In some instances, the cancer is a solid tumor. In other instances, the cancer is a hematologic malignancy. In some cases, the cancer is a metastatic cancer. In some cases, the cancer is a relapsed or refractory cancer. In some instances, the cancer is a solid tumor. Exemplary solid tumors include, but are not limited to, anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; gastroenterological cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; vulvar cancer; or glioblastoma. In some embodiments leukemia can be, for instance, acute lymphoblastic leukemia (ALL), acute myeloid leukemia (AML), chronic lymphocytic leukemia (CLL) and chronic myeloid leukemia (CML).

"Administering" is referred to herein as providing the compositions of the present disclosure to a patient. By way of example and not limitation, composition administration, e.g., injection, may be performed by intravenous (i.v.) injection, sub-cutaneous (s.c.) injection, intradermal (i.d.) injection, intraperitoneal (i.p.) injection, or intramuscular (i.m.) injection. One or more such routes may be employed. Parenteral administration can be, for example, by bolus injection or by gradual perfusion over time. Alternatively, or concurrently, administration may be by the oral route. Additionally, administration may also be by surgical deposition of a bolus or pellet of cells, or positioning of a medical device. In an embodiment, a composition of the present disclosure may comprise engineered cells or host cells expressing nucleic acid sequences described herein, or a vector comprising at least one nucleic acid sequence described herein, in an amount that is effective to treat or prevent proliferative disorders. A pharmaceutical composition may comprise a target cell population as described herein, in combination with one or more pharmaceutically or physiologically acceptable carriers, diluents or excipients. Such compositions may comprise buffers such as neutral buffered saline, phosphate buffered saline and the like, carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

As used herein, the terms "treatment," "treating," and its grammatical equivalents refer to obtaining a desired pharmacologic and/or physiologic effect. In embodiments, the effect is therapeutic, i.e., the effect partially or completely cures a disease and/or adverse symptom attributable to the disease. To this end, the method described herein comprises administering a "therapeutically effective amount" of the composition comprising the host cells expressing the nucleic acid sequence described herein, or a vector comprising the nucleic acid sequences described herein.

The terms "therapeutically effective amount", "therapeutic amount", "immunologically effective amount", anti-tumor effective amount", "tumor inhibiting effective amount" or their grammatical equivalents refers to an amount effective, at dosages and for periods of time necessary, to achieve a desired therapeutic result. The therapeutically effective amount may vary according to factors such as the disease state, age, sex, and weight of the individual and the ability of a composition described herein to elicit a desired response in the individual. The precise amount of the compositions of the present disclosure to be administered can be determined by a physician with consideration of individual differences in age, weight, tumor size, extent of infection or metastasis, and condition of the patient (subject).

Alternatively, the pharmacologic and/or physiologic effect of administration of one or more compositions described herein to a patient or a subject may be "prophylactic," i.e., the effect completely or partially prevents a disease or symptom thereof.

A "prophylactically effective amount" refers to an amount effective, at dosages and for periods of time necessary, to achieve a desired prophylactic result (e.g., prevention of disease onset).

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethyl cellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and An anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethyl cellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include CAR-T cells (e.g., CD19-specific CAR-T cells) encoding gene-switch polypeptides for regulated expression of CARs described herein, and optionally in addition with cytokines and/or chemotherapeutic agents disclosed herein. Such kits optionally include an identifying description or label or instructions relating to its use in the methods described herein.

A kit typically includes labels listing contents and/or instructions for use, and package inserts with instructions for use. A set of instructions will also typically be included.

In some embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

EXAMPLES

These examples are provided for illustrative purposes only and not to limit the scope of the claims provided herein.

Example 1. Nucleofection of PBMC with SB Gene Switch System

Various DNA plasmids expressing a SB transposon system, i.e. SB11, membrane bound IL-15 (mbIL-15), and chimeric antigen receptor (CAR), were transfected to peripheral blood mononuclear cells (PBMC) via nucleofection to redirect T cell specificity (FIG. 1).

On day 0, 20 million PBMC were resuspended in 100 μL of Amaxa Human T cell Nucleofector solution (Cat. no. VPA-1002; Lonza, Basel, Switzerland) mixed with a total of 15 μg of transposons and 5 μg of transposase (SB11) and electroporated.

The following day (day 1) cells were counted, and CAR expression was measured by flow cytometry. CAR T Cells were stimulated with either γ-irradiated (100 Gy) or mitomycin C treated AaPCs at a 1:1 ratio. The AaPC cells used were K562-AaPC expressing CD19 antigen. Cultures were supplemented with IL-21 (30 ng/ml) only for the first round of stimulation and subsequently with recombinant human IL-2 (50 IU/ml) and IL-21 (30 ng/ml) (Pepro Tech) for remaining stimulations. T cell cultures were phenotyped at the end of each stimulation cycle, which typically lasted 7 days. The cultures were phenotyped for CAR expression by multi-parameter flow cytometry utilizing either Protein L or anti-idiotype antibody that recognizes CD19-specific CAR. Cultures were also closely monitored for the outgrowth of NK cells (defined as CD3negCD56+ population) and were removed from the CAR T cell cultures when the percentage exceeded 10% of total cell populations using magnetic beads for specific for CD56 (Stem Cell Technologies and/or Miltenyi Biotec), according to the manufacturer's instructions.

Example 2. Flow Cytometry Analysis of ON-OFF SB Gene Switch System

CD19-specific T cells were generated from mononuclear cells (MNC) derived from PB or UCB using SB transposition to introduce the CAR followed by addition of AaPC to numerically expand the T cells in a CAR-dependent manner.

For flow cytometry analysis to assess expression of various markers and gene(s) of interest, cells were gently resuspended and cell number, and viability were measured using Trypan blue exclusion method with the Countess instrument. Cell diameter size was also recorded. $5\times10^5$ cells for each for the samples were harvested at 330×g for 4 min at 10° C. for antibody staining. Harvested cells were incubated on ice for at least 15 min with 10% human AB serum in HBSS. Antibody cocktails containing fluorescently conjugated antibodies included one or more of antibodies specific to CD4 (Clone RPA-T4), CD8 (Clone SK1), CD3 (Clone UCHT1), CD56, CD19-specific CAR (anti-idiotype antibody), IL-15, and IL-15Rα, in HBSS+0.1% BSA+2 mM EDTA. The prepared antibody cocktails and associated fluorescence minus one/isotype control were added to stain the cell samples, and then the samples were incubated on ice for 30 min. The samples were then washed then with FACS buffer (HBSS+0.5% BSA+2 mM EDTA) and stained with Fixable Viability Dye (eBiosciences) for 30 min on ice. Cells were washed with FACS buffer and then fixed with a 4% paraformaldehyde solution (BD Cytofix; BD Biosciences). All samples were run on a LSR II flow cytometer, a Fortessa X-20 flow cytometer (BD Biosciences) or iQue Screener Plus (Intellicyt) and data was analyzed using FlowJo V10 (TreeStar, Ashland, Oreg.) or iQue Screener software.

For induction of expression using ligand (veledimex), AaPC stimulated CAR-T cells were harvested at $1\times10^6$ cells/ml. Either veledimex or DMSO (to keep DMSO concentration constant in both cultures) was added to the cultures. Veledimex was used at a concentration of 20 nM, 50 nM, 100 nM or as described. Cells were then cultured at 37° C. in presence of veledimex or DMSO for 2-3 days. After 2-3 days in culture, $5\times10^5$ cells for each for the samples were harvested at 330×g for 4 min at 10° C. for antibody staining. Harvested cells were incubated on ice for at least 15 min with 10% human AB serum in HBSS. Antibody cocktails containing fluorescently conjugated antibodies included one of more of antibodies specific to CD4 (Clone RPA-T4), CD8 (Clone SK1), CD3 (Clone UCHT1), CD56, CD19-specific CAR (anti-idiotype antibody), IL-15, and IL-15Ra in HBSS+0.1% BSA+2 mM EDTA. The prepared antibody cocktails and associated isotype control were added to stain the cell samples, and then the samples were incubated on ice for 30 min. The samples were then washed with FACS buffer (HBSS+0.5% BSA+2 mM EDTA) and stained with Fixable Viability Dye (eBiosciences) for 30 min on ice. Cells were washed with FACS buffer and fixed with 4% paraformaldehyde solution (BD Cytofix; BD Biosciences). All samples were run on a LSR II flow cytometer, a Fortessa X-20 flow cytometer (BD Biosciences) or iQue Screener Plus (Intellicyt) and data was analyzed using FlowJo V10 (TreeStar, Ashland, Oreg.) or iQue Screener software.

For veledimex ON-OFF-ON experiments, veledimex was first added at mentioned concentration (typically between 20-100 nM) to cell cultures for 2-3 days. An aliquot of cells was harvested and analyzed for expression (ON) of various proteins by flow cytometry as noted above. Remaining cell culture was then washed and resuspended in complete medium without veledimex and cultured for up to 5 days. Aliquots of cells were harvested and analyzed for expression (OFF) at times mentioned by flow cytometry as noted above. Remaining cell culture was then washed and resuspended with complete medium containing veledimex to turn the expression of target gene(s) back on. After 2-3 days in culture, aliquot of cells were harvested and analyzed for expression by flow cytometry.

Example 3. Survival Experiments

Multiple Sleeping Beauty transposon DNA plasmids encoding for RTS-membrane bound IL-15 (RTS-mbIL-15), CD19-specific chimeric antigen receptor (CD19 CAR) (Design 9, FIG. 2) were transfected into peripheral blood mononuclear cells (PBMC) along with plasmid DNA encoding for Sleeping Beauty transposase SB11 via nucleofection (FIG. 1). On day 0, 20 million PBMC were resuspended in 100 μL of Amaxa Human T cell Nucleofector solution (Cat. no. VPA-1002; Lonza, Basel, Switzerland) mixed with a total of 15 μg of transposons and 5 μg of transposase and nucleofected into cells. The following day (day1) cells were counted, and CAR expression was measured using flow cytometry. Cells were stimulated with either γ-irradiated (100 Gy) or mitomycin C treated K562 based AaPCs expressing CD19 on their surface at a 1:1 ratio. Cultures were supplemented with IL-21 (30 ng/ml) only for the first round of stimulation and subsequently with recombinant human IL-2 (50 IU/ml) and IL-21 (30 ng/ml) (Pepro Tech) for remaining stimulations. T cell cultures were phenotyped at the end of each stimulation cycle, which typically lasted 7 days. The cultures were phenotyped for CAR expression, utilizing anti-idiotype antibody staining to detect CD19-specific CAR-T cells by multi-parameter flow cytometry. Cultures were also closely monitored for the outgrowth of NK cells (defined as CD3negCD56+ population) and were removed from the CAR T cell cultures when the percentage exceeded 10% of total cell populations using magnetic beads for CD56 (Stem Cell Technologies and/or Miltenyi Biotec), according to the manufacturer's instructions.

To measure persistence of CD19-specific CAR-T cells co-expressing RTS-mbIL-15 upon withdrawal of cytokines (IL-2 and IL-21) from culture media, CAR-T cells were harvested and seeded in complete RPMI medium with or without IL-2 and IL-21, at the concentration of $1\times10^6$ cells/ml in 6-well plates. Veledimex (50 nM final concentration) or DMSO control were added to the culture media. Culture medium was changed every 2-3 days and small aliquot of cells were harvested for flow analysis. Flow analysis was conducted to measure mbIL-15 expression as well as to measure the % of live cells in the culture in presence of absence of cytokines from media. Survival of CAR-T cells is shown in FIG. 12 in presence and absence of cytokines. In absence of cytokines in culture, improved survival of CAR-T cells was seen when veledimex was added to induce mbIL-15 expression. When veledimex was not added (mbIL-15 expression was not induced), cells did not survive in ex vivo culture.

Example 4. Western Blotting

PBMC were nucleofected with plasmids of Sleeping Beauty system to express CD19-specific CAR under constitutive promoter (CD19 CAR alone), or CD19-specific CAR and mbIL-15 both under constitutive promoters (CD19 CAR+constitutive-mbIL-15) or CD19-specific CAR under constitutive promoter and RTS-mbIL-15 (CD19 CAR+RTS-mbIL-15). Nucleofected cells were cultured in presence of AaPC as described in Example 1.

After four rounds of stimulations, cells were cultured in absence (CD19 CAR alone, CD19 CAR+constitutive-mbIL-15 and CD19 CAR+RTS-mbIL-15) or presence (CD19 CAR+RTS-mbIL-15) of veledimex for 2-3 days. Cell lysates were prepared for western blot analysis. Approximately 10 μg lysate/lane of NuPAGE 10% Bis-Tris gel was loaded. Proteins were transferred from gel to a polyvinylidene fluoride (PVDF) membranes using the iBlot® (Life Technologies) semi-dry transfer apparatus. Membrane was blocked using a 5% (w/v) powdered milk solution in a PBS+Tween-20 (PBST; 1×PBS+0.05% Tween-20) solution stained with goat anti-human IL-15 (R&D Systems) primary antibody and rabbit anti-goat IgG HRP (KPL Laboratories) secondary antibody. SuperSignal™ West Pico Chemiluminescent Substrate (Thermo Fisher Scientific) for enhanced chemiluminescence (ECL) detection was utilized.

Image of the western blot were captured on the FluorChem™ E Imager (ProteinSimple, San Jose, Calif.) system using the Digital Darkroom software and AlphaView® software (ProteinSimple). FIG. 14 shows image of western blot. mbIL-15 expression was not detected by western blot when veledimex was absent (CD19 CAR+RTS-mbIL-15), but strong expression of mbIL-15 was observed when veledimex was added to the culture. In CD19 CAR only negative control, no mbIL-15 expression was observed. In CD19 CAR+constitutive-mbIL-15 positive control, expression of mbIL-15 was detected.

Example 5. T Cell Activation and Ligand Specific Control of mbIL-15 Transgene Expression Sleeping Beauty transposons were designed to stably express CD19-specific CAR, a cell tag as well as gene switch-controlled mbIL-15. Expression of one or both of gene switch components (e.g. VP16/RxR and Gal4/EcR) were performed under the control of a T cell activation specific promoter. In this example, a T cell activation dependent promoter generated by 6×NFAT response element fused to minimal IL-2 promoter (NFAT6-IL2 promoter) was utilized to drive expression of gene switch components—VP16-RxR and/or Gal4-EcR fusion proteins for conditional expression of mbIL-15. When components of the gene switch are under the control of NFAT6-IL2 promoter, expression of mbIL-15 requires two conditions to be met: 1) T cells are activated; and 2) activator ligand, veledimex, to be present. SB transposons construct combinations shown in FIG. 20A were transfected along with SB11 transposase in donor T cells.

On day 0, 10-20 million T cells were resuspended in 100 μL of Amaxa Human T cell Nucleofector solution (Cat. no. VPA-1002; Lonza, Basel, Switzerland) mixed with a total of 15 μg of transposon(s) and 5 μg of transposase (SB11) and electroporated.

The following day (day 1) cells were counted, and CAR expression was measured by flow cytometry. CAR-T Cells were selectively expanded ex vivo by successive rounds of stimulations every 7-10 days for up to 4 cycles with either γ-irradiated (100 Gy) or mitomycin C treated AaPCs at a 1:1 ratio. The AaPC cells used were K562-AaPC expressing CD19 antigen. Cultures were supplemented with IL-21 (30 ng/ml) only for the first round of stimulation and subsequently with recombinant human IL-2 (50 IU/ml) and IL-21 (30 ng/ml) (Pepro Tech) for remaining stimulations.

For flow cytometry analysis to assess expression of various markers and gene(s) of interest cells were gently resuspended and cell number and viability were measured using Trypan blue exclusion method with the Countess instrument. Cell diameter size was also recorded. $5\times10^5$ cells for each for the samples were harvested at 330×g for 4 min at 10° C. for antibody staining. Harvested cells were incubated on ice for at least 15 min with 10% human AB serum in HBSS. Antibody cocktails containing fluorescently conjugated antibodies included one or more of antibodies specific to CD4, CD8, CD3, CD56, CD19-specific CAR (anti-idiotype antibody), IL-15 and/or IL-15Ra, in HBSS+0.1% BSA+2 mM EDTA. The prepared antibody cocktails and associated fluorescence minus one/isotype control were added to stain the cell samples, and then the samples were incubated on ice for 30 min. The samples were then washed then with FACS buffer (HBSS+0.5% BSA+2 mM EDTA) and stained with Fixable Viability Dye (eBiosciences) for 30 min on ice. Cells were washed with FACS buffer and then fixed with a 4% paraformaldehyde solution (BD Cytofix; BD Biosciences). All samples were run on a LSR II flow cytometer, a Fortessa X-20 flow cytometer (BD Biosciences) or iQue Screener Plus (Intellicyt) and data was analyzed using FlowJo V10 (TreeStar, Ashland, Oreg.) or iQue Screener software.

To assess the impact of T cell activation on mbIL-15 expression, cells were kept in culture media for at least 7 days post last AaPC stimulation to test baseline (no stimulation) expression levels. T cells were activated using different doses of ConA (1 or 5 μg/mL) for 48 hours or PMA/Ionomycin for 24 hours prior to treatment with veledimex or DMSO.

Non-activated or activated CAR-T cells were harvested and either 100 nM veledimex or DMSO (to keep DMSO concentration constant in both cultures) was added to the cultures. Cells were then cultured at 37° C. in presence of veledimex or DMSO for at least 24 hours before flow cytometry analysis to measure transgene expression. CAR and mbIL-15 expression was quantified in either resting (FIG. 20B) or activated T cells in presence of absence of veledimex (FIG. 20C: ConA 1 μg/mL; ConA 5 μg/mL: FIG. 20D, PMA/Ionomycin: FIG. 20E).

FIG. 20B shows that in absence of T cell activation, only CAR-T cells that harbor transposons for expression of gene switch components (e.g. VP16/RxR and Gal4/EcR) under a constitutive promoter were able to express mbIL-15 in when veledimex was added to the culture. As shown in FIGS. 20C through 20E, CAR-T cells harboring transposons for expression of one or more gene switch components under NFAT6-IL-2 promoter (constructs #3, 4 and 6) exhibited expression of mbIL-15 when veledimex was added to culture showing two conditions had to be met for inducible expression of mbIL-15 by CAR-T cells. Furthermore, levels of mbIL-15 expression in presence of veledimex at fixed concentration increased with level of T cells activation (FIG. 20C and FIG. 20D). Extremely low levels of mbIL-15 expression by flow cytometry were detected in absence of veledimex for all tested construct combinations. Consistent with the design of these ligand inducible switch systems, only $CAR^+$ T cells were able to induce mbIL-15 in presence of veledimex.

Example 6. Expression of IL-12 Using Gene Switch System

Sleeping Beauty transposons were designed as depicted in FIG. 22 to stably express EGFRvIII-specific CAR, a cell tag and RTS-IL-12. Transposon plasmids were electroporated in several donor T cells as previously described. EGFRvIII-CAR-T cells were selectively expanded ex vivo by successive rounds of stimulations every 7-10 days for up to 4 cycles with either γ-irradiated or mitomycin C treated AaPC that served as "feeder cells" at 1:1 ratio in media supplemented with IL-2 and IL-21. The AaPC cells used were K562-AaPC expressing EGFRvIII antigen. FIG. 26 depicts CAR expression in T cells from multiple donors as the CAR+ T cells are selectively expanded ex vivo.

Veledimex ON-OFF Cycling Experiments:

For each ON-OFF cycle, veledimex was first added (ON) at previously mentioned concentrations (typically between 20-100 nM) to cell cultures for 2-3 days. An aliquot of cells was harvested and analyzed for expression (ON) of various proteins by flow cytometry and/or ELISA at noted time points. Remaining cell culture was then washed and resuspended in complete medium without veledimex (OFF) and cultured for up to 5 days. Aliquots of cells were harvested and analyzed for expression (OFF) at times mentioned by flow cytometry and/or ELISA as noted above. Veledimex ON-OFF cycle(s) can be repeated again with remaining cell culture by repeating the process.

To assay IL-12 induction in EGFRvIII-CAR-T cells, Pan T-cells at 24 h post nucleofection were treated with DMSO (control) or veledemix in the presence of AaPCs in media containing IL-21. After 48 hours post-nucleofection, culture supernatants were analyzed for IL-12 levels by ELISA.

FIG. 27 shows that treatment with veledimex induced IL-12 expression by T cells that were transfected with SB transposons to co-express both CAR and RTS-IL-12. CAR-T cells lacking RTS-IL-12 however, failed to produce IL-12 in culture supernatant. Treatment with DMSO control showed low background levels of IL-12 induction.

Furthermore, the ability of RTS-IL-12/CAR-T cells to produce inducible IL-12 was assessed in presence or absence of antigen specific stimulation. EGFRvIII-CAR/RTS-IL-12 T cells were expanded ex vivo by three successive rounds of stimulation with $EGFRvIII^{+}$ AaPCs. Veledimex (100 nM) or DMSO (control) were added to the culture of EGFRvIII-CAR/RTS-IL-12 T cells in absence (FIG. 28A) or presence (FIG. 28B) of $EGFRvIII^{+}$ AaPCs for 48 hours before analysis of IL-12 levels in culture supernatant. As shown in FIG. 28A and FIG. 28B, the ability of EGFRvIII-CAR/RTS-IL-12 T cells to express veledimex induced IL-12 is greatly enhanced in presence of EGFRvIII antigen specific stimulation with low background levels of IL-12 expression in absence of veledimex.

Example 7. Veledimex ON-OFF Cycling in EGFRvIII CAR Expressing Cells Using RTS Gene Switch System The effect of repeated treatments and withdrawals of veledimex to EGFRvIII-CAR-T cells harboring an inducible IL-12 gene was determined in vitro both in the presence and absence of antigen specific T cell activation by co-culture with AaPCs. In the first cycle (ON-OFF) of ligand treatment, CAR-T cells ($10^{6}$/ml) expanded ex vivo by four successive rounds of stimulation with $EGFRvIII^{+}$ AaPCs were treated with DMSO or veledimex and cultured in the presence or absence of AaPCs in media containing IL-21 and IL-2. After 48 hours post-treatment, cells were washed thoroughly to remove ligand and cultured in a new culture vessel in media containing IL-21 and IL-2 for 5 days. Culture supernatants harvested between 24-120 hours post-treatment were then analyzed for expression of IL-12 and IFNγ.

In the second cycle (ON-OFF) of ligand treatment, CAR-T cells from cultures treated with DMSO or veledimex in the presence of AaPCs in cycle 1 were collected at 5 days after withdrawal of veledimex (in cycle 1) and subjected to a second cycle of ligand treatment with DMSO or veledimex in the presence or absence of antigen specific T cell activation by co-culture with AaPCs. After 48 hours post-treatment, cells were washed thoroughly to remove ligand and cultured in a new culture vessel in media containing IL-21 plus IL-2 for 5 days. Culture supernatants harvested between 24-120 hours post-treatment were then analyzed for expression of IL-12 and IFNγ.

FIG. 29A shows that treatment with veledimex in EGFRvIII-CAR-T cells also harboring inducible IL-12 constructs (XON-61 or XON-62; SEQ ID NO 135 or 136) results in an increase in IL-12 expression relative to treatment with DMSO in culture supernatants at 48 h post-treatment. Levels of IL-12 induction were enhanced in the presence of AaPC-mediated antigen-specific stimulation compared to the absence of antigen-specific stimulation. Very low background levels of IL-12 expression were observed in absence of veledimex in presence or absence of antigen specific stimulation. EGFRvIII-CAR-T cells without inducible IL-12 failed to express any IL-12 in presence or absence of antigen specific stimulation.

The effect of withdrawing veledimex on IL-12 expression is shown in FIG. 30A (cells cultured in the absence of AaPCs) and FIG. 30B (cells cultured in the presence of AaPCs). In both the presence and absence of AaPC-mediated antigen-specific stimulation, withdrawal of veledimex at 48 h-post-treatment resulted in a reduction of IL-12 expression. Levels of IL-12 induction were significantly lower in the absence of antigen-specific stimulation (FIG. 30A) compared to in the presence of antigen-specific stimulation (FIG. 30B). But levels of IL-12 gradually reduced back to the baseline levels upon withdrawal of veledimex exhibiting tight control of inducible gene expression.

FIG. 31A and FIG. 31B show levels of IL-12 induction in culture supernatants at 48 h post-ligand treatment during a second cycle with veledimex or DMSO following withdrawal of the agents during cycle 1. DMSO or veledimex treated cells cultured in the presence of EGFRvIII-expressing AaPCs in cycle 1 were treated with veledimex (or DMSO) in cycle 2 in the presence or absence of $EGFRvIII^{+}$ aAaPCs. Results show that cells treated with veledimex and $EGFRvIII^{+}$ AaPCs in cycle 2 show increased IL-12 induction when they were treated with veledimex and $EGFRvIII^{+}$-AaPCs during cycle 1 (FIG. 31B) relative to cells treated with DMSO and $EGFRvIII^{+}$ AaPCs during cycle 1 (FIG. 31A). Again very low background levels of IL-12 expression were observed in absence of veledimex.

Kinetics of RTS-IL-12 expression upon two cycles of treatment with veledimex is captured in FIG. 32A. EGFRvIII-CAR-T cells harboring inducible IL-12 constructs (XON-61 or XON-62: SEQ ID NO 135 or 136) were evaluated for their ability to induce IL-12 expression in presence of absence of veledimex by two cycles of ligand treatment as described above. Ligand inducible gene switch vectors in this example are designed such that only cells that express both transposons are capable of gene switch controlled expression of IL-12. Expression of EGFRvIII CAR was quantified by flow cytometry in T cells prior to start of cycle 1 of ligand treatment as shown in FIG. 34B. Cells were gated on CD3.

As shown in FIG. 32A, IL-12 expression by these CAR-T cells can be turned ON and OFF repeatedly by addition or withdrawal of activator ligand veledimex during prolonged culture period. IL-12 expression went down to baseline levels upon withdrawal of veledimex and can be turned back on upon addition of veledimex. The data is representative from one donor.

FIG. 33 shows another example of kinetics of RTS-IL-12 expression upon two cycles of treatment with veledimex. EGFRvIII-CAR-T cells harboring inducible IL-12 constructs (XON-61 or XON-62; SEQ ID NO 135 or 136) were evaluated for their ability to induce IL-12 expression in presence of absence of veledimex by two cycles of ligand treatment as described above. In this case, the first treatment cycle was carried out in the presence of $EGFRvIII^{+}$ AaPCs and the second cycle was in the absence of $EGFRvIII^{+}$ AaPCs. Consistent with previous finding, veledimex can regulate IL-12 expression by EGFRvIII-CAR-T cells upon repeated treatment and withdrawal during prolonged culture period. Removal of AaPC-mediated EGFRvIII-specific stimulation during cycle 2 leads to a corresponding reduction of IL-12 levels. The data is representative from a second donor.

Example 8. Veledimex Dose-Response

EGFRvIII-CAR T cells with or without RTS-IL-12 were expanded ex vi by three successive rounds of stimulation with $EGFRvIII^{+}$ AaPCs. T cells were then treated with varying doses of veledimex from 0 nM (DMSO control) to 100 nM. At 48 h post veledimex treatment, culture supernatants were harvested analyzed for IL-12 levels by ELISA. EGFRvIII-CAR expression in all groups was confirmed with flow cytometry and was stable with increasing doses of veledimex (data not shown) as expected with CAR expression under control of a constitutive promoter.

Results are shown in FIG. 34. Results show that, EGFRvIII-CAR/RTS-IL-12 T cells produced IL-12 in veledimex dose dependent manner. Lower levels of IL-12 expression was observed for a given veledimex concentration in cells transfected with transposons that express a cell tag in addition to CAR and IL-12 compared to cells lacking cell tag expression. EGFRvIII-CAR-T cells without RTS-IL-12 failed to express IL-12.

Example 9. Specific Cytotoxicity of EGFRvIII-CAR-T Cells Towards EGFRvIII$^+$ Target Cells The ability of T-cells expressing EGFRvIII-CAR to respond to EGFRvIII$^+$ target cells was tested. EGFRvIII-CAR T cells with or without RTS-IL-12 were expanded ex vivo by four successive rounds of stimulation with EGFRvIII$^+$ AaPCs. These effector EGFRvIII-CAR-T cells were rested for 48 h in RPMI containing 2% FBS and L-glutamine prior to co-culture with EGFRvIII$^+$ and EGFRvIII$^{neg}$ target cells at a 1:1 effector to target cell ratio in absence of veledimex. Culture supernatants were collected at 24 h post-culture and analyzed for IFNγ as a functional readout of specificity of EGFRvIII-CAR-T cells.

FIG. 35 shows EGFRvIII antigen specific IFNγ production by CAR-T cells at 24 h post co-culture with target cells. Co-culture with EGFRvIII$^{neg}$ EL4 cell line or effector CAR-T cells alone did not result in IFNγ expression.

FIG. 36A shows IFNγ in culture supernatants at 24 h post co-culture with EGFRvIII-expressing Glioblastoma target cells (no veledimex). Results show that EGFRvIII$^+$ Glioblastoma target cells (U251MG-EGFRvIII-Fluc-GFP and U87MG-EGFRvIII-Fluc-GFP) induced IFNγ secretion by EGFRvIII-CAR T-cells while EGFRvIII$^{neg}$ target cells (U251MG, U251MG-EGFRvIII-Fluc-GFP, U87MG, and U87MG-Fluc-GFP) or effector cells alone failed to induce IFNγ secretion.

Cytotoxicity of EGFRvII-CAR-T cells towards EGFRvIII$^+$ and EGFRvIII$^{neg}$ target cells was tested in a 2 hr Europium release assay. Target cell lines were labeled using the DELFIA BATDA reagent (DELFIA EuTDA Cytotoxicity assay; Perkin Elmer). EGFRvIII-CAR-T effector (E) cells were co-cultured with labeled target (T) cells at (E:T) ratios of 3:1, 1:1 or 0.3:1 in RPMI-1640+5% heat-inactivated FBS. After 2 hr, supernatant from the co-cultures were harvested and developed with addition of the DELFIA Europium assay and read on a time-resolved fluorescence instrument to measure cytotoxicity of target cells. The results from example experiments are depicted in FIG. 36B.

As shown in FIG. 36B, EGFRvIII-CAR-T cells with or without RTS-IL-12 showed EGFRvIII antigen specific, dose-dependent cytotoxicity of target cells.

Example 10. Nucleofection of PBMCs with Serine Recombinase System

Various DNA plasmids containing serine recombinase attachment sites and components of the gene switch system as depicted in FIG. 17 were transfected to peripheral blood mononuclear cells (PBMC) via nucleofection to redirect T cell specificity. Specifically, 3 single vectors were tested in the presence and absence of a serine recombinase, SF370:

(i) CAR:HER1t+constitutive mbIL15 (positive control)
(ii) CAR:HER1t+promoterless mbIL15 (negative control)
(iii) CAR:HER1t+RTS:mbIL15

The expression of the CAR and mbIL15 was evaluated weekly (at days 1, day 8, day 15 and day 22). Aliquots of cells were treated with either DMSO or veledimex 24-48 h prior to each flow to assess inducible mbIL15 expression. AaPC Clone 1 was added weekly at a 1:1 ratio with CAR+ cells.

Only cells receiving the CAR/mbIL15 vector construct+SF370 recombinase were observed to expand; all other cultures failed to expand within a week despite similar transfection efficiencies. This result is indicative of recombinase-mediated integration of the test construct. HER1t expression was only evaluated on days 22 & 29 and correlates well with CAR expression (data not shown).

Two weeks post-transfection, veledimex treatment (~48 h) was associated with an induction of mbIL-15 expression. In the absence of veledimex, mbIL-15 expression is in the range with the negative control "promoterless mbIL15" sample. Removal of veledimex was associated with complete loss of mbIL15 expression.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments described herein, or combinations of one or more of these embodiments or aspects described therein may be employed in practicing the present disclosure. It is intended that the following claims define the scope of the present disclosure and that methods and structures within the scope of these claims and their equivalents be covered thereby.

What is claimed is:

1. A vector comprising a polynucleotide encoding: (a) a first gene switch polypeptide comprising a transactivation domain fused to a first ligand binding domain; and (b) a second gene switch polypeptide comprising a DNA binding domain fused to a second ligand binding domain, wherein:

the first and second gene switch polypeptides are connected by a polypeptide linker; and the first gene switch polypeptide comprises an amino acid sequence having at least 90% identity with SEQ ID NO: 183 and/or the second gene switch polypeptide comprises an amino acid sequence having at least 90% identity with SEQ ID NO: 187 or 188.

2. The vector of claim 1, wherein the vector is a Sleeping Beauty transposon.

3. The vector of claim 1, wherein the vector comprises one or more recombinase attachment sites.

4. The vector of claim 1, wherein the polypeptide linker comprises a cleavable linker sequence.

5. The vector of claim 1, wherein expression of the first and second gene switch polypeptides are modulated by a constitutive promoter.

6. The vector of claim 1, wherein the vector is a lentivirus vector, a retroviral vector, or a non-viral vector.

7. A method of stimulating the proliferation and/or survival of engineered cells, the method comprising transfecting a cell obtained from a subject with:

(a) the vector of claim 1;

(b) a polynucleotide comprising a transposon encoding a chimeric antigen receptor or a T cell receptor; and (b) one or more polynucleotides encoding a cytokine, a cell tag and a transposase effective to integrate the transposon into the genome of the cell.

8. A gene switch system for ligand-inducible control of heterologous gene expression, the gene switch system comprising:

(a) the vector of claim 1; and (b) a vector comprising a heterologous gene under the control of a ligand-inducible promoter.

9. The gene switch system of claim 8, wherein the vector of (a) further comprises a polynucleotide sequence encoding a chimeric antigen receptor, the expression of which is modulated by a non-inducible promoter.

10. The gene switch system of claim 9, wherein the chimeric antigen receptor is capable of binding at least one of CD19, CD33, BCMA, CD44, a-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MAGE-Al, MUC-16, h5T4, PSMA, TAG-72, EGFRvIII, CD123, and VEGF-R2.

11. The gene switch system of claim 8, wherein the vector of (b) further comprises a polynucleotide sequence encoding a cell tag.

12. The gene switch system of claim 11, wherein the cell tag comprises a HER1 truncated variant and/or a CD20 truncated variant.

13. The gene switch system of claim 12, wherein the cell tag comprises an amino acid sequence that is at least 90% identical to SEQ ID NO: 189 or 190.

14. The gene switch system of claim 12, wherein the cell tag comprises an amino acid sequence that is at least 90% identical to SEQ ID NO: 190.

15. The gene switch system of claim 8, wherein the ligand-inducible promoter comprises the polynucleotide sequence of any one of SEQ ID NOs: 40-64.

16. The gene switch system of claim 8, wherein the DNA binding domain comprises the amino acid sequence of SEQ ID NO: 184.

17. The gene switch system of claim 8, wherein the transactivation domain comprises the amino acid sequence of SEQ ID NO: 181.

18. The gene switch system of claim 8, wherein at least one of the first and second ligand binding domains comprises an amino acid sequence that is at least 90% identical to any one of SEQ ID NOs: 182, 185, and 186.

19. The gene switch system of claim 8, wherein the heterologous gene encodes a cytokine.

20. The gene switch system of claim 19, wherein the cytokine is IL-1, IL-2, IL-15, IL-12, IL-21, a fusion of IL-15 and IL-15Ra, or an IL-15 variant.

21. The gene switch system of claim 19, wherein the heterologous gene encodes a fusion polypeptide comprising: IL-15 or a functional variant thereof; and IL-15Rα or a functional variant thereof.

22. The gene switch system of claim 21, wherein the fusion polypeptide is connected to a cell tag by a polypeptide linker.

23. The gene switch system of claim 21, wherein the fusion polypeptide comprises: (a) an amino acid sequence of SEQ ID NO: 203 or functional variant thereof; and (b) an amino acid sequence of SEQ ID NO: 204 or a functional variant thereof.

24. The gene switch system of claim 8, wherein the polypeptide linker comprises a 2A linker, a p2A linker, a T2A linker, a F2A linker, an E2A linker, a GSG-2A linker, or one or more derivatives thereof.

25. The gene switch system of claim 8, wherein the polypeptide linker comprises an amino acid sequence having at least 90% sequence identity with any one of SEQ ID NOs: 153-160.

26. The gene switch system of claim 8, wherein:

(a) the ligand-inducible promoter comprises the polynucleotide sequence of any one of SEQ ID NOs: 40-64; and (b) the polypeptide linker comprises a 2A linker, a p2A linker, a T2A linker, a F2A linker, an E2A linker, or a GSG-2A linker.

27. The gene switch system of claim 26, wherein expression of the first and second gene switch polypeptides are modulated by an EF1A promoter or a functional variant thereof.

28. The gene switch system of claim 27, wherein the EF1A promoter or functional variant thereof comprises a polynucleotide sequence of any one of SEQ ID NOs: 58-60.

29. A method of regulating the expression of a heterologous gene in an effector cell, the method comprising introducing into the effector cell the gene switch system of claim 8 and contacting the effector cell with a ligand in an amount sufficient to induce expression of the heterologous gene.

30. The method of claim 29, wherein the heterologous gene encodes an antigen-binding polypeptide.

31. The method of claim 30, wherein the antigen-binding polypeptide selectively binds a predetermined cell surface protein of a target cell.

32. The method of claim 31, wherein the target cell is a mammalian cell.

* * * * *